(12) United States Patent
Yamazaki et al.

(10) Patent No.: US 10,611,804 B2
(45) Date of Patent: *Apr. 7, 2020

(54) HEPAROSAN-PRODUCING BACTERIUM AND HEPAROSAN MANUFACTURING METHOD

(71) Applicant: AJINOMOTO CO., INC., Tokyo (JP)

(72) Inventors: Shunsuke Yamazaki, Kanagawa (JP); Tomoko Shimizu, Kanagawa (JP); Kenichi Mori, Kanagawa (JP); Naoto Tonouchi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,354

(22) Filed: Apr. 20, 2018

(65) Prior Publication Data

US 2018/0237479 A1 Aug. 23, 2018

Related U.S. Application Data

(63) Continuation of application No. 15/082,464, filed on Mar. 28, 2016, now Pat. No. 9,975,928, which is a continuation of application No. PCT/JP2014/076357, filed on Oct. 2, 2014.

(30) Foreign Application Priority Data

| Oct. 2, 2013 | (JP) | 2013-207003 |
| Dec. 16, 2013 | (JP) | 2013-259620 |
| Dec. 16, 2013 | (JP) | 2013-259621 |
| Feb. 28, 2014 | (JP) | 2014-039250 |

(51) Int. Cl.

| C07K 14/245 | (2006.01) |
| C08B 37/00 | (2006.01) |
| C12N 15/70 | (2006.01) |
| C12P 19/26 | (2006.01) |
| C12P 19/04 | (2006.01) |

(52) U.S. Cl.
CPC ........ *C07K 14/245* (2013.01); *C08B 37/0075* (2013.01); *C12N 15/70* (2013.01); *C12P 19/04* (2013.01); *C12P 19/26* (2013.01)

(58) Field of Classification Search
CPC .......... C12P 19/04; C12P 19/26; C12N 15/70; C08B 37/0075; C07K 14/245
See application file for complete search history.

(56) References Cited

U.S. PATENT DOCUMENTS

| 7,176,028 B2 | 2/2007 | Gowrishankar et al. |
| 8,460,903 B2 | 6/2013 | Savrasova et al. |
| 8,592,186 B2 * | 11/2013 | De Rosa ................. C12P 19/26 435/101 |
| 8,852,897 B2 | 10/2014 | Savrasova et al. |
| 8,883,452 B2 | 11/2014 | Wang et al. |
| 9,234,223 B2 | 1/2016 | Yamazaki et al. |
| 9,975,928 B2 * | 5/2018 | Yamazaki ................ C12P 19/04 |
| 2005/0181464 A1 * | 8/2005 | Edwards .............. C07K 14/205 435/7.32 |
| 2011/0111458 A1 | 5/2011 | Masuda et al. |
| 2012/0035078 A1 | 2/2012 | Papoutsakis et al. |
| 2012/0135470 A1 | 5/2012 | De Rosa et al. |
| 2012/0157669 A1 | 6/2012 | Wang et al. |
| 2016/0201103 A1 | 7/2016 | Yamazaki et al. |

FOREIGN PATENT DOCUMENTS

| JP | 2013-503606 | 2/2013 |
| WO | WO03/008607 | 1/2003 |
| WO | WO2009/014559 | 1/2009 |
| WO | WO2010/136435 | 12/2010 |

OTHER PUBLICATIONS

Bailey, M. J. A., et al., "RfaH and the ops element, components of a novel system controlling bacterial transcription elongation," Mol. Microbiol. 1997;26(5):845-851.

Hodson, N., et al., "Identification That KfiA, a Protein Essential for the Biosynthesis of the *Escherichia coli* K5 Capsular Polysaccharide, Is an α-UDP-GlcNAc Glycosyltransferase," J. Biol. Chem. 2000;275(35):27311-27315.

Jann, B., et al., "Structure and Biosynthesis of the Capsular Antigens of *Escherichia coli*," Current Topics in Microbiology and Immunology, vol. 150, 1990, pp. 19-42.

Kane, T. A., et al., "Functional Characterization of PmHS1, a *Pasteurella multocida* Heparosan Synthase," J. Biol. Chem. 2006;281(44):33192-33197.

Kang, M. J., et al., "Identification of Genes Affecting Lycopene Accumulation in *Escherichia coli* Using a Shot-Gun Method," Biotechnol. Bioeng. 2005;91(5):636-642.

(Continued)

*Primary Examiner* — Ganapathirama Raghu
(74) *Attorney, Agent, or Firm* — Cermak Nakajima & McGowan LLP; Shelly Guest Cermak

(57) ABSTRACT

A method for producing heparosan is provided. Heparosan is produced by culturing an *Escherichia* bacterium having a heparosan-producing ability and modified so that expression of one or more genes, such as rbsR, rbsK, rbsB, hsrA, glgB, glgX, micF, rcsD, rcsB, ybiX, ybiI, ybiJ, ybiC, ybiB, rfaH, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, ycfS, lepB, rnc, era, dapA, gcvR, bcp, hyfA, rpoE, nadB, yfiC, srmB, g1414, g1413, nuoE, nuoF, nuoG, glmZ, hemY, hemX, hemD, rlmL, artQ, artM, artJ, rlmC, ybjO, yejO, yejM, yejL, rpoS, ygbN, ygbM, ygbL, g3798, g3797, g3796, g3795, g3794, g3793, g3792, ryjA, soxR, soxS, yjcC, yjcB, efeU, and efeO, is/are increased in a medium, and collecting heparosan from the medium.

5 Claims, 1 Drawing Sheet
Specification includes a Sequence Listing.

(56) References Cited

OTHER PUBLICATIONS

Lindahl, U., et al., "Regulated Diversity of Heparan Sulfate," J. Biol. Chem. 1998;273(39):24979-24982.
Lindahl, U., et al., "Generation of "Neoheparin" from *E. coli* K5 Capsular Polysaccharide," J. Med. Chem. 2005;48:349-352.
McNulty, C., et al., "The cell surface expression of group 2 capsular polysaccharides in *Escherichia coli*: the role of KpsD, RhsA and a multi-protein complex at the pole of the cell," Mol. Microbiol. 2006;59(3):907-922.
Santos, C. N. S., et al., "Rational, combinatorial, and genomic approaches for engineering L-tyrosine production in *Escherichia coli*," PNAS 2012;109(34)13538-13543.
Wang, Z., et al., "*E. coli* K5 fermentation and the Preparation of Heparosan, a Bioengineered Heparin Precursor," Biotechnol. Bioeng. 2010;107(6):964-973.
Zhang, C., et al., "Metabolic engineering of *Escherichia coli* BL21 for biosynthesis of heparosan, a bioengineered heparin precursor," Metabolic Eng. 2012;14:521-527.
Zhang, Z., et al., "Solution Structures of Chemoenzymatically Synthesized Heparin and Its Precursors," J. Am. Chem. Soc. 2008;130(39):12998-13007.
International Search Report for PCT Patent App. No. PCT/JP2014/076357 (dated Dec. 22, 2014).
International Preliminary Report on Patentability for PCT Patent App. No. PCT/JP2014/076357 (dated Apr. 14, 2016).
Barreteau, H., et al., "Production of intracellular heparosan and derived oligosaccharides by lyase expression in metabolically engineered *E. coli* K-12," Carbohydrate Res. 2012;360:19-24.
Missiakas, D., et al., "The extracytoplasmic function sigma factors: role and regulation," Mol. Microbiol. 1998;28(6):1059-1066.
Rowe, S., et al., "Regulation of the *Escherichia coli* K5 Capsule Gene Cluster: Evidence for the Roles of H-NS, BipA, and Integration Host Factor in Regulation of Group 2 Capsule Gene Clusters in Pathogenic *E. coli*," J. Bacteriol. 2000;182(10):2741-2745.
Stevens, M. P., et al., "Regulation of the *Escherichia coli* K5 capsule gene cluster by transcription antitermination," Mol. Microbiol. 1997;24(5):1001-1012.
Supplemental Partial European Search Report for European Patent App. No. 14850420.2 (dated May 15, 2017).
Tomar, S. K., et al., "NusG-Spt5 Proteins—Universal Tools for Transcription Modification and Communication," Chem. Rev. 2013;113:8604-8619.
Leeds, J. A., et al., "RfaH Enhances Elongation of *Escherichia coli* hlyCABD mRNA," J. Bacteriol. 1996;178 (7):1850-1857.
Stevens, M. P., et al., "Regulation of *Escherichia coli* K5 capsular polysaccharide expression: Evidence for involvement of RfaH in the expression of group II capsules," FEMS Microbiol. Lett. 1994;124:93-98.
Xue, P., et al., "Regulation of Expression of the Region 3 Promoter of the *Escherichia coli* K5 Capsule Gene Cluster Involves H-NS, SlyA, and a Large 5' Untranslated Region," J. Bacteriol. 2009;191(6):1838-1846.
Li, J., et al., "NusG, a New *Escherichia coli* Elongation Factor Involved in Transcriptional Antitermination by the N Protein of Phage λ*," J. Biol. Chem. 1992;267(9):6012-6019.
Chatzidaki-Livanis, M., et al., "A Family of Transcriptional Antitermination Factors Necessary for Synthesis of the Capsular Polysaccharides of Bacteroides fragilis," J. Bacteriol. 2009;191(23):7288-7295.
Bailey, M. J. A., et al., "Increased distal gene transcription by the elongation factor RfaH, a specialized homologue of NusG," Mol. Microbiol. 1996;22(4):729-737.
Extended European Search Report for European Patent App. No. 19197639.8 (dated Feb. 2020).
Nagy, G., et al., "Transcriptional regulation through RfaH contributes to intestinal colonization by *Escherichia coli*," FEMS Microbiol. Lett. 2005;244:173-180.
Cress, B. F., et al., "Draft Genome Sequence of *Escherichia coli* Strain Nissle 1917 (Serovar O6:K5:H1)," Genome Announcements 2013;1(2):pp. 1-2.
Cimini, D., et al., "Homologous overexpression of rfaH in *E. coli* K4 improves the production of chondroitin-like capsular polysaccharide," Microbiol. Cell Factories 2013;12(1):pp. 1-12.

* cited by examiner

[Fig.1]

Sequence of native promoter Pnlp0

```
                        -35(Pnlp2)                  -10(Pnlp2)
aaaacgtgaggaaatacctggattttttcctggttattttgccgcaggtcagcgtatcgtg -35(Pnlp1)              -10(Pnlp1)    transcription start site
aagatcttttccagtgttcagtagggtgccttgcacggtaattatgtcactggttattaa M    S
ccaattttttcctgggggataaatgagc
```

[Fig.2]

Sequence of mutant promoter Pnlp8

```
                        -35(Pnlp2)                  -10(Pnlp2)
aaaacgtgaggaaatacctggattttttcctggttattttgccgcaggtcagcgtataatg -35(Pnlp1)              -10(Pnlp1)    transcription start site
aagatcttttccagtgttgacaagggtgccttgcacggttataatgtcactggttattaa M    S
ccaattttttcctgggggataaatgagc
```

HEPAROSAN-PRODUCING BACTERIUM AND HEPAROSAN MANUFACTURING METHOD

This application is a Continuation of, and claims priority under 35 U.S.C. § 120 to, U.S. patent application Ser. No. 15/082,464, filed Mar. 28, 2016, now U.S. Pat. No. 9,975, 928 which was a Continuation of, and claimed priority under 35 U.S.C. § 120 to, International Application No. PCT/JP2014/076357, filed Oct. 2, 2014, and claims priority therethrough under 35 U.S.C. § 119 to Japanese Patent Application No. 2013-207003, filed Oct. 2, 2013, Japanese Patent Application No. 2013-259620, filed Dec. 16, 2013, Japanese Patent Application No. 2013-259621, filed Dec. 16, 2013, and Japanese Patent Application No. 2014-039250, filed Feb. 28, 2014, the entireties of which are incorporated by reference herein. Also, the Sequence Listing filed electronically herewith is hereby incorporated by reference (File name: 2018-04-20T_US-545C_Seq_List; File size: 583 KB; Date recorded: Apr. 20, 2018).

BACKGROUND OF THE INVENTION

Field of the Invention

The present invention relates to a heparosan-producing bacterium and a method for producing heparosan.

Brief Description of the Related Art

Heparosan (also referred to as N-acetylheparosan) is a polysaccharide constituted by a repetition structure of a disaccharide having a glucuronic acid (GlcUA) residue and an N-acetyl-D-glucosamine (GlcNAc) residue [→4)-β-GlcUA-(1→4)-α-GlcNAc-(1→].

In nature, heparosan is produced by the *Escherichia coli* K5 strain and the *Pasteurella multocida* type D strain as a capsular polysaccharide (Lindahl U. et al. (1998) J. Biol. Chem., 273(39):24979-24982). These heparosan-producing bacteria are pathogenic and cause urinary tract infections, atrophic rhinitis, etc. in mammals.

In the *Escherichia coli* K5 strain, two kinds of glucosyltransferases, which are heparosan synthetases, and six kinds of heparosan efflux carriers are required for the biosynthesis of heparosan. That is, GlcNAc and GlcUA are first alternately added to a non-reducing end of the sugar chain by the glucosyltransferases (KfiA and KfiC), and the heparosan chain is thereby extended (Hodson N. et al. (2000) J. Biol. Chem., 275(35):27311-27315). Then, the heparosan chain is transported to the cell surface by the heparosan efflux carriers, which includeKpsC, KpsD, KpsE, KpsM, KpsS, and KpsT (McNulty C. et al. (2006) Mol. Microbiol., 59(3):907-22). It is thought that the heparosan chain is fixed to a phosphatidic acid molecule in the outer membrane of *Escherichia coli* on the cell surface through lipid substitution at the reducing end (Jann B., Jann K. (1990) Curr. Top Microbiol. Immunol., 150:19-42).

In the *Escherichia coli* K5 strain, the heparosan synthetase genes and the heparosan efflux carrier genes form a cluster on the chromosome. The cluster is divided into regions 1 to 3, and region 2, located at the center of the cluster, encodes the four proteins including the heparosan synthetases, KfiA, KfiB, KfiC, and KfiD.

The *Pasteurella multocida* type D strain has PmHS1, which acts as a heparosan synthetase (glucosyltransferase) (Kane T. A. et al. (2006) J. Biol. Chem., November 3; 281(44):33192-33197). PmHS1 has active domains homologous to both KfiA and KfiC of the *Escherichia coli* K5 strain, and it catalyzes a polymerization reaction using both UDP-glucuronic acid and UDP-N-acetylglucosamine as substrates. However, to date, no heparosan efflux carriers of the *Pasteurella multocida* type D strain have been elucidated.

Heparin is one of anticoagulants, and is useful in therapeutic treatments of thromboembolism and disseminated intravascular coagulation (DIC), prevention of blood coagulation during artificial dialysis and extracorporeal circulation, and so forth. Heparosan is a sugar chain structure of heparin, and can be converted into a heparin-like polysaccharide through such steps as deacetylation, epimerization, sulfation, and molecular weight adjustment (Lindahl U. et al. (2005) J. Med. Chem., 48(2):349-352 and Zhang Z. et al. (2008) Journal of the American Chemical Society, 130(39): 12998-13007).

Heparin exhibits an anticoagulant activity through activation of antithrombin III, which is an anticoagulant. Antithrombin III binds to the active serine moieties of thrombin, Xa factor (active type of X factor), and other serine proteases to inhibit them. Thrombin is a blood coagulation factor, and the Xa factor is a factor involved in the maturation of thrombin. Heparin binds to this antithrombin III to change the structure thereof, and thereby activates the inhibitory activity. Thrombin shows higher affinity for the heparin-antithrombin-III complex compared with the Xa factor.

Low molecular weight heparins having an average molecular weight of 4000 to 6000 Da, which are obtainable by enzymatic or chemical treatments of heparin and fractionation, show less adverse reaction of hemorrhage, and frequency of use thereof is increasing in recent years. Since the low molecular weight heparins have a short sugar chain length, they can barely bind with thrombin, although they can bind with antithrombin III. For the inhibition of thrombin by the heparin-antithrombin III complex, binding of thrombin to heparin is necessary, but for the inhibition of the Xa factor by the heparin-antithrombin III complex, binding of the Xa factor to heparin is unnecessary. Therefore, the low molecular weight heparins hardly inhibit the activity of thrombin, but can inhibit the activity of the Xa factor.

Most of the currently available heparin preparations utilize extracts of porcine intestinal mucosa. However, in 2008, a fatal accident occurred as a result of contamination of impurities, and therefore the production and development of quality-controlled non-animal heparin was investigated.

It has recently been demonstrated through laboratory scale research that heparosan obtained from the *Escherichia coli* K5 strain can be enzymatically converted into a heparin-like anticoagulant polysaccharide (Lindahl U. et al. (2005) J. Med. Chem., 48(2):349-352 and Zhang Z. et al. (2008) Journal of the American Chemical Society, 130(39):12998-13007). Furthermore, heparosan can also be utilized for uses other than heparin manufacture (WO2009/014559).

Large scale production of heparosan using *Escherichia coli* K5 is being investigated, and it has been reported that 15 g/L of heparosan was produced in a 7-L fermentation tank (Wang Z. et al. (2010) Biotechnol. Bioeng., 107(6):964-973, Japanese Patent Laid-open (Kohyo) No. 2013-503606). In order to supply heparosan on an industrial scale as a raw material of heparin production, it must be scaled up to the order of 100,000 L, but there are issues that must be resolved, particularly concerning improving the substrate consumption rate, increasing the oxygen supply in fermentation tank, etc.

Furthermore, a heparosan-producing bacterium produced from a nonpathogenic *Escherichia coli* BL21(DE3) host has very recently been reported (Zang C. et al. (2012) Metabolic Engineering, 14(5):521-527). That is, in flask culture of the BL21 strain that had been introduced with an expression vector pETDuet-1 carrying the four heparosan biosynthesis genes, kfiA, kfiB, kfiC, and kfiD, which constitute region 2 of the *Escherichia coli* K5 strain, production of 334 mg/L of heparosan was confirmed.

Although the factors required for the heparosan production have been elucidated, factors that improve heparosan-producing ability of a heparosan-producing bacterium have not been previously reported.

SUMMARY OF THE INVENTION

Aspects to be Achieved by the Invention

Aspects of the present invention are to develop a novel technique for improving heparosan-producing ability of bacteria, and thereby provide an efficient method for producing heparosan.

It has been found that, by increasing the expression of one or more of the genes depicted in Tables 1 to 3 in bacteria having a heparosan-producing ability, the heparosan-producing ability is improved.

TABLE 1

| Gene | Function of gene product |
| --- | --- |
| rbsR | DNA-binding transcriptional repressor of ribose metabolism |
| rbsK | enzyme; Degradation of small molecules: Carbon compounds |
| rbsB | D-ribose transporter subunit |
| hsrA | inner membrane protein, multidrug efflux pump |
| glgB | 1,4-alpha-glucan branching enzyme |
| glgX | glycogen debranching enzyme |
| micF | Regulatory antisense sRNA affecting ompF expression; member of soxRS regulon |
| rcsD | phosphotransfer intermediate protein in two-component regulatory system with RcsBC |
| rcsB | DNA-binding response regulator in two-component regulatory system with RcsC and YojN |
| ybiX | conserved protein |
| ybiI | DksA-type zinc finger protein, function unknown |
| ybiJ | predicted protein |
| ybiC | predicted dehydrogenase |
| ybiB | predicted transferase/phosphorylase |
| rfaH | transcriptional antiterminator |
| nusG | transcription terminator |

TABLE 2

| Gene | Function of gene product |
| --- | --- |
| pcoE | Probable copper-binding protein pcoE precursor |
| pcoS | Probable sensor protein pcoS |
| pcoR | Transcriptional regulatory protein pcoR |
| yhcN | conserved protein |
| yhcO | predicted barnase inhibitor |
| aaeB | p-hydroxybenzoic acid efflux system component |
| aaeA | p-hydroxybenzoic acid efflux system component |
| aaeX | membrane protein of efflux system |
| g1455 | hypothetical protein |
| alpA | Predicted transcriptional regulator |
| g1453 | Haemolysin expression modulating protein |
| yrbA | predicted DNA-binding transcriptional regulator, BolA family |
| mlaB | ABC transporter maintaining OM lipid asymmetry, cytoplasmic STAS component |
| mlaC | ABC transporter maintaining OM lipid asymmetry, periplasmic binding protein |
| mlaD | ABC transporter maintaining OM lipid asymmetry, anchored periplasmic binding protein |
| mlaE | ABC transporter maintaining OM lipid asymmetry, inner membrane permease protein |
| mlaF | ABC transporter maintaining OM lipid asymmetry, ATP-binding protein |
| yrbG | predicted calcium/sodium: proton antiporter |
| norW | NADH: flavorubredoxin oxidoreductase |
| ybjI | FMN and erythrose-4-P phosphatase |

TABLE 2-continued

| Gene | Function of gene product |
| --- | --- |
| ybjJ | predicted transporter |
| ybjK | predicted DNA-binding transcriptional regulator |
| rybB | sRNA effector of ompC and ompW mRNA instability; requires Hfq |
| thrB | homoserine kinase |
| thrA | fused aspartokinase I and homoserine dehydrogenase I |
| thrL | thr operon leader peptide |
| yjtD | predicted rRNA methyltransferase |
| yjjY | predicted protein |
| fruA | fused fructose-specific PTS enzymes: IIBcomponent/IIC components |
| psuK | pseudouridine kinase |
| ytfT | predicted sugar transporter subunit: membrane component of ABC superfamily |
| yjfF | predicted sugar transporter subunit: membrane component of ABC superfamily |
| fbp | fructose-1,6-bisphosphatase I |
| yagU | inner membrane protein, DUF1440 family |
| paoA | PaoABC aldehyde oxidoreductase, 2Fe—2S subunit |
| paoB | PaoABC aldehyde oxidoreductase, FAD-containing subunit |
| gsiC | glutathione transporter, permease component, ABC superfamily |
| gsiD | glutathione transporter, permease component, ABC superfamily |
| yliE | predicted cyclic-di-GMP phosphodiesterase, inner membrane protein |
| irp2 | non-ribosomal peptide synthase |
| irp1 | non-ribosomal peptide synthase |
| bhsA | biofilm, cell surface and signaling protein |
| ycfS | L,D-transpeptidase linking Lpp to murein |

TABLE 3

| Gene | Function of gene product |
| --- | --- |
| lepB | leader peptidase (signal peptidase I) |
| rnc | RNase III |
| era | factor; Global regulatory functions |
| dapA | dihydrodipicolinate synthase |
| gcvR | DNA-binding transcriptional repressor, regulatory protein accessory to GcvA |
| bcp | peroxiredoxin; thiol peroxidase, thioredoxin-dependent |
| hyfA | hydrogenase 4, 4Fe—4S subunit |
| rpoE | RNA polymerase, sigma 24 (sigma E) factor |
| nadB | quinolinate synthase, L-aspartate oxidase (B protein) subunit |
| yfiC | tRNA1(Val) (adenine(37)-N6)-methyltransferase |
| srmB | ATP-dependent RNA helicase |
| g1414 | Putative transposase |
| g1413 | putative transposase |
| nuoE | NADH: ubiquinone oxidoreductase, chain E |
| nuoF | NADH: ubiquinone oxidoreductase, chain F |
| nuoG | NADH: ubiquinone oxidoreductase, chain G |
| glmZ | sRNA antisense activator of glmS mRNA, Hfq-dependent |
| hemY | putative protoheme IX synthesis protein |
| hemX | putative uroporphyrinogen III methyltransferase |
| hemD | uroporphyrinogen III synthase |
| rlmL | fused 23S rRNA m(2)G2445 and m(7)G2069 methyltransferase, SAM-dependent |
| artQ | arginine transporter subunit |
| artM | arginine transporter subunit |
| artJ | arginine binding protein, periplasmic |
| rlmC | 23S rRNA m(5)U747 methyltransferase, SAM-dependent |
| ybjO | Inner membrane protein, DUF2593 family |
| yejO | autotransporter outer membrane homology |
| yejM | putative hydrolase, inner membrane |
| yejL | conserved protein, UPF0352 family |
| rpoS | RNA polymerase, sigma S (sigma 38) factor |
| ygbN | putative transporter |
| ygbM | hypothetical protein |
| ygbL | putative class II aldolase |
| g3798 | SOS-response transcriptional repressers (RecA-mediated autopeptidases) |
| g3797 | hypothetical protein |
| g3796 | hypothetical protein |
| g3795 | hypothetical protein |

TABLE 3-continued

| Gene | Function of gene product |
|---|---|
| g3794 | Superinfection exclusion protein B |
| g3793 | Restriction inhibitor protein ral (Antirestriction protein) |
| g3792 | hypothetical protein |
| ryjA | Novel sRNA, function unknown |
| soxR | DNA-binding transcriptional dual regulator, Fe—S center for redox-sensing |
| soxS | DNA-binding transcriptional dual regulator |
| yjcC | putative membrane-anchored cyclic-di-GMP phosphodiesterase |
| yjcB | hypothetical protein |
| efeU | ferrous iron permease (pseudogene) |
| efeO | inactive ferrous ion transporter EfeUOB |

It is an aspect of the present invention to provide an *Escherichia* bacterium having a heparosan-producing ability, wherein:

the bacterium has been modified so that expression is increased of a gene selected from the group consisting of rpoE, rbsR, rbsK, rbsB, hsrA, glgB, glgX, micF, rcsD, rcsB, ybiX, ybiI, ybiJ, ybiC, ybiB, rfaH, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, ycfS, lepB, rnc, era, dapA, gcvR, bcp, hyfA, nadB, yfiC, srmB, g1414, g1413, nuoE, nuoF, nuoG, glmZ, hemY, hemX, hemD, rlmL, artQ, artM, artJ, rlmC, ybjO, yejO, yejM, yejL, rpoS, ygbN, ygbM, ygbL, g3798, g3797, g3796, g3795, g3794, g3793, g3792, ryjA, soxR, soxS, yjcC, yjcB, efeU, efeO, and combinations thereof.

It is an aspect of the present invention to provide the the bacterium bacterium as described above, which has been modified so that expression of at least the rpoE gene is increased.

It is an aspect of the present invention to provide the the bacterium as described above, which has been modified so that expression of at least the rfaH gene is increased.

It is an aspect of the present invention to provide the the bacterium as described above, which has been further modified so that expression of a gene selected from the group consisting of rbsR, rbsK, rbsB, hsrA, glgB, glgX, micF, rcsD, rcsB, ybiX, ybiI, ybiJ, ybiC, ybiB, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, ycfS, and combinations thereof.

It is an aspect of the present invention to provide the the bacterium as described above, wherein said expression is increased by increasing the copy number of the gene(s), and/or modifying a gene expression control sequence of the gene(s).

It is an aspect of the present invention to provide the the bacterium as described above, which is *Escherichia coli*.

It is an aspect of the present invention to provide the the bacterium as described above, wherein:

the rbsB gene is a DNA comprising the nucleotide sequence of positions 800 to 1690 of SEQ ID NO: 29, or a DNA comprising a nucleotide sequence having an identity of 90% or higher to the nucleotide sequence of positions 800 to 1690 of SEQ ID NO: 29 and is able to increase heparosan-producing ability of an *Escherichia* bacterium having heparosan-producing ability when expression amount thereof is increased in the bacterium;

the rbsK gene is a DNA comprising the nucleotide sequence of positions 1816 to 2745 of SEQ ID NO: 29, or a DNA comprising a nucleotide sequence having an identity of 90% or higher to the nucleotide sequence of positions 1816 to 2745 of SEQ ID NO: 29 and is able to increase heparosan-producing ability of an *Escherichia* bacterium having heparosan-producing ability when expression amount thereof is increased in the bacterium;

the rbsR gene is a DNA comprising the nucleotide sequence of positions 2749 to 3741 of SEQ ID NO: 29, or a DNA comprising a nucleotide sequence having an identity of 90% or higher to the nucleotide sequence of positions 2749 to 3741 of SEQ ID NO: 29 and is able to increase heparosan-producing ability of an *Escherichia* bacterium having heparosan-producing ability when expression amount thereof is increased in the bacterium;

the hsrA gene is a DNA comprising the complementary sequence of the nucleotide sequence of positions 3707 to 5134 of SEQ ID NO: 29, or a DNA comprising a nucleotide sequence having an identity of 90% or higher to the complementary sequence of the nucleotide sequence of positions 3707 to 5134 of SEQ ID NO: 29 and is able to increase heparosan-producing ability of an *Escherichia* bacterium having heparosan-producing ability when expression amount thereof is increased in the bacterium;

the glgB gene is a DNA comprising the nucleotide sequence of positions 989 to 3175 of SEQ ID NO: 34, or a DNA comprising a nucleotide sequence having an identity of 90% or higher to the nucleotide sequence of positions 989 to 3175 of SEQ ID NO: 34 and is able to increase heparosan-producing ability of an *Escherichia* bacterium having heparosan-producing ability when expression amount thereof is increased in the bacterium;

the glgX gene is a DNA comprising the nucleotide sequence of positions 3172 to 5145 of SEQ ID NO: 34, or a DNA comprising a nucleotide sequence having an identity of 90% or higher to the nucleotide sequence of positions 3172 to 5145 of SEQ ID NO: 34 and is able to increase heparosan-producing ability of an *Escherichia* bacterium having heparosan-producing ability when expression amount thereof is increased in the bacterium;

the rcsB gene is a DNA comprising the nucleotide sequence of positions 3312 to 3962 of SEQ ID NO: 43, or a DNA comprising a nucleotide sequence having an identity of 90% or higher to the nucleotide sequence of positions 3312 to 3962 of SEQ ID NO: 43 and is able to increase heparosan-producing ability of an *Escherichia* bacterium having heparosan-producing ability when expression amount thereof is increased in the bacterium;

the rcsD gene is a DNA comprising the nucleotide sequence of positions 623 to 3295 of SEQ ID NO: 43, or a DNA comprising a nucleotide sequence having an identity of 90% or higher to the nucleotide sequence of positions 623 to 3295 of SEQ ID NO: 43 and is able to increase heparosan-producing ability of an *Escherichia* bacterium having heparosan-producing ability when expression amount thereof is increased in the bacterium;

the micF gene is a DNA comprising the nucleotide sequence of positions 219 to 311 of SEQ ID NO: 43, or a DNA comprising a nucleotide sequence having an identity of 90% or higher to the nucleotide sequence of positions 219 to 311 of SEQ ID NO: 43 and is able to increase heparosan-producing ability of an *Escherichia* bacterium having heparosan-producing ability when expression amount thereof is increased in the bacterium;

the ybiX gene is a DNA comprising the nucleotide sequence of positions 718 to 1395 of SEQ ID NO: 37, or a DNA comprising a nucleotide sequence having an identity of 90% or higher to the nucleotide sequence of positions 718 to 1395 of SEQ ID NO: 37 and is able to increase heparosan-producing ability of an *Escherichia* bacterium having heparosan-producing ability when expression amount thereof is increased in the bacterium;

the ybiI gene is a DNA comprising the nucleotide sequence of positions 1469 to 1735 of SEQ ID NO: 37, or a DNA comprising a nucleotide sequence having an identity of 90% or higher to the nucleotide sequence of positions 1469 to 1735 of SEQ ID NO: 37 and is able to increase heparosan-producing ability of an *Escherichia* bacterium having heparosan-producing ability when expression amount thereof is increased in the bacterium;

the ybiJ gene is a DNA comprising the nucleotide sequence of positions 2000 to 2260 of SEQ ID NO: 37, or a DNA comprising a nucleotide sequence having an identity of 90% or higher to the nucleotide sequence of positions 2000 to 2260 of SEQ ID NO: 37 and is able to increase heparosan-producing ability of an *Escherichia* bacterium having heparosan-producing ability when expression amount thereof is increased in the bacterium;

the ybiC gene is a DNA comprising the complementary sequence of the nucleotide sequence of positions 2488 to 3574 of SEQ ID NO: 37, or a DNA comprising a nucleotide sequence having an identity of 90% or higher to the complementary sequence of the nucleotide sequence of positions 2488 to 3574 of SEQ ID NO: 37 and is able to increase heparosan-producing ability of an *Escherichia* bacterium having heparosan-producing ability when expression amount thereof is increased in the bacterium;

the ybiB gene is a DNA comprising the complementary sequence of the nucleotide sequence of positions 3715 to 4677 of SEQ ID NO: 37, or a DNA comprising a nucleotide sequence having an identity of 90% or higher to the complementary sequence of the nucleotide sequence of positions 3715 to 4677 of SEQ ID NO: 37 and is able to increase heparosan-producing ability of an *Escherichia* bacterium having heparosan-producing ability when expression amount thereof is increased in the bacterium;

the rfaH gene is a DNA comprising the nucleotide sequence of SEQ ID NO: 46, or a DNA comprising a nucleotide sequence having an identity of 90% or higher to the nucleotide sequence of SEQ ID NO: 46 and is able to increase heparosan-producing ability of an *Escherichia* bacterium having heparosan-producing ability when expression amount thereof is increased in the bacterium;

the nusG gene is a DNA comprising the nucleotide sequence of SEQ ID NO: 48, or a DNA comprising a nucleotide sequence having an identity of 90% or higher to the nucleotide sequence of SEQ ID NO: 48 and is able to increase heparosan-producing ability of an *Escherichia* bacterium having heparosan-producing ability when expression amount thereof is increased in the bacterium;

the pcoR gene is a DNA comprising the nucleotide sequence of positions 128 to 808 of SEQ ID NO: 50, or a DNA comprising a nucleotide sequence having an identity of 90% or higher to the nucleotide sequence of positions 128 to 808 of SEQ ID NO: 50 and is able to increase heparosan-producing ability of an *Escherichia* bacterium having heparosan-producing ability when expression amount thereof is increased in the bacterium;

the pcoS gene is a DNA comprising the nucleotide sequence of positions 805 to 2205 of SEQ ID NO: 50, or a DNA comprising a nucleotide sequence having an identity of 90% or higher to the nucleotide sequence of positions 805 to 2205 of SEQ ID NO: 50 and is able to increase heparosan-producing ability of an *Escherichia* bacterium having heparosan-producing ability when expression amount thereof is increased in the bacterium;

the pcoE gene is a DNA comprising the nucleotide sequence of positions 2423 to 2857 of SEQ ID NO: 50, or a DNA comprising a nucleotide sequence having an identity of 90% or higher to the nucleotide sequence of positions 2423 to 2857 of SEQ ID NO: 50 and is able to increase heparosan-producing ability of an *Escherichia* bacterium having heparosan-producing ability when expression amount thereof is increased in the bacterium;

the yhcN gene is a DNA comprising the nucleotide sequence of positions 63 to 326 of SEQ ID NO: 54, or a DNA comprising a nucleotide sequence having an identity of 90% or higher to the nucleotide sequence of positions 63 to 326 of SEQ ID NO: 54 and is able to increase heparosan-producing ability of an *Escherichia* bacterium having heparosan-producing ability when expression amount thereof is increased in the bacterium;

the yhcO gene is a DNA comprising the complementary sequence of the nucleotide sequence of positions 382 to 654 of SEQ ID NO: 54, or a DNA comprising a nucleotide sequence having an identity of 90% or higher to the complementary sequence of the nucleotide sequence of positions 382 to 654 of SEQ ID NO: 54 and is able to increase heparosan-producing ability of an *Escherichia* bacterium having heparosan-producing ability when expression amount thereof is increased in the bacterium;

the aaeB gene is a DNA comprising the complementary sequence of the nucleotide sequence of positions 746 to 2713 of SEQ ID NO: 54, or a DNA comprising a nucleotide sequence having an identity of 90% or higher to the complementary sequence of the nucleotide sequence of positions 746 to 2713 of SEQ ID NO: 54 and is able to increase heparosan-producing ability of an *Escherichia* bacterium having heparosan-producing ability when expression amount thereof is increased in the bacterium;

the aaeA gene is a DNA comprising the complementary sequence of the nucleotide sequence of positions 2719 to 3651 of SEQ ID NO: 54, or a DNA comprising a nucleotide sequence having an identity of 90% or higher to the complementary sequence of the nucleotide sequence of positions 2719 to 3651 of SEQ ID NO: 54 and is able to increase heparosan-producing ability of an *Escherichia* bacterium having heparosan-producing ability when expression amount thereof is increased in the bacterium;

the aaeX gene is a DNA comprising the complementary sequence of the nucleotide sequence of positions 3659 to 3931 of SEQ ID NO: 54, or a DNA comprising a nucleotide sequence having an identity of 90% or higher to the complementary sequence of the nucleotide sequence of positions 3659 to 3931 of SEQ ID NO: 54 and is able to increase heparosan-producing ability of an *Escherichia* bacterium having heparosan-producing ability when expression amount thereof is increased in the bacterium;

the g1455 gene is a DNA comprising the complementary sequence of the nucleotide sequence of positions 568 to 1140 of SEQ ID NO: 60, or a DNA comprising a nucleotide sequence having an identity of 90% or higher to the complementary sequence of the nucleotide sequence of positions 568 to 1140 of SEQ ID NO: 60 and is able to increase heparosan-producing ability of an *Escherichia* bacterium having heparosan-producing ability when expression amount thereof is increased in the bacterium;

the alpA gene is a DNA comprising the complementary sequence of the nucleotide sequence of positions 1226 to 1486 of SEQ ID NO: 60, or a DNA comprising a nucleotide sequence having an identity of 90% or higher to the complementary sequence of the nucleotide sequence of positions 1226 to 1486 of SEQ ID NO: 60 and is able to increase heparosan-producing ability of an *Escherichia* bacterium having heparosan-producing ability when expression amount thereof is increased in the bacterium;

the g1453 gene is a DNA comprising the nucleotide sequence of positions 2389 to 2529 of SEQ ID NO: 60, or a DNA comprising a nucleotide sequence having an identity of 90% or higher to the nucleotide sequence of positions 2389 to 2529 of SEQ ID NO: 60 and is able to increase heparosan-producing ability of an *Escherichia* bacterium having heparosan-producing ability when expression amount thereof is increased in the bacterium;

the yrbA gene is a DNA comprising the complementary sequence of the nucleotide sequence of positions 977 to 1246 of SEQ ID NO: 64, or a DNA comprising a nucleotide sequence having an identity of 90% or higher to the complementary sequence of the nucleotide sequence of positions 977 to 1246 of SEQ ID NO: 64 and is able to increase heparosan-producing ability of an *Escherichia* bacterium having heparosan-producing ability when expression amount thereof is increased in the bacterium;

the mlaB gene is a DNA comprising the complementary sequence of the nucleotide sequence of positions 1391 to 1780 of SEQ ID NO: 64, or a DNA comprising a nucleotide sequence having an identity of 90% or higher to the complementary sequence of the nucleotide sequence of positions 1391 to 1780 of SEQ ID NO: 64 and is able to increase heparosan-producing ability of an *Escherichia* bacterium having heparosan-producing ability when expression amount thereof is increased in the bacterium;

the mlaC gene is a DNA comprising the complementary sequence of the nucleotide sequence of positions 1684 to 2319 of SEQ ID NO: 64, or a DNA comprising a nucleotide sequence having an identity of 90% or higher to the complementary sequence of the nucleotide sequence of positions 1684 to 2319 of SEQ ID NO: 64 and is able to increase heparosan-producing ability of an *Escherichia* bacterium having heparosan-producing ability when expression amount thereof is increased in the bacterium;

the mlaD gene is a DNA comprising the complementary sequence of the nucleotide sequence of positions 2338 to 2889 of SEQ ID NO: 64, or a DNA comprising a nucleotide sequence having an identity of 90% or higher to the complementary sequence of the nucleotide sequence of positions 2338 to 2889 of SEQ ID NO: 64 and is able to increase heparosan-producing ability of an *Escherichia* bacterium having heparosan-producing ability when expression amount thereof is increased in the bacterium;

the mlaE gene is a DNA comprising the complementary sequence of the nucleotide sequence of positions 2894 to 3676 of SEQ ID NO: 64, or a DNA comprising a nucleotide sequence having an identity of 90% or higher to the complementary sequence of the nucleotide sequence of positions 2894 to 3676 of SEQ ID NO: 64 and is able to increase heparosan-producing ability of an *Escherichia* bacterium having heparosan-producing ability when expression amount thereof is increased in the bacterium;

the mlaF gene is a DNA comprising the complementary sequence of the nucleotide sequence of positions 3684 to 4493 of SEQ ID NO: 64, or a DNA comprising a nucleotide sequence having an identity of 90% or higher to the complementary sequence of the nucleotide sequence of positions 3684 to 4493 of SEQ ID NO: 64 and is able to increase heparosan-producing ability of an *Escherichia* bacterium having heparosan-producing ability when expression amount thereof is increased in the bacterium;

the yrbG gene is a DNA comprising the nucleotide sequence of positions 4703 to 5680 of SEQ ID NO: 64, or a DNA comprising a nucleotide sequence having an identity of 90% or higher to the nucleotide sequence of positions 4703 to 5680 of SEQ ID NO: 64 and is able to increase heparosan-producing ability of an *Escherichia* bacterium having heparosan-producing ability when expression amount thereof is increased in the bacterium;

the norW gene is a DNA comprising the nucleotide sequence of positions 1201 to 2334 of SEQ ID NO: 72, or a DNA comprising a nucleotide sequence having an identity of 90% or higher to the nucleotide sequence of positions 1201 to 2334 of SEQ ID NO: 72 and is able to increase heparosan-producing ability of an *Escherichia* bacterium having heparosan-producing ability when expression amount thereof is increased in the bacterium;

the ybjI gene is a DNA comprising the complementary sequence of the nucleotide sequence of positions 117 to 932 of SEQ ID NO: 74, or a DNA comprising a nucleotide sequence having an identity of 90% or higher to the complementary sequence of the nucleotide sequence of positions 117 to 932 of SEQ ID NO: 74 and is able to increase heparosan-producing ability of an *Escherichia* bacterium having heparosan-producing ability when expression amount thereof is increased in the bacterium;

the ybjJ gene is a DNA comprising the complementary sequence of the nucleotide sequence of positions 932 to 2140 of SEQ ID NO: 74, or a DNA comprising a nucleotide sequence having an identity of 90% or higher to the complementary sequence of the nucleotide sequence of positions 932 to 2140 of SEQ ID NO: 74 and is able to increase heparosan-producing ability of an *Escherichia* bacterium having heparosan-producing ability when expression amount thereof is increased in the bacterium;

the ybjK gene is a DNA comprising the nucleotide sequence of positions 2224 to 2760 of SEQ ID NO: 74, or a DNA comprising a nucleotide sequence having an identity of 90% or higher to the nucleotide sequence of positions 2224 to 2760 of SEQ ID NO: 74 and is able to increase heparosan-producing ability of an *Escherichia* bacterium having heparosan-producing ability when expression amount thereof is increased in the bacterium;

the rybB gene is a DNA comprising the complementary sequence of the nucleotide sequence of positions 2777 to 2855 of SEQ ID NO: 74, or a DNA comprising a nucleotide sequence having an identity of 90% or higher to the complementary sequence of the nucleotide sequence of positions 2777 to 2855 of SEQ ID NO: 74 and is able to increase heparosan-producing ability of an *Escherichia* bacterium having heparosan-producing ability when expression amount thereof is increased in the bacterium;

the yjjY gene is a DNA comprising the nucleotide sequence of positions 124 to 264 of SEQ ID NO: 78, or a DNA comprising a nucleotide sequence having an identity of 90% or higher to the nucleotide sequence of positions 124 to 264 of SEQ ID NO: 78 and is able to increase heparosan-producing ability of an *Escherichia* bacterium having heparosan-producing ability when expression amount thereof is increased in the bacterium;

the yjtD gene is a DNA comprising the nucleotide sequence of positions 664 to 1350 of SEQ ID NO: 78, or a DNA comprising a nucleotide sequence having an identity of 90% or higher to the nucleotide sequence of positions 664 to 1350 of SEQ ID NO: 78 and is able to increase heparosan-producing ability of an *Escherichia* bacterium having heparosan-producing ability when expression amount thereof is increased in the bacterium;

the thrL gene is a DNA comprising the nucleotide sequence of positions 1564 to 1629 of SEQ ID NO: 78, or a DNA comprising a nucleotide sequence having an identity of 90% or higher to the nucleotide sequence of positions 1564 to 1629 of SEQ ID NO: 78 and is able to increase heparosan-producing ability of an *Escherichia* bacterium having heparosan-producing ability when expression amount thereof is increased in the bacterium;

the thrA gene is a DNA comprising the nucleotide sequence of positions 1711 to 4173 of SEQ ID NO: 78, or a DNA comprising a nucleotide sequence having an identity of 90% or higher to the nucleotide sequence of positions 1711 to 4173 of SEQ ID NO: 78 and is able to increase heparosan-producing ability of an *Escherichia* bacterium having heparosan-producing ability when expression amount thereof is increased in the bacterium;

the thrB gene is a DNA comprising the nucleotide sequence of positions 4175 to 5107 of SEQ ID NO: 78, or a DNA comprising a nucleotide sequence having an identity of 90% or higher to the nucleotide sequence of positions 4175 to 5107 of SEQ ID NO: 78 and is able to increase heparosan-producing ability of an *Escherichia* bacterium having heparosan-producing ability when expression amount thereof is increased in the bacterium;

the fruA gene is a DNA comprising the nucleotide sequence of positions 897 to 2588 of SEQ ID NO: 84, or a DNA comprising a nucleotide sequence having an identity of 90% or higher to the nucleotide sequence of positions 897 to 2588 of SEQ ID NO: 84 and is able to increase heparosan-producing ability of an *Escherichia* bacterium having heparosan-producing ability when expression amount thereof is increased in the bacterium;

the psuK gene is a DNA comprising the nucleotide sequence of positions 3165 to 3953 of SEQ ID NO: 84, or a DNA comprising a nucleotide sequence having an identity of 90% or higher to the nucleotide sequence of positions 3165 to 3953 of SEQ ID NO: 84 and is able to increase heparosan-producing ability of an *Escherichia* bacterium having heparosan-producing ability when expression amount thereof is increased in the bacterium;

the ytfT gene is a DNA comprising the nucleotide sequence of positions 252 to 1277 of SEQ ID NO: 87, or a DNA comprising a nucleotide sequence having an identity of 90% or higher to the nucleotide sequence of positions 252 to 1277 of SEQ ID NO: 87 and is able to increase heparosan-producing ability of an *Escherichia* bacterium having heparosan-producing ability when expression amount thereof is increased in the bacterium;

the yjfF gene is a DNA comprising the nucleotide sequence of positions 1264 to 2259 of SEQ ID NO: 87, or a DNA comprising a nucleotide sequence having an identity of 90% or higher to the nucleotide sequence of positions 1264 to 2259 of SEQ ID NO: 87 and is able to increase heparosan-producing ability of an *Escherichia* bacterium having heparosan-producing ability when expression amount thereof is increased in the bacterium;

the fbp gene is a DNA comprising the complementary sequence of the nucleotide sequence of positions 2292 to 3290 of SEQ ID NO: 87, or a DNA comprising a nucleotide sequence having an identity of 90% or higher to the complementary sequence of the nucleotide sequence of positions 2292 to 3290 of SEQ ID NO: 87 and is able to increase heparosan-producing ability of an *Escherichia* bacterium having heparosan-producing ability when expression amount thereof is increased in the bacterium;

the yagU gene is a DNA comprising the complementary sequence of the nucleotide sequence of positions 117 to 731 of SEQ ID NO: 91, or a DNA comprising a nucleotide sequence having an identity of 90% or higher to the complementary sequence of the nucleotide sequence of positions 117 to 731 of SEQ ID NO: 91 and is able to increase heparosan-producing ability of an *Escherichia* bacterium having heparosan-producing ability when expression amount thereof is increased in the bacterium;

the paoA gene is a DNA comprising the nucleotide sequence of positions 1149 to 1838 of SEQ ID NO: 91, or a DNA comprising a nucleotide sequence having an identity of 90% or higher to the nucleotide sequence of positions 1149 to 1838 of SEQ ID NO: 91 and is able to increase heparosan-producing ability of an *Escherichia* bacterium having heparosan-producing ability when expression amount thereof is increased in the bacterium;

the paoB gene is a DNA comprising the nucleotide sequence of positions 1835 to 2791 of SEQ ID NO: 91, or a DNA comprising a nucleotide sequence having an identity of 90% or higher to the nucleotide sequence of positions 1835 to 2791 of SEQ ID NO: 91 and is able to increase heparosan-producing ability of an *Escherichia* bacterium having heparosan-producing ability when expression amount thereof is increased in the bacterium;

the gsiC gene is a DNA comprising the nucleotide sequence of positions 264 to 1184 of SEQ ID NO: 95, or a DNA comprising a nucleotide sequence having an identity of 90% or higher to the nucleotide sequence of positions 264 to 1184 of SEQ ID NO: 95 and is able to increase heparosan-producing ability of an *Escherichia* bacterium having heparosan-producing ability when expression amount thereof is increased in the bacterium;

the gsiD gene is a DNA comprising the nucleotide sequence of positions 1187 to 2098 of SEQ ID NO: 95, or a DNA comprising a nucleotide sequence having an identity of 90% or higher to the nucleotide sequence of positions 1187 to 2098 of SEQ ID NO: 95 and is able to increase heparosan-producing ability of an *Escherichia* bacterium having heparosan-producing ability when expression amount thereof is increased in the bacterium;

the yliE gene is a DNA comprising the nucleotide sequence of positions 2276 to 4624 of SEQ ID NO: 95, or a DNA comprising a nucleotide sequence having an identity of 90% or higher to the nucleotide sequence of positions 2276 to 4624 of SEQ ID NO: 95 and is able to increase heparosan-producing ability of an *Escherichia* bacterium having heparosan-producing ability when expression amount thereof is increased in the bacterium;

the irp2 gene is a DNA comprising the nucleotide sequence of SEQ ID NO: 100, or a DNA comprising a nucleotide sequence having an identity of 90% or higher to the nucleotide sequence of SEQ ID NO: 100 and is able to increase heparosan-producing ability of an *Escherichia* bacterium having heparosan-producing ability when expression amount thereof is increased in the bacterium;

the irp1 gene is a DNA comprising the nucleotide sequence of SEQ ID NO: 102, or a DNA comprising a nucleotide sequence having an identity of 90% or higher to the nucleotide sequence of SEQ ID NO: 102 and is able to increase heparosan-producing ability of an *Escherichia* bacterium having heparosan-producing ability when expression amount thereof is increased in the bacterium;

the bhsA gene is a DNA comprising the nucleotide sequence of positions 440 to 697 of SEQ ID NO: 104, or a DNA comprising a nucleotide sequence having an identity of 90% or higher to the nucleotide sequence of positions 440 to 697 of SEQ ID NO: 104 and is able to increase heparosan-producing ability of an *Escherichia* bacterium having heparosan-producing ability when expression amount thereof is increased in the bacterium;

the ycfS gene is a DNA comprising the complementary sequence of the nucleotide sequence of positions 779 to 1741 of SEQ ID NO: 104, or a DNA comprising a nucleotide sequence having an identity of 90% or higher to the complementary sequence of the nucleotide sequence of positions 779 to 1741 of SEQ ID NO: 104 and is able to increase heparosan-producing ability of an *Escherichia* bacterium having heparosan-producing ability when expression amount thereof is increased in the bacterium;

the lepB gene is a DNA comprising the nucleotide sequence of positions 1344 to 2318 of SEQ ID NO: 107, or a DNA comprising a nucleotide sequence having an identity of 90% or higher to the nucleotide sequence of positions 1344 to 2318 of SEQ ID NO: 107 and is able to increase heparosan-producing ability of an *Escherichia* bacterium having heparosan-producing ability when expression amount thereof is increased in the bacterium;

the rnc gene is a DNA comprising the nucleotide sequence of positions 2590 to 3270 of SEQ ID NO: 107, or a DNA comprising a nucleotide sequence having an identity of 90% or higher to the nucleotide sequence of positions 2590 to 3270 of SEQ ID NO: 107 and is able to increase heparosan-producing ability of an *Escherichia* bacterium having heparosan-producing ability when expression amount thereof is increased in the bacterium;

the era gene is a DNA comprising the nucleotide sequence of positions 3267 to 4172 of SEQ ID NO: 107, or a DNA comprising a nucleotide sequence having an identity of 90% or higher to the nucleotide sequence of positions 3267 to 4172 of SEQ ID NO: 107 and is able to increase heparosan-producing ability of an *Escherichia* bacterium having heparosan-producing ability when expression amount thereof is increased in the bacterium;

the dapA gene is a DNA comprising the complementary sequence of the nucleotide sequence of positions 858 to 1736 of SEQ ID NO: 111, or a DNA comprising a nucleotide sequence having an identity of 90% or higher to the complementary sequence of the nucleotide sequence of positions 858 to 1736 of SEQ ID NO: 111 and is able to increase heparosan-producing ability of an *Escherichia* bacterium having heparosan-producing ability when expression amount thereof is increased in the bacterium;

the gcvR gene is a DNA comprising the nucleotide sequence of positions 1882 to 2454 of SEQ ID NO: 111, or a DNA comprising a nucleotide sequence having an identity of 90% or higher to the nucleotide sequence of positions 1882 to 2454 of SEQ ID NO: 111 and is able to increase heparosan-producing ability of an *Escherichia* bacterium having heparosan-producing ability when expression amount thereof is increased in the bacterium;

the bcp gene is a DNA comprising the nucleotide sequence of positions 2454 to 2924 of SEQ ID NO: 111, or a DNA comprising a nucleotide sequence having an identity of 90% or higher to the nucleotide sequence of positions 2454 to 2924 of SEQ ID NO: 111 and is able to increase heparosan-producing ability of an *Escherichia* bacterium having heparosan-producing ability when expression amount thereof is increased in the bacterium;

the hyfA gene is a DNA comprising the nucleotide sequence of positions 3177 to 3794 of SEQ ID NO: 111, or a DNA comprising a nucleotide sequence having an identity of 90% or higher to the nucleotide sequence of positions 3177 to 3794 of SEQ ID NO: 111 and is able to increase heparosan-producing ability of an *Escherichia* bacterium having heparosan-producing ability when expression amount thereof is increased in the bacterium;

the rpoE gene is a DNA comprising the complementary sequence of the nucleotide sequence of positions 355 to 930 of SEQ ID NO: 116, or a DNA comprising a nucleotide sequence having an identity of 90% or higher to the complementary sequence of the nucleotide sequence of positions 355 to 930 of SEQ ID NO: 116 and is able to increase heparosan-producing ability of an *Escherichia* bacterium having heparosan-producing ability when expression amount thereof is increased in the bacterium;

the nadB gene is a DNA comprising the nucleotide sequence of positions 1338 to 2960 of SEQ ID NO: 116, or a DNA comprising a nucleotide sequence having an identity of 90% or higher to the nucleotide sequence of positions 1338 to 2960 of SEQ ID NO: 116 and is able to increase heparosan-producing ability of an *Escherichia* bacterium having heparosan-producing ability when expression amount thereof is increased in the bacterium;

the yfiC gene is a DNA comprising the complementary sequence of the nucleotide sequence of positions 2945 to 3682 of SEQ ID NO: 116, or a DNA comprising a nucleotide sequence having an identity of 90% or higher to the complementary sequence of the nucleotide sequence of positions 2945 to 3682 of SEQ ID NO: 116 and is able to increase heparosan-producing ability of an *Escherichia* bacterium having heparosan-producing ability when expression amount thereof is increased in the bacterium;

the srmB gene is a DNA comprising the nucleotide sequence of positions 3814 to 5148 of SEQ ID NO: 116, or a DNA comprising a nucleotide sequence having an identity of 90% or higher to the nucleotide sequence of positions 3814 to 5148 of SEQ ID NO: 116 and is able to increase heparosan-producing ability of an *Escherichia* bacterium having heparosan-producing ability when expression amount thereof is increased in the bacterium;

the g1414 gene is a DNA comprising the nucleotide sequence of positions 28 to 699 of SEQ ID NO: 121, or a DNA comprising a nucleotide sequence having an identity of 90% or higher to the nucleotide sequence of positions 28 to 699 of SEQ ID NO: 121 and is able to increase heparosan-producing ability of an *Escherichia* bacterium having heparosan-producing ability when expression amount thereof is increased in the bacterium;

the g1413 gene is a DNA comprising the nucleotide sequence of positions 831 to 1157 of SEQ ID NO: 121, or a DNA comprising a nucleotide sequence having an identity of 90% or higher to the nucleotide sequence of positions 831 to 1157 of SEQ ID NO: 121 and is able to increase heparosan-producing ability of an *Escherichia* bacterium having heparosan-producing ability when expression amount thereof is increased in the bacterium;

the nuoE gene is a DNA comprising the complementary sequence of the nucleotide sequence of positions 796 to 1296 of SEQ ID NO: 124, or a DNA comprising a nucleotide sequence having an identity of 90% or higher to the complementary sequence of the nucleotide sequence of positions 796 to 1296 of SEQ ID NO: 124 and is able to increase heparosan-producing ability of an *Escherichia* bacterium having heparosan-producing ability when expression amount thereof is increased in the bacterium;

the nuoF gene is a DNA comprising the complementary sequence of the nucleotide sequence of positions 1293 to 2630 of SEQ ID NO: 124, or a DNA comprising a nucleotide sequence having an identity of 90% or higher to the complementary sequence of the nucleotide sequence of positions 1293 to 2630 of SEQ ID NO: 124 and is able to increase heparosan-producing ability of an *Escherichia* bacterium having heparosan-producing ability when expression amount thereof is increased in the bacterium;

the nuoG gene is a DNA comprising the complementary sequence of the nucleotide sequence of positions 2683 to 5409 of SEQ ID NO: 124, or a DNA comprising a nucleotide sequence having an identity of 90% or higher to the complementary sequence of the nucleotide sequence of positions 2683 to 5409 of SEQ ID NO: 124 and is able to increase heparosan-producing ability of an *Escherichia* bacterium having heparosan-producing ability when expression amount thereof is increased in the bacterium;

the glmZ gene is a DNA comprising the nucleotide sequence of positions 357 to 563 of SEQ ID NO: 128, or a DNA comprising a nucleotide sequence having an identity of 90% or higher to the nucleotide sequence of positions 357 to 563 of SEQ ID NO: 128 and is able to increase heparosan-producing ability of an *Escherichia* bacterium having heparosan-producing ability when expression amount thereof is increased in the bacterium;

the hemY gene is a DNA comprising the nucleotide sequence of positions 611 to 1807 of SEQ ID NO: 128, or a DNA comprising a nucleotide sequence having an identity of 90% or higher to the nucleotide sequence of positions 611 to 1807 of SEQ ID NO: 128 and is able to increase heparosan-producing ability of an *Escherichia* bacterium having heparosan-producing ability when expression amount thereof is increased in the bacterium;

the hemX gene is a DNA comprising the nucleotide sequence of positions 1810 to 2991 of SEQ ID NO: 128, or a DNA comprising a nucleotide sequence having an identity of 90% or higher to the nucleotide sequence of positions 1810 to 2991 of SEQ ID NO: 128 and is able to increase heparosan-producing ability of an *Escherichia* bacterium having heparosan-producing ability when expression amount thereof is increased in the bacterium;

the hemD gene is a DNA comprising the nucleotide sequence of positions 3013 to 3753 of SEQ ID NO: 128, or a DNA comprising a nucleotide sequence having an identity of 90% or higher to the nucleotide sequence of positions 3013 to 3753 of SEQ ID NO: 128 and is able to increase heparosan-producing ability of an *Escherichia* bacterium having heparosan-producing ability when expression amount thereof is increased in the bacterium;

the rlmL gene is a DNA comprising the nucleotide sequence of positions 571 to 2679 of SEQ ID NO: 132, or a DNA comprising a nucleotide sequence having an identity of 90% or higher to the nucleotide sequence of positions 571 to 2679 of SEQ ID NO: 132 and is able to increase heparosan-producing ability of an *Escherichia* bacterium having heparosan-producing ability when expression amount thereof is increased in the bacterium;

the artQ gene is a DNA comprising the nucleotide sequence of positions 386 to 1102 of SEQ ID NO: 134, or a DNA comprising a nucleotide sequence having an identity of 90% or higher to the nucleotide sequence of positions 386 to 1102 of SEQ ID NO: 134 and is able to increase heparosan-producing ability of an *Escherichia* bacterium having heparosan-producing ability when expression amount thereof is increased in the bacterium;

the artM gene is a DNA comprising the nucleotide sequence of positions 1102 to 1770 of SEQ ID NO: 134, or a DNA comprising a nucleotide sequence having an identity of 90% or higher to the nucleotide sequence of positions 1102 to 1770 of SEQ ID NO: 134 and is able to increase heparosan-producing ability of an *Escherichia* bacterium having heparosan-producing ability when expression amount thereof is increased in the bacterium;

the artJ gene is a DNA comprising the nucleotide sequence of positions 2061 to 2792 of SEQ ID NO: 134, or a DNA comprising a nucleotide sequence having an identity of 90% or higher to the nucleotide sequence of positions 2061 to 2792 of SEQ ID NO: 134 and is able to increase heparosan-producing ability of an *Escherichia* bacterium having heparosan-producing ability when expression amount thereof is increased in the bacterium;

the rlmC gene is a DNA comprising the complementary sequence of the nucleotide sequence of positions 2991 to 4118 of SEQ ID NO: 134, or a DNA comprising a nucleotide sequence having an identity of 90% or higher to the complementary sequence of the nucleotide sequence of positions 2991 to 4118 of SEQ ID NO: 134 and is able to increase heparosan-producing ability of an *Escherichia* bacterium having heparosan-producing ability when expression amount thereof is increased in the bacterium;

the ybjO gene is a DNA comprising the complementary sequence of the nucleotide sequence of positions 4159 to 4647 of SEQ ID NO: 134, or a DNA comprising a nucleotide sequence having an identity of 90% or higher to the complementary sequence of the nucleotide sequence of positions 4159 to 4647 of SEQ ID NO: 134 and is able to increase heparosan-producing ability of an *Escherichia* bacterium having heparosan-producing ability when expression amount thereof is increased in the bacterium;

the yejO gene is a DNA comprising the nucleotide sequence of positions 216 to 2807 of SEQ ID NO: 140, or a DNA comprising a nucleotide sequence having an identity of 90% or higher to the nucleotide sequence of positions 216 to 2807 of SEQ ID NO: 140 and is able to increase heparosan-producing ability of an *Escherichia* bacterium having heparosan-producing ability when expression amount thereof is increased in the bacterium;

the yejM gene is a DNA comprising the complementary sequence of the nucleotide sequence of positions 3061 to 4821 of SEQ ID NO: 140, or a DNA comprising a nucleotide sequence having an identity of 90% or higher to the complementary sequence of the nucleotide sequence of positions 3061 to 4821 of SEQ ID NO: 140 and is able to increase heparosan-producing ability of an *Escherichia* bacterium having heparosan-producing ability when expression amount thereof is increased in the bacterium;

the yejL gene is a DNA comprising the complementary sequence of the nucleotide sequence of positions 4841 to 5068 of SEQ ID NO: 140, or a DNA comprising a nucleotide sequence having an identity of 90% or higher to the complementary sequence of the nucleotide sequence of positions 4841 to 5068 of SEQ ID NO: 140 and is able to increase heparosan-producing ability of an *Escherichia* bacterium having heparosan-producing ability when expression amount thereof is increased in the bacterium;

the rpoS gene is a DNA comprising the nucleotide sequence of positions 318 to 1310 of SEQ ID NO: 144, or a DNA comprising a nucleotide sequence having an identity of 90% or higher to the nucleotide sequence of positions 318 to 1310 of SEQ ID NO: 144 and is able to increase heparosan-producing ability of an *Escherichia* bacterium having heparosan-producing ability when expression amount thereof is increased in the bacterium;

the ygbN gene is a DNA comprising the complementary sequence of the nucleotide sequence of positions 1404 to 2768 of SEQ ID NO: 144, or a DNA comprising a nucleotide sequence having an identity of 90% or higher to the complementary sequence of the nucleotide sequence of positions 1404 to 2768 of SEQ ID NO: 144 and is able to increase heparosan-producing ability of an *Escherichia* bacterium having heparosan-producing ability when expression amount thereof is increased in the bacterium;

the ygbM gene is a DNA comprising the complementary sequence of the nucleotide sequence of positions 2857 to 3633 of SEQ ID NO: 144, or a DNA comprising a nucleotide sequence having an identity of 90% or higher to the complementary sequence of the nucleotide sequence of positions 2857 to 3633 of SEQ ID NO: 144 and is able to increase heparosan-producing ability of an *Escherichia* bacterium having heparosan-producing ability when expression amount thereof is increased in the bacterium;

the ygbL gene is a DNA comprising the complementary sequence of the nucleotide sequence of positions 3638 to 4276 of SEQ ID NO: 144, or a DNA comprising a nucleotide sequence having an identity of 90% or higher to the complementary sequence of the nucleotide sequence of positions 3638 to 4276 of SEQ ID NO: 144 and is able to increase heparosan-producing ability of an *Escherichia* bacterium having heparosan-producing ability when expression amount thereof is increased in the bacterium;

the g3798 gene is a DNA comprising the nucleotide sequence of positions 615 to 1268 of SEQ ID NO: 149, or a DNA comprising a nucleotide sequence having an identity of 90% or higher to the nucleotide sequence of positions 615 to 1268 of SEQ ID NO: 149 and is able to increase heparosan-producing ability of an *Escherichia* bacterium having heparosan-producing ability when expression amount thereof is increased in the bacterium;

the g3797 gene is a DNA comprising the nucleotide sequence of positions 1368 to 2219 of SEQ ID NO: 149, or a DNA comprising a nucleotide sequence having an identity of 90% or higher to the nucleotide sequence of positions 1368 to 2219 of SEQ ID NO: 149 and is able to increase heparosan-producing ability of an *Escherichia* bacterium having heparosan-producing ability when expression amount thereof is increased in the bacterium;

the g3796 gene is a DNA comprising the nucleotide sequence of positions 2257 to 2748 of SEQ ID NO: 149, or a DNA comprising a nucleotide sequence having an identity of 90% or higher to the nucleotide sequence of positions 2257 to 2748 of SEQ ID NO: 149 and is able to increase heparosan-producing ability of an *Escherichia* bacterium having heparosan-producing ability when expression amount thereof is increased in the bacterium;

the g3795 gene is a DNA comprising the nucleotide sequence of positions 3021 to 3203 of SEQ ID NO: 149, or a DNA comprising a nucleotide sequence having an identity of 90% or higher to the nucleotide sequence of positions 3021 to 3203 of SEQ ID NO: 149 and is able to increase heparosan-producing ability of an *Escherichia* bacterium having heparosan-producing ability when expression amount thereof is increased in the bacterium;

the g3794 gene is a DNA comprising the complementary sequence of the nucleotide sequence of positions 3470 to 4051 of SEQ ID NO: 149, or a DNA comprising a nucleotide sequence having an identity of 90% or higher to the complementary sequence of the nucleotide sequence of positions 3470 to 4051 of SEQ ID NO: 149 and is able to increase heparosan-producing ability of an *Escherichia* bacterium having heparosan-producing ability when expression amount thereof is increased in the bacterium;

the g3793 gene is a DNA comprising the nucleotide sequence of positions 4280 to 4480 of SEQ ID NO: 149, or a DNA comprising a nucleotide sequence having an identity of 90% or higher to the nucleotide sequence of positions 4280 to 4480 of SEQ ID NO: 149 and is able to increase heparosan-producing ability of an *Escherichia* bacterium having heparosan-producing ability when expression amount thereof is increased in the bacterium;

the g3792 gene is a DNA comprising the nucleotide sequence of positions 4520 to 4717 of SEQ ID NO: 149, or a DNA comprising a nucleotide sequence having an identity of 90% or higher to the nucleotide sequence of positions 4520 to 4717 of SEQ ID NO: 149 and is able to increase heparosan-producing ability of an *Escherichia* bacterium having heparosan-producing ability when expression amount thereof is increased in the bacterium;

the ryjA gene is a DNA comprising the nucleotide sequence of positions 657 to 796 of SEQ ID NO: 157, or a DNA comprising a nucleotide sequence having an identity of 90% or higher to the nucleotide sequence of positions 657 to 796 of SEQ ID NO: 157 and is able to increase heparosan-producing ability of an *Escherichia* bacterium having heparosan-producing ability when expression amount thereof is increased in the bacterium;

the soxR gene is a DNA comprising the complementary sequence of the nucleotide sequence of positions 790 to 1254 of SEQ ID NO: 157, or a DNA comprising a nucleotide sequence having an identity of 90% or higher to the complementary sequence of the nucleotide sequence of positions 790 to 1254 of SEQ ID NO: 157 and is able to increase heparosan-producing ability of an *Escherichia* bacterium having heparosan-producing ability when expression amount thereof is increased in the bacterium;

the soxS gene is a DNA comprising the nucleotide sequence of positions 1340 to 1663 of SEQ ID NO: 157, or a DNA comprising a nucleotide sequence having an identity of 90% or higher to the nucleotide sequence of positions 1340 to 1663 of SEQ ID NO: 157 and is able to increase heparosan-producing ability of an *Escherichia* bacterium having heparosan-producing ability when expression amount thereof is increased in the bacterium;

the yjcC gene is a DNA comprising the complementary sequence of the nucleotide sequence of positions 1666 to 3252 of SEQ ID NO: 157, or a DNA comprising a nucleotide sequence having an identity of 90% or higher to the complementary sequence of the nucleotide sequence of positions 1666 to 3252 of SEQ ID NO: 157 and is able to increase heparosan-producing ability of an *Escherichia* bacterium having heparosan-producing ability when expression amount thereof is increased in the bacterium;

the yjcB gene is a DNA comprising the nucleotide sequence of positions 3682 to 3963 of SEQ ID NO: 157, or a DNA comprising a nucleotide sequence having an identity of 90% or higher to the nucleotide sequence of positions 3682 to 3963 of SEQ ID NO: 157 and is able to increase heparosan-producing ability of an *Escherichia* bacterium having heparosan-producing ability when expression amount thereof is increased in the bacterium;

the efeU gene is a DNA comprising the nucleotide sequence of positions 753 to 1583 of SEQ ID NO: 162, or a DNA comprising a nucleotide sequence having an identity of 90% or higher to the nucleotide sequence of positions 753 to 1583 of SEQ ID NO: 162 and is able to increase heparosan-producing ability of an *Escherichia* bacterium having heparosan-producing ability when expression amount thereof is increased in the bacterium; and the efeO gene is a DNA comprising the nucleotide sequence of positions 1641 to 2768 of SEQ ID NO: 162, or a DNA comprising a nucleotide sequence having an identity of 90% or higher to the nucleotide sequence of positions 1641 to 2768 of SEQ ID NO: 162 and is able to increase heparosan-producing ability of an *Escherichia* bacterium having heparosan-producing ability when expression amount thereof is increased in the bacterium.

It is a further aspect of the present invention to provide a method for producing heparosan, the method comprising:

culturing the bacterium as described above in a medium to produce and accumulate heparosan in the medium; and collecting the heparosan from the medium.

It is an aspect of the present invention to provide the method for producing heparin, the method comprising:

culturing the bacterium mentioned above in a medium to produce and accumulate heparosan in the medium;

chemically and/or enzymatically treating the heparosan to produce heparin; and collecting the heparin.

The functions of the gene products of the genes mentioned in Tables 1 to 3, and relations thereof with heparosan production will be described below.

RbsR, RbsK, and RbsB are factors that participate in incorporation and use of D-ribose. RbsR is a repressor of ribose metabolism, and negatively controls transcription of the rbs operon encoding proteins that participate in a catabolic reaction of ribose (Laikova O. N. et al. (2001) "Computational analysis of the transcriptional regulation of pentose utilization systems in the gamma subdivision of Proteobacteria", FEMS Microbiol Lett., 205(2):315-22). RbsK is a ribokinase, and catalyzes phosphorylation of D-ribose (Bork P. et al. (1993) "Convergent evolution of similar enzymatic function on different protein folds: the hexokinase, ribokinase, and galactokinase families of sugar kinases", Protein Sci., 2(1):31-40). RbsB is one of the subunits of the ribose ABC transporter, and the ribose ABC transporter carries out incorporation of D-ribose (Iida A. et al. (1984) "Molecular cloning and characterization of genes required for ribose transport and utilization in *Escherichia coli* K-12", J. Bacteriol., 158(2):674-82). There has not been any report indicating the relationship between these proteins and heparosan production.

HsrA is an inner membrane protein presumed to be a member of the major facilitator superfamily (MFS) (Pao S. S. et al. (1998) "Major facilitator superfamily", Microbiol. Mol. Biol. Rev., 62(1):1-34). HsrA is presumed to have a function of a proton-driven type drug efflux system on the basis of sequence homology, but the actual function thereof has not been identified. Therefore, there has not been any report indicating the relationship between this protein and heparosan production.

GlgB and GlgX are enzymes that participate in the biosynthesis and decomposition of glycogen, respectively. GlgB is a glycogen-branching enzyme (1,4-α-glucan-branching enzyme), and introduces branching into a polyglucose chain by forming α-1,6-glycosidic linkage during the glycogen biosynthesis process (Boyer C. and Preiss (1977) "Biosynthesis of bacterial glycogen: Purification and properties of the *Escherichia coli* b alpha-1,4,-glucan: alpha-1, 4-glucan 6-glycosyltansferase", J. Biochemistry, 16(16): 3693-9). GlgX is a glycogen-debranching enzyme, and it hydrolyzes α-1,6-glycosidic linkage to liberate a unit of 3 or 4 glucose residues, and thereby eliminates branching of glycogen (Dauvillee D. et al. (2005) "Role of the *Escherichia coli* glgX gene in glycogen metabolism", J. Bacteriol., 187(4):1465-73). There has not been any report indicating the relationship between these proteins and heparosan production.

It is known that micF is an antisense RNA that participates in the expression suppression of OmpF, and functions especially under an osmotic pressure condition (Ramani N. (1994) "micF antisense RNA has a major role in osmoregulation of OmpF in *Escherichia coli*", J. Bacteriol., 176:5005-5010). There has not been any report indicating the relationship between this nucleotide chain and heparosan production.

RcsB is a transcription control factor found in bacteria belonging to the genus *Escherichia*, *Salmonella*, *Klebsiella*, or the like, and it is considered to control mainly the biosynthesis of cholanic acid, which is a capsule constituent component (Majdalani N. et al. (2005) "The Rcs phosphorelay: a complex signal transduction system", Anuu. Rev. Microbiol., 59:379-405). It has been reported that RcsB participates in the Vi polysaccharide expression of Citrobacter freundii (Houng H. S. et al. (1992) "Expression of Vi antigen in *Escherichia coli* K-12: characterization of ViaB from Citrobacter freundii and identity of ViaA with RcsB", J. Bacteriol., 174:5910-5915), and expression of K2 capsule of *Klebsiella* bacteria (Rochaporn W. et al. (1992) "Involvement of rcsB in *Klebsiella* K2 Capsule Synthesis in *Escherichia coli* K-12", J. Bacteriol. 174:1063-1067). Moreover, it is known that overexpression of RcsB increases K30 capsular polysaccharide production, but it has been reported that RcsB does not participate in the transcription of the csp cluster encoding polymerization enzymes for the K30 capsular polysaccharide, but positively controls expression of the galF gene encoding a biosynthesis enzyme of UDP-glucose, which is a precursor of the polysaccharide (Andrea Rahn et al. (2003) "Transcriptional organization and regulation of The *Escherichia coli*", Mol. Microbiol., 47:1045-1060). It has also been reported that overexpression of RcsB does not increase production of K5 capsular polysaccharide (heparosan) or K1 capsular polysaccharide (Wendy J. Keenleyside et al. (1993) "Coexpression of Colanic Acid and Serotype-Specific Capsular Polysaccharides in *Escherichia coli* Strains with Group II K Antigens", J. Bacteriol., 175: 6725-6730). RcsD is a sensor protein having histidine kinase, and it is known to transfer a phosphate group to RcsB in response to an external stimulus.

YbiX, YbiI, YbiJ, YbiC, and YbiB are factors with unknown function. Therefore, there has not been any report indicating the relationship between these proteins and heparosan production.

RfaH is a transcription factor required for the biosynthesis of lipopolysaccharides, secretion of α-hemolysin, and production of the F factor in *Escherichia coli* and *Salmonella typhimurium* (Leeds J. A. and Welch R. A. (1996) "RfaH enhances elongation of *Escherichia coli* hlyCABD mRNA", J. Bacteriol., 178(7):1850-7). It is also known that, in the *Escherichia coli* K5 strain, RfaH is required for the K5 capsular formation (Stevens M. P. et al. (1994) "Regulation of *Escherichia coli* K5 capsular polysaccharide expression: Evidence for involvement of RfaH in the expression of group II capsules", FEMS Microbiol. Lett., 124(1):93-98), and RfaH binds to the promoter region of the region 3 (kpsM, kpsT) to positively control transcription of not only the region 3, but also the downstream region 2 (kfiA, kfiB, kfiC, and kfiD) (Xue P. et al. (2009) "Regulation of expression of the region 3 promoter of the *Escherichia coli* K5 capsule gene cluster involves H-NS, SlyA, and a large 5' untranslated region", J. Bacteriol., 191(6):1838-1846). However, influence of enhanced expression of the rfaH gene on the amount of heparosan production has not been examined in the *Escherichia coli* K5 strain nor any other heparosan-producing bacteria.

NusG is a transcription factor, and is considered to regulate transcription by interacting with RNA polymerase (Li J. et al. (1992) J. Biol. Chem., 267(9):6012-6019). It is also reported that NusG participates in the capsule biosynthesis of *Bacteroides fragilis* (Livanis M. et al. (2009) J. Bacteriol., 191(23):7288-7295). However, there has not so far been reported involvement thereof in the heparosan biosynthesis. It is considered that NusG is a homologue of RfaH, and NusG and RfaH have a common domain (Bailey M. et al. (1996) Mol. Microbiol., 22(4):7729-737). However, the amino acid sequence homology of NusG and RfaH is about 20% in all of the *Escherichia coli* K-12 strains, K5 strains, and B strains, and it cannot be said that these proteins are highly homologous.

PcoR, PcoS, and PcoE are factors that relate to copper resistance. PcoR and PcoS are highly homologous to the activator of the pco operon, and the sensor protein of the two-component control system that responds to environmental stimuli, respectively (Cooksey D. A. (2006) "Copper uptake and resistance in bacteria", Mol. Microbiol., 7(1):1-5). PcoE is a copper-binding protein. There has not been any report indicating the relationship between these proteins and heparosan production.

YhcN is a factor involved in response of bacterial cells to hydrogen peroxide stress. AyhcN gene-deficient strain shows improved sensitivity to hydrogen peroxide, and increased biofilm formation amount (Lee J. et al. (2010) "Identification of stress-related proteins in *Escherichia coli* using the pollutant cis-dichloroethylene", J. Appl. Microbiol., June; 108(6):2088-102). There has not been any report indicating the relationship between this protein and heparosan production.

YhcO shows homology to an inhibition factor for barnase, which is a toxic RNase derived from *Bacillus amyloliquefaciens*. However, *Escherichia* bacteria do not have an RNase of the barnase family, and the function of YhcO is unclear. Therefore, there has not been any report indicating the relationship between this protein and heparosan production.

AaeB and AaeA are subunits of an efflux carrier of 4-hydroxybenzoic acid. Although AaeX is also estimated to be an efflux carrier, actual function thereof is unknown (Van Dyk T. K. et al. (2004) "Characterization of the *Escherichia coli* AaeAB efflux pump: a metabolic relief valve?", J. Bacteriol., 186:7196-7204). There has not been any report indicating the relationship between these proteins and heparosan production.

The g1455 and g1453 genes are found in only the *Escherichia coli* K5 strain, and the functions of the proteins encoded by these genes are unknown. Therefore, there has not been any report indicating the relationship between these proteins and heparosan production.

AlpA is an expression regulator of the intA gene encoding a prophage integrase, and it has a function of complementing deficiency of the Lon protease through increase of expression of intA (Trempy J. E. et al. (1994) "Alp suppression of Lon: dependence on the slpA gene", J. Bacteriol., 176(7): 2061-7). Although AlpA may possibly relate to biofilm formation or capsule production (Herzberg M. et al. (2006) "YdgG (TqsA) controls biofilm formation in *Escherichia coli* K-12 through autoinducer 2 transport", J. Bacteriol., 188(2):587-98), there has not been any report indicating the relationship between AlpA and heparosan production.

YrbA (synonym is IbaG) is a factor presumed to be a DNA-binding type transcription factor, and expression amount thereof increases under acidity stress conditions (Guinote I. B. et al. (2012) "Characterization of the BolA homolog IbaG: a new gene involved in acid resistance", J. Microbiol. Biotechnol., 22(4):484-93). There has not been any report indicating the relationship between this protein and heparosan production.

MlaB, MlaC, MlaD, MlaE, and MlaF are constituent factors of a phospholipid ABC transporter, and participate in transportation of phospholipids and maintenance of lipid asymmetry (Malinverni J. C. and Silhavy T. J. (2009) "An ABC transport system that maintains lipid asymmetry in the gram-negative outer membrane", Proc. Natl. Acad. Sci. USA, 106(19):8009-14). There has not been any report indicating the relationship between these proteins and heparosan production.

YrbG is a 5-pass transmembrane type inner membrane protein, and it is presumed to be a $Na^+/Ca^{2+}$ antiporter on the basis of sequence homology. However, intracellular $Ca^{2+}$ level regulation ability of YrbG has not been confirmed, and actual function thereof is unknown (Naseem R. et al. (2008) "pH and monovalent cations regulate cytosolic free Ca(2+) in *E. coli*", Biochim. Biophys. Acta, 1778(6):1415-22). Therefore, there has not been any report indicating the relationship between this protein and heparosan production at all, either.

NorW is a nitric oxide (NO) reductase to be expressed in response to NO stress (Gardner A. M. et al. (2003) "Role of NorR and sigma54 in the nitric oxide stress response", J. Biol. Chem., 278(12):10081-6). There has not been any report indicating the relationship between this protein and heparosan production.

YbjI is a flavin mononucleotide (FMN) phosphorylation enzyme belonging to the haloacid dehalogenation enzyme-like hydrolase family (Kuznetsova E. et al. (2006) "Genome-wide analysis of substrate specificities of the *Escherichia coli* haloacid dehalogenase-like phosphatase family", J. Biol. Chem., 281(47):36149-61). There has not been any report indicating the relationship between this protein and heparosan production.

YbjJ and YbjK are proteins with unknown function. Therefore, there has not been any report indicating the relationship between these proteins and heparosan production, either.

RybB is a low molecular weight RNA, the expression of which is dependent on sigma factor σE, which is activated in response to cell surface stress, and suppresses synthesis of the sigma factor σE (Thompson K. M. et al. (2007) "SigmaE regulates and is regulated by a small RNA in *Escherichia coli*", J. Bacteriol., 189(11):4243-56). RybB also participates in expression inhibition of OmpC and OmpW (Johansen J. et al. (2006) "Conserved small noncoding RNAs that belong to the sigmaE regulon: role in down-regulation of outer membrane proteins", J. Mol. Biol., 364(1):1-8). There has not been any report indicating the relationship between RybB and heparosan production.

YjjY is a protein of unknown function. Therefore, there has not been any report indicating the relationship between this protein and heparosan production at all.

Although YjtD is presumed to be one of RNA methyltransferases, its actual function is unknown (Anantharaman V. et al. (2002) "SPOUT: a class of methyltransferases that includes spoU and trmD RNA methylase superfamilies, and novel superfamilies of predicted prokaryotic RNA methylases", J. Mol. Microbiol. Biotechnol., 4(1):71-5). Therefore, there has not been any report indicating the relationship between this protein and heparosan production.

ThrB, ThrA, and ThrL are enzymes of the threonine biosynthesis pathway. ThrB is a homoserine kinase that catalyzes the reaction of converting homoserine into O-phospho-L-homoserine, and participates in the biosynthesis of threonine (Burr B. et al. (1976) "Homoserine kinase from *Escherichia coli* K12", Eur. J. Biochem., 62(3):519-26). ThrA is an enzyme having the dual functions of aspartate kinase I and homoserine dehydrogenase I, and participates in the biosyntheses of lysine and methionine, in addition to that of threonine (Clark R. B., Ogilvie J. W. et al. (1972) "Aspartokinase I-homoserine dehydrogenase I of *Escherichia coli* K12: Subunit molecular weight and nicotinamide-adenine dinucleotide phosphate binding", Biochemistry, 11(7):1278-82). ThrL is a leader peptide of the thrLABC operon, and attenuates expression of the thrLABC operon depending on the concentrations of threonine and isoleucine (Lynn S. P. et al. (1982) "Attenuation regulation in the thr operon of *Escherichia coli* K-12: molecular cloning and transcription of the controlling region", J. Bacteriol., 152(1):363-71). There has not been any report indicating the relationship between these proteins and heparosan production.

FruA is a fructose PTS permease, and has the IIB domain and IIC domain (Prior T. I. and Kornberg H. L. (1988) "Nucleotide sequence of fruA, the gene specifying enzyme IIfru of the phosphoenolpyruvate-dependent sugar phosphotransferase system in *Escherichia coli* K12", J. Gen. Microbiol., 134(10):2757-68). There has not been any report indicating the relationship between this protein and heparosan production.

PsuK is a pseudouridine kinase and participates in catabolism of pseudouridine, which is a modified RNA frequently found in the TΨC loop of tRNA (Solomon L. R. and Breitman T. R. (1971) "Pseudouridine kinase of *Escherichia coli*: a new enzyme", Biochem. Biophys. Res. Commun., 44(2):299-304). There has not been any report indicating the relationship between this protein and heparosan production.

Although YtfT and YjfF are presumed to be membrane constituent components of the galactose ABC carrier, their actual function is unknown. Therefore, there has not been any report indicating the relationship between these proteins and heparosan production at all, either.

Fbp is a fructose-1,6-diphosphate phosphatase (fructose-1,6-bisphosphatase) that catalyzes the reaction of converting fructose-1,6-diphosphate into fructose-6-phosphate in the gluconeogenesis pathway (Fraenkel D. G. and Horecker B. L. (1965) "Fructose-1,6-diphosphatase and acid hexose phosphatase of *Escherichia coli*", J. Bacteriol., 90(4):837-42). There has not been any report indicating the relationship between this protein and heparosan production.

Although YagU is presumed to be an inner membrane protein, its function is unknown. Therefore, there has not been any report indicating the relationship between this protein and heparosan production, either.

PaoA (also called YagT) and PaoB (also called YagS) are constituent factors of the aldehyde oxidoreductase YagTSR. PaoA is an iron-binding subunit, and PaoB is a flavine-adenine dinucleotide (FAD)-binding subunit (Neumann M. et al. (2009) "A periplasmic aldehyde oxidoreductase represents the first molybdopterin cytosine dinucleotide cofactor containing molybdo-flavoenzyme from *Escherichia coli*", FEBS J., 276(10):2762-74). There has not been any report indicating the relationship between these proteins and heparosan production.

GsiC and GsiD are constituent factors of a glutathione ABC transport carrier. GsiC and GsiD localize in the inner membrane (Moussatova A. et al. (2008) "ATP-binding cassette transporters in *Escherichia coli*", Biochim. Biophys. Acta, 1778(9): 1757-71). There has not been any report indicating the relationship between these proteins and heparosan production.

YliE is presumed to be a c-di-GMP-specific phosphodiesterase, and overexpression thereof promotes biofilm formation (Boehm A. et al. (2009) "Second messenger signalling governs *Escherichia coli* biofilm induction upon ribosomal stress", Mol. Microbiol., 72(6): 1500-16). There has not been any report indicating the relationship between this protein and heparosan production.

Irp2 and Irp1 are non-ribosomal peptide synthases, and participate in iron incorporation (Pelludat C. et al. (1998) "The yersiniabactin biosynthetic gene cluster of *Yersinia enterocolitica*: organization and siderophore-dependent regulation", J. Bacteriol., 180(3):538-46). There has not been any report indicating the relationship between these proteins and heparosan production.

BhsA (synonym is YcfR) is presumed to be an outer membrane protein, and participates in biofilm formation and stress response (Zhang X. S. et al. (2007) "YcfR (BhsA) influences *Escherichia coli* biofilm formation through stress response and surface hydrophobicity", J. Bacteriol., 189(8): 3051-62). There has not been any report indicating the relationship between this protein and heparosan production.

YcfS is one of L,D-transpeptidases. YcfS catalyzes the reaction of removing a D-alanine residue from the meso-diaminopimelate (DAP) residue of peptidoglycan, and binding a lysine residue of the C-terminus of Braun lipoprotein to this meso-DAP residue. Through this reaction, the peptidoglycan covalently binds to the outer membrane via the Braun lipoprotein (Magnet S. et al. (2007) "Identification of the L,D-transpeptidases responsible for attachment of the Braun lipoprotein to *Escherichia coli* peptidoglycan", J. Bacteriol., 189(10):3927-31). There has not been any report indicating the relationship between this protein and heparosan production.

LepB is a signal peptidase that removes an N-terminus leader peptide from a secretory protein (Dalbey R. E. (1991) "Leader peptidase", Mol. Microbiol., 5(12):2855-60). There has not been any report indicating the relationship between this protein and heparosan production.

Rnc is an RNaseIII that cleaves double stranded RNA to produce 5' phosphate group and hydroxyl group, and is required for processing of rRNA or phage mRNA. The main roles of Rnc are regulation of gene expression, and functionalization of antisense RNA (Robertson H. D. and Dunn J. J. (1975) "Ribonucleic acid processing activity of *Escherichia coli* ribonuclease III", J. Biol. Chem., 25; 250(8):3050-6). There has not been any report indicating the relationship between this protein and heparosan production.

Era is a factor indispensable for survival (Takiff H. E. et al. (1992) "Locating essential *Escherichia coli* genes by using mini-Tn10 transposons: the pdxJ operon", J. Bacteriol., 174(5): 1544-53). It has been elucidated by the yeast two-hybrid method that Era interacts with MazG (Zhang J. and Inouye M., (2002) "MazG, a nucleoside triphosphate pyrophosphohydrolase, interacts with Era, an essential GTPase in *Escherichia coli*", J. Bacteriol., 184 (19):5323-9). There has not been any report indicating the relationship between this protein and heparosan production.

DapA is a 4-hydroxy-tetrahydrodipicolinate synthase. 4-Hydroxy-tetrahydrodipicolinate synthase is one of the lysine biosynthesis enzymes, and catalyzes the reaction of converting pyruvic acid and L-aspartic acid β-semialdehyde into (2S,4S)-4-hydroxy-2,3,4,5-tetrahydrodipicolinate. This reaction is considered to be a rate-limiting step of the lysine biosynthesis after the reaction with aspartate kinase III (Laber B. et al. (1992) "*Escherichia coli* dihydrodipicolinate synthase: Identification of the active site and crystallization", Biochem. J., 288(Pt 2):691-5). There has not been any report indicating the relationship between this protein and heparosan production.

GcvR is a protein presumed to be a transcriptional control factor, and participates in expression of glycine biosynthesis genes. In the absence of glycine, GcvR directly binds to GcvA to form a GlvR/GlvA complex, and inhibits expression of glycine decomposition genes. In the presence of glycine, glycine binds to GcvR to inhibit the formation of the GlvR/GlvA complex (Ghrist A. C. et al. (2001) "GcvR interacts with GcvA to inhibit activation of the *Escherichia coli* glycine cleavage operon", Microbiology, 147(Pt 8):2215-21). There has not been any report indicating the relationship between this protein and heparosan production.

Bcp is a thioredoxin 1-dependent thiol peroxidase (Clarke D. J. et al. (2009) "Interrogating the molecular details of the peroxiredoxin activity of the *Escherichia coli* bacterioferritin comigratory protein using high-resolution mass spectrometry", Biochemistry, 48(18):3904-14). There has not been any report indicating the relationship between this protein and heparosan production.

HyfA has four 4Fe-4S clusters, and is presumed to participate in electron transportation (Andrews S. C. et al. (1997) "A 12-cistron *Escherichia coli* operon (hyf) encoding a putative proton-translocating formate hydrogenlyase system", Microbiology, 143(Pt 11):3633-47). There has not been any report indicating the relationship between this protein and heparosan production.

RpoE is sigma E ($\sigma^E$), which is one of the sigma factors and functions as a subunit of RNA polymerase. RpoE controls expression of protease against membrane and intermembrane proteins in response to heat shock and stress (Ades S. E. et al. (2003) "Regulation of the alternative sigma factor sigma(E) during initiation, adaptation, and shutoff of the extracytoplasmic heat shock response in *Escherichia coli*", J. Bacteriol., 185(8):2512-9). There has not been any report indicating the relationship between this protein and heparosan production.

NadB is an L-aspartate oxidase. L-Aspartate oxidase is an initiation enzyme of the de novo NAD biosynthesis pathway, and catalyzes the reaction of converting L-aspartic acid to iminoaspartic acid in a FAD-dependent manner (Mortarino M. et al. (1996) "L-aspartate oxidase from *Escherichia coli*, I. Characterization of coenzyme binding and product inhibition", Eur. J. Biochem., 239(2):418-26). There has not been any report indicating the relationship between this protein and heparosan production.

YfiC is a methyltransferase that methylates N at the position 6 of A37 (adenine at the position 37) of valine tRNA (Golovina A. Y et al. (2009) RNA. "The yfiC gene of *E. coli* encodes an adenine-N6 methyltransferase that specifically modifies A37 of tRNA1Val(cmo5UAC)", 15(6): 1134-41). The nucleotide of the position 37 of tRNA is adjacent to the anticodon triplet, and is often modified. There has not been any report indicating the relationship between this protein and heparosan production.

SrmB is a DEAD-box type RNA helicase that promotes reactions of an early stage of 50S subunit assembly of ribosome (Charollais J. et al. (2003) "The DEAD-box RNA helicase SrmB is involved in the assembly of 50S ribosomal subunits in *Escherichia coli*", Mol. Microbiol., 48(5):1253-65). There has not been any report indicating the relationship between this protein and heparosan production.

G1414 and G1413 are proteins of unknown functions. Therefore, there has not been any report indicating the relationship between these proteins and heparosan production.

NuoE, NuoF, and NuoG are soluble fragments of an NADH dehydrogenase I, and function as the entrance of electrons into the electron transport system (Braun M. et al. (1998) "Characterization of the overproduced NADH dehydrogenase fragment of the NADH:ubiquinone oxidoreductase (complex I) from *Escherichia coli*", Biochemistry, 37(7): 1861-7). There has not been any report indicating the relationship between these proteins and heparosan production.

GlmZ is a low molecular weight RNA that controls expression and translation of glmS mRNA by posttranscriptional modification in response to the intracellular concentration of glucosamine-6-phosphate (Kalamorz F. et al. (2007) "Feedback control of glucosamine-6-phosphate synthase GlmS expression depends on the small RNA GlmZ and involves the novel protein YhbJ in *Escherichia coli*", Mol. Microbiol., 65(6):1518-33). GlmZ directly binds to 5'-UTR of glmS mRNA to liberate the SD region of glmS mRNA, which had formed a loop structure, and thereby activate translation of glmS mRNA (Urban J. H. and Vogel J. et al. (2008) "Two seemingly homologous noncoding RNAs act hierarchically to activate glmS mRNA translation", PLoS Biol., 6(3):e64). GlmS is L-glutamine:D-fructose-6-phosphate aminotransferase. L-Glutamine:D-fructose-6-phosphate aminotransferase is the first enzyme of the supply pathway of UDP-N-acetylglucosamine, which is a precursor of heparosan, and catalyzes the reaction of converting fructose-6-phosphate to glucosamine-6-phosphate. However, there has not been any report indicating the relationship between enhancement of the activity of GlmS and the heparosan-producing ability, and there has not been any report indicating the relationship between GlmZ and heparosan production.

HemY, HemX, and HemD are enzymes of the biosynthetic pathways of heme and choline. HemY is a protoporphyrinogen oxidase that oxidizes protoporphyrinogen IX to generate protoporphyrin IX in the heme biosynthesis pathway (Dailey T. A. et al. (1994) "Expression of a cloned protoporphyrinogen oxidase", The Journal of Biological Chemistry, 269:813-815). Although HemX is presumed to be an uroporphyrinogen III methylase that methylates uroporphyrinogen III to generate precholine II in the choline biosynthetic pathway, actual function thereof is unknown (Sasarman A. et al. (1988) "Nucleotide sequence of the hemX gene, the third member of the Uro operon of *Escherichia coli* K12", Nucleic Acids Res., 16(24): 11835). HemD is an uroporphyrinogen III synthase that generates uroporphyrinogen III, which is the last common metabolic intermediate in the biosynthetic pathways of heme and choline (Jordan P. M. and Woodcock S. C. (1991) "Mutagenesis of arginine residues in the catalytic cleft of *Escherichia coli* porphobilinogen deaminase that affects dipyrromethane cofactor assembly and tetrapyrrole chain initiation and elongation", Biochem. J., 280(Pt 2):445-9). There has not been any report indicating the relationship between these proteins and heparosan production.

RlmL (synonym is RlmKL) is a methyltransferase that methylates G2445 and G2069 of 23 S rRNA (Kimura S. et al. (2012) "Base methylations in the double-stranded RNA by a fused methyltransferase bearing unwinding activity", Nucleic Acids Res., 40(9):4071-85). RlmL is a fused protein, and the N-terminus domain may be especially referred to as RlmL, and the N-terminus domain as RlmK. There has not been any report indicating the relationship between this protein and heparosan production.

ArtQ, ArtM, and ArtJ are subunits of an arginine ABC transporter (Linton K. J. and Higgins C. F. (1998) "The *Escherichia coli* ATP-binding cassette (ABC) proteins", Mol. Microbiol., 28(1):5-13). It is estimated that ArtJ localizes in the periplasm. Since ArtM and Art are hydrophobic proteins, it is estimated that they localize in the inner membrane, and cooperate with ArtP, which is ATPase, to function as an inner membrane penetration device for arginine. There has not been any report indicating the relationship between these proteins and heparosan production.

RlmC (synonym is RumB) is a methyltransferase that methylates U747 of 23S rRNA (Madsen C. T. et al. (2003) "Identifying the methyltransferases for m(5)U747 and m(5) U1939 in 23S rRNA using MALDI mass spectrometry", Nucleic Acids Res., 31(16):4738-46). There has not been any report indicating the relationship between this protein and heparosan production.

Although YbjO is presumed to be an inner membrane protein, its function is unknown (Rapp M. et al. (2004) "Experimentally based topology models for *E. coli* inner membrane proteins", Protein Sci., 13(4):937-45). There has not been any report indicating the relationship between this protein and heparosan production.

YejO is an outer membrane protein, and has a function for phase-variable protein efflux (Henderson I. R. and Owen P. (1999) "The major phase-variable outer membrane protein of *Escherichia coli* structurally resembles the immunoglobulin A1 protease class of exported protein and is regulated by a novel mechanism involving Dam and oxyR", J. Bacteriol., 181(7):2132-41). There has not been any report indicating the relationship between this protein and heparosan production.

YejM is presumed to be a hydrolase, but its actual function is unknown. Therefore, there has not been any report indicating the relationship between this protein and heparosan production.

YejL is a protein of unknown function. Therefore, there has not been any report indicating the relationship between this protein and heparosan production.

RpoS is sigma S (σs), which is a sigma factor and acts as a subunit of RNA polymerase. RpoS globally controls expression of genes in response to stress (Maciag A. et al (2011) "In vitro transcription profiling of the σS subunit of bacterial RNA polymerase: Re-definition of the σS regulon and identification of σS-specific promoter sequence elements", Nucleic Acids Res., 39(13):5338-55). There has not been any report indicating the relationship between this protein and heparosan production.

YgbN is a protein presumed to be a transporter belonging to the Gnt family involved in the gluconic acid transport, and has been suggested to possibly be a proton-driven type metabolite uptake carrier (Peekhaus N. et al. (1997) "Characterization of a novel transporter family that includes multiple *Escherichia coli* gluconate transporters and their homologues", FEMS Microbiol. Lett., 147(2):233-8). There has not been any report indicating the relationship between this protein and heparosan production.

YgbM is a protein of unknown function. Therefore, there has not been any report indicating the relationship between this protein and heparosan production.

Although YbgL is presumed to be an aldolase, actual function thereof is unknown. Therefore, there has not been any report indicating the relationship between this protein and heparosan production.

G3798 is a protein presumed to be an SOS-response transcriptional repressor (RecA-mediated autopeptidase). G3794 is a protein presumed to be a superinfection exclusion protein B. G3793 is a protein presumed to be a restriction inhibitor protein ral (antirestriction protein). There has not been any report indicating the relationship between these proteins and heparosan production.

G3797, G3796, G3795, and G3792 are proteins of unknown function. Therefore, there has not been any report indicating the relationship between these proteins and heparosan production.

RyjA is a low molecular weight RNA of about 140 nt (Wassarman K. M. et al. (2001) "Identification of novel small RNAs using comparative genomics and microarrays", Genes, Dev. 15(13):1637-51). There has not been any report indicating the relationship between this RNA and heparosan.

SoxRS are transcriptional control factors that participate in response to oxidation stress. SoxR is activated by oxidation stress, and induces expression of SoxS, and SoxRS induce expression of the SoxRS regulon gene (Gu M. and Imlay J. A. (2011) "The SoxRS response of *Escherichia coli* is directly activated by redox-cycling drugs rather than by superoxide", Mol. Microbiol., 79(5):1136-50; Touati D. (2000) "Sensing and protecting against superoxide stress in *Escherichia coli*—how many ways are there to trigger soxRS response?", Redox Rep., 5(5):287-93). SoxRS are known to participate in generation of lipopolysaccharide (Lee J. H. et al. (2009) "SoxRS-mediated lipopolysaccharide modification enhances resistance against multiple drugs in *Escherichia coli*", J. Bacteriol., 191(13):4441-50). However, there has not been any report indicating the relationship between these proteins and heparosan production.

YjcC is a c-di-GMP-specific phosphodiesterase (Boehm A. et al. (2009) "Second messenger signaling governs *Escherichia coli* biofilm induction upon ribosomal stress", Mol. Microbiol., 72(6):1500-16). Although it is known that overexpression of YjcC decreases biofilm formation, there has not been any report indicating the relationship between this protein and heparosan production.

YjcB is a protein of unknown function. Therefore, there has not been any report indicating the relationship between this protein and heparosan production.

EfeU and EfeO are components of the divalent iron ion transport carrier EfeUOB. EfeU functions as a permease, and EfeO functions as a protein localizing in the periplasm (Cao J. et al. (2007) "EfeUOB (YcdNOB) is a tripartite, acid-induced and CpxAR-regulated, low-pH $Fe^{2+}$ transporter that iscryptic in *Escherichia coli* K-12 but functional in *E. coli* O-157:H7", Mol. Microbiol., 65:857-875). There has not been any report indicating the relationship between these proteins and heparosan production.

BRIEF DESCRIPTION OF THE DRAWINGS

FIG. 1 shows the structure of the wild-type nlpD promoter (Pnlp0). The nucleotide sequence shown in the figure is shown as SEQ ID NO: 165.

FIG. 2 shows the structure of a variant type nlpD promoter (Pnlp8). The nucleotide sequence shown in the figure is shown as SEQ ID NO: 168.

DETAILED DESCRIPTION OF THE INVENTION

Hereafter, the present invention will be explained in detail.

<1> Bacterium of the Present Invention

The bacterium of the present invention is an *Escherichia* bacterium having a heparosan-producing ability that has been modified so that expression of one or more of the genes depicted in Tables 1 to 3 is increased.

<1-1> Bacterium Having Heparosan-Producing Ability the phrase "bacterium having a heparosan-producing ability" can refer to a bacterium having an ability to produce and accumulate heparosan in a medium in such a degree that heparosan can be collected, when the bacterium is cultured in the medium. The bacterium having a heparosan-producing ability may be a bacterium that is able to accumulate heparosan in a medium in an amount larger than that obtainable with a non-modified strain. Examples of the non-modified strain include wild-type strains and parent strains of the bacterium. The bacterium having a heparosan-producing ability may be a bacterium that is able to accumulate heparosan in a medium in an amount of, for example, 50 mg/L or more, 100 mg/L or more, 200 mg/L or more, or 300 mg/L or more.

The *Escherichia* bacterium is not particularly limited, and examples thereof include those classified into the genus *Escherichia* according to the taxonomy known to those skilled in the field of microbiology. Examples of the *Escherichia* bacterium include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology, Second Edition, American Society for Microbiology Press, Washington, D.C.). Examples of *Escherichia* bacterium include, for example, *Escherichia coli*. Specific examples of *Escherichia coli* include, for example, *Escherichia coli* K-12 strains such as *Escherichia coli* W3110 strain (ATCC 27325) and MG1655 strain (ATCC 47076); *Escherichia coli* K5 strain (ATCC 23506); *Escherichia coli* B strains such as BL21(DE3) strain; and their derivative strains.

These strains are available from, for example, the American Type Culture Collection (Address: 12301 Parklawn Drive, Rockville, Md. 20852, P.O. Box 1549, Manassas, Va. 20108, United States of America). That is, registration numbers are given to the respective strains, and the strains can be ordered by using these registration numbers (refer to atcc.org/). The registration numbers of the strains are listed in the catalogue of the American Type Culture Collection. The BL21(DE3) strain is also available from, for example, Life Technologies (product number C6000-03).

The bacterium of the present invention may be a bacterium inherently having a heparosan-producing ability, or may be a bacterium modified so that it has a heparosan-producing ability. The bacterium having a heparosan-producing ability can be obtained by, for example, imparting a heparosan-producing ability to such a bacterium as mentioned above.

A heparosan-producing ability can be imparted by introducing a gene encoding a protein that participates in heparosan production. Examples of such a protein that participates in heparosan production include glycosyltransferase and heparosan efflux carrier protein. In the present invention, one gene or two or more different genes may be introduced. A gene may be introduced in the same manner as that of the method of increasing copy number of gene described later.

The term "glycosyltransferase" referred to herein means a protein having an activity for catalyzing a reaction of adding N-acetyl-D-glucosamine (GlcNAc) and/or glucuronic acid (GlcUA) to a non-reducing end of a sugar chain to thereby extend a heparosan chain. This activity is also referred to as "glycosyltransferase activity". Examples of the gene encoding glycosyltransferase include the kfiA gene, kfiC gene, and pmHS1 gene.

Examples of the kfiA gene and kfiC gene include the kfiA gene and kfiC gene of the *Escherichia coli* K5 strain. The KfiA protein encoded by the kfiA gene of the *Escherichia coli* K5 strain adds GlcNAc to a non-reducing end of a sugar chain by using UDP-GlcNAc as a substrate. The KfiC protein encoded by the kfiC gene of the *Escherichia coli* K5 strain adds GlcUA to a non-reducing end of a sugar chain by using UDP-GlcUA as a substrate. The kfiA and kfiC genes of the *Escherichia coli* K5 strain constitute the kfiABCD operon (also referred to as region 2) together with the kfiB and kfiD genes. The nucleotide sequence of a region containing the kfiABCD operon of the *Escherichia coli* K5 strain is shown as SEQ ID NO: 24. In the nucleotide sequence of SEQ ID NO: 24, the kfiA, kfiB, kfiC, and kfiD genes correspond to the sequence of the positions 445 to 1,164, the sequence of the positions 1,593 to 3,284, the sequence of the positions 4,576 to 6,138, and the sequence of the positions 6,180 to 7,358, respectively. The amino acid sequences of KfiA, KfiB, KfiC, and KfiD proteins of the *Escherichia coli* K5 strain are shown as SEQ ID NOS: 25 to 28, respectively.

Examples of the pmHS1 gene include the pmHS1 gene of the *Pasteurella multocida* type D strain. The PmHS1 protein encoded by the pmHS1 gene of the *Pasteurella multocida* type D strain alternately adds GlcNAc and GlcUA to a non-reducing end of a sugar chain by using both UDP-GlcNAc and UDP-GlcUA as substrates. The nucleotide sequence of the pmHS1 gene of the *Pasteurella multocida* type D strain and the amino acid sequence of the protein encoded by this gene can be obtained from public databases such as the NCBI database (ncbi.nlm.nih.gov/).

The phrase "heparosan efflux carrier protein" can mean a protein having the activity of excreting a heparosan chain out of a cell through cell membranes. This activity can also referred to as "heparosan efflux activity". Examples of a gene encoding the heparosan efflux carrier protein include the kpsC, kpsD, kpsE, kpsM, kpsS, and kpsT genes. Examples of the kpsC, kpsD, kpsE, kpsM, kpsS, and kpsT genes include the kpsC, kpsD, kpsE, kpsM, kpsS, and kpsT genes of the *Escherichia coli* K5 strain and *Escherichia coli* B strain. The kpsC, kpsD, kpsE, and kpsS genes of these strains constitute the kpsFEDUCS operon (also referred to as region 1) together with the kpsF and kpsU genes. The kpsM and kpsT genes of these strains constitute the kpsMT operon (also referred to as region 3). The nucleotide sequences of the kpsC, kpsD, kpsE, kpsM, kpsS, and kpsT genes of these strains, and the amino acid sequences of the proteins encoded by these genes can be obtained from public databases such as the NCBI database (ncbi.nlm.nih.gov/).

The gene to be introduced can be appropriately chosen according to type of the bacterium to be used, and so forth. For example, the *Escherichia coli* B strain has genes encoding a heparosan efflux carrier protein, but it does not have genes encoding glycosyltransferase. Therefore, a heparosan-producing ability can be imparted to the *Escherichia coli* B strain by introducing gene(s) encoding glycosyltransferase.

Furthermore, for example, the *Escherichia coli* K-12 strain does not have either genes encoding glycosyltransferase or genes encoding a heparosan efflux carrier protein. Therefore, a heparosan-producing ability can be imparted to the *Escherichia coli* K-12 strain by introducing both gene(s) encoding glycosyltransferase and genes encoding a heparosan efflux carrier protein.

Thus, examples of the *Escherichia* bacterium having a heparosan-producing ability include, for example, *Escherichia coli* K5 strain; *Escherichia coli* B strain such as BL21(DE3) strain introduced with the kfiA gene and kfiC gene of the *Escherichia coli* K5 strain; *Escherichia coli* K-12 strain such as W3110 strain and MG1655 strain introduced with the kfiA gene and kfiC gene of the *Escherichia coli* K5 strain, as well as the kpsC, kpsD, kpsE, kpsM, kpsS, and kpsT genes of the *Escherichia coli* K5 strain or *Escherichia coli* B strain; and derivative strains thereof. Specific examples of *Escherichia coli* B strain introduced with the kfiA gene and kfiC gene of the *Escherichia coli* K5 strain include, for example, the *Escherichia coli* BL21 (DE3)/pVK9-region2 described in Examples.

The bacterium having a heparosan-producing ability may also be a bacterium that has been modified so that expression is enhanced of a gene encoding a protein involved in the heparosan production and that is inherently present in the bacterium. That is, for example, the *Escherichia coli* K5 strain may be modified so that expression of one or more genes encoding a protein that participates in the heparosan production is enhanced. Furthermore, for example, the *Escherichia coli* B strain may be modified so that expression of one or more genes encoding a heparosan efflux carrier protein is enhanced.

The bacterium having a heparosan-producing ability may have been further modified in other ways so long as the heparosan-producing ability is not degraded. For example, the bacterium having a heparosan-producing ability may have been modified so that expression of one or more genes, such as kfiB, kfiD, kpsF, and kpsU, is enhanced. That is, when genes encoding glycosyltransferase are introduced, for example, region 2 may be entirely introduced, and when genes encoding glycosyltransferase and genes encoding a heparosan efflux carrier protein are introduced, regions 1 to 3 may be entirely introduced.

The gene used to modify a bacterium, so that, for example, impartation of a heparosan-producing ability, is not limited to the genes exemplified above or genes having a known nucleotide sequence, but may be a variant of such genes, so long as the variant encodes a protein that maintains the original function. The expression "protein maintains the original function" means that, in the case of the glycosyltransferase, for example, the variant of the protein has the glycosyltransferase activity, or in the case of the heparosan efflux carrier protein, the variant of the protein has the heparosan efflux activity. For example, the gene used for modification of the bacterium such as impartation of a heparosan-producing ability may be a gene encoding a protein having a known amino acid sequence including substitution, deletion, insertion, or addition of one or several amino acid residues at one or several positions. To variants of genes or proteins, the descriptions for conservative variants of the genes depicted in Tables 1 to 3 and the proteins encoded by them can be similarly applied.

<1-2> Increase in Expression of Genes Depicted in Tables 1 to 3

The bacterium of the present invention has been modified so that expression of one or more genes such as those depicted in Tables 1 to 3 is increased. The bacterium of the present invention can be obtained by modifying a bacterium having a heparosan-producing ability so that expression of one or more genes such as those depicted in Tables 1 to 3 is increased. The bacterium of the present invention can also be obtained by modifying a bacterium so that expression of one or more genes such as those depicted in Tables 1 to 3 is increased, and then imparting a heparosan-producing ability to the bacterium. The bacterium of the present invention may be a bacterium that has acquired a heparosan-producing ability as a result of the modification for increasing expression of one or more genes such as those depicted in Tables 1 to 3. In the present invention, modifications for constructing the bacterium of the present invention can be performed in an arbitrary order.

The "genes depicted in Tables 1 to 3" are, specifically, rbsR, rbsK, rbsB, hsrA, glgB, glgX, micF, rcsD, rcsB, ybiX, ybiI, ybiJ, ybiC, ybiB, rfaH, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, ycfS, lepB, rnc, era, dapA, gcvR, bcp, hyfA, rpoE, nadB, yfiC, srmB, g1414, g1413, nuoE, nuoF, nuoG, glmZ, hemY, hemX, hemD, rlmL, artQ, artM, artJ, rlmC, ybjO, yejO, yejM, yejL, rpoS, ygbN, ygbM, ygbL, g3798, g3797, g3796, g3795, g3794, g3793, g3792, ryjA, soxR, soxS, yjcC, yjcB, efeU, and efeO. The genes depicted in Tables 1 to 3 are also referred to as "the genes of Tables 1 to 3".

The rbsR, rbsK, and rbsB genes are genes encoding factors that participate in uptake of D-ribose. The rbsR gene encodes the repressor of the rbs operon. The rbsK gene encodes a ribokinase. The rbsB gene encodes one of the subunits of the ribose ABC transporter. The rbsR, rbsK, and rbsB genes of the *Escherichia coli* K-12 MG1655 strain correspond to the sequence of the positions 3,936,250 to 3,937,242, the sequence of the positions 3,935,317 to 3,936,246, and the sequence of the positions 3,934,301 to 3,935,191 of the genome sequence registered at the NCBI database as GenBank accession NC_000913 (VERSION NC_000913.2 GI: 49175990), respectively. The RbsR, RbsK, and RbsB proteins of the MG1655 strain are registered as GenBank accession NP_418209 (version NP_418209.1 GI: 16131621), GenBank accession NP_418208 (version NP_418208.1 GI: 16131620), and GenBank accession NP_418207 (version NP_418207.1 GI: 16131619), respectively.

The hsrA gene encodes an inner membrane protein presumed to be a member of the major facilitator superfamily (MFS). The hsrA gene of the *Escherichia coli* K-12 MG1655 strain corresponds to the complementary sequence of the sequence of the positions 3,937,208 to 3,938,635 in the genome sequence registered at the NCBI database as GenBank accession NC_000913 (VERSION NC_000913.2 GI: 49175990). The HsrA protein of the MG1655 strain is registered as GenBank accession NP_418210 (version NP_418210.1 GI: 16131622).

The nucleotide sequence of a region containing the rbsB, rbsK, rbsR, and hsrA genes of the *Escherichia coli* K5 strain is shown as SEQ ID NO: 29. In the nucleotide sequence shown as SEQ ID NO: 29, the rbsB, rbsK, and rbsR genes correspond to the sequence of the positions 800 to 1,690, the sequence of the positions 1,816 to 2,745, and the sequence of the positions 2,749 to 3,741, respectively. In the nucleotide sequence shown as SEQ ID NO: 29, the hsrA gene corresponds to the complementary sequence of the sequence of the positions 3,707 to 5,134. The amino acid sequences of RbsR, RbsK, RbsB, and HsrA proteins of the *Escherichia coli* K5 strain are shown as SEQ ID NOS: 30 to 33, respectively.

The glgB gene encodes a glycogen branching enzyme (1,4-α-glucan branching enzyme). The glgX gene encodes a glycogen debranching enzyme. The glgB and glgX genes of the *Escherichia coli* K-12 MG1655 strain correspond to the complementary sequence of the sequence of the positions 3,569,339 to 3,571,525, and the complementary sequence of the sequence of the positions 3,567,369 to 3,569,342 in the genome sequence registered at the NCBI database as GenBank accession NC_000913 (VERSION NC_000913.2 GI: 49175990), respectively. The GlgB and GlgX proteins of the MG1655 strain are registered as GenBank accession NP_417890 (version NP_417890.1 GI:16131306) and GenBank accession NP_417889 (version NP_417889.1 GI: 16131305), respectively.

The nucleotide sequence of a region containing the glgB and glgX genes of the *Escherichia coli* K5 strain is shown as SEQ ID NO: 34. In the nucleotide sequence shown as SEQ ID NO: 34, the glgB and glgX genes correspond to the sequence of the positions 989 to 3,175, and the sequence of the positions 3,172 to 5,145, respectively. The amino acid sequences of the GlgB and GlgX proteins of the *Escherichia coli* K5 strain are shown as SEQ ID NOS: 35 and 36, respectively.

The micF gene encodes an antisense RNA that participates in the expression inhibition of OmpF. The micF gene of the *Escherichia coli* K-12 MG1655 strain corresponds to the sequence of the positions 2,311,106 to 2,311,198 in the genome sequence registered at the NCBI database as GenBank accession NC_000913 (VERSION NC_000913.2 GI: 49175990).

The rcsD and rcsB genes encode a transcription factor. The rcsD and rcsB genes of the *Escherichia coli* K-12 MG1655 strain correspond to the sequences of the positions 2,311,510 to 2,314,182, and the positions 2,314,199 to 2,314,849 in the genome sequence registered at the NCBI database as GenBank accession NC_000913 (VERSION NC_000913.2 GI: 49175990), respectively. The RcsD and RcsB proteins of the MG1655 strain are registered as GenBank accession NP_416720 (version NP_416720.1 GI:16130153) and GenBank accession NP_416721 (version NP_416721.1 GI: 16130154), respectively.

The nucleotide sequence of a region containing the rcsB, rcsD, and micF genes of the *Escherichia coli* K5 strain is shown as SEQ ID NO: 43. In the nucleotide sequence shown as SEQ ID NO: 43, the rcsB, rcsD, and micF genes correspond to the sequence of the positions 3,312 to 3,962, the sequence of the positions 623 to 3,295, and the sequence of the positions 219 to 311, respectively. The amino acid sequences of RcsB and RcsD proteins of the *Escherichia coli* K5 strain are shown as SEQ ID NOS: 44 and 45, respectively.

The ybiX, ybiI, ybiJ, ybiC, and ybiB genes are genes of unknown functions. The ybiX, ybiI, ybiJ, ybiC, and ybiB genes of the *Escherichia coli* K-12 MG1655 strain correspond to the complementary sequence of the sequence of the positions 837,753 to 838,430, the complementary sequence of the sequence of the positions 837,413 to 837,679, the complementary sequence of the sequence of the positions 836,888 to 837,148, the sequence of the positions 835,574 to 836,659, and the sequence of the positions 834,471 to 835,433 in the genome sequence registered at the NCBI database as GenBank accession NC_000913 (VERSION NC_000913.2 GI: 49175990), respectively. The YbiX, YbiI, YbiJ, YbiC, and YbiB proteins of the MG1655 strain are registered as GenBank accession NP_415325 (version NP_415325.4 GI: 90111170), GenBank accession NP_415324 (version NP_415324.1 GI: 16128771), GenBank accession NP_415323 (version NP_415323.1 GI: 16128770), GenBank accession NP_415322 (version NP_415322.1 GI: 16128769), and GenBank accession NP_415321 (version NP_415321.1 GI: 16128768), respectively.

The nucleotide sequence of a region containing the ybiX, ybiI, ybiJ, ybiC, and ybiB genes of the *Escherichia coli* K5 strain is shown as SEQ ID NO: 37. In the nucleotide sequence shown as SEQ ID NO: 37, the ybiX, ybiI, and ybiJ genes correspond to the sequence of the positions 718 to 1,395, the sequence of the positions 1,469 to 1,735, and the sequence of the positions 2,000 to 2,260, respectively. In the nucleotide sequence shown as SEQ ID NO: 37, the ybiC and ybiB genes correspond to the complementary sequence of the sequence of the positions 2,488 to 3,574, and the complementary sequence of the sequence of the positions 3,715 to 4,677. The amino acid sequences of the YbiX, YbiI, YbiJ, YbiC, and YbiB proteins of the *Escherichia coli* K5 strain are shown as SEQ ID NOS: 38 to 42, respectively.

The rfaH and nusG genes encode a transcription factor. The rfaH and nusG genes of the *Escherichia coli* K-12 MG1655 strain correspond to the complementary sequence of the sequence of the positions 4,022,356 to 4,022,844, and the sequence of the positions 4,175,766 to 4,176,311 in the genome sequence registered at the NCBI database as GenBank accession NC_000913 (VERSION NC_000913.2 GI: 49175990), respectively. The RfaH and NusG proteins of the MG1655 strain are registered as GenBank accession NP_418284 (version NP_418284.1 GI: 16131688) and GenBank accession NP_418409 (version NP_418409.1 GI: 16131812), respectively.

The nucleotide sequence of the rfaH gene of the *Escherichia coli* BL21(DE3) strain, and the amino acid sequence of the RfaH protein encoded by this gene are shown as SEQ ID NOS: 46 and 47, respectively. The nucleotide sequence of the nusG gene of the *Escherichia coli* BL21(DE3) strain, and the amino acid sequence of the NusG protein encoded by this gene are shown as SEQ ID NOS: 48 and 49, respectively.

The pcoR, pcoS, and pcoE genes are genes encoding a factor that relates to copper resistance. The pcoR gene encodes a protein homologous to the activator of the pco operon. The pcoS gene encodes a protein homologous to the sensor protein of a two-component control system. The pcoE gene encodes a copper binding protein. These genes are not annotated in the genome of the *Escherichia coli* K-12 MG1655 strain.

The nucleotide sequence of a region containing the pcoR, pcoS, and pcoE genes of the *Escherichia coli* K5 strain is shown as SEQ ID NO: 50. In the nucleotide sequence shown as SEQ ID NO: 50, the pcoR, pcoS, and pcoE genes correspond to the sequence of the positions 128 to 808, the sequence of the positions 805 to 2,205, and the sequence of the positions 2,423 to 2,857, respectively. The amino acid sequences of the PcoR, PcoS, and PcoE proteins of the *Escherichia coli* K5 strain are shown as SEQ ID NOS: 51 to 53, respectively.

The yhcN gene encodes a factor that participates in stress response. The yhcN gene of the *Escherichia coli* K-12 MG1655 strain corresponds to the sequence of the positions 3,383,560 to 3,383,823 in the genome sequence registered at the NCBI database as GenBank accession NC_000913 (VERSION NC_000913.2 GI: 49175990). The YhcN protein of the MG1655 strain is registered as GenBank accession NP_417705 (version NP_417705.2 GI: 90111561).

The yhcO gene encodes a protein homologous to an inhibitor for RNase. The yhcO gene of the *Escherichia coli* K-12 MG1655 strain corresponds to the complementary sequence of the sequence of the positions 3,383,879 to 3,384,151 in the genome sequence registered at the NCBI database as GenBank accession NC_000913 (VERSION NC_000913.2 GI: 49175990). The YhcO protein of the MG1655 strain is registered as GenBank accession NP_417706 (version NP_417706.1 GI: 16131129).

The aaeB and aaeA genes encode a subunit of an efflux carrier of 4-hydroxybenzoic acid. The aaeX gene encodes a protein presumed to be an efflux carrier. The aaeB, aaeA, and aaeX genes of the *Escherichia coli* K-12 MG1655 strain correspond to the complementary sequence of the sequence of the positions 3,384,243 to 3,386,210, the complementary sequence of the sequence of the positions 3,386,216 to 3,387,148, and the complementary sequence of the sequence of the positions 3,387,156 to 3,387,359 in the genome sequence registered at the NCBI database as GenBank accession NC_000913 (VERSION NC_000913.2 GI: 49175990), respectively. The AaeB, AaeA, and AaeX proteins of the MG1655 strain are registered as GenBank accession NP_417707 (version NP_417707.1 GI: 16131130), GenBank accession NP_417708 (version NP_417708.1 GI: 16131131), and GenBank accession NP_417709 (version NP_417709.2 GI: 90111562), respectively.

The nucleotide sequence of a region containing the yhcN, yhcO, aaeB, aaeA, and aaeX genes of the *Escherichia coli* K5 strain is shown as SEQ ID NO: 54. In the nucleotide sequence shown as SEQ ID NO: 54, the yhcN, yhcO, aaeB, aaeA, and aaeX genes correspond to the sequence of the positions 63 to 326, the complementary sequence of the sequence of the positions 382 to 654, the complementary sequence of the sequence of the positions 746 to 2,713, the complementary sequence of the sequence of the positions 2,719 to 3,651, and the complementary sequence of the sequence of the positions 3,659 to 3,931, respectively. The amino acid sequences of the YhcN, YhcO, AaeB, AaeA, and AaeX proteins of the *Escherichia coli* K5 strain are shown as SEQ ID NOS: 55 to 59, respectively.

The g1455 and g1453 genes are genes of unknown functions. These genes are not annotated in the genome of the *Escherichia coli* K-12 MG1655 strain.

The alpA gene encodes an expression control factor of the intA gene. The alpA gene of the *Escherichia coli* K-12 MG1655 strain corresponds to the sequence of the positions 2,756,666 to 2,756,878 in the genome sequence registered at the NCBI database as GenBank accession NC_000913 (VERSION NC_000913.2 GI: 49175990). The AlpA protein of the MG1655 strain is registered as GenBank accession NP_417113 (version NP_417113.1 GI: 16130542).

The nucleotide sequence of a region containing the g1455, alpA, and g1453 genes of the *Escherichia coli* K5 strain is shown as SEQ ID NO: 60. In the nucleotide sequence shown as SEQ ID NO: 60, the g1455, alpA, and g1453 genes correspond to the complementary sequence of the sequence of the positions 568 to 1,140, the complementary sequence of the sequence of the positions 1,226 to 1,486, and the sequence of the positions 2,389 to 2,529, respectively. The amino acid sequences of G1455, AlpA, and G1453 proteins of the *Escherichia coli* K5 strain are shown as SEQ ID NOS: 61 to 63, respectively.

The yrbA gene (synonym is ibaG) encodes a protein presumed to be a DNA-binding type transcription factor. The yrbA gene of the *Escherichia coli* K-12 MG1655 strain corresponds to the complementary sequence of the sequence of the positions 3,334,571 to 3,334,825 in the genome sequence registered at the NCBI database as GenBank accession NC_000913 (VERSION NC_000913.2 GI: 49175990). The YrbA protein of the MG1655 strain is registered as GenBank accession NP_417657 (version NP_417657.2 GI: 90111555).

The mlaB, mlaC, mlaD, mlaE, and mlaF genes encode a constituent factor of a phospholipid ABC transporter. The mlaB, mlaC, mlaD, mlaE, and mlaF genes of the *Escherichia coli* K-12 MG1655 strain correspond to the complementary sequence of the sequence of the positions 3,334,985 to 3,335,278, the complementary sequence of the sequence of the positions 3,335,278 to 3,335,913, the complementary sequence of the sequence of the positions 3,335,932 to 3,336,483, the complementary sequence of the sequence of the positions 3,336,488 to 3,337,270, and the complementary sequence of the sequence of the positions 3,337,278 to 3,338,087 in the genome sequence registered at the NCBI database as GenBank accession NC_000913 (VERSION NC_000913.2 GI: 49175990), respectively. The MlaB, MlaC, MlaD, MlaE, and MlaF proteins of the MG1655 strain are registered as GenBank accession NP_417658 (version NP_417658.4 GI: 90111556), GenBank accession NP_417659 (version NP_417659.1 GI: 16131082), GenBank accession NP_417660 (version NP_417660.1 GI: 16131083), GenBank accession NP_417661 (version NP_417661.1 GI: 16131084), and GenBank accession NP_417662 (version NP_417662.1 GI: 16131085), respectively.

The yrbG gene encodes a protein presumed to be an $Na^+/Ca^{2+}$ antiporter. The yrbG gene of the *Escherichia coli* K-12 MG1655 strain corresponds to the sequence of the positions 3,338,297 to 3,339,274 in the genome sequence registered at the NCBI database as GenBank accession NC_000913 (VERSION NC_000913.2 GI: 49175990). The YrbG protein of the MG1655 strain is registered as GenBank accession NP_417663 (version NP_417663.1 GI: 16131086).

The nucleotide sequence of a region containing the yrbA, mlaB, mlaC, mlaD, mlaE, mlaF, and yrbG genes of the *Escherichia coli* K5 strain is shown as SEQ ID NO: 64. In the nucleotide sequence shown as SEQ ID NO: 64, the yrbA, mlaB, mlaC, mlaD, mlaE, mlaF, and yrbG genes correspond to the complementary sequence of the sequence of the positions 977 to 1,246, the complementary sequence of the sequence of the positions 1,391 to 1,780, the complementary sequence of the sequence of the positions 1,684 to 2,319, the complementary sequence of the sequence of the positions 2,338 to 2,889, the complementary sequence of the sequence of the positions 2,894 to 3,676, the complementary sequence of the sequence of the positions 3,684 to 4,493, and the sequence of the positions 4,703 to 5,680, respectively. The amino acid sequences of YrbA, MlaB, MlaC, MlaD, MlaE, MlaF, and YrbG proteins of the *Escherichia coli* K5 strain are shown as SEQ ID NOS: 65 to 71, respectively.

The norW gene encodes an NO reductase. The norW gene of the *Escherichia coli* K-12 MG1655 strain corresponds to the sequence of the positions 2,831,934 to 2,833,067 in the genome sequence registered at the NCBI database as GenBank accession NC_000913 (VERSION NC_000913.2 GI: 49175990). The NorW protein of the MG1655 strain is registered as GenBank accession NP_417191 (version NP_417191.1 GI: 16130618).

The nucleotide sequence of a region containing the norW gene of the *Escherichia coli* K5 strain is shown as SEQ ID NO: 72. In the nucleotide sequence shown as SEQ ID NO: 72, the norW gene corresponds to the sequence of the positions 1,201 to 2,334. The amino acid sequence of the NorW protein of the *Escherichia coli* K5 strain is shown as SEQ ID NO: 73.

The ybjI gene encodes a flavin mononucleotide (FMN) phosphorylating enzyme. The ybjI gene of the *Escherichia coli* K-12 MG1655 strain corresponds to the complementary sequence of the sequence of the positions 884,539 to 885,354 in the genome sequence registered at the NCBI database as GenBank accession NC_000913 (VERSION NC_000913.2 GI: 49175990). The YbjI protein of the MG1655 strain is registered as GenBank accession NP_415365 (version NP_415365.4 GI: 90111176).

The ybjJ and ybjK genes are genes of unknown function. The ybjJ and ybjK genes of the *Escherichia coli* K-12 MG1655 strain correspond to the complementary sequence of the sequence of the positions 885,354 to 886,562, and the sequence of the positions 886,646 to 887,182 in the genome sequence registered at the NCBI database as GenBank accession NC_000913 (VERSION NC_000913.2 GI: 49175990), respectively. The YbjJ and YbjK proteins of the MG1655 strain are registered as GenBank accession NP_415366 (version NP_415366.1 GI: 16128813) and GenBank accession NP_415367 (version NP_415367.1 GI: 16128814), respectively.

The rybB gene encodes a low molecular weight RNA that participates in expression inhibition of OmpC and OmpW. The rybB gene of the *Escherichia coli* K-12 MG1655 strain corresponds to the complementary sequence of the sequence of the positions 887,199 to 887,277 in the genome sequence registered at the NCBI database as GenBank accession NC_000913 (VERSION NC_000913.2 GI: 49175990).

The nucleotide sequence of a region containing the ybjI, ybjJ, ybjK, and rybB genes of the *Escherichia coli* K5 strain is shown as SEQ ID NO: 74. In the nucleotide sequence shown as SEQ ID NO: 74, the ybjI, ybjJ, ybjK, and rybB genes correspond to the complementary sequence of the sequence of the positions 117 to 932, the complementary sequence of the sequence of the positions 932 to 2,140, the sequence of the positions 2,224 to 2,760, and the complementary sequence of the sequence of the positions 2,777 to 2,855, respectively. The amino acid sequences of the YbjI, YbjJ, and YbjK proteins of the *Escherichia coli* K5 strain are shown as SEQ ID NOS: 75 to 77, respectively.

The yjjY gene is a gene of unknown function. The yjjY gene of the *Escherichia coli* K-12 MG1655 strain corresponds to the sequence of the positions 4,638,425 to 4,638,565 in the genome sequence registered at the NCBI database as GenBank accession NC_000913 (VERSION NC_000913.2 GI: 49175990). The YjjY protein of the MG1655 strain is registered as GenBank accession NP_418819 (version NP_418819.1 GI: 16132219).

The yjtD gene encodes a protein presumed to be one of RNA methyltransferases. The yjtD gene of the *Escherichia coli* K-12 MG1655 strain corresponds to the sequence of the positions 4,638,965 to 4,639,651 in the genome sequence registered at the NCBI database as GenBank accession NC_000913 (VERSION NC_000913.2 GI: 49175990). The YjtD protein of the MG1655 strain is registered as GenBank accession NP_418820 (version NP_418820.1 GI: 16132220).

The thrL, thrA, and thrB genes encode an enzyme of the threonine biosynthesis pathway. The thrB gene encodes a homoserine kinase. The thrA gene encodes an enzyme having two functions of aspartate kinase I and homoserine dehydrogenase I. The thrL gene encodes a leader peptide of the thrLABC operon. The thrL, thrA, and thrB genes of the *Escherichia coli* K-12 MG1655 strain correspond to the sequence of the positions 190 to 255, the sequence of the positions 337 to 2,799, and the sequence of the positions 2,801 to 3,733 in the genome sequence registered at the NCBI database as GenBank accession NC_000913 (VERSION NC_000913.2 GI: 49175990), respectively. The ThrL, ThrA, and ThrB proteins of the MG1655 strain are registered as GenBank accession NP_414542 (version NP_414542.1 GI: 16127995), GenBank accession NP_414543 (version NP_414543.1 GI: 16127996), and GenBank accession NP_414544 (version NP_414544.1 GI: 16127997), respectively.

The nucleotide sequence of a region containing the yjjY, yjtD, thrL, thrA, and thrB genes of the *Escherichia coli* K5 strain is shown as SEQ ID NO: 78. In the nucleotide sequence shown as SEQ ID NO: 78, the yjjY, yjtD, thrL, thrA, and thrB genes correspond to the sequence of the positions 124 to 264, the sequence of the positions 664 to 1,350, the sequence of the positions 1,564 to 1,629, the sequence of the positions 1,711 to 4,173, and the sequence of the positions 4,175 to 5,107, respectively. The amino acid sequences of the YjjY, YjtD, ThrL, ThrA, and ThrB proteins of the *Escherichia coli* K5 strain are shown as SEQ ID NOS: 79 to 83, respectively.

The fruA gene encodes a fructose PTS permease. The fruA gene of the *Escherichia coli* K-12 MG1655 strain corresponds to the complementary sequence of the sequence of the positions 2,257,741 to 2,259,432 in the genome sequence registered at the NCBI database as GenBank accession NC_000913 (VERSION NC_000913.2 GI: 49175990). The FruA protein of the MG1655 strain is registered as GenBank accession NP_416672 (version NP_416672.1 GI: 16130105).

The psuK gene encodes a pseudouridine kinase. The psuK gene of the *Escherichia coli* K-12 MG1655 strain corresponds to the complementary sequence of the sequence of the positions 2,256,377 to 2,257,318 in the genome sequence registered at the NCBI database as GenBank accession NC_000913 (VERSION NC_000913.2 GI: 49175990). The PsuK protein of the MG1655 strain is registered as GenBank accession NP_416671 (version NP_416671.1 GI: 16130104).

The nucleotide sequence of a region containing the fruA and psuK genes of the *Escherichia coli* K5 strain is shown as SEQ ID NO: 84. In the nucleotide sequence shown as SEQ ID NO: 84, the fruA and psuK genes correspond to the sequence of the positions 897 to 2588, and the sequence of the positions 3,165 to 3,953, respectively. The amino acid sequences of the FruA and PsuK proteins of the *Escherichia coli* K5 strain are shown as SEQ ID NOS: 85 and 86, respectively.

The ytfT and yjfF genes are genes encoding a protein presumed to be a membrane constituent component of the galactose ABC transport carrier. The ytfT and yjfF genes of the *Escherichia coli* K-12 MG1655 strain correspond to the sequence of the positions 4,450,594 to 4,451,619 and the sequence of the positions 4,451,606 to 4,452,601 in the genome sequence registered at the NCBI database as GenBank accession NC_000913 (VERSION NC_000913.2 GI: 49175990), respectively. The YtfT and YjfF proteins of the MG1655 strain are registered as GenBank accession NP_418651 (version NP_418651.3 GI:145698343) and GenBank accession NP_418652 (version NP_418652.2 GI: 90111710), respectively.

The fbp gene encodes a fructose-1,6-diphosphate phosphatase (fructose-1,6-bisphosphatase). The fbp gene of the

*Escherichia coli* K-12 MG1655 strain corresponds to the complementary sequence of the sequence of the positions 4,452,634 to 4,453,632 in the genome sequence registered at the NCBI database as GenBank accession NC_000913 (VERSION NC_000913.2 GI: 49175990). The Fbp protein of the MG1655 strain is registered as GenBank accession NP_418653 (version NP_418653.1 GI: 16132054).

The nucleotide sequence of a region containing the ytfT, yjfF, and fbp genes of the *Escherichia coli* K5 strain is shown as SEQ ID NO: 87. In the nucleotide sequence shown as SEQ ID NO: 87, the ytfT, yjfF, and fbp genes correspond to the sequence of the positions 252 to 1,277, the sequence of the positions 1,264 to 2,259, and the complementary sequence of the sequence of the positions 2,292 to 3,290, respectively. The amino acid sequences of the YtfT, YjfF, and Fbp proteins of the *Escherichia coli* K5 strain are shown as SEQ ID NOS: 88 to 90, respectively.

The yagU gene encodes a protein presumed to be an inner membrane protein. The yagU gene of the *Escherichia coli* K-12 MG1655 strain corresponds to the sequence of the positions 302,215 to 302,829 in the genome sequence registered at the NCBI database as GenBank accession NC_000913 (VERSION NC_000913.2 GI: 49175990). The YagU protein of the MG1655 strain is registered as GenBank accession NP_414821 (version NP_414821.1 GI: 16128272).

The paoA gene (also called yagT) and paoB gene (also called yagS) are genes encoding a constituent factor of an aldehyde oxidoreductase. The paoA and paoB genes of the *Escherichia coli* K-12 MG1655 strain correspond to the complementary sequence of the sequence of the positions 301,108 to 301,797, and the complementary sequence of the sequence of the positions 300,155 to 301,111 in the genome sequence registered at the NCBI database as GenBank accession NC_000913 (VERSION NC_000913.2 GI: 49175990), respectively. The PaoA and PaoB proteins of the MG1655 strain are registered as GenBank accession NP_414820 (version NP_414820.1 GI:16128271) and GenBank accession NP_414819 (version NP_414819.1 GI: 16128270), respectively.

The nucleotide sequence of a region containing the yagU, paoA, and paoB genes of the *Escherichia coli* K5 strain is shown as SEQ ID NO: 91. In the nucleotide sequence shown as SEQ ID NO: 91, the yagU, paoA, and paoB genes correspond to the complementary sequence of the sequence of the positions 117 to 731, the sequence of the positions 1,149 to 1,838, and the sequence of the positions 1,835 to 2,791, respectively. The amino acid sequences of the YagU, PaoA, and PaoB proteins of the *Escherichia coli* K5 strain are shown as SEQ ID NOS: 92 to 94, respectively.

The gsiC and gsiD genes are genes encoding a constituent factor of a glutathione ABC transport carrier. The gsiC and gsiD genes of the *Escherichia coli* K-12 MG1655 strain correspond to the sequence of the positions 870,190 to 871,110, and the sequence of the positions 871,113 to 872,024 in the genome sequence registered at the NCBI database as GenBank accession NC_000913 (VERSION NC_000913.2 GI: 49175990), respectively. The GsiC and GsiD proteins of the MG1655 strain are registered as GenBank accession NP_415352 (version NP_415352.1 GI:16128799) and GenBank accession NP_415353 (version NP_415353.1 GI: 16128800), respectively.

The yliE gene encodes a protein presumed to be a c-di-GMP-specific phosphodiesterase. The yliE gene of the *Escherichia coli* K-12 MG1655 strain corresponds to the sequence of the positions 872,202 to 874,550 in the genome sequence registered at the NCBI database as GenBank accession NC_000913 (VERSION NC_000913.2 GI: 49175990). The YliE protein of the MG1655 strain is registered as GenBank accession NP_415354 (version NP_415354.1 GI: 16128801).

The nucleotide sequence of a region containing the gsiC, gsiD, and yliE genes of the *Escherichia coli* K5 strain is shown as SEQ ID NO: 95. In the nucleotide sequence shown as SEQ ID NO: 95, the gsiC, gsiD, and yliE genes correspond to the sequence of the positions 264 to 1,184, the sequence of the positions 1,187 to 2,098, and the sequence of the positions 2,276 to 4,624, respectively. The amino acid sequences of the GsiC, GsiD, and YliE proteins of the *Escherichia coli* K5 strain are shown as SEQ ID NOS: 96 to 98, respectively.

The irp2 and irp1 genes encode a non-ribosormal peptide synthetase. The irp2 and irp1 genes are not annotated in the genome of the *Escherichia coli* K-12 MG1655 strain. In the present invention, the irp2 and irp1 gene may be generically called "irp gene".

The nucleotide sequence of a region containing a part of the irp gene of the *Escherichia coli* K5 strain is shown as SEQ ID NO: 99. This region contains the second half moiety of the irp2 gene (moiety of the positions 2,781 to 6,108 in the full length of 6108 bp, equivalent to about 54% of the full length), and the first half moiety of the irp1 gene (moiety of the positions 1 to 2,530 in the full length of 9492 bp, equivalent to about 27% of the full length). The nucleotide sequence of the irp2 gene of the *Escherichia coli* K5 strain and the amino acid sequence of the Irp2 protein encoded by that gene are shown as SEQ ID NOS: 100 and 101, respectively. The nucleotide sequence of the irp1 gene of the *Escherichia coli* K5 strain and the amino acid sequence of the Irp1 protein encoded by that gene are shown as SEQ ID NOS: 102 and 103, respectively.

The bhsA gene (synonym is ycfR) encodes a protein presumed to be an outer membrane protein. The bhsA gene of the *Escherichia coli* K-12 MG1655 strain corresponds to the sequence of the positions 1,168,296 to 1,168,553 in the genome sequence registered at the NCBI database as GenBank accession NC_000913 (VERSION NC_000913.2 GI: 49175990). The BhsA protein of the MG1655 strain is registered as GenBank accession NP_415630 (version NP_415630.1 GI: 16129075).

The ycfS gene encodes one of L,D-transpeptidases. The ycfS gene of the *Escherichia coli* K-12 MG1655 strain corresponds to the complementary sequence of the sequence of the positions 1,168,635 to 1,169,597 in the genome sequence registered at the NCBI database as GenBank accession NC_000913 (VERSION NC_000913.2 GI: 49175990). The YcfS protein of the MG1655 strain is registered as GenBank accession NP_415631 (version NP_415631.1 GI: 16129076).

The nucleotide sequence of a region containing the bhsA and ycfS genes of the *Escherichia coli* K5 strain is shown as SEQ ID NO: 104. In the nucleotide sequence shown as SEQ ID NO: 104, the bhsA and ycfS genes correspond to the sequence of the positions 440 to 697, and the complementary sequence of the sequence of the positions 779 to 1,741, respectively. The amino acid sequences of the BhsA and YcfS proteins of the *Escherichia coli* K5 strain are shown as SEQ ID NOS: 105 and 106, respectively.

The lepB gene encodes a signal peptidase. The lepB gene of the *Escherichia coli* K-12 MG1655 strain corresponds to the complementary sequence of the sequence of the positions 2,702,357 to 2,703,331 in the genome sequence registered at the NCBI database as GenBank accession NC_000913 (VERSION NC_000913.2 GI: 49175990). The LepB protein of the MG1655 strain is registered as GenBank accession NP_417063 (version NP_417063.1 GI: 16130493).

The rnc gene encodes an RNaseIII. The rnc gene of the *Escherichia coli* K-12 MG1655 strain corresponds to the complementary sequence of the sequence of the positions 2,701,405 to 2,702,085 in the genome sequence registered at the NCBI database as GenBank accession NC_000913 (VERSION NC_000913.2 GI: 49175990). The Rnc protein of the MG1655 strain is registered as GenBank accession NP_417062 (version NP_417062.1 GI: 16130492).

The era gene encodes a factor indispensable to survival. The era gene of the *Escherichia coli* K-12 MG1655 strain corresponds to the complementary sequence of the sequence of the positions 2,700,503 to 2,701,408 in the genome sequence registered at the NCBI database as GenBank accession NC_000913 (VERSION NC_000913.2 GI: 49175990). The Era protein of the MG1655 strain is registered as GenBank accession NP_417061 (version NP_417061.1 GI: 16130491).

The nucleotide sequence of a region containing the lepB, rnc, and era genes of the *Escherichia coli* K5 strain is shown as SEQ ID NO: 107. In the nucleotide sequence shown as SEQ ID NO: 107, the lepB, rnc, and era genes correspond to the sequence of the positions 1,344 to 2,318, the sequence of the positions 2,590 to 3,270, and the sequence of the positions 3,267 to 4,172, respectively. The amino acid sequences of the LepB, Rnc, and Era proteins of the *Escherichia coli* K5 strain are shown as SEQ ID NOS: 108 to 110, respectively.

The dapA gene encodes a 4-hydroxy-tetrahydrodipicolinate synthase. The dapA gene of the *Escherichia coli* K-12 MG1655 strain corresponds to the complementary sequence of the sequence of the positions 2,596,904 to 2,597,782 in the genome sequence registered at the NCBI database as GenBank accession NC_000913 (VERSION NC_000913.2 GI: 49175990). The DapA protein of the MG1655 strain is registered as GenBank accession NP_416973 (version NP_416973.1 GI: 16130403).

The gcvR gene encodes a protein presumed to be a transcription control factor. The gcvR gene of the *Escherichia coli* K-12 MG1655 strain corresponds to the sequence of the positions 2,597,928 to 2,598,500 in the genome sequence registered at the NCBI database as GenBank accession NC_000913 (VERSION NC_000913.2 GI: 49175990). The GcvR protein of the MG1655 strain is registered as GenBank accession NP_416974 (version NP_416974.4 GI: 90111443).

The bcp gene encodes a thiol peroxidase. The bcp gene of the *Escherichia coli* K-12 MG1655 strain corresponds to the sequence of the positions 2,598,500 to 2,598,970 in the genome sequence registered at the NCBI database as GenBank accession NC_000913 (VERSION NC_000913.2 GI: 49175990). The Bcp protein of the MG1655 strain is registered as GenBank accession NP_416975 (version NP_416975.1 GI: 16130405).

The hyfA gene encodes a protein presumed to participate in the electron transportation. The hyfA gene of the *Escherichia coli* K-12 MG1655 strain corresponds to the sequence of the positions 2,599,223 to 2,599,840 in the genome sequence registered at the NCBI database as GenBank accession NC_000913 (VERSION NC_000913.2 GI: 49175990). The HyfA protein of the MG1655 strain is registered as GenBank accession NP_416976 (version NP_416976.4 GI: 90111444).

The nucleotide sequence of a region containing the dapA, gcvR, bcp, and hyfA genes of the *Escherichia coli* K5 strain is shown as SEQ ID NO: 111. In the nucleotide sequence shown as SEQ ID NO: 111, the dapA, gcvR, bcp, and hyfA genes correspond to the complementary sequence of the sequence of the positions 858 to 1,736, the sequence of the positions 1,882 to 2,454, the sequence of the positions 2,454 to 2,924, and the sequence of the positions 3,177 to 3,794, respectively. The amino acid sequences of the DapA, GcvR, Bcp, and HyfA proteins of the *Escherichia coli* K5 strain are shown as SEQ ID NOS: 112 to 115, respectively.

The rpoE gene encodes SigmaE ($\sigma^E$). The rpoE gene of the *Escherichia coli* K-12 MG1655 strain corresponds to the complementary sequence of the sequence of the positions 2,707,459 to 2,708,034 in the genome sequence registered at the NCBI database as GenBank accession NC_000913 (VERSION NC_000913.2 GI: 49175990). The RpoE protein of the MG1655 strain is registered as GenBank accession NP_417068 (version NP_417068.1 GI: 16130498).

The nadB gene encodes an L-aspartic acid oxidase. The nadB gene of the *Escherichia coli* K-12 MG1655 strain corresponds to the sequence of the positions 2,708,442 to 2,710,064 in the genome sequence registered at the NCBI database as GenBank accession NC_000913 (VERSION NC_000913.2 GI: 49175990). The NadB protein of the MG1655 strain is registered as GenBank accession NP_417069 (version NP_417069.1 GI: 16130499).

The yfiC gene encodes a methyltransferase that methylates N at the position 6 of A37 (adenine at the position 37) of valine tRNA. The yfiC gene of the *Escherichia coli* K-12 MG1655 strain corresponds to the complementary sequence of the sequence of the positions 2,710,049 to 2,710,786 in the genome sequence registered at the NCBI database as GenBank accession NC_000913 (VERSION NC_000913.2 GI: 49175990). The YfiC protein of the MG1655 strain is registered as GenBank accession NP_417070 (version NP_417070.2 GI: 90111461).

The srmB gene encodes a DEAD-box type RNA helicase. The srmB gene of the *Escherichia coli* K-12 MG1655 strain corresponds to the sequence of the positions 2,710,918 to 2,712,252 in the genome sequence registered at the NCBI database as GenBank accession NC_000913 (VERSION NC_000913.2 GI: 49175990). The SrmB protein of the MG1655 strain is registered as GenBank accession NP_417071 (version NP_417071.1 GI: 16130501).

The nucleotide sequence of a region containing the rpoE, nadB, yfiC, and srmB genes of the *Escherichia coli* K5 strain is shown as SEQ ID NO: 116. In the nucleotide sequence shown as SEQ ID NO: 116, the rpoE, nadB, yfiC, and srmB genes correspond to the complementary sequence of the sequence of the positions 355 to 930, the sequence of the positions 1,338 to 2,960, the complementary sequence of the sequence of the positions 2,945 to 3,682, and the sequence of the positions 3,814 to 5,148, respectively. Among these, the nucleotide sequence of the rpoE gene of the *Escherichia coli* K5 strain is especially shown as SEQ ID NO: 174. The amino acid sequences of the RpoE, NadB, YfiC, and SrmB proteins of the *Escherichia coli* K5 strain are shown as SEQ ID NOS: 117 to 120, respectively.

The g1414 and g1413 genes are genes of unknown function. These genes are not annotated in the genome of the *Escherichia coli* K-12 MG1655 strain.

The nucleotide sequence of a region containing the g1414 and g1413 genes of the *Escherichia coli* K5 strain is shown as SEQ ID NO: 121. In the nucleotide sequence shown as SEQ ID NO: 121, the g1414 and g1413 genes correspond to the sequence of the positions 28 to 699, and the sequence of the positions 831 to 1,157, respectively. The amino acid sequences of the G1414 and G1413 proteins of the *Escherichia coli* K5 strain are shown as SEQ ID NOS: 122 and 123, respectively.

The nuoE, nuoF, and nuoG genes encode a soluble fragment of NADH dehydrogenase I. The nuoE, nuoF, and nuoG genes of the *Escherichia coli* K-12 MG1655 strain correspond to the complementary sequence of the sequence of the positions 2,399,574 to 2,400,074, the complementary sequence of the sequence of the positions 2,398,240 to 2,399,577, and the complementary sequence of the sequence of the positions 2,395,461 to 2,398,187 in the genome sequence registered at the NCBI database as GenBank accession NC_000913 (VERSION NC_000913.2 GI: 49175990), respectively. The NuoE, NuoF, and NuoG proteins of the MG1655 strain are registered as GenBank accession NP_416788 (version NP_416788.1 GI: 16130220), GenBank accession NP_416787 (version NP_416787.1 GI: 16130219), and GenBank accession NP_416786 (version NP_416786.4 GI: 145698290), respectively.

The nucleotide sequence of a region containing the nuoE, nuoF, and nuoG genes of the *Escherichia coli* K5 strain is shown as SEQ ID NO: 124. In the nucleotide sequence shown as SEQ ID NO: 124, the nuoE, nuoF, and nuoG genes correspond to the complementary sequence of the sequence of the positions 796 to 1,296, the complementary sequence of the sequence of the positions 1,293 to 2,630, and the complementary sequence of the sequence of the positions 2,683 to 5,409, respectively. The amino acid sequences of the NuoE, NuoF, and NuoG proteins of the *Escherichia coli* K5 strain are shown as SEQ ID NOS: 125 to 127, respectively.

The glmZ gene encodes a low molecular weight RNA. The glmZ gene of the *Escherichia coli* K-12 MG1655 strain corresponds to the sequence of the positions 3,984,455 to 3,984,626 in the genome sequence registered at the NCBI database as GenBank accession NC_000913 (VERSION NC_000913.2 GI: 49175990).

The hemY, hemX, and hemD genes encode enzymes of the biosynthesis pathways of heme and choline. The hemY gene encodes a protoporphyrinogen oxidase. The hemX gene encodes a protein presumed to be a uroporphyrinogen III methylase. The hemD gene encodes a uroporphyrinogen III synthase. The hemY, hemX, and hemD genes of the K-12 MG1655 strain correspond to the complementary sequence of the sequence of the positions 3,984,709 to 3,985,905, the complementary sequence of the sequence of the positions 3,985,908 to 3,987,089, and the complementary sequence of the sequence of the positions 3,987,111 to 3,987,851 in the genome sequence registered at the NCBI database as GenBank accession NC_000913 (VERSION NC_000913.2 GI: 49175990), respectively. The HemY, HemX, and HemD proteins of the MG1655 strain are registered as GenBank accession NP_418246 (version NP_418246.1 GI: 16131654), GenBank accession NP_418247 (version NP_418247.1 GI: 16131655), and GenBank accession NP_418248 (version NP_418248.1 GI: 16131656), respectively.

The nucleotide sequence of a region containing the glmZ, hemY, hemX, and hemD genes of the *Escherichia coli* K5 strain is shown as SEQ ID NO: 128. In the nucleotide sequence shown as SEQ ID NO: 128, the glmZ, hemY, hemX, and hemD genes correspond to the sequence of the positions 357 to 563, the sequence of the positions 611 to 1,807, the sequence of the positions 1,810 to 2,991, and the sequence of the positions 3,013 to 3,753, respectively. The amino acid sequences of the HemY, HemX, and HemD proteins of the *Escherichia coli* K5 strain are shown as SEQ ID NOS: 129 to 131, respectively.

The rlmL gene (synonym is rlmKL) encodes a methyltransferase that methylates G2445 and G2069 of 23 S rRNA. The rlmL gene of the *Escherichia coli* K-12 MG1655 strain corresponds to the sequence of the positions 1,007,067 to 1,009,175 in the genome sequence registered at the NCBI database as GenBank accession NC_000913 (VERSION NC_000913.2 GI: 49175990). The RlmL protein of the MG1655 strain is registered as GenBank accession NP_415468 (version NP_415468.1 GI: 16128915).

The nucleotide sequence of a region containing the rlmL gene of the *Escherichia coli* K5 strain is shown as SEQ ID NO: 132. In the nucleotide sequence shown as SEQ ID NO: 132, the rlmL gene corresponds to the sequence of the positions 571 to 2,679. The amino acid sequence of the RlmL protein of the *Escherichia coli* K5 strain is shown as SEQ ID NO: 133.

The artQ, artM, and artJ genes encode subunits of an arginine ABC transporter. The artQ, artM, and artJ genes of the *Escherichia coli* K-12 MG1655 strain correspond to the complementary sequence of the sequence of the positions 900,757 to 901,473, the complementary sequence of the sequence of the positions 900,089 to 900,757, and the complementary sequence of the sequence of the positions 899,067 to 899,798 in the genome sequence registered at the NCBI database as GenBank accession NC_000913 (VERSION NC_000913.2 GI: 49175990), respectively. The ArtQ, ArtM, and ArtJ proteins of the MG1655 strain are registered as GenBank accession NP_415383 (version NP_415383.1 GI: 16128830), GenBank accession NP_415382 (version NP_415382.1 GI: 16128829), and GenBank accession NP_415381 (version NP_415381.1 GI: 16128828), respectively.

The rlmC gene (synonym is rumB) encodes a methyltransferase that methylates U747 of 23 S rRNA. The rlmC gene of the *Escherichia coli* K-12 MG1655 strain corresponds to the sequence of the positions 897,741 to 898,868 in the genome sequence registered at the NCBI database as GenBank accession NC_000913 (VERSION NC_000913.2 GI: 49175990). The RlmC protein of the MG1655 strain is registered as GenBank accession NP_415380 (version NP_415380.1 GI: 16128827).

The ybjO gene encodes a protein presumed to be an inner membrane protein. The ybjO gene of the *Escherichia coli* K-12 MG1655 strain corresponds to the sequence of the positions 897,212 to 897,700 in the genome sequence registered at the NCBI database as GenBank accession NC_000913 (VERSION NC_000913.2 GI: 49175990). The YbjO protein of the MG1655 strain is registered as GenBank accession NP_415379 (version NP_415379.1 GI: 16128826).

The nucleotide sequence of a region containing the artQ, artM, artJ, rlmC, and ybjO genes of the *Escherichia coli* K5 strain is shown as SEQ ID NO: 134. In the nucleotide sequence shown as SEQ ID NO: 134, the artQ, artM, artJ, rlmC, and ybjO genes correspond to the sequence of the positions 386 to 1,102, the sequence of the positions 1,102 to 1,770, the sequence of the positions 2,061 to 2,792, the complementary sequence of the sequence of the positions 2,991 to 4,118, and the complementary sequence of the sequence of the positions 4,159 to 4,647, respectively. The amino acid sequences of the ArtQ, ArtM, ArtJ, RlmC, and YbjO proteins of the *Escherichia coli* K5 strain are shown as SEQ ID NOS: 135 to 139, respectively.

The yejO gene encodes an outer membrane protein. The yejO gene of the *Escherichia coli* K-12 MG1655 strain corresponds to the complementary sequence of the fused sequence consisting of the sequence of the positions 2,284,412 to 2,286,936 and the sequence of the positions 2,288,136 to 2,288,202 in the genome sequence registered at the NCBI database as GenBank accession NC_000913 (VERSION NC_000913.2 GI: 49175990). The yejO gene of the MG1655 strain is considered to be a pseudogene.

The yejM gene is a gene encoding a protein presumed to be one of hydrolases. The yejM gene of the *Escherichia coli* K-12 MG1655 strain corresponds to the sequence of the positions 2,282,398 to 2,284,158 in the genome sequence registered at the NCBI database as GenBank accession NC_000913 (VERSION NC_000913.2 GI: 49175990). The YejM protein of the MG1655 strain is registered as GenBank accession NP_416693 (version NP_416693.1 GI: 16130126).

The yejL gene is a gene of unknown function. The yejL gene of the *Escherichia coli* K-12 MG1655 strain corresponds to the sequence of the positions 2,282,151 to 2,282,378 in the genome sequence registered at the NCBI database as GenBank accession NC_000913 (VERSION NC_000913.2 GI: 49175990). The YejL protein of the MG1655 strain is registered as GenBank accession NP_416692 (version NP_416692.1 GI: 16130125).

The nucleotide sequence of a region containing the yejO, yejM, and yejL genes of the *Escherichia coli* K5 strain is shown as SEQ ID NO: 140. In the nucleotide sequence shown as SEQ ID NO: 140, the yejO, yejM, and yejL genes correspond to the sequence of the positions 216 to 2,807, the complementary sequence of the sequence of the positions 3,061 to 4,821, and the complementary sequence of the sequence of the positions 4,841 to 5,068, respectively. The amino acid sequences of the YejO, YejM, and YejL proteins of the *Escherichia coli* K5 strain are shown as SEQ ID NOS: 141 to 143, respectively.

The rpoS gene encodes SigmaS ($\sigma^s$). The rpoS gene of the *Escherichia coli* K-12 MG1655 strain corresponds to the complementary sequence of the sequence of the positions 2,864,581 to 2,865,573 in the genome sequence registered at the NCBI database as GenBank accession NC_000913 (VERSION NC_000913.2 GI: 49175990). The RpoS protein of the MG1655 strain is registered as GenBank accession NP_417221 (version NP_417221.1 GI: 16130648).

The ygbN gene encodes a protein presumed to be a transporter belonging to the Gnt family. The ygbN gene of the *Escherichia coli* K-12 MG1655 strain corresponds to the sequence of the positions 2,863,123 to 2,864,487 in the genome sequence registered at the NCBI database as GenBank accession NC_000913 (VERSION NC_000913.2 GI: 49175990). The YgbN protein of the MG1655 strain is registered as GenBank accession NP_417220 (version NP_417220.1 GI: 16130647).

The ygbM gene is a gene of unknown function. The ygbM gene of the *Escherichia coli* K-12 MG1655 strain corresponds to the sequence of the positions 2,862,258 to 2,863,034 in the genome sequence registered at the NCBI database as GenBank accession NC_000913 (VERSION NC_000913.2 GI: 49175990). The YgbM protein of the MG1655 strain is registered as GenBank accession NP_417219 (version NP_417219.1 GI: 16130646).

The ygbL gene encodes a protein presumed to be one of aldolases. The ygbL gene of the *Escherichia coli* K-12 MG1655 strain corresponds to the sequence of the positions 2,861,615 to 2,862,253 in the genome sequence registered at the NCBI database as GenBank accession NC_000913 (VERSION NC_000913.2 GI: 49175990). The YgbL protein of the MG1655 strain is registered as GenBank accession NP_417218 (version NP_417218.1 GI: 16130645).

The nucleotide sequence of a region containing the rpoS, ygbN, ygbM, and ygbL genes of the *Escherichia coli* K5 strain is shown as SEQ ID NO: 144. In the nucleotide sequence shown as SEQ ID NO: 144, the rpoS, ygbN, ygbM, and ygbL genes correspond to the sequence of the positions 318 to 1,310, the complementary sequence of the sequence of the positions 1,404 to 2,768, the complementary sequence of the sequence of the positions 2,857 to 3,633, and the complementary sequence of the sequence of the positions 3,638 to 4,276, respectively. The amino acid sequences of the RpoS, YgbN, YgbM, and YgbL proteins of the *Escherichia coli* K5 strain are shown as SEQ ID NOS: 145 to 148, respectively.

The g3798 gene encodes a protein presumed to be an SOS-response transcriptional repressor (RecA-mediated autopeptidase). The g3794 gene encodes a protein presumed to be a superinfection exclusion protein B. The g3793 gene encodes a protein presumed to be a restriction inhibitor protein ral (antirestriction protein). The g3797, g3796, g3795, and g3792 genes are genes of unknown functions. These genes are not annotated in the genome of the *Escherichia coli* K-12 MG1655 strain.

The nucleotide sequence of a region containing the g3798, g3797, g3796, g3795, g3794, g3793, and g3792 genes of the *Escherichia coli* K5 strain is shown as SEQ ID NO: 149. In the nucleotide sequence shown as SEQ ID NO: 149, the g3798, g3797, g3796, g3795, g3794, g3793, and g3792 genes correspond to the sequence of the positions 615 to 1,268, the sequence of the positions 1,368 to 2,219, the sequence of the positions 2,257 to 2,748, the sequence of the positions 3,021 to 3,203, the complementary sequence of the sequence of the positions 3,470 to 4,051, the sequence of the positions 4,280 to 4,480, and the sequence of the positions 4,520 to 4,717, respectively. The amino acid sequences of the G3798, G3797, G3796, G3795, G3794, G3793, and G3792 proteins of the *Escherichia coli* K5 strain are shown as SEQ ID NOS: 150 to 156, respectively.

The ryjA gene encodes a low molecular weight RNA. The ryjA gene of the *Escherichia coli* K-12 MG1655 strain corresponds to the complementary sequence of the sequence of the positions 4,275,950 to 4,276,089 in the genome sequence registered at the NCBI database as GenBank accession NC_000913 (VERSION NC_000913.2 GI: 49175990).

The soxR and soxS genes are genes encoding a transcriptional control factor. The soxR and soxS genes of the *Escherichia coli* K-12 MG1655 strain correspond to the sequence of the positions 4,275,492 to 4,275,956, and the complementary sequence of the sequence of the positions 4,275,083 to 4,275,406 in the genome sequence registered at the NCBI database as GenBank accession NC_000913 (VERSION NC_000913.2 GI: 49175990), respectively. The SoxR and SoxS proteins of the MG1655 strain are registered as GenBank accession NP_418487 (version NP_418487.1 GI:16131889) and GenBank accession NP_418486 (version NP_418486.1 GI: 16131888), respectively.

The yjcC gene encodes a c-di-GMP-specific phosphodiesterase. The yjcC gene of the *Escherichia coli* K-12 MG1655 strain corresponds to the sequence of the positions 4,273,494 to 4,275,080 in the genome sequence registered at the NCBI database as GenBank accession NC_000913 (VERSION NC_000913.2 GI: 49175990). The YjcC protein of the MG1655 strain is registered as GenBank accession NP_418485 (version NP_418485.1 GI: 16131887).

The yjcB gene is a gene of unknown function. The yjcB gene of the *Escherichia coli* K-12 MG1655 strain corresponds to the complementary sequence of the sequence of the positions 4,272,783 to 4,273,064 in the genome sequence registered at the NCBI database as GenBank accession NC_000913 (VERSION NC_000913.2 GI: 49175990). The YjcB protein of the MG1655 strain is registered as GenBank accession NP_418484 (version NP_418484.4 GI: 90111681).

The nucleotide sequence of a region containing the ryjA, soxR, soxS, yjcC, and yjcB genes of the *Escherichia coli* K5 strain is shown as SEQ ID NO: 157. In the nucleotide sequence shown as SEQ ID NO: 157, the ryjA, soxR, soxS, yjcC, and yjcB genes correspond to the sequence of the positions 657 to 796, the complementary sequence of the sequence of the positions 790 to 1,254, the sequence of the positions 1,340 to 1,663, the complementary sequence of the sequence of the positions 1,666 to 3,252, and the sequence of the positions 3,682 to 3,963, respectively. The amino acid sequences of the SoxR, SoxS, YjcC, and YjcB proteins of the *Escherichia coli* K5 strain are shown as SEQ ID NOS: 158 to 161, respectively.

The efeU and efeO genes are genes encoding a component of a divalent iron ion transport carrier. The efeU and efeO genes of the *Escherichia coli* K-12 MG1655 strain correspond to the sequence of the positions 1,080,579 to 1,081,408, and the sequence of the positions 1,081,466 to 1,082,593 in the genome sequence registered at the NCBI database as GenBank accession NC_000913 (VERSION NC_000913.2 GI: 49175990), respectively. The efeU gene of the MG1655 strain is considered to be a pseudogene. The EfeO protein of the MG1655 strain is registered as GenBank accession NP_415537 (version NP_415537.1 GI: 16128982).

The nucleotide sequence of a region containing the efeU and efeO genes of the *Escherichia coli* K5 strain is shown as SEQ ID NO: 162. In the nucleotide sequence shown as SEQ ID NO: 162, the efeU and efeO genes correspond to the sequence of the positions 753 to 1,583, and the sequence of the positions 1,641 to 2,768, respectively. The amino acid sequences of EfeU and EfeO proteins of the *Escherichia coli* K5 strain are shown as SEQ ID NOS: 163 and 164, respectively.

The bacterium of the present invention may have been modified so that, for example, expression of at least the rfaH gene among the genes of Tables 1 to 3 is increased, or expression of at least one or more genes among the genes of Tables 1 to 3 other than the rfaH gene is increased. The bacterium of the present invention may have been also modified so that expression of the rfaH gene and expression of one or more kinds of the genes of Tables 1 to 3 other than the rfaH gene are increased. Specifically, the bacterium of the present invention may have been modified so that, for example, expression of the rfaH gene and expression is increased of one or more genes such as rbsR, rbsK, rbsB, hsrA, glgB, glgX, micF, rcsD, rcsB, ybiX, ybiI, ybiJ, ybiC, ybiB, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, and ycfS. The bacterium of the present invention may have been also modified so that, for example, expression of at least the rpoE gene among the genes of Tables 1 to 3 is increased. The combination of the genes of Tables 1 to 3 of which expression is to be increased is not particularly limited. Examples of the combination include, for example, the combinations described in Examples depicted herein.

The methods for increasing gene expression will be described later. Expression of the gene(s) of Tables 1 to 3 may be increased by, for example, increasing the copy number of a DNA containing the gene(s) of Tables 1 to 3, such as a DNA having the nucleotide sequence shown as SEQ ID NO: 29, 34, 37, 43, 50, 54, 60, 64, 72, 74, 78, 84, 87, 91, 95, 99, 104, 107, 111, 116, 121, 124, 128, 132, 134, 140, 144, 149, 157, or 162. As for the irp gene, the copy number of a DNA containing a part of the irp gene, such as a DNA having the nucleotide sequence shown as SEQ ID NO: 99, may also be increased. Such DNA as mentioned above of which the copy number is to be increased may be a variant of a DNA having the nucleotide sequence shown as SEQ ID NO: 29, 34, 37, 43, 50, 54, 60, 64, 72, 74, 78, 84, 87, 91, 95, 99, 104, 107, 111, 116, 121, 124, 128, 132, 134, 140, 144, 149, 157, or 162. For variants of DNA, the descriptions about conservative variants of the genes mentioned in Tables 1 to 3 can be similarly applied. Namely, for example, the copy number of a DNA showing a homology of 90% or more to the nucleotide sequence shown as SEQ ID NOS: 29, 34, 37, 43, 50, 54, 60, 64, 72, 74, 78, 84, 87, 91, 95, 99, 104, 107, 111, 116, 121, 124, 128, 132, 134, 140, 144, 149, 157, or 162 may be increased.

These genes can be obtained by PCR using a chromosome of a strain having any of these genes as the template, and oligonucleotides produced on the basis of any of these known gene sequences as the primers.

The genes of Tables 1 to 3 each may be a variant of the genes exemplified above, so long as the variant maintains the original function. Similarly, the proteins encoded by the genes of Tables 1 to 3 each may be a variant of the proteins exemplified above, so long as the variant maintains the original function. Such a variant that maintains the original function may be referred to as a "conservative variant". In the present invention, the genes specified with the aforementioned gene names and the proteins specified with names corresponding to the gene names include the genes and proteins exemplified above, respectively, and in addition, conservative variants thereof. Namely, for example, the term "rpoE gene" includes the rpoE genes exemplified above (i.e. rpoE genes of the *Escherichia coli* K-12 MG1655 strain and the *Escherichia coli* K5 strain), and in addition, conservative variants thereof. Similarly, for example, the term "RpoE protein" includes the RpoE proteins exemplified above (i.e. RpoE proteins of the *Escherichia coli* K-12 MG1655 strain and the *Escherichia coli* K5 strain), and in addition, conservative variants thereof. Examples of the conservative variants include, for example, homologues and artificially modified variants of the genes and proteins exemplified above.

The expression "variant maintains the original function" means that the variant of a gene or protein has a function (such as activity or property) corresponding to the function (such as activity or property) of the original gene or protein.

That is, the expression "variant maintains the original function" means that, in the case of the genes of Tables 1 to 3, a variant of any of the genes has a property of increasing heparosan-producing ability of an *Escherichia* bacterium having heparosan-producing ability when expression amount of the variant is increased in the bacterium. Furthermore, the expression "variant maintains the original function" may also mean that, in the case of the genes of Tables 1 to 3, a variant of any of the genes encodes a protein that maintains the original function. That is, the genes of Tables 1 to 3 may encode a conservative variant of the proteins exemplified above.

Similarly, the expression "variant maintains the original function" means that, in the case of the proteins encoded by the genes of Tables 1 to 3, a variant of any of the proteins has a property of increasing heparosan-producing ability of an *Escherichia* bacterium having heparosan-producing ability when expression amount of the variant is increased in the bacterium. Further, the expression "variant maintains the original function" may also mean that, in the case of the proteins encoded by the genes of Tables 1 to 3, a variant of any of the proteins has the above-mentioned function of the corresponding protein, for example, the function of the sigmaE ($\sigma^E$) in the case of the RpoE protein.

Whether a variant of a gene or protein has the property of increasing heparosan-producing ability of an *Escherichia* bacterium having heparosan-producing ability when expression amount thereof is increased in the bacterium can be confirmed by introducing the gene or a gene encoding the protein into the *Escherichia* bacterium having heparosan-producing ability, and confirming whether the heparosan-producing ability is improved or not.

Homologues of the genes of Tables 1 to 3 can be easily obtained from public databases by, for example, BLAST search or FASTA search using any of the nucleotide sequences of the genes exemplified above as a query sequence. Further, homologues of the genes of Tables 1 to 3 can also be obtained by, for example, PCR using a chromosome of a microorganism such as bacterium as the template, and oligonucleotides prepared on the basis of any of these known gene sequences as the primers.

The genes of Tables 1 to 3 each may encode a protein having any of the aforementioned amino acid sequences including substitution, deletion, insertion, or addition of one or several amino acid residues at one or several positions, so long as the protein maintains the original function. For example, the N-terminus and/or C-terminus of the encoded protein may be extended or shortened. Although the number of "one or several" may differ depending on the positions in the three-dimensional structure of the protein or the types of amino acid residues, specifically, it is, for example, 1 to 50, 1 to 40, or 1 to 30, 1 to 20, 1 to 10, 1 to 5, or 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

The genes of Tables 1 to 3 each may be a gene encoding a protein showing a homology of, for example, 80% or more, preferably 90% or more, more preferably 95% or more, still more preferably 97% or more, particularly preferably 99% or more, to the total amino acid sequence of any of the amino acid sequences mentioned above, so long as the protein maintains the original function. In this description, "homology" may mean "identity".

The genes of Tables 1 to 3 each may also be a DNA that is able to hybridize under stringent conditions with a probe that can be prepared from a known gene sequence, for example, a sequence complementary to a partial or entire sequence of any of the aforementioned nucleotide sequences. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., or 0.1×SSC, 0.1% SDS at 60° C., or 0.1×SSC, 0.1% SDS at 68° C.

As described above, the probe used for the aforementioned hybridization may be a part of a sequence that is complementary to a gene. Such a probe can be prepared by PCR using oligonucleotides prepared on the basis of a known gene sequence as the primers and a DNA fragment containing any of the genes of Tables 1 to 3 as the template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, the genes of Tables 1 to 3 each may be a gene in which an arbitrary codon is replaced with an equivalent codon, so long as the original function is maintained. For example, the genes of Tables 1 to 3 each may be modified so that they have optimal codons according to codon usage of the host.

A variant of the genes of Tables 1 to 3 can be obtained by, for example, modifying a coding region of the genes by site-specific mutagenesis so that a specific site of the encoded protein include substitution, deletion, insertion, or addition of amino acid residues. Further, a variant of the genes of Tables 1 to 3 can also be obtained by the conventionally known mutagenesis. Examples of the mutagenesis include such methods as treating a DNA molecule having a nucleotide sequence of any of the genes of Tables 1 to 3 in vitro with hydroxylamine or the like, irradiating X-ray or ultraviolet ray on a microorganism such as a microorganism belonging to Enterobacteriaceae containing any of the genes of Tables 1 to 3, treating such a microorganism with a mutagen such as N-methyl-N'-nitro-N-nitrosoguanidine (NTG), ethyl methanesulfonate (EMS), and methyl methanesulfonate (MMS), performing error prone PCR (Cadwell, R. C., PCR Meth. Appl., 2, 28 (1992)), DNA shuffling (Stemmer, W. P., Nature, 370, 389 (1994)), and StEP-PCR (Zhao, H., Nature Biotechnol., 16, 258 (1998)), and so forth.

<1-3> Method for Increasing Expression of Gene

Hereafter, methods for increasing (rising) expression of a gene will be explained.

The expression of a gene may be increased 1.5 times or more, 2 times or more, or 3 times or more, as compared with that of a non-modified strain. Further, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein. The state that "the expression of a gene is increased" may also be referred to as "the expression of a gene is enhanced".

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the production of an objective substance as a target. Homologous recombination can be performed by, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, or a transduction method using a phage. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC 184, pMW219 (NIPPON GENE), pTrc99A (Pharmacia), pPROK series vectors (Clontech), pKK233-2 (Clontech), pET series vectors (Novagen), pQE series vectors (QIAGEN), and the broad host spectrum vector RSF 1010.

When a gene is introduced, it is sufficient that the gene is expressibly harbored by the bacterium of the present invention. Specifically, it is sufficient that the gene is introduced so that it is expressed under control by a promoter sequence that functions in the bacterium of the present invention. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in the bacterium of the present invention. The terminator may be a terminator derived from the host, or a heterogenous terminator. The terminator may be the native terminator of the gene to be introduced, or a terminator of another gene. Specific examples of the terminator include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the bacterium of the present invention. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The case of "introducing two or more genes" include, for example, introducing respective genes coding for two or more kinds of enzymes, introducing respective genes coding for two or more subunits constituting a single enzyme, and a combination of the foregoing cases.

The gene to be introduced is not particularly limited so long as it codes for a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)).

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that code for the subunits may be enhanced. It is usually preferable to enhance the expression of all of the plurality of genes coding for the subunits. Furthermore, the subunits constituting the complex may be derived from a single kind of organism or two or more kinds of organisms, so long as the complex has a function of the objective protein. That is, for example, genes of the same organism coding for a plurality of subunits may be introduced into a host, or genes of different organisms coding for a plurality of subunits may be introduced into a host.

Further, the expression of a gene can be increased by improving the transcription efficiency of the gene. The transcription efficiency of a gene can be improved by, for example, replacing the promoter of the gene on a chromosome with a stronger promoter. The "stronger promoter" means a promoter providing an improved transcription of a gene compared with an inherently existing wild-type promoter of the gene. Examples of stronger promoters include, for example, the known high expression promoters such as T7 promoter, trp promoter, lac promoter, thr promoter, tac promoter, trc promoter, tet promoter, araBAD promoter, rpoH promoter, PR promoter, and PL promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Furthermore, the expression of a gene can also be increased by improving the translation efficiency of the gene. The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

In the present invention, sites that affect the expression of a gene, such as promoter, SD sequence, and spacer region between RBS and the start codon, may also be collectively referred to as "expression control region". Expression control regions can be identified by using a promoter search vector or gene analysis software such as GENETYX. These expression control regions can be modified by, for example, a method of using a temperature sensitive vector, or the Red driven integration method (WO2005/010175).

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess amount of rare codons, a translational problem may arise. According to recent research, it is suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a synonymous codon more frequently used. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H. A. Eds., Stockton Press (1989); Carter, P., Meth. in Enzymol, 154, 382 (1987)), and the method utilizing phage (Kramer, W. and Frits, H. J., Meth. in Enzymol, 154, 350 (1987); Kunkel, T. A. et al., Meth. in Enzymol, 154, 367 (1987)). Alternatively, a gene fragment in which objective codons are replaced may be totally synthesized. Frequencies of codons in various organisms are disclosed in the "Codon Usage Database" (www.kazusa.or.jp/codon; Nakamura, Y et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in any arbitrary combination.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, the electric pulse method reported for coryneform bacteria (Japanese Patent Laid-open (Kokai) No. 2-207791) can also be used.

An increase in the expression of a gene can be confirmed by confirming an increase in the transcription amount of the gene, or by confirming an increase in the amount of a protein expressed from the gene. An increase in the expression of a gene can also be confirmed by confirming an increase in the activity of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

An increase in the activity of a protein can be confirmed by measuring the activity of the protein. The activity of the protein may increase, for example, 1.5 times or more, 2 times or more, or 3 times or more, as compared with that of a non-modified strain.

The aforementioned methods for increasing the expression of a gene can be used for enhancement of the expression of arbitrary genes such as the genes of Tables 1 to 3 and genes encoding a protein that participates in heparosan production.

<2> Method for Producing Heparosan

The method for producing heparosan of the present invention includes steps, for example, of culturing the bacterium of the present invention in a medium to produce and accumulate heparosan in the medium, and collecting heparosan from the medium.

The medium to be used is not particularly limited, so long as the bacterium of the present invention can proliferate in the medium, and heparosan is produced and accumulated. As the medium, for example, a usual medium used for culture of bacteria can be used. Specific examples of the medium include, for example, the LB medium (Luria-Bertani medium, containing 10.0 g of Bacto tryptone, 5.0 g of Bacto yeast extract, and 5.0 g of NaCl in 1 litter), but are not limited thereto. As the medium, for example, a medium containing carbon source, nitrogen source, phosphorus source, and sulfur source, as well as components selected from other various organic components and inorganic components as required can be used. Types and concentrations of the medium components may be arbitrarily determined by those skilled in the art.

The carbon source is not particularly limited, so long as the bacterium of the present invention can utilize it to generate heparosan. Specific examples of the carbon source include, for example, saccharides such as glucose, fructose, sucrose, lactose, galactose, xylose, arabinose, blackstrap molasses, starch hydrolysates, and hydrolysates of biomass, organic acids such as acetic acid, fumaric acid, citric acid, succinic acid, and malic acid, alcohols such as glycerol, crude glycerol, and ethanol, and aliphatic acids. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid or the like for growth thereof is used, it is preferable to supplement a required nutrient to the medium. Furthermore, when a gene is introduced by using a vector carrying an antibiotic resistance gene, it is preferable to add the corresponding antibiotic to the medium.

Culture conditions are not particularly limited, so long as the bacterium of the present invention can proliferate, and heparosan is produced and accumulated. The culture can be performed with, for example, usual conditions used for culture of bacteria. The culture conditions may be appropriately chosen by those skilled in the art.

The culture can be performed, for example, aerobically as aeration culture or shaking culture by using a liquid medium. The culture temperature may be, for example, 30 to 37° C. The culture period may be, for example, 16 to 72 hours. The culture can be performed as batch culture, fed-batch culture, continuous culture, or a combination of these. The culture may be performed as preculture and main culture. The preculture may be performed by using, for example, a plate medium or liquid medium.

As a result of culture of the bacterium of the present invention as described above, heparosan is accumulated in the medium.

The method for collecting heparosan from the culture broth is not particularly limited, so long as heparosan can be collected. Examples of the method for collecting heparosan from the culture broth include, for example, the method described in Examples. Specifically, for example, culture supernatant can be separated from the culture broth, and then heparosan contained in the supernatant can be precipitated by ethanol precipitation. The volume of ethanol to be added may be, for example, 2.5 to 3.5 times the volume of the supernatant. The solvent used for precipitating heparosan is not limited to ethanol, and organic solvents miscible with water in an arbitrary ratio can be used. Examples of such organic solvents include methanol, n-propanol, isopropanol, n-butanol, t-butanol, sec-butanol, propylene glycol, acetonitrile, acetone, DMF, DMSO, N-methylpyrrolidone, pyridine, 1,2-dimethoxyethane, 1,4-dioxane, and THF, as well as ethanol. Precipitated heparosan can be dissolved with, for example, water in a volume of 2 times the volume of the original supernatant. The collected heparosan may contain such components as bacterial cells, medium components, moisture, and by-product metabolites of the bacterium, in addition to heparosan. Heparosan may be purified in a desired degree. Purity of heparosan may be, for example, 30% (w/w) or higher, 50% (w/w) or higher, 70% (w/w) or higher, 80% (w/w) or higher, 90% (w/w) or higher, or 95% (w/w) or higher.

Detection and quantification of heparosan can be performed by a known method. Specifically, for example, heparosan can be detected and quantified by the carbazole method. The carbazole method is a technique widely used as a quantification method for uronic acid, in which a thermal reaction of heparosan and carbazole can be carried out in the presence of sulfuric acid, and absorption at 530 nm of the reaction mixture provided by the generated color substance can be measured to detect and quantify heparosan (Bitter T. and Muir H. M. (1962) "A modified uronic acid carbazole reaction", Analytical Biochemistry, 4(4):330-334). Heparosan can also be detected and quantified by, for example, treating heparosan with heparinase III, which is a heparosan decomposition enzyme, and performing disaccharide composition analysis.

<3> Method for Producing Heparin

Heparin can be produced by using heparosan produced by the bacterium of the present invention. That is, the method for producing heparin of the present invention is a method for producing heparin comprising culturing the bacterium of the present invention in a medium to produce and accumulate heparosan in the medium, chemically and/or enzymatically treating the heparosan to produce heparin, and collecting the heparin. Heparin has an anticoagulant activity, and can be used as an ingredient in drug formulations.

The method for producing heparin from heparosan has already been reported. Specifically, for example, by subjecting heparosan as a starting material to the steps of (1) N-deacetylation, (2) N-sulfation, (3) C5-epimerization, (4) 2-O-sulfation, (5) 6-O-sulfation, and (6) 3-O-sulfation, heparin having an anticoagulant activity can be produced (Zhang Z. et al. (2008) "Solution Structures of Chemoenzymatically Synthesized Heparin and Its Precursors", J. Am. Chem. Soc., 130(39):12998-13007). The method for producing heparin may further include a depolymerization step. Such steps as mentioned above for producing heparin from heparosan are also collectively referred to as "heparin production process". The implementation order of the steps in the heparin production process is not particularly limited, so long as heparin having desired properties can be obtained.

When heparosan is present in the medium, the medium may be subjected to the heparin production process, or heparosan collected from the medium may be subjected to the heparin production process. Furthermore, heparosan may be subjected to an arbitrary pretreatment, and then may be subjected to the heparin production process. Examples of the pretreatment include, for example, purification, dilution, concentration, drying, dissolution, and so forth. These pretreatments may also be performed in an appropriate combination. For example, a culture broth containing heparosan as it is, or heparosan purified from such a culture broth to a desired extent may be subjected to the heparin production process.

The N-deacetylation can be chemically performed by using, for example, sodium hydroxide. The reaction conditions can be appropriately determined by those skilled in the art. For example, conditions mentioned in the published reference (Kuberan B. et al. (2003) "Chemoenzymatic Synthesis of Classical and Non-classical Anticoagulant Heparan Sulfate Polysaccharides", J. Biol. Chem., 278(52):52613-52621) can be referred to.

The N-sulfation can be chemically performed by using, for example, sulfur trioxide/trimethylamine complex. The reaction conditions can be appropriately determined by those skilled in the art. For example, conditions mentioned in the published reference (Kuberan B. et al. (2003) "Chemoenzymatic Synthesis of Classical and Non-classical Anticoagulant Heparan Sulfate Polysaccharides", J. Biol. Chem., 278(52):52613-52621) can be referred to.

The C5-epimerization can be enzymatically performed by using, for example, C5-epimerase. The C5-epimerase is not particularly limited so long as a C5-epimerase that can catalyze the epimerization of the glucuronic acid (GlcUA) residue into the iduronic acid (IdoA) residue is chosen. Depending on the order of the C5-epimerization, N-deacetylation, and/or 0-sulfation, a C5-epimerase showing suitable substrate specificity can be chosen and used. The C5-epimerase may be derived from any origin such as animal, plant, and microorganism. As the C5-epimerase, for example, human C5-epimerase can be used. The reaction conditions can be appropriately determined by those skilled in the art. For example, conditions mentioned in the published reference (Chen J., et al., "Enzymatic redesigning of biologically active heparan sulfate", J. Biol. Chem., 2005 Dec., 30; 280(52):42817-25) can be referred to.

The 2-O-sulfation can be enzymatically performed by using, for example, a 2-O-sulfation enzyme (2-OST). 2-OST is not particularly limited, so long as the chosen 2-OST can catalyze sulfation of the 0-2 position of the IdoA residue. Depending on the order of the 2-O-sulfation, N-deacetylation, C5-epimerization, 6-O-sulfation, and/or 3-O-sulfation, 2-OST showing suitable substrate specificity can be chosen and used. 2-OST may be derived from any origin such as animal, plant, and microorganism. As 2-OST, for example, hamster 2-OST can be used. The reaction conditions can be appropriately determined by those skilled in the art. For example, conditions mentioned in the published reference (Chen J., et al., "Enzymatic redesigning of biologically active heparan sulfate", J. Biol. Chem., 2005 Dec., 30; 280(52):42817-25) can be referred to.

The 6-O-sulfation can be enzymatically performed by using, for example, a 6-O-sulfation enzyme (6-OST). 6-OST is not particularly limited so long as the chosen 6-OST can catalyze sulfation of the 0-6 position of N-sulfated glucosamine (GlcNS) residue. Depending on the order of the 6-O-sulfation, N-deacetylation, C5-epimerization, 2-O-sulfation, and/or 3-O-sulfation, 6-OST showing suitable substrate specificity can be chosen and used. 6-OST may be derived from any origin such as animal, plant, and microorganism. As 6-OST, for example, hamster 6-OST-1 or mouse 6-OST-3 can be used. The reaction conditions can be appropriately determined by those skilled in the art. For example, conditions mentioned in the published reference (Chen J., et al., "Enzymatic redesigning of biologically active heparan sulfate", J. Biol. Chem., 2005 Dec., 30; 280(52):42817-25) can be referred to.

The 3-O-sulfation can be enzymatically performed by using, for example, a 3-O-sulfation enzyme (3-OST). 3-OST is not particularly limited so long as 3-OST that can catalyze sulfation of the 0-3 position of N-sulfated and 6-O-sulfated glucosamine residue is chosen. Depending on the order of the 3-O-sulfation, N-deacetylation, C5-epimerization, 2-O-sulfation, and/or 6-O-sulfation, 3-OST showing suitable substrate specificity can be chosen and used. 3-OST may be derived from any origin such as animal, plant, and microorganism. As 3-OST, for example, mouse 3-OST-1 can be used. The reaction conditions can be appropriately determined by those skilled in the art. For example, conditions mentioned in the published reference (Chen J., et al., "Enzymatic redesigning of biologically active heparan sulfate", J. Biol. Chem., 2005 Dec., 30; 280(52):42817-25) can be referred to.

The depolymerization can be performed, for example, by using nitrous acid or by the photolysis method. Degree of the depolymerization is not particularly limited. The depolymerization may be performed so that heparin having a molecular weight of, for example, 1000 to 35000 Da is produced.

The produced heparin can be collected by known methods used for separation and purification of compounds. Examples of such methods include, for example, ion-exchange resin method, membrane treatment, precipitation, and crystallization. These methods can be used in an appropriate combination. The collected heparin may contain components such as those used for the heparin production process, and moisture, in addition to heparin. Heparin may be purified in a desired degree. Purity of heparin may be, for example, 30% (w/w) or higher, 50% (w/w) or higher, 70% (w/w) or higher, 80% (w/w) or higher, 90% (w/w) or higher, or 95% (w/w) or higher.

The obtained heparin can be further fractionated to obtain a low molecular weight heparin. Low molecular weight heparin means, for example, a fraction of a molecular weight of 1000 to 10000 Da (average molecular weight, 4000 to 6000 Da). Low molecular weight heparin has an advantage that it shows less adverse reaction of hemorrhage compared with a non-fractionated heparin.

EXAMPLES

Hereafter, the present invention will be more specifically explained with reference to Examples.

Example 1: Construction of Heparosan-producing Strain from *Escherichia coli* BL21(DE3) Strain Construction of expression plasmid for kfiABCD genes of *Escherichia coli* K5 strain From the *Escherichia coli* K5 strain (ATCC 23506), the kfiABCD genes (kfiABCD operon) were cloned into the pVK9 vector (SEQ ID NO: 1, U.S. Published Patent Application No. 20050196846) to construct a kfiABCD gene expression plasmid, pVK9-kfiABCD.

The details of the construction of the expression plasmid are described below. By PCR using the chromosomal DNA of the *Escherichia coli* K5 strain as the template, as well as the primer KfiABCD-kpnF (SEQ ID NO: 2) and primer KfiABCD-xbaR (SEQ ID NO: 3), a DNA fragment containing the kfiABCD genes and an upstream sequence thereof of about 450 bp was obtained. PrimeStar Polymerase (TaKaRa) was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 8 minutes, and final maintenance at 4° C. Further, by PCR using pVK9 as the template DNA and the oligonucleotides of SEQ ID NOS: 4 and 5 as the primers, a DNA fragment of pVK9 was obtained. PrimeStar Polymerase (TaKaRa) was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 6 minutes, and final maintenance at 4° C. Both the obtained DNA fragments were ligated by using In-Fusion (registered trademark) HD Cloning Kit (Clontech) to construct a kfiABCD gene expression plasmid, pVK9-kfiABCD. A nucleotide sequence containing the cloned kfiABCD genes and the upstream sequence thereof of about 450 bp is shown as SEQ ID NO: 24.

Construction of kfiABCD gene-expressing strain of *Escherichia coli* BL21(DE3)

The kfiABCD gene expression plasmid, pVK9-kfiABCD, was introduced into the *Escherichia coli* BL21(DE3) strain (Life Technologies) by electroporation (cell 80 μL, 200 Ω, 25 μF, 1.8 kV, cuvette 0.1 mL) to obtain *Escherichia coli* BL21(DE3)/pVK9-kfiABCD strain. This strain was spread on the LB agar medium containing 25 μg/mL kanamycin, and precultured overnight at 37° C. Then, the cells on the plate were scraped and inoculated into 2 mL of a production medium contained in a test tube. Shaking culture was performed at 37° C. for 40 hours, and the culture was finished when glycerol contained in the medium was completely consumed.

The composition of the production medium is shown below.

Production medium: (concentrations of components are final concentrations)
Component 1:

| Glycerol | 10 g/L |
|---|---|

Component 2:

| MOPS (3-N-morpholino-propanesulphonic acid) | 41.9 g/L |
|---|---|

Components 3:

| Tryptone | 8.8 g/L |
|---|---|
| Yeast extract | 4.4 g/L |
| Sodium chloride | 8.8 g/L |

Components 1 and 3 were separately sterilized by autoclaving at 120° C. for 20 minutes, and component 2 was sterilized by filter sterilization. After cooling to room temperature, three of the components were mixed.

Quantification of Polysaccharides by Carbazole Method

The produced polysaccharides were quantified by the carbazole method (Bitter, T. and Murir H. M., Anal. Biochem., 1962, 4:330-334). The procedures are shown below.

The culture supernatant was collected from the culture broth (fermentation broth) by centrifugation. To 150 μL of the culture supernatant, 500 μL of 100% ethanol was added, and the polysaccharide components were precipitated by centrifugation. The obtained precipitates were air-dried, and dissolved in 300 μL of 0.2 N aqueous sodium hydroxide solution. The obtained sample (solution, 30 μL) was calmly added to 150 μL of sulfuric acid containing 0.025 M tetraboronic acid, and the resulting mixture was heated at 100° C. for 10 minutes. After the mixture was cooled to room temperature, 30 μL of a 0.025% carbazole solution (obtained by dissolving 0.125 g of carbazole in 100 mL of 100% ethanol) was added. The resulting mixture was heated at 100° C. for 15 minutes, and then cooled to room temperature, and absorbance was measured at 530 nm. As a result of quantification performed by using a standard curve prepared with D-glucuronic acid, the concentration of the polysaccharides contained in the sample (solution) was calculated to be 140.5 mg/L in terms of glucuronic acid concentration.

Example 2: Structural Analysis of Produced Polysaccharides (2-1) Nuclear Magnetic Resonance (NMR) Spectrum Analysis The fermentation broth obtained in Example 1 was subjected to bactofugation, and the supernatant was filtered through a 0.45 m MF membrane. The obtained filtrate (31 g) was concentrated to 1.1 g by using a UF membrane of 100 KDa (Amicon-15K, 5000 rpm). The concentrate was further washed twice with 40 mL of water. The washed concentrate was further concentrated under reduced pressure in an evaporator, 600 μL of heavy water was added to the residue to prepare a solution, and then $^1$H-NMR measurement was performed.

The analysis conditions are shown below.
(A) Apparatus: AVANCE400 produced by Bruker; 1H, 400 MHz
(B) Solvent: Heavy water
(C) Temperature: Room temperature
(D) Number of times of measurement: 16 times As a result, there was observed a spectrum of $^1$H-NMR ($D_2O$) including peaks of σ: 1.9 (methyl proton of N-acetyl group), 3.3-4.5 (methylene and methine protons of C2 to C6), and 5.3 (methine proton of C1). This spectrum was the same as the $^1$H-NMR spectrum of heparosan produced by Iduron (lot number, B.N.4).

(2-2) Disaccharide Composition Analysis by Liquid Chromatography-Mass Spectrometry (LC-MS)

The fermentation broth obtained in Example 1 was subjected to bactofugation, and the supernatant was filtered through a 0.45 m MF membrane. The obtained filtrate (40 mL) was concentrated to 4 mL by using a UF membrane of 100 KDa (Amicon-15K, 5000 rpm). The concentrate was further washed twice with 40 mL of water. To 50 μL of the washed concentrate, 10 μL of Tris-buffer (200 mM Tris-HCl, 1 M NaCl, 15 mM $CaCl_2$, adjusted to pH 7 (25° C.) with 35% hydrochloric acid), 10 μL of heparinase III (0.005 unit/mL, produced by Iduron), and 30 μL of water were added, and enzyme treatment was performed at 37° C. for 16 hours. To the obtained enzyme-treated mixture, 900 μL of water was added, and used for LC-MS analysis.

The analysis conditions are shown below:
(A) Apparatus: LC-MS 2010 produced by Shimadzu
(B) Column: UG80 (SCX, Shiseido), 2.0 mm×250 mm, particle size 5 μm
(C) Mobile phase: $CH_3CN$/10 mM formic acid=8/2
(D) Flow rate: 0.2 mL/minute
(E) Column temperature: 40° C.
(F) Injection volume: 10 μL
(G) UV (PDA): 200 to 600 nm
(H) MS (ESI): 100 to 2000 (positive and negative)

As a result, fragment ions of [m/z]=362 (M+H—$H_2O$), 380 (M+H), and 418 (M+K) were detected at a retention time of 6 minutes. The retention time and fragment pattern of the enzyme-treated mixture agreed with the retention time and fragment pattern of a ΔGlcUA-GlcNAc standard sample (Heparin disaccharide IV-A sodium salt, Sigma-Aldrich), which is a heparinase decomposition product of heparin and heparan sulfate. The structural formula of the ΔGlcUA-GlcNAc standard sample is shown below as the formula (I).

Formula 1

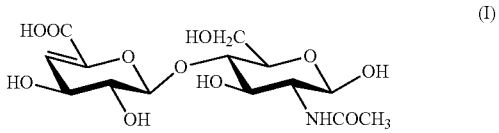

On the basis of the aforementioned results of NMR and LC-MS, it was identified that the polymer component obtained from the culture broth of the BL21(DE3)/pVK9-kfiABCD strain was objective heparosan. Therefore, the glucuronic acid concentration multiplied by a coefficient 2.067 was used as heparosan concentration measured by the carbazole method.

(2-3) Gel Filtration Chromatography (GPC) Analysis

The fermentation broth obtained in Example 1 was subjected to bactofugation, and the supernatant was filtered through a 0.45 μm MF membrane. The obtained filtrate (31 g) was concentrated to 1.1 g by using a UF membrane of 100 KDa (Amicon-15K, 5000 rpm). The concentrate was further washed twice with 40 mL of water. GPC measurement of the washed concentrate was performed.

Analysis conditions are shown below.
(A) Apparatus: HPLC produced by Shimadzu
(B) Column: Asahipak GS520HQ, 7.5 mm×300 mm
(C) Mobile phase: 100 mM $KH_2PO_4$
(D) Flow rate: 0.6 mL/minute
(E) Column temperature: 40° C.
(F) Injection volume: 20 μL
(G) UV: 200 nm
(H) Molecular weight standard sample: Pullulan (P-82, Showa Denko)

As a result, it was confirmed that retention time (peak top) was 8.3 minutes, number average molecular weight (Mn) was 240,000, weight average molecular weight (Mw) was 320,000, and Mw/Mn was 1.3.

Example 3: Screening for Factors that Improve Heparosan-producing Ability

In this example, screening was performed for factors that improve heparosan-producing ability by introducing a genomic library of the *Escherichia coli* K5 strain into a heparosan-producing strain.

(3-1) Construction of *Escherichia coli* BL21 (DE3)-Ptac-rfaH/pVK9-kfiABCD Strain As a heparosan-producing strain to be introduced with the genomic library, *Escherichia coli* BL21 (DE3)-Ptac-rfaH/pVK9-kfiABCD strain introduced with the kfiABCD gene and showing enhanced expression of the rfaH gene was constructed in accordance with the following procedures.

A rfaH gene expression-enhanced strain was obtained by replacing the native promoter region of the rfaH gene on the chromosome with a potent tac promoter (Amann E. et al. (1983) "Vectors bearing a hybrid trp-lac promoter useful for regulated expression of cloned genes in *Escherichia coli*", Gene, 25(2-3): 167-78). The rfaH promoter was replaced with the tac promoter by using the method called "Red-driven integration", which was originally developed by Datsenko and Wanner ("One-step inactivation of chromosomal genes in *Escherichia coli* K-12 using PCR products", Proc. Natl. Acad. Sci. USA, 2000, 97(12), 6640-6645). According to this technique, a strain in which a DNA fragment amplified by PCR is inserted into the genomic DNA can be obtained.

First, by PCR using the genomic DNA of the *Pantoea ananatis* NA1Δc1129 strain (WO2010/027022A1) as the template, as well as the primer rfaH-attL Fw (SEQ ID NO: 6) and primer rfaH-Ptac Rv (SEQ ID NO: 7), a DNA fragment for promoter substitution was amplified. PrimeStar Polymerase was used for PCR, and the PCR cycles consisted of 94° C. for 5 minutes, following 30 cycles of 98° C. for 5 seconds, 55° C. for 10 seconds, and 72° C. for 3 minutes, and final maintenance at 4° C. The primer rfaH-attL Fw (SEQ ID NO: 6) shows homology to both a region locating upstream from the rfaH gene, and a region adjacent to the gene that imparts kanamycin (km) resistance existing in the genomic DNA of the NA1Δc1129 strain. The Km resistance gene kan existing in the genomic DNA of the NA1Δc1129 strain is inserted between the attL and attR genes, which are the attachment sites of λ phage, and the tac promoter (Ptac, SEQ ID NO: 8) is inserted further downstream therefrom in the order of attL-kan-attR-Ptac. The primer rfaH-Ptac Rv (SEQ ID NO: 7) shows homology to both the rfaH region and a region locating downstream from the tac promoter in the genomic DNA of the NA1Δc1129 strain.

Then, into *Escherichia coli* BL21(DE3)/pKD46 strain obtained by introducing the plasmid pKD46 having a temperature sensitive replication origin (Datsenko and Wanner, Proc. Natl. Acad. Sci. USA, 2000, 97:12:6640-45) into *Escherichia coli* BL21(DE3) strain (C6000-03, Life Technologies), the PCR product obtained above was introduced by electroporation to attain substitution of the promoter region. The plasmid pKD46 contains the genes of the λ Red homologous recombination system (γ, β, and exo genes), i.e. a 2,154 nucleotide DNA fragment of phage λ (GenBank/EMBL Accession No. J02459, nucleotide positions 31088 to 33241), under the control of the arabinose-inducible $P_{araB}$ promoter. The plasmid pKD46 is necessary for integration of the PCR product into the chromosome of the BL21(DE3) strain. The *Escherichia coli* BL21(DE3)/pKD46 strain was grown overnight at 30° C. in the LB medium containing ampicillin (100 mg/L). This culture was diluted 100 times with the LB medium (100 mL) containing ampicillin and L-arabinose (1 mM). The cells were grown at 30° C. with aeration until OD600 became about 0.3, then concentrated 100 times, washed 3 times with ice-cooled aqueous glycerol solution (10%), and thereby made into electrocompetent cells. Electroporation was performed by using 70 μl of the competent cells and about 100 ng of the PCR product. After the electroporation, the cells were incubated in 1 mL of the SOC medium (Molecular Cloning A Laboratory Manual, 2nd edition, Sambrook, J. et al., Cold Spring Harbor Laboratory Press (1989)) at 37° C. for 2.5 hours, applied to the LB agar medium, and grown at 37° C. to select Km resistant strains.

The substitution of the tac promoter for the rfaH promoter was confirmed by PCR using the primer rfaH CF (SEQ ID NO: 9) and primer rfaH CR (SEQ ID NO: 10), which are specific to the nucleotide sequence after the promoter substitution. PrimeStar Polymerase was used for PCR. The PCR cycles consisted of 94° C. for 5 minutes, following 30 cycles of 98° C. for 5 seconds, 55° C. for 10 seconds, and 72° C. for 2 minutes, and final maintenance at 4° C. A strain in which amplification of a DNA fragment of 1.6 kbp could be confirmed was designated as BL21(DE3)-Ptac-rfaH(KmR) strain.

In order to remove the Km resistance marker from the BL21(DE3)-Ptac-rfaH(KmR) strain, plasmid pMW118-int-xis (ampicillin resistant (AmpR)) was introduced (WO2005/010175) to the strain. AmpR clones were grown at 30° C. on an LB agar plate containing 150 mg/L of ampicillin. Several tens of AmpR clones were picked up, and a Km-sensitive strain was selected. By incubating the Km sensitive strain at 42° C. on an LB agar plate, the plasmid pMW118-int-xis was removed from the Km-sensitive strain. An obtained Amp sensitive strain was designated as BL21(DE3)-Ptac-rfaH strain. The plasmid pVK9-kfiABCD produced in Example 1 was introduced into the BL21(DE3)-Ptac-rfaH strain by electroporation to obtain BL21(DE3)-Ptac-rfaH/pVK9-kfiABCD strain. Culture was performed in test tubes by using the same medium and culture method as those of Example 1, and heparosan production amount was determined by the carbazole method. The heparosan production amounts of the BL21(DE3)/pVK9-kfiABCD strain of which expression of the rfaH gene was not enhanced, and the BL21(DE3)-Ptac-rfaH/pVK9-kfiABCD strain of which expression of the rfaH gene was enhanced are shown in Table 4.

TABLE 4

| Heparosan production amount of BL21(DE3)-Ptac-rfaH/pVK9-kfiABCD strain | |
|---|---|
| Strain | Heparosan (mg/L) |
| BL21(DE3)/pVK9-kfiABCD | 290.4 ± 32.7 |
| BL21(DE3)-Ptac-rfaH/pVK9-kfiABCD | 506.2 ± 69.9 |

(3-2) Construction of Genomic Library of *Escherichia coli* K5 Strain

Fragments of the genomic DNA of the *Escherichia coli* K5 strain were cloned into the pSTV28 vector (SEQ ID NO: 11, TaKaRa) to constructed genomic library.

The details of the construction of the genomic library are shown below. The genomic DNA of the *Escherichia coli* K5 strain (3 μg) was randomly fragmented by using a DNA fragmentation apparatus (Hydro-Shear, Gene Machine), and fractionated by agarose electrophoresis. A portion containing DNAs of about 3 to 5 kb was cut out from the agarose gel, and DNAs were extracted, purified, and then blunt-ended. Then, the genomic DNA fragments were ligated with 50 ng of the plasmid vector pSTV28 (TaKaRa) digested with HincII and dephosphorylated with Alkaline Phosphatase (*E. coli* C75) (TaKaRa). The *Escherichia coli* HST08 strain (TaKaRa) was transformed with the ligation product by electroporation. Seventy percent or more of the obtained transformants contained inserts of about 3 to 5 kb. The transformants were cultured, and the plasmids were extracted to obtain a genomic library.

(3-3) Selection of Strains Showing Heparosan-Producing Ability Improved by Introduction of Genomic Library The genomic library or pSTV28 as a control was introduced into the BL21(DE3)-Ptac-rfaH/pVK9-kfiABCD strain by electroporation. One clone was selected from each of the obtained genomic library transformants, and used to perform fermentative production culture. Media of the following compositions were used for the culture.

Seed medium: (concentrations of components are final concentrations)

| | |
|---|---|
| Tryptone | 10 g/L |
| Yeast extract | 5 g/L |
| Sodium chloride | 10 g/L |

The seed medium was sterilized by autoclaving at 120° C. for 20 minutes.

Production medium: (concentrations of components are final concentrations)

Component 1:

| | |
|---|---|
| Glycerol | 10 g/L |

Component 2:

| | |
|---|---|
| MOPS (3-N-morpholino-propanesulphonic acid) | 41.9 g/L |

Components 3:

| | |
|---|---|
| Tryptone | 8.8 g/L |
| Yeast extract | 4.4 g/L |
| Sodium chloride | 8.8 g/L |

The components 1 and 3 were separately sterilized by autoclaving at 120° C. for 20 minutes, and the component 2 was sterilized by filter sterilization. After cooling to room temperature, three of the components were mixed.

The heparosan production culture was performed according to the following procedures. First, one colony of each transformant was inoculated into each well of a 96-well plate (MEDISCAN), which contained 750 μL of the seed medium, and shaking culture was performed overnight at 37° C. on a shaking machine (Tietech). Then, 20 μL of the seed culture broth was inoculated into 2 mL of the production medium contained in a test tube, shaking culture was performed at 37° C. for 30 hours, and the culture was terminated when the glycerol in the medium was completely consumed. In order to make the cells harbor the plasmids, kanamycin (25 mg/L) and chloramphenicol (25 mg/L) were added to the medium over the whole culture period. Heparosan produced in the medium was quantified by the carbazole method (Bitter, T. and Murir H. M., Anal. Biochem., 1962, 4:330-334). There were isolated clones that showed increased heparosan accumulation amounts as compared with the simultaneously cultured control vector (pSTV28)-introduced strain. In order to identify the genes inserted into the plasmids contained in the isolated clones, the nucleotide sequences of the inserted DNA fragments were determined by using the primer pSTV Fw (SEQ ID NO: 12) and primer pSTV Rv (SEQ ID NO: 13). As a result, it was revealed that the respective plasmids contained rbsBKR-hsrA, glgBX, ybiXIJCB, rcsBD-micF, pcoESR, yhcNO-aaeBAX, g1455-alpA-g1453, yrbA-mlaBCDEF-yrbG, norW, ybjIJK-rybB, thrBAL-yjtD-yjjY, fruA-psuK, ytfT-yjfF-fbp, yagU-paoAB, gsiCD-yliE, irp (part), bhsA-ycfS, lepB-rnc-era, dapA-gcvR-bcp-hyfA, rpoE-nadB-yfiC-srmB, g1414-g1413, nuoEFG, glmZ-hemYXD, rlmL, artQMJ-rlmC-ybjO, yejOML, rpoS-ygbNML, g3798-g3797-g3796-g3795-g3794-g3793-g3792, ryjA-soxRS-yjcCB, and efeUO. The irp (part) means a part of the irp2 gene and a part of the irp1 gene. The nucleotide sequences of the inserted fragments containing rbsBKR-hsrA, glgBX, ybiXIJCB, rcsBD-micF, pcoESR, yhcNO-aaeBAX, g1455-alpA-g1453, yrbA-mlaB-CDEF-yrbG, norW, ybjIJK-rybB, thrBAL-yjtD-yjjY, fruA-psuK, ytfT-yifF-fbp, yagU-paoAB, gsiCD-yliE, irp (part), bhsA-ycfS, lepB-rnc-era, dapA-gcvR-bcp-hyfA, rpoE-nadB-yfiC-srmB, g1414-g1413, nuoEFG, glmZ-hemYXD, rlmL, artQMJ-rlmC-ybjO, yejOML, rpoS-ygbNML, g3798-g3797-g3796-g3795-g3794-g3793-g3792, ryjA-soxRS-yjcCB, and efeUO are shown as SEQ ID NOS: 29, 34, 37, 43, 50, 54, 60, 64, 72, 74, 78, 84, 87, 91, 95, 99, 104, 107, 111, 116, 121, 124, 128, 132, 134, 140, 144, 149, 157, and 162, respectively. From the respective isolated clones, plasmids pSTV28-rbsBKR-hsrA, pSTV28-glgBX, pSTV28-ybiXIJCB, pSTV28-rcsBD-micF, pSTV28-pcoESR, pSTV28-yhcNO-aaeBAX, pSTV28-g1455-alpA-g1453, pSTV28-yrbA-mlaBCDEF-yrbG, pSTV28-norW, pSTV28-ybjIJK-rybB, pSTV28-thrBAL-yjtD-yjjY, pSTV28-fruA-psuK, pSTV28-ytfT-yjfF-fbp, pSTV28-yagU-paoAB, pSTV28-gsiCD-yliE, pSTV28-irp, pSTV28-bhsA-ycfS, pSTV28-lepB-rnc-era, pSTV28-dapA-gcvR-bcp-hyfA, pSTV28-rpoE-nadB-yfiC-srmB, pSTV28-g1414-g1413, pSTV28-nuoEFG, pSTV28-glmZ-hemYXD, pSTV28-rlmL, pSTV28-artQMJ-rlmC-ybjO, pSTV28-yejOML, pSTV28-rpoS-ygbNML, pSTV28-g3798-g3797-g3796-g3795-g3794-g3793-g3792, pSTV28-ryjA-soxRS-yjcCB, and pSTV28-efeUO were extracted.

Example 4: Heparosan Production Using rbsBKR-hsrA, glgBX, ybiXIJCB, and rcsBD-micF Gene Expression-enhanced Strains (1)

There were constructed respective strains from the *Escherichia coli* BL21(DE3)-Ptac-rfaH/pVK9-kfiABCD strain constructed in Example 1 by introducing thereto pSTV28-rbsBKR-hsrA, pSTV28-glgBX, pSTV28-ybiXIJCB, and pSTV28-rcsBD-micF isolated in Example 3, and pSTV28 as a control. Fermentative production culture was performed with these strains, and amounts of the produced heparosan were compared. The strains were cultured in test tubes in quadruplicate by using the same medium and culture method as those shown in Example 1, and heparosan was quantified by the carbazole method. Averages and standard deviations of the measured heparosan concentrations are shown in Table 5.

TABLE 5

Effect of enhancement of rbsBKR-hsrA, glgBX, ybiXIJCB, or micF-rcsDB gene expression in BL21(DE3)-Ptac-rfaH/pVK9-kfiABCD strain

| Strain | Heparosan (mg/L) |
|---|---|
| BL21(DE3)-Ptac-rfaH/pVK9-kfiABCD/pSTV28 | 529.6 ± 46.3 |
| BL21(DE3)-Ptac-rfaH/pVK9-kfiABCD/pSTV28-rbsBKR-hsrA | 766.4 ± 156.7 |
| BL21(DE3)-Ptac-rfaH/pVK9-kfiABCD/pSTV28-glgBX | 679.8 ± 9.7 |
| BL21(DE3)-Ptac-rfaH/pVK9-kfiABCD/pSTV28-ybiXIJCB | 753.4 ± 129.2 |
| BL21(DE3)-Ptac-rfaH/pVK9-kfiABCD/pSTV28-micF-rcsDB | 656.7 ± 57.7 |

Example 5: Heparosan Production Using rbsBKR-hsrA, glgBX, ybiXIJCB, and rcsBD-micF Gene Expression-enhanced Strains (2)

There were constructed respective strains from the *Escherichia coli* BL21(DE3)/pVK9-kfiABCD strain constructed in Example 1 by introducing thereto pSTV28-rbsBKR-hsrA, pSTV28-glgBX, pSTV28-ybiXIJCB, and pSTV28-rcsBD-micF isolated in Example 3, and pSTV28 as a control. Fermentative production culture was performed with these strains, and amounts of the produced heparosan were compared. The strains were cultured in test tubes in quadruplicate by using the same medium and culture method as those shown in Example 1, and heparosan was quantified by the carbazole method. Averages and standard deviations of the measured heparosan concentrations are shown in Table 6.

TABLE 6

Effect of enhancement of rbsBKR-hsrA, glgBX, ybiXIJCB, or micF-rcsDB gene expression in BL21(DE3)/pVK9-kfiABCD strain

| Strain | Heparosan (mg/L) |
| --- | --- |
| BL21(DE3)/pVK9-kfiABCD/pSTV28 | 145.3 ± 14.3 |
| BL21(DE3)/pVK9-kfiABCD/pSTV28-rbsBKR-hsrA | 286.9 ± 53.3 |
| BL21(DE3)/pVK9-kfiABCD/pSTV28-glgBX | 238.7 ± 44.2 |
| BL21(DE3)/pVK9-kfiABCD/pSTV28-ybiXIJCB | 238.1 ± 55.4 |
| BL21(DE3)/pVK9-kfiABCD/pSTV28-micF-rcsDB | 167.0 ± 7.0 |

Example 6: Heparosan Production Using rfaH Gene Expression-enhanced Strain (6-1) Construction of Expression Plasmid for rfaH Gene of *Escherichia coli* B Strain The rfaH gene was cloned from the *Escherichia coli* BL21(DE3) strain into pMIV-Pnlp0-ter to construct a rfaH gene expression plasmid, pMIV-Pnlp0-rfaH. pMIV-Pnlp0-ter contains the potent nlp0 promoter (Pnlp0) and the rrnB terminator, and the promoter and the terminator can function as an expression unit of a target gene when the target gene is inserted therebetween. "Pnlp0" means the wild-type promoter of the nlpD gene of the *Escherichia coli* K-12 strain.

The details of the construction of the expression plasmid are shown below. By PCR using the chromosomal DNA of *Escherichia coli* MG1655 as the template, as well as the primer P1 (SEQ ID NO: 14) and primer P2 (SEQ ID NO: 15), there was obtained a DNA fragment containing the promoter region of the nlpD gene of about 300 bp (wild-type nlpD gene promoter is henceforth referred to as "Pnlp0"). The sites for the restriction enzymes SalI and PaeI were designed in the 5' end regions of the respective primers. The PCR cycles consisted of 95° C. for 3 minutes, following 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and PaeI, and inserted into pMIV-5JS (Japanese Patent Laid-open (Kokai) No. 2008-99668) at the SalI-PaeI site to obtain plasmid pMIV-Pnlp0. The nucleotide sequence of the PaeI-SalI fragment of the Pnlp0 promoter inserted into this pMIV-Pnlp0 plasmid is as shown as SEQ ID NO: 16.

Then, by PCR using the chromosomal DNA of MG1655 as the template, as well as the primer P3 (SEQ ID NO: 17) and primer P4 (SEQ ID NO: 18), a DNA fragment (SEQ ID NO: 19) containing about 300 bp of the terminator region of the rrnB gene was obtained. The sites for the restriction enzymes XbaI and BamHI were designed in the 5' end regions of the respective primers. The PCR cycles consisted of 95° C. for 3 minutes, following 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and 72° C. for 5 minutes as the final cycle. The obtained fragment was treated with XbaI and BamHI, and inserted into pMIV-Pnlp0 at the XbaI-BamHI site to obtain plasmid pMIV-Pnlp0-ter.

Then, by PCR using the chromosomal DNA of the *Escherichia coli* BL21(DE3) strain as the template, as well as the primer rfaH Fw (SEQ ID NO: 20) and primer rfaH Rv (SEQ ID NO: 21), a rfaH gene fragment was obtained. The sites for the restriction enzymes SalI and XbaI were designed in the 5' end regions of the respective primers. PrimeStar Polymerase was used for PCR, and the PCR cycles consisted of 94° C. for 5 minutes, following 30 cycles of 98° C. for 5 seconds, 55° C. for 10 seconds, and 72° C. for 4 minutes, and final maintenance at 4° C. The obtained fragment was treated with SalI and XbaI, and inserted into pMIV-Pnlp0-ter at the SalI-XbaI site to obtain plasmid pMIV-Pnlp0-rfaH. As described above, there was constructed an rfaH expression unit comprising the nlpD promoter, rfaH gene, and rrnB terminator connected in this order in the pMIV-5JS vector. The nucleotide sequence of the rfaH gene of the *Escherichia coli* BL21(DE3) strain cloned in this experiment is shown as SEQ ID NO: 46.

(6-2) Heparosan Production Using rfaH Gene Expression-enhanced Strain

There were constructed respective strains from the *Escherichia coli* BL21(DE3)/pVK9-kfiABCD strain constructed in Example 1 by introducing thereto pMIV-Pnlp0-rfaH and pMIV-5JS as a control. Fermentative production culture was performed with these strains, and amounts of the produced heparosan were compared. The medium, culture method, and quantification method for heparosan were the same as those described above. Averages and standard deviations of the measured heparosan concentrations are shown in Table 7.

TABLE 7

Effect of enhancement of rfaH gene expression in BL21(DE3)/pVK9-kfiABCD strain

| Strain | Heparosan (mg/L) |
| --- | --- |
| BL21(DE3)/pVK9-kfiABCD/pMIV-5JS | 376.9 ± 48.3 |
| BL21(DE3)/pVK9-kfiABCD/pMIV-Pnlp0-rfaH | 857.9 ± 219.1 |

Example 7: Heparosan Production Using nusG Gene Expression-enhanced Strain (7-1) Construction of Expression Plasmid for nusG Gene of *Escherichia coli* B Strain By PCR using the chromosomal DNA of the *Escherichia coli* BL21(DE3) strain as the template, as well as the primer nusG Fw (SEQ ID NO: 22) and primer nusG Rv (SEQ ID NO: 23), a nusG gene fragment was obtained. The sites for the restriction enzymes SalI and XbaI were designed in the 5' end regions of the respective primers. PrimeStar Polymerase was used for PCR, and the PCR cycles consisted of 94° C. for 5 minutes, following 30 cycles of 98° C. for 5 seconds, 55° C. for 10 seconds, and 72° C. for 4 minutes, and final maintenance at 4° C. The obtained fragment was treated with SalI and XbaI, and inserted into pMIV-Pnlp0-ter treated with the same restriction enzymes at the SalI-XbaI site to obtain plasmid pMIV-Pnlp0-nusG, in which the nusG gene was cloned. The nucleotide sequence of the nusG gene of the *Escherichia coli* BL21(DE3) strain cloned in this experiment is shown as SEQ ID NO: 48.

(7-2) Heparosan Production Using nusG Gene Expression-Enhanced Strain

There were constructed respective strains from the *Escherichia coli* BL21(DE3)/pVK9-kfiABCD strain constructed in Example 1 by introducing thereto pMIV-Pnlp0-nusG and pMIV-5JS as a control. Fermentative production culture was performed with these strains, and amounts of the produced heparosan were compared. The medium, culture method, and quantification method for heparosan were the same as those described above. Averages and standard deviations of the measured heparosan concentrations are shown in Table 8.

TABLE 8

Effect of enhancement of nusG gene expression in BL21(DE3)/pVK9-kfiABCD strain

| Strain | Heparosan (mg/L) |
|---|---|
| BL21(DE3)/pVK9-kfiABCD/pMTV-5JS | 376.9 ± 48.3 |
| BL21(DE3)/pVK9-kfiABCD/pMTV-Pnlp0-nusG | 618.1 ± 14.6 |

Example 8: Heparosan Production Using pcoESR, yhcNO-aaeBAX, g1455-alpA-g1453, yrbA-mlaB-CDEF-yrbG, norW, ybjIJK-rybB, thrBAL-yjtD-yjjY, fruA-psuK, ytfT-yjfF-fbp, yagU-paoAB, gsiCD-yliE, Irp (Part), and bhsA-ycfS Gene Expression-Enhanced Strains (1)

There were constructed respective strains from the *Escherichia coli* BL21(DE3)-Ptac-rfaH/pVK9-kfiABCD strain constructed in Example 1 by introducing thereto pSTV28-pcoESR, pSTV28-yhcNO-aaeBAX, pSTV28-g1455-alpA-g1453, pSTV28-yrbA-mlaBCDEF-yrbG, pSTV28-norW, pSTV28-ybjIJK-rybB, pSTV28-thrBAL-yjtD-yjjY, pSTV28-fruA-psuK, pSTV28-ytfT-yjfF-fbp, pSTV28-yagU-paoAB, pSTV28-gsiCD-yliE, pSTV28-irp, and pSTV28-bhsA-ycfS isolated in Example 3, and pSTV28 as a control. Fermentative production culture was performed with these strains, and amounts of the produced heparosan were compared. The strains were cultured in test tubes in quadruplicate by using the same medium and culture method as those shown in Example 1, and heparosan was quantified by the carbazole method. Averages and standard deviations of the measured heparosan concentrations are shown in Table 9.

TABLE 9

Effect of enhancement of pcoESR, yhcNO-aaeBAX, g1455-alpA-g1453, yrbA-mlaBCDEF-yrbG, norW, ybjIJK-rybB, thrBAL-yjtD-yjjY, fruA-psuK, ytfT-yjfF-fbp, yagU-paoAB, gsiCD-yliE, irp (part), or bhsA-ycfS gene expression in BL21(DE3)-Ptac-rfaH/pVK9-kfiABCD strain

| Strain | Heparosan (mg/L) |
|---|---|
| BL21(DE3)-Ptac-rfaH/pVK9-kfiABCD/pSTV28 | 559.8 ± 72.6 |
| BL21(DE3)-Ptac-rfaH/pVK9-kfiABCD/pSTV28-pcoESR | 692.0 ± 95.1 |
| BL21(DE3)-Ptac-rfaH/pVK9-kfiABCD/pSTV28-yhcNO-aaeBAX | 663.3 ± 136.1 |
| BL21(DE3)-Ptac-rfaH/pVK9-kfiABCD/pSTV28-g1455-alpA-g1453 | 843.1 ± 81.5 |
| BL21(DE3)-Ptac-rfaH/pVK9-kfiABCD/pSTV28-yrbA-mlaBCDEF-yrbG | 877.8 ± 137.8 |
| BL21(DE3)-Ptac-rfaH/pVK9-kfiABCD/pSTV28-norW | 741.0 ± 21.1 |
| BL21(DE3)-Ptac-rfaH/pVK9-kfiABCD/pSTV28-ybjIJK-rybB | 796.0 ± 235.8 |
| BL21(DE3)-Ptac-rfaH/pVK9-kfiABCD/pSTV28-thrBAL-yjtD-yjjY | 635.1 ± 7.9 |
| BL21(DE3)-Ptac-rfaH/pVK9-kfiABCD/pSTV28-fruA-psuK | 826.0 ± 125.1 |
| BL21(DE3)-Ptac-rfaH/pVK9-kfiABCD/pSTV28-ytfT-yjfF-fbp | 872.3 ± 20.1 |
| BL21(DE3)-Ptac-rfaH/pVK9-kfiABCD/pSTV28-yagU-paoAB | 690.2 ± 63.1 |

TABLE 9-continued

Effect of enhancement of pcoESR, yhcNO-aaeBAX, g1455-alpA-g1453, yrbA-mlaBCDEF-yrbG, norW, ybjIJK-rybB, thrBAL-yjtD-yjjY, fruA-psuK, ytfT-yjfF-fbp, yagU-paoAB, gsiCD-yliE, irp (part), or bhsA-ycfS gene expression in BL21(DE3)-Ptac-rfaH/pVK9-kfiABCD strain

| Strain | Heparosan (mg/L) |
|---|---|
| BL21(DE3)-Ptac-rfaH/pVK9-kfiABCD/pSTV28-gsiCD-yliE | 804.1 ± 92.9 |
| BL21(DE3)-Ptac-rfaH/pVK9-kfiABCD/pSTV28-irp | 691.5 ± 92.4 |
| BL21(DE3)-Ptac-rfaH/pVK9-kfiABCD/pSTV28-bhsA-ycfS | 994.3 ± 124.1 |

Example 9: Heparosan Production Using pcoESR, yhcNO-aaeBAX, g1455-alpA-g1453, yrbA-mlaB-CDEF-yrbG, norW, ybjIJK-rybB, thrBAL-yjtD-yjjY, fruA-psuK, ytfT-yjfF-fbp, yagU-paoAB, gsiCD-yliE, irp (part), and bhsA-ycfS gene expression-enhanced strains (2)

There were constructed respective strains from the *Escherichia coli* BL21(DE3)/pVK9-kfiABCD strain constructed in Example 1 by introducing thereto pSTV28-pcoESR, pSTV28-yhcNO-aaeBAX, pSTV28-g1455-alpA-g1453, pSTV28-yrbA-mlaBCDEF-yrbG, pSTV28-norW, pSTV28-ybjIJK-rybB, pSTV28-thrBAL-yjtD-yjjY, pSTV28-fruA-psuK, pSTV28-ytfT-yjfF-fbp, pSTV28-yagU-paoAB, pSTV28-gsiCD-yliE, pSTV28-irp, and pSTV28-bhsA-ycfS isolated in Example 3, and pSTV28 as a control. Fermentative production culture was performed with these strains, and amounts of the produced heparosan were compared. The strains were cultured in test tubes in quadruplicate by using the same medium and culture method as those shown in Example 1, and heparosan was quantified by the carbazole method. Averages and standard deviations of the measured heparosan concentrations are shown in Table 10.

TABLE 10

Effect of enhancement of pcoESR, yhcNO-aaeBAX, g1455-alpA-g1453, yrbA-mlaBCDEF-yrbG, norW, ybjIJK-rybB, thrBAL-yjtD-yjjY, fruA-psuK, ytfT-yjfF-fbp, yagU-paoAB, gsiCD-yliE, irp (part), or bhsA-ycfS gene expression in BL21(DE3)/pVK9-kfiABCD strain

| Strain | Heparosan (mg/L) |
|---|---|
| BL21(DE3)/pVK9-kfiABCD/pSTV28 | 106.4 ± 12.4 |
| BL21(DE3)/pVK9-kfiABCD/pSTV28-pcoESR | 260.8 ± 47.8 |
| BL21(DE3)/pVK9-kfiABCD/pSTV28-yhcNO-aaeBAX | 237.2 ± 36.6 |
| BL21(DE3)/pVK9-kfiABCD/pSTV28-g1455-alpA-g1453 | 225.6 ± 8.5 |
| BL21(DE3)/pVK9-kfiABCD/pSTV28-yrbA-mlaBCDEF-yrbG | 215.2 ± 14.9 |
| BL21(DE3)/pVK9-kfiABCD/pSTV28-norW | 216.4 ± 36.6 |
| BL21(DE3)/pVK9-kfiABCD/pSTV28-ybjIJK-rybB | 301.9 ± 46.9 |
| BL21(DE3)/pVK9-kfiABCD/pSTV28-thrBAL-yjtD-yjjY | 327.2 ± 39.8 |
| BL21(DE3)/pVK9-kfiABCD/pSTV28-fruA-psuK | 209.3 ± 8.1 |
| BL21(DE3)/pVK9-kfiABCD/pSTV28-ytfT-yjfF-fbp | 220.1 ± 18.5 |
| BL21(DE3)/pVK9-kfiABCD/pSTV28-yagU-paoAB | 258.0 ± 26.4 |
| BL21(DE3)/pVK9-kfiABCD/pSTV28-gsiCD-yliE | 323.3 ± 15.5 |
| BL21(DE3)/pVK9-kfiABCD/pSTV28-irp | 202.0 ± 15.0 |
| BL21(DE3)/pVK9-kfiABCD/pSTV28-bhsA-ycfS | 225.5 ± 37.4 |

Example 10: Heparosan production using lepB-rnc-era, dapA-gcvR-bcp-hyfA, rpoE-nadB-yfiC-srmB, g1414-g1413, nuoEFG, glmZ-hemYXD, rlmL, artQMJ-rlmC-ybjO, yejOML, rpoS-ygbNML, g3798-g3797-g3796-g3795-g3794-g3793-g3792, ryjA-soxRS-yjcCB, and efeUO Gene Expression-enhanced Strains There were constructed respective strains from the Escherichia coli BL21(DE3)/pVK9-kfiABCD strain constructed in Example 1 by introducing thereto pSTV28-lepB-rnc-era, pSTV28-dapA-gcvR-bcp-hyfA, pSTV28-rpoE-nadB-yfiC-srmB, pSTV28-g1414-g1413, pSTV28-nuoEFG, pSTV28-glmZ-hemYXD, pSTV28-rlmL, pSTV28-artQMJ-rlmC-ybjO, pSTV28-yejOML, pSTV28-rpoS-ygbNML, pSTV28-g3798-g3797-g3796-g3795-g3794-g3793-g3792, pSTV28-ryjA-soxRS-yjcCB, and pSTV28-efeUO isolated in Example 3, and pSTV28 as a control. Fermentative production culture was performed with these strains, and amounts of the produced heparosan were compared. The strains were cultured in test tubes in quadruplicate by using the same medium and culture method as those shown in Example 1, and heparosan was quantified by the carbazole method. Averages and standard deviations of the measured heparosan concentrations are shown in Tables 11 and 12.

TABLE 11

Effect of enhancement of lepB-rnc-era, dapA-gcvR-bcp-hyfA, rpoE-nadB-yfiC-srmB, g1414-g1413, nuoEFG, or glmZ-hemYXD gene expression in BL21(DE3)/pVK9-kfiABCD strain

| Strain | Heparosan (mg/L) |
| --- | --- |
| BL21(DE3)/pVK9-kfiABCD/pSTV28 | 210.4 ± 23.6 |
| BL21(DE3)/pVK9-kfiABCD/pSTV28-lepB-rnc-era | 488.7 ± 83.5 |
| BL21(DE3)/pVK9-kfiABCD/pSTV28-dapA-gcvR-bcp-hyfA | 379.8 ± 49.1 |
| BL21(DE3)/pVK9-kfiABCD/pSTV28-rpoE-nadB-yfiC-srmB | 282.9 ± 54.1 |
| BL21(DE3)/pVK9-kfiABCD/pSTV28-g1414-g1413 | 423.9 ± 119.5 |
| BL21(DE3)/pVK9-kfiABCD/pSTV28-nuoEFG | 428.5 ± 64.6 |
| BL21(DE3)/pVK9-kfiABCD/pSTV28-glmZ-hemYXD | 604.2 ± 177.5 |

TABLE 12

Effect of enhancement of rlmL, artQMJ-rlmC-ybjO, yejOML, rpoS-ygbNML, g3798-g3797-g3796-g3795-g3794-g3793-g3792, ryjA-soxRS-yjcCB, or efeUO gene expression in BL21(DE3)/pVK9-kfiABCD strain

| Strain | Heparosan (mg/L) |
| --- | --- |
| BL21(DE3)/pVK9-kfiABCD/pSTV28 | 147.4 ± 16.3 |
| BL21(DE3)/pVK9-kfiABCD/pSTV28-rlmL | 242.7 ± 45.8 |
| BL21(DE3)/pVK9-kfiABCD/pSTV28-artQMJ-rlmC-ybjO | 243.4 ± 97.9 |
| BL21(DE3)/pVK9-kfiABCD/pSTV28-yejOML | 310.7 ± 40.8 |
| BL21(DE3)/pVK9-kfiABCD/pSTV28-rpoS-ygbNML | 257.1 ± 56.8 |
| BL21(DE3)/pVK9-kfiABCD/pSTV28-g3798-g3797-g3796-g3795-g3794-g3793-g3792 | 251.6 ± 68.5 |
| BL21(DE3)/pVK9-kfiABCD/pSTV28-ryjA-soxRS-yjcCB | 287.5 ± 46.0 |
| BL21(DE3)/pVK9-kfiABCD/pSTV28-efeUO | 385.7 ± 88.5 |

Example 11: Heparosan Production Using rpoE Gene Expression-enhanced Strain (11-1) Construction of Expression Plasmid for rpoE Gene of Escherichia coli K5 Strain The rpoE gene was cloned from the Escherichia coli K5 strain into pMIV-Pnlp8-ter to construct a rpoE gene expression plasmid, pMIV-Pnlp0-rpoE. pMIV-Pnlp0-ter contains the potent nlp8 promoter (Pnlp8), and the promoter and a terminator can function as an expression unit of a target gene when the target gene is inserted therebetween. "Pnlp8" means a variant promoter of the nlpD gene of the Escherichia coli K-12 strain.

The details of the construction of the expression vector pMIV-Pnlp8-ter are shown below. In order to make the wild-type nlpD promoter (Pnlp0) be a stronger promoter by modifying the −10 region thereof, the −10 region was randomized according to the following procedures. The wild-type nlpD promoter region (FIG. 1, SEQ ID NO: 165) contains two regions presumed to function as a promoter, and they are indicated as Pnlp1 and Pnlp2, respectively, in the drawing. By PCR using the plasmid pMIV-Pnlp0-ter constructed in Example 6 as the template, as well as the primer P1 (SEQ ID NO: 14) and primer P7 (SEQ ID NO: 166), there was obtained a DNA fragment of the wild-type nlpD promoter (Pnlp0) of which −10 region (−10(Pnlp1)) contained on the 3' end side was randomized. The PCR cycle consisted of 95° C. for 3 minutes, following 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

In the same manner, by PCR using the plasmid pMIV-Pnlp0-ter as the template, as well as the primer P2 (SEQ ID NO: 15) and primer P8 (SEQ ID NO: 167), there was obtained a DNA fragment of the wild-type nlpD promoter (Pnlp0) of which −10 region (−10(Pnlp2)) contained on the 5' end side was randomized. The PCR cycle consisted of 95° C. for 3 minutes, following 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

The obtained fragments for the 3' end side and 5' end side were ligated by using the BglII sites designed in the primers P7 and P8 to construct a DNA fragment containing a variant nlpD promoter in full length, of which two −10 regions were randomized. By PCR using this DNA fragment as the template, as well as the primer P1 and primer P2, the DNA fragment containing the full length of the variant nlpD promoter was amplified. The PCR cycles consisted of 95° C. for 3 minutes, following 2 cycles of 95° C. for 60 seconds, 50° C. for 30 seconds, and 72° C. for 40 seconds, 12 cycles of 94° C. for 20 seconds, 60° C. for 20 seconds, and 72° C. for 15 seconds, and 72° C. for 5 minutes as the final cycle.

The amplified DNA fragment containing the full length of the variant nlpD promoter was treated with the restriction enzymes SalI and PaeI designed in the 5' end regions of the primers, and inserted into the plasmid pMIV-Pnlp0-ter similarly treated with SalI and PaeI to replace the wild-type nlpD promoter (Pnlp0) on the plasmid with the variant nlpD promoter. From plasmids obtained as described above, one having the promoter sequence shown in FIG. 2 (Pnlp8, SEQ ID NO: 168) was chosen, and designated as pMIV-Pnlp8-ter. The nucleotide sequence of the PaeI-SalI fragment of the Pnlp8 promoter inserted into this plasmid was as shown as SEQ ID NO: 169.

The details of the construction of the rpoE gene expression plasmid, pMIV-Pnlp8-rpoE, are described below. By PCR using the chromosomal DNA of the *Escherichia coli* K5 strain as the template, as well as the primer rpoE-SalI Fw (SEQ ID NO: 170) and primer rpoE-xba Rv (SEQ ID NO: 171), a DNA fragment of the rpoE gene was obtained. PrimeStar Polymerase (TaKaRa) was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 2 minutes, and final maintenance at 4° C. Further, by PCR using pMIV-Pnlp8-ter as the template DNA, as well as the oligonucleotides of SEQ ID NOS: 172 and 173 as the primers, a DNA fragment of pMIV-Pnlp8-ter was obtained. PrimeStar Polymerase (TaKaRa) was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 6 minutes, and final maintenance at 4° C. Both the obtained DNA fragments were ligated by using In-Fusion (registered trademark) HD Cloning Kit (Clontech) to construct an rpoE gene expression plasmid, pMIV-Pnlp8-rpoE. The nucleotide sequence of the cloned rpoE gene is shown as SEQ ID NO: 174.

(11-2) Heparosan Production Using rpoE Gene Expression-enhanced Strain

There were constructed respective strains from the *Escherichia coli* BL21(DE3)/pVK9-kfiABCD strain constructed in Example 1 by introducing thereto pMIV-Pnlp8-rpoE and pMIV-5JS as a control. Fermentative production culture was performed with these strains, and amounts of the produced heparosan were compared. The medium, culture method, and quantification method for heparosan were the same as those described above. Averages and standard deviations of the measured heparosan concentrations are shown in Table 13.

TABLE 13

Effect of enhancement of rpoE gene expression in BL21(DE3)/pVK9-kfiABCD strain

| Strain | Heparosan (mg/L) |
|---|---|
| BL21(DE3)/pVK9-kfiABCD/pMIV-5JS | 96.1 ± 5.8 |
| BL21(DE3)/pVK9-kfiABCD/pMIV-Pnlp8-rpoE | 183.6 ± 7.8 |

While the invention has been described in detail with reference to the preferred embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

According to the present invention, heparosan-producing ability of bacteria can be improved, and heparosan can be efficiently produced.

Description of Sequence Listing

SEQ ID NO: 1, Nucleotide sequence of pVK9
SEQ ID NOS: 2 to 7, Primers
SEQ ID NO: 8, Nucleotide sequence of tac promoter
SEQ ID NOS: 9 and 10, Primers
SEQ ID NO: 11, Nucleotide sequence of pSTV28
SEQ ID NOS: 12 to 15, Primers
SEQ ID NO: 16, Nucleotide sequence of PaeI-SalI fragment containing wild-type nlpD promoter (Pnlp0)
SEQ ID NOS: 17 and 18, Primers
SEQ ID NO: 19, Nucleotide sequence of rrnB terminator
SEQ ID NOS: 20 to 23, Primers
SEQ ID NO: 24, Nucleotide sequence of kfiABCD operon of *Escherichia coli* K5 strain
SEQ ID NO: 25, Amino acid sequence of KfiA protein of *Escherichia coli* K5 strain
SEQ ID NO: 26, Amino acid sequence of KfiB protein of *Escherichia coli* K5 strain
SEQ ID NO: 27, Amino acid sequence of KfiC protein of *Escherichia coli* K5 strain
SEQ ID NO: 28, Amino acid sequence of KfiD protein of *Escherichia coli* K5 strain
SEQ ID NO: 29, Nucleotide sequence of region containing rbsBKR-hsrA genes of *Escherichia coli* K5 strain
SEQ ID NO: 30, Amino acid sequence of RbsB protein of *Escherichia coli* K5 strain
SEQ ID NO: 31, Amino acid sequence of RbsK protein of *Escherichia coli* K5 strain
SEQ ID NO: 32, Amino acid sequence of RbsR protein of *Escherichia coli* K5 strain
SEQ ID NO: 33, Amino acid sequence of HsrA protein of *Escherichia coli* K5 strain
SEQ ID NO: 34, Nucleotide sequence of region containing glgBX genes of *Escherichia coli* K5 strain
SEQ ID NO: 35, Amino acid sequence of GlgB protein of *Escherichia coli* K5 strain
SEQ ID NO: 36, Amino acid sequence of GlgX protein of *Escherichia coli* K5 strain
SEQ ID NO: 37, Nucleotide sequence of region containing ybiXIJCB genes of *Escherichia coli* K5 strain
SEQ ID NO: 38, Amino acid sequence of YbiX protein of *Escherichia coli* K5 strain
SEQ ID NO: 39, Amino acid sequence of YbiI protein of *Escherichia coli* K5 strain
SEQ ID NO: 40, Amino acid sequence of YbiJ protein of *Escherichia coli* K5 strain
SEQ ID NO: 41, Amino acid sequence of YbiC protein of *Escherichia coli* K5 strain
SEQ ID NO: 42, Amino acid sequence of YbiB protein of *Escherichia coli* K5 strain
SEQ ID NO: 43, Nucleotide sequence of region containing rcsBD-micF genes of *Escherichia coli* K5 strain
SEQ ID NO: 44, Amino acid sequence of RcsB protein of *Escherichia coli* K5 strain
SEQ ID NO: 45, Amino acid sequence of RcsD protein of *Escherichia coli* K5 strain
SEQ ID NO: 46, Nucleotide sequence of rfaH gene of *Escherichia coli* BL21(DE3) strain
SEQ ID NO: 47, Amino acid sequence of RfaH protein of *Escherichia coli* BL21(DE3) strain
SEQ ID NO: 48, Nucleotide sequence of nusG gene of *Escherichia coli* BL21(DE3) strain
SEQ ID NO: 49, Amino acid sequence of NusG protein of *Escherichia coli* BL21(DE3) strain
SEQ ID NO: 50, Nucleotide sequence of region containing pcoRSE genes of *Escherichia coli* K5 strain
SEQ ID NO: 51, Amino acid sequence of PcoR protein of *Escherichia coli* K5 strain
SEQ ID NO: 52, Amino acid sequence of PcoS protein of *Escherichia coli* K5 strain
SEQ ID NO: 53, Amino acid sequence of PcoE protein of *Escherichia coli* K5 strain SEQ ID NO: 54, Nucleotide sequence of region containing yhcNO-aaeBAX genes of *Escherichia coli* K5 strain SEQ ID NO: 55, Amino acid sequence of YchN protein of *Escherichia coli* K5 strain SEQ ID NO: 56, Amino acid sequence of YchO protein of *Escherichia coli* K5 strain SEQ ID NO: 57, Amino acid sequence of AaeB protein of *Escherichia coli* K5 strain SEQ ID NO: 58, Amino acid sequence of AaeA protein of *Escherichia coli* K5 strain SEQ ID NO: 59, Amino acid sequence of AaeX protein of *Escherichia coli* K5 strain SEQ ID NO: 60, Nucleotide sequence of region containing g1455-alpA-g1453 genes of *Escherichia coli* K5 strain SEQ ID NO: 61, Amino acid sequence of G1455 protein of *Escherichia coli* K5 strain SEQ ID NO: 62, Amino acid sequence of AlpA protein of *Escherichia coli* K5 strain SEQ ID NO: 63, Amino acid sequence of G1453 protein of *Escherichia coli* K5 strain SEQ ID NO: 64, Nucleotide sequence of region containing yrbA-mlaBCDEF-yrbG genes of *Escherichia coli* K5 strain SEQ ID NO: 65, Amino acid sequence of YrbA protein of *Escherichia coli* K5 strain SEQ ID NO: 66, Amino acid sequence of MlaB protein of *Escherichia coli* K5 strain SEQ ID NO: 67, Amino acid sequence of MlaC protein of *Escherichia coli* K5 strain SEQ ID NO: 68, Amino acid sequence of MlaD protein of *Escherichia coli* K5 strain SEQ ID NO: 69, Amino acid sequence of MlaE protein of *Escherichia coli* K5 strain SEQ ID NO: 70, Amino acid sequence of MlaF protein of *Escherichia coli* K5 strain SEQ ID NO: 71, Amino acid sequence of YrbG protein of *Escherichia coli* K5 strain SEQ ID NO: 72, Nucleotide sequence of region containing norW gene of *Escherichia coli* K5 strain SEQ ID NO: 73, Amino acid sequence of NorW protein of *Escherichia coli* K5 strain SEQ ID NO: 74, Nucleotide sequence of region containing ybjIJK-rybB genes of *Escherichia coli* K5 strain SEQ ID NO: 75, Amino acid sequence of YbjI protein of *Escherichia coli* K5 strain SEQ ID NO: 76, Amino acid sequence of YbjJ protein of *Escherichia coli* K5 strain SEQ ID NO: 77, Amino acid sequence of YbjK protein of *Escherichia coli* K5 strain SEQ ID NO: 78, Nucleotide sequence of region containing yjjY-yjtD-thrLAB genes of *Escherichia coli* K5 strain SEQ ID NO: 79, Amino acid sequence of YjjY protein of *Escherichia coli* K5 strain SEQ ID NO: 80, Amino acid sequence of YjtD protein of *Escherichia coli* K5 strain SEQ ID NO: 81, Amino acid sequence of ThrL protein of *Escherichia coli* K5 strain SEQ ID NO: 82, Amino acid sequence of ThrA protein of *Escherichia coli* K5 strain SEQ ID NO: 83, Amino acid sequence of ThrB protein of *Escherichia coli* K5 strain SEQ ID NO: 84, Nucleotide sequence of region containing fruA-psuK genes of *Escherichia coli* K5 strain SEQ ID NO: 85, Amino acid sequence of FruA protein of *Escherichia coli* K5 strain SEQ ID NO: 86, Amino acid sequence of PsuK protein of *Escherichia coli* K5 strain SEQ ID NO: 87, Nucleotide sequence of region containing ytfT-yjfF-fbp genes of *Escherichia coli* K5 strain SEQ ID NO: 88, Amino acid sequence of YtfT protein of *Escherichia coli* K5 strain SEQ ID NO: 89, Amino acid sequence of YjfF protein of *Escherichia coli* K5 strain SEQ ID NO: 90, Amino acid sequence of Fbp protein of *Escherichia coli* K5 strain SEQ ID NO: 91, Nucleotide sequence of region containing yagU-paoAB genes of *Escherichia coli* K5 strain SEQ ID NO: 92, Amino acid sequence of YagU protein of *Escherichia coli* K5 strain SEQ ID NO: 93, Amino acid sequence of PaoA protein of *Escherichia coli* K5 strain SEQ ID NO: 94, Amino acid sequence of PaoB protein of *Escherichia coli* K5 strain SEQ ID NO: 95, Nucleotide sequence of region containing gsiCD-yliE genes of *Escherichia coli* K5 strain SEQ ID NO: 96, Amino acid sequence of GsiC protein of *Escherichia coli* K5 strain SEQ ID NO: 97, Amino acid sequence of GsiD protein of *Escherichia coli* K5 strain SEQ ID NO: 98, Amino acid sequence of YliE protein of *Escherichia coli* K5 strain SEQ ID NO: 99, Nucleotide sequence of region containing a part of irp gene of *Escherichia coli* K5 strain SEQ ID NO: 100, Nucleotide sequence of irp2 gene of *Escherichia coli* K5 strain SEQ ID NO: 101, Amino acid sequence of Irp2 protein of *Escherichia coli* K5 strain SEQ ID NO: 102, Nucleotide sequence of irp1 gene of *Escherichia coli* K5 strain SEQ ID NO: 103, Amino acid sequence of Irp1 protein of *Escherichia coli* K5 strain SEQ ID NO: 104, Nucleotide sequence of region containing bhsA-ycfS genes of *Escherichia coli* K5 strain SEQ ID NO: 105, Amino acid sequence of BhsA protein of *Escherichia coli* K5 strain SEQ ID NO: 106, Amino acid sequence of YcfS protein of *Escherichia coli* K5 strain SEQ ID NO: 107, Nucleotide sequence of region containing lepB-rnc-era genes of *Escherichia coli* K5 strain SEQ ID NO: 108, Amino acid sequence of LepB protein of *Escherichia coli* K5 strain SEQ ID NO: 109, Amino acid sequence of Rnc protein of *Escherichia coli* K5 strain SEQ ID NO: 110, Amino acid sequence of Era protein of *Escherichia coli* K5 strain SEQ ID NO: 111, Nucleotide sequence of region containing dapA-gcvR-bcp-hyfA genes of *Escherichia coli* K5 strain SEQ ID NO: 112, Amino acid sequence of DapA protein of *Escherichia coli* K5 strain SEQ ID NO: 113, Amino acid sequence of GcvR protein of *Escherichia coli* K5 strain SEQ ID NO: 114, Amino acid sequence of Bcp protein of *Escherichia coli* K5 strain SEQ ID NO: 115, Amino acid sequence of HyfA protein of *Escherichia coli* K5 strain SEQ ID NO: 116, Nucleotide sequence of region containing rpoE-nadB-yfiC-srmB genes of *Escherichia coli* K5 strain SEQ ID NO: 117, Amino acid sequence of RpoE protein of *Escherichia coli* K5 strain SEQ ID NO: 118, Amino acid sequence of NadB protein of *Escherichia coli* K5 strain SEQ ID NO: 119, Amino acid sequence of YfiC protein of *Escherichia coli* K5 strain
SEQ ID NO: 120, Amino acid sequence of SrmB protein of *Escherichia coli* K5 strain
SEQ ID NO: 121, Nucleotide sequence of region containing g1414-g1413 genes of *Escherichia coli* K5 strain
SEQ ID NO: 122, Amino acid sequence of G1414 protein of *Escherichia coli* K5 strain
SEQ ID NO: 123, Amino acid sequence of G1413 protein of *Escherichia coli* K5 strain
SEQ ID NO: 124, Nucleotide sequence of region containing nuoEFG genes of *Escherichia coli* K5 strain
SEQ ID NO: 125, Amino acid sequence of NuoE protein of *Escherichia coli* K5 strain
SEQ ID NO: 126, Amino acid sequence of NuoF protein of *Escherichia coli* K5 strain
SEQ ID NO: 127, Amino acid sequence of NuoG protein of *Escherichia coli* K5 strain
SEQ ID NO: 128, Nucleotide sequence of region containing glmZ-hemYXD genes of *Escherichia coli* K5 strain
SEQ ID NO: 129, Amino acid sequence of HemY protein of *Escherichia coli* K5 strain
SEQ ID NO: 130, Amino acid sequence of HemX protein of *Escherichia coli* K5 strain
SEQ ID NO: 131, Amino acid sequence of HemD protein of *Escherichia coli* K5 strain
SEQ ID NO: 132, Nucleotide sequence of region containing rlmL gene of *Escherichia coli* K5 strain
SEQ ID NO: 133, Amino acid sequence of RlmL protein of *Escherichia coli* K5 strain
SEQ ID NO: 134, Nucleotide sequence of region containing artQMJ-rlmC-ybjO genes of *Escherichia coli* K5 strain
SEQ ID NO: 135, Amino acid sequence of ArtQ protein of *Escherichia coli* K5 strain
SEQ ID NO: 136, Amino acid sequence of ArtM protein of *Escherichia coli* K5 strain
SEQ ID NO: 137, Amino acid sequence of ArtJ protein of *Escherichia coli* K5 strain
SEQ ID NO: 138, Amino acid sequence of RlmC protein of *Escherichia coli* K5 strain
SEQ ID NO: 139, Amino acid sequence of YbjO protein of *Escherichia coli* K5 strain
SEQ ID NO: 140, Nucleotide sequence of region containing yejOML genes of *Escherichia coli* K5 strain
SEQ ID NO: 141, Amino acid sequence of YejO protein of *Escherichia coli* K5 strain
SEQ ID NO: 142, Amino acid sequence of YejM protein of *Escherichia coli* K5 strain
SEQ ID NO: 143, Amino acid sequence of YejL protein of *Escherichia coli* K5 strain
SEQ ID NO: 144, Nucleotide sequence of region containing rpoS-ygbNML genes of *Escherichia coli* K5 strain
SEQ ID NO: 145, Amino acid sequence of RpoS protein of *Escherichia coli* K5 strain
SEQ ID NO: 146, Amino acid sequence of YgbN protein of *Escherichia coli* K5 strain
SEQ ID NO: 147, Amino acid sequence of YgbM protein of *Escherichia coli* K5 strain
SEQ ID NO: 148, Amino acid sequence of YgbL protein of *Escherichia coli* K5 strain
SEQ ID NO: 149, Nucleotide sequence of region containing g3798-g3797-g3796-g3795-g3794-g3793-g3792 genes of *Escherichia coli* K5 strain
SEQ ID NO: 150, Amino acid sequence of G3798 protein of *Escherichia coli* K5 strain
SEQ ID NO: 151, Amino acid sequence of G3797 protein of *Escherichia coli* K5 strain
SEQ ID NO: 152, Amino acid sequence of G3796 protein of *Escherichia coli* K5 strain
SEQ ID NO: 153, Amino acid sequence of G3795 protein of *Escherichia coli* K5 strain
SEQ ID NO: 154, Amino acid sequence of G3794 protein of *Escherichia coli* K5 strain
SEQ ID NO: 155, Amino acid sequence of G3793 protein of *Escherichia coli* K5 strain
SEQ ID NO: 156, Amino acid sequence of G3792 protein of *Escherichia coli* K5 strain
SEQ ID NO: 157, Nucleotide sequence of region containing ryjA-soxRS-yjcCB genes of *Escherichia coli* K5 strain
SEQ ID NO: 158, Amino acid sequence of SoxR protein of *Escherichia coli* K5 strain
SEQ ID NO: 159, Amino acid sequence of SoxS protein of *Escherichia coli* K5 strain
SEQ ID NO: 160, Amino acid sequence of YjcC protein of *Escherichia coli* K5 strain
SEQ ID NO: 161, Amino acid sequence of YjcB protein of *Escherichia coli* K5 strain
SEQ ID NO: 162, Nucleotide sequence of region containing efeUO genes of *Escherichia coli* K5 strain
SEQ ID NO: 163, Amino acid sequence of EfeU protein of *Escherichia coli* K5 strain
SEQ ID NO: 164, Amino acid sequence of EfeO protein of *Escherichia coli* K5 strain
SEQ ID NO: 165, Nucleotide sequence of wild-type nlpD promoter (Pnlp0)
SEQ ID NOS: 166 and 167, Primers
SEQ ID NO: 168, Nucleotide sequence of variant nlpD promoter (Pnlp8)
SEQ ID NO: 169, Nucleotide sequence of PaeI-SalI fragment containing variant nlpD promoter (Pnlp8)
SEQ ID NOS: 170 to 173, Primers
SEQ ID NO: 174, Nucleotide sequence of rpoE gene of *Escherichia coli* K5 strain

The invention claimed is:

1. A method for producing heparin, the method comprising:

A) culturing an *Escherichia coli* bacterium having a heparosan-producing ability in a medium to produce and accumulate heparosan in the medium;

B) treating the heparosan using chemical methods, enzymatic methods, or both chemical and enzymatic methods to produce heparin; and C) collecting the heparin, wherein the bacterium has been modified so that expression is increased of an *Escherichia coli* rfaH gene; and wherein the bacterium has been further modified so that expression of an *Escherichia coli* heparosan biosynthesis enzyme gene is increased.

2. The method according to claim 1, wherein the bacterium has been further modified so that expression is increased of an *Escherichia coli* nusG gene.

3. The method according to claim 1, wherein said expression is increased by increasing the copy number of the gene(s), modifying a gene expression control sequence of the gene(s), or both.

4. The method according to claim 1, wherein the rfaH gene is a DNA comprising the nucleotide sequence of SEQ ID NO: 46, or a DNA comprising a nucleotide sequence having an identity of 90% or higher to the nucleotide sequence of SEQ ID NO: 46 and is able to increase heparosan-producing ability of an *Escherichia* bacterium having heparosan-producing ability when expression amount thereof is increased in the bacterium.

5. The method according to claim 2, wherein the nusG gene is a DNA comprising the nucleotide sequence of SEQ ID NO: 48, or a DNA comprising a nucleotide sequence having an identity of 90% or higher to the nucleotide sequence of SEQ ID NO: 48 and is able to increase heparosan-producing ability of an *Escherichia* bacterium having heparosan-producing ability when expression amount thereof is increased in the bacterium.

* * * * *

SEQUENCE LISTING

```
<160> NUMBER OF SEQ ID NOS: 174

<210> SEQ ID NO 1
<211> LENGTH: 5629
<212> TYPE: DNA
<213> ORGANISM: Artificial Sequence
<220> FEATURE:
<223> OTHER INFORMATION: vector

<400> SEQUENCE: 1
```

-continued

```
gaggtctgcc tcgtgaagaa ggtgttgctg actcatacca ggcctgaatc gccccatcat      60
ccagccagaa agtgagggag ccacggttga tgagagcttt gttgtaggtg gacgggatc     120 ttttctacgg ggtctgacgc tcagtggaac gaaaactcac gttaagggat tttggtcatg    180
agattatcaa aaaggatcat gcgagcaacc tccataagat cagctaggcg atctttggga    240
gcagtccttg tcgcgttacg aggtgagccg gtggggaacc gttagctgcc tatggtgtga    300 gccccctag agagcttcaa gagcaatcag cccgacctag aaaggaggcc aagagagaga     360
cctacggggg gaaccgtttt ctgcctacga gatgggcaca ttactgggaa gctttacggc    420
gtcctcgtgg aagttcaatg cccgcagact taagtgctct attcacgtc tgacgtgaca     480 cgctaaattc agacatagct tcattgattg tcggccacga gccagtctct ccctcaacag    540
tcataaacca acctgcaatg gtcaagcgat ttcctttagc tttcctagct tgtcgttgac    600
tggacttagc tagttttttct cgctgtgctc gggcgtactc actgtttggg tctttccagc    660
gttctgcggc cttttaccg ccacgtcttc ccatagtggc cagagctttt cgccctcggc      720
tgctctgcgt ctctgtctga cgagcaggga cgactggctg gcctttagcg acgtagccgc    780
gcacacgtcg cgccatcgtc tggcggtcac gcatcggcgg cagatcaggc tcacggccgt    840
ctgctccgac cgcctgagcg acggtgtagg cacgctcgta ggcgtcgatg atcttggtgt    900
cttttaggcg ctcaccagcc gcttttaact ggtatcccac agtcaaagcg tggcgaaaag    960
ccgtctcatc acgggcggca cgccctggag cagtccagag gacacggacg ccgtcgatca   1020
gctctccaga cgcttcagcg gcgctcggca ggcttgcttc aagcgtggca agtgcttttg   1080
cttccgcagt ggcttttctt gccgcttcga tacgtgcccg tccgctagaa aactcctgct   1140
catagcgttt tttaggtttt tctgtgcctg agatcatgcg agcaacctcc ataagatcag   1200
ctaggcgatc cacgcgattg tgctgggcat gccagcggta cgcggtggga tcgtcggaga   1260
cgtgcagtgg ccaccggctc agcctatgtg aaaaagcctg gtcagcgccg aaaacgcggg   1320
tcatttcctc ggtcgttgca gccagcaggc gcatattcgg gctgctcatg cctgctgcgg   1380
catacaccgg atcaatgagc cagatgagct ggcatttccc gctcagtgga ttcacgccga   1440
tccaagctgc cgcttttttcc aggcgtgccc agcgctccaa aatcgcgtag acctcggggt   1500
ttacgtgctc gattttcccg ccggcctggt ggctcggcac atcaatgtcc aggacaagca   1560
cggctgcgtg ctgcgcgtgc gtcagagcaa catactggca ccgggcaagc gattttgaac   1620
caactcggta taacttcggc tgtgtttctc ccgtgtccgg gtctttgatc caagcgctgg   1680
cgaagtcgcg ggtcttgctg ccctggaaat tttctctgcc caggtgagcg aggaattcgc   1740
ggcggtcttc gctcgtccag ccacgtgatc gcagcgcgag ctcgggatgg gtgtcgaaca   1800
gatcagcgga aaatttccag gccggtgtgt caatgtctcg tgaatccgct agagtcattt   1860
ttgagcgctt tctcccaggt ttggactggg ggttagccga cgccctgtga gttaccgctc   1920
acggggcgtt caacattttt caggtattcg tgcagcttat cgcttcttgc cgcctgtgcg   1980
ctttttcgac gcgcgacgct gctgccgatt cggtgcaggt ggtggcggcg ctgacacgtc   2040
ctgggcggcc acggccacac gaaacgcggc atttacgatg tttgtcatgc ctgcgggcac   2100
cgcgccacga tcgcggataa ttctcgctgc cgcttccagc tctgtgacga ccatggccaa   2160
aatttcgctc gggggacgca cttccagcgc catttgcgac ctagccgcct ccagctcctc   2220
ggcgtggcgt ttgttggcgc gctcgcggct ggctgcggca cgacacgcat ctgagcaata   2280
ttttgcgcgc cgtcctcgcg ggtcaggccg gggaggaatc aggccaccgc agtaggcgca   2340
actgattcga tcctccacta ctgtgcgtcc tcctggcgct gccgagcacg cagctcgtca   2400
```

```
gccagctcct caagatccgc cacgagagtt tctaggtcgc tcgcggcact ggcccagtct    2460
cgtgatgctg gcgcgtccgt cgtatcgaga gctcggaaaa atccgatcac cgttttttaaa   2520 tcgacggcag catcgagcgc gtcggactcc agcgcgacat cagagagatc catagctgat    2580
gattcgggcc aattttggta cttcgtcgtg aaggtcatga caccattata acgaacgttc    2640
gttaaagttt ttggcggaaa atcacgcggc acgaaaattt tcacgaagcg ggactttgcg    2700
cagctcaggg gtgctaaaaa ttttgtatcg cacttgattt ttccgaaaga cagattatct    2760
gcaaacggtg tgtcgtattt ctggcttggt ttttaaaaaa tctggaatcg aaaatttgcg    2820
gggcgaccga gaagtttttt acaaaaggca aaaactttt cgggatcagc taggcgatcc     2880
acgcgattgt gctgggcatg ccagcggtac gcggtgggat cgtcggagac gtgcagtggc    2940
caccggctca gcctatgtga aaaagcctgg tcagcgccga aaacgcgggt catttcctcg    3000
gtcgttgcag ccagcaggcg catattcggg ctgctcatgc ctgctgcggc atacaccgga    3060
tcggaccagt tggtgatttt gaacttttgc tttgccacgg aacggtctgc gttgtcggga    3120
agatgcgtga tctgatcctt caactcagca aaagttcgat ttattcaaca aagccacgtt    3180
gtgtctcaaa atctctgatg ttacattgca caagataaaa atatatcatc atgaacaata    3240
aaactgtctg cttacataaa cagtaataca aggggtgtta tgagccatat caacgggaa     3300 acgtcttgct cgaagccgcg attaaattcc aacatggatg ctgatttata tgggtataaa    3360
tgggctcgcg ataatgtcgg gcaatcaggt gcgacaatct atcgattgta tgggaagccc    3420
gatgcgccag agttgtttct gaaacatggc aaaggtagcg ttgccaatga tgttacagat    3480
gagatggtca gactaaactg gctgacggaa tttatgcctc ttccgaccat caagcatttt    3540
atccgtactc ctgatgatgc atggttactc accactgcga tccccgggaa aacagcattc    3600
caggtattag aagaatatcc tgattcaggt gaaaatattg ttgatgcgct ggcagtgttc    3660
ctgcgccggt tgcattcgat tcctgttttgt aattgtcctt ttaacagcga tcgcgtattt    3720
cgtctcgctc aggcgcaatc acgaatgaat aacggtttgg ttgatgcgag tgattttgat    3780
gacgagcgta atggctggcc tgttgaacaa gtctggaaag aaatgcataa gcttttgcca    3840
ttctcaccgg attcagtcgt cactcatggt gatttctcac ttgataacct tatttttgac    3900
gaggggaaat taataggttg tattgatgtt ggacgagtcg gaatcgcaga ccgataccag    3960
gatcttgcca tcctatggaa ctgcctcggt gagttttctc cttcattaca gaaacggctt    4020
tttcaaaaat atggtattga taatcctgat atgaataaat tgcagtttca tttgatgctc    4080
gatgagtttt tctaatcaga attggttaat tggttgtaac actggcagag cattacgctg    4140
acttgacggg acggcggctt tgttgaataa atcgcattcg ccattcaggc tgcgcaactg    4200
ttgggaaggg cgatcggtgc gggcctcttc gctattacgc cagctggcga aggggggatg    4260
tgctgcaagg cgattaagtt gggtaacgcc agggttttcc cagtcacgac gttgtaaaac    4320 gacgccagt gaattcgagc tcggtacccg gggatcctct agagtcgacc tgcaggcatg    4380
caagcttggc gtaatcatgg tcatagctgt ttcctgtgtg aaattgttat ccgctcacaa    4440
ttccacacaa catacgagcc ggaagcataa agtgtaaagc ctggggtgcc taatgagtga    4500
gctaactcac attaattgcg ttgcgctcac tgcccgcttt ccagtcggga aacctgtcgt    4560
gccagctgca ttaatgaatc ggccaacgcg cggggagagg cggtttgcgt attggcgaac    4620
ttttgctgag ttgaaggatc agatcacgca tcttcccgac aacgcagacc gttccgtggc    4680
aaagcaaaag ttcaaaatca gtaaccgtca gtgccgataa gttcaaagtt aaacctggtg    4740
```

-continued

```
ttgataccaa cattgaaacg ctgatcgaaa acgcgctgaa aaacgctgct gaatgtgcga    4800
gcttcttccg cttcctcgct cactgactcg ctgcgctcgg tcgttcggct gcggcgagcg    4860
gtatcagctc actcaaaggc ggtaatacgg ttatccacag aatcagggga taacgcagga    4920
aagaacatgt gagcaaaagg ccagcaaaag gccaggaacc gtaaaaaggc cgcgttgctg    4980 gcgttttttcc ataggctccg ccccctgac gagcatcaca aaaatcgacg ctcaagtcag    5040
aggtggcgaa acccgacagg actataaaga taccaggcgt ttccccctgg aagctccctc    5100
gtgcgctctc ctgttccgac cctgccgctt accggatacc tgtccgcctt tctcccttcg    5160
ggaagcgtgg cgctttctca atgctcacgc tgtaggtatc tcagttcggt gtaggtcgtt    5220
cgctccaagc tgggctgtgt gcacgaaccc cccgttcagc ccgaccgctg cgccttatcc    5280
ggtaactatc gtcttgagtc aacccggta agacacgact tatcgccact ggcagcagcc    5340
actggtaaca ggattagcag agcgaggtat gtaggcggtg ctacagagtt cttgaagtgg    5400
tggcctaact acggctacac tagaaggaca gtatttggta tctgcgctct gctgaagcca    5460
gttaccttcg gaaaaagagt tggtagctct tgatccggca acaaaccac cgctggtagc    5520 ggtggttttt ttgtttgcaa gcagcagatt acgcgcagaa aaaaaggatc tcaagaagat    5580
cctttgatct tttctacggg gtctgacgct cagtggaacg atccgtcga                5629
```

```
<210> SEQ ID NO 2
<211> LENGTH: 52
<212> TYPE: DNA
<213> ORGANISM: Artificial Sequence
<220> FEATURE:
<223> OTHER INFORMATION: primer

<400> SEQUENCE: 2
gtgaattcga gctcggtacc ggaggcctga ttactgttgc actaacagtg tc             52

<210> SEQ ID NO 3
<211> LENGTH: 48
<212> TYPE: DNA
<213> ORGANISM: Artificial Sequence
<220> FEATURE:
<223> OTHER INFORMATION: primer

<400> SEQUENCE: 3
gcaggtcgac tctagatctt attttacgat cgaggattaa taaagaac                  48

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tctagagtcg acctgcaggc                                                 20

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
cgagctcgaa ttcactggcc gt                                              22
```

```
<210> SEQ ID NO 6
<211> LENGTH: 80
<212> TYPE: DNA
<213> ORGANISM: Artificial Sequence
<220> FEATURE:
<223> OTHER INFORMATION: primer

<400> SEQUENCE: 6
cgtaaagctt ttgctatcct tgcgccccga ttaaacggat aagagtcatt tgaagcctgc      60 tttttatac taagttggca                                                   80

<210> SEQ ID NO 7
<211> LENGTH: 80
<212> TYPE: DNA
<213> ORGANISM: Artificial Sequence
<220> FEATURE:
<223> OTHER INFORMATION: primer

<400> SEQUENCE: 7
gcacgttgaa gttgcccgcg cttgcagtac agtaaatacc aggattgcat ggcagtctcc      60
ttgtgtgaaa ttgttatccg                                                  80

<210> SEQ ID NO 8
<211> LENGTH: 84
<212> TYPE: DNA
<213> ORGANISM: Artificial Sequence
<220> FEATURE:
<223> OTHER INFORMATION: promoter

<400> SEQUENCE: 8
agatctccct gttgacaatt aatcatcggc tcgtataatg tgtggaatcg tgagcggata      60
acaatttcac acaaggagac tgcc                                             84

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tggcgtccat tgtagcctct                                                  20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttagagtttg cggaactcgg                                                  20

<210> SEQ ID NO 11
<211> LENGTH: 2999
<212> TYPE: DNA
<213> ORGANISM: Artificial Sequence
<220> FEATURE:
<223> OTHER INFORMATION: vector

<400> SEQUENCE: 11
cgtatggcaa tgaaagacgg tgagctggtg atatgggata gtgttcaccc ttgttacacc      60
gttttccatg agcaaactga aacgttttca tcgctctgga gtgaatacca cgacgatttc     120
```

```
cggcagtttc tacacatata ttcgcaagat gtggcgtgtt acggtgaaaa cctggcctat    180
ttccctaaag ggtttattga gaatatgttt ttcgtctcag ccaatccctg ggtgagtttc    240
accagttttg atttaaacgt ggccaatatg gacaacttct tcgcccccgt tttcaccatg    300
ggcaaatatt atacgcaagg cgacaaggtg ctgatgccgc tggcgattca ggttcatcat    360
gccgtttgtg atggcttcca tgtcggcaga atgcttaatg aattacaaca gtactgcgat    420
gagtggcagg gcggggcgta attttttttaa ggcagttatt ggtgcccctta aacgcctggt    480 gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaacggttta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg tacccgggga tcctctagag tcgacctgca ggcatgcaag cttggcactg   1320
gccgtcgttt tacaacgtcg tgactgggaa accctggcg ttacccaact taatcgcctt   1380
gcagcacatc cccctttcgc cagctggcgt aatagcgaag aggcccgcac cgatcgccct   1440
tcccaacagt tgcgcagcct gaatggcgaa tgagcttatc gatgataagc tgtcaaacat   1500
gagaattaca acttatatcg tatggggctg acttcaggtg ctacatttga agagataaat   1560
tgcactgaaa tctagaaata ttttatctga ttaataagat gatcttcttg agatcgtttt   1620
ggtctgcgcg taatctcttg ctctgaaaac gaaaaaaccg ccttgcaggg cggttttttcg   1680 aaggttctct gagctaccaa ctctttgaac cgaggtaact ggcttggagg agcgcagtca   1740
ccaaaacttg tcctttcagt ttagccttaa ccggcgcatg acttcaagac taactcctct   1800
aaatcaatta ccagtggctg ctgccagtgg tgcttttgca tgtctttccg ggttggactc   1860
aagacgatag ttaccggata aggcgcagcg gtcggactga acgggggggtt cgtgcataca   1920 gtccagcttg gagcgaactg cctacccgga actgagtgtc aggcgtggaa tgagacaaac   1980
gcggccataa cagcggaatg acaccggtaa accgaaaggc aggaacagga gagcgcacga   2040
gggagccgcc aggggaaacg cctggtatct ttatagtcct gtcgggtttc gccaccactg   2100
atttgagcgt cagatttcgt gatgcttgtc aggggggcgg agcctatgga aaaacggctt   2160
tgccgcggcc ctctcacttc cctgttaagt atcttcctgg catcttccag gaaatctccg   2220
ccccgttcgt aagccatttc cgctcgccgc agtcgaacga ccgagcgtag cgagtcagtg   2280
agcgaggaag cggaatatat cctgtatcac atattctgct gacgcaccgg tgcagccttt   2340
tttctcctgc cacatgaagc acttcactga caccctcatc agtgccaaca tagtaagcca   2400
gtatacactc cgctagcgct gatgtccggc ggtgcttttg ccgttacgca ccaccccgtc   2460
agtagctgaa caggagggac agctgataga aacagaagcc actggagcac ctcaaaaaca   2520
```

```
ccatcataca ctaaatcagt aagttggcag catcacccga cgcactttgc gccgaataaa    2580
tacctgtgac ggaagatcac ttcgcagaat aaataaatcc tggtgtccct gttgataccg    2640
ggaagccctg ggccaacttt tggcgaaaat gagacgttga tcggcacgta agaggttcca    2700
actttcacca taatgaaata agatcactac cgggcgtatt ttttgagtta tcgagatttt    2760
caggagctaa ggaagctaaa atggagaaaa aaatcactgg atataccacc gttgatatat    2820
cccaatggca tcgtaaagaa catttttgagg catttcagtc agttgctcaa tgtacctata    2880
accagaccgt tcagctggat attacggcct ttttaaagac cgtaaagaaa aataagcaca    2940
agttttatcc ggcctttatt cacattcttg cccgcctgat gaatgctcat ccggaattt     2999
```

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12

```
gagcggataa caatttcaca caggaaacag                                       30
```

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13

```
cgcgcagacc aaaacgatct caagaagatc                                       30
```

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14

```
agctgagtcg acccccagga aaaattggtt aataac                                36
```

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15

```
agctgagcat gcttccaact gcgctaatga cgc                                   33
```

<210> SEQ ID NO 16
<211> LENGTH: 313
<212> TYPE: DNA
<213> ORGANISM: Artificial Sequence
<220> FEATURE:
<223> OTHER INFORMATION: promoter

<400> SEQUENCE: 16

```
gcatgcttcc aactgcgcta atgacgcagc tggacgaagg cgggattctc gtcttacccg     60 tagggggagga gcaccagtat ttgaaacggg tgcgtcgtcg gggaggcgaa tttattatcg    120
```

-continued

```
ataccgtgga ggccgtgcgc tttgtccctt tagtgaaggg tgagctggct taaaacgtga      180
ggaaatacct ggattttttcc tggttatttt gccgcaggtc agcgtatcgt gaacatcttt      240
tccagtgttc agtagggtgc cttgcacggt aattatgtca ctggttatta accaattttt      300 cctggggggtc gac                                                        313
```

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17

```
agctgatcta gaaaacagaa tttgcctggc ggc                                    33
```

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18

```
agctgaggat ccaggaagag tttgtagaaa cgc                                    33
```

<210> SEQ ID NO 19
<211> LENGTH: 369
<212> TYPE: DNA
<213> ORGANISM: Artificial Sequence
<220> FEATURE:
<223> OTHER INFORMATION: terminator

<400> SEQUENCE: 19

```
tctagaaaca gaatttgcct ggcggcagta gcgcggtggt cccacctgac cccatgccga       60
actcagaagt gaaacgccgt agcgccgatg gtagtgtggg gtctccccat gcgagagtag      120
ggaactgcca ggcatcaaat aaaacgaaag gctcagtcga agactgggc ctttcgtttt       180 atctgttgtt tgtcggtgaa cgctctcctg agtaggacaa atccgccggg agcggatttg      240
aacgttgcga agcaacggcc cggagggtgg cgggcaggac gcccgccata aactgccagg      300
catcaaatta gcagaaggc catcctgacg gatggccttt ttgcgtttct acaaactctt       360
cctggatcc                                                              369
```

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20

```
acgcgtcgac atgcaatcct ggtatttact                                        30
```

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21

```
gctctagatt agagtttgcg gaactcggta                                        30
```

```
<210> SEQ ID NO 22
<211> LENGTH: 28
<212> TYPE: DNA
<213> ORGANISM: Artificial Sequence
<220> FEATURE:
<223> OTHER INFORMATION: primer

<400> SEQUENCE: 22
gggtcgacat gtctgaagct cctaaaaa                                      28

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
tttctagatt aggcttttc aacctggc                                       28

<210> SEQ ID NO 24
<211> LENGTH: 7467
<212> TYPE: DNA
<213> ORGANISM: Escherichia coli
<220> FEATURE:
<221> NAME/KEY: CDS
<222> LOCATION: (445)..(1164)
<220> FEATURE:
<221> NAME/KEY: CDS
<222> LOCATION: (1593)..(3284)
<220> FEATURE:
<221> NAME/KEY: CDS
<222> LOCATION: (4576)..(6138)
<220> FEATURE:
<221> NAME/KEY: CDS
<222> LOCATION: (6180)..(7358)

<400> SEQUENCE: 24
ggaggcctga ttactgttgc actaacagtg tcattgccgg agattgtaat cacactctat    60
ataattatat aaactctatt gtatttagtg tatgaggagg atggacagta tactttgaac   120
taggtaatta tgaatttgat cgtgatctcg taatacgttg ctgttattct ttaattaatt   180
atctgccaat ttattttag atagttacag gaaatgttta tgcaaagagt ggtttgatat    240
ggtaagagta taatttaga tgaagataaa tatatcaaac gtacaccta gtagttattt     300 ttaattaaac atatcgtcca tgaggtgcgg agtcattcta atcaacttaa tgtgttctgt   360
ttattaagca tttcctataa ataaacgact atcaatacgt tgatagtttt cattaacatg   420
caatattaat taaaatatta cccc atg att gtt gca aat atg tca tca tac      471
                          Met Ile Val Ala Asn Met Ser Ser Tyr
                            1               5 cca cct cga aaa aaa gag ttg gtg cat tct ata caa agt tta cat gct     519
Pro Pro Arg Lys Lys Glu Leu Val His Ser Ile Gln Ser Leu His Ala
 10              15                  20                  25 caa gta gat aaa att aat ctt tgc ctg aat gag ttt gaa gaa att cct     567
Gln Val Asp Lys Ile Asn Leu Cys Leu Asn Glu Phe Glu Glu Ile Pro
             30                  35                  40 gag gaa tta gat ggt ttt tca aaa tta aat cca gtt att cca gat aaa     615
Glu Glu Leu Asp Gly Phe Ser Lys Leu Asn Pro Val Ile Pro Asp Lys
         45                  50                  55 gat tat aag gat gtg ggc aaa ttt ata ttt cct tgc gct aaa aat gat     663
Asp Tyr Lys Asp Val Gly Lys Phe Ile Phe Pro Cys Ala Lys Asn Asp
     60                  65                  70
```

-continued

| | |
|---|---|
| atg atc gta ctt aca gat gat gat att att tac cct ccc gat tat gta<br>Met Ile Val Leu Thr Asp Asp Asp Ile Ile Tyr Pro Pro Asp Tyr Val<br>75                        80                      85 | 711 |
| gaa aaa atg ctc aat ttt tat aat tcc ttt gca ata ttc aat tgc att<br>Glu Lys Met Leu Asn Phe Tyr Asn Ser Phe Ala Ile Phe Asn Cys Ile<br>90                        95                     100                  105 | 759 |
| gtt ggg att cat ggc tgt ata tac ata gat gca ttt gat gga gat cag<br>Val Gly Ile His Gly Cys Ile Tyr Ile Asp Ala Phe Asp Gly Asp Gln<br>110                     115                     120 | 807 |
| tct aaa aga aaa gta ttt tca ttt act caa ggg cta ttg cga ccg aga<br>Ser Lys Arg Lys Val Phe Ser Phe Thr Gln Gly Leu Leu Arg Pro Arg<br>125                     130                     135 | 855 |
| gtt gta aat caa tta ggt aca ggg act gtt ttt ctt aag gca gat caa<br>Val Val Asn Gln Leu Gly Thr Gly Thr Val Phe Leu Lys Ala Asp Gln<br>140                     145                     150 | 903 |
| tta cca tct tta aaa tat atg gat ggt tct caa cga ttc gtc gat gtt<br>Leu Pro Ser Leu Lys Tyr Met Asp Gly Ser Gln Arg Phe Val Asp Val<br>155                     160                     165 | 951 |
| aga ttt tct cgc tat atg tta gag aat gaa att ggt atg ata tgt gtt<br>Arg Phe Ser Arg Tyr Met Leu Glu Asn Glu Ile Gly Met Ile Cys Val<br>170                     175                     180                  185 | 999 |
| ccc aga gaa aaa aac tgg cta aga gag gtc tca tca ggt tca atg gaa<br>Pro Arg Glu Lys Asn Trp Leu Arg Glu Val Ser Ser Gly Ser Met Glu<br>190                     195                     200 | 1047 |
| gga ctt tgg aac aca ttt aca aaa aaa tgg cct tta gac atc ata aaa<br>Gly Leu Trp Asn Thr Phe Thr Lys Lys Trp Pro Leu Asp Ile Ile Lys<br>205                     210                     215 | 1095 |
| gaa aca caa gca atc gca gga tat tca aaa ctt aac ctc gaa tta gtg<br>Glu Thr Gln Ala Ile Ala Gly Tyr Ser Lys Leu Asn Leu Glu Leu Val<br>220                     225                     230 | 1143 |
| tat aat gtg gaa ggg taa aaa cttactttt tattcacatt cctgtatttt<br>Tyr Asn Val Glu Gly    Lys<br>235 | 1194 |
| gtgttggttt ctgaagttta tagtataaat acttgtttta aatagttgta cgttgatatt | 1254 |
| ttgttatata cttatttaaa ccatttgttt tatgattttg aaaaatatca gcgttagttt | 1314 |
| ggtagagttt ataattaaga tttttgtcta aaagaaggtg gtaacgcaat atgtcaatta | 1374 |
| ttaggaggtg ctctgagtta tattgatatt gtttattgat gaatggctat accaaataaa | 1434 |
| tcagatgtgc tattgagata tagatagttt catttagtat tatcacataa cgccacctaa | 1494 |
| attacattac agatttgaaa tatatgtctg caatatcacc attacgataa acgacagtgt | 1554 |
| ttaaaataaa gtaatcttgt agataataaa gaggaaat atg atg aat aaa tta gtg<br>                                                                Met Met Asn Lys Leu Val<br>                                                                240                                 245 | 1610 |
| cta gtc gga cat cct ggc tca aag tat cag ata gtt gaa cat ttt ttg<br>Leu Val Gly His Pro Gly Ser Lys Tyr Gln Ile Val Glu His Phe Leu<br>250                     255                     260 | 1658 |
| aaa gaa att ggc atg aac tca cca aat tat tct aca agt aat aaa att<br>Lys Glu Ile Gly Met Asn Ser Pro Asn Tyr Ser Thr Ser Asn Lys Ile<br>265                     270                     275 | 1706 |
| tcc cca gaa tat atc acc gct tca tta tgt caa ttt tat caa aca cca<br>Ser Pro Glu Tyr Ile Thr Ala Ser Leu Cys Gln Phe Tyr Gln Thr Pro<br>280                     285                     290 | 1754 |
| gaa gtt aat gat gta gta gat gag aga gaa ttc tca gct gtt caa gtc<br>Glu Val Asn Asp Val Val Asp Glu Arg Glu Phe Ser Ala Val Gln Val<br>295                     300                     305 | 1802 |
| tca acc atg tgg gat agc atg gtt ctt gaa cta atg atg aac aat cta<br>Ser Thr Met Trp Asp Ser Met Val Leu Glu Leu Met Met Asn Asn Leu<br>310                     315                     320                     325 | 1850 |

```
aat aac aaa ctt tgg ggg tgg gca gat cca tct ata ata ttt ttt ctt    1898
Asn Asn Lys Leu Trp Gly Trp Ala Asp Pro Ser Ile Ile Phe Phe Leu
            330                 335                 340 gat ttt tgg aaa aat ata gat aaa agc ata aaa ttc atc atg ata tat    1946
Asp Phe Trp Lys Asn Ile Asp Lys Ser Ile Lys Phe Ile Met Ile Tyr
            345                 350                 355 gat cac cct aaa tat aat tta atg cgt tca gta aat aat gcc cct ctc    1994
Asp His Pro Lys Tyr Asn Leu Met Arg Ser Val Asn Asn Ala Pro Leu
            360                 365                 370 tct tta aat ata aat aat agt gta gat aac tgg att gca tat aat aaa    2042
Ser Leu Asn Ile Asn Asn Ser Val Asp Asn Trp Ile Ala Tyr Asn Lys
        375                 380                 385 aga ttg ctt gat ttt ttt ttg gag aat aaa gaa cga tgt gtg ttg att    2090
Arg Leu Leu Asp Phe Phe Leu Glu Asn Lys Glu Arg Cys Val Leu Ile
390                 395                 400                 405 aat ttt gag gcg ttt caa agc aat aag aaa aat att ata aag cca ttg    2138
Asn Phe Glu Ala Phe Gln Ser Asn Lys Lys Asn Ile Ile Lys Pro Leu
                410                 415                 420 agt aat att ata aaa ata gat aat cta atg tct gcg cat tac aaa aat    2186
Ser Asn Ile Ile Lys Ile Asp Asn Leu Met Ser Ala His Tyr Lys Asn
                425                 430                 435 tca ata ttg ttt gat gtg gtt gag aat aat gat tat aca aaa tca aat    2234
Ser Ile Leu Phe Asp Val Val Glu Asn Asn Asp Tyr Thr Lys Ser Asn
            440                 445                 450 gaa att gcc ctg ctt gaa aaa tat aca act tta ttt tct tta agt gca    2282
Glu Ile Ala Leu Leu Glu Lys Tyr Thr Thr Leu Phe Ser Leu Ser Ala
        455                 460                 465 aat gag act gaa att aca ttt aat gat aca aag gtt agt gag tac tta    2330
Asn Glu Thr Glu Ile Thr Phe Asn Asp Thr Lys Val Ser Glu Tyr Leu
470                 475                 480                 485 gta tct gaa tta ata aaa gaa aga acc gag gtt ctg aag ctt tat aat    2378
Val Ser Glu Leu Ile Lys Glu Arg Thr Glu Val Leu Lys Leu Tyr Asn
                490                 495                 500 gag tta caa gcc tat gca aac cta cct tat ata gaa aca tcg aaa gat    2426
Glu Leu Gln Ala Tyr Ala Asn Leu Pro Tyr Ile Glu Thr Ser Lys Asp
            505                 510                 515 aac gtt tcg gct gag gct gca tta tgg gag gta gtc gaa gag aga aat    2474
Asn Val Ser Ala Glu Ala Ala Leu Trp Glu Val Val Glu Glu Arg Asn
        520                 525                 530 tct atc ttc aat att gta tct cat ttg gtg caa gag tca aaa aag aag    2522
Ser Ile Phe Asn Ile Val Ser His Leu Val Gln Glu Ser Lys Lys Lys
535                 540                 545 gat gca gat att gaa ttg act aaa tct ata ttt aag aaa aga caa ttt    2570
Asp Ala Asp Ile Glu Leu Thr Lys Ser Ile Phe Lys Lys Arg Gln Phe
550                 555                 560                 565 tta tta ttg aac agg att aat gag cta aaa aaa gaa aag gaa gag gta    2618
Leu Leu Leu Asn Arg Ile Asn Glu Leu Lys Lys Glu Lys Glu Glu Val
                570                 575                 580 att aaa ctt tca aaa ata aat cac aac gat gtt gtg aga caa gaa aaa    2666
Ile Lys Leu Ser Lys Ile Asn His Asn Asp Val Val Arg Gln Glu Lys
            585                 590                 595 tat cca gat gat att gaa aaa aaa ata aat gac ata cag aaa tat gaa    2714
Tyr Pro Asp Asp Ile Glu Lys Lys Ile Asn Asp Ile Gln Lys Tyr Glu
        600                 605                 610 gaa gag ata agc gaa aaa gaa tca aaa ctc act cag gca ata tca gaa    2762
Glu Glu Ile Ser Glu Lys Glu Ser Lys Leu Thr Gln Ala Ile Ser Glu
        615                 620                 625 aaa gaa cag att tta aaa caa ttg cat aaa tat gaa gag gag ata agc    2810
Lys Glu Gln Ile Leu Lys Gln Leu His Lys Tyr Glu Glu Glu Ile Ser
```

```
                630             635             640             645
gaa aaa gaa tca aaa ctc act cag gca ata tca gaa aaa gaa cag att    2858
Glu Lys Glu Ser Lys Leu Thr Gln Ala Ile Ser Glu Lys Glu Gln Ile
                650                 655                 660 tta aaa caa ttg cat ata gtg caa gag cag ttg gaa cac tat ttt ata    2906
Leu Lys Gln Leu His Ile Val Gln Glu Gln Leu Glu His Tyr Phe Ile
                665                 670                 675 gaa aat cag gaa att aaa aag aaa ctt cca cct gtg cta tat gga gca    2954
Glu Asn Gln Glu Ile Lys Lys Lys Leu Pro Pro Val Leu Tyr Gly Ala
            680                 685                 690 gct gag cag ata aaa caa gag tta ggt tat cga ctt ggt tat att ata    3002
Ala Glu Gln Ile Lys Gln Glu Leu Gly Tyr Arg Leu Gly Tyr Ile Ile
            695                 700                 705 gtc tcg tat tct aaa tcc ctc aag ggg att att acc atg cca ttt gca    3050
Val Ser Tyr Ser Lys Ser Leu Lys Gly Ile Ile Thr Met Pro Phe Ala
710                 715                 720                 725 ctt atc cgt gag tgt gtt ttt gaa aaa aaa cgt aag aag agt tat ggc    3098
Leu Ile Arg Glu Cys Val Phe Glu Lys Lys Arg Lys Lys Ser Tyr Gly
                730                 735                 740 gtt gat gtg cca ctc tat tta tat gct gat gct gat aag gct gaa aga    3146
Val Asp Val Pro Leu Tyr Leu Tyr Ala Asp Ala Asp Lys Ala Glu Arg
                745                 750                 755 gtt aag aaa cat tta tct tat caa tta ggg cag gct att atc tcc agt    3194
Val Lys Lys His Leu Ser Tyr Gln Leu Gly Gln Ala Ile Ile Ser Ser
                760                 765                 770 gct aat tcg ata ttt gga ttc att acc ctt cca ttt aag tta att gtt    3242
Ala Asn Ser Ile Phe Gly Phe Ile Thr Leu Pro Phe Lys Leu Ile Val
            775                 780                 785 gtt gtt tat aaa tat agg aga gct aaa atc aag ggc tgt taa            3284
Val Val Tyr Lys Tyr Arg Arg Ala Lys Ile Lys Gly Cys
790                 795                 800 aaatgtgaac cctaatgaga tatattgcaa attttatttt tctctttgtg gtgttttgct  3344
ttcgttaaaa tagttagtta ttttatttat ataatatcac gcattataat accaatttat  3404
acttttgcaa gtgaccgtat agattcgcca catattgcaa attttgttct ctcgtaaaat  3464
attttcttct ggtgtcagta attcgagcac ttcatgctgt cttttactgc agtatagtac  3524
taggttttca gctagtttct gattaaatat gtttagctct ttaaagagtc tatttattta  3584
aattcaatga actgttcttt cggcgttcgc ttaaaacgtt cagaggtgcg ttctaggcgt  3644
aaaggggtag gtccataggg cttgctagcg gattcctgcg gtgctttgtc gaagtttcct  3704
gggaactctt tcccgttatc tgcgatgccc tggttgatat cgatagggaa tagccggtct  3764
gcacggcaaa agaagagttt gatgatatca cagttaagtg acggcacggc ctgtgccaga  3824
gcgtagttgc tgtgttcgtc gatcatggta atgacataac agcgcagctc gcccattctg  3884
agctcaatag catctatacc aacgagctca ctgctcttta ccgggcgata gcgttttgat  3944
ctgcgggttg gaggattgta tttttttatga acagtgtttt tccttgggga ggcagtcaca  4004
tcggtatcag tcgcatttta tcgtgtgcgg ccgtgaacat cctgccgatg gttgaaatgc  4064
tcggacagac caggcggtgc tgttcactcc acggcttcaa gcaaacaaaa atctgttctt  4124
ctaggttggg aagctctatt ctcagtcgac gtatttctta cagaattacg agatgccatt  4184
gctttgtgcg atgtactagc ggagctttgc tacgcgaaat aggtgcctct gggccataat  4244
acagcgttcg tgtggataca gcaaaaactt ccgcaactgt attgatctca tgttctcccc  4304
agaagtatat ttttcatcc ttaattttgt aatctcaggt ataacaaagt gtttcatcac   4364
atagatgttg gcatggtaat gcctcaaata tccgccgcag atacgttgca tcaacttagc  4424
```

```
atttccctcg cttgtccgga gataattgca atatctctgt gagcttacac tgtgacattc      4484
gttgagtttt agtgatgttt ttaaagattt atatttataa tatttagtaa atgcagtttt      4544
attctcattt tatttatcat taagtgaatg t atg aac gca gaa tat ata aat         4596
                                   Met Asn Ala Glu Tyr Ile Asn
                                   805 tta gtt gaa cgt aaa aag aaa tta ggg aca aat att ggt gct ctt gat        4644
Leu Val Glu Arg Lys Lys Lys Leu Gly Thr Asn Ile Gly Ala Leu Asp
810             815                 820                 825 ttt tta tta tca att cat aag gag aaa gtt gat ctt caa cat aaa aac        4692
Phe Leu Leu Ser Ile His Lys Glu Lys Val Asp Leu Gln His Lys Asn
                830                 835                 840 tcg cct tta aaa ggt aac gat aac ctt att cac aaa aga ata aac gaa        4740
Ser Pro Leu Lys Gly Asn Asp Asn Leu Ile His Lys Arg Ile Asn Glu
845                 850                 855 tac gac aat gta ctt gaa cta tct aag aat gta tca gct cag aat tct        4788
Tyr Asp Asn Val Leu Glu Leu Ser Lys Asn Val Ser Ala Gln Asn Ser
        860                 865                 870 ggc aat gag ttt tct tat tta ttg gga tat gca gat tct ctt aga aaa        4836
Gly Asn Glu Phe Ser Tyr Leu Leu Gly Tyr Ala Asp Ser Leu Arg Lys
875                 880                 885 gtt ggt atg ttg gat act tat att aaa att gtt tgt tat cta aca att        4884
Val Gly Met Leu Asp Thr Tyr Ile Lys Ile Val Cys Tyr Leu Thr Ile
890                 895                 900                 905 caa tct cgt tat ttt aaa aat ggc gaa cga gtt aag ctt ttt gaa cat        4932
Gln Ser Arg Tyr Phe Lys Asn Gly Glu Arg Val Lys Leu Phe Glu His
                910                 915                 920 ata agt aac gct cta cgg tat tca agg agt gat ttt ctc att aat ctt        4980
Ile Ser Asn Ala Leu Arg Tyr Ser Arg Ser Asp Phe Leu Ile Asn Leu
                925                 930                 935 att ttt gaa cga tat atc gaa tat ata aac cat cta aaa ttg tcg ccc        5028
Ile Phe Glu Arg Tyr Ile Glu Tyr Ile Asn His Leu Lys Leu Ser Pro
            940                 945                 950 aaa caa aaa gat ttt tat ttt tgt acg aag ttt tca aaa ttt cat gat        5076
Lys Gln Lys Asp Phe Tyr Phe Cys Thr Lys Phe Ser Lys Phe His Asp
955                 960                 965 tat act aaa aat gga tat aaa tat tta gca ttt gat aat caa gcc gat        5124
Tyr Thr Lys Asn Gly Tyr Lys Tyr Leu Ala Phe Asp Asn Gln Ala Asp
970                 975                 980                 985 gca ggg tat ggc ctg act tta tta tta aat gca aac gat gat atg  caa       5172
Ala Gly Tyr Gly Leu Thr Leu Leu Leu Asn Ala Asn Asp Asp Met  Gln
                990                 995                 1000 gat agt tat aat  cta ctc cct gag caa  gaa ctt ttt att tgt  aat         5217
Asp Ser Tyr Asn  Leu Leu Pro Glu Gln  Glu Leu Phe Ile Cys  Asn
                 1005                 1010                 1015 gct gta ata gat  aat atg aat att tat  agg agt caa ttt aac  aaa         5262
Ala Val Ile Asp  Asn Met Asn Ile Tyr  Arg Ser Gln Phe Asn  Lys
                 1020                 1025                 1030 tgt cta cga aaa  tac gat tta tca gaa  ata act gat ata tac  cca         5307
Cys Leu Arg Lys  Tyr Asp Leu Ser Glu  Ile Thr Asp Ile Tyr  Pro
                 1035                 1040                 1045 aat aaa att ata  ttg caa gga att aag  ttc gat aag aaa aaa  aat         5352
Asn Lys Ile Ile  Leu Gln Gly Ile Lys  Phe Asp Lys Lys Lys  Asn
                 1050                 1055                 1060 gtt tat gga aaa  gat ctt gtt agt ata  ata atg tca gta ttc  aat         5397
Val Tyr Gly Lys  Asp Leu Val Ser Ile  Ile Met Ser Val Phe  Asn
                 1065                 1070                 1075 tca gaa gat act  att gca tac tca tta  cat tca ttg ttg aat  caa         5442
Ser Glu Asp Thr  Ile Ala Tyr Ser Leu  His Ser Leu Leu Asn  Gln
```

|     |     |     |     |     |     |     |     |     |     |     |     |     |     |      |
|-----|-----|-----|-----|-----|-----|-----|-----|-----|-----|-----|-----|-----|-----|------|
|     |     |     |     |     | 1080 |    |     |     | 1085 |    |     |     | 1090 |      |
| aca | tat | gaa | aat | att | gaa | att | ctc | gtg | tgc | gat | gat | tgt | tca | tcg | 5487 |
| Thr | Tyr | Glu | Asn | Ile | Glu | Ile | Leu | Val | Cys | Asp | Asp | Cys | Ser | Ser |      |
|     |     |     |     | 1095 |   |     |     |     | 1100 |   |     |     | 1105 |     |      |
| gac | aaa | agc | ctt | gaa | ata | att | aag | agc | ata | gct | tat | tct | gat | tca | 5532 |
| Asp | Lys | Ser | Leu | Glu | Ile | Ile | Lys | Ser | Ile | Ala | Tyr | Ser | Asp | Ser |      |
|     |     |     | 1110 |   |     |     |     | 1115 |   |     |     |     | 1120 |     |      |
| aga | gtg | aaa | gta | tat | agc | tca | cga | aaa | aac | caa | ggc | cct | tat | aat | 5577 |
| Arg | Val | Lys | Val | Tyr | Ser | Ser | Arg | Lys | Asn | Gln | Gly | Pro | Tyr | Asn |      |
|     |     | 1125 |   |     |     |     | 1130 |   |     |     |     | 1135 |   |     |      |
| ata | aga | aat | gag | cta | ata | aaa | aaa | gca | cac | ggt | aat | ttc | atc | acc | 5622 |
| Ile | Arg | Asn | Glu | Leu | Ile | Lys | Lys | Ala | His | Gly | Asn | Phe | Ile | Thr |      |
|     |     |     | 1140 |   |     |     |     | 1145 |   |     |     |     | 1150 |     |      |
| ttt | caa | gat | gca | gat | gat | ctt | tct | cat | ccg | gag | aga | ata | caa | aga | 5667 |
| Phe | Gln | Asp | Ala | Asp | Asp | Leu | Ser | His | Pro | Glu | Arg | Ile | Gln | Arg |      |
|     |     |     | 1155 |   |     |     |     | 1160 |   |     |     |     | 1165 |     |      |
| caa | gtt | gag | gtt | ctt | cgc | aat | aat | aag | gct | gta | atc | tgt | atg | gct | 5712 |
| Gln | Val | Glu | Val | Leu | Arg | Asn | Asn | Lys | Ala | Val | Ile | Cys | Met | Ala |      |
|     |     |     | 1170 |   |     |     |     | 1175 |   |     |     |     | 1180 |     |      |
| aac | tgg | atc | cgt | gtt | gcg | tca | aat | gga | aaa | att | caa | ttc | ttc | tat | 5757 |
| Asn | Trp | Ile | Arg | Val | Ala | Ser | Asn | Gly | Lys | Ile | Gln | Phe | Phe | Tyr |      |
|     |     |     | 1185 |   |     |     |     | 1190 |   |     |     |     | 1195 |     |      |
| gat | gat | aaa | gcc | aca | aga | atg | tct | gtt | gta | tcg | tca | atg | ata | aaa | 5802 |
| Asp | Asp | Lys | Ala | Thr | Arg | Met | Ser | Val | Val | Ser | Ser | Met | Ile | Lys |      |
|     |     |     | 1200 |   |     |     |     | 1205 |   |     |     |     | 1210 |     |      |
| aaa | gat | att | ttt | gcg | aca | gtt | ggt | ggc | tat | aga | caa | tct | tta | att | 5847 |
| Lys | Asp | Ile | Phe | Ala | Thr | Val | Gly | Gly | Tyr | Arg | Gln | Ser | Leu | Ile |      |
|     |     |     | 1215 |   |     |     |     | 1220 |   |     |     |     | 1225 |     |      |
| ggt | gca | gat | acg | gag | ttt | tat | gaa | aca | gta | ata | atg | cgt | tat | ggg | 5892 |
| Gly | Ala | Asp | Thr | Glu | Phe | Tyr | Glu | Thr | Val | Ile | Met | Arg | Tyr | Gly |      |
|     |     |     | 1230 |   |     |     |     | 1235 |   |     |     |     | 1240 |     |      |
| cga | gaa | agt | att | gta | aga | tta | ctg | cag | cca | ttg | ata | ttg | ggg | tta | 5937 |
| Arg | Glu | Ser | Ile | Val | Arg | Leu | Leu | Gln | Pro | Leu | Ile | Leu | Gly | Leu |      |
|     |     |     | 1245 |   |     |     |     | 1250 |   |     |     |     | 1255 |     |      |
| tgg | gga | gac | tcc | gga | ctt | acc | agg | aat | aaa | gga | aca | gaa | gct | cta | 5982 |
| Trp | Gly | Asp | Ser | Gly | Leu | Thr | Arg | Asn | Lys | Gly | Thr | Glu | Ala | Leu |      |
|     |     |     | 1260 |   |     |     |     | 1265 |   |     |     |     | 1270 |     |      |
| cct | gat | gga | tat | ata | tca | caa | tct | cga | aga | gaa | tat | agt | gat | atc | 6027 |
| Pro | Asp | Gly | Tyr | Ile | Ser | Gln | Ser | Arg | Arg | Glu | Tyr | Ser | Asp | Ile |      |
|     |     |     | 1275 |   |     |     |     | 1280 |   |     |     |     | 1285 |     |      |
| gcg | gca | aga | caa | cga | gtg | tta | ggg | aaa | agt | atc | gta | agt | gat | aaa | 6072 |
| Ala | Ala | Arg | Gln | Arg | Val | Leu | Gly | Lys | Ser | Ile | Val | Ser | Asp | Lys |      |
|     |     |     | 1290 |   |     |     |     | 1295 |   |     |     |     | 1300 |     |      |
| gat | gta | cgt | ggt | tta | tta | tct | cgc | tat | ggt | ttg | ttt | aaa | gat | gta | 6117 |
| Asp | Val | Arg | Gly | Leu | Leu | Ser | Arg | Tyr | Gly | Leu | Phe | Lys | Asp | Val |      |
|     |     |     | 1305 |   |     |     |     | 1310 |   |     |     |     | 1315 |     |      |
| tca | gga | ata | att | gaa | caa | tag | tttgttattc | tatatatatt | aaattttttgg | | | | | | 6168 |
| Ser | Gly | Ile | Ile | Glu | Gln |     |     |     |     |     |     |     |     |     |      |
|     |     |     | 1320 |   |     |     |     |     |     |     |     |     |     |     |      |
| ggctatataa | a atg | ttc | gga | aca | cta | aaa | ata | act | gtt | tca | ggc | gct | | | 6215 |
|     | Met | Phe | Gly | Thr | Leu | Lys | Ile | Thr | Val | Ser | Gly | Ala |     |     |      |
|     |     |     |     | 1325 |   |     |     |     |     | 1330 |   |     |     |     |      |
| ggt | tac | gtt | ggg | ctt | tca | aat | gga | att | cta | atg | gct | caa | aat | cat | 6260 |
| Gly | Tyr | Val | Gly | Leu | Ser | Asn | Gly | Ile | Leu | Met | Ala | Gln | Asn | His |      |
| 1335 |   |     |     |     | 1340 |   |     |     |     | 1345 |   |     |     |     |      |
| gaa | gtg | gtt | gca | ttt | gat | acc | cat | caa | aaa | aaa | gtt | gac | tta | ctt | 6305 |
| Glu | Val | Val | Ala | Phe | Asp | Thr | His | Gln | Lys | Lys | Val | Asp | Leu | Leu |      |
| 1350 |   |     |     |     | 1355 |   |     |     |     | 1360 |   |     |     |     |      |
| aat | gat | aaa | ctc | tct | cct | ata | gag | gat | aag | gaa | att | gaa | aat | tat | 6350 |

```
            Asn Asp Lys Leu Ser Pro Ile Glu Asp Lys Glu Ile Glu Asn Tyr
            1365            1370            1375 ctt tca act aaa ata ctt aat ttt cgc gca act act aac aaa tat    6395
Leu Ser Thr Lys Ile Leu Asn Phe Arg Ala Thr Thr Asn Lys Tyr
1380            1385            1390 gaa gcc tat aaa aat gcc aat tac gtt att att gct aca cca acg    6440
Glu Ala Tyr Lys Asn Ala Asn Tyr Val Ile Ile Ala Thr Pro Thr
1395            1400            1405 aat tat gac cca ggt tca aat tac ttt gat aca tca agc gtt gaa    6485
Asn Tyr Asp Pro Gly Ser Asn Tyr Phe Asp Thr Ser Ser Val Glu
1410            1415            1420 gct gtc att cgt gac gta acg gaa atc aac cca aac gca att atg    6530
Ala Val Ile Arg Asp Val Thr Glu Ile Asn Pro Asn Ala Ile Met
1425            1430            1435 gtg gtt aaa tct acg gtc cca gta ggt ttc aca aaa aca att aaa    6575
Val Val Lys Ser Thr Val Pro Val Gly Phe Thr Lys Thr Ile Lys
1440            1445            1450 gaa cat tta ggt att aat aat att atc ttc tct cca gaa ttt tta    6620
Glu His Leu Gly Ile Asn Asn Ile Ile Phe Ser Pro Glu Phe Leu
1455            1460            1465 cga gaa gga aga gcc cta tac gat aat ctc cat cca tct cgc att    6665
Arg Glu Gly Arg Ala Leu Tyr Asp Asn Leu His Pro Ser Arg Ile
1470            1475            1480 att atc ggt gaa tgt tct gaa cgg gca gaa cgt ttg gca gtg tta    6710
Ile Ile Gly Glu Cys Ser Glu Arg Ala Glu Arg Leu Ala Val Leu
1485            1490            1495 ttt cag gaa gga gcg att aaa caa aat ata ccc gtt tta ttt aca    6755
Phe Gln Glu Gly Ala Ile Lys Gln Asn Ile Pro Val Leu Phe Thr
1500            1505            1510 gat tct acg gaa gcg gaa gcg att aag tta ttt tca aat act tat    6800
Asp Ser Thr Glu Ala Glu Ala Ile Lys Leu Phe Ser Asn Thr Tyr
1515            1520            1525 ttg gct atg cga gtt gca ttt ttt aat gaa ttg gat agt tac gca    6845
Leu Ala Met Arg Val Ala Phe Phe Asn Glu Leu Asp Ser Tyr Ala
1530            1535            1540 gaa agt ttt ggt ctg aat acg cgt cag att att gac ggt gtt tgt    6890
Glu Ser Phe Gly Leu Asn Thr Arg Gln Ile Ile Asp Gly Val Cys
1545            1550            1555 ttg gat ccg cgc att ggt aat tac tac aat aat cct tct ttt ggt    6935
Leu Asp Pro Arg Ile Gly Asn Tyr Tyr Asn Asn Pro Ser Phe Gly
1560            1565            1570 tat ggt ggc tac tgt ttg cca aaa gat acc aag caa tta tta gcc    6980
Tyr Gly Gly Tyr Cys Leu Pro Lys Asp Thr Lys Gln Leu Leu Ala
1575            1580            1585 aac tat cag tct gtt ccg aat aaa ctt ata tct gca att gtt gat    7025
Asn Tyr Gln Ser Val Pro Asn Lys Leu Ile Ser Ala Ile Val Asp
1590            1595            1600 gct aac cgt aca cgt aag gac ttt atc act aat gtt att ttg aaa    7070
Ala Asn Arg Thr Arg Lys Asp Phe Ile Thr Asn Val Ile Leu Lys
1605            1610            1615 cat aga cca caa gtt gtg ggg gtt tat cgt ttg att atg aaa agt    7115
His Arg Pro Gln Val Val Gly Val Tyr Arg Leu Ile Met Lys Ser
1620            1625            1630 ggt tca gat aat ttt aga gat tct tct att ctt ggt att ata aag    7160
Gly Ser Asp Asn Phe Arg Asp Ser Ser Ile Leu Gly Ile Ile Lys
1635            1640            1645 cgt atc aag aaa aaa ggc gtg aaa gta att att tat gag ccg ctt    7205
Arg Ile Lys Lys Lys Gly Val Lys Val Ile Ile Tyr Glu Pro Leu
1650            1655            1660
```

-continued

```
att tct gga gat aca ttc ttt aac tca cct ttg gaa cgg gag ctg         7250
Ile Ser Gly Asp Thr Phe Phe Asn Ser Pro Leu Glu Arg Glu Leu
1665            1670            1675 gcg atc ttt aaa ggg aaa gct gat att att atc act aac cga atg         7295
Ala Ile Phe Lys Gly Lys Ala Asp Ile Ile Ile Thr Asn Arg Met
1680            1685            1690 tca gag gag ttg aac gat gtg gtc gac aaa gtc tat agt cgc gat         7340
Ser Glu Glu Leu Asn Asp Val Val Asp Lys Val Tyr Ser Arg Asp
1695            1700            1705 ttg ttt aaa tgt gac taa tgtattgtta tatactatta actattaaga            7388
Leu Phe Lys Cys Asp
1710 gaaggaaatg cattatttaa tccgttaaaa atatgcctcg ttggtatgtt ctttattaat    7448 cctcgatcgt aaaataaga                                                7467

<210> SEQ ID NO 25
<211> LENGTH: 238
<212> TYPE: PRT
<213> ORGANISM: Escherichia coli

<400> SEQUENCE: 25

Met Ile Val Ala Asn Met Ser Ser Tyr Pro Pro Arg Lys Lys Glu Leu
1               5                   10                  15

Val His Ser Ile Gln Ser Leu His Ala Gln Val Asp Lys Ile Asn Leu
            20                  25                  30

Cys Leu Asn Glu Phe Glu Glu Ile Pro Glu Glu Leu Asp Gly Phe Ser
        35                  40                  45

Lys Leu Asn Pro Val Ile Pro Asp Lys Asp Tyr Lys Asp Val Gly Lys
    50                  55                  60

Phe Ile Phe Pro Cys Ala Lys Asn Asp Met Ile Val Leu Thr Asp Asp
65                  70                  75                  80

Asp Ile Ile Tyr Pro Pro Asp Tyr Val Glu Lys Met Leu Asn Phe Tyr
                85                  90                  95

Asn Ser Phe Ala Ile Phe Asn Cys Ile Val Gly Ile His Gly Cys Ile
            100                 105                 110

Tyr Ile Asp Ala Phe Asp Gly Asp Gln Ser Lys Arg Lys Val Phe Ser
        115                 120                 125

Phe Thr Gln Gly Leu Leu Arg Pro Arg Val Val Asn Gln Leu Gly Thr
    130                 135                 140

Gly Thr Val Phe Leu Lys Ala Asp Gln Leu Pro Ser Leu Lys Tyr Met
145                 150                 155                 160

Asp Gly Ser Gln Arg Phe Val Asp Val Arg Phe Ser Arg Tyr Met Leu
                165                 170                 175

Glu Asn Glu Ile Gly Met Ile Cys Val Pro Arg Glu Lys Asn Trp Leu
            180                 185                 190

Arg Glu Val Ser Ser Gly Ser Met Glu Gly Leu Trp Asn Thr Phe Thr
        195                 200                 205

Lys Lys Trp Pro Leu Asp Ile Ile Lys Glu Thr Gln Ala Ile Ala Gly
    210                 215                 220

Tyr Ser Lys Leu Asn Leu Glu Leu Val Tyr Asn Val Glu Gly
225                 230                 235

<210> SEQ ID NO 26
<211> LENGTH: 563
<212> TYPE: PRT
<213> ORGANISM: Escherichia coli
```

<400> SEQUENCE: 26

```
Met Met Asn Lys Leu Val Leu Val Gly His Pro Gly Ser Lys Tyr Gln
1               5                   10                  15

Ile Val Glu His Phe Leu Lys Glu Ile Gly Met Asn Ser Pro Asn Tyr
            20                  25                  30

Ser Thr Ser Asn Lys Ile Ser Pro Glu Tyr Ile Thr Ala Ser Leu Cys
        35                  40                  45

Gln Phe Tyr Gln Thr Pro Glu Val Asn Asp Val Val Asp Glu Arg Glu
    50                  55                  60

Phe Ser Ala Val Gln Val Ser Thr Met Trp Asp Ser Met Val Leu Glu
65                  70                  75                  80

Leu Met Met Asn Asn Leu Asn Asn Lys Leu Trp Gly Trp Ala Asp Pro
                85                  90                  95

Ser Ile Ile Phe Phe Leu Asp Phe Trp Lys Asn Ile Asp Lys Ser Ile
            100                 105                 110

Lys Phe Ile Met Ile Tyr Asp His Pro Lys Tyr Asn Leu Met Arg Ser
        115                 120                 125

Val Asn Asn Ala Pro Leu Ser Leu Asn Ile Asn Asn Ser Val Asp Asn
    130                 135                 140

Trp Ile Ala Tyr Asn Lys Arg Leu Leu Asp Phe Phe Leu Glu Asn Lys
145                 150                 155                 160

Glu Arg Cys Val Leu Ile Asn Phe Glu Ala Phe Gln Ser Asn Lys Lys
                165                 170                 175

Asn Ile Ile Lys Pro Leu Ser Asn Ile Ile Lys Ile Asp Asn Leu Met
            180                 185                 190

Ser Ala His Tyr Lys Asn Ser Ile Leu Phe Asp Val Val Glu Asn Asn
        195                 200                 205

Asp Tyr Thr Lys Ser Asn Glu Ile Ala Leu Leu Glu Lys Tyr Thr Thr
    210                 215                 220

Leu Phe Ser Leu Ser Ala Asn Glu Thr Glu Ile Thr Phe Asn Asp Thr
225                 230                 235                 240

Lys Val Ser Glu Tyr Leu Val Ser Glu Leu Ile Lys Glu Arg Thr Glu
                245                 250                 255

Val Leu Lys Leu Tyr Asn Glu Leu Gln Ala Tyr Ala Asn Leu Pro Tyr
            260                 265                 270

Ile Glu Thr Ser Lys Asp Asn Val Ser Ala Glu Ala Ala Leu Trp Glu
        275                 280                 285

Val Val Glu Glu Arg Asn Ser Ile Phe Asn Ile Val Ser His Leu Val
    290                 295                 300

Gln Glu Ser Lys Lys Lys Asp Ala Asp Ile Glu Leu Thr Lys Ser Ile
305                 310                 315                 320

Phe Lys Lys Arg Gln Phe Leu Leu Leu Asn Arg Ile Asn Glu Leu Lys
                325                 330                 335

Lys Glu Lys Glu Glu Val Ile Lys Leu Ser Lys Ile Asn His Asn Asp
            340                 345                 350

Val Val Arg Gln Glu Lys Tyr Pro Asp Asp Ile Glu Lys Lys Ile Asn
        355                 360                 365

Asp Ile Gln Lys Tyr Glu Glu Ile Ser Glu Lys Glu Ser Lys Leu
    370                 375                 380

Thr Gln Ala Ile Ser Glu Lys Glu Gln Ile Leu Lys Gln Leu His Lys
385                 390                 395                 400

Tyr Glu Glu Glu Ile Ser Glu Lys Glu Ser Lys Leu Thr Gln Ala Ile
                405                 410                 415
```

Ser Glu Lys Glu Gln Ile Leu Lys Gln Leu His Ile Val Gln Glu Gln
          420                 425                 430

Leu Glu His Tyr Phe Ile Glu Asn Gln Glu Ile Lys Lys Leu Pro
          435                 440                 445

Pro Val Leu Tyr Gly Ala Ala Glu Gln Ile Lys Gln Glu Leu Gly Tyr
450                 455                 460

Arg Leu Gly Tyr Ile Ile Val Ser Tyr Ser Lys Ser Leu Lys Gly Ile
465                 470                 475                 480

Ile Thr Met Pro Phe Ala Leu Ile Arg Glu Cys Val Phe Glu Lys Lys
                485                 490                 495

Arg Lys Lys Ser Tyr Gly Val Asp Val Pro Leu Tyr Leu Tyr Ala Asp
                500                 505                 510

Ala Asp Lys Ala Glu Arg Val Lys Lys His Leu Ser Tyr Gln Leu Gly
                515                 520                 525

Gln Ala Ile Ile Ser Ser Ala Asn Ser Ile Phe Gly Phe Ile Thr Leu
530                 535                 540

Pro Phe Lys Leu Ile Val Val Tyr Lys Tyr Arg Arg Ala Lys Ile
545                 550                 555                 560

Lys Gly Cys

<210> SEQ ID NO 27
<211> LENGTH: 520
<212> TYPE: PRT
<213> ORGANISM: Escherichia coli

<400> SEQUENCE: 27

Met Asn Ala Glu Tyr Ile Asn Leu Val Glu Arg Lys Lys Lys Leu Gly
1               5                   10                  15

Thr Asn Ile Gly Ala Leu Asp Phe Leu Leu Ser Ile His Lys Glu Lys
                20                  25                  30

Val Asp Leu Gln His Lys Asn Ser Pro Leu Lys Gly Asn Asp Asn Leu
            35                  40                  45

Ile His Lys Arg Ile Asn Glu Tyr Asp Asn Val Leu Glu Leu Ser Lys
        50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
210                 215                 220

Ser Gln Phe Asn Lys Cys Leu Arg Lys Tyr Asp Leu Ser Glu Ile Thr
225                 230                 235                 240

Asp Ile Tyr Pro Asn Lys Ile Ile Leu Gln Gly Ile Lys Phe Asp Lys
            245                 250                 255

Lys Lys Asn Val Tyr Gly Lys Asp Leu Val Ser Ile Ile Met Ser Val
            260                 265                 270

Phe Asn Ser Glu Asp Thr Ile Ala Tyr Ser Leu His Ser Leu Leu Asn
            275                 280                 285

Gln Thr Tyr Glu Asn Ile Glu Ile Leu Val Cys Asp Asp Cys Ser Ser
            290                 295                 300

Asp Lys Ser Leu Glu Ile Ile Lys Ser Ile Ala Tyr Ser Asp Ser Arg
305                 310                 315                 320

Val Lys Val Tyr Ser Ser Arg Lys Asn Gln Gly Pro Tyr Asn Ile Arg
            325                 330                 335

Asn Glu Leu Ile Lys Lys Ala His Gly Asn Phe Ile Thr Phe Gln Asp
            340                 345                 350

Ala Asp Asp Leu Ser His Pro Glu Arg Ile Gln Arg Gln Val Glu Val
            355                 360                 365

Leu Arg Asn Asn Lys Ala Val Ile Cys Met Ala Asn Trp Ile Arg Val
370                 375                 380

Ala Ser Asn Gly Lys Ile Gln Phe Phe Tyr Asp Asp Lys Ala Thr Arg
385                 390                 395                 400

Met Ser Val Val Ser Ser Met Ile Lys Lys Asp Ile Phe Ala Thr Val
            405                 410                 415

Gly Gly Tyr Arg Gln Ser Leu Ile Gly Ala Asp Thr Glu Phe Tyr Glu
            420                 425                 430

Thr Val Ile Met Arg Tyr Gly Arg Glu Ser Ile Val Arg Leu Leu Gln
            435                 440                 445

Pro Leu Ile Leu Gly Leu Trp Gly Asp Ser Gly Leu Thr Arg Asn Lys
            450                 455                 460

Gly Thr Glu Ala Leu Pro Asp Gly Tyr Ile Ser Gln Ser Arg Arg Glu
465                 470                 475                 480

Tyr Ser Asp Ile Ala Ala Arg Gln Arg Val Leu Gly Lys Ser Ile Val
            485                 490                 495

Ser Asp Lys Asp Val Arg Gly Leu Leu Ser Arg Tyr Gly Leu Phe Lys
            500                 505                 510

Asp Val Ser Gly Ile Ile Glu Gln
            515                 520

<210> SEQ ID NO 28
<211> LENGTH: 392
<212> TYPE: PRT
<213> ORGANISM: Escherichia coli

<400> SEQUENCE: 28

Met Phe Gly Thr Leu Lys Ile Thr Val Ser Gly Ala Gly Tyr Val Gly
1               5                   10                  15

Leu Ser Asn Gly Ile Leu Met Ala Gln Asn His Glu Val Val Ala Phe
            20                  25                  30

Asp Thr His Gln Lys Lys Val Asp Leu Leu Asn Asp Lys Leu Ser Pro
            35                  40                  45

Ile Glu Asp Lys Glu Ile Glu Asn Tyr Leu Ser Thr Lys Ile Leu Asn
50                  55                  60

Phe Arg Ala Thr Thr Asn Lys Tyr Glu Ala Tyr Lys Asn Ala Asn Tyr

```
                65                  70                  75                  80
Val Ile Ile Ala Thr Pro Thr Asn Tyr Asp Pro Gly Ser Asn Tyr Phe
                    85                  90                  95

Asp Thr Ser Ser Val Glu Ala Val Ile Arg Asp Val Thr Glu Ile Asn
                100                 105                 110

Pro Asn Ala Ile Met Val Val Lys Ser Thr Val Pro Val Gly Phe Thr
                115                 120                 125

Lys Thr Ile Lys Glu His Leu Gly Ile Asn Asn Ile Ile Phe Ser Pro
130                 135                 140

Glu Phe Leu Arg Glu Gly Arg Ala Leu Tyr Asp Asn Leu His Pro Ser
145                 150                 155                 160

Arg Ile Ile Ile Gly Glu Cys Ser Glu Arg Ala Glu Arg Leu Ala Val
                165                 170                 175

Leu Phe Gln Glu Gly Ala Ile Lys Gln Asn Ile Pro Val Leu Phe Thr
                180                 185                 190

Asp Ser Thr Glu Ala Glu Ala Ile Lys Leu Phe Ser Asn Thr Tyr Leu
                195                 200                 205

Ala Met Arg Val Ala Phe Phe Asn Glu Leu Asp Ser Tyr Ala Glu Ser
210                 215                 220

Phe Gly Leu Asn Thr Arg Gln Ile Ile Asp Gly Val Cys Leu Asp Pro
225                 230                 235                 240

Arg Ile Gly Asn Tyr Tyr Asn Asn Pro Ser Phe Gly Tyr Gly Gly Tyr
                245                 250                 255

Cys Leu Pro Lys Asp Thr Lys Gln Leu Leu Ala Asn Tyr Gln Ser Val
                260                 265                 270

Pro Asn Lys Leu Ile Ser Ala Ile Val Asp Ala Asn Arg Thr Arg Lys
                275                 280                 285

Asp Phe Ile Thr Asn Val Ile Leu Lys His Arg Pro Gln Val Val Gly
                290                 295                 300

Val Tyr Arg Leu Ile Met Lys Ser Gly Ser Asp Asn Phe Arg Asp Ser
305                 310                 315                 320

Ser Ile Leu Gly Ile Ile Lys Arg Ile Lys Lys Gly Val Lys Val
                325                 330                 335

Ile Ile Tyr Glu Pro Leu Ile Ser Gly Asp Thr Phe Phe Asn Ser Pro
                340                 345                 350

Leu Glu Arg Glu Leu Ala Ile Phe Lys Gly Lys Ala Asp Ile Ile Ile
                355                 360                 365

Thr Asn Arg Met Ser Glu Glu Leu Asn Asp Val Val Asp Lys Val Tyr
                370                 375                 380

Ser Arg Asp Leu Phe Lys Cys Asp
385                 390

<210> SEQ ID NO 29
<211> LENGTH: 5624
<212> TYPE: DNA
<213> ORGANISM: Escherichia coli
<220> FEATURE:
<221> NAME/KEY: CDS
<222> LOCATION: (800)..(1690)
<220> FEATURE:
<221> NAME/KEY: CDS
<222> LOCATION: (1816)..(2745)
<220> FEATURE:
<221> NAME/KEY: CDS
<222> LOCATION: (2749)..(3741)

<400> SEQUENCE: 29
```

-continued

```
gctggtgatc ctgacgtcgg gcatcgactt atcggtaggt tctctgttgg cgctgaccgg      60
cgcagttgct gcatctatcg tcggcattga agtcaatgcg ctggtggctg tcgctgctgc     120
tctcgcgtta ggtgccgcaa ttggtgcggt aaccggggtg attgtagcga aggtcgcgt     180 ccaggcgttt atcgctacgc tggttatgat gcttttactg cgcggcgtga ccatggttta     240
taccaacggt agcccagtga ataccggctt tactgagaac gccgatctgt ttggctggtt     300
tggtattggt cgtccgctgg gcgtaccgac gccagtctgg atcatgggga ttgtcttcct     360
cgcggcctgg tacatgctgc atcacacgcg tctggggcgt tacatctacg cgctgggcgg     420
caacgaagcg gcaacgcgtc tttctggtat caacgtcaat aaaatcaaaa tcatcgtcta     480
ttctctttgt ggtctgctgg catcgctggc cgggatcatt gaagtggcgc gtctctcctc     540
cgcacaaccc acggcgggga ctggctatga gctggatgct attgctgcgg tggttctggg     600
cggtacgagt ctggcgggcg aaaaggtcg cattgttggg acgttgatcg cgcattaat      660 tcttggcttc cttaataatg gattgaattt gttaggtgtt tcctcctatt accagatgat     720
cgtcaaagcg gtggtgattt tgctggcggt gctggtagaa acaaaaagc agtaataacg     780 actacaggac atcttgaat atg aac atg aaa aaa ctg gct acc ctg gtt tcc     832
                     Met Asn Met Lys Lys Leu Ala Thr Leu Val Ser
                      1               5                  10 gct gtt gcg cta agc gcc acc gtc agt gcg aat gcg atg gca aaa gac     880
Ala Val Ala Leu Ser Ala Thr Val Ser Ala Asn Ala Met Ala Lys Asp
         15                  20                  25 acc atc gcg ctg gtg gtc tcc acg ctt aac aac ccg ttc ttt gta tcg     928
Thr Ile Ala Leu Val Val Ser Thr Leu Asn Asn Pro Phe Phe Val Ser
     30                  35                  40 ctg aaa gat ggc gcg cag aaa gag gcg gat aaa ctt ggc tat aac ctg     976
Leu Lys Asp Gly Ala Gln Lys Glu Ala Asp Lys Leu Gly Tyr Asn Leu
 45                  50                  55 gtg gtg ctg gac tcc cag aac aac ccg gcg aaa gag ctg gcg aac gtg    1024
Val Val Leu Asp Ser Gln Asn Asn Pro Ala Lys Glu Leu Ala Asn Val
 60                  65                  70                  75 cag gac tta acc gtt cgc ggc aca aaa att ctg ctg att aac ccg acc    1072
Gln Asp Leu Thr Val Arg Gly Thr Lys Ile Leu Leu Ile Asn Pro Thr
             80                  85                  90 gac tcc gac gca gtg ggt aat gct gtg aag atg gct aac cag gcg aac    1120
Asp Ser Asp Ala Val Gly Asn Ala Val Lys Met Ala Asn Gln Ala Asn
         95                 100                 105 atc ccg gtt atc act ctt gac cgc cag gca acg aaa ggt gaa gtg gtg    1168
Ile Pro Val Ile Thr Leu Asp Arg Gln Ala Thr Lys Gly Glu Val Val
     110                 115                 120 agc cac att gct tct gat aac gta ctg ggc ggc aaa atc gct ggt gat    1216
Ser His Ile Ala Ser Asp Asn Val Leu Gly Gly Lys Ile Ala Gly Asp
 125                 130                 135 tac atc gcg aag aaa gcg ggt gaa ggt gcc aaa gtt atc gag ctg caa    1264
Tyr Ile Ala Lys Lys Ala Gly Glu Gly Ala Lys Val Ile Glu Leu Gln
140                 145                 150                 155 ggc att gct ggt aca tcc gca gcc cgt gaa cgt ggc gaa ggc ttc cag    1312
Gly Ile Ala Gly Thr Ser Ala Ala Arg Glu Arg Gly Glu Gly Phe Gln
                 160                 165                 170 cag gcc gtt gct gct cac aag ttt aat gtt ctt gcc agc cag cca gca    1360
Gln Ala Val Ala Ala His Lys Phe Asn Val Leu Ala Ser Gln Pro Ala
             175                 180                 185 gat ttt gat cgc act aaa ggt ttg aac gta atg cag aac ctg ttg acc    1408
Asp Phe Asp Arg Thr Lys Gly Leu Asn Val Met Gln Asn Leu Leu Thr
         190                 195                 200 gct cat ccg gat gtt cag gct gta ttc gcg cag aat gat gaa atg gcg    1456
```

```
                Ala His Pro Asp Val Gln Ala Val Phe Ala Gln Asn Asp Glu Met Ala
                    205                 210                 215 ctg ggc gcg ctg cgc gca ctg caa act gcc ggt aaa tcg gat gtg atg              1504
Leu Gly Ala Leu Arg Ala Leu Gln Thr Ala Gly Lys Ser Asp Val Met
220                 225                 230                 235 gtc gtc gga ttt gac ggt aca ccg gat ggc gaa aaa gcg gtg aat gat              1552
Val Val Gly Phe Asp Gly Thr Pro Asp Gly Glu Lys Ala Val Asn Asp
                    240                 245                 250 ggc aaa cta gca gcg act atc gct cag cta ccc gat cag att ggc gcg              1600
Gly Lys Leu Ala Ala Thr Ile Ala Gln Leu Pro Asp Gln Ile Gly Ala
                255                 260                 265 aaa ggc gtc gaa acc gca gat aaa gtg ctg aaa ggc gag aaa gtt cag              1648
Lys Gly Val Glu Thr Ala Asp Lys Val Leu Lys Gly Glu Lys Val Gln
            270                 275                 280 gct aag tat ccg gtt gat ctg aaa ctg gtt gtt aag cag tag                      1690
Ala Lys Tyr Pro Val Asp Leu Lys Leu Val Val Lys Gln
285                 290                 295 ttttaatcag gttgtatgac ctgatggtga cataaatacg tcatcgacag atgaacgtgt            1750
aatataaaga aaagcagggc acgcgccacc ctaacacggt ggcgcatttt atggacatcc            1810 cgaat atg caa aac gca ggc agc ctc gtt gtt ctt ggc agc att aat gct            1860
      Met Gln Asn Ala Gly Ser Leu Val Val Leu Gly Ser Ile Asn Ala
          300                 305                 310 gac cac att ctt aat ctt caa tct ttt cct act cca ggc gaa acc gta              1908
Asp His Ile Leu Asn Leu Gln Ser Phe Pro Thr Pro Gly Glu Thr Val
                315                 320                 325 acc ggt aac cac tat cag gtt gca ttt ggc ggc aaa ggc gcg aat cag              1956
Thr Gly Asn His Tyr Gln Val Ala Phe Gly Gly Lys Gly Ala Asn Gln
            330                 335                 340 gct gtg gct gct ggg cgt agc ggt gcg aat atc gcg ttt att gcc tgt              2004
Ala Val Ala Ala Gly Arg Ser Gly Ala Asn Ile Ala Phe Ile Ala Cys
345                 350                 355 acg ggt gat gac agc att ggt gag agc gtt cgc cag cag ctc gcc act              2052
Thr Gly Asp Asp Ser Ile Gly Glu Ser Val Arg Gln Gln Leu Ala Thr
360                 365                 370                 375 gat aac att gat att act ccg gtc agc gtg atc aaa ggc gaa tca aca              2100
Asp Asn Ile Asp Ile Thr Pro Val Ser Val Ile Lys Gly Glu Ser Thr
                380                 385                 390 ggt gtg gcg ctg att ttt gtt aat ggc gaa ggt gag aat gtc atc ggt              2148
Gly Val Ala Leu Ile Phe Val Asn Gly Glu Gly Glu Asn Val Ile Gly
                395                 400                 405 att cat gcc ggc gct aat gct gcc ctt tcc ccg gcg ctg gtg gaa gcg              2196
Ile His Ala Gly Ala Asn Ala Ala Leu Ser Pro Ala Leu Val Glu Ala
            410                 415                 420 caa cgt gag cgt att gcc aac gcg tca gca tta tta atg cag ctg gaa              2244
Gln Arg Glu Arg Ile Ala Asn Ala Ser Ala Leu Leu Met Gln Leu Glu
425                 430                 435 tca cca ctc gaa agt gtg atg gca gcg gcg aaa atc gcc cat caa aat              2292
Ser Pro Leu Glu Ser Val Met Ala Ala Ala Lys Ile Ala His Gln Asn
440                 445                 450                 455 aag act atc gtt gcg ctt aac ccg gct ccg gct cgc gaa ctt cct gac              2340
Lys Thr Ile Val Ala Leu Asn Pro Ala Pro Ala Arg Glu Leu Pro Asp
                460                 465                 470 gaa ctg ctg gcg ctg gtg gac att att acg cca aac gaa acg gaa gca              2388
Glu Leu Leu Ala Leu Val Asp Ile Ile Thr Pro Asn Glu Thr Glu Ala
                475                 480                 485 gaa aag ctc acc ggt att cgt gtt gaa aat gat gaa gat gca gcg aag              2436
Glu Lys Leu Thr Gly Ile Arg Val Glu Asn Asp Glu Asp Ala Ala Lys
            490                 495                 500
```

-continued

| | |
|---|---|
| gcg gcg cag gta ctg cat gaa aaa ggt atc cgt act gta ctg att act<br>Ala Ala Gln Val Leu His Glu Lys Gly Ile Arg Thr Val Leu Ile Thr<br>505                    510                    515 | 2484 |
| tta gga agt cgt ggt gta tgg gct agc gtg aat ggt gaa ggt cag cgc<br>Leu Gly Ser Arg Gly Val Trp Ala Ser Val Asn Gly Glu Gly Gln Arg<br>520                    525                    530                    535 | 2532 |
| gtt cct gga ttc cgg gtg cag gct gtc gat acc att gct gcc gga gat<br>Val Pro Gly Phe Arg Val Gln Ala Val Asp Thr Ile Ala Ala Gly Asp<br>540                    545                    550 | 2580 |
| acc ttt aac ggt gcg tta atc acg gca ttg gaa gaa aaa cca ttg<br>Thr Phe Asn Gly Ala Leu Ile Thr Ala Leu Glu Glu Lys Pro Leu<br>555                    560                    565 | 2628 |
| cca gag gcg att cgt ttt gcc cat gct gcc gct gcg att gcc gta aca<br>Pro Glu Ala Ile Arg Phe Ala His Ala Ala Ala Ala Ile Ala Val Thr<br>570                    575                    580 | 2676 |
| cgt aaa ggc gca caa cct tcc gta ccg tgg cgt gaa gag atc gac gca<br>Arg Lys Gly Ala Gln Pro Ser Val Pro Trp Arg Glu Glu Ile Asp Ala<br>585                    590                    595 | 2724 |
| ttt tta gac agg cag agg tga cgc ttg gct aca atg aaa gat gtt gcc<br>Phe Leu Asp Arg Gln Arg       Met Ala Thr Met Lys Asp Val Ala<br>600                    605                                610 | 2772 |
| cgc ctg gcg ggc gtt tct acc tca aca gtt tct cac gtt atc aat aaa<br>Arg Leu Ala Gly Val Ser Thr Ser Thr Val Ser His Val Ile Asn Lys<br>615                    620                    625 | 2820 |
| gat cgc ttc gtc agt gaa gcg att acc gcc aaa gtt gaa gcg gcg att<br>Asp Arg Phe Val Ser Glu Ala Ile Thr Ala Lys Val Glu Ala Ala Ile<br>630                    635                    640                    645 | 2868 |
| aaa gaa ctc aat tac gcg cca tca gct ctg gcg cgt agc ctc aaa ctc<br>Lys Glu Leu Asn Tyr Ala Pro Ser Ala Leu Ala Arg Ser Leu Lys Leu<br>650                    655                    660 | 2916 |
| aat caa aca cat acc att ggc atg ttg atc act gcc agt acc aat cct<br>Asn Gln Thr His Thr Ile Gly Met Leu Ile Thr Ala Ser Thr Asn Pro<br>665                    670                    675 | 2964 |
| ttc tat tca gaa ctg gtg cgt ggc gtt gaa cgc agc tgc ttc gaa cgc<br>Phe Tyr Ser Glu Leu Val Arg Gly Val Glu Arg Ser Cys Phe Glu Arg<br>680                    685                    690 | 3012 |
| ggt tat agt ctc gtc ctt tgc aat acc gaa ggc gat gaa cag cgg atg<br>Gly Tyr Ser Leu Val Leu Cys Asn Thr Glu Gly Asp Glu Gln Arg Met<br>695                    700                    705 | 3060 |
| aat cgc aat ctg gaa acg ctg atg caa aaa cgc gtt gat ggc ttg ctg<br>Asn Arg Asn Leu Glu Thr Leu Met Gln Lys Arg Val Asp Gly Leu Leu<br>710                    715                    720                    725 | 3108 |
| tta ctg tgc acc gaa acg cat caa cct tcg cgt gaa atc atg caa cgt<br>Leu Leu Cys Thr Glu Thr His Gln Pro Ser Arg Glu Ile Met Gln Arg<br>730                    735                    740 | 3156 |
| tat ccg aca gtg cct act gtg atg atg gac tgg gct ccg ttc gat ggc<br>Tyr Pro Thr Val Pro Thr Val Met Met Asp Trp Ala Pro Phe Asp Gly<br>745                    750                    755 | 3204 |
| gac agc gat ctt att cag gat aac tcg ttg ctg gga gga gac tta gca<br>Asp Ser Asp Leu Ile Gln Asp Asn Ser Leu Leu Gly Gly Asp Leu Ala<br>760                    765                    770 | 3252 |
| acg caa tat ctg atc gat aaa ggt cat acc cgt atc gcc tgt att acc<br>Thr Gln Tyr Leu Ile Asp Lys Gly His Thr Arg Ile Ala Cys Ile Thr<br>775                    780                    785 | 3300 |
| ggc ccg ctg gat aaa act ccg gcg cgc ctg cgg ttg gaa ggt tat cgg<br>Gly Pro Leu Asp Lys Thr Pro Ala Arg Leu Arg Leu Glu Gly Tyr Arg<br>790                    795                    800                    805 | 3348 |
| gcg gcg atg aaa cgt gcg ggt ctc aac att cct gat ggc tat gaa gtc<br>Ala Ala Met Lys Arg Ala Gly Leu Asn Ile Pro Asp Gly Tyr Glu Val<br>810                    815                    820 | 3396 |

```
act ggt gat ttt gaa ttt aac ggc ggg ttt gac gct atg cgc caa ctg    3444
Thr Gly Asp Phe Glu Phe Asn Gly Gly Phe Asp Ala Met Arg Gln Leu
            825                 830                 835 cta tca cat ccg ctg cgt cct cag gcc gtc ttt acc gga aat gac gct    3492
Leu Ser His Pro Leu Arg Pro Gln Ala Val Phe Thr Gly Asn Asp Ala
        840                 845                 850 atg gct gtt ggc gtt tac cag gcg tta tat cag gca gag tta cag gtt    3540
Met Ala Val Gly Val Tyr Gln Ala Leu Tyr Gln Ala Glu Leu Gln Val
855                 860                 865 ccg cag gat atc gcg gtg att ggc tat gac gat atc gaa ctg gca agc    3588
Pro Gln Asp Ile Ala Val Ile Gly Tyr Asp Asp Ile Glu Leu Ala Ser
870                 875                 880                 885 ttt atg acg cca cca tta acc act atc cac caa ccg aaa gat gaa ctg    3636
Phe Met Thr Pro Pro Leu Thr Thr Ile His Gln Pro Lys Asp Glu Leu
                890                 895                 900 ggg gag ctg gcg att gat gta ctc atc cat cgg ata acc cag ccg acc    3684
Gly Glu Leu Ala Ile Asp Val Leu Ile His Arg Ile Thr Gln Pro Thr
            905                 910                 915 ctt cag caa caa cga tta caa ctt act ccg att ctg atg gaa cgc ggt    3732
Leu Gln Gln Gln Arg Leu Gln Leu Thr Pro Ile Leu Met Glu Arg Gly
        920                 925                 930 tcg gct tag atttacgctg tcttttgatc aaattattac catcggttgt             3781
Ser Ala
    935 tttcagaagc atgaacattg ctgctgaagc aacagtaata atgcccattg tgataaacgt   3841
atagtggaat tgttcgacag tcgttgtgcc ttccattcct tcataaacgc gaaggacggc   3901
cgcacttaca gcaacgccta aactaatcga cagttgctgc gtgaccgcca gaacactgtt   3961
accgctgctg gcattgtcat cggtcagatc ggcaagtgtg atggtattca tcgcggtaaa   4021
ctgcgtcgac atagccatcc ctaatataaa caacggcaag atcagcatcc atatagccat   4081
tgctggtgat tgcaaagaga actgagcgat cattagccca ataatcaccg tgatccccac   4141
taacgtatgg cgatagccca gacgacgtaa gacttgggta accatcgatt ttgcaataat   4201
ggaacctaac gctgtcggtg ccatcataca gccagccata aacgcctgat aaccaaatcc   4261
tacctgtaac atcaatggca taaggaacgg tacacagccg gtccccagac gggttgcaat   4321
attgcctacg ataccgatcg agaaagtgcg ggttttaaat aaatctaatg aaattaatgg   4381
gtttggcgtg cgtcgtgcat ggagaatata gagaagcagt aacccgatgc tggtgacaat   4441
taccgtcaag gcaatccagc tggcgacaat cttttcccg aatagctcta ttccgcttga    4501
gaagagaaca aggctgaggc caaacagcaa aaagccagtg atatcgaatc tgcgtcgtgc   4561
ggtggtgaaa ttgggcatat gtttgcgcgc gtaaagaagg cccgcaatac ctatggggat   4621
attgattaaa aatatccagt gccaggttgc ccaggtgacc agcacgccgc caagaacggg   4681
gcctaaaatt ggccccacca gacccggcat ggcgacaaaa ttcaatactg gaagaagttc   4741
attacgagga taagcgcgca gtaaggccag ccgagcaaca ggcatcatca ttgcgccgcc   4801
tatcccctga ataacccgga agacaaccag ctgtggtagc gaattagaaa gtgcgcaggc   4861
cagagaaccc aatgtgaaca gactcacggc aagggtaaaa atgcgacgcg taccgaagcg   4921
atcggctagc catccgctta ccggaataag catcgccacc gtcagcgtat aactgatgat   4981
ggctgattgc atcgcgagag gagaacgatt aaggctatga gcggttgcgg gtaaggcggt   5041
attaagaata gtggcatcaa gtgcctgcat gaagaaggcc atcgccgcga tccacggcaa   5101
acccgccata ctgcgcttct ttttatcgct cattcaatgt cctgttatcg ggttatcact   5161
```

```
tatcaggtga gcgtagcagc gcctgacaag ctttaaatgc cgcgtcgcca tcgctttgga   5221
taatcgcatc gacaatcgcc tgatgcagat ccagctttat cactgtgtcg ctggtaattg   5281
acgtgaagta agtgtgataa accgaatgga atagcgaggc gaatgaggtc aaaaacggat   5341
tggcgctcat ttcatagata tgctcatgcc aggccatatc gacttcgatc cagcgttcac   5401
ggcgaaagtt ctcttttaat gccgccattt cggccattaa cgtattgaga tgcgctttct   5461
gttccgcggt gccaaccgtt gctgccagta ggcaggcttg cggctccaga cagatacgca   5521
taaccagaaa gtgatcgatg acctgatgaa agttctcttc tgtcatccac caggtaagca   5581
attcctgatc aagaaaattc cagttcgatt gtggcatgac ccg                     5624
```

<210> SEQ ID NO 30
<211> LENGTH: 296
<212> TYPE: PRT
<213> ORGANISM: Escherichia coli

<400> SEQUENCE: 30

```
Met Asn Met Lys Lys Leu Ala Thr Leu Val Ser Ala Val Ala Leu Ser
1               5                   10                  15

Ala Thr Val Ser Ala Asn Ala Met Ala Lys Asp Thr Ile Ala Leu Val
            20                  25                  30

Val Ser Thr Leu Asn Asn Pro Phe Phe Val Ser Leu Lys Asp Gly Ala
        35                  40                  45

Gln Lys Glu Ala Asp Lys Leu Gly Tyr Asn Leu Val Val Leu Asp Ser
    50                  55                  60

Gln Asn Asn Pro Ala Lys Glu Leu Ala Asn Val Gln Asp Leu Thr Val
65                  70                  75                  80

Arg Gly Thr Lys Ile Leu Leu Ile Asn Pro Thr Asp Ser Asp Ala Val
                85                  90                  95

Gly Asn Ala Val Lys Met Ala Asn Gln Ala Asn Ile Pro Val Ile Thr
            100                 105                 110

Leu Asp Arg Gln Ala Thr Lys Gly Glu Val Val Ser His Ile Ala Ser
        115                 120                 125

Asp Asn Val Leu Gly Gly Lys Ile Ala Gly Asp Tyr Ile Ala Lys Lys
    130                 135                 140

Ala Gly Glu Gly Ala Lys Val Ile Glu Leu Gln Gly Ile Ala Gly Thr
145                 150                 155                 160

Ser Ala Ala Arg Glu Arg Gly Glu Gly Phe Gln Ala Val Ala Ala
                165                 170                 175

His Lys Phe Asn Val Leu Ala Ser Gln Pro Ala Asp Phe Asp Arg Thr
            180                 185                 190

Lys Gly Leu Asn Val Met Gln Asn Leu Leu Thr Ala His Pro Asp Val
        195                 200                 205

Gln Ala Val Phe Ala Gln Asn Asp Glu Met Ala Leu Gly Ala Leu Arg
    210                 215                 220

Ala Leu Gln Thr Ala Gly Lys Ser Asp Val Met Val Val Gly Phe Asp
225                 230                 235                 240

Gly Thr Pro Asp Gly Glu Lys Ala Val Asn Asp Gly Lys Leu Ala Ala
                245                 250                 255

Thr Ile Ala Gln Leu Pro Asp Gln Ile Gly Ala Lys Gly Val Glu Thr
            260                 265                 270

Ala Asp Lys Val Leu Lys Gly Glu Lys Val Gln Ala Lys Tyr Pro Val
        275                 280                 285

Asp Leu Lys Leu Val Val Lys Gln
```

<210> SEQ ID NO 31
<211> LENGTH: 309
<212> TYPE: PRT
<213> ORGANISM: Escherichia coli

<400> SEQUENCE: 31

Met Gln Asn Ala Gly Ser Leu Val Val Leu Gly Ser Ile Asn Ala Asp
1               5                   10                  15

His Ile Leu Asn Leu Gln Ser Phe Pro Thr Pro Gly Glu Thr Val Thr
            20                  25                  30

Gly Asn His Tyr Gln Val Ala Phe Gly Gly Lys Gly Ala Asn Gln Ala
        35                  40                  45

Val Ala Ala Gly Arg Ser Gly Ala Asn Ile Ala Phe Ile Ala Cys Thr
    50                  55                  60

Gly Asp Asp Ser Ile Gly Glu Ser Val Arg Gln Gln Leu Ala Thr Asp
65                  70                  75                  80

Asn Ile Asp Ile Thr Pro Val Ser Val Ile Lys Gly Glu Ser Thr Gly
                85                  90                  95

Val Ala Leu Ile Phe Val Asn Gly Glu Gly Glu Asn Val Ile Gly Ile
            100                 105                 110

His Ala Gly Ala Asn Ala Ala Leu Ser Pro Ala Leu Val Glu Ala Gln
        115                 120                 125

Arg Glu Arg Ile Ala Asn Ala Ser Ala Leu Leu Met Gln Leu Glu Ser
    130                 135                 140

Pro Leu Glu Ser Val Met Ala Ala Lys Ile Ala His Gln Asn Lys
145                 150                 155                 160

Thr Ile Val Ala Leu Asn Pro Ala Pro Ala Arg Glu Leu Pro Asp Glu
                165                 170                 175

Leu Leu Ala Leu Val Asp Ile Ile Thr Pro Asn Glu Thr Glu Ala Glu
            180                 185                 190

Lys Leu Thr Gly Ile Arg Val Glu Asn Asp Glu Asp Ala Ala Lys Ala
        195                 200                 205

Ala Gln Val Leu His Glu Lys Gly Ile Arg Thr Val Leu Ile Thr Leu
    210                 215                 220

Gly Ser Arg Gly Val Trp Ala Ser Val Asn Gly Glu Gly Gln Arg Val
225                 230                 235                 240

Pro Gly Phe Arg Val Gln Ala Val Asp Thr Ile Ala Ala Gly Asp Thr
                245                 250                 255

Phe Asn Gly Ala Leu Ile Thr Ala Leu Leu Glu Glu Lys Pro Leu Pro
            260                 265                 270

Glu Ala Ile Arg Phe Ala His Ala Ala Ala Ile Ala Val Thr Arg
        275                 280                 285

Lys Gly Ala Gln Pro Ser Val Pro Trp Arg Glu Glu Ile Asp Ala Phe
    290                 295                 300

Leu Asp Arg Gln Arg
305

<210> SEQ ID NO 32
<211> LENGTH: 330
<212> TYPE: PRT
<213> ORGANISM: Escherichia coli

<400> SEQUENCE: 32

Met Ala Thr Met Lys Asp Val Ala Arg Leu Ala Gly Val Ser Thr Ser

```
            1               5                  10                 15
         Thr Val Ser His Val Ile Asn Lys Asp Arg Phe Val Ser Glu Ala Ile
                         20                 25                 30

Thr Ala Lys Val Glu Ala Ala Ile Lys Glu Leu Asn Tyr Ala Pro Ser
                         35                 40                 45

Ala Leu Ala Arg Ser Leu Lys Leu Asn Gln Thr His Thr Ile Gly Met
         50                  55                 60

Leu Ile Thr Ala Ser Thr Asn Pro Phe Tyr Ser Glu Leu Val Arg Gly
         65                  70                 75                 80

Val Glu Arg Ser Cys Phe Glu Arg Gly Tyr Ser Leu Val Leu Cys Asn
                         85                 90                 95

Thr Glu Gly Asp Glu Gln Arg Met Asn Arg Asn Leu Glu Thr Leu Met
                        100                105                110

Gln Lys Arg Val Asp Gly Leu Leu Leu Cys Thr Glu Thr His Gln
                        115                120                125

Pro Ser Arg Glu Ile Met Gln Arg Tyr Pro Thr Val Pro Thr Val Met
         130                 135                140

Met Asp Trp Ala Pro Phe Asp Gly Asp Ser Asp Leu Ile Gln Asp Asn
         145                 150                155                160

Ser Leu Leu Gly Gly Asp Leu Ala Thr Gln Tyr Leu Ile Asp Lys Gly
                        165                170                175

His Thr Arg Ile Ala Cys Ile Thr Gly Pro Leu Asp Lys Thr Pro Ala
                        180                185                190

Arg Leu Arg Leu Glu Gly Tyr Arg Ala Ala Met Lys Arg Ala Gly Leu
                        195                200                205

Asn Ile Pro Asp Gly Tyr Glu Val Thr Gly Asp Phe Glu Phe Asn Gly
         210                 215                220

Gly Phe Asp Ala Met Arg Gln Leu Leu Ser His Pro Leu Arg Pro Gln
         225                 230                235                240

Ala Val Phe Thr Gly Asn Asp Ala Met Ala Val Gly Val Tyr Gln Ala
                        245                250                255

Leu Tyr Gln Ala Glu Leu Gln Val Pro Gln Asp Ile Ala Val Ile Gly
                        260                265                270

Tyr Asp Asp Ile Glu Leu Ala Ser Phe Met Thr Pro Pro Leu Thr Thr
                        275                280                285

Ile His Gln Pro Lys Asp Glu Leu Gly Glu Leu Ala Ile Asp Val Leu
                        290                295                300

Ile His Arg Ile Thr Gln Pro Thr Leu Gln Gln Arg Leu Gln Leu
         305                 310                315                320

Thr Pro Ile Leu Met Glu Arg Gly Ser Ala
                        325                330

<210> SEQ ID NO 33
<211> LENGTH: 475
<212> TYPE: PRT
<213> ORGANISM: Escherichia coli

<400> SEQUENCE: 33

Met Ser Asp Lys Lys Arg Ser Met Ala Gly Leu Pro Trp Ile Ala
         1               5                  10                 15

Ala Met Ala Phe Phe Met Gln Ala Leu Asp Ala Thr Ile Leu Asn Thr
                         20                 25                 30

Ala Leu Pro Ala Thr Ala His Ser Leu Asn Arg Ser Pro Leu Ala Met
                         35                 40                 45
```

```
Gln Ser Ala Ile Ile Ser Tyr Thr Leu Thr Val Ala Met Leu Ile Pro
    50                  55                  60

Val Ser Gly Trp Leu Ala Asp Arg Phe Gly Thr Arg Arg Ile Phe Thr
65                  70                  75                  80

Leu Ala Val Ser Leu Phe Thr Leu Gly Ser Leu Ala Cys Ala Leu Ser
                85                  90                  95

Asn Ser Leu Pro Gln Leu Val Val Phe Arg Val Ile Gln Gly Ile Gly
                100                 105                 110

Gly Ala Met Met Met Pro Val Ala Arg Leu Ala Leu Leu Arg Ala Tyr
                115                 120                 125

Pro Arg Asn Glu Leu Leu Pro Val Leu Asn Phe Val Ala Met Pro Gly
130                 135                 140

Leu Val Gly Pro Ile Leu Gly Pro Val Leu Gly Val Leu Val Thr
145                 150                 155                 160

Trp Ala Thr Trp His Trp Ile Phe Leu Ile Asn Ile Pro Ile Gly Ile
                165                 170                 175

Ala Gly Leu Leu Tyr Ala Arg Lys His Met Pro Asn Phe Thr Thr Ala
                180                 185                 190

Arg Arg Arg Phe Asp Ile Thr Gly Phe Leu Leu Phe Gly Leu Ser Leu
                195                 200                 205

Val Leu Phe Ser Ser Gly Ile Glu Leu Phe Gly Glu Lys Ile Val Ala
                210                 215                 220

Ser Trp Ile Ala Leu Thr Val Ile Val Thr Ser Ile Gly Leu Leu Leu
225                 230                 235                 240

Leu Tyr Ile Leu His Ala Arg Arg Thr Pro Asn Pro Leu Ile Ser Leu
                245                 250                 255

Asp Leu Phe Lys Thr Arg Thr Phe Ser Ile Gly Ile Val Gly Asn Ile
                260                 265                 270

Ala Thr Arg Leu Gly Thr Gly Cys Val Pro Phe Leu Met Pro Leu Met
                275                 280                 285

Leu Gln Val Gly Phe Gly Tyr Gln Ala Phe Met Ala Gly Cys Met Met
                290                 295                 300

Ala Pro Thr Ala Leu Gly Ser Ile Ile Ala Lys Ser Met Val Thr Gln
305                 310                 315                 320

Val Leu Arg Arg Leu Gly Tyr Arg His Thr Leu Val Gly Ile Thr Val
                325                 330                 335

Ile Ile Gly Leu Met Ile Ala Gln Phe Ser Leu Gln Ser Pro Ala Met
                340                 345                 350

Ala Ile Trp Met Leu Ile Leu Pro Leu Phe Ile Leu Gly Met Ala Met
                355                 360                 365

Ser Thr Gln Phe Thr Ala Met Asn Thr Ile Thr Leu Ala Asp Leu Thr
370                 375                 380

Asp Asp Asn Ala Ser Ser Gly Asn Ser Val Leu Ala Val Thr Gln Gln
385                 390                 395                 400

Leu Ser Ile Ser Leu Gly Val Ala Val Ser Ala Val Leu Arg Val
                405                 410                 415

Tyr Glu Gly Met Glu Gly Thr Thr Thr Val Glu Gln Phe His Tyr Thr
                420                 425                 430

Phe Ile Thr Met Gly Ile Ile Thr Val Ala Ser Ala Ala Met Phe Met
                435                 440                 445

Leu Leu Lys Thr Thr Asp Gly Asn Asn Leu Ile Lys Arg Gln Arg Lys
450                 455                 460

Ser Lys Pro Asn Arg Val Pro Ser Glu Ser Glu
```

<210> SEQ ID NO 34
<211> LENGTH: 5145
<212> TYPE: DNA
<213> ORGANISM: Escherichia coli

<400> SEQUENCE: 34

| | | | | | |
|---|---|---|---|---|---|
| ttgttggcgg | taactgtacc | gtaagcctga | tgttgatgtc | gttgggtggt | ttattcgcca | 60 |
| atgatcttgt | tgattgggtg | tccgttgcaa | cctaccaggc | cgcttccggc | ggtggtgcgc | 120 |
| gacatatgcg | tgagttatta | acccagatgg | gccatctgta | tggccatgtg | gcagatgaac | 180 |
| tcgcgacccc | gtcctctgct | attctcgata | tcgaacgcaa | agtcacaacc | ttaacccgta | 240 |
| gcggtgagct | gccggtggat | aactttggcg | tgccgctggc | gggtagcctg | attccgtgga | 300 |
| tcgacaaaca | gctcgataac | ggtcagagcc | gcgaagagtg | gaaagggcag | gcggaaacca | 360 |
| acaagatcct | caacacatct | tccgtaattc | cggtagatgg | tttatgtgtg | cgtgtcgggg | 420 |
| cattgcgctg | ccacagccag | gcattcacta | ttaaattgaa | aaaagatgtg | tctattccga | 480 |
| ccgtggaaga | actgctggct | gcgcacaatc | cgtgggcgaa | agtcgttccg | aacgatcggg | 540 |
| aaatcactat | gcgtgagcta | accccagctg | ccgttaccgg | cacgctgacc | acgccggtag | 600 |
| gccgcctgcg | taagctgaat | atgggaccag | agttcctgtc | agcctttacc | gtgggcgacc | 660 |
| agctgctgtg | ggggccgcg | gagccgctgc | gtcggatgct | tcgtcaactg | gcgtaatctt | 720 |
| tattcattaa | atctggggcg | cgatgccgcc | cctgttagtg | cgtaatacag | gagtaagcgc | 780 |
| agatgtttca | tgatttaccg | ggagttaaat | agagcattgg | ctattcttta | agggtggctg | 840 |
| aatacatgag | tattcacagc | cttacctgaa | gtgaggacga | cgcagagagg | atgcacagag | 900 |
| tgctgcgccg | ttcaggtcaa | aaaatgtca | caaccagaag | tcaaaaatcc | aattggatgg | 960 |
| ggtgacacaa | taaaacagga | agacaagcat | gtccgatcgt | atcgatagag | acgtgattaa | 1020 |
| cgcgctaatt | gcaggccatt | tgcggatcc | ttttccgta | ctgggaatgc | ataaaaccac | 1080 |
| cgcgggactg | gaagtccgtg | cccttttacc | cgacgctacc | gatgtgtggg | tgattgaacc | 1140 |
| gaaaaccggg | cgcaaactcg | caaaactgga | gtgtctcgac | tcacggggat | tctttagcgg | 1200 |
| cgtcattccg | cgacgtaaga | attttttccg | ctatcagttg | gctgttgtct | ggcatggtca | 1260 |
| gcaaaacctg | attgatgatc | cttaccgttt | tggtccgcta | atccaggaaa | tggatgcctg | 1320 |
| gctattatct | gaaggtactc | acctgcgccc | gtatgaaacc | ttaggcgcgc | atgcagatac | 1380 |
| tatggatggc | gtcacaggta | cgcgtttctc | tgtctgggct | ccaaacgccc | gtcgggtctc | 1440 |
| ggtggttggg | caattcaact | actgggacgg | tcgccgtcac | ccgatgcgcc | tgcgtaaaga | 1500 |
| gagcggcatc | tgggaactgt | ttatccctgg | ggcgcataac | ggtcagctct | ataaatacga | 1560 |
| gatgattgat | gccaatggca | acttgcgtct | gaagtccgac | ccttatgcct | ttgaagcgca | 1620 |
| aatgcgcccg | gaaaccgcgt | ctcttatttg | cgggctgccg | gaaaaggttg | tacagactga | 1680 |
| agagcgcaaa | aaagcgaatc | agtttgatgc | gccaatctct | atttatgaag | ttcacctggg | 1740 |
| gtcctggcgt | cgccacaccg | acaacaattt | ctggttgagc | taccgcgagc | tggccgatca | 1800 |
| actggtgcct | tatgctaaat | ggatgggctt | tacccacctc | gaactactgc | cattaacga | 1860 |
| gcatccttc | gatggcagtt | ggggttatca | gccaaccggc | ctgtatgcgc | caacccgccg | 1920 |
| ttttggtact | cgcgacgact | tccgttattt | cattgatgcc | gcacacgcag | ctggtctgaa | 1980 |
| cgtgattctc | gactgggtgc | caggccactt | cccgactgat | gactttgcgc | ttgccgaatt | 2040 |
| tgatggcacg | aacttgtatg | aacacagcga | tccgcgtgaa | ggctatcatc | aggactggaa | 2100 |

```
cacgctgatc tacaactatg gtcgccgtga agtcagtaac ttcctcgtcg gtaacgcgct    2160
ttactggatt gaacgttttg gtattgatgc gctgcgcgtc gatgcggtgg cgtcaatgat    2220
ttatcgcgac tacagccgta aagaggggga gtggatcccg aacgaatttg gcgggcgcga    2280
gaatcttgaa gcgattgaat tcttgcgtaa taccaaccgt attcttggtg agcaggtttc    2340
cggtgcggtg acaatggctg aggagtctac cgatttccct ggcgtttctc gtccgcagga    2400
tatgggcggt ctgggcttct ggtacaagtg gaacctcggc tggatgcatg acaccctgga    2460
ctacatgaag ctcgacccgg tttatcgtca gtatcatcac gataaactga ccttcgggat    2520
tctctacaac tacactgaaa acttcgtcct gccgttgtcg catgatgaag tggtccacgg    2580
taaaaaatcg attctcgacc gcatgccggg cgacgcatgg cagaaattcg cgaacctgcg    2640
cgcctactat ggctggatgt gggcattccc gggcaagaaa ctactgttca tgggtaacga    2700
atttgcccag ggccgcgagt ggaaccatga cgccagcctc gactggcatc tgttggaagg    2760
cggcgataac tggcaccacg gtgtccagcg tctggtgcgc gatctgaacc tcacctaccg    2820
ccaccataaa gcaatgcatg aactggattt tgacccgtac ggctttgaat ggctggtggt    2880
ggatgacaaa gaacgctcgg tgctgatctt tgtgcgtcgc gataaagagg gtaacgaaat    2940
catcgttgcc agtaacttta cgccggtacc gcgtcatgat tatcgcttcg gcataaacca    3000
gccgggcaaa tggcgtgaaa tcctcaatac cgattccatg cactatcacg gcagtaatgc    3060
aggcaatggc ggcacggtac acagcgatga gattgccagc cacggtcgtc agcattcact    3120
aagcctgacg ctaccaccgc tggccactat ctggctggtt cgggaggcag aatgacacaa    3180
ctcgccattg gcaaacccgc tcccctcggc gcgcattacg acggtcaggg cgtcaacttc    3240
acacttttct ccgctcatgc cgagcgggta gaactgtgtg tctttgacgc caatggccag    3300
gaacatcgct atgacttgcc agggcacagt ggcgacattt ggcacggtta tctgccggat    3360
gcgcgcccgg gtttgcgtta tggttatcgc gttcatggcc cctggcaacc cgccgagggg    3420
catcgcttta acccggcgaa gttgttgatt gatccttgcg cgcggcaaat tgacggggag    3480
tttaaagata acccgctgct gcacgccggt cataatgaac ctgactatcg cgacaacgcc    3540
gccattgcgc cgaaatgcgt agtggtggtt gatcactatg actgggaaga tgatgccccg    3600
ccgcgcacgc cgtggggcag caccatcatt tatgaagccc atgtcaaagg attaacgtac    3660
ttgcacccgg agatcccggt cgagatccgt ggcacttata aagccctcgg catccggtg    3720
atgatcaact atttgaaaca attgggcatt accgcgctgg aactgctgcc agtggcgcag    3780
tttgccagtg aaccacgtct gcaacgcatg gggctaagta actactgggg ttacaacccg    3840
gtggcgatgt ttgcgctgca tccggcgtat gcctgctcgc cagaaacggc gctggatgag    3900
tttcgcgatg caatcaaagc actgcataaa gcgggtatcg aagtcattct tgatatcgtg    3960
ctcaaccata gtgcggaact ggacctcgac ggcccgttat tctcgctgcg tgggatcgat    4020
aaccgtagct attattggat aagagaagac ggcgattatc acaactggac cggttgcggc    4080
aacacgctca atttgagtca tccggcggtg gtggattatg ccagcgcctg cctgcgttat    4140
tgggtagaaa cctgccacgt cgatggtttc cgctttgatc tggcggcagt catgggccgt    4200
acgccagagt tccgtcagga tgcgccgttg tttaccgcta tccagaactg cccggtgctc    4260
tcgcaggtga agttaattgc tgaaccgtgg gatatcgctc tggtggtta tcaggtggga    4320
aatttcccgc cgctgtttgc cgagtggaac gatcatttcc gcgatgctgc ccgtcgtttc    4380
tggctacatt atgatttgcc tctggggggcg tttgccgggc gttttgctgc ctccagcgat    4440
```

```
gtttttaaac gtaatggtcg tctgccgagt gccgcgatta atctcgtcac cgcgcatgac    4500
ggttttacgc ttcgcgactg cgtttgcttc aaccataaac acaatgaagc aaacggagaa    4560
gaaaatcgcg acgggaccaa caacaattac agtaacaatc atggtaaaga agggttaggc    4620
ggttctcttg acctggttga acggcggcgc gacagcattc acgccctgtt aacaacgttg    4680
ttgctctccc agggtacgcc gatgttactg gccggtgacg aacatggtca cagccagcat    4740
ggcaataaca atgcctactg tcaggataac caattaacct ggttggactg gtcgcaggca    4800
agcagtggtt taaccgcatt taccgccgcg ttaatccatc tgcgcaagcg cattcccgct    4860
ttggtggaga atcgctggtg ggaagaaggc gacggcaatg tccgttggct aaatcgatat    4920
gctcaacctt taagcacgga tgagtggcaa acgggccga aacagctgca aattctgctc    4980
tcggatcgct ttttgatcgc aattaacgcc acgcttgagg taacagagat tgttttacct    5040
gctggggagt ggcacgccat tcccccattc gctggagagg ataacccagt gattacggct    5100
gtctggcagg gacctgcaca cggattgtgt gtgttccaga gatga                    5145
```

<210> SEQ ID NO 35
<211> LENGTH: 728
<212> TYPE: PRT
<213> ORGANISM: Escherichia coli

<400> SEQUENCE: 35

```
Met Ser Asp Arg Ile Asp Arg Asp Val Ile Asn Ala Leu Ile Ala Gly
1               5                   10                  15

His Phe Ala Asp Pro Phe Ser Val Leu Gly Met His Lys Thr Thr Ala
            20                  25                  30

Gly Leu Glu Val Arg Ala Leu Leu Pro Asp Ala Thr Asp Val Trp Val
        35                  40                  45

Ile Glu Pro Lys Thr Gly Arg Lys Leu Ala Lys Leu Glu Cys Leu Asp
    50                  55                  60

Ser Arg Gly Phe Phe Ser Gly Val Ile Pro Arg Arg Lys Asn Phe Phe
65                  70                  75                  80

Arg Tyr Gln Leu Ala Val Val Trp His Gly Gln Gln Asn Leu Ile Asp
                85                  90                  95

Asp Pro Tyr Arg Phe Gly Pro Leu Ile Gln Glu Met Asp Ala Trp Leu
            100                 105                 110

Leu Ser Glu Gly Thr His Leu Arg Pro Tyr Glu Thr Leu Gly Ala His
        115                 120                 125

Ala Asp Thr Met Asp Gly Val Thr Gly Thr Arg Phe Ser Val Trp Ala
    130                 135                 140

Pro Asn Ala Arg Arg Val Ser Val Val Gly Gln Phe Asn Tyr Trp Asp
145                 150                 155                 160

Gly Arg Arg His Pro Met Arg Leu Arg Lys Glu Ser Gly Ile Trp Glu
                165                 170                 175

Leu Phe Ile Pro Gly Ala His Asn Gly Gln Leu Tyr Lys Tyr Glu Met
            180                 185                 190

Ile Asp Ala Asn Gly Asn Leu Arg Leu Lys Ser Asp Pro Tyr Ala Phe
        195                 200                 205

Glu Ala Gln Met Arg Pro Glu Thr Ala Ser Leu Ile Cys Gly Leu Pro
    210                 215                 220

Glu Lys Val Val Gln Thr Glu Arg Lys Lys Ala Asn Gln Phe Asp
225                 230                 235                 240

Ala Pro Ile Ser Ile Tyr Glu Val His Leu Gly Ser Trp Arg Arg His
                245                 250                 255
```

```
Thr Asp Asn Asn Phe Trp Leu Ser Tyr Arg Glu Leu Ala Asp Gln Leu
                260                 265                 270

Val Pro Tyr Ala Lys Trp Met Gly Phe Thr His Leu Glu Leu Leu Pro
            275                 280                 285

Ile Asn Glu His Pro Phe Asp Gly Ser Trp Gly Tyr Gln Pro Thr Gly
        290                 295                 300

Leu Tyr Ala Pro Thr Arg Arg Phe Gly Thr Arg Asp Asp Phe Arg Tyr
305                 310                 315                 320

Phe Ile Asp Ala Ala His Ala Ala Gly Leu Asn Val Ile Leu Asp Trp
                325                 330                 335

Val Pro Gly His Phe Pro Thr Asp Asp Phe Ala Leu Ala Glu Phe Asp
            340                 345                 350

Gly Thr Asn Leu Tyr Glu His Ser Asp Pro Arg Glu Gly Tyr His Gln
        355                 360                 365

Asp Trp Asn Thr Leu Ile Tyr Asn Tyr Gly Arg Arg Glu Val Ser Asn
    370                 375                 380

Phe Leu Val Gly Asn Ala Leu Tyr Trp Ile Glu Arg Phe Gly Ile Asp
385                 390                 395                 400

Ala Leu Arg Val Asp Ala Val Ala Ser Met Ile Tyr Arg Asp Tyr Ser
                405                 410                 415

Arg Lys Glu Gly Glu Trp Ile Pro Asn Glu Phe Gly Gly Arg Glu Asn
            420                 425                 430

Leu Glu Ala Ile Glu Phe Leu Arg Asn Thr Asn Arg Ile Leu Gly Glu
        435                 440                 445

Gln Val Ser Gly Ala Val Thr Met Ala Glu Glu Ser Thr Asp Phe Pro
    450                 455                 460

Gly Val Ser Arg Pro Gln Asp Met Gly Gly Leu Gly Phe Trp Tyr Lys
465                 470                 475                 480

Trp Asn Leu Gly Trp Met His Asp Thr Leu Asp Tyr Met Lys Leu Asp
                485                 490                 495

Pro Val Tyr Arg Gln Tyr His His Asp Lys Leu Thr Phe Gly Ile Leu
            500                 505                 510

Tyr Asn Tyr Thr Glu Asn Phe Val Leu Pro Leu Ser His Asp Glu Val
        515                 520                 525

Val His Gly Lys Lys Ser Ile Leu Asp Arg Met Pro Gly Asp Ala Trp
    530                 535                 540

Gln Lys Phe Ala Asn Leu Arg Ala Tyr Tyr Gly Trp Met Trp Ala Phe
545                 550                 555                 560

Pro Gly Lys Lys Leu Leu Phe Met Gly Asn Glu Phe Ala Gln Gly Arg
                565                 570                 575

Glu Trp Asn His Asp Ala Ser Leu Asp Trp His Leu Leu Glu Gly Gly
            580                 585                 590

Asp Asn Trp His His Gly Val Gln Arg Leu Val Arg Asp Leu Asn Leu
        595                 600                 605

Thr Tyr Arg His His Lys Ala Met His Glu Leu Asp Phe Asp Pro Tyr
    610                 615                 620

Gly Phe Glu Trp Leu Val Val Asp Asp Lys Glu Arg Ser Val Leu Ile
625                 630                 635                 640

Phe Val Arg Arg Asp Lys Glu Gly Asn Glu Ile Ile Val Ala Ser Asn
                645                 650                 655

Phe Thr Pro Val Pro Arg His Asp Tyr Arg Phe Gly Ile Asn Gln Pro
            660                 665                 670
```

```
Gly Lys Trp Arg Glu Ile Leu Asn Thr Asp Ser Met His Tyr His Gly
            675                 680                 685

Ser Asn Ala Gly Asn Gly Thr Val His Ser Asp Glu Ile Ala Ser
        690                 695                 700

His Gly Arg Gln His Ser Leu Ser Leu Thr Leu Pro Pro Leu Ala Thr
705                 710                 715                 720

Ile Trp Leu Val Arg Glu Ala Glu
                725

<210> SEQ ID NO 36
<211> LENGTH: 657
<212> TYPE: PRT
<213> ORGANISM: Escherichia coli

<400> SEQUENCE: 36

Met Thr Gln Leu Ala Ile Gly Lys Pro Ala Pro Leu Gly Ala His Tyr
1               5                   10                  15

Asp Gly Gln Gly Val Asn Phe Thr Leu Phe Ser Ala His Ala Glu Arg
            20                  25                  30

Val Glu Leu Cys Val Phe Asp Ala Asn Gly Gln Glu His Arg Tyr Asp
        35                  40                  45

Leu Pro Gly His Ser Gly Asp Ile Trp His Gly Tyr Leu Pro Asp Ala
    50                  55                  60

Arg Pro Gly Leu Arg Tyr Gly Tyr Arg Val His Gly Pro Trp Gln Pro
65                  70                  75                  80

Ala Glu Gly His Arg Phe Asn Pro Ala Lys Leu Leu Ile Asp Pro Cys
                85                  90                  95

Ala Arg Gln Ile Asp Gly Glu Phe Lys Asp Asn Pro Leu Leu His Ala
            100                 105                 110

Gly His Asn Glu Pro Asp Tyr Arg Asp Asn Ala Ala Ile Ala Pro Lys
        115                 120                 125

Cys Val Val Val Asp His Tyr Asp Trp Glu Asp Asp Ala Pro Pro
    130                 135                 140

Arg Thr Pro Trp Gly Ser Thr Ile Ile Tyr Glu Ala His Val Lys Gly
145                 150                 155                 160

Leu Thr Tyr Leu His Pro Glu Ile Pro Val Glu Ile Arg Gly Thr Tyr
                165                 170                 175

Lys Ala Leu Gly His Pro Val Met Ile Asn Tyr Leu Lys Gln Leu Gly
            180                 185                 190

Ile Thr Ala Leu Glu Leu Leu Pro Val Ala Gln Phe Ala Ser Glu Pro
        195                 200                 205

Arg Leu Gln Arg Met Gly Leu Ser Asn Tyr Trp Gly Tyr Asn Pro Val
    210                 215                 220

Ala Met Phe Ala Leu His Pro Ala Tyr Ala Cys Ser Pro Glu Thr Ala
225                 230                 235                 240

Leu Asp Glu Phe Arg Asp Ala Ile Lys Ala Leu His Lys Ala Gly Ile
                245                 250                 255

Glu Val Ile Leu Asp Ile Val Leu Asn His Ser Ala Glu Leu Asp Leu
            260                 265                 270

Asp Gly Pro Leu Phe Ser Leu Arg Gly Ile Asp Asn Arg Ser Tyr Tyr
        275                 280                 285

Trp Ile Arg Glu Asp Gly Asp Tyr His Asn Trp Thr Gly Cys Gly Asn
    290                 295                 300

Thr Leu Asn Leu Ser His Pro Ala Val Val Asp Tyr Ala Ser Ala Cys
305                 310                 315                 320
```

-continued

```
Leu Arg Tyr Trp Val Glu Thr Cys His Val Asp Gly Phe Arg Phe Asp
            325                 330                 335

Leu Ala Ala Val Met Gly Arg Thr Pro Glu Phe Arg Gln Asp Ala Pro
        340                 345                 350

Leu Phe Thr Ala Ile Gln Asn Cys Pro Val Leu Ser Gln Val Lys Leu
    355                 360                 365

Ile Ala Glu Pro Trp Asp Ile Ala Pro Gly Gly Tyr Gln Val Gly Asn
370                 375                 380

Phe Pro Pro Leu Phe Ala Glu Trp Asn Asp His Phe Arg Asp Ala Ala
385                 390                 395                 400

Arg Arg Phe Trp Leu His Tyr Asp Leu Pro Leu Gly Ala Phe Ala Gly
                405                 410                 415

Arg Phe Ala Ala Ser Ser Asp Val Phe Lys Arg Asn Gly Arg Leu Pro
            420                 425                 430

Ser Ala Ala Ile Asn Leu Val Thr Ala His Asp Gly Phe Thr Leu Arg
        435                 440                 445

Asp Cys Val Cys Phe Asn His Lys His Asn Glu Ala Asn Gly Glu Glu
    450                 455                 460

Asn Arg Asp Gly Thr Asn Asn Asn Tyr Ser Asn Asn His Gly Lys Glu
465                 470                 475                 480

Gly Leu Gly Gly Ser Leu Asp Leu Val Glu Arg Arg Arg Asp Ser Ile
                485                 490                 495

His Ala Leu Leu Thr Thr Leu Leu Leu Ser Gln Gly Thr Pro Met Leu
            500                 505                 510

Leu Ala Gly Asp Glu His Gly His Ser Gln His Gly Asn Asn Asn Ala
        515                 520                 525

Tyr Cys Gln Asp Asn Gln Leu Thr Trp Leu Asp Trp Ser Gln Ala Ser
    530                 535                 540

Ser Gly Leu Thr Ala Phe Thr Ala Leu Ile His Leu Arg Lys Arg
545                 550                 555                 560

Ile Pro Ala Leu Val Glu Asn Arg Trp Trp Glu Gly Asp Gly Asn
                565                 570                 575

Val Arg Trp Leu Asn Arg Tyr Ala Gln Pro Leu Ser Thr Asp Glu Trp
            580                 585                 590

Gln Asn Gly Pro Lys Gln Leu Gln Ile Leu Leu Ser Asp Arg Phe Leu
        595                 600                 605

Ile Ala Ile Asn Ala Thr Leu Glu Val Thr Glu Ile Val Leu Pro Ala
    610                 615                 620

Gly Glu Trp His Ala Ile Pro Pro Phe Ala Gly Glu Asp Asn Pro Val
625                 630                 635                 640

Ile Thr Ala Val Trp Gln Gly Pro Ala His Gly Leu Cys Val Phe Gln
                645                 650                 655

Arg
```

```
<210> SEQ ID NO 37
<211> LENGTH: 5455
<212> TYPE: DNA
<213> ORGANISM: Escherichia coli
<220> FEATURE:
<221> NAME/KEY: CDS
<222> LOCATION: (718)..(1395)
<220> FEATURE:
<221> NAME/KEY: CDS
<222> LOCATION: (1469)..(1735)
<220> FEATURE:
<221> NAME/KEY: CDS
```

<222> LOCATION: (2000)..(2260)

<400> SEQUENCE: 37

| | |
|---|---:|
| ccagcagcct ccgggcggca acaacttcgc ccttgcgcag tctggcagcg gtaacagtgc | 60 |
| caaccgcacc gattttaaac cgcaaaaagc caacaccagc gagattggca ccaaatggca | 120 |
| ggttctggat aaacgtctgt tgctcaccgc cgcgctgttc cgcactgata tcgaaaatga | 180 |
| agttgagcaa aatgatgacg gaacttactc gcaatacggt aagaaacgcg tcgaaggcta | 240 |
| tgagatatcc gtggccggga atatcactcc cgcgtggcag gtgattggcg gctataccca | 300 |
| gcaaaaagca accatcaaaa acggcaaaga tgttgcccag gatggttcct catcgctgcc | 360 |
| gtataccccg gagcacgcct tcaccttatg gagccaatat caggcaaccg acgatatctc | 420 |
| tgttggcgcg ggcgcacgct atatcggcag tatgcataaa ggttcagacg gcgcggtggg | 480 |
| aacgccagcg tttaccgaag gttactgggt cgccgatgcc aaactggggt atcgagttaa | 540 |
| tcgcaatctc gacttccagc taaacgttta caacctgttt gataccgatt acgtcgcctc | 600 |
| aatcaacaag agcggctacc gttatcaccc gggcgagcca agaaccttct tgctcacagc | 660 |
| caatatgcat ttctgattca gatgtggggc gcaggcccca cttttttggag aaattgt | 717 |

| | | | | | | | | | | | | | | | | |
|---|---|---|---|---|---|---|---|---|---|---|---|---|---|---|---|---:|
| atg | atg | tac | cac | att | ccc | ggc | gtg | tta | tcg | cca | cag | gac | gtc | gct | cgt | 765 |
| Met | Met | Tyr | His | Ile | Pro | Gly | Val | Leu | Ser | Pro | Gln | Asp | Val | Ala | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---:|
| ttt | cgc | gaa | caa | ctg | gaa | caa | gcc | gaa | tgg | gtg | gat | gga | cgc | gtc | acc | 813 |
| Phe | Arg | Glu | Gln | Leu | Glu | Gln | Ala | Glu | Trp | Val | Asp | Gly | Arg | Val | Thr | |
| | | | 20 | | | | | 25 | | | | | 30 | | | |

| | | | | | | | | | | | | | | | | |
|---|---|---|---|---|---|---|---|---|---|---|---|---|---|---|---|---:|
| acc | ggc | gca | caa | ggt | gcg | caa | gtt | aag | aac | aat | caa | cag | gtc | gac | acc | 861 |
| Thr | Gly | Ala | Gln | Gly | Ala | Gln | Val | Lys | Asn | Asn | Gln | Gln | Val | Asp | Thr | |
| | | 35 | | | | | 40 | | | | | 45 | | | | |

| | | | | | | | | | | | | | | | | |
|---|---|---|---|---|---|---|---|---|---|---|---|---|---|---|---|---:|
| cgc | agc | acg | tta | tac | gcc | gcc | ctg | caa | aat | gag | gtg | ctg | aac | gcg | gtt | 909 |
| Arg | Ser | Thr | Leu | Tyr | Ala | Ala | Leu | Gln | Asn | Glu | Val | Leu | Asn | Ala | Val | |
| | 50 | | | | | 55 | | | | | 60 | | | | | |

| | | | | | | | | | | | | | | | | |
|---|---|---|---|---|---|---|---|---|---|---|---|---|---|---|---|---:|
| aac | caa | cat | gct | tta | ttc | ttt | gcc | gcg | gcc | ttg | ccg | cgt | acc | ctt | tcc | 957 |
| Asn | Gln | His | Ala | Leu | Phe | Phe | Ala | Ala | Ala | Leu | Pro | Arg | Thr | Leu | Ser | |
| 65 | | | | 70 | | | | | 75 | | | | | 80 | | |

| | | | | | | | | | | | | | | | | |
|---|---|---|---|---|---|---|---|---|---|---|---|---|---|---|---|---:|
| acg | ccg | ctg | ttt | aat | cgc | tat | cag | aac | aat | gaa | acc | tat | ggt | ttc | cat | 1005 |
| Thr | Pro | Leu | Phe | Asn | Arg | Tyr | Gln | Asn | Asn | Glu | Thr | Tyr | Gly | Phe | His | |
| | | | | 85 | | | | | 90 | | | | | 95 | | |

| | | | | | | | | | | | | | | | | |
|---|---|---|---|---|---|---|---|---|---|---|---|---|---|---|---|---:|
| gtg | gat | ggc | gca | gta | cgc | agc | cat | cca | caa | aac | ggc | tgg | atg | cgt | act | 1053 |
| Val | Asp | Gly | Ala | Val | Arg | Ser | His | Pro | Gln | Asn | Gly | Trp | Met | Arg | Thr | |
| | | | 100 | | | | | 105 | | | | | 110 | | | |

| | | | | | | | | | | | | | | | | |
|---|---|---|---|---|---|---|---|---|---|---|---|---|---|---|---|---:|
| gac | ctt | tct | gcc | acg | ctg | ttt | tta | agc | gat | cca | caa | agc | tac | gac | ggc | 1101 |
| Asp | Leu | Ser | Ala | Thr | Leu | Phe | Leu | Ser | Asp | Pro | Gln | Ser | Tyr | Asp | Gly | |
| | | 115 | | | | | 120 | | | | | 125 | | | | |

| | | | | | | | | | | | | | | | | |
|---|---|---|---|---|---|---|---|---|---|---|---|---|---|---|---|---:|
| ggc | gaa | ctg | gtc | gtt | aat | gac | acc | ttc | gga | caa | cat | cgg | gta | aaa | ctc | 1149 |
| Gly | Glu | Leu | Val | Val | Asn | Asp | Thr | Phe | Gly | Gln | His | Arg | Val | Lys | Leu | |
| | 130 | | | | | 135 | | | | | 140 | | | | | |

| | | | | | | | | | | | | | | | | |
|---|---|---|---|---|---|---|---|---|---|---|---|---|---|---|---|---:|
| ccg | gca | ggc | gat | ctc | gtg | ttg | tat | ccc | tcc | agc | agc | ctg | cat | tgc | gtg | 1197 |
| Pro | Ala | Gly | Asp | Leu | Val | Leu | Tyr | Pro | Ser | Ser | Ser | Leu | His | Cys | Val | |
| 145 | | | | 150 | | | | | 155 | | | | | 160 | | |

| | | | | | | | | | | | | | | | | |
|---|---|---|---|---|---|---|---|---|---|---|---|---|---|---|---|---:|
| aca | ccc | gta | acc | cgc | ggc | gta | cga | gtg | gca | tca | ttt | atg | tgg | atc | cag | 1245 |
| Thr | Pro | Val | Thr | Arg | Gly | Val | Arg | Val | Ala | Ser | Phe | Met | Trp | Ile | Gln | |
| | | | | 165 | | | | | 170 | | | | | 175 | | |

| | | | | | | | | | | | | | | | | |
|---|---|---|---|---|---|---|---|---|---|---|---|---|---|---|---|---:|
| tcg | atg | atc | cgc | gat | gat | aaa | aag | cgc | gcc | atg | ctg | ttt | gaa | ctg | gac | 1293 |
| Ser | Met | Ile | Arg | Asp | Asp | Lys | Lys | Arg | Ala | Met | Leu | Phe | Glu | Leu | Asp | |
| | | | 180 | | | | | 185 | | | | | 190 | | | |

| | | | | | | | | | | | | | | | | |
|---|---|---|---|---|---|---|---|---|---|---|---|---|---|---|---|---:|
| aac | aat | att | cag | tcg | ctg | aaa | agc | cgc | tac | ggc | gaa | agt | gaa | gag | atc | 1341 |
| Asn | Asn | Ile | Gln | Ser | Leu | Lys | Ser | Arg | Tyr | Gly | Glu | Ser | Glu | Glu | Ile | |
| | | 195 | | | | | 200 | | | | | 205 | | | | |

```
ctg tcg ctg ctt aat ctt tat cat aat ctg ctg cgg gaa tgg tcg gag    1389
Leu Ser Leu Leu Asn Leu Tyr His Asn Leu Leu Arg Glu Trp Ser Glu
    210                 215                 220 atc tga tgcttgaact gcccgagttc gtccctggat tagctacact taactgtaca    1445
Ile
225 agtattgata tggggaggtc gat atg gca tcc ggt tgg gct aac gat gac gcc  1498
                        Met Ala Ser Gly Trp Ala Asn Asp Asp Ala
                                        230                 235 gtc aac gaa cag atc aac agt aca att gaa gat gcg att gcc cgc gct    1546
Val Asn Glu Gln Ile Asn Ser Thr Ile Glu Asp Ala Ile Ala Arg Ala
                240                 245                 250 cgg ggt gaa att ccg cgc ggc gaa agc ctg gat gaa tgt gaa gag tgc    1594
Arg Gly Glu Ile Pro Arg Gly Glu Ser Leu Asp Glu Cys Glu Glu Cys
            255                 260                 265 ggt gcc ccc atc ccg cag gcc cgt cgg gaa gcc att cct ggc gtg cgc    1642
Gly Ala Pro Ile Pro Gln Ala Arg Arg Glu Ala Ile Pro Gly Val Arg
        270                 275                 280 tta tgt att cat tgt cag cag gag aaa gat tta caa aaa cca gct tat    1690
Leu Cys Ile His Cys Gln Gln Glu Lys Asp Leu Gln Lys Pro Ala Tyr
    285                 290                 295 aca gga tat aat cgc aga ggt tcg aaa gac agc cag tta cgt taa        1735
Thr Gly Tyr Asn Arg Arg Gly Ser Lys Asp Ser Gln Leu Arg
300                 305                 310 ctacaactgg cgagatgcat agcgagtata atttgtattt tgcgtgtcat tccgtgcctt  1795
taacgctgct gtgactgcca cgcggtataa aacaagttca taagtacaac aaataaatgg  1855
tttatcagta ggttagatat caatcaattt atttgaacaa ggcggtcaat tctcttcgat  1915
tttatctctc gtaaaaaaac gtgatactca tcacatcgac gaaacaacgt cacttataca  1975 aaaatcaccct gcgagagatt aatt atg aaa act atc aat act gtt gtt gct    2026
                              Met Lys Thr Ile Asn Thr Val Val Ala
                                          315                 320 gct atg gct ctt tca act ctg tca ttt ggc gtg ttc gcg gcg gaa ccg    2074
Ala Met Ala Leu Ser Thr Leu Ser Phe Gly Val Phe Ala Ala Glu Pro
                325                 330                 335 gta acg gca tcc cag gca cag aac atg aat aaa atc ggc gtg gtt tct    2122
Val Thr Ala Ser Gln Ala Gln Asn Met Asn Lys Ile Gly Val Val Ser
            340                 345                 350 gcc gat ggc gca tcc acc ctc gat gcc ctg gaa gcg aaa ctg gct gag    2170
Ala Asp Gly Ala Ser Thr Leu Asp Ala Leu Glu Ala Lys Leu Ala Glu
355                 360                 365                 370 aaa gcc gcg gca gcc ggt gcc agt gga tac agc atc act tcc gcc acc    2218
Lys Ala Ala Ala Ala Gly Ala Ser Gly Tyr Ser Ile Thr Ser Ala Thr
                375                 380                 385 aac aac aat aaa tta agc ggt act gcg gta att tat aag taa            2260
Asn Asn Asn Lys Leu Ser Gly Thr Ala Val Ile Tyr Lys
                390                 395 ttcgtaggac ggataaggcg tttacgccgc atccggcaac agatgcctga tgcgacgcta  2320
ccgcgtctta tcaggcctac aaaatccgaa ccgttggacg gatcaggcgt ttacgctacg  2380
tccagcacaa gtatttccct gtctgtttgc cgacagacgc atatgctcta accctcattg  2440
atcctatgtt acccttgttt gcccgtccgc cactggacgg ctttttttt agctggctaa  2500 ctgctgacag aaagcctgca acgtctcttc cggcatacca atctgccgcg ctgcatcaca  2560
aatggcctgc cagcttcccg catccagtgg aatcccctgc ttctgccgtt cgcgacgcgt  2620
gttcacttcc cactcgcccg gtagcaaaat cggcttatca tcatcatgcg gcgaggcttt  2680
```

```
cacccactcg gcaaaggctt cggtctgcgc gttacaatcc ggcgcgccga agagttccgg      2740
gttgatgatg atagtggtca tgcagttaag aatggcatcg ggactggttt gtaacgtttc      2800
ctgatgcgtc gttttaccgc cggaaagcgc cccgccaaga atttcacaca tcgctgcaag      2860
ggcgtagcct ttatgttcgg caaaggtcaa cagcgaaccc aacggcgact cctgcattac      2920
cgccggattg gtcgtcggca cgccgttaac gtcaatcagg caacctggcg gcacggggac      2980
gcctttatgc caggcgacgc gggttttgcc aaatgcaatg cgctggtgg cgtaatcaag       3040 caacagcggg aaattatctt tacgagggaa aaccacacag aacggattgg tgccaaagcg      3100
gctgtcgcga ccgtggaacg gcgcgaccat tggaataccg accacgctaa caaagtggat      3160
agagacaaac cccgccgctg cacactgctc cgcccagtaa ccgatacggc cgatatgatg      3220
cgagttatgt agcgccacgg cggcaatacc gtgctgatgc gctttctcaa tccccagcgc      3280
catcgcttca tgtgccgcga cctgaccaaa tgcgcgatcc ccatcgagcg tgaccgccgc      3340
ccccgcctct ttaacggttt tggcatgatg gttaatttgc aggtgcccct gactccagga      3400
gcgtacatag cttgggatca tgccaatacc atgtgaatca tgcccctgcca ggtttgccgc     3460 gattaaatga tcggcaacta atttcgcttc ttgttcctcg ctacccatct gacgaaatac      3520
agcctgaata aaactgtgca gcgtctgagc atcaaagcga tgaccacttt ccatggttaa      3580
ctcctgttta tgttatgtgt ttgttgtatt tttatgctgc acgccgggcg tgggaaggtc      3640
aataaagatg caggaatttc atattgcggt ggggtaaaag ccggatgaca tggctcatcc      3700
ggctgagaaa agaattaaaa tgcctgatta acgcgcgcca ggccgtcgct gatagttgcc      3760
gcttcacccg tagccaccag gcagcaagcc atctggattt tcagcgattc gggaatcggt      3820
tcgctgccag caaggcaacg ctcaatccac tgcgccgtgg tttccggatc ttttgcttgt      3880
ggcagtaact cgctaccagc agtgtcctgt ttttcataca gcacccgcat cccttcacgg      3940
tcaatgagat tgatctgcgg gcagcgctgc ggattagcat acacttcacc ttcagtacca      4000
tgcattagta gcgcccgccc gccgatatcg ctaaagaact cgcgacgcg tccaatgtat       4060 tccggatgcg aaacgctgga agacgcagc gcctcacctt cggcaaatgg cgtcgccagt       4120
ttcgccaggg tatgtgcact gttacgcacg cccatccgcc agcgcatcgc cagttgttt      4180 tccagcggcg ggcaaaacgc gccgactggc ataaacaccg gttgatgttc gtcgagcttc      4240
gcctgcgcct gcccgccgtg caacgttggc gtaatacccca tcaattcaaa atgtttca     4300 gtcagcacgc gggttggatc ttcgctaacc ccgtgaacca ccacaggaaa accgagtttg      4360
tgcaggagaa tcgccaacaa cggcgtcagg ttggcctgtt tacgcgcgcc gttgtaactg      4420
gggatgacaa tcggcatcgg cttgcctgct ggcggcgtca gcttgatggt gtgattttgc      4480
atggcttcgt aaaagccgag catctctgct tccccttctc ctttgatacg cagcgcaatc      4540
aatacgccgc ccaactcaag gtcagggact tcaccattga gcatatgagc atacagaccg      4600
cgcgcagtat cccggtctaa atcgcgcgcg tggttttttcc cgcgcccgat ctctttaatg      4660
attttgcgat agtccattta cgactcctta cctgactcac atcattaacg ccgccgacgg      4720
cgtggggatt tcgttttttc tttcttttta actataccct cagggacttc cggttgctct      4780
atcggaaata ccgtaatgc atccagtagt cgcttgccat aattttggt cagcaagcgt       4840 ttgtcgtaga taaccacttc gccccagcaa ccgtggcttc gaatcagtcg cccaacctgc      4900
tgaatcaggt taacgaggc gctcggcagg ctttgcacct caaacggata gcggttgagg       4960
cttttcagcc attcccctt cggtgatcacc accgggctgt cgatgggcgg aaaagcgatt     5020
ttgtggatat gcacctggct gagcagatca cctttcaaat caagtccttc ggcaaatgac      5080
```

-continued

```
tgtaagccca ccagcacgct gcgctcaccg ttggcgacgc gtttgcggtg cagttcaact    5140
aaacggtaac gcggctgatc gccctgaacc agcaacatca gacgtaaatc cgtcacatag    5200
tcgagaaagc gctgcatcgc ccgtccgctg caaacagta ccaacatacc gagatgtttt    5260
ttgctctcca cctgcttacg gaaaaaggcc gccatttcgg caatatgctg ctcttcgttg    5320
tcgatggaag gctcaacgcg catccgggga ataacaattt tgccctgttc gcagtggtta    5380 aaggggaat ccagcgccac aaaacggtcg cccgctttct ctttcagacc actcatctcc    5440
tgcaaacgcg aaaaa                                                     5455
```

<210> SEQ ID NO 38
<211> LENGTH: 225
<212> TYPE: PRT
<213> ORGANISM: Escherichia coli

<400> SEQUENCE: 38

Met Met Tyr His Ile Pro Gly Val Leu Ser Pro Gln Asp Val Ala Arg
1               5                   10                  15

Phe Arg Glu Gln Leu Glu Gln Ala Glu Trp Val Asp Gly Arg Val Thr
            20                  25                  30

Thr Gly Ala Gln Gly Ala Gln Val Lys Asn Asn Gln Val Asp Thr
        35                  40                  45

Arg Ser Thr Leu Tyr Ala Ala Leu Gln Asn Glu Val Leu Asn Ala Val
    50                  55                  60

Asn Gln His Ala Leu Phe Phe Ala Ala Leu Pro Arg Thr Leu Ser
65                  70                  75                  80

Thr Pro Leu Phe Asn Arg Tyr Gln Asn Asn Glu Thr Tyr Gly Phe His
                85                  90                  95

Val Asp Gly Ala Val Arg Ser His Pro Gln Asn Gly Trp Met Arg Thr
            100                 105                 110

Asp Leu Ser Ala Thr Leu Phe Leu Ser Asp Pro Gln Ser Tyr Asp Gly
        115                 120                 125

Gly Glu Leu Val Val Asn Asp Thr Phe Gly Gln His Arg Val Lys Leu
    130                 135                 140

Pro Ala Gly Asp Leu Val Leu Tyr Pro Ser Ser Ser Leu His Cys Val
145                 150                 155                 160

Thr Pro Val Thr Arg Gly Val Arg Val Ala Ser Phe Met Trp Ile Gln
                165                 170                 175

Ser Met Ile Arg Asp Asp Lys Lys Arg Ala Met Leu Phe Glu Leu Asp
            180                 185                 190

Asn Asn Ile Gln Ser Leu Lys Ser Arg Tyr Gly Glu Ser Glu Glu Ile
        195                 200                 205

Leu Ser Leu Leu Asn Leu Tyr His Asn Leu Leu Arg Glu Trp Ser Glu
    210                 215                 220

Ile
225

<210> SEQ ID NO 39
<211> LENGTH: 88
<212> TYPE: PRT
<213> ORGANISM: Escherichia coli

<400> SEQUENCE: 39

Met Ala Ser Gly Trp Ala Asn Asp Asp Ala Val Asn Glu Gln Ile Asn
1               5                   10                  15

```
Ser Thr Ile Glu Asp Ala Ile Ala Arg Ala Arg Gly Glu Ile Pro Arg
            20                  25                  30

Gly Glu Ser Leu Asp Glu Cys Glu Cys Gly Ala Pro Ile Pro Gln
        35                  40                  45

Ala Arg Arg Glu Ala Ile Pro Gly Val Arg Leu Cys Ile His Cys Gln
 50                  55                  60

Gln Glu Lys Asp Leu Gln Lys Pro Ala Tyr Thr Gly Tyr Asn Arg Arg
 65                  70                  75                  80

Gly Ser Lys Asp Ser Gln Leu Arg
                85

<210> SEQ ID NO 40
<211> LENGTH: 86
<212> TYPE: PRT
<213> ORGANISM: Escherichia coli

<400> SEQUENCE: 40

Met Lys Thr Ile Asn Thr Val Ala Ala Met Ala Leu Ser Thr Leu
 1               5                  10                  15

Ser Phe Gly Val Phe Ala Ala Glu Pro Val Thr Ala Ser Gln Ala Gln
            20                  25                  30

Asn Met Asn Lys Ile Gly Val Val Ser Ala Asp Gly Ala Ser Thr Leu
        35                  40                  45

Asp Ala Leu Glu Ala Lys Leu Ala Glu Lys Ala Ala Ala Gly Ala
 50                  55                  60

Ser Gly Tyr Ser Ile Thr Ser Ala Thr Asn Asn Asn Lys Leu Ser Gly
 65                  70                  75                  80

Thr Ala Val Ile Tyr Lys
                85

<210> SEQ ID NO 41
<211> LENGTH: 361
<212> TYPE: PRT
<213> ORGANISM: Escherichia coli

<400> SEQUENCE: 41

Met Glu Ser Gly His Arg Phe Asp Ala Gln Thr Leu His Ser Phe Ile
 1               5                  10                  15

Gln Ala Val Phe Arg Gln Met Gly Ser Glu Glu Gln Glu Ala Lys Leu
            20                  25                  30

Val Ala Asp His Leu Ile Ala Ala Asn Leu Ala Gly His Asp Ser His
        35                  40                  45

Gly Ile Gly Met Ile Pro Ser Tyr Val Arg Ser Trp Ser Gln Gly His
 50                  55                  60

Leu Gln Ile Asn His His Ala Lys Thr Val Lys Glu Ala Gly Ala Ala
 65                  70                  75                  80

Val Thr Leu Asp Gly Asp Arg Ala Phe Gly Gln Val Ala Ala His Glu
                85                  90                  95

Ala Met Ala Leu Gly Ile Glu Lys Ala His Gln His Gly Ile Ala Ala
                100                 105                 110

Val Ala Leu His Asn Ser His His Ile Gly Arg Ile Gly Tyr Trp Ala
            115                 120                 125

Glu Gln Cys Ala Ala Ala Gly Phe Val Ser Ile His Phe Val Ser Val
        130                 135                 140

Val Gly Ile Pro Met Val Ala Pro Phe His Gly Arg Asp Ser Arg Phe
145                 150                 155                 160
```

```
Gly Thr Asn Pro Phe Cys Val Val Phe Pro Arg Lys Asp Asn Phe Pro
                165                 170                 175

Leu Leu Leu Asp Tyr Ala Thr Ser Ala Ile Ala Phe Gly Lys Thr Arg
            180                 185                 190

Val Ala Trp His Lys Gly Val Pro Val Pro Pro Gly Cys Leu Ile Asp
        195                 200                 205

Val Asn Gly Val Pro Thr Thr Asn Pro Ala Val Met Gln Glu Ser Pro
    210                 215                 220

Leu Gly Ser Leu Leu Thr Phe Ala Glu His Lys Gly Tyr Ala Leu Ala
225                 230                 235                 240

Ala Met Cys Glu Ile Leu Gly Gly Ala Leu Ser Gly Gly Lys Thr Thr
                245                 250                 255

His Gln Glu Thr Leu Gln Thr Ser Pro Asp Ala Ile Leu Asn Cys Met
                260                 265                 270

Thr Thr Ile Ile Ile Asn Pro Glu Leu Phe Gly Ala Pro Asp Cys Asn
            275                 280                 285

Ala Gln Thr Glu Ala Phe Ala Glu Trp Val Lys Ala Ser Pro His Asp
        290                 295                 300

Asp Asp Lys Pro Ile Leu Leu Pro Gly Glu Trp Glu Val Asn Thr Arg
305                 310                 315                 320

Arg Glu Arg Gln Lys Gln Gly Ile Pro Leu Asp Ala Gly Ser Trp Gln
                325                 330                 335

Ala Ile Cys Asp Ala Ala Arg Gln Ile Gly Met Pro Glu Glu Thr Leu
                340                 345                 350

Gln Ala Phe Cys Gln Gln Leu Ala Ser
                355                 360

<210> SEQ ID NO 42
<211> LENGTH: 320
<212> TYPE: PRT
<213> ORGANISM: Escherichia coli

<400> SEQUENCE: 42

Met Asp Tyr Arg Lys Ile Ile Lys Glu Ile Gly Arg Gly Lys Asn His
1               5                   10                  15

Ala Arg Asp Leu Asp Arg Asp Thr Ala Arg Gly Leu Tyr Ala His Met
                20                  25                  30

Leu Asn Gly Glu Val Pro Asp Leu Glu Leu Gly Gly Val Leu Ile Ala
            35                  40                  45

Leu Arg Ile Lys Gly Glu Gly Glu Ala Glu Met Leu Gly Phe Tyr Glu
        50                  55                  60

Ala Met Gln Asn His Thr Ile Lys Leu Thr Pro Pro Ala Gly Lys Pro
65                  70                  75                  80

Met Pro Ile Val Ile Pro Ser Tyr Asn Gly Ala Arg Lys Gln Ala Asn
                85                  90                  95

Leu Thr Pro Leu Leu Ala Ile Leu Leu His Lys Leu Gly Phe Pro Val
                100                 105                 110

Val Val His Gly Val Ser Glu Asp Pro Thr Arg Val Leu Thr Glu Thr
            115                 120                 125

Ile Phe Glu Leu Met Gly Ile Thr Pro Thr Leu His Gly Gly Gln Ala
        130                 135                 140

Gln Ala Lys Leu Asp Glu His Gln Pro Val Phe Met Pro Val Gly Ala
145                 150                 155                 160

Phe Cys Pro Pro Leu Glu Lys Gln Leu Ala Met Arg Trp Arg Met Gly
                165                 170                 175
```

```
Val Arg Asn Ser Ala His Thr Leu Ala Lys Leu Ala Thr Pro Phe Ala
            180                 185                 190

Glu Gly Glu Ala Leu Arg Leu Ser Val Ser His Pro Glu Tyr Ile
        195                 200                 205

Gly Arg Val Ala Lys Phe Phe Ser Asp Ile Gly Arg Ala Leu Leu
210                 215                 220

Met His Gly Thr Glu Gly Val Tyr Ala Asn Pro Gln Arg Cys Pro
225                 230                 235                 240

Gln Ile Asn Leu Ile Asp Arg Glu Gly Met Arg Val Leu Tyr Glu Lys
            245                 250                 255

Gln Asp Thr Ala Gly Ser Glu Leu Leu Pro Gln Ala Lys Asp Pro Glu
            260                 265                 270

Thr Thr Ala Gln Trp Ile Glu Arg Cys Leu Ala Gly Ser Glu Pro Ile
            275                 280                 285

Pro Glu Ser Leu Lys Ile Gln Met Ala Cys Cys Leu Val Ala Thr Gly
            290                 295                 300

Glu Ala Ala Thr Ile Ser Asp Gly Leu Ala Arg Val Asn Gln Ala Phe
305                 310                 315                 320

<210> SEQ ID NO 43
<211> LENGTH: 6281
<212> TYPE: DNA
<213> ORGANISM: Escherichia coli
<220> FEATURE:
<221> NAME/KEY: CDS
<222> LOCATION: (623)..(3295)
<220> FEATURE:
<221> NAME/KEY: CDS
<222> LOCATION: (3312)..(3962)

<400> SEQUENCE: 43
cgaatatgat actaaaactt ttaagatgtt tcatttatcg ctatagatgt ttcaaaatgt      60
aaatgcaagg gaactttta agattattgc ggaatggcga ataagcacc taacatcaag      120 caataataat tcaaggttaa aatcaataac ttattcttaa gtatttgaca gcactgaatg     180
tcaaaacaaa accttcactc gcaactagaa taactcccgc tatcatcatt aactttattt    240
attaccgtca ttcatttctg aatgtctgtt taccccatt tcaaccggat gcctcgcatt    300
cggttttttt tacccttctt tacacacttt tcattattct gtgctaccac agaaaaacta    360
taacgcttgt taactatttc acaaataatt aacatccgca taatttccag caatctttgt    420
ttatttgcaa ttatttttgt tgggcttttt gtaggttatt tgtacagcaa aatggcgctt    480
gtacatctat ttcccccaat gcaggatgat aaatatcacg ggagaataga gaatcatcaa    540
tcaggtaaga gtctggaatt tcacactgta cccctttatac tgccctatca cttcgcgaag    600
ttttaacagg tcataaacac ga atg cgt cag aaa gag aca acg gcc acg acc       652
                        Met Arg Gln Lys Glu Thr Thr Ala Thr Thr
                          1               5                  10 cgc ttt tca ctc cta ccg ggg agc att acc cgc ttc ttt tta ctg ttg       700
Arg Phe Ser Leu Leu Pro Gly Ser Ile Thr Arg Phe Phe Leu Leu Leu
                15                  20                  25 atc att gtg tta ctg gtg acg atg ggt gta atg gta caa agc gcc gtt       748
Ile Ile Val Leu Leu Val Thr Met Gly Val Met Val Gln Ser Ala Val
            30                  35                  40 aac gcc tgg ctg aaa gat aaa agt tac cag att gtc gac att acc cat       796
Asn Ala Trp Leu Lys Asp Lys Ser Tyr Gln Ile Val Asp Ile Thr His
        45                  50                  55 gct atc caa aag cgc gtc gat aac tgg cgt tac gtg acc tgg cag atc       844
```

```
Ala Ile Gln Lys Arg Val Asp Asn Trp Arg Tyr Val Thr Trp Gln Ile
     60                  65                  70 tac gac aac att gcc gcg acg acc tcc ccc tcc tcc ggc gaa ggt tta    892
Tyr Asp Asn Ile Ala Ala Thr Thr Ser Pro Ser Ser Gly Glu Gly Leu
 75                  80                  85                  90 caa gag acg cgc ctg aaa cag gat gtc tac tat ctg gag aaa cca cgc    940
Gln Glu Thr Arg Leu Lys Gln Asp Val Tyr Tyr Leu Glu Lys Pro Arg
                 95                 100                 105 cgc aaa acg gaa gcg tta atc ttt ggc tct cac gac aac tca acg ctt    988
Arg Lys Thr Glu Ala Leu Ile Phe Gly Ser His Asp Asn Ser Thr Leu
            110                 115                 120 gag atg act cag cgg atg tcc act tat ctg gat aca ttg tgg ggc gca   1036
Glu Met Thr Gln Arg Met Ser Thr Tyr Leu Asp Thr Leu Trp Gly Ala
        125                 130                 135 gaa aat gta ccg tgg tcg atg tat tac ctg aat ggt cag gat aac agt   1084
Glu Asn Val Pro Trp Ser Met Tyr Tyr Leu Asn Gly Gln Asp Asn Ser
    140                 145                 150 ctg gtg ctg atc tca acc cta ccc ctt aaa gat ctc acc tcc gga ttt   1132
Leu Val Leu Ile Ser Thr Leu Pro Leu Lys Asp Leu Thr Ser Gly Phe
155                 160                 165                 170 aaa gaa tcg acc gtc agc gac att gtt gat tca cgt cgt gca gag atg   1180
Lys Glu Ser Thr Val Ser Asp Ile Val Asp Ser Arg Arg Ala Glu Met
                175                 180                 185 ttg caa cag gcc aac gcc ctc gat gaa cgc gaa agc ttt tct aac atg   1228
Leu Gln Gln Ala Asn Ala Leu Asp Glu Arg Glu Ser Phe Ser Asn Met
            190                 195                 200 cgc cgc ctg gcc tgg cag aac ggt cat tac ttt aca ttg cgt act acc   1276
Arg Arg Leu Ala Trp Gln Asn Gly His Tyr Phe Thr Leu Arg Thr Thr
        205                 210                 215 ttt aac cag cca gga cat ctg gca acg gtc gtg gct ttt gat ctg ccg   1324
Phe Asn Gln Pro Gly His Leu Ala Thr Val Val Ala Phe Asp Leu Pro
    220                 225                 230 att aat gat ttg atc cca ccg ggt atg ccg ctg gac agt ttc cgc ctt   1372
Ile Asn Asp Leu Ile Pro Pro Gly Met Pro Leu Asp Ser Phe Arg Leu
235                 240                 245                 250 gag cca gac gcg acg gca acg gga aac aat gat aat gag aaa gaa ggg   1420
Glu Pro Asp Ala Thr Ala Thr Gly Asn Asn Asp Asn Glu Lys Glu Gly
                255                 260                 265 acg gat agc gtc agt atc cac ttt aac agt acg aag att gaa atc tcc   1468
Thr Asp Ser Val Ser Ile His Phe Asn Ser Thr Lys Ile Glu Ile Ser
            270                 275                 280 tcg gca ctc aac tct acc gat atg cgc ctg gtc tgg cag gtt cct tat   1516
Ser Ala Leu Asn Ser Thr Asp Met Arg Leu Val Trp Gln Val Pro Tyr
        285                 290                 295 ggc acc tta ttg ctg gat acg ttg caa aac att ctg ctg cca ctg ctg   1564
Gly Thr Leu Leu Leu Asp Thr Leu Gln Asn Ile Leu Leu Pro Leu Leu
    300                 305                 310 ctg aac atc ggt ttg ctg gcg ctg gcg tta ttt ggc tat acc aca ttc   1612
Leu Asn Ile Gly Leu Leu Ala Leu Ala Leu Phe Gly Tyr Thr Thr Phe
315                 320                 325                 330 cgc cat ttc tcc agc cgc agt aca gaa aac gtc ccc agc acg gcg gtc   1660
Arg His Phe Ser Ser Arg Ser Thr Glu Asn Val Pro Ser Thr Ala Val
                335                 340                 345 aat aac gaa ttg cgc att tta cgg gca atc aat gaa gag ata gtc tca   1708
Asn Asn Glu Leu Arg Ile Leu Arg Ala Ile Asn Glu Glu Ile Val Ser
            350                 355                 360 ctg ctg ccg ctc ggc ctg ctg gtt cac gat cag gaa tcg aac cgc act   1756
Leu Leu Pro Leu Gly Leu Leu Val His Asp Gln Glu Ser Asn Arg Thr
        365                 370                 375
```

-continued

| | |
|---|---|
| gtc ata agt aac aaa att gcc gat cat ttg ctg ccg cat ttg aat ctg<br>Val Ile Ser Asn Lys Ile Ala Asp His Leu Leu Pro His Leu Asn Leu<br>380              385                    390 | 1804 |
| caa aac atc acc acc atg gcg gaa cag cat cag ggg att att cag gcg<br>Gln Asn Ile Thr Thr Met Ala Glu Gln His Gln Gly Ile Ile Gln Ala<br>395                   400                  405                  410 | 1852 |
| acg atc aat aac gag ctg tat gag atc cgc atg ttc cgc agc cag gtc<br>Thr Ile Asn Asn Glu Leu Tyr Glu Ile Arg Met Phe Arg Ser Gln Val<br>415              420                    425 | 1900 |
| gcg ccg cgc aca caa att ttc att att cgc gat cag gat cgc gaa gtg<br>Ala Pro Arg Thr Gln Ile Phe Ile Ile Arg Asp Gln Asp Arg Glu Val<br>430              435                    440 | 1948 |
| ctg gta aac aag aaa ctc aag cag gcg cag cgt ctg tat gag aaa aac<br>Leu Val Asn Lys Lys Leu Lys Gln Ala Gln Arg Leu Tyr Glu Lys Asn<br>445              450                    455 | 1996 |
| cag cag ggg cgg atg atc ttt atg aaa aac att ggc gat gcg ctg aaa<br>Gln Gln Gly Arg Met Ile Phe Met Lys Asn Ile Gly Asp Ala Leu Lys<br>460              465                    470 | 2044 |
| gaa ccc gca cag tcc ctg gcg gag agc gcg gct aaa ctc aac gcc ccg<br>Glu Pro Ala Gln Ser Leu Ala Glu Ser Ala Ala Lys Leu Asn Ala Pro<br>475              480                  485                  490 | 2092 |
| gaa agc aaa caa ctg gcg aat cag gca gat gtg ctg gtg cgg ctg gtt<br>Glu Ser Lys Gln Leu Ala Asn Gln Ala Asp Val Leu Val Arg Leu Val<br>495              500                    505 | 2140 |
| gat gaa ata cag tta gcg aac atg ctt gcg gat gat agc tgg aaa agt<br>Asp Glu Ile Gln Leu Ala Asn Met Leu Ala Asp Asp Ser Trp Lys Ser<br>510              515                    520 | 2188 |
| gag acg gtg ctg ttc tcc gtg cag gat tta att gat gaa gtt gtg cct<br>Glu Thr Val Leu Phe Ser Val Gln Asp Leu Ile Asp Glu Val Val Pro<br>525              530                    535 | 2236 |
| tca gtg ttg cct gcc atc aag cgt aaa ggt ctg caa ctg ctg att aac<br>Ser Val Leu Pro Ala Ile Lys Arg Lys Gly Leu Gln Leu Leu Ile Asn<br>540              545                    550 | 2284 |
| aat cat ctg aaa gca cac gat atg cgc cgc ggc gat cgc gat gcc tta<br>Asn His Leu Lys Ala His Asp Met Arg Arg Gly Asp Arg Asp Ala Leu<br>555              560                  565                  570 | 2332 |
| cga cgt att ttg ctg cta ctg atg caa tat gcc gtg acc tca acg caa<br>Arg Arg Ile Leu Leu Leu Leu Met Gln Tyr Ala Val Thr Ser Thr Gln<br>575              580                    585 | 2380 |
| ttg gga aaa atc acc ctt gag gtt gat cag gat gag tcc tcc gaa gac<br>Leu Gly Lys Ile Thr Leu Glu Val Asp Gln Asp Glu Ser Ser Glu Asp<br>590              595                    600 | 2428 |
| cgc ctg acg ttc cgc att ctg gac acg gga gaa ggc gta agt att cat<br>Arg Leu Thr Phe Arg Ile Leu Asp Thr Gly Glu Gly Val Ser Ile His<br>605              610                    615 | 2476 |
| gaa atg gat aat ttg cac ttc ccg ttt atc aac cag acc caa aac gat<br>Glu Met Asp Asn Leu His Phe Pro Phe Ile Asn Gln Thr Gln Asn Asp<br>620              625                    630 | 2524 |
| cgc tat ggc aag gcg gac ccg ctg gca ttc tgg ctg agc gat caa ctg<br>Arg Tyr Gly Lys Ala Asp Pro Leu Ala Phe Trp Leu Ser Asp Gln Leu<br>635              640                  645                  650 | 2572 |
| gca cgt aaa ctg ggc ggt cat tta aac atc aaa acg cgg gat ggg ctt<br>Ala Arg Lys Leu Gly Gly His Leu Asn Ile Lys Thr Arg Asp Gly Leu<br>655              660                  665 | 2620 |
| ggt aca cgc tac tct gtg cat atc aaa atg ctc gca gct gac ccg gaa<br>Gly Thr Arg Tyr Ser Val His Ile Lys Met Leu Ala Ala Asp Pro Glu<br>670              675                  680 | 2668 |
| gtt gaa gag gaa gaa gag cgt tta ctg gat gat gtc tgc gta atg gtg<br>Val Glu Glu Glu Glu Glu Arg Leu Leu Asp Asp Val Cys Val Met Val<br>685              690                  695 | 2716 |

```
gat gtt act tcg gca gaa att cgg aat att gtc act cgc cag tta gaa      2764
Asp Val Thr Ser Ala Glu Ile Arg Asn Ile Val Thr Arg Gln Leu Glu
    700                 705                 710 aat tgg ggt gca acc tgt atc aca ccc gat gaa aga tta att agt caa      2812
Asn Trp Gly Ala Thr Cys Ile Thr Pro Asp Glu Arg Leu Ile Ser Gln
715                 720                 725                 730 gat tat ggt atc ttt tta acg gat aat ccg tct aat ctt act gcc tct      2860
Asp Tyr Gly Ile Phe Leu Thr Asp Asn Pro Ser Asn Leu Thr Ala Ser
                735                 740                 745 ggc ttg ctt tta agc gat gat gag tct ggc gta cgg gaa att ggg cct      2908
Gly Leu Leu Leu Ser Asp Asp Glu Ser Gly Val Arg Glu Ile Gly Pro
            750                 755                 760 ggt caa ttg tgc gtc aac ttc aat atg agc aac gct atg cag gaa gcg      2956
Gly Gln Leu Cys Val Asn Phe Asn Met Ser Asn Ala Met Gln Glu Ala
        765                 770                 775 gtc tta caa tta att gaa gtg caa ctg gcg cag gaa gag gtg aca gaa      3004
Val Leu Gln Leu Ile Glu Val Gln Leu Ala Gln Glu Glu Val Thr Glu
    780                 785                 790 tcg cct ctg ggc gga gat gaa aat gcg caa ctc cat gcc agc ggc tat      3052
Ser Pro Leu Gly Gly Asp Glu Asn Ala Gln Leu His Ala Ser Gly Tyr
795                 800                 805                 810 tat gcg ctc ttt gta gac aca gta ccg gat gat gtt aag agg ctg tat      3100
Tyr Ala Leu Phe Val Asp Thr Val Pro Asp Asp Val Lys Arg Leu Tyr
                815                 820                 825 act gaa gca gca acc agt gac ttt gct gcg tta gcc caa acg gct cat      3148
Thr Glu Ala Ala Thr Ser Asp Phe Ala Ala Leu Ala Gln Thr Ala His
            830                 835                 840 cgt ctt aaa ggc gta ttt gcc atg cta aat ctg gta ccc ggc aag cag      3196
Arg Leu Lys Gly Val Phe Ala Met Leu Asn Leu Val Pro Gly Lys Gln
        845                 850                 855 tta tgt gaa acg ctg gaa cat ctg att cgt gag aag gat gtt cca gga      3244
Leu Cys Glu Thr Leu Glu His Leu Ile Arg Glu Lys Asp Val Pro Gly
    860                 865                 870 ata gaa aaa tac atc agc gac att gac agt tat gtc aag agc ttg ctg      3292
Ile Glu Lys Tyr Ile Ser Asp Ile Asp Ser Tyr Val Lys Ser Leu Leu
875                 880                 885                 890 tag caaggtagcc tattac atg aac aat atg aac gta att att gcc gat gac   3344
                       Met Asn Asn Met Asn Val Ile Ile Ala Asp Asp
                                        895                 900 cat ccg ata gtc ttg ttc ggt att cgc aaa tca ctt gag caa att gag      3392
His Pro Ile Val Leu Phe Gly Ile Arg Lys Ser Leu Glu Gln Ile Glu
            905                 910                 915 tgg gtg aat gtt gtc ggc gaa ttt gaa gac tct aca gca ctg atc aac      3440
Trp Val Asn Val Val Gly Glu Phe Glu Asp Ser Thr Ala Leu Ile Asn
        920                 925                 930 aac ctg ccg aaa ctg gat gcg cat gtg ttg att acc gat ctc tcc atg      3488
Asn Leu Pro Lys Leu Asp Ala His Val Leu Ile Thr Asp Leu Ser Met
    935                 940                 945 cct ggc gat aag tac ggc gat ggc att acc tta atc aag tac atc aag      3536
Pro Gly Asp Lys Tyr Gly Asp Gly Ile Thr Leu Ile Lys Tyr Ile Lys
950                 955                 960                 965 cgc cat ttc cca agc ctg tcg atc att gtt ctg act atg aac aac aac      3584
Arg His Phe Pro Ser Leu Ser Ile Ile Val Leu Thr Met Asn Asn Asn
                970                 975                 980 ccg gcg att ctt agt gcg gta ttg gat ctg gat atc gaa ggg atc gtg      3632
Pro Ala Ile Leu Ser Ala Val Leu Asp Leu Asp Ile Glu Gly Ile Val
            985                 990                 995 ctg aaa caa  ggt gca ccg acc gat  ctg ccg aaa gct ctc  gcc gcg       3677
Leu Lys Gln  Gly Ala Pro Thr Asp  Leu Pro Lys Ala Leu  Ala Ala
```

-continued

```
             1000                 1005                 1010
ctg cag aaa ggg aag aaa ttt acc ccg gaa agc gtt tct cgc ctg       3722
Leu Gln Lys Gly Lys Lys Phe Thr Pro Glu Ser Val Ser Arg Leu
        1015                 1020                 1025 ttg gaa aaa atc agt gct ggt ggt tac ggt gac aag cgt ctc tcg       3767
Leu Glu Lys Ile Ser Ala Gly Gly Tyr Gly Asp Lys Arg Leu Ser
    1030                 1035                 1040 cca aaa gag agt gaa gtt ctg cgc ctg ttt gcg gaa ggc ttc ctg       3812
Pro Lys Glu Ser Glu Val Leu Arg Leu Phe Ala Glu Gly Phe Leu
1045                 1050                 1055 gtg acc gag atc gct aaa aag ctg aac cgc agt att aaa acc atc       3857
Val Thr Glu Ile Ala Lys Lys Leu Asn Arg Ser Ile Lys Thr Ile
            1060                 1065                 1070 agt agc cag aag aaa tct gcg atg atg aag ctg ggt gtc gag aac       3902
Ser Ser Gln Lys Lys Ser Ala Met Met Lys Leu Gly Val Glu Asn
        1075                 1080                 1085 gat atc gcc ctg ctg aat tat ctc tct tca gtg acc tta agt ccg       3947
Asp Ile Ala Leu Leu Asn Tyr Leu Ser Ser Val Thr Leu Ser Pro
    1090                 1095                 1100 gca gat aaa gac taa tcacctgtag gccagataag acgcgttagt gtcttatctg   4002
Ala Asp Lys Asp
        1105 gcatttgcac cgattgccgg atgcggcgta acgccttat  ccggcctacg attcccatta  4062
tttcaacaaa ttacattaaa gtaggccaga taagacgcgt cagcgtcgca tctggcattt  4122
gcactgaatg ccggatgcgg cgtaaacgcc ttatccgtcc tacgaatccc gcgatttcct  4182
gaccctctcg gcatataacg tcagcgtctg ttttatcaca tccagcgtta ccggcttcga  4242
caggcagctg tccataccgg actccagaca ccgctgcttc tcttcagcca acgcattagc  4302
agttactccg attaccggca acgtcagtcc caactgacga atgcgttgcg tcaagcggta  4362
accatccata tttggcatgt tgacgtcgct aagcacgata tcaatatgat tcttgctaag  4422
tacattaagc gcatcgacgc catcattcgc ggttttacat tgatagccca acgatcccaa  4482
ctgatctgcc agcaaacgcc ggttaatcgg atgatcatcc acgaccagaa tcatcatatc  4542
gtcattatcg ctgaccgctt tgtccgttga cggcagagcg ttagcaggat cgtcgctctc  4602
catctcgatc aaataaatac gcgccaacaa tgccggtagc tcatgcggag cagccacact  4662
gtgtacccac tccctggcg cttttctccag cggaataca atatggcgac gacagaaggt  4722
cactaccgct ctgccctgcc atttttttact cactacctcg tcagtgatca acacatcttc  4782
gggagtcggt tcctgccctt cgtatgttgt aacgacgatg ccgctgcgct gcaaactggt  4842
ttccaggaac tgacagagcg acgcattgcg gaccgccagc cagcagcgtt taccactcaa  4902
cccttccacg cctttttttct gcgggtactg agcgccgtac aacggaatac gcacggtaaa  4962
ctggctgccc attcccggtt ctgaatctac cgagatatcg ccgtccatca tgctgatcag  5022
tttttcacaa atcgccagac ccagaccggt cccctggaaa ttacgctgta cgcccgttcc  5082
gacctggaag aagggatcaa acaagcgcac cacttctttc gccggtatcc ccacgccggt  5142
atcgcgaaca cggatagaga gataatcgcc atccgcgcga acatgcaaaa ctatacagcc  5202
ggtatcggtg aatttatgg cgttactcaa caggttggag atgacctgct gtaaacgcat  5262
cgggtcgcca tttaaggcca ctggcacatc cggttcaata aagcagtaca agcctaactg  5322
cttgcgtacc accagcggta aatagttggc ggtgatgtgg ttcatcactt cacgcggtga  5382
aaactcacgc ggttcgatct tcaactgttc cgattcaatc ttcgagaaat cgagaatatc  5442
gctgataatt ttcaacaaca ggctggaaga gttgttcatt gccgtcacca gccgatcgac  5502
```

-continued

```
gcctttcggt aactctttgg tttgcaacag atccaggtta ccgataatgc catacagcgg    5562
cgttcgcagc tcatgactga cggtggcaag gaacatcgat tttgactggc tcgcctgttc    5622
cgctgcttgt gccatctcct gcaacgactc ttccatcttc acgcgcgaag aaacatccac    5682
cagcacacaa atggccacgt tttcattacg atagcgcgaa tggacgaagc tgatttgcag    5742
attggtattg ttgctggtca ggacatcaac aaaattgacc tgctgcccac agataatttg    5802
cgtcagtcgt tggcggtcct catgcgtaag catattgaga taggtatgcg ccagttcgtt    5862
acttaaaata ttgacgccat cagcggtacg caaaatgcag atacccactg cgcggaggc     5922 gacaatcttg cgattgaact gctcatgttc ttccagtcgc agggcgtcgt tttccgccgg    5982
aatgaaaata cgtcgctcgt acatccgtgc gagagtaaac aatgcagctc cggcaagcac    6042
attcagcaaa attgcgttaa ggatcaacat gcgaatgcgt tccagcacct tatcaaccgg    6102
caccgaatac acgatgctta gcgatgaggg tggcagattt ttcttcagca ccagctcccg    6162
gaacccttcc gtatagccaa accaggagcg ttcctgcatc cagcgaggat cgcccttaat    6222
tttactttct ggtccggtaa gcgaaatcag ggtatgacca ttttcatcaa gaatggtaa     6281
```

<210> SEQ ID NO 44
<211> LENGTH: 890
<212> TYPE: PRT
<213> ORGANISM: Escherichia coli

<400> SEQUENCE: 44

```
Met Arg Gln Lys Glu Thr Thr Ala Thr Thr Arg Phe Ser Leu Leu Pro
1               5                   10                  15

Gly Ser Ile Thr Arg Phe Phe Leu Leu Ile Ile Val Leu Leu Val
            20                  25                  30

Thr Met Gly Val Met Val Gln Ser Ala Val Asn Ala Trp Leu Lys Asp
        35                  40                  45

Lys Ser Tyr Gln Ile Val Asp Ile Thr His Ala Ile Gln Lys Arg Val
    50                  55                  60

Asp Asn Trp Arg Tyr Val Thr Trp Gln Ile Tyr Asp Asn Ile Ala Ala
65                  70                  75                  80

Thr Thr Ser Pro Ser Ser Gly Glu Gly Leu Gln Glu Thr Arg Leu Lys
                85                  90                  95

Gln Asp Val Tyr Tyr Leu Glu Lys Pro Arg Arg Lys Thr Glu Ala Leu
            100                 105                 110

Ile Phe Gly Ser His Asp Asn Ser Thr Leu Glu Met Thr Gln Arg Met
        115                 120                 125

Ser Thr Tyr Leu Asp Thr Leu Trp Gly Ala Glu Asn Val Pro Trp Ser
    130                 135                 140

Met Tyr Tyr Leu Asn Gly Gln Asp Asn Ser Leu Val Leu Ile Ser Thr
145                 150                 155                 160

Leu Pro Leu Lys Asp Leu Thr Ser Gly Phe Lys Glu Ser Thr Val Ser
                165                 170                 175

Asp Ile Val Asp Ser Arg Arg Ala Glu Met Leu Gln Gln Ala Asn Ala
            180                 185                 190

Leu Asp Glu Arg Glu Ser Phe Ser Asn Met Arg Arg Leu Ala Trp Gln
        195                 200                 205

Asn Gly His Tyr Phe Thr Leu Arg Thr Thr Phe Asn Gln Pro Gly His
    210                 215                 220

Leu Ala Thr Val Val Ala Phe Asp Leu Pro Ile Asn Asp Leu Ile Pro
225                 230                 235                 240
```

```
Pro Gly Met Pro Leu Asp Ser Phe Arg Leu Glu Pro Asp Ala Thr Ala
            245                 250                 255

Thr Gly Asn Asn Asp Asn Glu Lys Glu Gly Thr Asp Ser Val Ser Ile
        260                 265                 270

His Phe Asn Ser Thr Lys Ile Glu Ile Ser Ser Ala Leu Asn Ser Thr
    275                 280                 285

Asp Met Arg Leu Val Trp Gln Val Pro Tyr Gly Thr Leu Leu Leu Asp
290                 295                 300

Thr Leu Gln Asn Ile Leu Leu Pro Leu Leu Leu Asn Ile Gly Leu Leu
305                 310                 315                 320

Ala Leu Ala Leu Phe Gly Tyr Thr Thr Phe Arg His Phe Ser Ser Arg
                325                 330                 335

Ser Thr Glu Asn Val Pro Ser Thr Ala Val Asn Asn Glu Leu Arg Ile
            340                 345                 350

Leu Arg Ala Ile Asn Glu Glu Ile Val Ser Leu Leu Pro Leu Gly Leu
        355                 360                 365

Leu Val His Asp Gln Glu Ser Asn Arg Thr Val Ile Ser Asn Lys Ile
    370                 375                 380

Ala Asp His Leu Leu Pro His Leu Asn Leu Gln Asn Ile Thr Thr Met
385                 390                 395                 400

Ala Glu Gln His Gln Gly Ile Ile Gln Ala Thr Ile Asn Asn Glu Leu
                405                 410                 415

Tyr Glu Ile Arg Met Phe Arg Ser Gln Val Ala Pro Arg Thr Gln Ile
            420                 425                 430

Phe Ile Ile Arg Asp Gln Asp Arg Glu Val Leu Val Asn Lys Lys Leu
        435                 440                 445

Lys Gln Ala Gln Arg Leu Tyr Glu Lys Asn Gln Gln Gly Arg Met Ile
    450                 455                 460

Phe Met Lys Asn Ile Gly Asp Ala Leu Lys Glu Pro Ala Gln Ser Leu
465                 470                 475                 480

Ala Glu Ser Ala Ala Lys Leu Asn Ala Pro Glu Ser Lys Gln Leu Ala
                485                 490                 495

Asn Gln Ala Asp Val Leu Val Arg Leu Val Asp Glu Ile Gln Leu Ala
            500                 505                 510

Asn Met Leu Ala Asp Asp Ser Trp Lys Ser Glu Thr Val Leu Phe Ser
        515                 520                 525

Val Gln Asp Leu Ile Asp Glu Val Pro Ser Val Leu Pro Ala Ile
    530                 535                 540

Lys Arg Lys Gly Leu Gln Leu Leu Ile Asn Asn His Leu Lys Ala His
545                 550                 555                 560

Asp Met Arg Arg Gly Asp Arg Asp Ala Leu Arg Ile Leu Leu Leu
                565                 570                 575

Leu Met Gln Tyr Ala Val Thr Ser Thr Gln Leu Gly Lys Ile Thr Leu
            580                 585                 590

Glu Val Asp Gln Asp Glu Ser Ser Glu Asp Arg Leu Thr Phe Arg Ile
        595                 600                 605

Leu Asp Thr Gly Glu Gly Val Ser Ile His Glu Met Asp Asn Leu His
    610                 615                 620

Phe Pro Phe Ile Asn Gln Thr Gln Asn Asp Arg Tyr Gly Lys Ala Asp
625                 630                 635                 640

Pro Leu Ala Phe Trp Leu Ser Asp Gln Leu Ala Arg Lys Leu Gly Gly
                645                 650                 655
```

-continued

His Leu Asn Ile Lys Thr Arg Asp Gly Leu Gly Thr Arg Tyr Ser Val
            660                 665                 670

His Ile Lys Met Leu Ala Ala Asp Pro Glu Val Glu Glu Glu Glu Glu
        675                 680                 685

Arg Leu Leu Asp Asp Val Cys Val Met Val Asp Val Thr Ser Ala Glu
    690                 695                 700

Ile Arg Asn Ile Val Thr Arg Gln Leu Glu Asn Trp Gly Ala Thr Cys
705                 710                 715                 720

Ile Thr Pro Asp Glu Arg Leu Ile Ser Gln Asp Tyr Gly Ile Phe Leu
                725                 730                 735

Thr Asp Asn Pro Ser Asn Leu Thr Ala Ser Gly Leu Leu Ser Asp
            740                 745                 750

Asp Glu Ser Gly Val Arg Glu Ile Gly Pro Gly Gln Leu Cys Val Asn
        755                 760                 765

Phe Asn Met Ser Asn Ala Met Gln Glu Ala Val Leu Gln Leu Ile Glu
    770                 775                 780

Val Gln Leu Ala Gln Glu Glu Val Thr Glu Ser Pro Leu Gly Gly Asp
785                 790                 795                 800

Glu Asn Ala Gln Leu His Ala Ser Gly Tyr Tyr Ala Leu Phe Val Asp
                805                 810                 815

Thr Val Pro Asp Asp Val Lys Arg Leu Tyr Thr Glu Ala Ala Thr Ser
            820                 825                 830

Asp Phe Ala Ala Leu Ala Gln Thr Ala His Arg Leu Lys Gly Val Phe
        835                 840                 845

Ala Met Leu Asn Leu Val Pro Gly Lys Gln Leu Cys Glu Thr Leu Glu
    850                 855                 860

His Leu Ile Arg Glu Lys Asp Val Pro Gly Ile Glu Lys Tyr Ile Ser
865                 870                 875                 880

Asp Ile Asp Ser Tyr Val Lys Ser Leu Leu
                885                 890

<210> SEQ ID NO 45
<211> LENGTH: 216
<212> TYPE: PRT
<213> ORGANISM: Escherichia coli

<400> SEQUENCE: 45

Met Asn Asn Met Asn Val Ile Ile Ala Asp Asp His Pro Ile Val Leu
1               5                   10                  15

Phe Gly Ile Arg Lys Ser Leu Glu Gln Ile Glu Trp Val Asn Val Val
            20                  25                  30

Gly Glu Phe Glu Asp Ser Thr Ala Leu Ile Asn Asn Leu Pro Lys Leu
        35                  40                  45

Asp Ala His Val Leu Ile Thr Asp Leu Ser Met Pro Gly Asp Lys Tyr
    50                  55                  60

Gly Asp Gly Ile Thr Leu Ile Lys Tyr Ile Lys Arg His Phe Pro Ser
65                  70                  75                  80

Leu Ser Ile Ile Val Leu Thr Met Asn Asn Asn Pro Ala Ile Leu Ser
                85                  90                  95

Ala Val Leu Asp Leu Asp Ile Glu Gly Ile Val Leu Lys Gln Gly Ala
            100                 105                 110

Pro Thr Asp Leu Pro Lys Ala Leu Ala Ala Leu Gln Lys Gly Lys Lys
        115                 120                 125

Phe Thr Pro Glu Ser Val Ser Arg Leu Leu Glu Lys Ile Ser Ala Gly
    130                 135                 140

Gly Tyr Gly Asp Lys Arg Leu Ser Pro Lys Glu Ser Glu Val Leu Arg
145                 150                 155                 160

Leu Phe Ala Glu Gly Phe Leu Val Thr Glu Ile Ala Lys Lys Leu Asn
                165                 170                 175

Arg Ser Ile Lys Thr Ile Ser Ser Gln Lys Lys Ser Ala Met Met Lys
            180                 185                 190

Leu Gly Val Glu Asn Asp Ile Ala Leu Leu Asn Tyr Leu Ser Ser Val
        195                 200                 205

Thr Leu Ser Pro Ala Asp Lys Asp
    210                 215

<210> SEQ ID NO 46
<211> LENGTH: 489
<212> TYPE: DNA
<213> ORGANISM: Escherichia coli
<220> FEATURE:
<221> NAME/KEY: CDS
<222> LOCATION: (1)..(489)

<400> SEQUENCE: 46

| | |
|---|---|
| atg caa tcc tgg tat tta ctg tac tgc aag cgc ggg caa ctt caa cgt<br>Met Gln Ser Trp Tyr Leu Leu Tyr Cys Lys Arg Gly Gln Leu Gln Arg<br>1               5                   10                  15 | 48 |
| gcc cag gaa cac ctc gaa aga cag gct gtg aat tgc ctg gca ccg atg<br>Ala Gln Glu His Leu Glu Arg Gln Ala Val Asn Cys Leu Ala Pro Met<br>            20                  25                  30 | 96 |
| atc acc ctg gaa aaa atc gtg cgt gga aaa cgt act gca gtc agt gag<br>Ile Thr Leu Glu Lys Ile Val Arg Gly Lys Arg Thr Ala Val Ser Glu<br>        35                  40                  45 | 144 |
| cca ttg ttt ccc aac tac ctg ttt gtc gaa ttt gat cca gaa gtg att<br>Pro Leu Phe Pro Asn Tyr Leu Phe Val Glu Phe Asp Pro Glu Val Ile<br>    50                  55                  60 | 192 |
| cat acc acg act atc aac gcg acc cgc ggt gtc agt cac ttc gtg cgc<br>His Thr Thr Thr Ile Asn Ala Thr Arg Gly Val Ser His Phe Val Arg<br>65                  70                  75                  80 | 240 |
| ttt ggc gcg tcg cca gcg ata gtc cca tcg gcg gtg att cat cag cta<br>Phe Gly Ala Ser Pro Ala Ile Val Pro Ser Ala Val Ile His Gln Leu<br>                85                  90                  95 | 288 |
| tcg gta tat aaa ccg aaa gac att gtc gat ccg gca acc cct tat ccg<br>Ser Val Tyr Lys Pro Lys Asp Ile Val Asp Pro Ala Thr Pro Tyr Pro<br>            100                 105                 110 | 336 |
| gga gat aag gtg att att acc gaa ggc gcg ttc gaa ggc ttt cag gcc<br>Gly Asp Lys Val Ile Ile Thr Glu Gly Ala Phe Glu Gly Phe Gln Ala<br>        115                 120                 125 | 384 |
| att ttc acc gaa ccc gat ggt gag gct cgc tcc atg cta ttg ctt aat<br>Ile Phe Thr Glu Pro Asp Gly Glu Ala Arg Ser Met Leu Leu Leu Asn<br>    130                 135                 140 | 432 |
| ctt att aat aaa gag att aag cac agt gtg aag aac acc gag ttc cgc<br>Leu Ile Asn Lys Glu Ile Lys His Ser Val Lys Asn Thr Glu Phe Arg<br>145                 150                 155                 160 | 480 |
| aaa ctc taa<br>Lys Leu | 489 |

<210> SEQ ID NO 47
<211> LENGTH: 162
<212> TYPE: PRT
<213> ORGANISM: Escherichia coli

<400> SEQUENCE: 47

Met Gln Ser Trp Tyr Leu Leu Tyr Cys Lys Arg Gly Gln Leu Gln Arg

```
              1               5                    10                   15
            Ala Gln Glu His Leu Glu Arg Gln Ala Val Asn Cys Leu Ala Pro Met
                          20                  25                  30
            Ile Thr Leu Glu Lys Ile Val Arg Gly Lys Arg Thr Ala Val Ser Glu
                          35                  40                  45
            Pro Leu Phe Pro Asn Tyr Leu Phe Val Glu Phe Pro Glu Val Ile
                50                  55                  60
            His Thr Thr Thr Ile Asn Ala Thr Arg Gly Val Ser His Phe Val Arg
            65                  70                  75                  80
            Phe Gly Ala Ser Pro Ala Ile Val Pro Ser Ala Val Ile His Gln Leu
                            85                  90                  95
            Ser Val Tyr Lys Pro Lys Asp Ile Val Asp Pro Ala Thr Pro Tyr Pro
                           100                 105                 110
            Gly Asp Lys Val Ile Ile Thr Glu Gly Ala Phe Glu Gly Phe Gln Ala
                           115                 120                 125
            Ile Phe Thr Glu Pro Asp Gly Glu Ala Arg Ser Met Leu Leu Leu Asn
                        130                 135                 140
            Leu Ile Asn Lys Glu Ile Lys His Ser Val Lys Asn Thr Glu Phe Arg
            145                 150                 155                 160
            Lys Leu

<210> SEQ ID NO 48
<211> LENGTH: 546
<212> TYPE: DNA
<213> ORGANISM: Escherichia coli
<220> FEATURE:
<221> NAME/KEY: CDS
<222> LOCATION: (1)..(546)

<400> SEQUENCE: 48 atg tct gaa gct cct aaa aag cgc tgg tac gtc gtt cag gcg ttt tcc        48
Met Ser Glu Ala Pro Lys Lys Arg Trp Tyr Val Val Gln Ala Phe Ser
1               5                   10                  15 ggt ttt gaa ggc cgc gta gca acg tcg ctg cgt gag cat atc aaa tta       96
Gly Phe Glu Gly Arg Val Ala Thr Ser Leu Arg Glu His Ile Lys Leu
                20                  25                  30 cac aac atg gaa gat ttg ttt ggt gaa gtc atg gta cca acc gaa gaa      144
His Asn Met Glu Asp Leu Phe Gly Glu Val Met Val Pro Thr Glu Glu
            35                  40                  45 gtg gtt gaa atc cgt ggc ggt cag cgt cgc aaa agc gaa cgt aaa ttc      192
Val Val Glu Ile Arg Gly Gly Gln Arg Arg Lys Ser Glu Arg Lys Phe
        50                  55                  60 ttc cct ggc tac gtc ctc gtt cag atg gtg atg aac gac gcg agc tgg      240
Phe Pro Gly Tyr Val Leu Val Gln Met Val Met Asn Asp Ala Ser Trp
65                  70                  75                  80 cac ctg gtg cgc agc gta ccg cgt gtg atg ggc ttc atc ggc ggt act      288
His Leu Val Arg Ser Val Pro Arg Val Met Gly Phe Ile Gly Gly Thr
                85                  90                  95 tcc gat cgt cct gcg cca atc agc gat aaa gaa gtc gat gcg att atg      336
Ser Asp Arg Pro Ala Pro Ile Ser Asp Lys Glu Val Asp Ala Ile Met
                100                 105                 110 aac cgc ctg cag cag gtt ggt gat aag ccg cgt ccg aaa acg ctg ttt      384
Asn Arg Leu Gln Gln Val Gly Asp Lys Pro Arg Pro Lys Thr Leu Phe
            115                 120                 125 gaa ccg ggt gaa atg gtc cgt gtt aat gat ggt ccg ttc gct gac ttc      432
Glu Pro Gly Glu Met Val Arg Val Asn Asp Gly Pro Phe Ala Asp Phe
        130                 135                 140 aac ggt gtt gtt gaa gaa gtg gat tac gag aaa tct cgt ctg aaa gtg      480
```

| | | | | | | | | | | | | | | | |
|---|---|---|---|---|---|---|---|---|---|---|---|---|---|---|---|
|Asn|Gly|Val|Val|Glu|Glu|Val|Asp|Tyr|Glu|Lys|Ser|Arg|Leu|Lys|Val|
|145| | | |150| | | | |155| | | | |160| |

| | | | | | | | | | | | | |
|---|---|---|---|---|---|---|---|---|---|---|---|---|
|tct|gtt|tct|atc|ttc|ggt|cgt|gcg|acc|ccg|gta|gag|ctg|gac|ttc|agc|528|
|Ser|Val|Ser|Ile|Phe|Gly|Arg|Ala|Thr|Pro|Val|Glu|Leu|Asp|Phe|Ser| |
| | | |165| | | | |170| | | | |175| | | | cag gtt gaa aaa gcc taa 546
Gln Val Glu Lys Ala
        180

<210> SEQ ID NO 49
<211> LENGTH: 181
<212> TYPE: PRT
<213> ORGANISM: Escherichia coli

<400> SEQUENCE: 49

Met Ser Glu Ala Pro Lys Lys Arg Trp Tyr Val Val Gln Ala Phe Ser
1               5                   10                  15

Gly Phe Glu Gly Arg Val Ala Thr Ser Leu Arg Glu His Ile Lys Leu
            20                  25                  30

His Asn Met Glu Asp Leu Phe Gly Glu Val Met Val Pro Thr Glu Glu
        35                  40                  45

Val Val Glu Ile Arg Gly Gly Gln Arg Arg Lys Ser Glu Arg Lys Phe
    50                  55                  60

Phe Pro Gly Tyr Val Leu Val Gln Met Val Met Asn Asp Ala Ser Trp
65                  70                  75                  80

His Leu Val Arg Ser Val Pro Arg Val Met Gly Phe Ile Gly Gly Thr
                85                  90                  95

Ser Asp Arg Pro Ala Pro Ile Ser Asp Lys Val Asp Ala Ile Met
            100                 105                 110

Asn Arg Leu Gln Gln Val Gly Asp Lys Pro Arg Pro Lys Thr Leu Phe
        115                 120                 125

Glu Pro Gly Glu Met Val Arg Val Asn Asp Gly Pro Phe Ala Asp Phe
    130                 135                 140

Asn Gly Val Val Glu Glu Val Asp Tyr Glu Lys Ser Arg Leu Lys Val
145                 150                 155                 160

Ser Val Ser Ile Phe Gly Arg Ala Thr Pro Val Glu Leu Asp Phe Ser
                165                 170                 175

Gln Val Glu Lys Ala
            180

<210> SEQ ID NO 50
<211> LENGTH: 4181
<212> TYPE: DNA
<213> ORGANISM: Escherichia coli

<400> SEQUENCE: 50
attcgttgtt gcgattatca ttctgggcgc cgtagcgtgg ctcggaatgc ttgctccgtc    60
tcaggtcagc tagggacag ccaaagctca tgcgtgagat tttactttc atatcagcga    120 gttgaccatg cagcgtattt taatcgttga agacgaacaa aaaacaggtc gttacctgca    180
gcagggactg gttgaggaag ctatcaggc cgatctcttt aataatggcc gcgatggtct    240
cggggccgcg tcgaagggac agtatgattt gataatactg gacgtgatgc tgccttttcct    300 cgacgggtgg caaatcatca gcgcactgag ggagtccggg cacgaagaac cggtcctgtt    360
tttaaccgca aaggacaacg tgcgggacaa agtgaaagga ctggagcttg cgcagatga    420 ctacctgatt aagccctttg attttacgga gctggttgca cgtgtaagaa ccctactgcg    480

```
ccgggcacgc tcgcaggccg caacagtctg caccatcgcc gatatgaccg ttgatatggt    540
gcgccggacc gtgatccgtt cggggaagaa gatccatctc accggtaaag aatacgttct    600
gcttgagttg ctgctgcaac gcaccggaga agtgttaccc aggagtctta tctcgtccct    660
ggtctggaac atgaattttg acagtgatac gaatgtgatt gatgtcgccg tgagacgtct    720
gagaagtaaa attgatgatg actttgagcc aaaactgatc cataccgttc gcggtgccgg    780
atatgtcctg gagatcagag aagagtgagg ttcaaaattt ccctgaccac acgcctgagc    840
ctgatttttt ctgcggtgat gcttacggta tggtggttat caagttttat cctgattagc    900
acccttaatg gctatttcga taatcaggac cgcgattttc tgacaggtaa acttcagctc    960
accgaagagt ttcttaaaac agagacgttc aggaacaaaa cggatattaa gtcattatca   1020
gaaaaaataa acgatgcgat ggtggggcac aatggcttat tcatttctat aaaaaacatg   1080
gaaaatgaaa aaattgttga actctatgcc aaaaattctg ttgttccagc ggtcctgctt   1140
aataagtcgg gtgatattct cgactatatg atccagacgg aagaaaataa caccgtgtac   1200
cgcagtatct cgcggcgggt tgccgtgacg ccggaacagg gtaaaagcaa acatgtcatc   1260
attacggttg ccacggatac tgggtatcac accctgttta tggacaaaact cagtacctgg   1320
ctgttctggt tcaatatcgg tctggtcttt atttctgttt ttctgggctg gctgaccaca   1380
cgtattggtc tgaaaccgct acgggaaatg accagtctgg cttcctccat gaccgtacac   1440
agcctggatc agcgtctaaa tcccgatctg gctccgccgg aaatctctga gaccatgcag   1500
gagttcaata atatgtttga tcgcctggag ggggcattcc ggaaactgtc agatttctcg   1560
tctgacatcg cgcatgagct gcgcacacca gtcagtaatc tgatgatgca gacgcagttt   1620
gcactggcta aggaagggga tgtttcgcat taccgcgaaa ttttattcgc taacctggaa   1680
gaactgaaaa ggttgtcacg aatgaccagt gacatgcttt ttctggcacg ttcagagcat   1740
ggtctgctgc ggctggataa acatgatgtg gatctggcag ccgaactgaa tgaattacgt   1800
gagttgttcg agcccctggc agacgaaaca ggaaagacaa tcacggttga aggagagggc   1860
gttgttgccg gagacagcga tatgctccga cgtgctttca gtaacctgct ttccaatgca   1920
atcaagtatt ctcccgataa cacctgtaca gcgatacacc ttgagcgtga cagtgactgt   1980
gtgaacgtga tgattacgaa tacgatgtcc ggccaggttc ccgctaatct ggaacgtttg   2040
tttgaccggt ctatcgcgc agactcatca aggttctaca acacggaagg cgcggggctg   2100
ggattatcaa ttacaaggtc gatcattcat gctcacggcg gcgagctgtc agcagaacag   2160
caggggcgtg aaattgtgtt caaagtgcgc ctgttaatgg attaatcccg ttgttcagga   2220
gaaacctgga aggtgacaaa attgtcatca ttcagtcacg cgataaacag aggcggtttt   2280
ttataattat tcataaatca ggagcagcgt gataacacaa tcacctggtt cctggagtga   2340
tgattaaccc gccctgagat caactgcttt ctctgttata agccattgat tgtttgggta   2400
tgtaaacacc ggagacccaa ccatgaaaaa gattctcgta tcatttgttg ccattatggc   2460
tgccgcttca tctgccatgg ctgcagagac aatgaacatg catgaccagg taaataatgc   2520
acaggcacct gcccaccaga tgcagtcatc tgctgaaaaa agtgcaattc agggagacag   2580
catgacaatg atggatatga gcagtcacga tcaggccgca atgtcccatg acatgatgca   2640
aaacagcaat tctgctgccc accaggacat ggctgaaatg cataaaaaaa tgatgaaagc   2700
taaacccgga gctaccaacg aaacagcaaa gtcatttttct gaaatgagcg agcatgagaa   2760
ggccgcagct gtacatgaga aggcgaataa tggtcagtct tccgttgttc accagcagca   2820
ggctgataag catcgcagtc agatcaccca gaattaaccc gcagctccac ttgttagacc   2880
```

```
ctcatttgac gccgaagtca ctggcttacg ctcccgtccg ggagcgtttt ttttcccata    2940
tatcaaactt taactctgaa gaggtggaag tatctgacca acactgtcac gtaacgccag    3000
ataactacaa aaacacctttt ttcctcctgt aaattgcagt tcctgcaaga acatcaaggc    3060
```

```
ctcatttgac gccgaagtca ctggcttacg ctcccgtccg ggagcgtttt ttttcccata    2940
tatcaaactt taactctgaa gaggtggaag tatctgacca acactgtcac gtaacgccag    3000
ataactacaa aaacaccttt ttcctcctgt aaattgcagt tcctgcaaga acatcaaggc    3060
ataatgttgg aacagcgtgt gatacacact tagcatcatg ttttgtatgt gttttttttaa   3120
aactttacaa ctttaaagtc tttttcaggt taaggatac aactttaatg tctctacaca    3180
attgcagcaa agtcgtcctg acctatttcc taaagatgaa aattattaga gtcgcattaa    3240
aaatgagcta attttgatag tggttatctt gtgattattt tctaatgagc ccgtgaactg    3300
aaaccctcca tgcttaatat aaggtggatg gaaaggtgat tgaaaactca cccagtggcc    3360
agatctttat gaaatatgaa caggttgaaa aaaacagtaa ctttgctgtt ttttatactt    3420
aaccactatg cattaatgct gcgttatttc atgatgccta agaaaaacca gcgttacgca    3480
aatggtcaac gctggtttta tccggtacgt tgcaattatt ttttagcaga accgcttct    3540
aatattgaaa cgattgagaa caacgtaaag catccgctc ccaaaccgac cagaactcgc    3600
gaaggaataa aatatcccat gtcggtctgc gccatttccg caagaaacga tgccaggaaa    3660
aggcaaaaca ggcaggtgaa gacgggaatc atcggtattc tgttggctaa cgaacaggta    3720
cgtctccata ccagtgccag tagccagact tttgagaata tgctgtaaca gatcattccg    3780
aggcaaataa gaataatgcc gggagccagt cgggcgcttg catcggaact gactaagacg    3840
tatatcccct gcagtaccgt gattgagccg agaaaaataa cccaataaca ccacagccag    3900
tgttctttag ttgaaaacgt attacgtgtt tgatggacaa ttgtggcaac aaggccaatt    3960
agacaggcac agattgcggt taacccaagc aatacgtgac ccgcgacata atgcggagtt    4020
atgtcagcac tacgtaacag cgtaatagac caaatgaaac cgagcagggt gagtaaaacg    4080
ggaacggcaa tgaggcagtt accgattaat gaagaataag cctgtaccgg tgttccgtcg    4140
ctcttgctcc ccgctgcatt tttgggaatg agcagaaagt g                       4181
```

<210> SEQ ID NO 51
<211> LENGTH: 226
<212> TYPE: PRT
<213> ORGANISM: Escherichia coli
<400> SEQUENCE: 51

```
Met Gln Arg Ile Leu Ile Val Glu Asp Glu Gln Lys Thr Gly Arg Tyr
1               5                   10                  15

Leu Gln Gln Gly Leu Val Glu Glu Gly Tyr Gln Ala Asp Leu Phe Asn
            20                  25                  30

Asn Gly Arg Asp Gly Leu Gly Ala Ala Ser Lys Gly Gln Tyr Asp Leu
        35                  40                  45

Ile Ile Leu Asp Val Met Leu Pro Phe Leu Asp Gly Trp Gln Ile Ile
    50                  55                  60

Ser Ala Leu Arg Glu Ser Gly His Glu Glu Pro Val Leu Phe Leu Thr
65                  70                  75                  80

Ala Lys Asp Asn Val Arg Asp Lys Val Lys Gly Leu Glu Leu Gly Ala
                85                  90                  95

Asp Asp Tyr Leu Ile Lys Pro Phe Asp Phe Thr Glu Leu Val Ala Arg
            100                 105                 110

Val Arg Thr Leu Leu Arg Arg Ala Arg Ser Gln Ala Ala Thr Val Cys
        115                 120                 125

Thr Ile Ala Asp Met Thr Val Asp Met Val Arg Arg Thr Val Ile Arg
    130                 135                 140
```

```
Ser Gly Lys Lys Ile His Leu Thr Gly Lys Glu Tyr Val Leu Leu Glu
145                 150                 155                 160

Leu Leu Leu Gln Arg Thr Gly Glu Val Leu Pro Arg Ser Leu Ile Ser
                165                 170                 175

Ser Leu Val Trp Asn Met Asn Phe Asp Ser Asp Thr Asn Val Ile Asp
            180                 185                 190

Val Ala Val Arg Arg Leu Arg Ser Lys Ile Asp Asp Phe Glu Pro
        195                 200                 205

Lys Leu Ile His Thr Val Arg Gly Ala Gly Tyr Val Leu Glu Ile Arg
    210                 215                 220

Glu Glu
225

<210> SEQ ID NO 52
<211> LENGTH: 466
<212> TYPE: PRT
<213> ORGANISM: Escherichia coli

<400> SEQUENCE: 52

Met Arg Phe Lys Ile Ser Leu Thr Thr Arg Leu Ser Leu Ile Phe Ser
1               5                   10                  15

Ala Val Met Leu Thr Val Trp Trp Leu Ser Ser Phe Ile Leu Ile Ser
                20                  25                  30

Thr Leu Asn Gly Tyr Phe Asp Asn Gln Asp Arg Asp Phe Leu Thr Gly
            35                  40                  45

Lys Leu Gln Leu Thr Glu Glu Phe Leu Lys Thr Glu Thr Phe Arg Asn
50                  55                  60

Lys Thr Asp Ile Lys Ser Leu Ser Glu Lys Ile Asn Asp Ala Met Val
65                  70                  75                  80

Gly His Asn Gly Leu Phe Ile Ser Ile Lys Asn Met Glu Asn Glu Lys
                85                  90                  95

Ile Val Glu Leu Tyr Ala Lys Asn Ser Val Val Pro Ala Val Leu Leu
                100                 105                 110

Asn Lys Ser Gly Asp Ile Leu Asp Tyr Met Ile Gln Thr Glu Glu Asn
            115                 120                 125

Asn Thr Val Tyr Arg Ser Ile Ser Arg Arg Val Ala Val Thr Pro Glu
        130                 135                 140

Gln Gly Lys Ser Lys His Val Ile Ile Thr Val Ala Thr Asp Thr Gly
145                 150                 155                 160

Tyr His Thr Leu Phe Met Asp Lys Leu Ser Thr Trp Leu Phe Trp Phe
                165                 170                 175

Asn Ile Gly Leu Val Phe Ile Ser Val Phe Leu Gly Trp Leu Thr Thr
            180                 185                 190

Arg Ile Gly Leu Lys Pro Leu Arg Glu Met Thr Ser Leu Ala Ser Ser
        195                 200                 205

Met Thr Val His Ser Leu Asp Gln Arg Leu Asn Pro Asp Leu Ala Pro
    210                 215                 220

Pro Glu Ile Ser Glu Thr Met Gln Glu Phe Asn Asn Met Phe Asp Arg
225                 230                 235                 240

Leu Glu Gly Ala Phe Arg Lys Leu Ser Asp Phe Ser Ser Asp Ile Ala
                245                 250                 255

His Glu Leu Arg Thr Pro Val Ser Asn Leu Met Met Gln Thr Gln Phe
            260                 265                 270

Ala Leu Ala Lys Glu Arg Asp Val Ser His Tyr Arg Glu Ile Leu Phe
```

```
            275                 280                 285
Ala Asn Leu Glu Glu Leu Lys Arg Leu Ser Arg Met Thr Ser Asp Met
290                 295                 300

Leu Phe Leu Ala Arg Ser Glu His Gly Leu Leu Arg Leu Asp Lys His
305                 310                 315                 320

Asp Val Asp Leu Ala Ala Glu Leu Asn Glu Leu Arg Glu Leu Phe Glu
                325                 330                 335

Pro Leu Ala Asp Glu Thr Gly Lys Thr Ile Thr Val Glu Gly Glu Gly
                340                 345                 350

Val Val Ala Gly Asp Ser Asp Met Leu Arg Arg Ala Phe Ser Asn Leu
                355                 360                 365

Leu Ser Asn Ala Ile Lys Tyr Ser Pro Asp Asn Thr Cys Thr Ala Ile
370                 375                 380

His Leu Glu Arg Asp Ser Asp Cys Val Asn Val Met Ile Thr Asn Thr
385                 390                 395                 400

Met Ser Gly Gln Val Pro Ala Asn Leu Glu Arg Leu Phe Asp Arg Phe
                405                 410                 415

Tyr Arg Ala Asp Ser Ser Arg Phe Tyr Asn Thr Glu Gly Ala Gly Leu
                420                 425                 430

Gly Leu Ser Ile Thr Arg Ser Ile Ile His Ala His Gly Gly Glu Leu
                435                 440                 445

Ser Ala Glu Gln Gln Gly Arg Glu Ile Val Phe Lys Val Arg Leu Leu
                450                 455                 460

Met Asp
465

<210> SEQ ID NO 53
<211> LENGTH: 144
<212> TYPE: PRT
<213> ORGANISM: Escherichia coli

<400> SEQUENCE: 53

Met Lys Lys Ile Leu Val Ser Phe Val Ala Ile Met Ala Ala Ala Ser
1               5                   10                  15

Ser Ala Met Ala Ala Glu Thr Met Asn Met His Asp Gln Val Asn Asn
                20                  25                  30

Ala Gln Ala Pro Ala His Gln Met Gln Ser Ser Ala Glu Lys Ser Ala
                35                  40                  45

Ile Gln Gly Asp Ser Met Thr Met Met Asp Met Ser Ser His Asp Gln
            50                  55                  60

Ala Ala Met Ser His Asp Met Met Gln Asn Ser Asn Ser Ala Ala His
65                  70                  75                  80

Gln Asp Met Ala Glu Met His Lys Lys Met Met Lys Ala Lys Pro Gly
                85                  90                  95

Ala Thr Asn Glu Thr Ala Lys Ser Phe Ser Glu Met Ser Glu His Glu
                100                 105                 110

Lys Ala Ala Ala Val His Glu Lys Ala Asn Asn Gly Gln Ser Ser Val
                115                 120                 125

Val His Gln Gln Gln Ala Asp Lys His Arg Ser Gln Ile Thr Gln Asn
                130                 135                 140

<210> SEQ ID NO 54
<211> LENGTH: 4048
<212> TYPE: DNA
<213> ORGANISM: Escherichia coli
```

<400> SEQUENCE: 54

```
gattttgtga tatgggtcac gaaacaaagg cccagctaaa agattatgtc gaggtaaaaa      60
tcatgaaaat caaaccact gttgctgcat taagcgtact ttctgttctc tctttcggtg     120
cattcgctgc cgactccatt gatgctgcac aagcacaaaa tcgtgaagca atcgggaccg     180
tatccgtaag tggtgtggcg tcttcgccaa tggatatgcg tgaaatgctg aacaaaaaag     240
cggaagagaa aggcgcaacg gcctaccaga ttactgaagc tcgtagcggt gacacctggc     300
acgctacggc tgaactgtac aaataaaccc tcatcgtctt gtccgacgat attgccccg      360
gttcgggggc ttttttttgc gctaatgacg aacattaaaa cgcaaatgcc cttccagctc     420
ttcctctgcc tcatcaaaca gcaatattaa cgcgccaaaa cggcgacgcg ttttctctcc     480
cagatgaaca aattcaatct caagtggtag cggcaggaca tcgttcatta acacatccca     540
tagtgagtcg agatcgcgta ccttatcttt cgccagacca aaggtttggc taaagtcacg     600
ataaaaatcc tcctgactct caatctcatc aaaatcaaag gtataaatat tcatctgttg     660
ccaccgtcac gtttcgcggc gagttctgcc gtgcatcgct aagtatagcc atgaaaaaac     720
cgacgctttt ggcgtcggtt ttgacttaac tatcggtcaa cgcatgttga tacttatgga     780
gcatccccgc cagccgattt accggttccg tcacctgcgg tggcgcttgc cagatgcgta     840
gcttttcctg gtagatttcc agttcttcca gcaactggcc aaagtaccga cgacgtttat     900
catcgctacg gcagatatca catggtctg ctgtgcggcg catttgtcgg tgaaacgccg      960
ataaatcctc gttaaccggg atcggtgcat cacgcaggcg ctggtgcgcg ataatcatcg    1020
tcagcgccag gcgaaatttc ggcaaatccc ctgggaactt attcatcagc aaaaacagct    1080
gctgataaag tgccgggagg tggttctctt tacgacgtgc cacattggta gtcatcgcgg    1140
aaacagcgga agaaacaaac tgattaagca gtacacgtcc ggtcctgtcg cgcgatttat    1200
cccgcaccag caaaataacg gtgaacgcga gcacacagcc gacgatttgc cctaatgcgc    1260
tgtcgagaaa ctgactgaaa tggaaagtca tcgggttatc cagcacgata atatttatgg    1320
tgctggccag tgccccatc gagcccagtc gccgtttctg tacttctata ccgaggaaga     1380
atcccagcac tgccaggcta atgcacagca gcaacatgct ctgttgggta ttagggataa    1440
tcaccaaaaa gtagagcagc cctaacggca gcgcggccag cgtcccgtag ataaagtcga    1500
tcgccaccat gcgtggattc ggcaaacgca ttgccagtga cgtcactacc gcaatcatca    1560
ccattgcacc actgccggaa gtccagcccg tccacagcca gaaaagcgtg cccagaatgc    1620
aggaaagtgt ggttcgccag aagttaacca ttgcatgatg acgttcggct gactctactt    1680
ttacttccgg ttcgccttgc aggatctctt cttcggtggc gttgattttt gtgttactga    1740
taacgccgcg cttgagaagc tgataacgcg ttgccgccgc gacccagcta taatggtga    1800
caggcgtttc ccgttccccg gtccaggcga taactctccg caggcgtttg agctgcttgt    1860
ggacgtcctg cgcggtttct accggcgtgt caaaaaattc gcggaaagta tcagtgatca    1920
attccgggcg cgtattctga ataagataag tttcgcagga ttgggtaatc agcgtcagcg    1980
atagcgtatt gatcgctttt aaacgtcgat tggcccgcgc ccagcgggaa gattccatat    2040
tcaggttgct gcgcatgcct tgtagcgccg tggtgcgtcg caccaggtcg ccccaggctt    2100
tatcgacaac ttcaccatcg ccatgcttga tacagagttg cattaattga tattgcgcga    2160
ccagcaaact ttccagctct cgatccactt cttgtttgat cgatcgcgga gaaagagca    2220
aatccgccat aatcgcacac acaataccga taacgatctc gctacaacgt tcgacggcaa    2280
actgcggcgt aagcaatggt tccggctgaa tggtgatcac aatgatcagc gcggtataac    2340
```

```
cggccagccc ccacgcatac gagttttcta ttcgtaccag cgaggatatc caggtacaaa    2400
aaccggccca gatacagcac accagaatca tcaataatgg tgcgcggatc atcgcaatga    2460
tgatcaccag tccggcaata cagccaataa atgtgccgat gatgcgcaaa agccacgat    2520 agcgaatagc gccagaatac ggttcacctc ccgcagcaaa ggccgaccg gcggcaacaa    2580 tcgccgctgt cagtaccgcc cagcgtggcg tttccagctg gaagtgaaag ccaacaaaca    2640
gcgccagtac aatggcggtc gccagtttta ccgcaaagcg aatatgttgg ttagcaatgg    2700
agaaaatacc catcgtgatt aaccaaactc acgcaggcga tgggccattt tacggaagaa    2760
cgaatcctgg ctttcgtcgc gatcttgttt gccagtgacc accactgtag cagtggtgcc    2820
cgcaggccag atgttctctt gctggttgtc gagacgaata cgaaccggaa cacgttgcgc    2880
aagacgcacc cattcaaggt tagagtctat agtcgccatc cctttgtcgt cacgcgtgct    2940
gctggcgttg gtgacccctg cggcaacact atcaacagtc cctttcagca ctttgttact    3000
gccaagcggc gtgatctctg cacgataccc cggacgcacc ccttccagct tagttttcttc    3060 catataggcc agtacataga aggagttctg tttcaccagc gcaaccgccg ttgatcctcg    3120
agtaataaac tcaccggtat agacgttgag gttggtcacc cagccatctg ctggcgcgcg    3180
gatcaccgtg cgttcaagat ccagttttgc cagatcgcgg gtcgcctgcg ctttcgctaa    3240
ctgatgcaga accgtttgta gtacgttgtt ggcctggtcg atctcttcgc gagacatcgc    3300
ctgcacaccg agacggttac gacgtccggc ctcctggcgt ttctcctgtg ccagtacctg    3360
ataataagca acatcggctt gcgcttcctc aagcgccttt tgatagcgcg gctggtcgat    3420
ggtgaacagt atctgtcctt ttttcaccag ctggttatca tgaacattca cctgggtaat    3480
gagtccagaa acgtccggcg cgatcgcaac gacgtcagcg ctaaagcgcg cgtcacgcgt    3540 ccaggggat tcggtgtaat agacccaggc attaaaaatt gcgatgaagg ccagaatgac    3600
taatacgacc gtgatggccg tacgggagaa ttttcttatt agtgttttca cttcaacctc    3660
aaacgaacag tcgcgatatc aaataaaaca agcagcaata gagcgcggtg ttgaacaacg    3720
ccggatgcca gacaaagtcg tagataccctg ttggcacaag tacccggcgc accagccaga    3780
aaatcgccag tgataaaagc aattcaaaaa atatcggtgg gaaggacagc ccaaacacca    3840
cgataacggg aaacagactc atgttgacct tggttgtaaa gagagagcag gcgttattat    3900
tttcagcatc tgtcgccgca gagaagggca tggaaagccg ggcgagagca acattgctgt    3960
agattgatat ttaatatatt agcgtaactg ttatgctgtt atctatatta tgtgatctaa    4020 atcacttttta agtcagagtg aataatgg                                      4048

<210> SEQ ID NO 55
<211> LENGTH: 87
<212> TYPE: PRT
<213> ORGANISM: Escherichia coli

<400> SEQUENCE: 55

Met Lys Ile Lys Thr Thr Val Ala Ala Leu Ser Val Leu Ser Val Leu
1               5                   10                  15

Ser Phe Gly Ala Phe Ala Ala Asp Ser Ile Asp Ala Ala Gln Ala Gln
            20                  25                  30

Asn Arg Glu Ala Ile Gly Thr Val Ser Val Ser Gly Val Ala Ser Ser
        35                  40                  45

Pro Met Asp Met Arg Glu Met Leu Asn Lys Lys Ala Glu Glu Lys Gly
    50                  55                  60
```

```
Ala Thr Ala Tyr Gln Ile Thr Glu Ala Arg Ser Gly Asp Thr Trp His
 65                  70                  75                  80

Ala Thr Ala Glu Leu Tyr Lys
                 85

<210> SEQ ID NO 56
<211> LENGTH: 90
<212> TYPE: PRT
<213> ORGANISM: Escherichia coli

<400> SEQUENCE: 56

Met Asn Ile Tyr Thr Phe Asp Phe Asp Glu Ile Glu Ser Gln Glu Asp
  1               5                  10                  15

Phe Tyr Arg Asp Phe Ser Gln Thr Phe Gly Leu Ala Lys Asp Lys Val
             20                  25                  30

Arg Asp Leu Asp Ser Leu Trp Asp Val Leu Met Asn Asp Val Leu Pro
         35                  40                  45

Leu Pro Leu Glu Ile Glu Phe Val His Leu Gly Glu Lys Thr Arg Arg
     50                  55                  60

Arg Phe Gly Ala Leu Ile Leu Phe Asp Glu Ala Glu Glu Glu Leu
 65                  70                  75                  80

Glu Gly His Leu Arg Phe Asn Val Arg His
                 85                  90

<210> SEQ ID NO 57
<211> LENGTH: 655
<212> TYPE: PRT
<213> ORGANISM: Escherichia coli

<400> SEQUENCE: 57

Met Gly Ile Phe Ser Ile Ala Asn Gln His Ile Arg Phe Ala Val Lys
  1               5                  10                  15

Leu Ala Thr Ala Ile Val Leu Ala Leu Phe Val Gly Phe His Phe Gln
             20                  25                  30

Leu Glu Thr Pro Arg Trp Ala Val Leu Thr Ala Ala Ile Val Ala Ala
         35                  40                  45

Gly Pro Ala Phe Ala Ala Gly Gly Glu Pro Tyr Ser Gly Ala Ile Arg
     50                  55                  60

Tyr Arg Gly Phe Leu Arg Ile Ile Gly Thr Phe Ile Gly Cys Ile Ala
 65                  70                  75                  80

Gly Leu Val Ile Ile Ile Ala Met Ile Arg Ala Pro Leu Leu Met Ile
                 85                  90                  95

Leu Val Cys Cys Ile Trp Ala Gly Phe Cys Thr Trp Ile Ser Ser Leu
                100                 105                 110

Val Arg Ile Glu Asn Ser Tyr Ala Trp Gly Leu Ala Gly Tyr Thr Ala
                115                 120                 125

Leu Ile Ile Val Ile Thr Ile Gln Pro Glu Pro Leu Leu Thr Pro Gln
                130                 135                 140

Phe Ala Val Glu Arg Cys Ser Glu Ile Val Gly Ile Val Cys Ala
145                 150                 155                 160

Ile Met Ala Asp Leu Leu Phe Ser Pro Arg Ser Ile Lys Gln Glu Val
                165                 170                 175

Asp Arg Glu Leu Glu Ser Leu Leu Val Ala Gln Tyr Gln Leu Met Gln
                180                 185                 190

Leu Cys Ile Lys His Gly Asp Gly Glu Val Val Asp Lys Ala Trp Gly
                195                 200                 205
```

-continued

```
Asp Leu Val Arg Arg Thr Thr Ala Leu Gln Gly Met Arg Ser Asn Leu
    210                 215                 220
Asn Met Glu Ser Ser Arg Trp Ala Arg Ala Asn Arg Arg Leu Lys Ala
225                 230                 235                 240
Ile Asn Thr Leu Ser Leu Thr Leu Ile Thr Gln Ser Cys Glu Thr Tyr
                245                 250                 255
Leu Ile Gln Asn Thr Arg Pro Glu Leu Ile Thr Asp Thr Phe Arg Glu
            260                 265                 270
Phe Phe Asp Thr Pro Val Glu Thr Ala Gln Asp Val His Lys Gln Leu
        275                 280                 285
Lys Arg Leu Arg Arg Val Ile Ala Trp Thr Gly Glu Arg Glu Thr Pro
290                 295                 300
Val Thr Ile Tyr Ser Trp Val Ala Ala Thr Arg Tyr Gln Leu Leu
305                 310                 315                 320
Lys Arg Gly Val Ile Ser Asn Thr Lys Ile Asn Ala Thr Glu Glu Glu
                325                 330                 335
Ile Leu Gln Gly Glu Pro Glu Val Lys Val Glu Ser Ala Glu Arg His
            340                 345                 350
His Ala Met Val Asn Phe Trp Arg Thr Thr Leu Ser Cys Ile Leu Gly
        355                 360                 365
Thr Leu Phe Trp Leu Trp Thr Gly Trp Thr Ser Gly Ser Gly Ala Met
    370                 375                 380
Val Met Ile Ala Val Val Thr Ser Leu Ala Met Arg Leu Pro Asn Pro
385                 390                 395                 400
Arg Met Val Ala Ile Asp Phe Ile Tyr Gly Thr Leu Ala Ala Leu Pro
                405                 410                 415
Leu Gly Leu Leu Tyr Phe Leu Val Ile Ile Pro Asn Thr Gln Gln Ser
            420                 425                 430
Met Leu Leu Leu Cys Ile Ser Leu Ala Val Leu Gly Phe Phe Leu Gly
        435                 440                 445
Ile Glu Val Gln Lys Arg Arg Leu Gly Ser Met Gly Ala Leu Ala Ser
    450                 455                 460
Thr Ile Asn Ile Ile Val Leu Asp Asn Pro Met Thr Phe His Phe Ser
465                 470                 475                 480
Gln Phe Leu Asp Ser Ala Leu Gly Gln Ile Val Gly Cys Val Leu Ala
                485                 490                 495
Phe Thr Val Ile Leu Leu Val Arg Asp Lys Ser Arg Asp Arg Thr Gly
            500                 505                 510
Arg Val Leu Leu Asn Gln Phe Val Ser Ala Ala Val Ser Ala Met Thr
        515                 520                 525
Thr Asn Val Ala Arg Arg Lys Glu Asn His Leu Pro Ala Leu Tyr Gln
    530                 535                 540
Gln Leu Phe Leu Leu Met Asn Lys Phe Pro Gly Asp Leu Pro Lys Phe
545                 550                 555                 560
Arg Leu Ala Leu Thr Met Ile Ile Ala His Gln Arg Leu Arg Asp Ala
                565                 570                 575
Pro Ile Pro Val Asn Glu Asp Leu Ser Ala Phe His Arg Gln Met Arg
            580                 585                 590
Arg Thr Ala Asp His Val Ile Ser Ala Arg Ser Asp Asp Lys Arg Arg
        595                 600                 605
Arg Tyr Phe Gly Gln Leu Leu Glu Glu Leu Glu Ile Tyr Gln Glu Lys
    610                 615                 620
Leu Arg Ile Trp Gln Ala Pro Pro Gln Val Thr Glu Pro Val Asn Arg
```

```
                    625                 630                 635                 640
Leu Ala Gly Met Leu His Lys Tyr Gln His Ala Leu Thr Asp Ser
                645                 650                 655

<210> SEQ ID NO 58
<211> LENGTH: 310
<212> TYPE: PRT
<213> ORGANISM: Escherichia coli

<400> SEQUENCE: 58

Met Lys Thr Leu Ile Arg Lys Phe Ser Arg Thr Ala Ile Thr Val Val
1               5                   10                  15

Leu Val Ile Leu Ala Phe Ile Ala Ile Phe Asn Ala Trp Val Tyr Tyr
            20                  25                  30

Thr Glu Ser Pro Trp Thr Arg Asp Ala Arg Phe Ser Ala Asp Val Val
        35                  40                  45

Ala Ile Ala Pro Asp Val Ser Gly Leu Ile Thr Gln Val Asn Val His
    50                  55                  60

Asp Asn Gln Leu Val Lys Lys Gly Gln Ile Leu Phe Thr Ile Asp Gln
65                  70                  75                  80

Pro Arg Tyr Gln Lys Ala Leu Glu Glu Ala Gln Ala Asp Val Ala Tyr
                85                  90                  95

Tyr Gln Val Leu Ala Gln Glu Lys Arg Gln Glu Ala Gly Arg Arg Asn
            100                 105                 110

Arg Leu Gly Val Gln Ala Met Ser Arg Glu Glu Ile Asp Gln Ala Asn
        115                 120                 125

Asn Val Leu Gln Thr Val Leu His Gln Leu Ala Lys Ala Gln Ala Thr
    130                 135                 140

Arg Asp Leu Ala Lys Leu Asp Leu Glu Arg Thr Val Ile Arg Ala Pro
145                 150                 155                 160

Ala Asp Gly Trp Val Thr Asn Leu Asn Val Tyr Thr Gly Glu Phe Ile
                165                 170                 175

Thr Arg Gly Ser Thr Ala Val Ala Leu Val Lys Gln Asn Ser Phe Tyr
            180                 185                 190

Val Leu Ala Tyr Met Glu Glu Thr Lys Leu Glu Gly Val Arg Pro Gly
        195                 200                 205

Tyr Arg Ala Glu Ile Thr Pro Leu Gly Ser Asn Lys Met Leu Lys Gly
    210                 215                 220

Thr Val Asp Ser Val Ala Ala Gly Val Thr Asn Ala Ser Ser Thr Arg
225                 230                 235                 240

Asp Asp Lys Gly Met Ala Thr Ile Asp Ser Asn Leu Glu Trp Val Arg
                245                 250                 255

Leu Ala Gln Arg Val Pro Val Arg Ile Arg Leu Asp Asn Gln Gln Glu
            260                 265                 270

Asn Ile Trp Pro Ala Gly Thr Thr Ala Thr Val Val Val Thr Gly Lys
        275                 280                 285

Gln Asp Arg Asp Glu Ser Gln Asp Ser Phe Phe Arg Lys Met Ala His
    290                 295                 300

Arg Leu Arg Glu Phe Gly
305                 310

<210> SEQ ID NO 59
<211> LENGTH: 90
<212> TYPE: PRT
<213> ORGANISM: Escherichia coli
```

<400> SEQUENCE: 59

```
Met Pro Phe Ser Ala Ala Thr Asp Ala Glu Asn Asn Asn Ala Cys Ser
1               5                   10                  15

Leu Phe Thr Thr Lys Val Asn Met Ser Leu Phe Pro Val Ile Val Val
            20                  25                  30

Phe Gly Leu Ser Phe Pro Pro Ile Phe Phe Glu Leu Leu Leu Ser Leu
        35                  40                  45

Ala Ile Phe Trp Leu Val Arg Arg Val Leu Val Pro Thr Gly Ile Tyr
    50                  55                  60

Asp Phe Val Trp His Pro Ala Leu Phe Asn Thr Ala Leu Tyr Cys Cys
65                  70                  75                  80

Leu Phe Tyr Leu Ile Ser Arg Leu Phe Val
                85                  90
```

<210> SEQ ID NO 60
<211> LENGTH: 2529
<212> TYPE: DNA
<213> ORGANISM: Escherichia coli

<400> SEQUENCE: 60

| | |
|---|---|
| aacattgcga gaattgctgc gttattgcag tatttcagtc agggtgaagg gaaaatctct | 60 |
| gccgatatca tgacgtctgc tgtcgtaata agttcgtggt acacagatga atataaaaaa | 120 |
| ttatttgcgt tacctgatga atctgaactg cagctgcagg acgcccggga gctgctcgac | 180 |
| tggctcattg aggagtgccg cggagaatgc cgccccgtg tcaggaaaaa ttatattctc | 240 |
| cagtgtggcc cgggccggtt ccggaacagg aaaaagctga acgtcctgct gaacattctt | 300 |
| gcatctcaac tcaggctctc tgtcgtgcag gaggaaaaa ccacctatgt cctgctttcc | 360 |
| gaaataaaca atatcacgct gcctgaactg aatgcgtgct acagccagaa actgataaga | 420 |
| tggcatgagc aatcctttgg cttataatgt tccctgttgc tgagacggat tattcagtgg | 480 |
| tggtatcgca gtatgcccgt caccccgct tctgcatgag ggtgacggag gaaaagtaag | 540 |
| tgtgcggagg cccgggagcg ttatgaatca acaggcgtat aacaggtact cgtcaatcat | 600 |
| cagttccagc tcgcgctttt cccgtttgcg cgccacagcc cagttttcaa gctctgcatg | 660 |
| tgatttatgc tttaactctt cagtccaggg ctgcatggag tgggcacaca tcagatcata | 720 |
| ccagcacagc catatcagcg tgtggtagag atcacgatcg tcgaaacgcc ggagcaggct | 780 |
| gttcagcctg tttgccagcc ggttttcacc cagacgatgt agctcactga gtaaaacgcc | 840 |
| gcccagatta aatgtgtaa gcagcatgat tcatgggtc tgaatgctgg tcattaaccc | 900 |
| ttcctgaatg gcaggaatga acggtggtgt tcccggggttg acgacctgat agagtccctg | 960 |
| tggtgccact gagatgatgg tgccttttc tggcagaaaa aagtgggcca gggtcaggcg | 1020 |
| gtgataacca tgaagatgcg gagcccccat tccatgagcg acgataagcc tcgtcacgtt | 1080 |
| tgtcatccat ttctgatgct ggatgagcag cagctcacac cggttttcaa gttttttgcat | 1140 |
| aatattctct cctttagcgc gcagcaaaat gcctccgggg gccggatcat gcctttgctg | 1200 |
| cggttgaacg gataacggtc aggaattacg gacgggactg tgtaatacgt gcctgcaacc | 1260 |
| aggcttccac ttcactttc agccatcggg agctacggcc cagtttgatg ggggcaggaa | 1320 |
| aggcaccatc cttgatgagc ttgtaaaacc atttatcggt caggccggtc agctgagtga | 1380 |
| taaacgacat gtcgaccatc tggtcatcca tcagtgaaac tggggtattc atgaaaatgt | 1440 |
| tcctccggat gttgttaatc tcaaccgcg ttggtgatga aaacaacgca ccaccttccc | 1500 |
| cggcataaca accggggaaa aacgtaaaaa ataatcggga atgtgaccgt caggagataa | 1560 |

-continued

```
acgggggat tgcggtggct gagccgtacc ggtatgtcgg gtgattgttg cgaaacgatg    1620
cttccgcacg cgcacgtgat aaaggaggga ggactttcgt gagacaaggg gaaaactggc    1680
gttctgataa ttgcagagtt gtttttgaag gcggttgtgg tgcatcagcc cgtgacctgt    1740
gggcaggcga caggtatcac tggtgggata agactgtctg attggtatta taaatatata    1800
agagagctca acacatgag ttcatatatg tgaaataaat ctgtgagtgt gatcagcaga    1860
ccagtctacc cagtagcaac agattgcgtt gtactcacag ggttatccct gataactggc    1920
gtataacctg cgtacataaa acgtacctgc aatgcacctg aacagagtgc attaagcatc    1980
cgcctgagcg gtaaacgtat ccgatctggt gagtgacagt ctgagagcat tctcagtaat    2040
cgcccccttg tatcctggaa attggttaag ataacagcga ttagatttgg caaggtgtat    2100
gcagccagca gcttaacatc tcagctaact ggctggttac cttcaggttg tcgcaatggc    2160
atcggacatc cggtgtcgga taactaaacg tagcgttaag gcgatattgc tgagagactg    2220
gttaagtggt tgcacgggag taatgagttt ggggagggta ccagaatgtc agtctggtgc    2280
ggtatgctgg cagtatcacg ttgattacag cataaagtaa cgagagacga atggaagtta    2340
aaaccagagc agttccgtcg ttgttcatcc cgggagacgc tggaaaaagt gatttcccac    2400
acacgttata aacttacccc tgcggagctg gaagccttta actctgcggt cgatcaccgg    2460
ctggcagaac tgacaatgaa caaactttac gatcgcgtgc cggcttccgt ctggaaatat    2520
gtcacctga                                                            2529
```

<210> SEQ ID NO 61
<211> LENGTH: 190
<212> TYPE: PRT
<213> ORGANISM: Escherichia coli

<400> SEQUENCE: 61

```
Met Gln Lys Leu Glu Asn Arg Cys Glu Leu Leu Leu Ile Gln His Gln
1               5                   10                  15

Lys Trp Met Thr Asn Val Thr Arg Leu Ile Val Ala His Gly Met Gly
            20                  25                  30

Ala Pro His Leu His Gly Tyr His Arg Leu Thr Leu Ala His Phe Phe
        35                  40                  45

Leu Pro Glu Lys Gly Thr Ile Ile Ser Val Ala Pro Gln Gly Leu Tyr
    50                  55                  60

Gln Val Val Asn Pro Gly Thr Pro Pro Phe Ile Pro Ala Ile Gln Glu
65                  70                  75                  80

Gly Leu Met Thr Ser Ile Gln Thr His Glu Ile Met Leu Leu Thr His
                85                  90                  95

Phe Asn Leu Gly Gly Val Leu Leu Ser Glu Leu His Arg Leu Gly Glu
            100                 105                 110

Asn Arg Leu Ala Asn Arg Leu Asn Ser Leu Leu Arg Arg Phe Asp Asp
        115                 120                 125

Arg Asp Leu Tyr His Thr Leu Ile Trp Leu Cys Trp Tyr Asp Leu Met
    130                 135                 140

Cys Ala His Ser Met Gln Pro Trp Thr Glu Glu Leu Lys His Lys Ser
145                 150                 155                 160

His Ala Glu Leu Glu Asn Trp Ala Val Ala Arg Lys Arg Glu Lys Arg
                165                 170                 175

Glu Leu Glu Leu Met Ile Asp Glu Tyr Leu Leu Tyr Ala Cys
            180                 185                 190
```

<210> SEQ ID NO 62
<211> LENGTH: 86
<212> TYPE: PRT
<213> ORGANISM: Escherichia coli

<400> SEQUENCE: 62

Met Phe Ser Ser Pro Thr Pro Val Glu Ile Asn Asn Ile Arg Arg Asn
1               5                   10                  15

Ile Phe Met Asn Thr Pro Val Ser Leu Met Asp Asp Gln Met Val Asp
            20                  25                  30

Met Ser Phe Ile Thr Gln Leu Thr Gly Leu Thr Asp Lys Trp Phe Tyr
        35                  40                  45

Lys Leu Ile Lys Asp Gly Ala Phe Pro Ala Pro Ile Lys Leu Gly Arg
    50                  55                  60

Ser Ser Arg Trp Leu Lys Ser Glu Val Glu Ala Trp Leu Gln Ala Arg
65                  70                  75                  80

Ile Thr Gln Ser Arg Pro
                85

<210> SEQ ID NO 63
<211> LENGTH: 46
<212> TYPE: PRT
<213> ORGANISM: Escherichia coli

<400> SEQUENCE: 63

Met Ile Ser His Thr Arg Tyr Lys Leu Thr Pro Ala Glu Leu Glu Ala
1               5                   10                  15

Phe Asn Ser Ala Val Asp His Arg Leu Ala Glu Leu Thr Met Asn Lys
            20                  25                  30

Leu Tyr Asp Arg Val Pro Ala Ser Val Trp Lys Tyr Val Thr
        35                  40                  45

<210> SEQ ID NO 64
<211> LENGTH: 5775
<212> TYPE: DNA
<213> ORGANISM: Escherichia coli

<400> SEQUENCE: 64
cctgcatatc ggtcgggaat gccggatgcg gcgcggtacg tacgttaaca gccttcggac      60
gtttgccatg catatccagg ctaatccagt cttcgccgac ttcgatgtcc gctccagcgt     120
cacgcagttt cgccagcacg cgtcgagag tatctggctg cgcgttacgg cagataattt     180
tgccgcgaga atcgccgcc gccaccagga agtaccggt ttcgatacga tccggcagaa      240
cgcgatagac accgccgcct aaacgttcca caccttcgat gacgatacga tcggtgccct     300
gaccgctaat tttcgcaccc agcgtaatca ggaagttcgc ggtatcgacg atttccggtt     360
cacgcgctgc gtttttcaata atcgtggtgc cttccgccag ggttgcagca cacatgatgg     420
tcaccgttgc gccaacgctg actttatcca tcacgatatg tgcacctttc aaacgaccat     480
cgacggaagc tttaacgtaa ccttcttcca gtttgatggt cgcgcctaat tgttcgaggc     540
cagaaatgtg tagatcaacc ggacgcgcac cgatcgtaca accgccaggt agtgaaactt     600
gcccctgacc aaagcgcgct accagcggcc ccagcgccca gatagaagca cgcatggttt     660
taaccagatc gtaaggtgcg cagaatacat taacgtcgcg ggcatcaata tgcacagaac     720
cattacgttc tactttcgca cccagctggc ttagcagctt cattgatgta tcgacgtctt     780
tcagtttcgg gacgttctgg atctctaccg gttcttccgc cagtagtgcg gcaaaaagga     840

```
taggcagagc agcattttta gcgccggaaa ttgtgacttc gccctggagc ttcgttggcc    900
cctgaacacg aaatttatcc atttagtttg ttctcagtta acaattcata tccgctaccg    960
gcgaatcgcc catagctcaa aagccgttca gtttgcgatc gcgcgcccac tccgcagggg   1020
tatacgcttt gatcgacaca gcatgaatgc ggttatccgc aatatattcc atcagcggac   1080
catagaccgt ctgctgtttt ttaacccgac tcatgccgtc aaacaactca cccacggcaa   1140
taacctgaaa gtggctgcca tcgcggaaa cgtggacttc ctggagggag agagcgttca   1200
tcaacacgct ctgaatttca ttattttcca tgggatcttc aatcatcagt taataaacca   1260
gcgaaacatc ttagagcaaa gttgcgctgg cataaataag caaaaagcct cgctgataaa   1320
tcagacaagg ctcgacttgc aggcaggttt gccggacagg cggttaacgc catatccggc   1380
ctgaaaaaat ttaacgaggc agaacatcag caggcaaatt atacaatttc gccagggtat   1440
acactttgtc gtttaccccc tgaagcgtca cattgttgcc ctgcttttc gccagatcga   1500
taagatggag cagcagtgcc agtcccccg tatccacgcg ggagacacgg ctaagatcga   1560
tgcaggtaat ccccttcacc gcttcctcac gcatttccca aagcggtagc aaaacgtcct   1620
gatccagctc tccggataac gccagcgtgt cacccgtctg catccagctc agtgactcgc   1680
tcattatttt ttctcttcca gagtgatttt ctgttgagaa atcgatttca gttgcgcagt   1740
caggccgtcg atacctttgg tacgcagcag cgttccccac tcgttttgtt tggtggtgat   1800
catactgacg ccttcagcaa tcatgtcgta agcctgccaa ttgcccgtct gggagttttt   1860
acgccactgg aagtccagac gcaccggcgg acggccattc gggtcaataa tggtaacgcg   1920
aataggcaca atggttttat cgcccagcgg ctgttctggc gcaatctgat aggtttgacc   1980
gtgatacatc gccagcgcct gaccgtaagc ctgcttcagg tactcacgga aagcggcaaa   2040
gtaggcttca cgttgagcag gggtcgcact cttgtaatac tggcccagca ccagcgcacc   2100
ggcgtatttc acctgtacgt atggcagcag ttcctgatca acaatggtac gcagataatc   2160
cgggttggcc cgaatttgcg gttgctcatt cttcaggcga tcgaacgttt tctgcgccgc   2220
ctcgtccatc agcttatacg gattggtctg gtctgccgcg gttgccgcac tcagaggtgc   2280
aatcaccagc aaagcgacca tcattaaacg tttaaacatg cgtcggttct cctgaaatta   2340
tttcgttgta cccacaggtt cagtggtttc attattacct ggcgcagcag ctggcgcatc   2400
gccactattc ttattgtcat cgcctttact accgtaaagg aactgaccaa tgagatcttc   2460
cagcaccatc gcagacttag tgtcctgaat tgtatcgcca tccttcagga tagcagtccc   2520
cagttccggg tcttcaaaac cgacgtttaa tgccagatat tgttccccca gcaggccgga   2580
agtacgaatg ctcagcgaac tggtatctgg aatgtggtta taacgttgtt caatttccag   2640
cgttacgcgc ggcagatagg ttttcgggtc cagcgtaata tccgccaccc gacccacaac   2700
aacgccacca atactgaccg gagagcgcgc tttcaggccg ccaatgttat cgaacgtcgc   2760
ataaagcgtg taggtcggtt cagtacgtat ggacgtcacg ttcgccgcct tcaggcaaac   2820
aaacagcgcc gccagcagtg ctgctaataa aaagataccc acccaaattt catttttttt   2880
cgtttgcatg aactcaattc ccaaacatca atgcggtcag cacaaaatcc agccccagaa   2940
cagccagaga cgagtggaca acggtgcgag tggttgcccg gctaatcccg gcagacgtcg   3000
ggatggcgtc gtagccgtta aacaacgaaa tccacgtcac cgtgatggcg aacaccacgc   3060
tcttaatcag acagttgacc agatccatac gccagtcgac ggcattttgc attgccgacc   3120
agaagaaccc gctatcaatg ccttttccaac tgacgccgac cagagatccg ccccagatcc   3180
ccacggcgac gaaaataacc gtcaacagtg gtaatgaaat aaccccagcc cagaaacggg   3240
```

```
gagaaataac cgacgcagc ggatccaccg ccatcatctc catactggag agttgctctg     3300
tagcgcgcat caggccgatt tctgcggtta gcgccgaacc agcacgcccg gcaaacaaca     3360
acgcggcaac caccggcccc agttcacgca gtagcgataa cgccaccagc atacccagac     3420
tggtttccgc actataagtg gtcagaacca gataaccttg cagccccaac accattccga     3480
tgaacacgcc agaaaccaca ataatcagca tcgacaggac gccgacatta tagagctggc     3540
gcaccagcag cggcgcatgt tgcgaaatt ccggtttgcc gaccagcgca ttgaataaca      3600
ttaacccggc ccgcccgaac gttctcaggg ttttaatccc tttatgtccg agcgacgcca     3660
gcgcatttaa cagcatgagt ggcttaactc cctggtaaaa gatcagcgtg ataatcgccg     3720
gcaggatagc ggaacggaac aggcccgtca gctatcccgt ccagaaactg acgtacgcgc     3780
ggatcaggat tcgcctgcaa cgcctgggca ctgccatgag cgacaatttt tttgtccgcc     3840
aggatccagg cgtgatccgc aatacttaac acttccggca catcgtgaga aaccaccaca     3900
caagtcacgc ccagcgcgct gttcagctca gaaatcagct tcaccagtac gcccatggtg     3960
atgggatctt gcccaacaaa aggttcatca acatgatga gatccggctc cagcgcaatc      4020
gcacgcgcca gcgctgcacg ccgcgccatc ccaccggaaa gttcagaagg cattagttta     4080
gccgctccac gcagccccac ggcctccagc ttcatcatca ccgtactatg caacaatggc     4140
gcgggaagtt gggtatgttc gcgcagtgga taggcgacgt tgtcaaatac gttcatatca     4200
gtgaacaacg ccccggactg aaataacatg ctcatccgtt tgcgcactgt atacaggcgc     4260
gaacgagaca tcgccggaat attctcacca tcgaaaagga tctcaccatg atctggtgcg     4320
atttgcccgc caatcagacg gagtagcgtc gttttaccga tgcccgatgg ccccatgatc     4380
gccgtgatct tccctcgcgg cacggtcagg gaaatattat cgaagatgca gcgattgcca     4440
cgcgtaaaac tgacatcgcg catatcgact aaattcgcca cagactgctc cataattcac     4500
ccttcgtctt gcgttgattt tctaagcatg gcgctcaatt taaccttgaa cccaacatat     4560
ttacagaata ttacccgccg tggttagcga aagctggcat ttgttttact ttttagccgc     4620
ataaagtcaa aattaagcat ccgttacggc tttctgaaaa tcttcagcgg accggcgagt     4680
atacctgaag aaaggacgtt agatgctttt agctacggca ctgttaattg ttggtttact     4740
tttggtcgtt tacagtgccg accgcctggt ttttgccgcg tctattcttt gccgaaccttt    4800 tggcatcccg ccgctgatca tcggcatgac ggtggtcagt attggtacat cgttaccaga    4860
agtcatcgtc tcgcttgccg cgtctctgca cgaacaacgc gatttagccg ttggtacagc     4920
cctcggctca aacattatca atatattgct gatcctcggt ctggctgcgc tggttcgtcc     4980
ttttaccgtc cattctgatg ttctacgccg tgaattaccc ttaatgttgt tggtcagcgt     5040
ggtggccggt tccgtactct atgacggaca acttagtcgc agcgatggta tctttctcct     5100
ctttctggct gtgctatggc tgctgttcat tgttaaactt gcacgtcagg ctgaacgtca     5160
ggggactgac agcctgacca gagagcagct tgcagagctg ccgcgtgacg gcggattgcc     5220
cgtcgcgttt ttatggctcg gcattgcgct tatcatcatg ccagtggcca cgcggatggt     5280
ggttgataac gccacggtgc tggcgaatta ctttgccatc agcgagttga cgatgggtct     5340
gacggcaatt gctatcggaa ccagcctgcc ggaactggca accgcaatag cggggggttcg    5400 caaaggtgaa aacgacattg ctgtcggaaa tatcattggc gcaaacattt taatattgt      5460 catcgtgttg ggtttacccg cgctgataac gccaggagag attgatccac tggcgtacag     5520
tcgtgactac agcgtgatgt tgctggtgag cattattttt gcgttgctgt gctggcggcg     5580
```

```
ctccccgcaa ccgggccgtg gtgtaggggt attattaact ggcggattta tcgtatggct    5640
ggcgatgttg tactggttat cgccaatact cgttgaataa ctggaaacgc attatgtcgc    5700
acgtagagtt acaaccgggt tttgactttc agcaagcagg taaagaagtc ctggcgattg    5760
aacgtgaatg cctgg                                                    5775
```

<210> SEQ ID NO 65
<211> LENGTH: 89
<212> TYPE: PRT
<213> ORGANISM: Escherichia coli

<400> SEQUENCE: 65

Met Ile Glu Asp Pro Met Glu Asn Asn Glu Ile Gln Ser Val Leu Met
1               5                   10                  15

Asn Ala Leu Ser Leu Gln Glu Val His Val Ser Gly Asp Gly Ser His
            20                  25                  30

Phe Gln Val Ile Ala Val Gly Glu Leu Phe Asp Gly Met Ser Arg Val
        35                  40                  45

Lys Lys Gln Gln Thr Val Tyr Gly Pro Leu Met Glu Tyr Ile Ala Asp
    50                  55                  60

Asn Arg Ile His Ala Val Ser Ile Lys Ala Tyr Thr Pro Ala Glu Trp
65                  70                  75                  80

Ala Arg Asp Arg Lys Leu Asn Gly Phe
                85

<210> SEQ ID NO 66
<211> LENGTH: 129
<212> TYPE: PRT
<213> ORGANISM: Escherichia coli

<400> SEQUENCE: 66

Met Gly Asn Ala Ala Ala Tyr Gln Arg Tyr Arg Arg Pro Asp Cys Ala
1               5                   10                  15

Thr Glu Ile Asp Phe Ser Thr Glu Asn His Ser Gly Arg Glu Lys Ile
            20                  25                  30

Met Ser Glu Ser Leu Ser Trp Met Gln Thr Gly Asp Thr Leu Ala Leu
        35                  40                  45

Ser Gly Glu Leu Asp Gln Asp Val Leu Leu Pro Leu Trp Glu Met Arg
    50                  55                  60

Glu Glu Ala Val Lys Gly Ile Thr Cys Ile Asp Leu Ser Arg Val Ser
65                  70                  75                  80

Arg Val Asp Thr Gly Gly Leu Ala Leu Leu Leu His Leu Ile Asp Leu
                85                  90                  95

Ala Lys Lys Gln Gly Asn Asn Val Thr Leu Gln Gly Val Asn Asp Lys
            100                 105                 110

Val Tyr Thr Leu Ala Lys Leu Tyr Asn Leu Pro Ala Asp Val Leu Pro
        115                 120                 125

Arg

<210> SEQ ID NO 67
<211> LENGTH: 211
<212> TYPE: PRT
<213> ORGANISM: Escherichia coli

<400> SEQUENCE: 67

Met Phe Lys Arg Leu Met Met Val Ala Leu Leu Val Ile Ala Pro Leu
1               5                   10                  15

```
Ser Ala Ala Thr Ala Ala Asp Gln Thr Asn Pro Tyr Lys Leu Met Asp
            20                  25                  30

Glu Ala Ala Gln Lys Thr Phe Asp Arg Leu Lys Asn Glu Gln Pro Gln
        35                  40                  45

Ile Arg Ala Asn Pro Asp Tyr Leu Arg Thr Ile Val Asp Gln Glu Leu
    50                  55                  60

Leu Pro Tyr Val Gln Val Lys Tyr Ala Gly Ala Leu Val Leu Gly Gln
65                  70                  75                  80

Tyr Tyr Lys Ser Ala Thr Pro Ala Gln Arg Glu Ala Tyr Phe Ala Ala
                85                  90                  95

Phe Arg Glu Tyr Leu Lys Gln Ala Tyr Gly Gln Ala Leu Ala Met Tyr
            100                 105                 110

His Gly Gln Thr Tyr Gln Ile Ala Pro Glu Gln Pro Leu Gly Asp Lys
        115                 120                 125

Thr Ile Val Pro Ile Arg Val Thr Ile Ile Asp Pro Asn Gly Arg Pro
    130                 135                 140

Pro Val Arg Leu Asp Phe Gln Trp Arg Lys Asn Ser Gln Thr Gly Asn
145                 150                 155                 160

Trp Gln Ala Tyr Asp Met Ile Ala Glu Gly Val Ser Met Ile Thr Thr
                165                 170                 175

Lys Gln Asn Glu Trp Gly Thr Leu Leu Arg Thr Lys Gly Ile Asp Gly
            180                 185                 190

Leu Thr Ala Gln Leu Lys Ser Ile Ser Gln Gln Lys Ile Thr Leu Glu
        195                 200                 205

Glu Lys Lys
    210

<210> SEQ ID NO 68
<211> LENGTH: 183
<212> TYPE: PRT
<213> ORGANISM: Escherichia coli

<400> SEQUENCE: 68

Met Gln Thr Lys Lys Asn Glu Ile Trp Val Gly Ile Phe Leu Leu Ala
1               5                   10                  15

Ala Leu Leu Ala Ala Leu Phe Val Cys Leu Lys Ala Ala Asn Val Thr
            20                  25                  30

Ser Ile Arg Thr Glu Pro Thr Tyr Thr Leu Tyr Ala Thr Phe Asp Asn
        35                  40                  45

Ile Gly Gly Leu Lys Ala Arg Ser Pro Val Ser Ile Gly Gly Val Val
    50                  55                  60

Val Gly Arg Val Ala Asp Ile Thr Leu Asp Pro Lys Thr Tyr Leu Pro
65                  70                  75                  80

Arg Val Thr Leu Glu Ile Glu Gln Arg Tyr Asn His Ile Pro Asp Thr
                85                  90                  95

Ser Ser Leu Ser Ile Arg Thr Ser Gly Leu Leu Gly Glu Gln Tyr Leu
            100                 105                 110

Ala Leu Asn Val Gly Phe Glu Asp Pro Glu Leu Gly Thr Ala Ile Leu
        115                 120                 125

Lys Asp Gly Asp Thr Ile Gln Asp Thr Lys Ser Ala Met Val Leu Glu
    130                 135                 140

Asp Leu Ile Gly Gln Phe Leu Tyr Gly Ser Lys Gly Asp Asp Asn Lys
145                 150                 155                 160

Asn Ser Gly Asp Ala Pro Ala Ala Pro Gly Asn Asn Glu Thr Thr
                165                 170                 175
```

-continued

```
Glu Pro Val Gly Thr Thr Lys
            180

<210> SEQ ID NO 69
<211> LENGTH: 260
<212> TYPE: PRT
<213> ORGANISM: Escherichia coli

<400> SEQUENCE: 69

Met Leu Leu Asn Ala Leu Ala Ser Leu Gly His Lys Gly Ile Lys Thr
1               5                   10                  15

Leu Arg Thr Phe Gly Arg Ala Gly Leu Met Leu Phe Asn Ala Leu Val
            20                  25                  30

Gly Lys Pro Glu Phe Arg Lys His Ala Pro Leu Leu Val Arg Gln Leu
        35                  40                  45

Tyr Asn Val Gly Val Leu Ser Met Leu Ile Val Val Ser Gly Val
    50                  55                  60

Phe Ile Gly Met Val Leu Gly Leu Gln Gly Tyr Leu Val Leu Thr Thr
65                  70                  75                  80

Tyr Ser Ala Glu Thr Ser Leu Gly Met Leu Val Ala Leu Ser Leu Leu
                85                  90                  95

Arg Glu Leu Gly Pro Val Val Ala Ala Leu Leu Phe Ala Gly Arg Ala
            100                 105                 110

Gly Ser Ala Leu Thr Ala Glu Ile Gly Leu Met Arg Ala Thr Glu Gln
        115                 120                 125

Leu Ser Ser Met Glu Met Met Ala Val Asp Pro Leu Arg Arg Val Ile
    130                 135                 140

Ser Pro Arg Phe Trp Ala Gly Val Ile Ser Leu Pro Leu Leu Thr Val
145                 150                 155                 160

Ile Phe Val Ala Val Gly Ile Trp Gly Gly Ser Leu Val Gly Val Ser
                165                 170                 175

Trp Lys Gly Ile Asp Ser Gly Phe Phe Trp Ser Ala Met Gln Asn Ala
            180                 185                 190

Val Asp Trp Arg Met Asp Leu Val Asn Cys Leu Ile Lys Ser Val Val
        195                 200                 205

Phe Ala Ile Thr Val Thr Trp Ile Ser Leu Phe Asn Gly Tyr Asp Ala
    210                 215                 220

Ile Pro Thr Ser Ala Gly Ile Ser Arg Ala Thr Thr Arg Thr Val Val
225                 230                 235                 240

His Ser Ser Leu Ala Val Leu Gly Leu Asp Phe Val Leu Thr Ala Leu
                245                 250                 255

Met Phe Gly Asn
            260

<210> SEQ ID NO 70
<211> LENGTH: 269
<212> TYPE: PRT
<213> ORGANISM: Escherichia coli

<400> SEQUENCE: 70

Met Glu Gln Ser Val Ala Asn Leu Val Asp Met Arg Asp Val Ser Phe
1               5                   10                  15

Thr Arg Gly Asn Arg Cys Ile Phe Asp Asn Ile Ser Leu Thr Val Pro
            20                  25                  30

Arg Gly Lys Ile Thr Ala Ile Met Gly Pro Ser Gly Ile Gly Lys Thr
        35                  40                  45
```

```
Thr Leu Leu Arg Leu Ile Gly Gln Ile Ala Pro Asp His Gly Glu
        50                  55                  60

Ile Leu Phe Asp Gly Glu Asn Ile Pro Ala Met Ser Arg Ser Arg Leu
65                  70                  75                  80

Tyr Thr Val Arg Lys Arg Met Ser Met Leu Phe Gln Ser Gly Ala Leu
                85                  90                  95

Phe Thr Asp Met Asn Val Phe Asp Asn Val Ala Tyr Pro Leu Arg Glu
            100                 105                 110

His Thr Gln Leu Pro Ala Pro Leu Leu His Ser Thr Val Met Met Lys
            115                 120                 125

Leu Glu Ala Val Gly Leu Arg Gly Ala Ala Lys Leu Met Pro Ser Glu
130                 135                 140

Leu Ser Gly Gly Met Ala Arg Arg Ala Ala Leu Ala Arg Ala Ile Ala
145                 150                 155                 160

Leu Glu Pro Asp Leu Ile Met Phe Asp Glu Pro Phe Val Gly Gln Asp
            165                 170                 175

Pro Ile Thr Met Gly Val Leu Val Lys Leu Ile Ser Glu Leu Asn Ser
            180                 185                 190

Ala Leu Gly Val Thr Cys Val Val Val Ser His Asp Val Pro Glu Val
            195                 200                 205

Leu Ser Ile Ala Asp His Ala Trp Ile Leu Ala Asp Lys Lys Ile Val
210                 215                 220

Ala His Gly Ser Ala Gln Ala Leu Gln Ala Asn Pro Asp Pro Arg Val
225                 230                 235                 240

Arg Gln Phe Leu Asp Gly Ile Ala Asp Gly Pro Val Pro Phe Arg Tyr
                245                 250                 255

Pro Ala Gly Asp Tyr His Ala Asp Leu Leu Pro Gly Ser
            260                 265

<210> SEQ ID NO 71
<211> LENGTH: 325
<212> TYPE: PRT
<213> ORGANISM: Escherichia coli

<400> SEQUENCE: 71

Met Leu Leu Ala Thr Ala Leu Leu Ile Val Gly Leu Leu Val Val
1               5                   10                  15

Tyr Ser Ala Asp Arg Leu Val Phe Ala Ala Ser Ile Leu Cys Arg Thr
                20                  25                  30

Phe Gly Ile Pro Pro Leu Ile Ile Gly Met Thr Val Val Ser Ile Gly
            35                  40                  45

Thr Ser Leu Pro Glu Val Ile Val Ser Leu Ala Ser Leu His Glu
        50                  55                  60

Gln Arg Asp Leu Ala Val Gly Thr Ala Leu Gly Ser Asn Ile Ile Asn
65                  70                  75                  80

Ile Leu Leu Ile Leu Gly Leu Ala Ala Leu Val Arg Pro Phe Thr Val
                85                  90                  95

His Ser Asp Val Leu Arg Arg Glu Leu Pro Leu Met Leu Leu Val Ser
            100                 105                 110

Val Val Ala Gly Ser Val Leu Tyr Asp Gly Gln Leu Ser Arg Ser Asp
            115                 120                 125

Gly Ile Phe Leu Leu Phe Leu Ala Val Leu Trp Leu Leu Phe Ile Val
        130                 135                 140

Lys Leu Ala Arg Gln Ala Glu Arg Gln Gly Thr Asp Ser Leu Thr Arg
```

|   |   |   |   |   |   |   |   |   |   |   |   |   |   |   |
|---|---|---|---|---|---|---|---|---|---|---|---|---|---|---|
| 145 | | | | | 150 | | | | | 155 | | | | 160 |

Glu Gln Leu Ala Glu Leu Pro Arg Asp Gly Gly Leu Pro Val Ala Phe
                165                170                175

Leu Trp Leu Gly Ile Ala Leu Ile Ile Met Pro Val Ala Thr Arg Met
            180                185                190

Val Val Asp Asn Ala Thr Val Leu Ala Asn Tyr Phe Ala Ile Ser Glu
            195                200                205

Leu Thr Met Gly Leu Thr Ala Ile Ala Ile Gly Thr Ser Leu Pro Glu
            210                215                220

Leu Ala Thr Ala Ile Ala Gly Val Arg Lys Gly Glu Asn Asp Ile Ala
225                230                235                240

Val Gly Asn Ile Ile Gly Ala Asn Ile Phe Asn Ile Val Ile Val Leu
            245                250                255

Gly Leu Pro Ala Leu Ile Thr Pro Gly Glu Ile Asp Pro Leu Ala Tyr
            260                265                270

Ser Arg Asp Tyr Ser Val Met Leu Leu Val Ser Ile Ile Phe Ala Leu
            275                280                285

Leu Cys Trp Arg Arg Ser Pro Gln Pro Gly Arg Gly Val Gly Val Leu
            290                295                300

Leu Thr Gly Gly Phe Ile Val Trp Leu Ala Met Leu Tyr Trp Leu Ser
305                310                315                320

Pro Ile Leu Val Glu
            325

<210> SEQ ID NO 72
<211> LENGTH: 3719
<212> TYPE: DNA
<213> ORGANISM: Escherichia coli

<400> SEQUENCE: 72

```
tgcagaagag gaccacgctg gggcgctgac cgaactgatg gcacaaattc ccgatacgcc      60
gatctactgt acagccaacg ctatcgactc gataaatggt catcaccatc atccggagtg     120
gaatttaat gtggtgaaaa ctggcgacac gctggatatc ggcaacggca aacagctcat     180
ttttgtcgaa acaccaatgc tgcactggcc ggacagcatg atgacttacc tgacaggcga     240
cgcggtgctg ttcagtaacg atgctttcgg tcaacactac tgcgacgagc atctgttcaa     300
cgatgaagtg gatcagacgg agcttttcga gcagtgccag cgttactacg ccaatatcct     360
gacgccgttc agccgcctgg taacaccgaa aattaccgag atcctgggct taacttacc     420
agtcgatatg atagccactt cccacggcgt ggtatggcgc gataacccga cgcaaattgt     480
cgagctgtac ctgaaatggg cggctgatta tcaggaagac agaatcacca ttttctacga     540
caccatgtcg aataacaccc gcatgatggc tgacgctatc gcccagggga ttgcggaaac     600
cgacccacgc gtggcggtga aaattttcaa cgtcgcccga agcgataaaa acgaaatcct     660
gactaatgtc ttccgctcaa aaggcgtgct ggtcggcact cgacgatga ataacgtgat     720
gatgccgaaa atcgccgggc tggtggagga gatgactggt ttacgcttcc gtaacaaacg     780
cgccagtgct ttcggctctc acggctggag cggcggtgcg gtggatcgtc tttccacgcg     840
cctgcaggat gcgggtttcg aaatgtcgct tagcctgaaa gcgaaatggc gaccagacca     900
ggacgctctg aagttatgcc gtgaacacgg tcgcgaaatc gcccgtcagt gggcgctcgc     960
gccgctgccg cagagcacgg tgaatacggt agttaaagaa gaaacctctg ccaccacgac    1020
ggctgacctc ggcccacgga tgcagtgcag cgtctgccag tggatttacg atccggcaaa    1080
```

```
aggcgagcca atgcaggacg ttgcgccagg aacgccgtgg agtgaagtcc cggataactt    1140
cctctgcccg gaatgctccc tcggcaaaga cgtctttgaa gaactggcat cggaggcaaa    1200
atgagtaacg gcattgtgat catcggttcg ggcttcgccg cccgccaact ggtgaaaaat    1260
attcgcaaac aggacgccac tattccatta accctgattg ccgccgacag catggatgag    1320
tacaacaaac ctgacctcag ccatgttatc agtcaggggc aacgtgccga tgaccttacc    1380
cgccagacgg cgggtgaatt tgccgagcag tttaatctgc acctgttttcc acaaacctgg    1440 gtgacggata tcgatgccga agcccgtgtg gtgaaaagcc agaataatca gtggcaatac    1500
gacaagctag tactgcaaac cggtgccagt gcctttgtcc cgcctgtgcc tgggcgtgag    1560
ttaatgctga cgttaaatag tcagcaagag tatcgcgcct gtgaaacgca actgcgggat    1620
gcccgacgcg tgttgattgt tggcggtggt ttgattggta cgaactggc gatggatttt    1680 tgtcgtgcag gcaaagcggt cacgctaatc gacaacgctg ccagtattct ggcgtcgtta    1740
atgccaccgg aagtaagcag ccgcttgcag catcggttga cggagatggg cgttcatctg    1800
ctgttgaaat ctcagttaca ggggctggaa aaaacggatt ctggcattca ggcaacgctg    1860
gaccgccagc gcaatatcga agtggatgcg gtaattgccg ccaccggact gcgcccggaa    1920
accgccctgg cacgacgcgc cgggctgacg attaatcgcg gcgtttgcgt cgatagttat    1980 ctgcaaaacca gtaataccga tatttacgcg ctgggcgatt gcgcggaaat taacggtcag    2040
gtattgccgt tcctccagcc gattcaactt agcgcgatgg tgctggcaaa aaatcttctc    2100
ggcaataaca cgccgctgaa actcccggcg atgctggtga aaatcaaaac gccggaatta    2160
ccgctgcatc tggcaggcga aacccagcgt caggatttac gctggcaaat taataccgaa    2220
cgccagggaa tggtggcgcg cggcgttgac gatgctgacc agcttcgcgc ctttgtggtc    2280
agtgaggatc ggatgaaaga ggctttggaa ttgttgaaaa cattgccgat gtaggtgggc    2340
tactgtgcct aaaatgtcgg atgcgacgct ggcgcgtctt atccgaccta cggggacgca    2400
tgtgtaggcc ggataaggcg tttacgccgc atccggcaat ggtgtccaaa tgcaacacgt    2460
tttatccgtt ctggacttca cccgctaacc aacgcgccgc agcaataacc ccctgcccca    2520
gagacaaacc gccatcaccc gccggtaaac tctgtggaaa gagcaatgtg aaatcagcga    2580
gataatgcgc cagacgtgca cgcagcaaac ggttatgaat aaccccgccg ctaaatacca    2640
gcgtagtgat accacgcatc gtggcctgct cacgcatcaa cgcggcaaaa ccctgcgcca    2700
gcgcatcatg aaacgcccac gcgcgttgat taaccggtgc ctgccagttc agccactgct    2760
gccagaaagt ggcgagatcc agttgattgt ccacccgcgg cattgtcacc ggatgcgtca    2820
ctccgtggca tgaggctgcg agcgcctcca gagcacaagc cgcttcacct tcataactta    2880
acgtggctgg cgcacagccc agtgccgccg ccactgcatc gaaaaaacgc ccacacgatg    2940
acgccagcgg cgcgttaatt ccacgctcaa tggcccgcgc cagcacgctc cagttttgct    3000
gttgcacact tgctgtttca gagtaattct gccactccgg cacaaagcgc aggcactgcg    3060
ccagcaggtt tcgccacggc tgcttcgctg ccaaatcgcc accggaagc gccactgcag    3120 gcaagccgcc caggtgctca cattcgcgat agttcacccg caggcactcg ccgccccaca    3180
aagcgccgtt ctcccccata ccgataccgt cgagcgtcaa agcaatgaca tcaccgccat    3240
ccagcggcca ctgatgctct gccagacacg ccgctgcatg gcatgatga tgcagtaccg    3300 tttgcgtcgg cagattcatt tcacgcgccc actggctgga gacatagccc ggatgcgcgt    3360
catgcacaac gtattgcggg gtaaaatcgt agatgttttg catcaggcgt aacgcttcgc    3420
gccactgcat ctggatgcca tcgtcactta aatcgcccag atgctgactc aacaccgctt    3480
```

```
gttcaccgcg caccaggcag aaggtatttt tcagatccgc gccgagacac agcacaggcg    3540
gaacattttt aaagcccgga ggcaaagcca gcgcatccgg cacataccc cgcgaacggc     3600 gcagcatttc gccgctttcg cgcaccaccg aatcatccat ccgctgcacg atgtcgcggt   3660
tatgtatcaa gaatccgtcg gcaatgccct gcaaatccgc cagcgcctgt tcgttgctg    3719
```

<210> SEQ ID NO 73
<211> LENGTH: 377
<212> TYPE: PRT
<213> ORGANISM: Escherichia coli

<400> SEQUENCE: 73

```
Met Ser Asn Gly Ile Val Ile Ile Gly Ser Gly Phe Ala Ala Arg Gln
1               5                   10                  15

Leu Val Lys Asn Ile Arg Lys Gln Asp Ala Thr Ile Pro Leu Thr Leu
            20                  25                  30

Ile Ala Ala Asp Ser Met Asp Glu Tyr Asn Lys Pro Asp Leu Ser His
        35                  40                  45

Val Ile Ser Gln Gly Gln Arg Ala Asp Asp Leu Thr Arg Gln Thr Ala
    50                  55                  60

Gly Glu Phe Ala Glu Gln Phe Asn Leu His Leu Phe Pro Gln Thr Trp
65                  70                  75                  80

Val Thr Asp Ile Asp Ala Glu Ala Arg Val Val Lys Ser Gln Asn Asn
                85                  90                  95

Gln Trp Gln Tyr Asp Lys Leu Val Leu Ala Thr Gly Ala Ser Ala Phe
            100                 105                 110

Val Pro Pro Val Pro Gly Arg Glu Leu Met Leu Thr Leu Asn Ser Gln
        115                 120                 125

Gln Glu Tyr Arg Ala Cys Glu Thr Gln Leu Arg Asp Ala Arg Arg Val
    130                 135                 140

Leu Ile Val Gly Gly Gly Leu Ile Gly Ser Glu Leu Ala Met Asp Phe
145                 150                 155                 160

Cys Arg Ala Gly Lys Ala Val Thr Leu Ile Asp Asn Ala Ala Ser Ile
                165                 170                 175

Leu Ala Ser Leu Met Pro Pro Glu Val Ser Ser Arg Leu Gln His Arg
            180                 185                 190

Leu Thr Glu Met Gly Val His Leu Leu Leu Lys Ser Gln Leu Gln Gly
        195                 200                 205

Leu Glu Lys Thr Asp Ser Gly Ile Gln Ala Thr Leu Asp Arg Gln Arg
    210                 215                 220

Asn Ile Glu Val Asp Ala Val Ile Ala Ala Thr Gly Leu Arg Pro Glu
225                 230                 235                 240

Thr Ala Leu Ala Arg Arg Ala Gly Leu Thr Ile Asn Arg Gly Val Cys
                245                 250                 255

Val Asp Ser Tyr Leu Gln Thr Ser Asn Thr Asp Ile Tyr Ala Leu Gly
            260                 265                 270

Asp Cys Ala Glu Ile Asn Gly Gln Val Leu Pro Phe Leu Gln Pro Ile
        275                 280                 285

Gln Leu Ser Ala Met Val Leu Ala Lys Asn Leu Gly Asn Asn
    290                 295                 300

Pro Leu Lys Leu Pro Ala Met Leu Val Lys Ile Lys Thr Pro Glu Leu
305                 310                 315                 320

Pro Leu His Leu Ala Gly Glu Thr Gln Arg Gln Asp Leu Arg Trp Gln
                325                 330                 335
```

```
Ile Asn Thr Glu Arg Gln Gly Met Val Ala Arg Gly Val Asp Asp Ala
            340                 345                 350

Asp Gln Leu Arg Ala Phe Val Val Ser Glu Asp Arg Met Lys Glu Ala
            355                 360                 365

Phe Gly Leu Leu Lys Thr Leu Pro Met
            370             375
```

<210> SEQ ID NO 74
<211> LENGTH: 2934
<212> TYPE: DNA
<213> ORGANISM: Escherichia coli

<400> SEQUENCE: 74

| | | |
|---|---|---|
| cgcccaacag tagacaattt ttcataatca tttcgcctga aataatgcag cgggttaatt | 60 |
| tccgcgaatt atgcagcctt cattcaggca ttgtgttgcc gggcgtgctg ccggttttat | 120 |
| tggtcaaatg gcgcttcgtg tttaagaact ttatcgatca catccagtac gccttcacgg | 180 |
| ttattggagc ctgcgcggta ttttgccgct gcgacgaccg cgctaccggc attttccatt | 240 |
| gcaaaactaa agcctgcctg acgcagcatc tcaatatcgt taccgccatc gccaaagacc | 300 |
| accacttcgc tgtcgtctat tccccataat ttctgcagtt ggcgaaggcc attggcttta | 360 |
| tgtacgccgg ggataatcag atcgatgctg ccgttgccgg tgtggaccga caccataata | 420 |
| tcgccgatgg cctcatgtaa tgctttttgt acttgtggaa tcagttcatc ggaaagattc | 480 |
| aggccaaact taagaagat atcctctaag ttgtcaaagt tatcgacgta ttccagacgg | 540 |
| tgataataca tttccgccac cgttttcatg gcatcgtcat attttttgag tgtataggca | 600 |
| ctatttttc cgcaggcaat aatttccact tccgggcgcg tcagcaaatg ttccacgaca | 660 |
| gtagcaaacg catccttcga tagctcgcca ttaaaaacat ctttgccttc gctcactacc | 720 |
| cagccgccgt tttcagccac aaaggcaatt tcattagcaa tttcagggaa gaaagagatc | 780 |
| aactgataat attgattccc gctggcgact acaaagcgaa ttccttgtgc tttcatttgc | 840 |
| tgatactgag ccataaaccg ctcacggtta taggttttt gatcgcttaa gaaagtacca | 900 |
| tccatgtcta ccgcaattaa tttaatgctc atcaactatt ctccatcgcc gtctgcgttt | 960 |
| tggtatcggg tttggcgacg gctttcgcga caatagccgc gagaataacc agcgccagta | 1020 |
| caaccagcat tgcactacgt aatccataat gttcgccgag atagcccagc agcggcggcc | 1080 |
| cgacgaggaa agccagataa ccggtcgttg ctaccacact gacgcgggtt ggtgcatcgg | 1140 |
| ggccggtatc gctggcggca gaatggtca gcgggaagcc cagcgaggca cccagtcccc | 1200 |
| agagtacaac agacacccca gcgacccagg cgctatcgac aaaaataatc agcccaatac | 1260 |
| ccaacgcccc cattagtgca ctggcccgaa ccacggcaac gcgactgtaa cggtcgatga | 1320 |
| accaaccgcc ggtgaagcgt ccaacggtca tccccagggt aaaaccggca taaatcagcg | 1380 |
| agccggaagt agggctaaaa ccgtgaccgt caaccattaa taagggtaac cagtcgttgg | 1440 |
| cagaaccttc ggcaaaggcc atcgccagca ccacaacacc tatcagcagc aactggatat | 1500 |
| cgcgataaaa aggtacgcct ttttcgccat gctgggtgcc atcggcagca ttttgcccg | 1560 |
| taccgtcagg gattgcctga atggcgatat aaataggtgc gatacctacc agcgccgcca | 1620 |
| ataaaatgtg caccgttgcc ggaacgccaa aggccgtcag tgccatcccg acacctgcgc | 1680 |
| ctgccagcgt gcccaggcta taaaaaccgt gcatcatcgg caaaccgtc ttattcattt | 1740 |
| ctcgctcaac ggcagcacct tcaacgttta tcgccacttc cgcagaacca aaacttgccc | 1800 |
| caaagacgcc gagaccaacg gcaaagagca ggggcgatgt cagccagagt gccagactta | 1860 |

```
atatcatcat cccgatcaat gcgcaggaca tcgtgaccag gatgacatta cgtgtcccaa    1920
agcgtttcac taaccacgcc gagcagagaa taccgctcat cgaaccgatc gacagaccaa    1980
agagaacacc gcccatttca gcgatcgaga cagagagaat atcgcggata gcaggcgtac    2040
gggttgccca ggatgccatt aacaggcctg caaaaagaa gaacataaac agcgcccagg     2100
ttcggcgttt caatgcatta cgtgaagaat ttacggtcat agatcacgtc aaaataagaa    2160
gagggaagac aacattagca aggttgtgta catttgtaca caattgcaga gagggaaat    2220 gacatgcgtc gcgctaacga tccgcaacgg cgagaaaaaa ttatccaggc cacgctggag    2280
gcggtgaaac tttacggaat acatgctgtt acgcaccgca aaattgctac ccttgccggg    2340
gtaccgttgg gatcgatgac ctactatttt tcaggaattg atgagttgtt actggaggcg    2400
ttcagcagtt ttactgagat catgtcccgg caatatcagg cattttttag cgatgttagt    2460
gatgctccgg gcgcatgcca ggctatcacc gatatgatct acagctcaca ggttgcaacg    2520
ccggataaca tggagctgat gtaccagctc tacgcgctgg ctagccgaaa accgctatta    2580
aaaacggtaa tgcaaaactg gatgcagcgc agtcagcaaa cgctcgaaca atggtttgaa    2640
cccggaaccg cccgcgcgct tgatgcgttt attgagggga tgacgctgca ttttgtcacc    2700
gaccgtaagc cgctatcgcg cgaggagatt ttgaggatgg ttgagagggt tgcagggtag    2760
tagataagtt ttagataaca aaaaacccat caaccttgaa ccgaaatggc ggggttgatg    2820
ggctccacaa aatgggaca tcaaagaaaa gcagtggcac taattaagac tgatgccctg    2880
cggaaaagtt ctgcggttgt gcaaaaaaat ttcattttca gggcaacttc agtt          2934
```

<210> SEQ ID NO 75
<211> LENGTH: 271
<212> TYPE: PRT
<213> ORGANISM: Escherichia coli

<400> SEQUENCE: 75

```
Met Ser Ile Lys Leu Ile Ala Val Asp Met Asp Gly Thr Phe Leu Ser
1               5                   10                  15

Asp Gln Lys Thr Tyr Asn Arg Glu Arg Phe Met Ala Gln Tyr Gln Gln
            20                  25                  30

Met Lys Ala Gln Gly Ile Arg Phe Val Val Ala Ser Gly Asn Gln Tyr
        35                  40                  45

Tyr Gln Leu Ile Ser Phe Phe Pro Glu Ile Ala Asn Glu Ile Ala Phe
    50                  55                  60

Val Ala Glu Asn Gly Gly Trp Val Val Ser Glu Gly Lys Asp Val Phe
65                  70                  75                  80

Asn Gly Glu Leu Ser Lys Asp Ala Phe Ala Thr Val Val Glu His Leu
                85                  90                  95

Leu Thr Arg Pro Glu Val Glu Ile Ile Ala Cys Gly Lys Asn Ser Ala
            100                 105                 110

Tyr Thr Leu Lys Lys Tyr Asp Asp Ala Met Lys Thr Val Ala Glu Met
        115                 120                 125

Tyr Tyr His Arg Leu Glu Tyr Val Asp Asn Phe Asp Asn Leu Glu Asp
    130                 135                 140

Ile Phe Phe Lys Phe Gly Leu Asn Leu Ser Asp Glu Leu Ile Pro Gln
145                 150                 155                 160

Val Gln Lys Ala Leu His Glu Ala Ile Gly Asp Ile Met Val Ser Val
                165                 170                 175

His Thr Gly Asn Gly Ser Ile Asp Leu Ile Ile Pro Gly Val His Lys
```

```
                 180                 185                 190
Ala Asn Gly Leu Arg Gln Leu Gln Lys Leu Trp Gly Ile Asp Asp Ser
            195                 200                 205

Glu Val Val Phe Gly Asp Gly Asn Asp Ile Glu Met Leu Arg
210                 215                 220

Gln Ala Gly Phe Ser Phe Ala Met Glu Asn Ala Gly Ser Ala Val Val
225                 230                 235                 240

Ala Ala Ala Lys Tyr Arg Ala Gly Ser Asn Asn Arg Glu Gly Val Leu
            245                 250                 255

Asp Val Ile Asp Lys Val Leu Lys His Glu Ala Pro Phe Asp Gln
            260                 265                 270

<210> SEQ ID NO 76
<211> LENGTH: 402
<212> TYPE: PRT
<213> ORGANISM: Escherichia coli

<400> SEQUENCE: 76

Met Thr Val Asn Ser Ser Arg Asn Ala Leu Lys Arg Arg Thr Trp Ala
1               5                   10                  15

Leu Phe Met Phe Phe Phe Leu Pro Gly Leu Leu Met Ala Ser Trp Ala
            20                  25                  30

Thr Arg Thr Pro Ala Ile Arg Asp Ile Leu Ser Val Ser Ile Ala Glu
        35                  40                  45

Met Gly Gly Val Leu Phe Gly Leu Ser Ile Gly Ser Met Ser Gly Ile
    50                  55                  60

Leu Cys Ser Ala Trp Leu Val Lys Arg Phe Gly Thr Arg Asn Val Ile
65                  70                  75                  80

Leu Val Thr Met Ser Cys Ala Leu Ile Gly Met Met Ile Leu Ser Leu
                85                  90                  95

Ala Leu Trp Leu Thr Ser Pro Leu Leu Phe Ala Val Gly Leu Gly Val
            100                 105                 110

Phe Gly Ala Ser Phe Gly Ser Ala Glu Val Ala Ile Asn Val Glu Gly
        115                 120                 125

Ala Ala Val Glu Arg Glu Met Asn Lys Thr Val Leu Pro Met Met His
    130                 135                 140

Gly Phe Tyr Ser Leu Gly Thr Leu Ala Gly Ala Gly Val Gly Met Ala
145                 150                 155                 160

Leu Thr Ala Phe Gly Val Pro Ala Thr Val His Ile Leu Leu Ala Ala
                165                 170                 175

Leu Val Gly Ile Ala Pro Ile Tyr Ile Ala Ile Gln Ala Ile Pro Asp
            180                 185                 190

Gly Thr Gly Lys Asn Ala Ala Asp Gly Thr Gln His Gly Glu Lys Gly
        195                 200                 205

Val Pro Phe Tyr Arg Asp Ile Gln Leu Leu Ile Gly Val Val Val
    210                 215                 220

Leu Ala Met Ala Phe Ala Glu Gly Ser Ala Asn Asp Trp Leu Pro Leu
225                 230                 235                 240

Leu Met Val Asp Gly His Gly Phe Ser Pro Thr Ser Gly Ser Leu Ile
                245                 250                 255

Tyr Ala Gly Phe Thr Leu Gly Met Thr Val Gly Arg Phe Thr Gly Gly
            260                 265                 270

Trp Phe Ile Asp Arg Tyr Ser Arg Val Ala Val Arg Ala Ser Ala
            275                 280                 285
```

```
Leu Met Gly Ala Leu Gly Ile Gly Leu Ile Ile Phe Val Asp Ser Ala
    290             295                 300

Trp Val Ala Gly Val Ser Val Val Leu Trp Gly Leu Gly Ala Ser Leu
305             310                 315                 320

Gly Phe Pro Leu Thr Ile Ser Ala Ala Ser Asp Thr Gly Pro Asp Ala
                325                 330                 335

Pro Thr Arg Val Ser Val Val Ala Thr Thr Gly Tyr Leu Ala Phe Leu
            340                 345                 350

Val Gly Pro Pro Leu Leu Gly Tyr Leu Gly Glu His Tyr Gly Leu Arg
        355                 360                 365

Ser Ala Met Leu Val Val Leu Ala Leu Val Ile Leu Ala Ala Ile Val
370                 375                 380

Ala Lys Ala Val Ala Lys Pro Asp Thr Lys Thr Gln Thr Ala Met Glu
385                 390                 395                 400

Asn Ser
```

<210> SEQ ID NO 77
<211> LENGTH: 178
<212> TYPE: PRT
<213> ORGANISM: Escherichia coli

<400> SEQUENCE: 77

```
Met Arg Arg Ala Asn Asp Pro Gln Arg Arg Glu Lys Ile Ile Gln Ala
1               5                   10                  15

Thr Leu Glu Ala Val Lys Leu Tyr Gly Ile His Ala Val Thr His Arg
            20                  25                  30

Lys Ile Ala Thr Leu Ala Gly Val Pro Leu Gly Ser Met Thr Tyr Tyr
        35                  40                  45

Phe Ser Gly Ile Asp Glu Leu Leu Leu Glu Ala Phe Ser Ser Phe Thr
    50                  55                  60

Glu Ile Met Ser Arg Gln Tyr Gln Ala Phe Phe Ser Asp Val Ser Asp
65                  70                  75                  80

Ala Pro Gly Ala Cys Gln Ala Ile Thr Asp Met Ile Tyr Ser Ser Gln
                85                  90                  95

Val Ala Thr Pro Asp Asn Met Glu Leu Met Tyr Gln Leu Tyr Ala Leu
            100                 105                 110

Ala Ser Arg Lys Pro Leu Leu Lys Thr Val Met Gln Asn Trp Met Gln
        115                 120                 125

Arg Ser Gln Gln Thr Leu Glu Gln Trp Phe Glu Pro Gly Thr Ala Arg
    130                 135                 140

Ala Leu Asp Ala Phe Ile Glu Gly Met Thr Leu His Phe Val Thr Asp
145                 150                 155                 160

Arg Lys Pro Leu Ser Arg Glu Glu Ile Leu Arg Met Val Glu Arg Val
                165                 170                 175

Ala Gly
```

<210> SEQ ID NO 78
<211> LENGTH: 5687
<212> TYPE: DNA
<213> ORGANISM: Escherichia coli

<400> SEQUENCE: 78

```
caacgataag aatgtgcggg gtctgcatgt tgctacccta aattgccaac taaatcgaaa      60
caggaagtac aaaagtccct gacctgcctg atgcatgctg caaattaaca tgatcggcgt     120
aacatgacta agtacgtaa ttgcgttctt gatgcacttt ccatcaacgt caacaacatc      180
```

```
attagcttgg tcgtgggtac tttccctcag gacccgacag tgtcaaaaac ggctgtcatc      240
ctaaccattt taacagcaac ataacaggct aagaggggcc ggacacccaa taaaactacg      300
cttcgttgac atatatcaag ttcaattgta gcacgttaac agtttgatga aatcatcgta      360
tctaaatgct agctttcgtc acattatttt aataatccaa ctagttgcat catacaacta      420
ataaacgtgg tgaatccaat tgtcgagatt tatttttat aaaattatcc taagtaaaca       480
gaaggatatg tagcattttt taacaactca accgttagta cagtcaggaa atagtttagc      540
cttttttaag ctaagtaaag ggcttttttct gcgacttacg ttaagaattt gtaaattcgc     600
accgcgtaat aagttgacag tgatcacccg gttcgcggtt atttgatcaa gaagagtggc     660
aatatgcgta taacgattat tctggtcgca cccgccagag cagaaaatat gggggcagcg     720
gcgcgggcaa tgaaaacgat gggtttagc gatctgcgga ttgtcgatag tcaggcacac      780
ctggagccag ccacccgctg ggtcgcacat ggatctggtg atattattga taatattaaa     840
gttttcccga cactggctga atcgttacac gatgtcgatt tcactgtcgc caccactgcg     900
cgcagtcggg cgaaatatca ttactacgcc acgccagttg aactggtgcc gctgttagag     960
gaaaaatctt catggatgag ccatgccgcg ctggtgtttg gtcgcgaaga ttccgggttg    1020
actaacgaag agttagcgtt ggctgacgtt cttactggtg tgccgatggt ggcggattat    1080
ccttcgctca atctggggca ggcggtgatg gtctattgct atcaattagc aacattaata    1140
caacaaccgg cgaaaagtga tgcaacggca gaccaacatc aactgcaagc tttacgcgaa    1200
cgagccatga gattgctgac gactctggca gtggcagatg acataaaact ggtcgactgg    1260
ttacaacaac gcctggggct tttagagcaa cgagacacgg caatgttgca ccgtttgctg    1320
catgatattg aaaaaaatat caccaaataa aaaacgcctt agtaagtatt tttcagcttt    1380
tcattctgac tgcaacgggc aatatgtctc tgtgtggatt aaaaaaagag tgtctgatag    1440
cagcttctga actggttacc tgccgtgagt aaattaaaat tttattgact taggtcacta    1500
aatactttaa ccaatatagg catagcgcac agacagataa aaataacaga gtacacaaca    1560
tccatgaaac gcattagcac caccattacc accaccatca ccattaccac aggtaacggt    1620
gcgggctgac gcgtacagga aacacagaaa aaagcccgca cctgacagtg cgggcttttt    1680
ttttcgacca aggtaacga ggtaacaacc atgcgagtgt tgaagttcgg cggtacatca     1740
gtggcaaatg cagaacgttt tctgcgtgtt gccgatattc tggaaagcaa tgccaggcag    1800
gggcaggtgg ccaccgtcct ctctgccccc gccaaaatca ccaaccacct ggtggcgatg    1860
attgaaaaaa ccattagcgg ccaggatgct tacccaata tcagcgatgc cgaacgtatt     1920
tttgccgaac ttttgacggg actcgccgcc gcccagccgg ggttcccgct ggcgcaattg    1980
aaaactttcg tcgatcagga atttgcccaa ataaacatg tcctgcatgg cattagtttg     2040
ttggggcagt gcccggatag catcaacgct gcgctgattt gccgtggcga aaaatgtcg     2100 atcgccatta tggccggcgt gttagaagcg cgtggtcaca acgttaccgt tatcgatccg    2160
gtcgaaaaac tgctggctgt ggggcattac ctcgaatcta ccgtcgatat tgctgagtcc    2220
acccgccgta ttgcggcaag ccgcattccg gctgatcaca tggtgttgat ggcaggtttc    2280
accgccggta atgaaaaagg cgaactggtg gtgcttggac gtaacggttc cgactactcc    2340
gctgcggtgc tggctgcctg tttacgcgcc gattgttgcg agatttggac ggacgttgac    2400
ggggtctata cctgcgaccc cgtcaggtg cccgatgcga ggttgttgaa gtcgatgtcc     2460
taccaggaag cgatggagct ttcctacttc ggcgctaaag ttcttcaccc ccgcaccatt    2520
```

```
accccccatcg cccagttcca gatcccttgc ctgattaaaa ataccggaaa tcctcaagca    2580
ccaggtacgc tcattggcgc cagccgtgat gaagacgaat taccagtcaa gggcatttcc    2640
aatctgaata acatggcaat gtttagcgtt tccggtccgg gaatgaaagg gatggtcggc    2700
atggcggcgc gcgtctttgc agcgatgtca cgcgctcgca tttcagtggt gctgattacg    2760
caatcgtctt ctgaatacag tatcagtttc tgcgttccac aaagcgactg tgtgcgagct    2820
gaacgggcga tgcaggaaga gttctatctt gaactgaagg aaggcttgct ggagccgctg    2880
gcggtgacgg aacggctagc cattatctcg gtggtaggtg atggtatgcg caccttgcgt    2940
gggatctcgg cgaaattctt tgccgcgctg gcccgcgcca atatcaacat tgtcgccatt    3000
gctcagggat cttctgaacg ctcaatctct gtcgtggtaa ataacgatga tgcgaccact    3060
ggtgtgcgcg ttactcatca gatgctgttc aataccgatc aggttatcga agtgtttgta    3120
attggtgtcg gtggcgttgg cggtgcgctg ctggagcaac tgaagcgtca gcaaagctgg    3180
ttgaagaata acatatcga cttacgtgtc tgcggcgttg ccaactcaaa ggctctgctc    3240
accaatgtgc atggccttaa tctggagaac tggcaggaag aactgtcgca agccaaagag    3300
ccgtttaacc tcgggcgctt aattcgcctg gtgaaagaat atcatttgct gaatccggtg    3360
attgtcgact gtacctccag ccaggcggtg gcggatcagt atgctgactt cctgcgcgaa    3420
ggtttccacg tggttacgcc aaacaaaaag gccaacacct cgtcgatgga ttactaccat    3480
cagttgcgtt atgcggcgga aaatcgcgcg cgtaaattcc tctatgacac taacgttggg    3540
gctggattac cggttattga gaacctgcaa aatctgctca acgcaggtga tgaattaatg    3600
aagttctccg gcattctttc cggttcgctt tcttatatct tcggcaagtt agacgaaggc    3660
atgagtttct ccgaggcgac cacgctggcg cgggaaatgg gttataccga accggacccg    3720
cgagatgatc tttctggtat ggatgtggcg cgtaagctat tgattctcgc ccgtgaaacg    3780
ggacgtgaac tggaactggc ggatattgaa attgaacctg tgctgcccgc agagtttaac    3840
gcagagggtg atgttgcagc ttttatggcg aatctgtcac agctcgacga tctctttgcc    3900
gcacgcgtgg cgaaggctcg tgatgagggc aaagttttgc gctatgttgg caatattgat    3960
gaagatggca tctgccgcgt gaagattgcc gaagtggatg gcaatgatcc gctgttcaaa    4020
gtgaaaaatg gcgaaaacgc cctggccttc tatagccact attatcagcc gctgccgttg    4080
gttctgcgcg gatatggcgc gggcaatgac gttacagctg ctggtgtctt tgccgatctg    4140
ctacgtaccc tctcatggaa gttaggagtc tgacatggtt aaagtttatg ccccggcttc    4200
cagtgccaat atgagcgtcg ggtttgatgt gctcggggcg gcggtgacac ctgttgatgg    4260
tgcattgctc ggagatgtag taacggttga ggcggcagag acattcagtc tcaacaatct    4320
cggacgcttt gccgataagc tgccatcaga accacgggaa aatatcgttt atcagtgctg    4380
ggagcgtttt tgccaggagc tgggcaagca aattccagtg gcaatgacgc tggaaaagaa    4440
tatgccgatc ggttcgggtt taggatccag cgcttgttcg gtggtggcgg cgctgatggc    4500
gatgaatgaa cattgcggca agccgcttaa tgacacccgt ttgctggctt tgatgggcga    4560
gctggaaggg cgtatctccg gcagcattca ttacgacaac gtggcaccgt gttttcttgg    4620
tggtatgcag ttgatgatcg aagaaaacga catcatcagc cagcaagtgc cagggtttga    4680
tgagtggctg tgggtgctgg cgtatccggg gattaaagtc tcgacggcag aagccagggc    4740
tattttaccg gcgcagtatc gccgccagga ttgcattgcg cacgggcgac atctggcagg    4800
cttcattcac gcctgctatt cccgtcagcc tgagcttgcc gcgaagctga tgaaagatgt    4860
tatcgctgaa ccctaccgtg aacggttact gccaggcttc cggcaggcgc ggcaggcggt    4920
```

```
cgcggaaatc ggcgcggtag cgagcggtat ctccggctcc ggcccgacct tgttcgctct    4980
gtgtgacaag ccggaaaccg cccagcgcgt tgccgactgg ttgggtaaga actacctgca    5040
aaatcaggaa ggttttgttc atatttgccg gctggatacg gcgggcgcac gagtactgga    5100
aaactaaatg aaactctaca atctgaaaga tcacaacgag caggtcagct ttgcgcaagc    5160
cgtaacccag gggttgggca aaaatcaggg gctgtttttt ccgcacgacc tgccggaatt    5220
cagcctgact gaaattgatg agatgctgaa gctggatttt gtcacccgca gtgcgaagat    5280
cctctcggcg tttattggtg atgaaatccc acaggaaatc ctggaagagc gcgtgcgcgc    5340
ggcgtttgcc ttcccggctc cggtcgccaa tgttgaaagc gatgtcggtt gtctggaatt    5400
gttccacggg ccaacgctgg catttaaaga tttcggcggt cgctttatgg cacaaatgct    5460
gacccatatt gcgggtgata agccagtgac cattctgacc gcgacctccg gtgataccgg    5520
agcggcagtg gctcatgctt tctacggttt accgaatgtg aaagtggtta tcctctatcc    5580
acgaggcaaa atcagtccac tgcaagaaaa actgttctgt acattgggcg gcaatatcga    5640
aactgttgcc atcgacggcg atttcgatgc ctgtcaggcg ctggtga                  5687
```

<210> SEQ ID NO 79
<211> LENGTH: 46
<212> TYPE: PRT
<213> ORGANISM: Escherichia coli

<400> SEQUENCE: 79

Met Thr Lys Val Arg Asn Cys Val Leu Asp Ala Leu Ser Ile Asn Val
1               5                   10                  15

Asn Asn Ile Ile Ser Leu Val Val Gly Thr Phe Pro Gln Asp Pro Thr
            20                  25                  30

Val Ser Lys Thr Ala Val Ile Leu Thr Ile Leu Thr Ala Thr
        35                  40                  45

<210> SEQ ID NO 80
<211> LENGTH: 228
<212> TYPE: PRT
<213> ORGANISM: Escherichia coli

<400> SEQUENCE: 80

Met Arg Ile Thr Ile Ile Leu Val Ala Pro Ala Arg Ala Glu Asn Ile
1               5                   10                  15

Gly Ala Ala Ala Arg Ala Met Lys Thr Met Gly Phe Ser Asp Leu Arg
            20                  25                  30

Ile Val Asp Ser Gln Ala His Leu Glu Pro Ala Thr Arg Trp Val Ala
        35                  40                  45

His Gly Ser Gly Asp Ile Ile Asp Asn Ile Lys Val Phe Pro Thr Leu
    50                  55                  60

Ala Glu Ser Leu His Asp Val Asp Phe Thr Val Ala Thr Thr Ala Arg
65                  70                  75                  80

Ser Arg Ala Lys Tyr His Tyr Tyr Ala Thr Pro Val Glu Leu Val Pro
                85                  90                  95

Leu Leu Glu Glu Lys Ser Ser Trp Met Ser His Ala Ala Leu Val Phe
            100                 105                 110

Gly Arg Glu Asp Ser Gly Leu Thr Asn Glu Glu Leu Ala Leu Ala Asp
        115                 120                 125

Val Leu Thr Gly Val Pro Met Val Ala Asp Tyr Pro Ser Leu Asn Leu
    130                 135                 140

Gly Gln Ala Val Met Val Tyr Cys Tyr Gln Leu Ala Thr Leu Ile Gln
145                 150                 155                 160

Gln Pro Ala Lys Ser Asp Ala Thr Ala Asp Gln His Gln Leu Gln Ala
            165                 170                 175

Leu Arg Glu Arg Ala Met Arg Leu Leu Thr Thr Leu Ala Val Ala Asp
        180                 185                 190

Asp Ile Lys Leu Val Asp Trp Leu Gln Gln Arg Leu Gly Leu Leu Glu
    195                 200                 205

Gln Arg Asp Thr Ala Met Leu His Arg Leu Leu His Asp Ile Glu Lys
    210                 215                 220

Asn Ile Thr Lys
225

<210> SEQ ID NO 81
<211> LENGTH: 21
<212> TYPE: PRT
<213> ORGANISM: Escherichia coli

<400> SEQUENCE: 81

Met Lys Arg Ile Ser Thr Thr Ile Thr Thr Thr Ile Thr Ile Thr Thr
1               5                   10                  15

Gly Asn Gly Ala Gly
            20

<210> SEQ ID NO 82
<211> LENGTH: 820
<212> TYPE: PRT
<213> ORGANISM: Escherichia coli

<400> SEQUENCE: 82

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
            85                  90                  95

Glu Phe Ala Gln Ile Lys His Val Leu His Gly Ile Ser Leu Leu Gly
        100                 105                 110

Gln Cys Pro Asp Ser Ile Asn Ala Ala Leu Ile Cys Arg Gly Glu Lys
    115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
            165                 170                 175

Ser Arg Ile Pro Ala Asp His Met Val Leu Met Ala Gly Phe Thr Ala
        180                 185                 190

Gly Asn Glu Lys Gly Glu Leu Val Val Leu Gly Arg Asn Gly Ser Asp
    195                 200                 205

-continued

```
Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ser Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
```

```
            625                 630                 635                 640
      Ser Tyr Ile Phe Gly Lys Leu Asp Glu Gly Met Ser Phe Ser Glu Ala
                          645                 650                 655

Thr Thr Leu Ala Arg Glu Met Gly Tyr Thr Glu Pro Asp Pro Arg Asp
                          660                 665                 670

Asp Leu Ser Gly Met Asp Val Ala Arg Lys Leu Leu Ile Leu Ala Arg
                          675                 680                 685

Glu Thr Gly Arg Glu Leu Glu Leu Ala Asp Ile Glu Ile Glu Pro Val
                          690                 695                 700

Leu Pro Ala Glu Phe Asn Ala Glu Gly Asp Val Ala Ala Phe Met Ala
      705                 710                 715                 720

Asn Leu Ser Gln Leu Asp Asp Leu Phe Ala Ala Arg Val Ala Lys Ala
                          725                 730                 735

Arg Asp Glu Gly Lys Val Leu Arg Tyr Val Gly Asn Ile Asp Glu Asp
                          740                 745                 750

Gly Ile Cys Arg Val Lys Ile Ala Glu Val Asp Gly Asn Asp Pro Leu
                          755                 760                 765

Phe Lys Val Lys Asn Gly Glu Asn Ala Leu Ala Phe Tyr Ser His Tyr
          770                 775                 780

Tyr Gln Pro Leu Pro Leu Val Leu Arg Gly Tyr Gly Ala Gly Asn Asp
      785                 790                 795                 800

Val Thr Ala Ala Gly Val Phe Asp Leu Leu Arg Thr Leu Ser Trp
                          805                 810                 815

Lys Leu Gly Val
                  820

<210> SEQ ID NO 83
<211> LENGTH: 310
<212> TYPE: PRT
<213> ORGANISM: Escherichia coli

<400> SEQUENCE: 83

Met Val Lys Val Tyr Ala Pro Ala Ser Ser Ala Asn Met Ser Val Gly
      1               5                   10                  15

Phe Asp Val Leu Gly Ala Ala Val Thr Pro Val Asp Gly Ala Leu Leu
                      20                  25                  30

Gly Asp Val Val Thr Val Glu Ala Ala Glu Thr Phe Ser Leu Asn Asn
                  35                  40                  45

Leu Gly Arg Phe Ala Asp Lys Leu Pro Ser Glu Pro Arg Glu Asn Ile
          50                  55                  60

Val Tyr Gln Cys Trp Glu Arg Phe Cys Gln Glu Leu Gly Lys Gln Ile
      65                  70                  75                  80

Pro Val Ala Met Thr Leu Glu Lys Asn Met Pro Ile Gly Ser Gly Leu
                      85                  90                  95

Gly Ser Ser Ala Cys Ser Val Val Ala Ala Leu Met Ala Met Asn Glu
                  100                 105                 110

His Cys Gly Lys Pro Leu Asn Asp Thr Arg Leu Leu Ala Leu Met Gly
                  115                 120                 125

Glu Leu Glu Gly Arg Ile Ser Gly Ser Ile His Tyr Asp Asn Val Ala
          130                 135                 140

Pro Cys Phe Leu Gly Gly Met Gln Leu Met Ile Glu Glu Asn Asp Ile
      145                 150                 155                 160

Ile Ser Gln Gln Val Pro Gly Phe Asp Glu Trp Leu Trp Val Leu Ala
                      165                 170                 175
```

```
Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305                 310

<210> SEQ ID NO 84
<211> LENGTH: 4543
<212> TYPE: DNA
<213> ORGANISM: Escherichia coli

<400> SEQUENCE: 84
cccggaaatt gaacgcggcg aagtgaacct ggtgaaaacc accggtctgc atgcggcggg      60
taaaggcatc aacgtggcca agtattaaa agacctggga attgatgtca ccgttggcgg     120
cttcctcggt aaagacaatc aggatggttt tcagcaactg ttcagcgagc tgggcattgc     180
caaccgtttc caggttgtac aggggcgcac tcgaattaac gttaagctga cggaaaaaga     240
cggcgaagtg accgacttca acttctcggg ttttgaagtc accccgccg actgggaacg     300 ctttgtgact gattctctga ctggctcgg tcagttcgat atggtctgtg tcagcggaag     360
cttaccgtca ggcgtcagcc cggaagcgtt caccgactgg atgactcgcc tgcgtagtca     420
gtgtccttgc attatctttg atagtagccg tgaagcgtta gtagcaggtt tgaaagcggc     480
accatggctg gtgaaaccta accgccgcga gctggaaatc tgggcaggcc gtaaactgcc     540
tgaaatgaaa gatgtgattg aagctgcgca tgcgctgcgt gaacaaggta tcgcgcatgt     600
tgttatttca ctgggtgccg aaggcgcgct ttgggttaat gcctccggcg aatggatcgc     660
caaaccaccg tcagtcgatg tcgtaagcac cgttggcgca ggggattcta tggttggtgg     720
cctgatttat ggcttgctga tgcgtgaatc cagtgaacac acactgcgtc tggcgacagc     780
tgttgcagcc ctggcggtaa gtcaaagcaa tgtgggtatt accgatcgtc cgcagttggc     840
cgcaatgatg gcgcgcgtcg acttacaacc ttttaactga cagcaggaga ggcataatga     900
aaacgctgct gattattgac gctaatctcg gtcaggcacg cgcctatatg gcgaagaccc     960
tgctgggcgc ggcggcgcga aaagcaaaac tggaaatcat cgacaatccg aacgacgctg    1020
aaatggcgat tgttctcggt gattccatcc gaatgacag cgcgctgaac ggtaaaaatg    1080
tctggctggg tgatatttcc cggcagttg cgcaccctga ctgttcctg agtgaagcca    1140 aaggccatgc gaaaccttac actgcgccgg tcactgcgac agcaccggtt gccgccagcg    1200
gtccgaaacg cgtagttgcg gtgactgctt gcccgactgg cgtagcacac acctttatgg    1260
cggctgaagc cattgaaacc gaagcgaaaa acgtggctgt gggtgaaa gttgaaaccc    1320
```

```
gtggttctgt tggcgcgggt aatgcaatca ctcccgagga agtagccgca gcggatctgg    1380
tgattgtggc ggcagatatc gaagtggatc tggcgaaatt tgctggtaaa ccgatgtatc    1440
gtacctctac cggtctggcg ctgaagaaaa ccgcgcagga actggataaa gcggttgctg    1500
aagcaacgcc gtatgaaccg gcgggcaaag ctcaaacggc gaccactgaa ggtaagaaag    1560
agagtgcagg cgcttatcgt cacttgctaa cgggcgtctc ttacatgctg ccgatggtcg    1620
ttgctggtgg tctgtgtatc gcgctttctt ttgcttttgg tatcgaagcg tttaaagagc    1680
cgggtacgtt ggcagcggcg ctgatgcaga ttggcggtgg ttcagccttt gcgctgatgg    1740
tgccggtact ggcaggttat attgccttct ccattgccga tcgtccgggc ctcacgccgg    1800
gtctgattgg cggtatgctg gctgtcagca ccggttctgg cttcattggc ggtattattg    1860
cgggcttcct ggctgttac attgcgaagt taatcagtac gcaactgaaa ctgccacaga    1920
gtatggaggc gctgaaacca atcctgatca ttccgctaat ttccagtctg gtggtcggtc    1980
tggcgatgat ctacctgatc ggtaaaccag ttgctggcat tctcgaaggg ttgactcact    2040
ggctgcaaac catggggact gcgaatgcgg ttctgctggg ggcgatcctc ggtggcatga    2100
tgtgtactga catgggcggt ccggtaaaca aagcagcgta cgcattcggt gtgggtctgc    2160
tgagtactca aacctatggc ccgatggcgg cgattatggc ggcaggtatg gtgccaccgc    2220
tggcaatggg tctggcaaca atggtggcgc gtcgcaaatt cgacaaagcg cagcaggaag    2280
gtggcaaagc cgctctggta ttgggactgt gcttcatttc ggaaggtgca attccgtttg    2340
ctgctcgtga tccgatgcgt gtgctgccgt gctgtatcgt gggtggggcg ctgactggcg    2400
caatctcaat ggcgattggt gcgaaactga tggcaccgca cggtggtctg tttgttctgc    2460
tgatccctgg cgctattacg ccggtactgg gttacctggt agcaattatt gccggtacgc    2520
tggtggcggg tttggcctat gccttcctga acgtccgga agtggacgca gtagcgaaag    2580
cagcgtaata aaaggtatgt tacagggcag aaatttcctg ccctgtatca ttggatgagc    2640
gcaaagggaa tgaccggttt gtaaatgtaa ttttatgaat ttaaatggtt ttatctttca    2700
gtagaaacct gaaacgttca tcaaacacta aggttatttc ctcaagggca gattattttc    2760
tgccctttttt tagtgttcct gttctgtgca tcccgtcaca aattcctcgc ttttgtaatt    2820
caggcatttta atcgcatttt gtgagcctgc tcaaatctgc ccattttgcc tctctggcgg    2880
taatttactt tacgtaaaac atgcatacta tgagcacatg tttaaatatg aacacatgtt    2940
taaaccgtct ttgcagtatc tatattcttg tggattgaca gggttggtaa ttttttacca    3000
gaggacgtgc tatgcgcgaa aaggattatg tcgtaattat aggttcggcg aatattgatg    3060
tcgccggata ttcacatgaa tcattaaatt atgcggatta aaatccaggt aaaataaaat    3120
ttacgcctgg tggagtaggg cgcaatattg cacaaaacct ggcgttgctg ggtaacaaag    3180
cctggctact gagcgcagta ggcagtgatt tttatggtca atcgctgcta acgcaaacca    3240
atcaatctgg cgtttatgtc gataaatgcc tgattgtgcc gggagaaaat acgtctagtt    3300
atttatcatt actcgataat accggtgaaa tgctggttgc tataaatgac atgaatatta    3360
gcaacgctat tacagctgaa tatctcgcac agcaccgtga atttattcag agggcaaagg    3420
tcattgttgc ggactgtaat atcagtgaag aggcactggc atggattctg ataatgccg    3480
ccaacgtacc cgtatttgtc gatccggttt ccgcatggaa atgtgtcaaa gtgcgcgacc    3540
gtctaaatca gatccacact ctcaagccaa accgccttga agcggaaacc ctgagtggga    3600
ttgcgctgtc agggcgtgac gatgtggcaa aagttgctgc ctggttccat caacatggcc    3660
tgaaccgact ggtattgagc atgggcggcg acggcgttta ttacagcgat atcagcggtg    3720
```

-continued

```
aaaatggctg gtctgcgccg atcaaaacca atgttattaa tgttaccgga gcgggcgatg    3780
ccatgatggc gggacttgct tcgtgttggg tagacggaat gccgtttgcc gaatctgttc    3840
gtttcgcaca gggatgttcg tcaatggcgc tctcctgtga atacaccaat aaccccgatt    3900
tatcgattgc caacgttata tcgttagtgg agaacgcaga atgtctgaat taaaaatttc    3960
ccctgaatta ttacaaattt ccccggaagt gcaggacgct ttaaaaaaca aaaaaccggt    4020
tgtggcgctg aatcgacca ttatttctca cgggatgccg ttcccacaaa atgcccagac    4080
cgcaattgaa gtagaagaaa ctattcgtaa acagggcgct gtacctgcca ctatcgccat    4140
tattggcggc gtgatgaaag tgggtttaag caaagaagaa attgaattac tgggtcgtga    4200
agggcataac gtgaccaaag ttagtcgtcg cgatttacct tttgttgttg ccgccggaaa    4260
aaatggcgca accactgtgg cttcaacgat gattattgcg gcgcttgccg gaattaaagt    4320
atttgccacc gggggaattg gtggtgtgca tcgcggggcg aacataacct tcgatatttc    4380
tgccgatttg caagaactgg caaatactaa tgtcaccgtt gtttgtgccg gggcgaaatc    4440
tattctcgat ttaggattaa ccactgagta tttagaaacc ttcggtgtgc cgttaattgg    4500
ctatcagact aaagcgctgc ctgcgttttt ctgccgtacc agc                      4543
```

<210> SEQ ID NO 85
<211> LENGTH: 563
<212> TYPE: PRT
<213> ORGANISM: Escherichia coli

<400> SEQUENCE: 85

```
Met Lys Thr Leu Leu Ile Ile Asp Ala Asn Leu Gly Gln Ala Arg Ala
1               5                   10                  15

Tyr Met Ala Lys Thr Leu Leu Gly Ala Ala Ala Arg Lys Ala Lys Leu
            20                  25                  30

Glu Ile Ile Asp Asn Pro Asn Asp Ala Glu Met Ala Ile Val Leu Gly
        35                  40                  45

Asp Ser Ile Pro Asn Asp Ser Ala Leu Asn Gly Lys Asn Val Trp Leu
    50                  55                  60

Gly Asp Ile Ser Arg Ala Val Ala His Pro Glu Leu Phe Leu Ser Glu
65                  70                  75                  80

Ala Lys Gly His Ala Lys Pro Tyr Thr Ala Pro Val Thr Ala Thr Ala
                85                  90                  95

Pro Val Ala Ala Ser Gly Pro Lys Arg Val Val Ala Val Thr Ala Cys
            100                 105                 110

Pro Thr Gly Val Ala His Thr Phe Met Ala Ala Glu Ala Ile Glu Thr
        115                 120                 125

Glu Ala Lys Lys Arg Gly Trp Trp Val Lys Val Glu Thr Arg Gly Ser
    130                 135                 140

Val Gly Ala Gly Asn Ala Ile Thr Pro Glu Glu Val Ala Ala Ala Asp
145                 150                 155                 160

Leu Val Ile Val Ala Ala Asp Ile Glu Val Asp Leu Ala Lys Phe Ala
                165                 170                 175

Gly Lys Pro Met Tyr Arg Thr Ser Thr Gly Leu Ala Leu Lys Lys Thr
            180                 185                 190

Ala Gln Glu Leu Asp Lys Ala Val Ala Glu Ala Thr Pro Tyr Glu Pro
        195                 200                 205

Ala Gly Lys Ala Gln Thr Ala Thr Thr Glu Gly Lys Lys Glu Ser Ala
    210                 215                 220
```

Gly Ala Tyr Arg His Leu Leu Thr Gly Val Ser Tyr Met Leu Pro Met
225                 230                 235                 240

Val Val Ala Gly Gly Leu Cys Ile Ala Leu Ser Phe Ala Phe Gly Ile
            245                 250                 255

Glu Ala Phe Lys Glu Pro Gly Thr Leu Ala Ala Leu Met Gln Ile
        260                 265                 270

Gly Gly Gly Ser Ala Phe Ala Leu Met Val Pro Val Leu Ala Gly Tyr
    275                 280                 285

Ile Ala Phe Ser Ile Ala Asp Arg Pro Gly Leu Thr Pro Gly Leu Ile
        290                 295                 300

Gly Gly Met Leu Ala Val Ser Thr Gly Ser Gly Phe Ile Gly Gly Ile
305                 310                 315                 320

Ile Ala Gly Phe Leu Ala Gly Tyr Ile Ala Lys Leu Ile Ser Thr Gln
            325                 330                 335

Leu Lys Leu Pro Gln Ser Met Glu Ala Leu Lys Pro Ile Leu Ile Ile
        340                 345                 350

Pro Leu Ile Ser Ser Leu Val Val Gly Leu Ala Met Ile Tyr Leu Ile
            355                 360                 365

Gly Lys Pro Val Ala Gly Ile Leu Glu Gly Leu Thr His Trp Leu Gln
        370                 375                 380

Thr Met Gly Thr Ala Asn Ala Val Leu Leu Gly Ala Ile Leu Gly Gly
385                 390                 395                 400

Met Met Cys Thr Asp Met Gly Gly Pro Val Asn Lys Ala Ala Tyr Ala
                405                 410                 415

Phe Gly Val Gly Leu Leu Ser Thr Gln Thr Tyr Gly Pro Met Ala Ala
            420                 425                 430

Ile Met Ala Ala Gly Met Val Pro Pro Leu Ala Met Gly Leu Ala Thr
        435                 440                 445

Met Val Ala Arg Arg Lys Phe Asp Lys Ala Gln Gln Glu Gly Gly Lys
    450                 455                 460

Ala Ala Leu Val Leu Gly Leu Cys Phe Ile Ser Glu Gly Ala Ile Pro
465                 470                 475                 480

Phe Ala Ala Arg Asp Pro Met Arg Val Leu Pro Cys Cys Ile Val Gly
            485                 490                 495

Gly Ala Leu Thr Gly Ala Ile Ser Met Ala Ile Gly Ala Lys Leu Met
        500                 505                 510

Ala Pro His Gly Gly Leu Phe Val Leu Leu Ile Pro Gly Ala Ile Thr
    515                 520                 525

Pro Val Leu Gly Tyr Leu Val Ala Ile Ile Ala Gly Thr Leu Val Ala
    530                 535                 540

Gly Leu Ala Tyr Ala Phe Leu Lys Arg Pro Glu Val Asp Ala Val Ala
545                 550                 555                 560

Lys Ala Ala

<210> SEQ ID NO 86
<211> LENGTH: 262
<212> TYPE: PRT
<213> ORGANISM: Escherichia coli

<400> SEQUENCE: 86

Met Leu Gly Asn Lys Ala Trp Leu Leu Ser Ala Val Gly Ser Asp Phe
1               5                   10                  15

Tyr Gly Gln Ser Leu Leu Thr Gln Thr Asn Gln Ser Gly Val Tyr Val
            20                  25                  30

Asp Lys Cys Leu Ile Val Pro Gly Glu Asn Thr Ser Ser Tyr Leu Ser
           35                  40                  45

Leu Leu Asp Asn Thr Gly Glu Met Leu Val Ala Ile Asn Asp Met Asn
 50                  55                  60

Ile Ser Asn Ala Ile Thr Ala Glu Tyr Leu Ala Gln His Arg Glu Phe
 65                  70                  75                  80

Ile Gln Arg Ala Lys Val Ile Ala Asp Cys Asn Ile Ser Glu Glu
                 85                  90                  95

Ala Leu Ala Trp Ile Leu Asp Asn Ala Ala Asn Val Pro Val Phe Val
            100                 105                 110

Asp Pro Val Ser Ala Trp Lys Cys Val Lys Val Arg Asp Arg Leu Asn
            115                 120                 125

Gln Ile His Thr Leu Lys Pro Asn Arg Leu Glu Ala Glu Thr Leu Ser
130                 135                 140

Gly Ile Ala Leu Ser Gly Arg Asp Asp Val Ala Lys Val Ala Ala Trp
145                 150                 155                 160

Phe His Gln His Gly Leu Asn Arg Leu Val Leu Ser Met Gly Gly Asp
                165                 170                 175

Gly Val Tyr Tyr Ser Asp Ile Ser Gly Glu Asn Gly Trp Ser Ala Pro
            180                 185                 190

Ile Lys Thr Asn Val Ile Asn Val Thr Gly Ala Gly Asp Ala Met Met
            195                 200                 205

Ala Gly Leu Ala Ser Cys Trp Val Asp Gly Met Pro Phe Ala Glu Ser
            210                 215                 220

Val Arg Phe Ala Gln Gly Cys Ser Ser Met Ala Leu Ser Cys Glu Tyr
225                 230                 235                 240

Thr Asn Asn Pro Asp Leu Ser Ile Ala Asn Val Ile Ser Leu Val Glu
                245                 250                 255

Asn Ala Glu Cys Leu Asn
            260

<210> SEQ ID NO 87
<211> LENGTH: 4534
<212> TYPE: DNA
<213> ORGANISM: Escherichia coli

<400> SEQUENCE: 87
gcaatttctg atccttgatg agccaactcg cggcattgat gttggtgccc acgccgagat     60
catccgcctg attgaaacgc tatgcgccga tggtctggcg ctgctggtga tctcctccga    120
actggaagaa ctggtgggct atgccgaccg ggtgatcatc atgcgcgatc gcaaacaggt    180
ggcggagatc ccgctggcag agctttccgt tccggcgatc atgaacgcca ttgcggcgta    240
aggagaacag tgtgatgcct caatctctcc cggacactac gccgccgaaa aggcgctttc    300
gctggccaac gggaatgccg cagctggcgg cactgttgct ggtgctgctg gtcgatagcc    360
tggtggcccc gcattctgg caggtggtgc tccaggatgg gcgtttattc ggtagcccca    420
tagacattct taaccgtgcg gccccgttg cgctgttggc tatcggaatg acgctggtga    480
tcgcaacagg tgggattgat ctctccgtgg gggcggtgat ggctatcgcc ggagccacaa    540
cggctgcgat gacggtcgcg ggattcagcc tgccgattgt tttgttaagc gccctgggca    600
ctggcatcct ggcgggattg tgaacggca tactggtagc gatcctcaaa attcagccgt    660 tgttgccac cctgatcctg atggtcgccg gcgcggcgt ggcgcaactg atcacctccg    720
gacagatcgt cacgtttaac tcgccggatc tctcatggtt tggcagtgga tcgctgttgt    780

```
tcctgccaac gccggtcatt atcgcggtgc tgacgcttat cctgttctgg ctgttgaccc     840
gcaaaacggc gctggggatg tttatcgaag ccgttggtat caacattcgg gcggcaaaaa     900
atgccgggt aaacacgcgg atcatcgtca tgcttaccta cgtgttgagc gggctgtgtg      960
cggcgattgc gggcattatc gtggcggcgg atattcgcgg tgccgatgcc aataacgccg    1020
ggttatggct ggagctggac gccattctcg cggtggttat tggcggcgga tcgctgatgg    1080
gcggacgttt taacctactg ctttcggtgg tgggggcgct gattattcag gggatgaaca    1140
ccggaatttt gctttcgggc tttccgccag agatgaacca ggttgtaaaa gcggtggtgg    1200
ttctttgcgt gctgattgtc cagtcgcaac gctttatcag tctgattaaa ggagtacgta    1260
gccgtgataa aacgtaattt gccactgatg atcaccatcg gcgtctttgt gttgggttat    1320
ctttactgcc tgacccagtt tcccggtttt gcttccacaa gagtgatctg caatatcctg    1380
accgataacg cctttcttgg gatcattgcc gttggcatga cctttgtgat cctctccggt    1440
gggatcgatc tctccgtcgg ttcggtgatc gcctttactg gcgtgtttct ggcaaaagtg    1500
attggcgatt tcggcctctc gccgctactg gcgtttccgc tagtgctggt gatgggctgt    1560
gccttcggcg catttatggg cttttgatc gacgccctga agatcccggc atttatcatt    1620
accctggcgg ggatgttctt tttgcgcggt gtcagctatc tcgtttcgga agagtcgatt    1680
ccgataaacc atcccattta tgacacgctc tcaagccttg cgtggaaaat ccctggcggc    1740
ggtcgcttaa gtgcgatggg actgctgatg ttggcggtgg tggttatcgg tattttcctc    1800
gcgcatcgta cccgttttgg taatcaggta tacgccattg gcggcaacgc aacgtcggcg    1860
aacctgatgg ggatttccac tcgcagcacc actattcgca tttatatgct ctccaccgga    1920
ctggcaacgc tggcggggat tgtcttctcg atttataccc aggccggata tgcgctggcg    1980
ggcgtaggtg tggaactgga tgctatcgcc tcagtggtaa ttggcggtac gcttctgagc    2040
ggtggcgttg aacggtatt agggacgctt tttggcgtgg cgattcaggg gctaatacag    2100
acttatatca actttgatgg cacgctgagc tcatggtgga cgaaaatcgc catcggtatt    2160
ttgttattta tttttatagc attacagcgt ggattaacgg tgctgtggga aatcgtcag    2220
agttcgcctg tgacaagagt caacattgcg cagcgataaa aacgcctctc cgtgtgagaa    2280
ggcgcaggag attacgcgtc cgggaactca cggataaagc gttcgacatc ttcaaccata    2340
tggtcgttgc cgacaaagaa cgaacggcgc tggtgcaaag tttccgggat gatatccaga    2400
atacgctctt tgccatcgct cgctttaccg cccgcttgtt ccgccaggaa tgccatcggg    2460
ttgcactcat acagcaaacg cagtttgccg tccgggtggc tggcggtgct gggtagaga     2520
taaataccgc ctttcagcag gttacggtgg aaatccgcga ccagtgaacc gatataacgt    2580
gaggtataag ggcggttggt ggacttatct tcttcctggc agaatttaat gtacttcttc    2640
accccgttcg gaaacttaat gtagtttcct tcgttgatgg agtaggtttt gcctttctcc    2700
gggaagcgca tccgttcctg gcacagacag aaaacgccca gcgaaggatc gtaagtaaag    2760
gcgtgaacac cgcatccgt ggtgtaaacc agcatggtag aggagccgta taccacgtaa     2820
cctgccgcaa cctgtttgtt accaggctgg aggaaatctt cttccgttac cggcgtgcca    2880
acaggcgtaa cgcggcggta gatggagaaa atggtaccga cagagacgtt aacatcgatg    2940
ttggacgagc catccagtgg gtccatcagc accacgtatt ttgcgtgttc acagccttca    3000
aagacgacaa tctcatcttc ttcttcagag gcaatgcccg caacgatatc gcgtgctttc    3060
agtgcggctt tcagtttttc attagcgaac aagtcgagtt tctgctgaac ctcgccctgc    3120
acgttctcag caccgctggc acccaggata tcaaccagtc ctgctttgtt gatatcgcga    3180
```

```
tggataatct tggcgcccag ttttattgcc gacagcaaag cagtgagctc accggtagca    3240
tgagaaaact cgtgctgctt ttcgacaata aattcaccta acgttttcat aaaactttcc    3300
ctgcaatgtt tatggagtaa agcgaccgca acaatcttaa caaataatct caatgttgcg    3360
ctcaggtgaa tcgcgccagc aaattgcgga ttatcctgaa atgcgtttct cacttgcccg    3420
acatatgcgt aaaatgagcg gcagattaaa aaaggatagt gacgtatgcg cattcatatt    3480
ttaggaattt gtggcacgtt tatgggcggt ctggcgatgc tggcgcgcca gttaggccat    3540
gaagtaacgg gttcggacgc caatgtgtat ccgccgatga gcaccttact tgagaagcaa    3600
ggcattgaac tgattcaggg ttacgatgcc agccagctcg atccgcagcc ggatctggtg    3660
attattggca acgccatgac ccgtggaaat ccgtgtgtgg aagcggtact ggaaaaaaac    3720
atcccttata tgtcaggtcc acagtggctg cacgattttg tgctgcgcga ccgctgggtg    3780
ctggccgttg ccggtacaca tgcaaaaacc accaccgcgg gaatggcaac ctggattctg    3840
gaacagtgcg gttacaaacc gggatttgtg atcggcggtg tgccggggaa ctttgaggtt    3900
tcggcgcgtc tgggcgaaag cgacttcttt gttatcgaag cggatgagta tgactgcgcc    3960
ttcttcgaca aacgctctaa atttgtccat tactgcccac gtacgctgat cctcaacaac    4020
cttgagttcg atcacgccga tatctttgac gacctgaaag cgatccagaa acagttccac    4080
catctggtgc gtatcgttcc ggggcagggc cgtattatct ggccagaaaa cgacatcaac    4140
ctgaaacaga ccatggcgat gggctgctgg agcgagcagg agctggtggg tgagcagggg    4200
cactggcagg cgaaaaagct gaccaccgat gcttccgaat gggaagtttt gctggatggc    4260
gaaaaagtgg gcgaagtgaa atggtcgctg gtaggcgaac ataatatgca caatggcctg    4320
atggcgattg cggcggctcg ccatgttggt gtagcgccgg cagatgccgc taacgcgctg    4380
ggttcgttta ttaacgctcg tcgccgtctg gagttgcgtg gtgaagcgaa tggcgtcacg    4440
gtatatgacg attttgccca tcacccaacg gcgattctgg caacgcttgc ggcgctgcgt    4500
ggcaaagttg gcggtacggc gcgcattatt gccg                                4534
```

<210> SEQ ID NO 88
<211> LENGTH: 341
<212> TYPE: PRT
<213> ORGANISM: Escherichia coli

<400> SEQUENCE: 88

Met Met Pro Gln Ser Leu Pro Asp Thr Thr Pro Pro Lys Arg Arg Phe
1               5                   10                  15

Arg Trp Pro Thr Gly Met Pro Gln Leu Ala Ala Leu Leu Val Leu
            20                  25                  30

Leu Val Asp Ser Leu Val Ala Pro His Phe Trp Gln Val Val Leu Gln
        35                  40                  45

Asp Gly Arg Leu Phe Gly Ser Pro Ile Asp Ile Leu Asn Arg Ala Ala
    50                  55                  60

Pro Val Ala Leu Leu Ala Ile Gly Met Thr Leu Val Ile Ala Thr Gly
65                  70                  75                  80

Gly Ile Asp Leu Ser Val Gly Ala Val Met Ala Ile Ala Gly Ala Thr
                85                  90                  95

Thr Ala Ala Met Thr Val Ala Gly Phe Ser Leu Pro Ile Val Leu Leu
            100                 105                 110

Ser Ala Leu Gly Thr Gly Ile Leu Ala Gly Leu Trp Asn Gly Ile Leu
        115                 120                 125

```
Val Ala Ile Leu Lys Ile Gln Pro Phe Val Ala Thr Leu Ile Leu Met
130                 135                 140

Val Ala Gly Arg Gly Val Ala Gln Leu Ile Thr Ser Gly Gln Ile Val
145                 150                 155                 160

Thr Phe Asn Ser Pro Asp Leu Ser Trp Phe Gly Ser Gly Ser Leu Leu
                165                 170                 175

Phe Leu Pro Thr Pro Val Ile Ile Ala Val Leu Thr Leu Ile Leu Phe
            180                 185                 190

Trp Leu Leu Thr Arg Lys Thr Ala Leu Gly Met Phe Ile Glu Ala Val
        195                 200                 205

Gly Ile Asn Ile Arg Ala Ala Lys Asn Ala Gly Val Asn Thr Arg Ile
210                 215                 220

Ile Val Met Leu Thr Tyr Val Leu Ser Gly Leu Cys Ala Ala Ile Ala
225                 230                 235                 240

Gly Ile Ile Val Ala Ala Asp Ile Arg Gly Ala Asp Ala Asn Asn Ala
                245                 250                 255

Gly Leu Trp Leu Glu Leu Asp Ala Ile Leu Ala Val Val Ile Gly Gly
            260                 265                 270

Gly Ser Leu Met Gly Gly Arg Phe Asn Leu Leu Ser Val Val Gly
        275                 280                 285

Ala Leu Ile Ile Gln Gly Met Asn Thr Gly Ile Leu Leu Ser Gly Phe
290                 295                 300

Pro Pro Glu Met Asn Gln Val Val Lys Ala Val Val Leu Cys Val
305                 310                 315                 320

Leu Ile Val Gln Ser Gln Arg Phe Ile Ser Leu Ile Lys Gly Val Arg
                325                 330                 335

Ser Arg Asp Lys Thr
            340

<210> SEQ ID NO 89
<211> LENGTH: 331
<212> TYPE: PRT
<213> ORGANISM: Escherichia coli

<400> SEQUENCE: 89

Met Ile Lys Arg Asn Leu Pro Leu Met Ile Thr Ile Gly Val Phe Val
1               5                   10                  15

Leu Gly Tyr Leu Tyr Cys Leu Thr Gln Phe Pro Gly Phe Ala Ser Thr
                20                  25                  30

Arg Val Ile Cys Asn Ile Leu Thr Asp Asn Ala Phe Leu Gly Ile Ile
            35                  40                  45

Ala Val Gly Met Thr Phe Val Ile Leu Ser Gly Gly Ile Asp Leu Ser
        50                  55                  60

Val Gly Ser Val Ile Ala Phe Thr Gly Val Phe Leu Ala Lys Val Ile
65                  70                  75                  80

Gly Asp Phe Gly Leu Ser Pro Leu Leu Ala Phe Pro Leu Val Leu Val
                85                  90                  95

Met Gly Cys Ala Phe Gly Ala Phe Met Gly Leu Leu Ile Asp Ala Leu
            100                 105                 110

Lys Ile Pro Ala Phe Ile Ile Thr Leu Ala Gly Met Phe Phe Leu Arg
        115                 120                 125

Gly Val Ser Tyr Leu Val Ser Glu Glu Ser Ile Pro Ile Asn His Pro
130                 135                 140

Ile Tyr Asp Thr Leu Ser Ser Leu Ala Trp Lys Ile Pro Gly Gly Gly
145                 150                 155                 160
```

```
Arg Leu Ser Ala Met Gly Leu Met Leu Ala Val Val Ile Gly
                165                 170                 175

Ile Phe Leu Ala His Arg Thr Arg Phe Gly Asn Gln Val Tyr Ala Ile
                180                 185                 190

Gly Gly Asn Ala Thr Ser Ala Asn Leu Met Gly Ile Ser Thr Arg Ser
                195                 200                 205

Thr Thr Ile Arg Ile Tyr Met Leu Ser Thr Gly Leu Ala Thr Leu Ala
    210                 215                 220

Gly Ile Val Phe Ser Ile Tyr Thr Gln Ala Gly Tyr Ala Leu Ala Gly
225                 230                 235                 240

Val Gly Val Glu Leu Asp Ala Ile Ala Ser Val Ile Gly Gly Thr
                245                 250                 255

Leu Leu Ser Gly Gly Val Gly Thr Val Leu Gly Thr Leu Phe Gly Val
                260                 265                 270

Ala Ile Gln Gly Leu Ile Gln Thr Tyr Ile Asn Phe Asp Gly Thr Leu
                275                 280                 285

Ser Ser Trp Trp Thr Lys Ile Ala Ile Gly Ile Leu Leu Phe Ile Phe
                290                 295                 300

Ile Ala Leu Gln Arg Gly Leu Thr Val Leu Trp Glu Asn Arg Gln Ser
305                 310                 315                 320

Ser Pro Val Thr Arg Val Asn Ile Ala Gln Arg
                325                 330

<210> SEQ ID NO 90
<211> LENGTH: 332
<212> TYPE: PRT
<213> ORGANISM: Escherichia coli

<400> SEQUENCE: 90

Met Lys Thr Leu Gly Glu Phe Ile Val Glu Lys Gln His Glu Phe Ser
1               5                   10                  15

His Ala Thr Gly Glu Leu Thr Ala Leu Leu Ser Ala Ile Lys Leu Gly
                20                  25                  30

Ala Lys Ile Ile His Arg Asp Ile Asn Lys Ala Gly Leu Val Asp Ile
            35                  40                  45

Leu Gly Ala Ser Gly Ala Glu Asn Val Gln Gly Glu Val Gln Gln Lys
    50                  55                  60

Leu Asp Leu Phe Ala Asn Glu Lys Leu Lys Ala Ala Leu Lys Ala Arg
65                  70                  75                  80

Asp Ile Val Ala Gly Ile Ala Ser Glu Glu Asp Glu Ile Val Val
                85                  90                  95

Phe Glu Gly Cys Glu His Ala Lys Tyr Val Val Leu Met Asp Pro Leu
                100                 105                 110

Asp Gly Ser Ser Asn Ile Asp Val Asn Val Ser Val Gly Thr Ile Phe
            115                 120                 125

Ser Ile Tyr Arg Arg Val Thr Pro Val Gly Thr Pro Val Thr Glu Glu
    130                 135                 140

Asp Phe Leu Gln Pro Gly Asn Lys Gln Val Ala Ala Gly Tyr Val Val
145                 150                 155                 160

Tyr Gly Ser Ser Thr Met Leu Val Tyr Thr Thr Gly Cys Gly Val His
                165                 170                 175

Ala Phe Thr Tyr Asp Pro Ser Leu Gly Val Phe Cys Leu Cys Gln Glu
                180                 185                 190

Arg Met Arg Phe Pro Glu Lys Gly Lys Thr Tyr Ser Ile Asn Glu Gly
```

```
                195                 200                 205
Asn Tyr Ile Lys Phe Pro Asn Gly Val Lys Lys Tyr Ile Lys Phe Cys
    210                 215                 220

Gln Glu Glu Asp Lys Ser Thr Asn Arg Pro Tyr Thr Ser Arg Tyr Ile
225                 230                 235                 240

Gly Ser Leu Val Ala Asp Phe His Arg Asn Leu Leu Lys Gly Gly Ile
                245                 250                 255

Tyr Leu Tyr Pro Ser Thr Ala Ser His Pro Asp Gly Lys Leu Arg Leu
            260                 265                 270

Leu Tyr Glu Cys Asn Pro Met Ala Phe Leu Ala Glu Gln Ala Gly Gly
        275                 280                 285

Lys Ala Ser Asp Gly Lys Glu Arg Ile Leu Asp Ile Ile Pro Glu Thr
    290                 295                 300

Leu His Gln Arg Arg Ser Phe Phe Val Gly Asn Asp His Met Val Glu
305                 310                 315                 320

Asp Val Glu Arg Phe Ile Arg Glu Phe Pro Asp Ala
                325                 330
```

<210> SEQ ID NO 91
<211> LENGTH: 4537
<212> TYPE: DNA
<213> ORGANISM: Escherichia coli

<400> SEQUENCE: 91

```
catcatcctg aagtagcgcg atatactcac tgactatctg catcagaata taaaaagcaa      60
tgttttttaac ctataaaaat ggcgctgtat ttgcgccatt tttatcattc aatgcattat    120
ctgtttgagc ctaaagggat ctcagggtct ggctcatgag taattctgtt tcgtaaatct    180
ctgcgaataa tttcaataga ccagaaccag actaaatgtc caaaaatttc agaaacattc    240
tcataccacg ggagatcaaa cagaggtggc gtcagtccca tgagagggaa tgaaatcata    300
tgaacaaaaa gttgggctaa agcacctgcc agtaagccct gccagagttt aattttttgga   360
aatacttcag cgaccacaca ataaccgaca gcaaacacta tcgaaaagat aatgtgcgta    420
acaccaaccc agttaaagac atgcccggca aggtataaa cagccgcatt gggatctgtc     480
agccccaacc agtctcgaag aaaaatatac ggtggattga aaaattacg cgagcaatca     540
atttggcctg cagccctgat taatgattcc gggccacacg ctgcattaaa catatccacc    600
gggctacgtg gcggcaatgg aacttcagcc ccccacttca cgaatgcgga acaacgcca     660
gcaatcagcc caatgaatgc agcaagacca taacgtctgc ggttcggtgg agttgttca     720
aatatattca tatctacccct gcttgtacca ttatgttata cacctcttca ggagtattca   780
taaaacaagg caaatgtaaa gaactgtatt gttttgtata acaagatagt ttcctaatcg    840
ccaatgaata taagctccat catttctccc tatttttata ttagaagtga cagagatttg    900
cagggtgatg tagagctgaa atcacaggt ttccttattg gttttgcat cgtacaacta      960
aagcaataaa ccagctccca tcatcatcaa catcccggcg aacatgaatt tattagccgg   1020
gctcatagct gcattcgcgt tttaagaata atcctcctgc tgtcgccgac tatgcttaac    1080
gtttaaaaaa gcatcagcac tctcgcaacg cactcttatt ttccccttta gaataccgga   1140
ggcctggtat gagcaaccaa ggcgaatacc ccgaagataa tcgggttggg aagcacgagc    1200
cgcacgattt aagtttgacc cgtcgcgatc tgattaaagt gagcgccgca acagcggcga   1260
ccgccgtggt ttatcctcat tctacgctgg cggcaagcgt tccggcagct accccgcgc    1320
cagagataat gcccctgaca ctgaaggtga acggcaaaac cgagcagctt gaggtggata   1380
```

```
cccgaaccac gctactggac actttgcgtg aaaatctgca tttgatcggt accaagaaag    1440
gttgcgatca cggacagtgc ggagcctgta ccgtgctggt caatggtcgc aggcttaatg    1500
cctgcctgac gcttgcagtc atgcatcagg gggccgagat caccaccatt gaaggcctgg    1560
gttcgccaga taatcttcac cccatgcagg cggcctttat caagcatgat ggcttccagt    1620
gcggctactg cacctccggg caaatttgct catcagtagc ggtgctaaaa gagattcagg    1680
acggcattcc cagtcacgtc acggtcgatt tggtttccgc tccagaaaca actgccgatg    1740
agatccgtga acgtatgagc ggcaacatct gtcgctgtgg tgcatacgct aacatccttg    1800
ccgccattga agatgctgcg ggggagataa aatcatgaag gcgtttaccct atgaacgagt    1860
gaatacccca gccgaggcgg cacttagcgc tcagcgcgta cccggcgcaa aatttatcgc    1920
gggcgggacc aatctgctgg acctgatgaa gctggaaatt gaaacgccca cccaccttat    1980
cgatgtgaac ggcctcgggc tcgataagat tgaagtgacc gacgcgggtg ggctgcgcat    2040
cggcgcactg gtacggaaca ccgacctggc ggctcacgag cgcgtgcgtc gtgattacgc    2100
ggtactctcc cgcgccctgc tcgctggcgc gtctggtcag ttacgtaatc aggcaaccac    2160
cgcaggtaat ctgctccagc gcacgcgctg cccctatttt tacgacacca atcagccctg    2220
caataagcgc ctgcccggga gcggctgcgc ggcgcttgaa ggctttagcc gtcagcacgc    2280
ggtggtaggc gtaagcgaag cctgcattgc cacccatccg agcgatatgg cggtcgcaat    2340
gcggttgctg gatgcggtgg tggaaaccat cacgccggag ggaaagactc gcagtatcac    2400
actggctgat ttttatcacc ctccgggaaa aacgccgcac attgaaaccg ccctgcttcc    2460
cggtgagctt atcgttgcgg tgacgttacc tccaccgctc ggcggaaaac atatctaccg    2520
taaggtgcgc gatcgcgcct cctacgcctt tgccctggta tcggtcgcgg cgattattca    2580
gcctgacggc agcgggcgcg tcgcgctggg cggagtagca cataagccct ggcgcattga    2640
ggctgcggat gctcagctat cccaggggc gcaggccgta tatgacacgc tgttcgccag    2700
cgcccatccc accgctgaaa acacctttaa actcctgttg gcgaagcgaa cgcttgcctc    2760
cgtactggct gaagcgaggg cacaggcatg aaatttgata atccgcagg ggaaaaaccg    2820
atcgatcagc tgaaggttgt cggtcgtccc catgaccgca tcgacggacc gctgaaaact    2880
accggcacgg cacgctacgc ctacgaatgg catgaagaag cccccaacgc gcctatggc    2940
tatatcgtcg gttccgccat tgccaaagga cgcctcaccg cccttgatac ggacgccgcg    3000
caaaaagcgc cgggcgtact ggctgtcatt accgccagta acgccggggc actcggcaaa    3060
ggcgacaaaa acaccgccag gctgttaggc ggccccacta ttgagcacta tcatcaggcc    3120
attgcgctgg tagtggccga gaccttcgaa caggcgcgag cggcggcctc gctggtgcag    3180
gcacactatc gccgtaataa aggagcttac tccctggcgg acgaaaaaca ggccgtcaat    3240
cagccgccgg aagacacgcc cgacaaaaac gtcggtgact ttgacggggc tttcacctcc    3300
gctgcggtga agattgatgc tacctacacg accccgacc agagccatat ggcgatggag    3360
ccgcatgcct cgatggccgt ctgggatgga aataagctta ccctctggac ctcaaatcag    3420
atgattgact ggtgccgcac cgatctggca aaaacgctga agttcccgt ggagaatgtg    3480
cgtattatct ccccgtatat cggcggaggg tttggcggca gctgttcct gagaagcgat    3540
gcgctgctgg cggccctcgc cgcccgagcg gtgaaacgtc cggttaaagt gatgctcccc    3600
cgcccctcta ttcccaataa caccacgcac cgccccgcca cccttcagca cttgcgtatc    3660
ggtgccgacc agagcgggaa aatcaccgct atctcacatg aaagctggtc tggaaacctg    3720
```

```
cccggcggca cgccggaaac ggcggtacag caaagcgaat tactctacgc cggggcgaat    3780
cgtcataccg gcctgcggct cgccacgctt gatttgccgg aagggaacgc catgcgtgcg    3840
cccggcgaag ccccggtct gatggcgctc gaaatcgcga tcgacgaact ggcggaaaaa    3900 gcggcatcg atcccgtcga gtttcgcatc ctgaatgaca ctcaggttga ccccgccgac    3960
ccgacgcgct gcttctctcg ccgtcagctt atcgagtgct gcgcaccgg agcggataaa    4020 tttggctgga agcagcgcaa cgccaccccc ggacaggtgc gcgacgggga gtggctagtc    4080
ggccacggtg ttgcggcggg ctttcgcaat aatctgctgg aaaaatcggg tgctcgggtt    4140
cacctcgaac aaaacggcac cgttaccgta gaaacggaca tgaccgacat ggcaccggc    4200 agctacacca ttctggccca cggcagcg gaaatgcttg gcgtaccgct ggagcaggtt    4260
gcggttcacc tcggcgattc cagtttcccg gtttctgcgg gttctggtgg acaatggggc    4320 gcgaataccct ccacctccgg cgtttacgcc gcctgtatga agcttcgcga aatgattgcc    4380
tcggcagtcg ggtttgatcc tgagcagtcg cagtttgccg acggcaagat taccaacggt    4440
acccgaagcg ccacgctaca tgaagccacc gcaggcggca gactgacagc ggaagagagc    4500
attgaattcg gaacactgag caaagagtac cagcagt                              4537
```

<210> SEQ ID NO 92
<211> LENGTH: 204
<212> TYPE: PRT
<213> ORGANISM: Escherichia coli

<400> SEQUENCE: 92

```
Met Asn Ile Phe Glu Gln Thr Pro Pro Asn Arg Arg Tyr Gly Leu
1               5                   10                  15

Ala Ala Phe Ile Gly Leu Ile Ala Gly Val Val Ser Ala Phe Val Lys
                20                  25                  30

Trp Gly Ala Glu Val Pro Leu Pro Pro Arg Ser Pro Val Asp Met Phe
            35                  40                  45

Asn Ala Ala Cys Gly Pro Glu Ser Leu Ile Arg Ala Ala Gly Gln Ile
50                  55                  60

Asp Cys Ser Arg Asn Phe Leu Asn Pro Pro Tyr Ile Phe Leu Arg Asp
65                  70                  75                  80

Trp Leu Gly Leu Thr Asp Pro Asn Ala Ala Val Tyr Thr Phe Ala Gly
                85                  90                  95

His Val Phe Asn Trp Val Gly Val Thr His Ile Ile Phe Ser Ile Val
                100                 105                 110

Phe Ala Val Gly Tyr Cys Val Val Ala Glu Val Phe Pro Lys Ile Lys
            115                 120                 125

Leu Trp Gln Gly Leu Leu Ala Gly Ala Leu Ala Gln Leu Phe Val His
130                 135                 140

Met Ile Ser Phe Pro Leu Met Gly Leu Thr Pro Pro Leu Phe Asp Leu
145                 150                 155                 160

Pro Trp Tyr Glu Asn Val Ser Glu Ile Phe Gly His Leu Val Trp Phe
                165                 170                 175

Trp Ser Ile Glu Ile Ile Arg Arg Asp Leu Arg Asn Arg Ile Thr His
            180                 185                 190

Glu Pro Asp Pro Glu Ile Pro Leu Gly Ser Asn Arg
            195                 200
```

<210> SEQ ID NO 93
<211> LENGTH: 229
<212> TYPE: PRT

<213> ORGANISM: Escherichia coli

<400> SEQUENCE: 93

Met Ser Asn Gln Gly Glu Tyr Pro Glu Asp Asn Arg Val Gly Lys His
1               5                   10                  15

Glu Pro His Asp Leu Ser Leu Thr Arg Arg Asp Leu Ile Lys Val Ser
            20                  25                  30

Ala Ala Thr Ala Ala Thr Ala Val Val Tyr Pro His Ser Thr Leu Ala
        35                  40                  45

Ala Ser Val Pro Ala Ala Thr Pro Ala Pro Glu Ile Met Pro Leu Thr
    50                  55                  60

Leu Lys Val Asn Gly Lys Thr Glu Gln Leu Glu Val Asp Thr Arg Thr
65                  70                  75                  80

Thr Leu Leu Asp Thr Leu Arg Glu Asn Leu His Leu Ile Gly Thr Lys
                85                  90                  95

Lys Gly Cys Asp His Gly Gln Cys Gly Ala Cys Thr Val Leu Val Asn
            100                 105                 110

Gly Arg Arg Leu Asn Ala Cys Leu Thr Leu Ala Val Met His Gln Gly
        115                 120                 125

Ala Glu Ile Thr Thr Ile Glu Gly Leu Gly Ser Pro Asp Asn Leu His
    130                 135                 140

Pro Met Gln Ala Ala Phe Ile Lys His Asp Gly Phe Gln Cys Gly Tyr
145                 150                 155                 160

Cys Thr Ser Gly Gln Ile Cys Ser Ser Val Ala Val Leu Lys Glu Ile
                165                 170                 175

Gln Asp Gly Ile Pro Ser His Val Thr Val Asp Leu Val Ser Ala Pro
            180                 185                 190

Glu Thr Thr Ala Asp Glu Ile Arg Glu Arg Met Ser Gly Asn Ile Cys
        195                 200                 205

Arg Cys Gly Ala Tyr Ala Asn Ile Leu Ala Ala Ile Glu Asp Ala Ala
    210                 215                 220

Gly Glu Ile Lys Ser
225

<210> SEQ ID NO 94
<211> LENGTH: 318
<212> TYPE: PRT
<213> ORGANISM: Escherichia coli

<400> SEQUENCE: 94

Met Lys Ala Phe Thr Tyr Glu Arg Val Asn Thr Pro Ala Glu Ala Ala
1               5                   10                  15

Leu Ser Ala Gln Arg Val Pro Gly Ala Lys Phe Ile Ala Gly Gly Thr
            20                  25                  30

Asn Leu Leu Asp Leu Met Lys Leu Glu Ile Glu Thr Pro Thr His Leu
        35                  40                  45

Ile Asp Val Asn Gly Leu Gly Leu Asp Lys Ile Glu Val Thr Asp Ala
    50                  55                  60

Gly Gly Leu Arg Ile Gly Ala Leu Val Arg Asn Thr Asp Leu Ala Ala
65                  70                  75                  80

His Glu Arg Val Arg Arg Asp Tyr Ala Val Leu Ser Arg Ala Leu Leu
                85                  90                  95

Ala Gly Ala Ser Gly Gln Leu Arg Asn Gln Ala Thr Thr Ala Gly Asn
            100                 105                 110

Leu Leu Gln Arg Thr Arg Cys Pro Tyr Phe Tyr Asp Thr Asn Gln Pro

```
            115                 120                 125
Cys Asn Lys Arg Leu Pro Gly Ser Gly Cys Ala Ala Leu Glu Gly Phe
    130                 135                 140

Ser Arg Gln His Ala Val Val Gly Val Ser Glu Ala Cys Ile Ala Thr
145                 150                 155                 160

His Pro Ser Asp Met Ala Val Ala Met Arg Leu Leu Asp Ala Val Val
                165                 170                 175

Glu Thr Ile Thr Pro Glu Gly Lys Thr Arg Ser Ile Thr Leu Ala Asp
                180                 185                 190

Phe Tyr His Pro Pro Gly Lys Thr Pro His Ile Glu Thr Ala Leu Leu
                195                 200                 205

Pro Gly Glu Leu Ile Val Ala Val Thr Leu Pro Pro Leu Gly Gly
    210                 215                 220

Lys His Ile Tyr Arg Lys Val Arg Asp Arg Ala Ser Tyr Ala Phe Ala
225                 230                 235                 240

Leu Val Ser Val Ala Ala Ile Ile Gln Pro Asp Gly Ser Gly Arg Val
                245                 250                 255

Ala Leu Gly Gly Val Ala His Lys Pro Trp Arg Ile Glu Ala Ala Asp
                260                 265                 270

Ala Gln Leu Ser Gln Gly Ala Gln Ala Val Tyr Asp Thr Leu Phe Ala
    275                 280                 285

Ser Ala His Pro Thr Ala Glu Asn Thr Phe Lys Leu Leu Leu Ala Lys
    290                 295                 300

Arg Thr Leu Ala Ser Val Leu Ala Glu Ala Arg Ala Gln Ala
305                 310                 315

<210> SEQ ID NO 95
<211> LENGTH: 5291
<212> TYPE: DNA
<213> ORGANISM: Escherichia coli

<400> SEQUENCE: 95
acgctgttta ataccgcgtt ttacagcaat aaacaggtgg atgacttcct ggctcaggca      60
ctgaaaacta atgatccggc ggaaaagacc cgcttatata aggcggcgca ggatatcatc     120
tggcaagaat cgccgtggat cccgctggtg gtagaaaaac tggtgtcggc acacagtaaa     180
aacctgaccg ttttggat catgccagac accggcttca gctttgaaga cgcggatttg      240
caataagcaa cgcagggagt ggaatgctta attacgttat caaacgctta ctggggttga     300
ttccgacgct gtttatcgtc tcggtgctgg tgttttatt tgtccatatg ctgcccggcg      360
atccggcgcg attgattgcc gggcccgaag ctgatgcgca ggttatagaa ctggtgcgtc     420
agcagctggg gttggatcag ccgctgtatc accagttctg gcactatatc agcaatgctg     480
tgcaggggga ttttggcctg tcgatggtgt cgcgtcgtcc ggttgccgat gagattgcca     540
gccgctttat gccaacgctg tggctgacca taaccagtat ggtctgggcg gttatatttg     600
gtatggcggc gggaattatc gccgccgtct ggcgtaaccg ttggccggat cgattgagta     660
tgaccattgc ggtgtcgggg atctcgtttc ggcatttgc tctggggatg ctttttaattc     720 aggtattctc cgttgaactg ggctggctgc ctaccgtggg agcagacagt tggcagcact     780 acatttttacc ctccctgacg ctcggcgcgg cagtggccgc cgtgatggcg cgctttaccc     840
gcgcgtcgtt tgtcgatgtt ttaagcgaag attatatgcg taccgcgagg gcgaaggggg     900
tgagcgaaac ctgggttgtc ctcaaacacg ggctacgtaa cgcgatgatc ccggtagtga     960
ccatgatggg cttacagttt ggcttttttgc tcggtggttc catcgttgtg gagaaagttt    1020
```

```
tcaactggcc gggacttgga cgcttactcg ttgactccgt agaaatgcgt gattacccgg    1080
tgattcaggc ggaaattctg cttttctcgc tggaatttat tcttatcaac ttagtggtgg    1140
atgtgcttta cgccgccatt aacccggcta tcaggtacaa gtaaggatgc gactatttaa    1200
ctggcgacgt caggcggtgt taaacgccat gccactggtc aaacctgacc aggtacgtac    1260
accgtggcat gaattctggc gacgatttcg ccgtcagcat atggcgatga ccgccgcatt    1320
attcgttatt ttattgattg tggtggccat ttttgcacgc tggatcgctc cctatgacgc    1380
cgaaaattat tttgattatg acaatctgaa taacggacct tctttgcagc actggtttgg    1440
cgtcgattca ctggggcgtg acattttcag ccgtgtcctg gttggtgcgc aaatctcgct    1500
ggcggcgggc gtgtttgccg tgtttatcgg tgcggcgatc gggacgttgc tgggcttgct    1560
cgctggatat tatgaaggct ggtgggatcg gctgatcatg cgcatttgcg atgtgctgtt    1620
tgccttcccg ggtatttac tggcgatcgc tgttgttgcg gtgttgggaa gcggcattgc    1680
taacgtgatt attgcagtcg ccattttttc catccccgcg tttgcccgcc tggtgcgcgg    1740
caacacgctg gtgttgaaac agcaaacctt tattgagtca gcacgcagta ttggtgccag    1800
cgatatgacc gttttgttgc gtcatatcct gcctgggacc gtctcttcta tcgtggtgtt    1860
tttcaccatg cgcattggta cctcgattat ctctgccgcc agcctctcat ttctcggcct    1920
cggtgcgcag ccgccgacac cagagtgggg agcaatgctc aatgaggctc gagcggatat    1980
ggttatcgcg ccgcatgtcg ctgttttttcc ggccctggct attttttctga ccgtactggc    2040 gttcaatttg ttgggcgatg gtttacgcga tgcgctggat ccgaaaatta aaggatagtt    2100
acgtttgaat attgcttgaa agggtaatca cctcacagga aattattgcc ctaagcaagt    2160
gttgtaactt tctgctgatt ttgtagaatc gggtaatttg gttaaaaagc cgcagcaagg    2220
gacaattttt gcagcggcac agcgttcaga tagttatttt gttaaatgta ttaacatgct    2280
gagtttatac gaaagataaa agataaggct gataattttta ttttattgg cagcactgtc    2340 atttattggt cttttttttca tcattaacta tcaactggta tcggagcgcg cggtaaaacg    2400
tgccgatagc cgcttgaac ttattcagaa aaacgttggc tatttcttta aagatattga    2460
acgttcggcc ctgacattaa aggactcact gtatttatta aaaaatacag aggagattca    2520
acgcgccgtg attcttaaaa tggaaatgat gccatttttta gactcggtgg gactggtact    2580
tgatgataat aaatattatc ttttttcgcg gagggcgaat gataaaatcg ttgtttatca    2640
tcaggaacaa gtaaatggac cgcttgtcga cgagtcaggg cgggttattt ttgccgattt    2700
taacccatcg aaacgaccgt ggtcggtggc ttcagatgac tctaacaaca gctggaatcc    2760
ggcatacaat tgctttgatc gtccgggtaa aaaatgtatc tctttttacgc tacacatcaa    2820 cggcaaagat cacgatttgt tagcggtgga taaaattcat gtcgatttaa actggcgata    2880
tctgaacgag tatcttgatc aaatcagcgc taatgatgaa gttctatttt tgaaacaagg    2940
ccatgagatc attgccaaga atcaactcgc tcgtgaaaaa ctgattattt ataatagcga    3000
aggtaattat aatattattg attctgtcga tactgaacat atcgaaaaaa catcagcggt    3060
gccaaacaac gcattattcg aaatctattt ttattatcct ggcggtaatt tattgaacgc    3120
atcagataaa ctttttttatc tgccgtttgc gttcattatt atcgtattgc tggtggttta    3180
tttaatgacc actcgtgtgt tccgtcggca attttctgaa atgacagagc tggttaatac    3240
gctggcgttt ttgcctgact caacggatca aatcgaggct ctgaaaattc gtgaaggcga    3300
tgcgaaagag attatcagca tcaaaaattc gatcgcggaa atgaaagatg ccgaaattga    3360
```

```
acggtcaaat aaattgctct cactgatctc ttacgatcag gaaagtggtt ttattaaaaa    3420
tatggcgatt attgagtcta acaataatca gtatctggct gtggggatca tcaaactgtg    3480
tggtctggaa gccgtggaag cggtgtttgg tgttgatgag cgcaataaaa tcgtcaggaa    3540
attgtgtcag cgaattgccg agaaatatgc gcaatgctgc gatatcgtga cattcaatgc    3600
cgatctctat ttacttctgt gtcgggaaaa tgtacagaca tttacccgta aaatagcgat    3660
ggtaaacgat tttgacagca gctttggcta ccgcaatctg cgcatccata gtctgccat    3720 ttgtgaacct ttgcaggggg aaaacgcctg gagttacgca gaaaaactga actggcgat    3780 ttccagtatc cgtgaccata tgttctcaga gtttatttc tgtgatgacg cgaaactcaa    3840
cgaaatagaa gagaatatct ggattgcgcg taatattcgc catgcaatgg aaattggcga    3900
actattcctc gtctatcaac cgatcgttga tattaacacc cgcgccattc tgggcgcgga    3960
ggcgttgtgc cgttgggtgt ctgcggagcg ggggatcatt tcaccgctga agttcattac    4020
cattgctgaa gatatcgggt ttatcaatga gctgggttat cagattatta aaacggcaat    4080
gggtgaattc agacattta gtcagcgtgc gtcgctgaag gatgatttct tactgcatat    4140
taatgtttcg ccctggcagt taaacgaacc acactttcat gagcgtttta ccaccatcat    4200
gaaagaaaat ggcctgaagg cgaacagcct ctgtgttgag atcactgaaa ccgtgatcga    4260
gcgaattaat gaacattttt atctcaatat tgaacaactg cgtaaacaag ggtacggat    4320 atcgattgat gactttggca ccggtttgtc aaacctgaaa cgttttatg aaattaatcc    4380 agacagcata aaggtggact cgcaattcac cggcgatatt ttcggtactg cgggaaaaat    4440
tgtgcgcatt attttcgacc tggcacgcta taaccggatc ccggtgattg cggaaggcgt    4500
agagagcgaa gacgttgcgc gcgaattaat caaattagga tgtgttcagg ctcagggta    4560 tctgtaccag aaacccatgc cattctccgc ctgggataaa agtggaaaat tagtaaaaga    4620
gtagtttacg tatgtccaga atcaataagt tcgtacttac agtcagtctg ctgatttta    4680 tcatgattc agcagttgcc tgcgggatct acactcaaat ggtaaaggaa cgggtgtata    4740
gcctgaaaca gtccgttatt gatactgctt tgcggtggc aaatattgct gaatatcggc    4800
gtagcgtggc aattgatctt atcaacacgc taaatcccac ggaggaacag ctgttggttg    4860
gtttgcgcac agcttacgcc gactcggttt cccctctta tttgtacgat gtcggtcctt    4920
atctgatttc cagtgacgaa tgtattcagg taaggagtt cgagaaaaat tatttgtgcag    4980 atattatgca ggttgtgaag tatcgacatg tcaaaaatac agggtttatc tcttttgacg    5040
gtaaaacctt cgtctattac ctctatccgg taactcacaa tcgtagtctg atattttgc    5100 ttggtctgga gcgttttct ttactgtcaa atcgctggc gatggacagc gagaacctga    5160
tgttctctct atttaagaac ggtaaaccgg tgaccggtga tgaatataat gctaaaaacg    5220
ccatcttcac cgtttcggaa gcgatggagc acttcgccta tttgccgacc ggattgtatg    5280
tatttgcgta t                                                        5291
```

<210> SEQ ID NO 96
<211> LENGTH: 306
<212> TYPE: PRT
<213> ORGANISM: Escherichia coli

<400> SEQUENCE: 96

Met Leu Asn Tyr Val Ile Lys Arg Leu Leu Gly Leu Ile Pro Thr Leu
1               5                   10                  15

Phe Ile Val Ser Val Leu Val Phe Leu Phe Val His Met Leu Pro Gly
            20                  25                  30

Asp Pro Ala Arg Leu Ile Ala Gly Pro Glu Ala Asp Ala Gln Val Ile
                35                  40                  45

Glu Leu Val Arg Gln Gln Leu Gly Leu Asp Gln Pro Leu Tyr His Gln
 50                  55                  60

Phe Trp His Tyr Ile Ser Asn Ala Val Gln Gly Asp Phe Gly Leu Ser
 65                  70                  75                  80

Met Val Ser Arg Arg Pro Val Ala Asp Glu Ile Ala Ser Arg Phe Met
                85                  90                  95

Pro Thr Leu Trp Leu Thr Ile Thr Ser Met Val Trp Ala Val Ile Phe
                100                 105                 110

Gly Met Ala Ala Gly Ile Ile Ala Ala Val Trp Arg Asn Arg Trp Pro
                115                 120                 125

Asp Arg Leu Ser Met Thr Ile Ala Val Ser Gly Ile Ser Phe Pro Ala
                130                 135                 140

Phe Ala Leu Gly Met Leu Leu Ile Gln Val Phe Ser Val Glu Leu Gly
145                 150                 155                 160

Trp Leu Pro Thr Val Gly Ala Asp Ser Trp Gln His Tyr Ile Leu Pro
                165                 170                 175

Ser Leu Thr Leu Gly Ala Ala Val Ala Ala Val Met Ala Arg Phe Thr
                180                 185                 190

Arg Ala Ser Phe Val Asp Val Leu Ser Glu Asp Tyr Met Arg Thr Ala
                195                 200                 205

Arg Ala Lys Gly Val Ser Glu Thr Trp Val Val Leu Lys His Gly Leu
                210                 215                 220

Arg Asn Ala Met Ile Pro Val Val Thr Met Met Gly Leu Gln Phe Gly
225                 230                 235                 240

Phe Leu Leu Gly Gly Ser Ile Val Val Glu Lys Val Phe Asn Trp Pro
                245                 250                 255

Gly Leu Gly Arg Leu Leu Val Asp Ser Val Glu Met Arg Asp Tyr Pro
                260                 265                 270

Val Ile Gln Ala Glu Ile Leu Leu Phe Ser Leu Glu Phe Ile Leu Ile
                275                 280                 285

Asn Leu Val Val Asp Val Leu Tyr Ala Ala Ile Asn Pro Ala Ile Arg
                290                 295                 300

Tyr Lys
305

<210> SEQ ID NO 97
<211> LENGTH: 303
<212> TYPE: PRT
<213> ORGANISM: Escherichia coli

<400> SEQUENCE: 97

Met Arg Leu Phe Asn Trp Arg Arg Gln Ala Val Leu Asn Ala Met Pro
1                5                  10                  15

Leu Val Lys Pro Asp Gln Val Arg Thr Pro Trp His Glu Phe Trp Arg
                20                  25                  30

Arg Phe Arg Arg Gln His Met Ala Met Thr Ala Ala Leu Phe Val Ile
                35                  40                  45

Leu Leu Ile Val Val Ala Ile Phe Ala Arg Trp Ile Ala Pro Tyr Asp
 50                  55                  60

Ala Glu Asn Tyr Phe Asp Tyr Asp Asn Leu Asn Asn Gly Pro Ser Leu
 65                  70                  75                  80

Gln His Trp Phe Gly Val Asp Ser Leu Gly Arg Asp Ile Phe Ser Arg

```
                    85                  90                  95
Val Leu Val Gly Ala Gln Ile Ser Leu Ala Ala Gly Val Phe Ala Val
                100                 105                 110

Phe Ile Gly Ala Ala Ile Gly Thr Leu Leu Gly Leu Leu Ala Gly Tyr
                115                 120                 125

Tyr Glu Gly Trp Trp Asp Arg Leu Ile Met Arg Ile Cys Asp Val Leu
            130                 135                 140

Phe Ala Phe Pro Gly Ile Leu Leu Ala Ile Ala Val Val Ala Val Leu
145                 150                 155                 160

Gly Ser Gly Ile Ala Asn Val Ile Ile Ala Val Ala Ile Phe Ser Ile
                165                 170                 175

Pro Ala Phe Ala Arg Leu Val Arg Gly Asn Thr Leu Val Leu Lys Gln
                180                 185                 190

Gln Thr Phe Ile Glu Ser Ala Arg Ser Ile Gly Ala Ser Asp Met Thr
            195                 200                 205

Val Leu Leu Arg His Ile Leu Pro Gly Thr Val Ser Ser Ile Val Val
        210                 215                 220

Phe Phe Thr Met Arg Ile Gly Thr Ser Ile Ile Ser Ala Ala Ser Leu
225                 230                 235                 240

Ser Phe Leu Gly Leu Gly Ala Gln Pro Pro Thr Pro Glu Trp Gly Ala
                245                 250                 255

Met Leu Asn Glu Ala Arg Ala Asp Met Val Ile Ala Pro His Val Ala
            260                 265                 270

Val Phe Pro Ala Leu Ala Ile Phe Leu Thr Val Leu Ala Phe Asn Leu
        275                 280                 285

Leu Gly Asp Gly Leu Arg Asp Ala Leu Asp Pro Lys Ile Lys Gly
        290                 295                 300

<210> SEQ ID NO 98
<211> LENGTH: 782
<212> TYPE: PRT
<213> ORGANISM: Escherichia coli

<400> SEQUENCE: 98

Met Leu Ser Leu Tyr Glu Lys Ile Lys Ile Arg Leu Ile Ile Leu Phe
1               5                   10                  15

Leu Leu Ala Ala Leu Ser Phe Ile Gly Leu Phe Phe Ile Ile Asn Tyr
            20                  25                  30

Gln Leu Val Ser Glu Arg Ala Val Lys Arg Ala Asp Ser Arg Phe Glu
        35                  40                  45

Leu Ile Gln Lys Asn Val Gly Tyr Phe Phe Lys Asp Ile Glu Arg Ser
    50                  55                  60

Ala Leu Thr Leu Lys Asp Ser Leu Tyr Leu Leu Lys Asn Thr Glu Glu
65                  70                  75                  80

Ile Gln Arg Ala Val Ile Leu Lys Met Glu Met Pro Phe Leu Asp
                85                  90                  95

Ser Val Gly Leu Val Leu Asp Asp Asn Lys Tyr Tyr Leu Phe Ser Arg
                100                 105                 110

Arg Ala Asn Asp Lys Ile Val Val Tyr His Gln Glu Gln Val Asn Gly
            115                 120                 125

Pro Leu Val Asp Glu Ser Gly Arg Val Ile Phe Ala Asp Phe Asn Pro
        130                 135                 140

Ser Lys Arg Pro Trp Ser Val Ala Ser Asp Asp Ser Asn Asn Ser Trp
145                 150                 155                 160
```

-continued

```
Asn Pro Ala Tyr Asn Cys Phe Asp Arg Pro Gly Lys Lys Cys Ile Ser
                165                 170                 175

Phe Thr Leu His Ile Asn Gly Lys Asp His Asp Leu Leu Ala Val Asp
            180                 185                 190

Lys Ile His Val Asp Leu Asn Trp Arg Tyr Leu Asn Glu Tyr Leu Asp
        195                 200                 205

Gln Ile Ser Ala Asn Asp Glu Val Leu Phe Leu Lys Gln Gly His Glu
    210                 215                 220

Ile Ile Ala Lys Asn Gln Leu Ala Arg Glu Lys Leu Ile Ile Tyr Asn
225                 230                 235                 240

Ser Glu Gly Asn Tyr Asn Ile Ile Asp Ser Val Asp Thr Glu His Ile
                245                 250                 255

Glu Lys Thr Ser Ala Val Pro Asn Asn Ala Leu Phe Glu Ile Tyr Phe
            260                 265                 270

Tyr Tyr Pro Gly Gly Asn Leu Leu Asn Ala Ser Asp Lys Leu Phe Tyr
        275                 280                 285

Leu Pro Phe Ala Phe Ile Ile Val Leu Leu Val Val Tyr Leu Met
    290                 295                 300

Thr Thr Arg Val Phe Arg Arg Gln Phe Ser Glu Met Thr Glu Leu Val
305                 310                 315                 320

Asn Thr Leu Ala Phe Leu Pro Asp Ser Thr Asp Gln Ile Glu Ala Leu
                325                 330                 335

Lys Ile Arg Glu Gly Asp Ala Lys Glu Ile Ile Ser Ile Lys Asn Ser
            340                 345                 350

Ile Ala Glu Met Lys Asp Ala Glu Ile Glu Arg Ser Asn Lys Leu Leu
        355                 360                 365

Ser Leu Ile Ser Tyr Asp Gln Glu Ser Gly Phe Ile Lys Asn Met Ala
    370                 375                 380

Ile Ile Glu Ser Asn Asn Asn Gln Tyr Leu Ala Val Gly Ile Ile Lys
385                 390                 395                 400

Leu Cys Gly Leu Glu Ala Val Glu Ala Val Phe Gly Val Asp Glu Arg
                405                 410                 415

Asn Lys Ile Val Arg Lys Leu Cys Gln Arg Ile Ala Glu Lys Tyr Ala
            420                 425                 430

Gln Cys Cys Asp Ile Val Thr Phe Asn Ala Asp Leu Tyr Leu Leu Leu
        435                 440                 445

Cys Arg Glu Asn Val Gln Thr Phe Thr Arg Lys Ile Ala Met Val Asn
    450                 455                 460

Asp Phe Asp Ser Ser Phe Gly Tyr Arg Asn Leu Arg Ile His Lys Ser
465                 470                 475                 480

Ala Ile Cys Glu Pro Leu Gln Gly Glu Asn Ala Trp Ser Tyr Ala Glu
                485                 490                 495

Lys Leu Lys Leu Ala Ile Ser Ser Ile Arg Asp His Met Phe Ser Glu
            500                 505                 510

Phe Ile Phe Cys Asp Asp Ala Lys Leu Asn Glu Ile Glu Glu Asn Ile
        515                 520                 525

Trp Ile Ala Arg Asn Ile Arg His Ala Met Glu Ile Gly Glu Leu Phe
    530                 535                 540

Leu Val Tyr Gln Pro Ile Val Asp Ile Asn Thr Arg Ala Ile Leu Gly
545                 550                 555                 560

Ala Glu Ala Leu Cys Arg Trp Val Ser Ala Glu Arg Gly Ile Ile Ser
                565                 570                 575

Pro Leu Lys Phe Ile Thr Ile Ala Glu Asp Ile Gly Phe Ile Asn Glu
```

```
            580                 585                 590
Leu Gly Tyr Gln Ile Ile Lys Thr Ala Met Gly Glu Phe Arg His Phe
            595                 600                 605

Ser Gln Arg Ala Ser Leu Lys Asp Asp Phe Leu Leu His Ile Asn Val
            610                 615                 620

Ser Pro Trp Gln Leu Asn Glu Pro His Phe His Glu Arg Phe Thr Thr
625                 630                 635                 640

Ile Met Lys Glu Asn Gly Leu Lys Ala Asn Ser Leu Cys Val Glu Ile
                645                 650                 655

Thr Glu Thr Val Ile Glu Arg Ile Asn Glu His Phe Tyr Leu Asn Ile
            660                 665                 670

Glu Gln Leu Arg Lys Gln Gly Val Arg Ile Ser Ile Asp Asp Phe Gly
            675                 680                 685

Thr Gly Leu Ser Asn Leu Lys Arg Phe Tyr Glu Ile Asn Pro Asp Ser
            690                 695                 700

Ile Lys Val Asp Ser Gln Phe Thr Gly Asp Ile Phe Gly Thr Ala Gly
705                 710                 715                 720

Lys Ile Val Arg Ile Ile Phe Asp Leu Ala Arg Tyr Asn Arg Ile Pro
                725                 730                 735

Val Ile Ala Glu Gly Val Glu Ser Glu Asp Val Ala Arg Glu Leu Ile
            740                 745                 750

Lys Leu Gly Cys Val Gln Ala Gln Gly Tyr Leu Tyr Gln Lys Pro Met
            755                 760                 765

Pro Phe Ser Ala Trp Asp Lys Ser Gly Lys Leu Val Lys Glu
770                 775                 780

<210> SEQ ID NO 99
<211> LENGTH: 5945
<212> TYPE: DNA
<213> ORGANISM: Escherichia coli

<400> SEQUENCE: 99
gcagcaattt ttgacgctcc cggacgagcg ctggtatcgc accggcgatc tcggctgcta      60
ctggccagat ggcacaatcg agttcctcgg tcgtcgcgac aagcaggtca agtcggagg      120 atatcgcatc gagctgggcg aaatcgaaag cgcgctcagc cagctggcgg gggtgaaaca      180
agcaaccgtt ctggcgatcg gcgaaaaaga aaaaacgctg gcggcatacg ttgttcctca      240
gggcgaggct ttttgcgtta ccgatcatcg gaacccggca ctgccgcagg cgtggcacac      300
gcttgcggga acgttgccct gttgcgccat ctcgccagag atctccgcag aacaggtagc      360
cgatttcctt cagcatcgcc tgctaaaact gaagccgggt cacaccgctg cgccgatcc      420 tctcccctg atgaactcac tcgctatcca gccgcgctgg caggccgtgg tggaacgctg      480
gttagcattt ctggtgacac aacggcgact gaagcccgct gctgaaggtt atcaggtctg      540
cgctggtgaa gaacgcgagg atgagcaccc gcacttcagc ggacatgatt taacgttatc      600
gcaaattctt cgcggtgccc gtaacgaact gtcgttactg aacgacgcgc agtggtcgcc      660
ggaaagcctg gcctttaacc atccggccag cgccccgtat attcaggaac tggcgacaat      720
ttgccaacag cttgcacagc gcttacagcg cccggtacgc ctgcttgagg tgggaacccg      780
cactggccgc gccgcagaat cgctgttagc acagctcaac gccggacaga ttgagtatgt      840
cgggcttgag cagagccagg agatgctgct gagcgcccgg cagaggctcg ccccctggcc      900
tggcgcccgt ctgtccctct ggaatgcaga cacgctggcg acgcacgctc actcggcgga      960
cattatctgg cttaataacg ccctgcatcg tctgctgccg gaagatcccg ggctccttgc      1020
```

```
gacattacaa cagcttgccg ttcccggcgc gctgctctac gtgatggagt ttcgccagtt   1080
aacgccgtcc gccctactca gcacgctcct gttaaccaat gggcagccgg aggccttgct   1140
gcataacagc gccgactggg cggcattatt tagcgcggcc ggcttcaact gtcagcatgg   1200
cgatgaggtc gcggggttac aacgcttcct cgtacaatgt cctgacaggc aggtgcgccg   1260
cgatccccgt caacttcagg ccgccctcgc cgggcgtctg ccggggtgga tggtgccgca   1320
acggatcgta ttcctcgacg ccttaccgct gatggctaac gggaaaattg actaccaggc   1380
gctgaagcgt cgtcataccc ctgaagcgga aaacccggcc gaagcggatt taccccaggg   1440
cgacattgaa aaacaggttg ccgccctctg gcagcaactc ttatcaactg caatgtcac    1500
cagagaaacc gacttcttcc agcaaggcgg cgatagcctg ctggcgaccc gtctgaccgg   1560
gcaacttcat caggcaggtt atgaagcgca attaagcgac ctgtttaatc atccccggct   1620
ggcggatttt gccgccacgc tgcggaaaac cgacgtcccg gtcgaacaac cattcgtcca   1680
ctcccctgaa gatcgctacc agcccttttgc gcttaccgac gtgcagcagg cttacctggt   1740
ggggcgtcag ccgggctttg ccctgggcgg cgtcggctca catttctttg ttgaatttga   1800
aattgccgat ctggacctca cccggctgga cacggtctgg aaccgattaa tcgcccgcca   1860
cgatatgctg cgcgccatcg tgcgtgatgg acagcaacag gtgctcgaac agacgccccc   1920
ttgggtgata cccgcacaca ccctccatac gcctgaagag gcgttgcggg tgcgcgaaaa   1980
actggcgcat caggtactca accccgaagt gtggccggta ttcgatctcc aggtcggata   2040
cgtggacggg atgcctgccc gcctgtggct gtgtctggat aacctgttgc ttgacggtct   2100
gagcatgcag atcctgctgg cggagctgga gcacggctac cgctacccgc aacagctgct   2160
tccgccgctg cccgtcacct tcagggatta tctgcaacaa ccctcgctac agtcgcccaa   2220
tccagattct ctggcatggt ggcaggcgca gcttgatgat attcctccgg cgcctgcgtt   2280
gccgctgcgc tgcttgcctc aggaggttga aacaccgcgc ttcgcccgcc tgaacgcgc    2340
actggacagc acgcgctggc atcggctgaa aaaacgggcg gctgacgccc atctcacccc   2400
gtcggccgta ctgttgtcgg tgtggtcaac ggttctctct gcatggagtg cacagcctga   2460
gttcacgctt aaccttacgc ttttcgacag gcgaccgctg caccccgcaaa tcaaccagat   2520
tctgggcgat ttcacctcgc tgatgctgct gagctggcat cccggcgaaa gctggctgca   2580
cagcgcgcag tcactacagc agcggctgag ccagaacctc aaccaccgcg atgtgtcagc   2640
catccgcgtg atgcgtcaac tggtgcaacg gcaaaacgtg cctgccgttc cgatgcccgt   2700
cgtctttacc agcgcactgg gctttgagca ggataacttc ctcgcccggc gtaatctgct   2760
caaaccggtc tggggcatct cccagacgcc gcaggtctgg ctcgatcacc agatttatga   2820
atccgaaggc gaactgcgct ttaactggga ttttgtcgcc gcgctgtttc ctgccgggca   2880
ggtggagcgc cagtttgaac agtattgcgc attgctaaac cgaatggccg aggatgaaag   2940
cggctggcaa ctgccgctcg ccgcgctggt gcctcccgtt aaacacgcag gcaatgcgc    3000
agagcgctca ccgcgcgtat gccctgagca ctctcagcca cacattgcgg cggacgagag   3060
caccgtcagc ctgatttgcg acgccttccg cgaggtggtt ggcgagtctg tcacgcccgc   3120
agaaaacttc tttgaggcgg gcgcaacgtc gctgaatctg gtgcaactgc acgttttgtt   3180
acaacgtcac gaattttcca ccctgacgtt gcttgacctc ttcacccacc cttctcctgc   3240
tgccctggcc gattatctgg ccggcgtcgc cacggtggag aaaacaaaac gacctcgccc   3300
tgttcgccgt cgtcagcggc ggatatagcg cgaagcaaac tgattttccc cggaacgcca   3360
```

```
tcgcgaacgc atggcgttcc attgactttg tgaatcttag gaaacgggac cgattatgga   3420
taacttgcgc ttctcttctg cgccgacagc agattccatt gatgcatcga tcgctcaaca   3480
ctacccggac tgcgaacctg tcgcggttat cggctacgcc tgccattttc ctgaatcgcc   3540
ggatggcgaa acgttctggc aaaatctgct ggaaggtcgt gaatgcagcc gacgctttac   3600
gcgcgaagag cttctggccg tcggtctgga tgccgccatc attgacgatc ctcattatgt   3660
caatatcggt acggtgttag acaacgccga ctgcttcgac gccaccctgt ttggctattc   3720
gcgacaggaa gcggagtcga tggacccgca gcagcgcctg tttttgcagg cggtctggca   3780
tgcgctggaa catgccggtt atgccccggg cgccgtcccc cataagaccg gcgttttcgc   3840
ctcttcccgg atgagtacct accccggtcg cgaagcattg aacgtgacag aagtcgcgca   3900
ggtaaaaggt ctgcaatctc tgatgggcaa tgataaagac tatattgcca cccgcgccgc   3960
gtacaaactc aacctgcacg gcccggcgtt atcggtacag accgcctgct ccagctcgct   4020
ggttgccgtg catcttgcct gtgaaagcct gcgcgcaggc gaatccgata tggcggtggc   4080
cggcggcgtg gcgctctctt tcccccagca ggcaggctac cgctaccagc ccggaatgat   4140
tttctctcct gatggtcact gtcgtccctt tgacgcctcg gctgagggca cctgggccgg   4200
taacggtctc ggctgcgtgg tgctgcgtcg cctgagagac gcgctgctgt caggcgatcc   4260
gattatctcg gtgatcctct ccagcgcggt caacaacgac ggcaacagaa aggtcggcta   4320
taccgcccct tccgtcgcag ggcaacaggc agtcatcgaa gaggcgttaa tgctggcggc   4380
catcgacgac aggcaggtag gttacattga aacccacggc accggcacac gctgggcgaa   4440
cgcgattgaa attgaagcgt tacgcaacgt ctatgcgcct cgcccgcagg atcagcgctg   4500
tgcgctcggt tccgtgaaaa gtaacatggg ccatctggat accgcggcgg gcattgccgg   4560
actgctgaaa accgttctgg cagtcagtcg cgggcaaatt cctcccttac tgaattttca   4620
cacccccaac ccggcgctga acttgaaga gagccccttt accataccgg tgtcggcaca   4680
ggcatggcag gacgaaatgc gctatgcggg cgtctcctcc tttggtattg gcggcaccaa   4740
ctgccatatg atcgtcgcct cgctgcccga cgcgctcaac gcgcgcctcc caatacgga   4800
tagcggcaga aaaagtaccg cgctgctgct cagcgccgcc agcgacagcg cgttgcggcg   4860
gctggcgacg gattatgccg gggcgctgag agagaatgcg gatgccagct ctctggcctt   4920
cacagccctg cacgcgcgcc gtctcgatct ccccttccgc ctggcggcgc cattaaaccg   4980
tgaaaccgcc gaggcgctca cgcgctgggc cggtgagaaa tcggggcgc tggtttacag   5040
cggccacggc gccagcggca agcaggtgtg gctgtttacc ggccagggct cgcactggcg   5100
cactatgggt caaacgatgt accatcactc aacggcgttt gccgacacgc tggatcgctg   5160
ttttccgcc tgtagcgaaa tgctcacgcc gtcactgcgc gaagcgatgt ttaaccccga   5220
ttcggcgcag ctgacaata tggcctgggc gcagccggcg attgtcgcgt ttgaaatcgc   5280
gatggcggcg cactggcgtg ctgaaggact gaagccagac ttcgccattg ggcattccgt   5340
cggtgaattt gccgctgccg ttgtctgcgg acactatacg attgaacagg tcatgccact   5400
ggtttgtcgg cgcggcgcgc taatgcagca gtgcgcaagc ggcgcgatgg tggcggtatt   5460
tgcagacgaa gacacgctga tgccgctggc tcgccagttt gagctggatc tcgccgccaa   5520
caacggtacg caacatacgg tattttccgg gccggaagcc cgtctcgcgg tattttgcgc   5580
cacgctctcg cagcatgaca ttaactatcg tcgcctgagc gtaaccggtg cggcgcactc   5640
cgctttactg gagccgatac tcgatcggtt ccaggacgcc tgcgcgggac tgcacgcgga   5700
gccggggcaa ataccgatta tttccacgct caccgccgac gtcattgatg agtcaacgct   5760
```

```
caaccaggcg gattactggc gccgacacat gcgccagccg gtgcgtttta tccagagtat    5820
tcaggtggcg catcagctcg gcgcccgcgt ttttctggag atggggcccg atgcccagtt    5880
ggttgcttgc gggcagcgcg aataccgcga taacgcatac tggatagcca gcgcccggcg    5940
taaca                                                                5945
```

<210> SEQ ID NO 100
<211> LENGTH: 6108
<212> TYPE: DNA
<213> ORGANISM: Escherichia coli

<400> SEQUENCE: 100

```
atgatttctg gcgcaccatc tcaggattcg ctgttaccgg acaaccgcca cgcggctgat      60
taccaacaat tacgcgagcg gctcatacag gaactgaatt taacgccgca gcagttacat     120
gaagagagca acctgatcca ggccggcctg gattccataa gattgatgag atggttacac     180
tggtttcgta aaaatggcta ccgccttacc cttcgcgagc tgtatgccgc ccccacgctg     240
gcggcatgga accagttaat gctcagccgg tcgccggaga acgcggaaga agaaacgccg     300
cccgacgaat catcctggcc gaacatgacc gaaagtaccc ccttcccatt gacgccagta     360
cagcacgcct acctgacggg ccgcatgccg gggcagacgc ttggcggcgt gggttgccac     420
ctgtatcagg agtttgaagg ccattgtctg acggcgtcgc agctggagca ggccatcacg     480
accttgctgc aacgccaccc aacgctgcat atcgcctttc gccccgacgg gcagcaggtc     540
tggctaccgc aaccttactg gaacggcgtc accgttcatg atttacgcca taacgacgct     600
gaaagccgcc aggcctatct ggacgcactg cgccagcgcc tgagccaccg tcttttacgc     660
gtggaaatcg gcgaaacgtt tgattttcag ctgacgctct gccggacaa tcgccaccgc     720 ctccatgtca atattgacct gctgattatg gatgcctcca gctttacgct tttcttcgat     780
gagcttaacg ccctgctggc cggagaatcg ctgccggcta tcgacacccg ctatgatttc     840
cgctcgtatt tgctgcacca gcagaagatc aatcaaccac tgagagacga cgcgcgcgct     900
tactggctgg cgaaagcatc gacgcttccc cccgcgcccg tcttgccgct ggcctgcgaa     960
cccgccacgc tacgtgaagt ccgtaatacc cgacgccgca tgattgtccc ggcaacacgc    1020
tggcacgcct ttagcaaccg ggccggcgag tatgcgtga cgccgacaat ggcactggcg    1080
acctgttttt ctgccgtgct ggctcgctgg ggcggcctga cgcgtctgct gcttaacatc    1140
accttattcg accgccagcc gctgcacccg gcggttggcg cgatgcttgc cgacttcacc    1200
aatattcttc tgctggatac cgcctgcgat ggcgataccg tcagcaacct ggcgcgtaaa    1260
aaccagctca cgtttacgga ggactgggag catcgccact ggtccggcgt cgaattactc    1320
cgtgaactca aacgccagca cgctacccc cacgcgcgcc cggtggtatt taccagcaat    1380
ctggggcgtt ccctctacag cagccgcgca gaatcgccgt tgggcgagcc ggaatggggc    1440
atctcgcaaa cgccgcaggt ctggatagat catctggcgt tcgagcatca cggcgaggtc    1500
tggctacaat gggacagcaa cgacgcgctg ttccctccgg cgttagtcga acattgttc     1560 gacgcctact gccagttgat taaccaactc tgcgatgacg aaagcgcctg caaaagccg    1620 ttcgcagata tgatgcccgc cagccagcgc gcgatacgcg aacgggtcaa cgccaccggc    1680
gcccccattc ccgaaggctt gctgcatgaa ggcattttcc gtatcgctct gcaacagccg    1740
caggcgctgg cggtaacgga catgcgttat cagtggaatt atcatgagct gacagactat    1800
gcccgccgtt gcgcgggcag gttaatcgag tgcggggttc agcccggcga taatgtggct    1860
```

```
atcacgatgt cgaaaggcgc aggacaactt gttgcggttc tggccgtcct gctggccggg    1920
gcggtttacg ttccggtttc gctggatcag cctgccgcac ggcgcgagaa aatctacgct    1980
gacgccagcg tccggctggt gctcatttgt cagcacgacg ccagcgccgg gtcagacgat    2040
attcccgtcc ttgcctggca gcaggccatt gaggcggagc cgatcgccaa cccggtagta    2100
cgcgccccca cgcaaccggc ctacattatc tacacctccg gctctaccgg tacgccgaaa    2160
ggggtagtca tttctcaccg gggagcgctt aacacctgtt gcgatatcaa tacccgctat    2220
caggttggcc cgcatgacag ggtgctggcc ctctccgccc tacattttga tttatcggtt    2280
tacgacattt ttggcgtact gcgcgcgggc ggcgcgctgg tgatggtgat ggaaaatcaa    2340
cggcgcgatc ctcacgcatg gtgtgagctg atccagcgcc atcaggtcac gctctggaac    2400
agcgtcccgg cgctgttcga tatgctgctg acctggtgtg aaggtttcgc cgacgccacg    2460
ccggaaaacc tgcgcgcagt gatgctttcc ggcgactgga tcgggcttga cctccccgcc    2520
cgttatcggg ccttccggcc acaaggacaa tttatcgcga tgggcggcgc caccgaggcg    2580
tctatctggt ctaacgcctg cgaaattcac gacgtccccg cccactggcg ctccatccct    2640
tacggttttc cgctaaccaa ccaacgctac cgggtggtgg atgaacaggg ccggactgc    2700
cctgactggg tgccgggtga attatggatt ggcggcattg gggtcgcgga aggctatttc    2760
aacgatcccc tgcgtagcga gcagcaattt ttgacgctcc cggacgagcg ctggtatcgc    2820
accggcgatc tcggctgcta ctggccagat ggcacaatcg agttcctcgg tcgtcgcgac    2880
aagcaggtca agtcggagg atatcgcatc gagctgggcg aaatcgaaag cgcgctcagc    2940
cagctggcgg gggtgaaaca agcaaccgtt ctggcgatcg gcgaaaaaga aaaacgctg    3000
gcggcatacg ttgttcctca gggcgaggct ttttgcgtta ccgatcatcg gaacccggca    3060
ctgccgcagg cgtggcacac gcttgcggga acgttgccct gttgcgccat ctcgccagag    3120
atctccgcag aacaggtagc cgatttcctt cagcatcgcc tgctaaaact gaagccgggt    3180
cacaccgctg gcgccgatcc tctcccctg atgaactcac tcgctatcca gccgcgctgg    3240
caggccgtgg tggaacgctg gttagcattt ctggtgacac aacggcgact gaagcccgct    3300
gctgaaggtt atcaggtctg cgctggtgaa gaacgcgagg atgagcaccc gcacttcagc    3360
ggacatgatt taacgttatc gcaaattctt cgcggtgccc gtaacgaact gtcgttactg    3420
aacgacgcgc agtggtcgcc ggaaaagcctg gcctttaacc atccggccag cgccccgtat    3480
attcaggaac tggcgacaat tgccaacag cttgcacagc gcttacagcg cccggtacgc    3540
ctgcttgagg tgggaacccg cactggccgc gccgcagaat cgctgttagc acagctcaac    3600
gccggacaga ttgagtatgt cgggcttgag cagagccagg agatgctgct gagcgcccgg    3660
cagaggctcg ccccctggcc tggcgcccgt ctgtccctct ggaatgcaga cacgctggcg    3720
acgcacgctc actcggcgga cattatctgg cttaataacg ccctgcatcg tctgctgccg    3780
gaagatcccg ggctccttgc gacattacaa cagcttgccg ttcccggcgc gctgctctac    3840
gtgatggagt ttcgccagtt aacgccgtcc gccctactca gcacgctcct gttaaccaat    3900
gggcagccgg aggccttgct gcataacagc gccgactggg cggcattatt tagcgcggcc    3960
ggcttcaact gtcagcatgg cgatgaggtc gcggggttac aacgcttcct cgtacaatgt    4020
cctgacaggc aggtgcgccg cgatccccgt caacttcagg ccgccctcgc cgggcgtctg    4080
ccggggtgga tggtgccgca acggatcgta ttcctcgacg ccttaccgct gatggctaac    4140
gggaaaattg actaccaggc gctgaagcgt cgtcataccc ctgaagcgga aaacccggcc    4200
gaagcggatt taccccaggg cgacattgaa aaacaggttg ccgccctctg gcagcaactc    4260
```

-continued

```
ttatcaactg gcaatgtcac cagagaaacc gacttcttcc agcaaggcgg cgatagcctg    4320
ctggcgaccc gtctgaccgg gcaacttcat caggcaggtt atgaagcgca attaagcgac    4380
ctgtttaatc atccccggct ggcggatttt gccgccacgc tgcggaaaac cgacgtcccg    4440
gtcgaacaac cattcgtcca ctcccctgaa gatcgctacc agcccttttgc gcttaccgac    4500 gtgcagcagg cttacctggt ggggcgtcag ccgggctttg ccctgggcgg cgtcggctca    4560
catttctttg ttgaatttga aattgccgat ctggacctca cccggctgga gacggtctgg    4620
aaccgattaa tcgcccgcca cgatatgctg cgcgccatcg tgcgtgatgg acagcaacag    4680
gtgctcgaac agacgccccc ttgggtgata cccgcacaca ccctccatac gcctgaagag    4740
gcgttgcggg tgcgcgaaaa actggcgcat caggtactca accccgaagt gtggccggta    4800
ttcgatctcc aggtcggata cgtggacggg atgcctgccc gctgtgtggct gtgtctggat    4860 aacctgttgc ttgacggtct gagcatgcag atcctgctgg cggagctgga gcacggctac    4920 cgctaccccgc aacagctgct tccgccgctg cccgtcacct tcagggatta tctgcaacaa    4980
ccctcgctac agtcgcccaa tccagattct ctggcatggt ggcaggcgca gcttgatgat    5040
attcctccgg cgcctgcgtt gccgctgcgc tgcttgcctc aggaggttga aacaccgcgc    5100
ttcgcccgcc tgaacggcgc actggacagc acgcgctggc atcggctgaa aaaacgggcg    5160
gctgacgccc atctcacccc gtcggccgta ctgttgtcgg tgtggtcaac ggttctctct    5220
gcatggagtg cacagcctga gttcacgctt aaccttacgc ttttcgacag cgaccgctg    5280 cacccgcaaa tcaaccagat tctgggcgat ttcacctcgc tgatgctgct gagctggcat    5340
cccggcgaaa gctggctgca cagcgcgcag tcactacagc agcggctgag ccagaacctc    5400
aaccaccgcg atgtgtcagc catccgctgt atgcgtcaac tggtgcaacg gcaaaacgtg    5460
cctgccgttc cgatgcccgt cgtctttacc agcgcactgg gctttgagca ggataacttc    5520
ctcgcccggc gtaatctgct caaaccggtc tggggcatct cccagacgcc gcaggtctgg    5580
ctcgatcacc agatttatga atccgaaggc gaactgcgct ttaactggga ttttgtcgcc    5640
gcgctgtttc ctgccgggca ggtggagcgc cagtttgaac agtattgcgc attgctaaac    5700
cgaatggccg aggatgaaag cggctggcaa ctgccgctcg ccgcgctggt gcctcccgtt    5760
aaacacgcag ggcaatgcgc agagcgctca ccgcgcgtat gccctgagca ctctcagcca    5820
cacattgcgc cggacgagag caccgtcagc ctgatttgcg acgccttccg cgaggtggtt    5880
ggcgagtctg tcacgcccgc agaaaacttc tttgaggcgg cgcaacgtc gctgaatctg    5940 gtgcaactgc acgtttttgtt acaacgtcac gaatttttcca ccctgacgtt gcttgacctc    6000
ttcacccacc cttctcctgc tgccctggcc gattatctgg ccggcgtcgc cacggtggag    6060
aaaacaaaac gacctcgccc tgttcgccgt cgtcagcggc ggatatag                 6108
```

<210> SEQ ID NO 101
<211> LENGTH: 2035
<212> TYPE: PRT
<213> ORGANISM: Escherichia coli

<400> SEQUENCE: 101

Met Ile Ser Gly Ala Pro Ser Gln Asp Ser Leu Leu Pro Asp Asn Arg
1               5                   10                  15

His Ala Ala Asp Tyr Gln Gln Leu Arg Glu Arg Leu Ile Gln Glu Leu
            20                  25                  30

Asn Leu Thr Pro Gln Gln Leu His Glu Glu Ser Asn Leu Ile Gln Ala
        35                  40                  45

Gly Leu Asp Ser Ile Arg Leu Met Arg Trp Leu His Trp Phe Arg Lys
    50                  55                  60

Asn Gly Tyr Arg Leu Thr Leu Arg Glu Leu Tyr Ala Ala Pro Thr Leu
65                  70                  75                  80

Ala Ala Trp Asn Gln Leu Met Leu Ser Arg Ser Pro Glu Asn Ala Glu
                85                  90                  95

Glu Glu Thr Pro Pro Asp Glu Ser Ser Trp Pro Asn Met Thr Glu Ser
            100                 105                 110

Thr Pro Phe Pro Leu Thr Pro Val Gln His Ala Tyr Leu Thr Gly Arg
        115                 120                 125

Met Pro Gly Gln Thr Leu Gly Gly Val Gly Cys His Leu Tyr Gln Glu
    130                 135                 140

Phe Glu Gly His Cys Leu Thr Ala Ser Gln Leu Glu Gln Ala Ile Thr
145                 150                 155                 160

Thr Leu Leu Gln Arg His Pro Thr Leu His Ile Ala Phe Arg Pro Asp
                165                 170                 175

Gly Gln Gln Val Trp Leu Pro Gln Pro Tyr Trp Asn Gly Val Thr Val
            180                 185                 190

His Asp Leu Arg His Asn Asp Ala Glu Ser Arg Gln Ala Tyr Leu Asp
        195                 200                 205

Ala Leu Arg Gln Arg Leu Ser His Arg Leu Leu Arg Val Glu Ile Gly
    210                 215                 220

Glu Thr Phe Asp Phe Gln Leu Thr Leu Leu Pro Asp Asn Arg His Arg
225                 230                 235                 240

Leu His Val Asn Ile Asp Leu Leu Ile Met Asp Ala Ser Ser Phe Thr
                245                 250                 255

Leu Phe Phe Asp Glu Leu Asn Ala Leu Leu Ala Gly Glu Ser Leu Pro
            260                 265                 270

Ala Ile Asp Thr Arg Tyr Asp Phe Arg Ser Tyr Leu Leu His Gln Gln
        275                 280                 285

Lys Ile Asn Gln Pro Leu Arg Asp Asp Ala Arg Ala Tyr Trp Leu Ala
    290                 295                 300

Lys Ala Ser Thr Leu Pro Pro Ala Pro Val Leu Pro Leu Ala Cys Glu
305                 310                 315                 320

Pro Ala Thr Leu Arg Glu Val Arg Asn Thr Arg Arg Met Ile Val
                325                 330                 335

Pro Ala Thr Arg Trp His Ala Phe Ser Asn Arg Ala Gly Glu Tyr Gly
            340                 345                 350

Val Thr Pro Thr Met Ala Leu Ala Thr Cys Phe Ser Ala Val Leu Ala
        355                 360                 365

Arg Trp Gly Gly Leu Thr Arg Leu Leu Leu Asn Ile Thr Leu Phe Asp
    370                 375                 380

Arg Gln Pro Leu His Pro Ala Val Gly Ala Met Leu Ala Asp Phe Thr
385                 390                 395                 400

Asn Ile Leu Leu Leu Asp Thr Ala Cys Asp Gly Asp Thr Val Ser Asn
                405                 410                 415

Leu Ala Arg Lys Asn Gln Leu Thr Phe Thr Glu Asp Trp Glu His Arg
            420                 425                 430

His Trp Ser Gly Val Glu Leu Leu Arg Glu Leu Lys Arg Gln Gln Arg
        435                 440                 445

Tyr Pro His Gly Ala Pro Val Val Phe Thr Ser Asn Leu Gly Arg Ser
    450                 455                 460

-continued

Leu Tyr Ser Ser Arg Ala Glu Ser Pro Leu Gly Glu Pro Glu Trp Gly
465                 470                 475                 480

Ile Ser Gln Thr Pro Gln Val Trp Ile Asp His Leu Ala Phe Glu His
            485                 490                 495

His Gly Glu Val Trp Leu Gln Trp Asp Ser Asn Asp Ala Leu Phe Pro
        500                 505                 510

Pro Ala Leu Val Glu Thr Leu Phe Asp Ala Tyr Cys Gln Leu Ile Asn
    515                 520                 525

Gln Leu Cys Asp Asp Glu Ser Ala Trp Gln Lys Pro Phe Ala Asp Met
530                 535                 540

Met Pro Ala Ser Gln Arg Ala Ile Arg Glu Arg Val Asn Ala Thr Gly
545                 550                 555                 560

Ala Pro Ile Pro Glu Gly Leu Leu His Glu Gly Ile Phe Arg Ile Ala
            565                 570                 575

Leu Gln Gln Pro Gln Ala Leu Ala Val Thr Asp Met Arg Tyr Gln Trp
        580                 585                 590

Asn Tyr His Glu Leu Thr Asp Tyr Ala Arg Arg Cys Ala Gly Arg Leu
    595                 600                 605

Ile Glu Cys Gly Val Gln Pro Gly Asp Asn Val Ala Ile Thr Met Ser
610                 615                 620

Lys Gly Ala Gly Gln Leu Val Ala Val Leu Ala Val Leu Leu Ala Gly
625                 630                 635                 640

Ala Val Tyr Val Pro Val Ser Leu Asp Gln Pro Ala Ala Arg Arg Glu
            645                 650                 655

Lys Ile Tyr Ala Asp Ala Ser Val Arg Leu Val Leu Ile Cys Gln His
        660                 665                 670

Asp Ala Ser Ala Gly Ser Asp Asp Ile Pro Val Leu Ala Trp Gln Gln
    675                 680                 685

Ala Ile Glu Ala Glu Pro Ile Ala Asn Pro Val Val Arg Ala Pro Thr
690                 695                 700

Gln Pro Ala Tyr Ile Ile Tyr Thr Ser Gly Ser Thr Gly Thr Pro Lys
705                 710                 715                 720

Gly Val Val Ile Ser His Arg Gly Ala Leu Asn Thr Cys Cys Asp Ile
            725                 730                 735

Asn Thr Arg Tyr Gln Val Gly Pro His Asp Arg Val Leu Ala Leu Ser
        740                 745                 750

Ala Leu His Phe Asp Leu Ser Val Tyr Asp Ile Phe Gly Val Leu Arg
    755                 760                 765

Ala Gly Gly Ala Leu Val Met Val Met Glu Asn Gln Arg Arg Asp Pro
770                 775                 780

His Ala Trp Cys Glu Leu Ile Gln Arg His Gln Val Thr Leu Trp Asn
785                 790                 795                 800

Ser Val Pro Ala Leu Phe Asp Met Leu Leu Thr Trp Cys Glu Gly Phe
            805                 810                 815

Ala Asp Ala Thr Pro Glu Asn Leu Arg Ala Val Met Leu Ser Gly Asp
        820                 825                 830

Trp Ile Gly Leu Asp Leu Pro Ala Arg Tyr Arg Ala Phe Arg Pro Gln
    835                 840                 845

Gly Gln Phe Ile Ala Met Gly Gly Ala Thr Glu Ala Ser Ile Trp Ser
850                 855                 860

Asn Ala Cys Glu Ile His Asp Val Pro Ala His Trp Arg Ser Ile Pro
865                 870                 875                 880

Tyr Gly Phe Pro Leu Thr Asn Gln Arg Tyr Arg Val Val Asp Glu Gln

```
                885             890             895
Gly Arg Asp Cys Pro Asp Trp Val Pro Gly Glu Leu Trp Ile Gly Gly
            900             905             910
Ile Gly Val Ala Glu Gly Tyr Phe Asn Asp Pro Leu Arg Ser Glu Gln
            915             920             925
Gln Phe Leu Thr Leu Pro Asp Glu Arg Trp Tyr Arg Thr Gly Asp Leu
    930             935             940
Gly Cys Tyr Trp Pro Asp Gly Thr Ile Glu Phe Leu Gly Arg Arg Asp
945             950             955             960
Lys Gln Val Lys Val Gly Gly Tyr Arg Ile Glu Leu Gly Glu Ile Glu
            965             970             975
Ser Ala Leu Ser Gln Leu Ala Gly Val Lys Gln Ala Thr Val Leu Ala
            980             985             990
Ile Gly Glu Lys Glu Lys Thr Leu Ala Ala Tyr Val Val Pro Gln Gly
            995             1000            1005
Glu Ala Phe Cys Val Thr Asp His Arg Asn Pro Ala Leu Pro Gln
        1010            1015            1020
Ala Trp His Thr Leu Ala Gly Thr Leu Pro Cys Cys Ala Ile Ser
        1025            1030            1035
Pro Glu Ile Ser Ala Glu Gln Val Ala Asp Phe Leu Gln His Arg
        1040            1045            1050
Leu Leu Lys Leu Lys Pro Gly His Thr Ala Gly Ala Asp Pro Leu
        1055            1060            1065
Pro Leu Met Asn Ser Leu Ala Ile Gln Pro Arg Trp Gln Ala Val
        1070            1075            1080
Val Glu Arg Trp Leu Ala Phe Leu Val Thr Gln Arg Arg Leu Lys
        1085            1090            1095
Pro Ala Ala Glu Gly Tyr Gln Val Cys Ala Gly Glu Glu Arg Glu
        1100            1105            1110
Asp Glu His Pro His Phe Ser Gly His Asp Leu Thr Leu Ser Gln
        1115            1120            1125
Ile Leu Arg Gly Ala Arg Asn Glu Leu Ser Leu Leu Asn Asp Ala
        1130            1135            1140
Gln Trp Ser Pro Glu Ser Leu Ala Phe Asn His Pro Ala Ser Ala
        1145            1150            1155
Pro Tyr Ile Gln Glu Leu Ala Thr Ile Cys Gln Gln Leu Ala Gln
        1160            1165            1170
Arg Leu Gln Arg Pro Val Arg Leu Leu Glu Val Gly Thr Arg Thr
        1175            1180            1185
Gly Arg Ala Ala Glu Ser Leu Leu Ala Gln Leu Asn Ala Gly Gln
        1190            1195            1200
Ile Glu Tyr Val Gly Leu Glu Gln Ser Gln Glu Met Leu Leu Ser
        1205            1210            1215
Ala Arg Gln Arg Leu Ala Pro Trp Pro Gly Ala Arg Leu Ser Leu
        1220            1225            1230
Trp Asn Ala Asp Thr Leu Ala Thr His Ala His Ser Ala Asp Ile
        1235            1240            1245
Ile Trp Leu Asn Asn Ala Leu His Arg Leu Leu Pro Glu Asp Pro
        1250            1255            1260
Gly Leu Leu Ala Thr Leu Gln Gln Leu Ala Val Pro Gly Ala Leu
        1265            1270            1275
Leu Tyr Val Met Glu Phe Arg Gln Leu Thr Pro Ser Ala Leu Leu
        1280            1285            1290
```

```
Ser Thr Leu Leu Leu Thr Asn Gly Gln Pro Glu Ala Leu Leu His
    1295             1300            1305

Asn Ser Ala Asp Trp Ala Ala Leu Phe Ser Ala Ala Gly Phe Asn
    1310             1315            1320

Cys Gln His Gly Asp Glu Val Ala Gly Leu Gln Arg Phe Leu Val
    1325             1330            1335

Gln Cys Pro Asp Arg Gln Val Arg Arg Asp Pro Arg Gln Leu Gln
    1340             1345            1350

Ala Ala Leu Ala Gly Arg Leu Pro Gly Trp Met Val Pro Gln Arg
    1355             1360            1365

Ile Val Phe Leu Asp Ala Leu Pro Leu Met Ala Asn Gly Lys Ile
    1370             1375            1380

Asp Tyr Gln Ala Leu Lys Arg Arg His Thr Pro Glu Ala Glu Asn
    1385             1390            1395

Pro Ala Glu Ala Asp Leu Pro Gln Gly Asp Ile Glu Lys Gln Val
    1400             1405            1410

Ala Ala Leu Trp Gln Gln Leu Leu Ser Thr Gly Asn Val Thr Arg
    1415             1420            1425

Glu Thr Asp Phe Phe Gln Gln Gly Gly Asp Ser Leu Leu Ala Thr
    1430             1435            1440

Arg Leu Thr Gly Gln Leu His Gln Ala Gly Tyr Glu Ala Gln Leu
    1445             1450            1455

Ser Asp Leu Phe Asn His Pro Arg Leu Ala Asp Phe Ala Ala Thr
    1460             1465            1470

Leu Arg Lys Thr Asp Val Pro Val Glu Gln Pro Phe Val His Ser
    1475             1480            1485

Pro Glu Asp Arg Tyr Gln Pro Phe Ala Leu Thr Asp Val Gln Gln
    1490             1495            1500

Ala Tyr Leu Val Gly Arg Gln Pro Gly Phe Ala Leu Gly Gly Val
    1505             1510            1515

Gly Ser His Phe Phe Val Glu Phe Glu Ile Ala Asp Leu Asp Leu
    1520             1525            1530

Thr Arg Leu Glu Thr Val Trp Asn Arg Leu Ile Ala Arg His Asp
    1535             1540            1545

Met Leu Arg Ala Ile Val Arg Asp Gly Gln Gln Gln Val Leu Glu
    1550             1555            1560

Gln Thr Pro Pro Trp Val Ile Pro Ala His Thr Leu His Thr Pro
    1565             1570            1575

Glu Glu Ala Leu Arg Val Arg Glu Lys Leu Ala His Gln Val Leu
    1580             1585            1590

Asn Pro Glu Val Trp Pro Val Phe Asp Leu Gln Val Gly Tyr Val
    1595             1600            1605

Asp Gly Met Pro Ala Arg Leu Trp Leu Cys Leu Asp Asn Leu Leu
    1610             1615            1620

Leu Asp Gly Leu Ser Met Gln Ile Leu Leu Ala Glu Leu Glu His
    1625             1630            1635

Gly Tyr Arg Tyr Pro Gln Gln Leu Leu Pro Pro Leu Pro Val Thr
    1640             1645            1650

Phe Arg Asp Tyr Leu Gln Gln Pro Ser Leu Gln Ser Pro Asn Pro
    1655             1660            1665

Asp Ser Leu Ala Trp Trp Gln Ala Gln Leu Asp Asp Ile Pro Pro
    1670             1675            1680
```

Ala Pro Ala Leu Pro Leu Arg Cys Leu Pro Gln Glu Val Glu Thr
1685                1690                1695

Pro Arg Phe Ala Arg Leu Asn Gly Ala Leu Asp Ser Thr Arg Trp
1700                1705                1710

His Arg Leu Lys Lys Arg Ala Ala Asp Ala His Leu Thr Pro Ser
1715                1720                1725

Ala Val Leu Leu Ser Val Trp Ser Thr Val Leu Ser Ala Trp Ser
1730                1735                1740

Ala Gln Pro Glu Phe Thr Leu Asn Leu Thr Leu Phe Asp Arg Arg
1745                1750                1755

Pro Leu His Pro Gln Ile Asn Gln Ile Leu Gly Asp Phe Thr Ser
1760                1765                1770

Leu Met Leu Leu Ser Trp His Pro Gly Glu Ser Trp Leu His Ser
1775                1780                1785

Ala Gln Ser Leu Gln Gln Arg Leu Ser Gln Asn Leu Asn His Arg
1790                1795                1800

Asp Val Ser Ala Ile Arg Val Met Arg Gln Leu Val Gln Arg Gln
1805                1810                1815

Asn Val Pro Ala Val Pro Met Pro Val Val Phe Thr Ser Ala Leu
1820                1825                1830

Gly Phe Glu Gln Asp Asn Phe Leu Ala Arg Arg Asn Leu Leu Lys
1835                1840                1845

Pro Val Trp Gly Ile Ser Gln Thr Pro Gln Val Trp Leu Asp His
1850                1855                1860

Gln Ile Tyr Glu Ser Glu Gly Glu Leu Arg Phe Asn Trp Asp Phe
1865                1870                1875

Val Ala Ala Leu Phe Pro Ala Gly Gln Val Glu Arg Gln Phe Glu
1880                1885                1890

Gln Tyr Cys Ala Leu Leu Asn Arg Met Ala Glu Asp Glu Ser Gly
1895                1900                1905

Trp Gln Leu Pro Leu Ala Ala Leu Val Pro Pro Val Lys His Ala
1910                1915                1920

Gly Gln Cys Ala Glu Arg Ser Pro Arg Val Cys Pro Glu His Ser
1925                1930                1935

Gln Pro His Ile Ala Ala Asp Glu Ser Thr Val Ser Leu Ile Cys
1940                1945                1950

Asp Ala Phe Arg Glu Val Val Gly Glu Ser Val Thr Pro Ala Glu
1955                1960                1965

Asn Phe Phe Glu Ala Gly Ala Thr Ser Leu Asn Leu Val Gln Leu
1970                1975                1980

His Val Leu Leu Gln Arg His Glu Phe Ser Thr Leu Thr Leu Leu
1985                1990                1995

Asp Leu Phe Thr His Pro Ser Pro Ala Ala Leu Ala Asp Tyr Leu
2000                2005                2010

Ala Gly Val Ala Thr Val Glu Lys Thr Lys Arg Pro Arg Pro Val
2015                2020                2025

Arg Arg Arg Gln Arg Arg Ile
2030                2035

<210> SEQ ID NO 102
<211> LENGTH: 9492
<212> TYPE: DNA
<213> ORGANISM: Escherichia coli

<400> SEQUENCE: 102

-continued

```
atggataact tgcgcttctc ttctgcgccg acagcagatt ccattgatgc atcgatcgct      60
caacactacc cggactgcga acctgtcgcg gttatcggct acgcctgcca ttttcctgaa     120
tcgccggatg gcgaaacgtt ctggcaaaat ctgctggaag gtcgtgaatg cagccgacgc     180
tttacgcgcg aagagcttct ggccgtcggt ctggatgccg ccatcattga cgatcctcat     240
tatgtcaata tcggtacggt gttagacaac gccgactgct tcgacgccac cctgtttggc     300
tattcgcgac aggaagcgga gtcgatggac ccgcagcagc gcctgttttt gcaggcggtc     360
tggcatgcgc tggaacatgc cggttatgcc cccggcgccg tccccataa gaccggcgtt     420 ttcgcctctt cccggatgag tacctacccc ggtcgcgaag cattgaacgt gacagaagtc     480
gcgcaggtaa aaggtctgca atctctgatg ggcaatgata agactatat tgccacccgc     540 gccgcgtaca aactcaacct gcacggcccg gcgttatcgg tacagaccgc ctgctccagc     600
tcgctggttg ccgtgcatct tgcctgtgaa agcctgcgcg caggcgaatc cgatatggcg     660
gtggccggcg gcgtggcgct ctcttccccc cagcaggcag gctaccgcta ccagcccgga     720 atgatttct ctcctgatgg tcactgtcgt cctttgacg cctcggctga gggcacctgg     780
gccggtaacg gtctcggctg cgtggtgctg cgtcgcctga gagacgcgct gctgtcaggc     840
gatccgatta tctcggtgat cctctccagc gcggtcaaca acgacggcaa cagaaaggtc     900
ggctataccg ccccttccgt cgcagggcaa caggcagtca tcgaagaggc gttaatgctg     960
gcggccatcg acgacaggca ggtaggttac attgaaaccc acggcaccgg cacaccgctg    1020
ggcgacgcga ttgaaattga agcgttacgc aacgtctatg cgcctcgccc gcaggatcag    1080
cgctgtgcgc tcggttccgt gaaaagtaac atgggccatc tggataccgc ggcgggcatt    1140
gccggactgc tgaaaaccgt tctggcagtc agtcgcgggc aaattcctcc cttactgaat    1200
tttcacaccc ccaacccggc gctgaaactt gaagagagcc cctttaccat accggtgtcg    1260
gcacaggcat ggcaggacga aatgcgctat gcgggcgtct cctccttgg tattggcggc    1320 accaactgcc atatgatcgt cgcctcgctg cccgacgcgc tcaacgcgcg cctccccaat    1380
acggatagcg gcagaaaaag taccgcgctg ctgctcagcg ccgccagcga cagcgcgttg    1440
cggcggctgg cgacggatta tgccggggcg ctgagagaga atgcggatgc cagctctctg    1500
gccttcacag ccctgcacgc gcgccgtctc gatctcccct tccgcctggc ggcgccatta    1560
aaccgtgaaa ccgccgaggc gctcagcgcc tgggccggtg agaaatcggg ggcgctggtt    1620
tacagcggcc acggcgccag cggcaagcag gtgtggctgt ttaccggcca gggctcgcac    1680
tggcgcacta tgggtcaaac gatgtaccat cactcaacgg cgtttgccga cacgctggat    1740
cgctgttttt ccgcctgtag cgaaatgctc acgccgtcac tgcgcgaagc gatgtttaac    1800
cccgattcgg cgcagctgga caatatggcc tgggcgcagc cggcgattgt cgcgtttgaa    1860
atcgcgatgg cggcgcactg gcgtgctgaa ggactgaagc cagacttcgc cattgggcat    1920
tccgtcggtg aatttgccgc tgccgttgtc tgcggacact atacgattga acaggtcatg    1980
ccactggttt gtcggcgcgg cgcgctaatg cagcagtgcg caagcggcgc gatggtggcg    2040
gtatttgcag acgaagacac gctgatgccg ctggctcgcc agtttgagct ggatctcgcc    2100
gccaacaacg gtacgcaaca tacgcgtattt tccgggccgg aagcccgtct cgcggtatt    2160 tgcgccacgc tctcgcagca tgacattaac tatcgtcgcc tgagcgtaac cggtgcggcg    2220
cactccgctt tactgagcc gatactcgat cggttccagg acgcctgcgc gggactgcac    2280
gcggagccgg ggcaaatacc gattatttcc acgctcaccg ccgacgtcat tgatgagtca    2340
```

```
acgctcaacc aggcggatta ctggcgccga cacatgcgcc agccggtgcg ttttatccag    2400
agtattcagg tggcgcatca gctcggcgcc cgcgtttttc tggagatggg gcccgatgcc    2460
cagttggttg cttgcgggca gcgcgaatac cgcgataacg catactggat agccagcgcc    2520
cggcgtaaca aagaggcgag cgatgtcctc aatcaggccc tgctccagct ttacgctgcc    2580
ggcgtcgccc taccgtgggc cgacctgctg gcgggcgatg acaacgtat cgctgcgcca    2640 tgttatccgt ttgatactga acgttactgg aaagagcgcg tctccccggc ctgcgagcct    2700
gccgacgcag cgctgtctgc cgggctggag gtggcgagtc gcgccgcgac agcgctcgat    2760
ctccctcgcc tggaagcgct taaacagtgc gccacgcgac tgcacgccat ctacgtcgat    2820
caactggtac aacgctgtac cggcgatgcc attgagaacg gcgtggacgc catgaccatc    2880
atgcgccgtg gacgtctgct gccccgctac cagcagctac tccagcgcct gctgaataac    2940
tgcgtggtcg acggcgatta ccgctgcacc gacgggcgat acgtccgcgc ccgccccatt    3000
gaacatcaac agcgggaatc actgctgacg gaacttgccg ttattgtga aggttttcag    3060 gctattcccg acaccatcgc ccgtgccggc gatcggttat atgaaatgat gagcggcgcg    3120
gaagaaccgg tggcgattat cttcccgcaa agcgcctccg acggcgtgga agtgctgtat    3180
caggaattca gctttggccg ctatttcaac caaatcgccg ccggggtatt acgcggcatt    3240
gtccagacgc gtcagccccg ccagccgttg cgtattcttg aagttggcgg cggaaccggc    3300
ggcaccaccg cgtggctgct gccggaactc aacggcgttc cggcactgga gtaccatttc    3360
accgatatct cggcgctgtt cacccgtcgc gcccagcaga aattcgccga ctacgatttt    3420
gtgaagtata gcgagctgga tctcgaaaaa gaggcgcagt ctcagggttt ccaggcacag    3480
tcttacgatc ttatcgtggc agcgaacgtg attcacgcca cccgccatat tggccgcacg    3540
ctcgataatc tgcgccccct gctcaagcca ggcgggcgcc tgctgatgcg cgaaatcacc    3600
cagccaatgc gtctgtttga cttcgttttc ggcccgctgg ttcttccgct acaggatctc    3660
gacgcccgcg aaggtgagtt attcctcacc accgctcagt ggcaacaaca gtgccgccac    3720
gccggattca gcaaagtggc gtggctaccg caggatggca gcccgaacgc cgggatgagc    3780
gaacatatca ttctcgccac gctgcccggt caggcggtta cgccgtaac attcaccgcg    3840 ccatcagaac ccgtgttggg gcaggcgctg acggataacg gtgattatct cgccgactgg    3900
tctgattgcg caggtcagcc cgaacagttt aacgcccgct ggcaggaggc atggcgtctg    3960
ctttcacagc gtcatggcga cgctctgcct gtggaaccgc cccccgtcgc cgccccggag    4020
tggctgggga aggttcgctt aagctggcaa aacgaagcct ttcccgcgg tcagatgcgc    4080 gttgaagccc gtcatcctgc tggcgagtgg ctgccgctat cgcccgccgc gcctcttcct    4140
gcgccgcaaa cgcattatca atggcgctgg acgcccctca cgtcgccag cattgaccat    4200 ccgcttacct ttagcttcag cgccggtacg cttgcgcgca gcgacgagct ggcgcaatac    4260
ggcatcattc acgatccgca cgcctcttca cgactgatga ttgttgagga gagcgaggat    4320
acgctggcct tagcggagaa agtgatagca gcgctcaccg ccagcgcagc cggattgatt    4380
gtggttactc gccgcgcgtg gcgagtcgag gaaaatgaag cactctctgc atcccatcac    4440
gcgctatggg ccttgcttcg cgtcgcgccc aacgaacagc cggaacggtt gcttgccgcc    4500
atcgatctcg ccgaaaacac cccgtgggaa acgctgcatc aagggttgag cgcagtctca    4560
ctaccacagc gctggctcgc cgcacggggt gacaccctt ggcttccttc actgtcgccc    4620
aatacgggat gcgccgctga attaccggca aacgtgttta ccggcgatag ccgctggcat    4680
ctggtgaccg gagcgtttgg cggattaggc cgccttgccg tgaactggct cagagaaaaa    4740
```

-continued

```
ggggcgcgac gcatcgccct gctggcgccg cgcgtggatg agtcatggct acgcgacgtg    4800
gagggcgggc agacgcgcgt ctgccgttgt gatgtgggcg atgccgggca actggccacg    4860
gttcttgacg atctggcggc caacggcggc attgccggag cgattcatgc cgctggcgta    4920
ttggctgacg cgcccttgca ggagcttgat gaccaccagc tggctgccgt tttcgcggta    4980
aaagcgcagg cggcaagcca gctgttgcaa accctgcgca accacgacgg acgctatctt    5040
attctctact cttccgctgc cgccaccctc ggcgcgccgg gtcagagcgc ccatgcgctg    5100
gcctgcggct acctggacgg gctggcccag cagttttcca cccttgatgc gccgaaaacg    5160
ctctctgtcg cctggggcgc atggggagaa agccggtcggg cggccacgcc ggaaatgctg    5220
gcgacgctcg ccagccgagg tatgggcgcg ttaagcgatg ccgaaggctg ctggcacctg    5280
gaacaggcgt tgatgcgcgg cgcccgtgg cgactggcga tgcgcgtttt taccgacaaa    5340
atgcccccgt tacaacaggc tctgtttaac atcagcgcca cagaaaaagc cgcaacgccg    5400
gtcattcctc ctgctgatga caacgccttt aacggcagcc tgagcgatga acagcggtg    5460
atggcatggc tgaaaaagcg gattgcggtt cagctaaggc tgagcgatcc ggcgtcactg    5520
catccaaacc aggatctgtt gcaactcggc atggactcgc tgctcttcct tgaactcagt    5580
agcgatattc agcactacct gggtgtacgc atcaatgcgg aacgggcgtg gcaggatctg    5640
tctcctcatg gactcacgca gcttatctgt tctaagccag aggcgacgcc tgccgcttcg    5700
cagccggaag tgttgcggca cgacgccgac gagcgttatg cgcccttccc tttgacgccc    5760
attcagcacg cctactggct ggggcgaacc cacttcattg gctatggcgg cgtcgcctgt    5820
cacgtcctgt ttgagtggga taaacgccac gatgagttcg atctcgccat actgagaaaa    5880
gcatggaacc agctcatcgc acgccacgat atgttgcgta tggtggttga tgccgacggg    5940
cagcagcgaa tcctggcgac aacgccggag tatcacatcc cgcgtgacga tctgcgcgcg    6000
cttttccccgg aagaacagcg catcgcgctg aaaaacggc ggcatgaact gagctatcgc    6060
gttttgcctg ccgaccagtg gcctcttttt gagctggtgg tcagcgaaat cgacgattgc    6120
cattaccgtc tgcatatgaa cctcgacctt ttgcagtttg atgtgcagag tttttaaagtc    6180
atgatggacg acctggcgca ggtctggcgc ggtgaaacgc tggcaccgct cgctattacc    6240
ttccgtgatt atgtgatggc tgaacaggcg cgccgacaga catcggcatg gcacgatgcc    6300
tgggattact ggcaggaaaa actgccgcaa ctgcccttag cgccagagct gccggtggtt    6360
gagacgcccc cggaaacgcc acacttcacc accttcaaat cgacgatcgg caagacagaa    6420
tggcaggccg tgaaacagcg ctggcagcag caaggcgtca caccgtctgc cgcgctgctc    6480
acgctgtttg ccgccaccct tgagcgctgg agccgtacca caacatttac gctgaacctg    6540
acgttcttca atcgccagcc gatccatccg caaatcaacc agttgattgg tgattttacc    6600
tccgtcacgc tggttgattt taacttctca gcgccggtga cgttgcaaga gcagatgcaa    6660
cagacccaac agcgcctctg gcaaaacatg gcgcacagtg aaatgaacgg tgttgaggtg    6720
atccgtgagc tgggccgcct gcgcggatca caacgtcaac cgctgatgcc ggtagtgttt    6780
accagtatgc tggggatgac gctggaaggc atgactatcg atcaggcgat gagccatctg    6840
ttcggcgaac cctgctatgt attcacgcaa acgccgcagg tctggctgga tcatcaggtc    6900
atggagagcg acggcgagtt gatgtttagc tggtactgca tggacaacgt gctggaaccc    6960
ggcgctgccg aggcgatgtt taatgactat tgcgccatcc tgcaagccgt catcgccgcc    7020
cctgaaagcc tgaagactct cgccagcggc atcgccaggc acattccccg ccgacgctgg    7080
```

```
ccgctgaacg cgcaggcgga ctacgacctg cgggatattg agcaggcgac gctcgaatac   7140
cccggcatcc ggcaggccag agcggaaata accgaacagg gcgcgttgac gctggatatc   7200
gtgatggccg acgatccttc gccatcagcg gcgatgcctg atgagcacga acttacccaa   7260
ctggcgctgc cgttgcctga gcaggcgcag cttgatgagc tggaggcgac ctggcgctgg   7320
ctggaggcgc gtgcgctaca ggggatcgcg gctacgctaa atcgtcacgg cctgtttacc   7380
acgccggaga tcgcccatcg ctttagcgca atagtacagg cgctgtccgc gcaagcgtct   7440
caccagcgtc tgctgcgcca gtggctacag tgtctgacgg aaagagagtg gttaatccgc   7500
gaaggtgaaa gctggcgctg ccgcattccg ctcagcgaga ttcctgagcc tcaggaagcg   7560
tgcccgcaaa gccaatggag ccgggcgctg gcgcagtatc tggaaacctg catcgcccgg   7620
cacgacgccc ttttctccgg gcagtgttct ccgctggaat tgctgttcaa cgagcagcat   7680
cgcgttaccg acgcgctgta tcgcgacaac cccgccagcg cctgtctgaa tcgctatacc   7740
gcgcagattg ccgccttgtg cagcgcgaaa cggattctgg aggttggcgc cggaaccgca   7800
gccactaccg cgccggtgct gaaggccacg cggaacacgc gacagtcgta ccacttcacg   7860
gacgtctccg cgcagttcct caatgacgcc agagcccgtt ccatgatgaa atcgcaggtg   7920
tcttatgcct tgttcgacat caaccagccg ctggatttca ccgccacccc ggaggcgggt   7980
tacgacctga tcgttgccgt caatgtgctc cacgacgcca gccatgtcgt ccagacgttg   8040
cgcagattaa aactgttgct gaaagccggc ggacgtttgc tgatcgttga agcgacggag   8100
cgaaacagcg tattccagct ggcgagcgtg ggctttattg agggattaag cggataccgc   8160
gatttccgcc gccgggatga gaaaccgatg ctcacccgct ccgcatggca ggaggttctc   8220
gttcaggccg ggtttgcaaa cgagctggcg tggcccgcgc aggaatcgtc gccgctgcgc   8280
cagcatctgc tggtagcgcg ttcgcctggc gtaaatcgcc cggataaaaa agccgtgagc   8340
cgctatttac agcagcgctt tggcaccggt ctgcccattt tacagatccg gcaaagagaa   8400
gcgttattta cgccgctgca tgccccgtct gatgcgccga ctgagccagc caaacccacg   8460
ccagttgccg gggggaatcc ggcgctggaa aaacaggtgg ctgaactctg gcaatcgctg   8520
ctgtctcgcc ccgtggcaag gcatcacgac tttttcgaac tgggcggcga cagcctgatg   8580
gcgacaagga tggtcgcgca gctaaaccgg agagggattg ccagggctaa ccttcaggat   8640
ctgttcagcc attcgacgct gagcgacttc tgcgcccatc tacaggcggc tacgtcagga   8700
gaggacaacc cgatacccct tgccagggc gacggtgagg aaaccctgtt tgtcttccac   8760
gcttcagacg gcgatatcag cgcctggctg ccgctcgcta gcgcgttgaa caggcgcgtt   8820
ttcggcctgc aagcaaaatc gccgcagcgc tttgccacgc tcgaccagat gatcgatgag   8880
tatgtcgggt gcatccgtcg tcagcagcct cacggccctt atgtgctggc gggttggtcg   8940
tatggcgcgt ttcttgcggc gggcgccgca cagcgcctgt acgccaaagg caagcaggtt   9000
cggatggtgt taatcgatcc cgtgtgccga caggatttct gttgcgaaaa ccgggcggcc   9060
ctgctgcgcc tgttagccga aggacaaacg cctctggcac tgcccgaaca tttcgaccag   9120
cagacgcccg acagccagct tgccgacttt atcagcctcg ctaaaacggc cggtatggtg   9180
tcgcaaaacc tgacgctgca agcggcagaa acgtggctcg acaacatcgc gcatctgctg   9240
cgtttactga ctgagcatac gccgggcgaa agcgttccgg tccctgtct catggtgtat   9300 gccgccggga gacccgagcg ctggacgcca gcagaaaccg agtggcaggg ctggataaac   9360
aacgccgacg acgctgtgat tgaagccagc cactggcaaa tcatgatgga agcccccac   9420 gttcaggctt gtgcgcaaca cattacgcgc tggctttgcg caacctcaac gcaaccggag   9480
```
aacacgttat ga                                                          9492

<210> SEQ ID NO 103
<211> LENGTH: 3163
<212> TYPE: PRT
<213> ORGANISM: Escherichia coli

<400> SEQUENCE: 103

Met Asp Asn Leu Arg Phe Ser Ser Ala Pro Thr Ala Asp Ser Ile Asp
1               5                   10                  15

Ala Ser Ile Ala Gln His Tyr Pro Asp Cys Glu Pro Val Ala Val Ile
            20                  25                  30

Gly Tyr Ala Cys His Phe Pro Glu Ser Pro Asp Gly Glu Thr Phe Trp
        35                  40                  45

Gln Asn Leu Leu Glu Gly Arg Glu Cys Ser Arg Arg Phe Thr Arg Glu
    50                  55                  60

Glu Leu Leu Ala Val Gly Leu Asp Ala Ala Ile Ile Asp Asp Pro His
65                  70                  75                  80

Tyr Val Asn Ile Gly Thr Val Leu Asp Asn Ala Asp Cys Phe Asp Ala
                85                  90                  95

Thr Leu Phe Gly Tyr Ser Arg Gln Glu Ala Glu Ser Met Asp Pro Gln
            100                 105                 110

Gln Arg Leu Phe Leu Gln Ala Val Trp His Ala Leu Glu His Ala Gly
        115                 120                 125

Tyr Ala Pro Gly Ala Val Pro His Lys Thr Gly Val Phe Ala Ser Ser
    130                 135                 140

Arg Met Ser Thr Tyr Pro Gly Arg Glu Ala Leu Asn Val Thr Glu Val
145                 150                 155                 160

Ala Gln Val Lys Gly Leu Gln Ser Leu Met Gly Asn Asp Lys Asp Tyr
                165                 170                 175

Ile Ala Thr Arg Ala Ala Tyr Lys Leu Asn Leu His Gly Pro Ala Leu
            180                 185                 190

Ser Val Gln Thr Ala Cys Ser Ser Leu Val Ala Val His Leu Ala
        195                 200                 205

Cys Glu Ser Leu Arg Ala Gly Glu Ser Asp Met Ala Val Ala Gly Gly
    210                 215                 220

Val Ala Leu Ser Phe Pro Gln Gln Ala Gly Tyr Arg Tyr Gln Pro Gly
225                 230                 235                 240

Met Ile Phe Ser Pro Asp Gly His Cys Arg Pro Phe Asp Ala Ser Ala
                245                 250                 255

Glu Gly Thr Trp Ala Gly Asn Gly Leu Gly Cys Val Val Leu Arg Arg
            260                 265                 270

Leu Arg Asp Ala Leu Leu Ser Gly Asp Pro Ile Ile Ser Val Ile Leu
        275                 280                 285

Ser Ser Ala Val Asn Asn Asp Gly Asn Arg Lys Val Gly Tyr Thr Ala
    290                 295                 300

Pro Ser Val Ala Gly Gln Gln Ala Val Ile Glu Glu Ala Leu Met Leu
305                 310                 315                 320

Ala Ala Ile Asp Asp Arg Gln Val Gly Tyr Ile Glu Thr His Gly Thr
                325                 330                 335

Gly Thr Pro Leu Gly Asp Ala Ile Glu Ile Glu Ala Leu Arg Asn Val
            340                 345                 350

Tyr Ala Pro Arg Pro Gln Asp Gln Arg Cys Ala Leu Gly Ser Val Lys
        355                 360                 365

```
Ser Asn Met Gly His Leu Asp Thr Ala Ala Gly Ile Ala Gly Leu Leu
    370                 375                 380

Lys Thr Val Leu Ala Val Ser Arg Gly Gln Ile Pro Pro Leu Leu Asn
385                 390                 395                 400

Phe His Thr Pro Asn Pro Ala Leu Lys Leu Glu Glu Ser Pro Phe Thr
                405                 410                 415

Ile Pro Val Ser Ala Gln Ala Trp Gln Asp Glu Met Arg Tyr Ala Gly
                420                 425                 430

Val Ser Ser Phe Gly Ile Gly Gly Thr Asn Cys His Met Ile Val Ala
                435                 440                 445

Ser Leu Pro Asp Ala Leu Asn Ala Arg Leu Pro Asn Thr Asp Ser Gly
    450                 455                 460

Arg Lys Ser Thr Ala Leu Leu Leu Ser Ala Ala Ser Asp Ser Ala Leu
465                 470                 475                 480

Arg Arg Leu Ala Thr Asp Tyr Ala Gly Ala Leu Arg Glu Asn Ala Asp
                485                 490                 495

Ala Ser Ser Leu Ala Phe Thr Ala Leu His Ala Arg Arg Leu Asp Leu
                500                 505                 510

Pro Phe Arg Leu Ala Ala Pro Leu Asn Arg Glu Thr Ala Glu Ala Leu
    515                 520                 525

Ser Ala Trp Ala Gly Glu Lys Ser Gly Ala Leu Val Tyr Ser Gly His
    530                 535                 540

Gly Ala Ser Gly Lys Gln Val Trp Leu Phe Thr Gly Gln Gly Ser His
545                 550                 555                 560

Trp Arg Thr Met Gly Gln Thr Met Tyr His His Ser Thr Ala Phe Ala
                565                 570                 575

Asp Thr Leu Asp Arg Cys Phe Ser Ala Cys Ser Glu Met Leu Thr Pro
                580                 585                 590

Ser Leu Arg Glu Ala Met Phe Asn Pro Asp Ser Ala Gln Leu Asp Asn
    595                 600                 605

Met Ala Trp Ala Gln Pro Ala Ile Val Ala Phe Glu Ile Ala Met Ala
    610                 615                 620

Ala His Trp Arg Ala Glu Gly Leu Lys Pro Asp Phe Ala Ile Gly His
625                 630                 635                 640

Ser Val Gly Glu Phe Ala Ala Ala Val Val Cys Gly His Tyr Thr Ile
                645                 650                 655

Glu Gln Val Met Pro Leu Val Cys Arg Arg Gly Ala Leu Met Gln Gln
                660                 665                 670

Cys Ala Ser Gly Ala Met Val Ala Val Phe Ala Asp Glu Asp Thr Leu
    675                 680                 685

Met Pro Leu Ala Arg Gln Phe Glu Leu Asp Leu Ala Ala Asn Asn Gly
    690                 695                 700

Thr Gln His Thr Val Phe Ser Gly Pro Glu Ala Arg Leu Ala Val Phe
705                 710                 715                 720

Cys Ala Thr Leu Ser Gln His Asp Ile Asn Tyr Arg Arg Leu Ser Val
                725                 730                 735

Thr Gly Ala Ala His Ser Ala Leu Leu Glu Pro Ile Leu Asp Arg Phe
                740                 745                 750

Gln Asp Ala Cys Ala Gly Leu His Ala Glu Pro Gly Gln Ile Pro Ile
                755                 760                 765

Ile Ser Thr Leu Thr Ala Asp Val Ile Asp Glu Ser Thr Leu Asn Gln
    770                 775                 780
```

```
Ala Asp Tyr Trp Arg Arg His Met Arg Gln Pro Val Arg Phe Ile Gln
785                 790                 795                 800

Ser Ile Gln Val Ala His Gln Leu Gly Ala Arg Val Phe Leu Glu Met
            805                 810                 815

Gly Pro Asp Ala Gln Leu Val Ala Cys Gly Gln Arg Glu Tyr Arg Asp
        820                 825                 830

Asn Ala Tyr Trp Ile Ala Ser Ala Arg Arg Asn Lys Glu Ala Ser Asp
            835                 840                 845

Val Leu Asn Gln Ala Leu Leu Gln Leu Tyr Ala Ala Gly Val Ala Leu
        850                 855                 860

Pro Trp Ala Asp Leu Leu Ala Gly Asp Gly Gln Arg Ile Ala Ala Pro
865                 870                 875                 880

Cys Tyr Pro Phe Asp Thr Glu Arg Tyr Trp Lys Glu Arg Val Ser Pro
                885                 890                 895

Ala Cys Glu Pro Ala Asp Ala Ala Leu Ser Ala Gly Leu Glu Val Ala
                900                 905                 910

Ser Arg Ala Ala Thr Ala Leu Asp Leu Pro Arg Leu Glu Ala Leu Lys
            915                 920                 925

Gln Cys Ala Thr Arg Leu His Ala Ile Tyr Val Asp Gln Leu Val Gln
930                 935                 940

Arg Cys Thr Gly Asp Ala Ile Glu Asn Gly Val Asp Ala Met Thr Ile
945                 950                 955                 960

Met Arg Arg Gly Arg Leu Leu Pro Arg Tyr Gln Leu Leu Gln Arg
                965                 970                 975

Leu Leu Asn Asn Cys Val Val Asp Gly Asp Tyr Arg Cys Thr Asp Gly
            980                 985                 990

Arg Tyr Val Arg Ala Arg Pro Ile Glu His Gln Gln Arg Glu Ser Leu
        995                 1000                1005

Leu Thr Glu Leu Ala Gly Tyr Cys Glu Gly Phe Gln Ala Ile Pro
    1010                1015                1020

Asp Thr Ile Ala Arg Ala Gly Asp Arg Leu Tyr Glu Met Met Ser
    1025                1030                1035

Gly Ala Glu Glu Pro Val Ala Ile Ile Phe Pro Gln Ser Ala Ser
    1040                1045                1050

Asp Gly Val Glu Val Leu Tyr Gln Glu Phe Ser Phe Gly Arg Tyr
    1055                1060                1065

Phe Asn Gln Ile Ala Ala Gly Val Leu Arg Gly Ile Val Gln Thr
    1070                1075                1080

Arg Gln Pro Arg Gln Pro Leu Arg Ile Leu Glu Val Gly Gly Gly
    1085                1090                1095

Thr Gly Gly Thr Thr Ala Trp Leu Leu Pro Glu Leu Asn Gly Val
    1100                1105                1110

Pro Ala Leu Glu Tyr His Phe Thr Asp Ile Ser Ala Leu Phe Thr
    1115                1120                1125

Arg Arg Ala Gln Gln Lys Phe Ala Asp Tyr Asp Phe Val Lys Tyr
    1130                1135                1140

Ser Glu Leu Asp Leu Glu Lys Glu Ala Gln Ser Gln Gly Phe Gln
    1145                1150                1155

Ala Gln Ser Tyr Asp Leu Ile Val Ala Ala Asn Val Ile His Ala
    1160                1165                1170

Thr Arg His Ile Gly Arg Thr Leu Asp Asn Leu Arg Pro Leu Leu
    1175                1180                1185

Lys Pro Gly Gly Arg Leu Leu Met Arg Glu Ile Thr Gln Pro Met
```

-continued

```
            1190                1195                1200
Arg Leu Phe Asp Phe Val Phe Gly Pro Leu Val Leu Pro Leu Gln
    1205                1210                1215
Asp Leu Asp Ala Arg Glu Gly Glu Leu Phe Leu Thr Thr Ala Gln
    1220                1225                1230
Trp Gln Gln Gln Cys Arg His Ala Gly Phe Ser Lys Val Ala Trp
    1235                1240                1245
Leu Pro Gln Asp Gly Ser Pro Asn Ala Gly Met Ser Glu His Ile
    1250                1255                1260
Ile Leu Ala Thr Leu Pro Gly Gln Ala Val Ser Ala Val Thr Phe
    1265                1270                1275
Thr Ala Pro Ser Glu Pro Val Leu Gly Gln Ala Leu Thr Asp Asn
    1280                1285                1290
Gly Asp Tyr Leu Ala Asp Trp Ser Asp Cys Ala Gly Gln Pro Glu
    1295                1300                1305
Gln Phe Asn Ala Arg Trp Gln Glu Ala Trp Arg Leu Leu Ser Gln
    1310                1315                1320
Arg His Gly Asp Ala Leu Pro Val Glu Pro Pro Val Ala Ala
    1325                1330                1335
Pro Glu Trp Leu Gly Lys Val Arg Leu Ser Trp Gln Asn Glu Ala
    1340                1345                1350
Phe Ser Arg Gly Gln Met Arg Val Glu Ala Arg His Pro Ala Gly
    1355                1360                1365
Glu Trp Leu Pro Leu Ser Pro Ala Ala Pro Leu Pro Ala Pro Gln
    1370                1375                1380
Thr His Tyr Gln Trp Arg Trp Thr Pro Leu Asn Val Ala Ser Ile
    1385                1390                1395
Asp His Pro Leu Thr Phe Ser Phe Ser Ala Gly Thr Leu Ala Arg
    1400                1405                1410
Ser Asp Glu Leu Ala Gln Tyr Gly Ile Ile His Asp Pro His Ala
    1415                1420                1425
Ser Ser Arg Leu Met Ile Val Glu Glu Ser Glu Asp Thr Leu Ala
    1430                1435                1440
Leu Ala Glu Lys Val Ile Ala Ala Leu Thr Ala Ser Ala Ala Gly
    1445                1450                1455
Leu Ile Val Val Thr Arg Arg Ala Trp Arg Val Glu Glu Asn Glu
    1460                1465                1470
Ala Leu Ser Ala Ser His His Ala Leu Trp Ala Leu Leu Arg Val
    1475                1480                1485
Ala Ala Asn Glu Gln Pro Glu Arg Leu Leu Ala Ala Ile Asp Leu
    1490                1495                1500
Ala Glu Asn Thr Pro Trp Glu Thr Leu His Gln Gly Leu Ser Ala
    1505                1510                1515
Val Ser Leu Pro Gln Arg Trp Leu Ala Ala Arg Gly Asp Thr Leu
    1520                1525                1530
Trp Leu Pro Ser Leu Ser Pro Asn Thr Gly Cys Ala Ala Glu Leu
    1535                1540                1545
Pro Ala Asn Val Phe Thr Gly Asp Ser Arg Trp His Leu Val Thr
    1550                1555                1560
Gly Ala Phe Gly Gly Leu Gly Arg Leu Ala Val Asn Trp Leu Arg
    1565                1570                1575
Glu Lys Gly Ala Arg Arg Ile Ala Leu Leu Ala Pro Arg Val Asp
    1580                1585                1590
```

```
Glu Ser Trp Leu Arg Asp Val Glu Gly Gln Thr Arg Val Cys
    1595                1600                1605

Arg Cys Asp Val Gly Asp Ala Gly Gln Leu Ala Thr Val Leu Asp
1610                1615                1620

Asp Leu Ala Ala Asn Gly Gly Ile Ala Gly Ala Ile His Ala Ala
    1625                1630                1635

Gly Val Leu Ala Asp Ala Pro Leu Gln Glu Leu Asp Asp His Gln
    1640                1645                1650

Leu Ala Ala Val Phe Ala Val Lys Ala Gln Ala Ala Ser Gln Leu
    1655                1660                1665

Leu Gln Thr Leu Arg Asn His Asp Gly Arg Tyr Leu Ile Leu Tyr
    1670                1675                1680

Ser Ser Ala Ala Ala Thr Leu Gly Ala Pro Gly Gln Ser Ala His
    1685                1690                1695

Ala Leu Ala Cys Gly Tyr Leu Asp Gly Leu Ala Gln Gln Phe Ser
    1700                1705                1710

Thr Leu Asp Ala Pro Lys Thr Leu Ser Val Ala Trp Gly Ala Trp
    1715                1720                1725

Gly Glu Ser Gly Arg Ala Ala Thr Pro Glu Met Leu Ala Thr Leu
    1730                1735                1740

Ala Ser Arg Gly Met Gly Ala Leu Ser Asp Ala Glu Gly Cys Trp
    1745                1750                1755

His Leu Glu Gln Ala Val Met Arg Gly Ala Pro Trp Arg Leu Ala
    1760                1765                1770

Met Arg Val Phe Thr Asp Lys Met Pro Pro Leu Gln Gln Ala Leu
    1775                1780                1785

Phe Asn Ile Ser Ala Thr Glu Lys Ala Ala Thr Pro Val Ile Pro
    1790                1795                1800

Pro Ala Asp Asp Asn Ala Phe Asn Gly Ser Leu Ser Asp Glu Thr
1805                1810                1815

Ala Val Met Ala Trp Leu Lys Lys Arg Ile Ala Val Gln Leu Arg
    1820                1825                1830

Leu Ser Asp Pro Ala Ser Leu His Pro Asn Gln Asp Leu Leu Gln
    1835                1840                1845

Leu Gly Met Asp Ser Leu Leu Phe Leu Glu Leu Ser Ser Asp Ile
    1850                1855                1860

Gln His Tyr Leu Gly Val Arg Ile Asn Ala Glu Arg Ala Trp Gln
    1865                1870                1875

Asp Leu Ser Pro His Gly Leu Thr Gln Leu Ile Cys Ser Lys Pro
    1880                1885                1890

Glu Ala Thr Pro Ala Ala Ser Gln Pro Glu Val Leu Arg His Asp
    1895                1900                1905

Ala Asp Glu Arg Tyr Ala Pro Phe Pro Leu Thr Pro Ile Gln His
    1910                1915                1920

Ala Tyr Trp Leu Gly Arg Thr His Phe Ile Gly Tyr Gly Gly Val
    1925                1930                1935

Ala Cys His Val Leu Phe Glu Trp Asp Lys Arg His Asp Glu Phe
    1940                1945                1950

Asp Leu Ala Ile Leu Glu Lys Ala Trp Asn Gln Leu Ile Ala Arg
    1955                1960                1965

His Asp Met Leu Arg Met Val Val Asp Ala Asp Gly Gln Gln Arg
    1970                1975                1980
```

-continued

```
Ile Leu Ala Thr Thr Pro Glu Tyr His Ile Pro Arg Asp Asp Leu
1985                1990                1995

Arg Ala Leu Ser Pro Glu Glu Gln Arg Ile Ala Leu Glu Lys Arg
2000                2005                2010

Arg His Glu Leu Ser Tyr Arg Val Leu Pro Ala Asp Gln Trp Pro
2015                2020                2025

Leu Phe Glu Leu Val Val Ser Glu Ile Asp Asp Cys His Tyr Arg
2030                2035                2040

Leu His Met Asn Leu Asp Leu Leu Gln Phe Asp Val Gln Ser Phe
2045                2050                2055

Lys Val Met Met Asp Asp Leu Ala Gln Val Trp Arg Gly Glu Thr
2060                2065                2070

Leu Ala Pro Leu Ala Ile Thr Phe Arg Asp Tyr Val Met Ala Glu
2075                2080                2085

Gln Ala Arg Arg Gln Thr Ser Ala Trp His Asp Ala Trp Asp Tyr
2090                2095                2100

Trp Gln Glu Lys Leu Pro Gln Leu Pro Leu Ala Pro Glu Leu Pro
2105                2110                2115

Val Val Glu Thr Pro Pro Glu Thr Pro His Phe Thr Thr Phe Lys
2120                2125                2130

Ser Thr Ile Gly Lys Thr Glu Trp Gln Ala Val Lys Gln Arg Trp
2135                2140                2145

Gln Gln Gln Gly Val Thr Pro Ser Ala Ala Leu Leu Thr Leu Phe
2150                2155                2160

Ala Ala Thr Leu Glu Arg Trp Ser Arg Thr Thr Thr Phe Thr Leu
2165                2170                2175

Asn Leu Thr Phe Phe Asn Arg Gln Pro Ile His Pro Gln Ile Asn
2180                2185                2190

Gln Leu Ile Gly Asp Phe Thr Ser Val Thr Leu Val Asp Phe Asn
2195                2200                2205

Phe Ser Ala Pro Val Thr Leu Gln Glu Gln Met Gln Gln Thr Gln
2210                2215                2220

Gln Arg Leu Trp Gln Asn Met Ala His Ser Glu Met Asn Gly Val
2225                2230                2235

Glu Val Ile Arg Glu Leu Gly Arg Leu Arg Gly Ser Gln Arg Gln
2240                2245                2250

Pro Leu Met Pro Val Val Phe Thr Ser Met Leu Gly Met Thr Leu
2255                2260                2265

Glu Gly Met Thr Ile Asp Gln Ala Met Ser His Leu Phe Gly Glu
2270                2275                2280

Pro Cys Tyr Val Phe Thr Gln Thr Pro Gln Val Trp Leu Asp His
2285                2290                2295

Gln Val Met Glu Ser Asp Gly Glu Leu Met Phe Ser Trp Tyr Cys
2300                2305                2310

Met Asp Asn Val Leu Glu Pro Gly Ala Ala Glu Ala Met Phe Asn
2315                2320                2325

Asp Tyr Cys Ala Ile Leu Gln Ala Val Ile Ala Ala Pro Glu Ser
2330                2335                2340

Leu Lys Thr Leu Ala Ser Gly Ile Ala Arg His Ile Pro Arg Arg
2345                2350                2355

Arg Trp Pro Leu Asn Ala Gln Ala Asp Tyr Asp Leu Arg Asp Ile
2360                2365                2370

Glu Gln Ala Thr Leu Glu Tyr Pro Gly Ile Arg Gln Ala Arg Ala
```

-continued

```
              2375                2380                2385
Glu  Ile  Thr  Glu  Gln  Gly  Ala  Leu  Thr  Leu  Asp  Ile  Val  Met  Ala
              2390                2395                2400

Asp  Asp  Pro  Ser  Pro  Ser  Ala  Ala  Met  Pro  Asp  Glu  His  Glu  Leu
              2405                2410                2415

Thr  Gln  Leu  Ala  Leu  Pro  Leu  Pro  Glu  Gln  Ala  Gln  Leu  Asp  Glu
              2420                2425                2430

Leu  Glu  Ala  Thr  Trp  Arg  Trp  Leu  Glu  Ala  Arg  Ala  Leu  Gln  Gly
              2435                2440                2445

Ile  Ala  Ala  Thr  Leu  Asn  Arg  His  Gly  Leu  Phe  Thr  Thr  Pro  Glu
              2450                2455                2460

Ile  Ala  His  Arg  Phe  Ser  Ala  Ile  Val  Gln  Ala  Leu  Ser  Ala  Gln
              2465                2470                2475

Ala  Ser  His  Gln  Arg  Leu  Leu  Arg  Gln  Trp  Leu  Gln  Cys  Leu  Thr
              2480                2485                2490

Glu  Arg  Glu  Trp  Leu  Ile  Arg  Glu  Gly  Glu  Ser  Trp  Arg  Cys  Arg
              2495                2500                2505

Ile  Pro  Leu  Ser  Glu  Ile  Pro  Glu  Pro  Gln  Glu  Ala  Cys  Pro  Gln
              2510                2515                2520

Ser  Gln  Trp  Ser  Arg  Ala  Leu  Ala  Gln  Tyr  Leu  Glu  Thr  Cys  Ile
              2525                2530                2535

Ala  Arg  His  Asp  Ala  Leu  Phe  Ser  Gly  Gln  Cys  Ser  Pro  Leu  Glu
              2540                2545                2550

Leu  Leu  Phe  Asn  Glu  Gln  His  Arg  Val  Thr  Asp  Ala  Leu  Tyr  Arg
              2555                2560                2565

Asp  Asn  Pro  Ala  Ser  Ala  Cys  Leu  Asn  Arg  Tyr  Thr  Ala  Gln  Ile
              2570                2575                2580

Ala  Ala  Leu  Cys  Ser  Ala  Glu  Arg  Ile  Leu  Glu  Val  Gly  Ala  Gly
              2585                2590                2595

Thr  Ala  Ala  Thr  Thr  Ala  Pro  Val  Leu  Lys  Ala  Thr  Arg  Asn  Thr
              2600                2605                2610

Arg  Gln  Ser  Tyr  His  Phe  Thr  Asp  Val  Ser  Ala  Gln  Phe  Leu  Asn
              2615                2620                2625

Asp  Ala  Arg  Ala  Arg  Phe  His  Asp  Glu  Ser  Gln  Val  Ser  Tyr  Ala
              2630                2635                2640

Leu  Phe  Asp  Ile  Asn  Gln  Pro  Leu  Asp  Phe  Thr  Ala  His  Pro  Glu
              2645                2650                2655

Ala  Gly  Tyr  Asp  Leu  Ile  Val  Ala  Val  Asn  Val  Leu  His  Asp  Ala
              2660                2665                2670

Ser  His  Val  Val  Gln  Thr  Leu  Arg  Arg  Leu  Lys  Leu  Leu  Leu  Lys
              2675                2680                2685

Ala  Gly  Gly  Arg  Leu  Leu  Ile  Val  Glu  Ala  Thr  Glu  Arg  Asn  Ser
              2690                2695                2700

Val  Phe  Gln  Leu  Ala  Ser  Val  Gly  Phe  Ile  Glu  Gly  Leu  Ser  Gly
              2705                2710                2715

Tyr  Arg  Asp  Phe  Arg  Arg  Arg  Asp  Glu  Lys  Pro  Met  Leu  Thr  Arg
              2720                2725                2730

Ser  Ala  Trp  Gln  Glu  Val  Leu  Val  Gln  Ala  Gly  Phe  Ala  Asn  Glu
              2735                2740                2745

Leu  Ala  Trp  Pro  Ala  Gln  Glu  Ser  Ser  Pro  Leu  Arg  Gln  His  Leu
              2750                2755                2760

Leu  Val  Ala  Arg  Ser  Pro  Gly  Val  Asn  Arg  Pro  Asp  Lys  Lys  Ala
              2765                2770                2775
```

-continued

```
Val Ser Arg Tyr Leu Gln Gln Arg Phe Gly Thr Gly Leu Pro Ile
    2780            2785            2790

Leu Gln Ile Arg Gln Arg Glu Ala Leu Phe Thr Pro Leu His Ala
    2795            2800            2805

Pro Ser Asp Ala Pro Thr Glu Pro Ala Lys Pro Thr Pro Val Ala
    2810            2815            2820

Gly Gly Asn Pro Ala Leu Glu Lys Gln Val Ala Glu Leu Trp Gln
    2825            2830            2835

Ser Leu Leu Ser Arg Pro Val Ala Arg His His Asp Phe Phe Glu
    2840            2845            2850

Leu Gly Gly Asp Ser Leu Met Ala Thr Arg Met Val Ala Gln Leu
    2855            2860            2865

Asn Arg Arg Gly Ile Ala Arg Ala Asn Leu Gln Asp Leu Phe Ser
    2870            2875            2880

His Ser Thr Leu Ser Asp Phe Cys Ala His Leu Gln Ala Ala Thr
    2885            2890            2895

Ser Gly Glu Asp Asn Pro Ile Pro Leu Cys Gln Gly Asp Gly Glu
    2900            2905            2910

Glu Thr Leu Phe Val Phe His Ala Ser Asp Gly Asp Ile Ser Ala
    2915            2920            2925

Trp Leu Pro Leu Ala Ser Ala Leu Asn Arg Arg Val Phe Gly Leu
    2930            2935            2940

Gln Ala Lys Ser Pro Gln Arg Phe Ala Thr Leu Asp Gln Met Ile
    2945            2950            2955

Asp Glu Tyr Val Gly Cys Ile Arg Arg Gln Gln Pro His Gly Pro
    2960            2965            2970

Tyr Val Leu Ala Gly Trp Ser Tyr Gly Ala Phe Leu Ala Ala Gly
    2975            2980            2985

Ala Ala Gln Arg Leu Tyr Ala Lys Gly Lys Gln Val Arg Met Val
    2990            2995            3000

Leu Ile Asp Pro Val Cys Arg Gln Asp Phe Cys Cys Glu Asn Arg
    3005            3010            3015

Ala Ala Leu Leu Arg Leu Leu Ala Glu Gly Gln Thr Pro Leu Ala
    3020            3025            3030

Leu Pro Glu His Phe Asp Gln Gln Thr Pro Asp Ser Gln Leu Ala
    3035            3040            3045

Asp Phe Ile Ser Leu Ala Lys Thr Ala Gly Met Val Ser Gln Asn
    3050            3055            3060

Leu Thr Leu Gln Ala Ala Glu Thr Trp Leu Asp Asn Ile Ala His
    3065            3070            3075

Leu Leu Arg Leu Leu Thr Glu His Thr Pro Gly Glu Ser Val Pro
    3080            3085            3090

Val Pro Cys Leu Met Val Tyr Ala Ala Gly Arg Pro Glu Arg Trp
    3095            3100            3105

Thr Pro Ala Glu Thr Glu Trp Gln Gly Trp Ile Asn Asn Ala Asp
    3110            3115            3120

Asp Ala Val Ile Glu Ala Ser His Trp Gln Ile Met Met Glu Ala
    3125            3130            3135

Pro His Val Gln Ala Cys Ala Gln His Ile Thr Arg Trp Leu Cys
    3140            3145            3150

Ala Thr Ser Thr Gln Pro Glu Asn Thr Leu
    3155            3160
```

<210> SEQ ID NO 104
<211> LENGTH: 5331
<212> TYPE: DNA
<213> ORGANISM: Escherichia coli

<400> SEQUENCE: 104

| | | | | | |
|---|---|---|---|---|---|
| ataacccctc | tttgttggta | aattccgcgt | atagcgtggg | cgctttggct | ccggtcgctt | 60 |
| cgacgaggtc | cgcaagagaa | gtcgcttcat | aaccgtgttg | ccagaacaat | ttcatggcct | 120 |
| tatcaagcgc | ggcatccctg | tcgaacactt | ttgggcggcc | acggcttttt | tttacacatt | 180 |
| gtgttgagtc | agttgccatg | atgccgttgt | acctggtgac | tgtgaatgaa | aggttattat | 240 |
| aaaaataatc | acctccgttc | accagtccag | atcccataaa | aataattgct | ttctatttaa | 300 |
| ctgaaattta | aagattttta | aattaattaa | tgattgttat | aaaaaatatc | ttgtatgtga | 360 |
| tccagatcac | atctatcatt | tagttatcga | tcgttaagta | attgcttgcg | acgtcattca | 420 |
| tctgcataag | gccactatta | tgaaaaacgt | aaaaccctc | atcgctgcgg | cgattttaag | 480 |
| ctccatgtca | tttgccagct | ttgcggctgt | cgaagttcag | tcaacgccag | aaggccaaca | 540 |
| aaaagtcggt | acaatcagtg | ctaacgcggg | gacaaatctg | ggatcgctgg | aagagcagct | 600 |
| ggcgcaaaaa | gcggatgaga | tgggcgcaaa | atctttccgt | attacttctg | taaccggtcc | 660 |
| gaatacccctc | catggaacag | cagtaattta | taaataagca | ttaaccctca | ttaatgcctg | 720 |
| ctactgctga | ttttttcccc | gcgacatgcc | gtgtcgcggg | gattttttta | tccgggcttt | 780 |
| acagcgtttg | tgggctcact | tgatgacggc | ggacatccac | cggcatcccg | gaacggacat | 840 |
| ccatcacatg | ttgcatcact | tcagcgtcag | tttgtgctgc | atctttaaat | gattgcattg | 900 |
| cgctattcag | cgtaattggc | agcagctgcg | gatcgtcatc | aatcttctct | gacagcggct | 960 |
| gatgtacttc | aaccagacgc | gcaccgtttg | gttcggcaga | gacttttatc | ggagtgttga | 1020 |
| tgatattcac | tttggtgcct | ggggtgacct | ggctaaagag | tgttttgata | tcgtcatccc | 1080 |
| gcagacgaat | acagccagaa | cttacccgca | tgccaatgcc | gaaatcggcg | ttcgtaccat | 1140 |
| gaagcaaata | aacgccgcca | taggccgcca | gacgaatcgc | atgatggccc | attgggttat | 1200 |
| ccggtccagc | cggcactacc | gcaggcaact | caattccctg | tgctttataa | cgggcgcgga | 1260 |
| tgtttgccgt | tggcgtccag | gttgggtttg | cacgtttgtc | tgaaacggtg | gtcaccattg | 1320 |
| tcggtgtcag | cgtgtcacca | cctaactgac | caatacctat | tggatacacg | gttaccgaat | 1380 |
| ttttacccgg | cgggtagtaa | tagagacgca | gctccgcaat | gttgatcaca | atgccttcgc | 1440 |
| gcggcgcatc | tggaagtagg | gtttgcaacg | ggatcgttaa | cacgctgccc | gcgcgcggta | 1500 |
| cgtaaggatc | aacgccgggg | ttagcctgta | acagagcgag | aaagccgacg | ttgtattttt | 1560 |
| tggcgatggc | ttccagagaa | ccaccgtcat | tttccaccac | atgaaatttg | ttttcgccaa | 1620 |
| ccagacgact | gcccgctggc | ggcagcggcc | aggtgttggc | ttttgccggt | agcgccagcg | 1680 |
| ccacggcagc | ggcgaacgta | aaaaacgtta | gccagcgaga | aaacgcgtt | ttgatcatca | 1740 |
| ccaaaaatcc | ataataaata | taaggttatt | gtaataaaca | gataagcctg | aattatggat | 1800 |
| ggtgacagtg | tcggatagtg | cagggaagtg | caaagaattt | gtaaatgttg | cagatggggg | 1860 |
| cgcagaaacg | cccccgattt | accattaagc | gatcgcgttc | tcttccagtt | cacgcataaa | 1920 |
| ctggcgtacc | cattcgatac | gcgttttccg | ctcactcaaa | tcctgaataa | atttcaggcg | 1980 |
| cgtcggacca | tcaaggcggt | aatgctgcgg | ctgttttttgc | agcaaaccaa | tcaaccaggc | 2040 |
| cggattaacg | tgattcttct | cggcaaattc | gatcaccccg | cctttctcat | taccttccag | 2100 |
| cttcctgatc | cccagtttct | gcgcttgctg | gcgcagacgg | gcaatatcca | gcagggtacg | 2160 |

```
cgccggatct ggcagcaggc cgaagcgatc gataagctcg actttgatct cttccagttc    2220
gttttccgtt ttggcgctgg caatacgttt gtagaacgac agacgcgtgt tcacgtcagg    2280
gatgaaatca tctggcaata gcgacggcat ccgcagctcg acttctgttt gctggctggt    2340
gagatcttcc agcgacggct cgcgtccggc tttcagtgca tcgacggcgt tttccagcaa    2400
ctccatatac agcgagaaac cgatggtttc cattgagccg ctttgttctt cgccaagcag    2460
ttcacccgcg ccgcgaatct ccagatcgtg cgttgccagc gcaaaacctg ccccgagatc    2520
ttccagcgag gcaattgctt caagacgttt ttgtgcatcg gtagtcatcg cttttggatg    2580
cggtgtcagc aaccatgcat atgcctgatg atgcgaacgt ccgacgcgac cgcgtaactg    2640
gtgcagctgc gccagaccga agtgatccgc gcgttcaatg ataatagtgt tggctgtcgg    2700
gatgtcgatc ccggtttcga taatggttgt acaaaccagc acgttgaaac gttgatgatg    2760
gaaatcattc atcacccgtt ccagttcgcg ctcgcgcatc tgcccgtgac cgatggcgat    2820
ccgcgcttct ggaccagtt ctgccagccg ttcggcggct ttctgaatgt tttccacatc    2880
attgtagaga taataaacct gtcctccgcg caaaatttca cgcaggatcg cctcccggac    2940
caccatgctg tcatactcac ggacaaaggt tttaactgcc agacgacggg cgggcggcgt    3000
ggcgataatc gacaggtcac gcattccgct cattgccata ttcagcgtac gtgggatcgg    3060
cgttgcagta agcgtcagaa tatccacgtt cgcgcgcatc gctttaatgc gctctttatg    3120
acgcaccccg aagcggtgtt cttcatcgac aatcagcagg cctaaatctt taaacttgac    3180
gtcactttgc agcagtttgt gcgtaccgat cagaatatcg attttccctt ccgccacttc    3240
cgcaaggatt tgcgtctgct ctttggcgct gcggaaacgg gagatcattt cgatacgtac    3300
cggccagttg gcgaaacggt cgcggaagtt gtcgtaatgc tgctgcgcga aagggtggt    3360
aggcaccagc accgccacct gcttgtggtt atctactgcc aggaaagctg cgcgcatcgc    3420
cacttctgtt ttaccaaagc caacatcgcc gcacaccaga cgatccattg ccagcggctg    3480
acacatgtcg ctaagtaccg cattaatggc ctgcgcctga tccggcgtgg tttcaaacgg    3540
gaagctgtcg cagaacaact gatactgctc acgatcgtat ttaaacgcga agccctcttt    3600
ggcggcgcgt tgcgcgtaga tatccagcaa ttccgccgcc acatcacgca ctttttccgc    3660
cgctttctgc cgcgcgcgtg accacgcatc gccgccaagt ttatgcagcg ggcgttttc    3720
ttccgcgcca cctgcgtaac ggctaatcag atgcagtgac gacaccggaa catacagttt    3780
ggcgtcgttg gcataggtga gcatcagata ctcgccagta atgccacccg cttccagcgt    3840
ggtcattccg gcataacgac cgacgccgtg ctccagatgg accaccggct gaccaatatg    3900
cagttccgca aggttacgga tcagtgtatc ggggttgatg gtgcggcgag aatcctgacg    3960
acgacgggca acgcgttcac cgagcagatc gctttcgcaa atcagcgcca gattacgcac    4020
cgtatcgaca aaaccatgtt cggcagcgcc aatcatcaga taacgcccac ggtcgctggc    4080
ttcatcaaga cgcataatgc gttgcggagc aattttaatt cgtgcgagca gttcacccag    4140
cgcttcacgg cgaccttcac tttctaccga gaacaccacc ggaccgtcga agtctcgag    4200
gaacttacgc agcgcatcca gcggcgcttt ttgttgtgcc tgaacggcca ggtctggcag    4260
tttctggaaa cctaaattgg cattcgcggc ttttgtcggt aaatgttcag tttttagctg    4320
caccccgggc cagttttttca gctctgagaa gagctcgtcc acccgcagcc agagcgattg    4380
tggtggcaac agcgggcgca tcggatcgac gccgcgattc tcaaaacgcg ccagcgtgtc    4440
agcctggaaa cgttcggcac tggtttccag atcgccagta ttcacgagca aggtattggc    4500
```

```
agggaaataa ctgaacagcg gcagcagtgg ttcgctgaag aacaatggct gccagtactc    4560
gatcccggca ggtaatgtgc ctttactcac ttgctggtaa atatgttctg gatcgcgctt    4620
cacttcgaag gtatcgcgcc actggctgcg gaacagttca attgccgctt tatcggtcgg    4680
aaattcgtgc gcgggcagca gattgatcgc ttctacttcc tccagcgtgc gctggctgtc    4740
gacgtcaaac acccgcaggc tgtcgatttc atcatcaaag aaatcaagac gataaggcag    4800
ctcactcccc atcgggaaga gatccagcaa cgcgccgcgc gtggcgtatt cgccgtgctc    4860
catcacctgg tcaacatggc gataaccggc gctgtccagt tgggttcgta atgcatctcg    4920
tgacaggcgc tgaccttttt tcatcaccag cgcatgaccg tggagaaaac tgtgtgggca    4980
aacgcgctgc ataagcgtat tcaccggaac aatcagtacg ccacgctgca tcgtcggtag    5040
ctggtaaagg gtggaaaggc gcgaggagat aatgtcctga tgaggcgaaa aactgtcgta    5100
gggaagagtt tcccagtccg ccagattcat caccatttga tcggtaaact ggctgatttc    5160
atcatgcaaa cgcagagcat tttgcatatc tggtgcaatg agtaccaccg gaccggcgtg    5220
acgttcggca atttccgcta ccagcgttgc acaggctgcg ccggttaact cgcccagcag    5280
acgctgctca cccgctttga cgggcagcgt ataacgatat tgttcaggca t             5331
```

<210> SEQ ID NO 105
<211> LENGTH: 85
<212> TYPE: PRT
<213> ORGANISM: Escherichia coli

<400> SEQUENCE: 105

```
Met Lys Asn Val Lys Thr Leu Ile Ala Ala Ile Leu Ser Ser Met
1               5                   10                  15

Ser Phe Ala Ser Phe Ala Ala Val Glu Val Gln Ser Thr Pro Glu Gly
                20                  25                  30

Gln Gln Lys Val Gly Thr Ile Ser Ala Asn Ala Gly Thr Asn Leu Gly
            35                  40                  45

Ser Leu Glu Glu Gln Leu Ala Gln Lys Ala Asp Glu Met Gly Ala Lys
        50                  55                  60

Ser Phe Arg Ile Thr Ser Val Thr Gly Pro Asn Thr Leu His Gly Thr
65                  70                  75                  80

Ala Val Ile Tyr Lys
                85
```

<210> SEQ ID NO 106
<211> LENGTH: 320
<212> TYPE: PRT
<213> ORGANISM: Escherichia coli

<400> SEQUENCE: 106

```
Met Met Ile Lys Thr Arg Phe Ser Arg Trp Leu Thr Phe Phe Thr Phe
1               5                   10                  15

Ala Ala Ala Val Ala Leu Ala Leu Pro Ala Lys Ala Asn Thr Trp Pro
                20                  25                  30

Leu Pro Pro Ala Gly Ser Arg Leu Val Gly Glu Asn Lys Phe His Val
            35                  40                  45

Val Glu Asn Asp Gly Gly Ser Leu Glu Ala Ile Ala Lys Lys Tyr Asn
        50                  55                  60

Val Gly Phe Leu Ala Leu Leu Gln Ala Asn Pro Gly Val Asp Pro Tyr
65                  70                  75                  80

Val Pro Arg Ala Gly Ser Val Leu Thr Ile Pro Leu Gln Thr Leu Leu
                85                  90                  95
```

Pro Asp Ala Pro Arg Glu Gly Ile Val Ile Asn Ile Ala Glu Leu Arg
                100                 105                 110

Leu Tyr Tyr Tyr Pro Pro Gly Lys Asn Ser Val Thr Val Tyr Pro Ile
            115                 120                 125

Gly Ile Gly Gln Leu Gly Gly Asp Thr Leu Thr Pro Thr Met Val Thr
130                 135                 140

Thr Val Ser Asp Lys Arg Ala Asn Pro Thr Trp Thr Pro Thr Ala Asn
145                 150                 155                 160

Ile Arg Ala Arg Tyr Lys Ala Gln Gly Ile Glu Leu Pro Ala Val Val
                165                 170                 175

Pro Ala Gly Pro Asp Asn Pro Met Gly His His Ala Ile Arg Leu Ala
            180                 185                 190

Ala Tyr Gly Gly Val Tyr Leu Leu His Gly Thr Asn Ala Asp Phe Gly
        195                 200                 205

Ile Gly Met Arg Val Ser Ser Gly Cys Ile Arg Leu Arg Asp Asp Asp
210                 215                 220

Ile Lys Thr Leu Phe Ser Gln Val Thr Pro Gly Thr Lys Val Asn Ile
225                 230                 235                 240

Ile Asn Thr Pro Ile Lys Val Ser Ala Glu Pro Asn Gly Ala Arg Leu
                245                 250                 255

Val Glu Val His Gln Pro Leu Ser Glu Lys Ile Asp Asp Pro Gln
            260                 265                 270

Leu Leu Pro Ile Thr Leu Asn Ser Ala Met Gln Ser Phe Lys Asp Ala
        275                 280                 285

Ala Gln Thr Asp Ala Glu Val Met Gln His Val Met Asp Val Arg Ser
290                 295                 300

Gly Met Pro Val Asp Val Arg Arg His Gln Val Ser Pro Gln Thr Leu
305                 310                 315                 320

<210> SEQ ID NO 107
<211> LENGTH: 4553
<212> TYPE: DNA
<213> ORGANISM: Escherichia coli

<400> SEQUENCE: 107
cggtgcgctg ttcagcgaaa accggcgttg gtgtgcagga cgttctcgaa cgtctggtgc      60
gcgacattcc gccgccggaa ggcgatccgg aaggcccgtt gcaggcacta attatcgact     120
catggttcga caactacctg gcgttgtttc acttatccg tattaaaaac ggcaccctgc     180
gtaagggcga caaagtgaaa gtcatgagta ccgggcagac ctataacgcc gaccgtctgg     240
gcatcttcac gccgaaacag gttgaccgca ctgaactgaa atgtggcgaa gtaggctggc     300
tcgtatgtgc gattaaagat atccacggcg ctccagtcgg cgatacctta acgctggcgc     360
gtaatccggc agaaaaggcg ctgcctggct ttaagaaagt caaaccgcag gtatacgccg     420
gtctgttccc ggtaagttcc gacgactatg aagccttccg tgacgcgctg gtaaactca     480
gcctgaacga tgcctcactg ttctatgagc cggaaagctc cagcgcgctg ggctttggtt     540
tccgctgcgg cttcctcggc ctgctgcaca tggagatcat ccaggaacgt ctggaacgtg     600
aatacgatct ggatcgatc accactgcgc cgaccgtagt gtatgaagtt gaaaccacgt     660
caagagaagt tatctacgtc gacagcccat ccaagctgcc tgcggtaaat aacatctacg     720
aactgcgcga ccgattgca gagtgtcaca tgctgctgcc gcaggcatat ctcggcaacg     780
ttattacgtt gtgcgtagaa aaacgcggcg tgcagaccaa tatggtttac cacggtaatc     840

```
aggtggcgct gacgtacgag atcccgatgg cggaagtggt gctcgacttc ttcgatcgcc    900
tgaaatctac ctcgcgtggt tatgcgtctc tggattacaa cttcaagcgc ttccaggcgt    960
ccgacatggt acgtgtagac gtattaatca acggtgaacg tgttgatgcg ctggcgttga   1020
tcacccaccg tgataattcg caaaaccgcg gtcgcgagtt ggtggagaag atgaaagatc   1080
tgatcccacg ccagcagttt gatatcgcca ttcaggcagc gattggtacg cacatcattg   1140
cgcgatccac cgtgaaacag ctgcgtaaaa acgtactggc taaatgttat ggcggcgata   1200
tcagccgtaa gaaaaagctg ctgcagaagc agaaagaagg taagaaacgc atgaagcaga   1260
tcggtaacgt cgagctgccg caggaagcgt tcctcgccat tctgcacgtc ggcaaagaca   1320
acaaataacc cttaggagtt ggcatggcga atatgtttgc cctgattctg gtgattgcca   1380
cactggtgac gggcatttta tggtgcgtgg ataaattctt tttcgcacct aaacggcggg   1440
aacgtcaggc agcggcgcag gcggctgccg gggactcact ggataaagca acgttgaaaa   1500
aggttgcgcc gaagcctggc tggctggaaa ccggtgcttc tgttttccg gtactggcta   1560
tcgtattgat tgtgcgttcg tttatttatg aaccgttcca gatcccgtca ggttcgatga   1620
tgccgactct gttaattggt gattttattc tggtagagaa gtttgcttat ggcattaaag   1680
atcctatcta ccagaaaacg ctgatcgaaa ccggtcatcc gaaacgcggc gatatcgtgg   1740
tctttaaata tccggaagat ccaaagcttg attacatcaa gcgcgcggtg ggtttaccgg   1800
gcgataaagt cacttacgat ccggtctcaa aagagctgac gattcaaccg ggatgcagtt   1860
ccggccaggc gtgtgaaaac gcgctgccgg tcacctactc aaacgtggaa ccgagcgatt   1920
tcgttcagac cttctcacgc cgtaatggtg gggaagcgac cagcggattc tttgaagtgc   1980
cgaaaaacga aaccaaagaa aatggaattc gtctttccga gcgtaaagag acactgggtg   2040
atgtgacgca ccgcattctg acagtgccga ttgcgcagga tcaggtgggg atgtattacc   2100
agcagccagg gcaacaactg gcaacctgga ttgttcctcc gggacaatac ttcatgatgg   2160
gcgacaaccg cgacaacagc gcggacagcc gttactgggg cttttgtgccg gaagcgaatc   2220
tggtcggtcg ggcaacggct atctggatga gcttcgataa gcaagaaggc gaatggccga   2280
ctggtctgcg cttaagtcgc attggcggca tccattaata gccatcttcg ttcacgttgt   2340
cgccgttatg gcgacaacgt gaattatta tgagataaat ctcccgtggc taacgacatc   2400
ccccgtcgtt gtgtatagaa tattcccccg aagtttaagg ttggcacctc caggttgcca   2460
cggcacacga aacagcgttg gtccccatat accggtaaac tgaaactgca gcgaagcagt   2520
tagcagaacc atgtatatca ggtctgtttc gtgtgctgaa ttgttgacgc atttatttat   2580
tggtatcgca tgaaccccat cgtaattaat cggcttcaac ggaagctggg ctacacttt   2640
aatcatcagg aactgttgca gcaggcatta actcatcgta gtgccagcag taaacataac   2700
gagcgtttag aattttagg cgactctatt ctgagctacg ttatcgccaa tgcgctttat   2760
caccgtttcc ctcgtgtgga tgaaggcgat atgagccgga tgcgcgccac gctggtccgt   2820
ggcaatacgc tggcggaact ggcgcgcgaa tttgagttag gcgagtgctt acgtttaggg   2880
ccaggtgaac ttaaaagcgg tggatttcgt cgtgagtcaa ttctcgccga caccgtcgaa   2940
gcattaattg gtggcgtatt cctcgacagt gatattcaaa ccgtcgagaa attaatcctc   3000
aactggtatc aaactcgttt ggacgaaatt agcccaggcg ataaacaaaa agatccgaaa   3060
acgcgcttgc aagaatattt gcagggtcgc catctgccgc tgccgactta tctggtagtc   3120
caggtacgtg gcgaagcgca cgatcaggaa tttactatcc actgccaggt cagcggcctg   3180
agtgaaccgg tggttggcac aggttcaagc cgtcgtaagg ctgagcaggc tgccgccgaa   3240
```

```
caggcgttga aaaaactgga gctggaatga gcatcgataa aagttactgc ggatttattg    3300
ccatcgtcgg acgtccgaac gttggcaaat ccacattgtt gaacaaactg ctggggcaga    3360
aaatctccat cacttcccgc aaggcgcaga caactcgtca ccgcattgtg gggatccata    3420
ctgaaggcgc gtatcaggcg atctacgtcg atacaccggg cctgcatatg gaagaaaaac    3480
gcgccattaa ccgcctgatg aacaaagcgg cgagcagctc tattggcgat gttgagctgg    3540 tgattttgt cgttgaaggc acccgctgga cgccggacga cgaaatggtg ctcaacaaac    3600
tgcgcgaagg caaagcgccg gtaatcctcg cggtgaacaa agtggacaac gtgcaggaga    3660
aagccgatct gctgccgcac ctgcagttcc tggcaagcca gatgaacttc ctcgatatcg    3720
tgccaatctc tgccgaaacc gggctgaatg ttgacactat tgcggcaatc gtgcgtaagc    3780
atctacctga agcgactcat cacttcccgg aagattacat caccgatcgc tcacagcgtt    3840
ttatggcgtc tgaaatcatc cgcgaaaaac tgatgcgttt cctcggcgct gaactgccgt    3900
actccgtgac cgtggagatc gaacgtttcg tctctaacga acgcggtggt tatgacatca    3960
acggtttgat tctcgttgag cgtgaagggc agaagaagat ggtcattggc aacaaagggg    4020
ccaagatcaa aaccatcggg attgaagcgc gtaaagacat gcaggaaatg ttcgaagcgc    4080
ctgttcacct tgaactgtgg gtaaaagtga atccggttg ggccgacgac gaacgcgcac    4140
tgcgcagtct cggttacgtt gacgatcttt aagagtaact ccgatggaag gctggcagcg    4200
cgcatttgtc ctgcatagtc gcccgtggag cgaaaccagc ctgatgctgg acgtcttcac    4260
ggaggaatcg gggcgcgtgc gtctggttgc caaaggcgca cgctctaaac gctctaccct    4320
gaaaggtgca ttacagcctt tcaccctct cttgctacgt tttggcgggc gtggcgaagt    4380
caaaacgctg cgcagtgctg aagccgtctc gctggcgctg ccattaagcg gtatcacgct    4440
ttacagcggt ctgtacatca cgaacttct ctcccgcgta ctggaatacg agacgcgctt    4500
ctctgaactt tttttcgatt acttgcactg cattcagtct cttgcagggg tca           4553
```

<210> SEQ ID NO 108
<211> LENGTH: 324
<212> TYPE: PRT
<213> ORGANISM: Escherichia coli

<400> SEQUENCE: 108

```
Met Ala Asn Met Phe Ala Leu Ile Leu Val Ile Ala Thr Leu Val Thr
1               5                   10                  15

Gly Ile Leu Trp Cys Val Asp Lys Phe Phe Phe Ala Pro Lys Arg Arg
            20                  25                  30

Glu Arg Gln Ala Ala Ala Gln Ala Ala Ala Gly Asp Ser Leu Asp Lys
        35                  40                  45

Ala Thr Leu Lys Lys Val Ala Pro Lys Pro Gly Trp Leu Glu Thr Gly
    50                  55                  60

Ala Ser Val Phe Pro Val Leu Ala Ile Val Leu Ile Val Arg Ser Phe
65                  70                  75                  80

Ile Tyr Glu Pro Phe Gln Ile Pro Ser Gly Ser Met Met Pro Thr Leu
                85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Lys Leu Asp Tyr
    130                 135                 140
```

```
Ile Lys Arg Ala Val Gly Leu Pro Gly Asp Lys Val Thr Tyr Asp Pro
145                 150                 155                 160

Val Ser Lys Glu Leu Thr Ile Gln Pro Gly Cys Ser Ser Gly Gln Ala
                165                 170                 175

Cys Glu Asn Ala Leu Pro Val Thr Tyr Ser Asn Val Glu Pro Ser Asp
            180                 185                 190

Phe Val Gln Thr Phe Ser Arg Arg Asn Gly Gly Glu Ala Thr Ser Gly
        195                 200                 205

Phe Phe Glu Val Pro Lys Asn Glu Thr Lys Glu Asn Gly Ile Arg Leu
210                 215                 220

Ser Glu Arg Lys Glu Thr Leu Gly Asp Val Thr His Arg Ile Leu Thr
225                 230                 235                 240

Val Pro Ile Ala Gln Asp Gln Val Gly Met Tyr Tyr Gln Gln Pro Gly
                245                 250                 255

Gln Gln Leu Ala Thr Trp Ile Val Pro Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Arg Ala Thr Ala Ile Trp Met Ser Phe
290                 295                 300

Asp Lys Gln Glu Gly Glu Trp Pro Thr Gly Leu Arg Leu Ser Arg Ile
305                 310                 315                 320

Gly Gly Ile His

<210> SEQ ID NO 109
<211> LENGTH: 226
<212> TYPE: PRT
<213> ORGANISM: Escherichia coli

<400> SEQUENCE: 109

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
                20                  25                  30

Ser Ser Lys His Asn Glu Arg Leu Glu Phe Leu Gly Asp Ser Ile Leu
            35                  40                  45

Ser Tyr Val Ile Ala Asn Ala Leu Tyr His Arg Phe Pro Arg Val Asp
        50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190
```

Gln Val Ser Gly Leu Ser Glu Pro Val Gly Thr Gly Ser Ser Arg
    195                 200                 205

Arg Lys Ala Glu Gln Ala Ala Glu Gln Ala Leu Lys Lys Leu Glu
210                 215                 220

Leu Glu
225

<210> SEQ ID NO 110
<211> LENGTH: 301
<212> TYPE: PRT
<213> ORGANISM: Escherichia coli

<400> SEQUENCE: 110

Met Ser Ile Asp Lys Ser Tyr Cys Gly Phe Ile Ala Ile Val Gly Arg
1               5                   10                  15

Pro Asn Val Gly Lys Ser Thr Leu Leu Asn Lys Leu Leu Gly Gln Lys
            20                  25                  30

Ile Ser Ile Thr Ser Arg Lys Ala Gln Thr Thr Arg His Arg Ile Val
        35                  40                  45

Gly Ile His Thr Glu Gly Ala Tyr Gln Ala Ile Tyr Val Asp Thr Pro
    50                  55                  60

Gly Leu His Met Glu Glu Lys Arg Ala Ile Asn Arg Leu Met Asn Lys
65                  70                  75                  80

Ala Ala Ser Ser Ser Ile Gly Asp Val Glu Leu Val Ile Phe Val Val
                85                  90                  95

Glu Gly Thr Arg Trp Thr Pro Asp Asp Glu Met Val Leu Asn Lys Leu
            100                 105                 110

Arg Glu Gly Lys Ala Pro Val Ile Leu Ala Val Asn Lys Val Asp Asn
        115                 120                 125

Val Gln Glu Lys Ala Asp Leu Leu Pro His Leu Gln Phe Leu Ala Ser
    130                 135                 140

Gln Met Asn Phe Leu Asp Ile Val Pro Ile Ser Ala Glu Thr Gly Leu
145                 150                 155                 160

Asn Val Asp Thr Ile Ala Ala Ile Val Arg Lys His Leu Pro Glu Ala
                165                 170                 175

Thr His His Phe Pro Glu Asp Tyr Ile Thr Asp Arg Ser Gln Arg Phe
            180                 185                 190

Met Ala Ser Glu Ile Ile Arg Glu Lys Leu Met Arg Phe Leu Gly Ala
        195                 200                 205

Glu Leu Pro Tyr Ser Val Thr Val Glu Ile Glu Arg Phe Val Ser Asn
    210                 215                 220

Glu Arg Gly Gly Tyr Asp Ile Asn Gly Leu Ile Leu Val Glu Arg Glu
225                 230                 235                 240

Gly Gln Lys Lys Met Val Ile Gly Asn Lys Gly Ala Lys Ile Lys Thr
                245                 250                 255

Ile Gly Ile Glu Ala Arg Lys Asp Met Gln Glu Met Phe Glu Ala Pro
            260                 265                 270

Val His Leu Glu Leu Trp Val Lys Val Lys Ser Gly Trp Ala Asp Asp
        275                 280                 285

Glu Arg Ala Leu Arg Ser Leu Gly Tyr Val Asp Asp Leu
    290                 295                 300

<210> SEQ ID NO 111
<211> LENGTH: 5262
<212> TYPE: DNA

<213> ORGANISM: Escherichia coli

<400> SEQUENCE: 111

| | | | | | |
|---|---|---|---|---|---|
| tataagttac | ggccatgttg | ccctgcgaac | gggtgctgtc | ggtcactttc | atgcccactt | 60 |
| tttccagcgc | cgctggcaga | cgttgccaaa | ccacattgaa | cggcccgcgt | acgaccagca | 120 |
| ttggtaaacc | ggtgtcatca | gctgcacttt | gtacgtccat | agtggtggag | gcacgatttt | 180 |
| gcgcagcgtt | cgcggcgtca | gtggcagatt | tatccagacc | ggcggaaata | acgttcatca | 240 |
| tctccgtgct | gtaacgctgc | atggaagccg | cgtctgcaac | cggtttgccc | gcctgttcca | 300 |
| ggttcagcag | tttaaccgta | accgctgct | gataaccctg | cggcttaaca | gagatttgat | 360 |
| aacgaccacg | atactgctcg | tcttcgtcca | gacggttcca | ttgtacccaa | tcggtggtca | 420 |
| gtgtctgacc | agcatcatca | cgttgggtga | tggtgtagtt | tttcgcctgc | agcacgctaa | 480 |
| ccacctgcgg | ccacagagta | ttgccacgac | cattttccac | cagcaatgaa | gcggtatcgc | 540 |
| ccgtgaactg | ggtacgcgcg | ccagaaacca | gtgccagcgg | ctgggctggt | ggacgaatgt | 600 |
| ccagcgcctt | accgacagca | ccactaccgt | tggtcaccgg | gattgcataa | tcaccggagg | 660 |
| tcaccggcaa | aatcattcca | gccggggcat | gaagctccgc | aagcggtgcc | gcttccaggt | 720 |
| aggcttcatc | accactgacc | tgacgcttat | agcgtgagtc | agaactacag | gcagcgagta | 780 |
| ataaaacaag | cgaaacaccc | gcaacctttg | ccaggcgcga | cttttgaaca | gagtaagcca | 840 |
| tcaaatctcc | ctaaacttta | cagcaaaccg | gcatgcttaa | gcgccgctct | gaccgtctca | 900 |
| cgaccactgt | cggtgattgg | tgtcattggc | aggcgcagcg | tatcggtcgc | cacaagaccc | 960 |
| agttccttac | atgcccattt | caccgggatt | ggattgggtt | cgacaaatag | tttgttgtgt | 1020 |
| aatggcatca | gacgctgatt | aataacgcgt | gcctcggcaa | aatgcccttc | tgctgccagt | 1080 |
| ttgcacatct | gggccatatc | acgcgctgcg | acgttagccg | taacggaaat | aaccccatga | 1140 |
| ccgcccaatt | gcatgaagtc | cagcgcgctc | gcatcatcgc | cgctcagcag | aacaaaatca | 1200 |
| tctgaaacca | gctctttgat | ctggtttaca | cgcgttaagt | tccctgttgc | ctctttgatt | 1260 |
| ccgataatat | tttttacttt | cgccagacgg | cccaccgttt | ccgggagcag | atcgcagcca | 1320 |
| gtacgggacg | gcacattata | cagaatttgc | ggcaggtcag | tatgctcagc | gatggctttg | 1380 |
| aaatgctgat | acaaaccttc | ttgcgacgga | cgattgtagt | aaggggttac | cgtcaggcag | 1440 |
| ccgacgatac | cactgtcatt | gaagcgctgc | gtcaggctaa | tggcttccgc | agtagcgtta | 1500 |
| gcgccggtcc | cggcaattac | cggaatgcgc | ccatcagcca | gatccagcgt | catcatcacc | 1560 |
| acatcagcat | gttcgtcatg | atttaaggta | gcggactcgc | cagtggtgcc | aacagaaacg | 1620 |
| atcgccgaag | taccgctggc | gacatgataa | tcaatcagtt | ttttcaagct | agcccgacag | 1680 |
| acattacctt | tttcatccat | cggagtaaca | atcgcgacaa | tacttcccgt | gaacatgggc | 1740 |
| catcctctgt | gcaaacaagt | gtctcaatgg | tacgtttggt | atggcattaa | aagcaagcag | 1800 |
| acagaaccgt | tctgattgtt | gtatgcatgt | ttttttatg | ctttccttaa | gaacaactca | 1860 |
| cccccttaaag | gaataaccag | tttgacactg | tcatcgcaac | attatctggt | gatcactgcg | 1920 |
| ttgggtgccg | atcgccctgg | aattgtgaac | accatcaccc | gtcatgtcag | tagttgcggc | 1980 |
| tgtaatattg | aagacagtcg | cctggcgatg | ctggagaag | agttcacgtt | tattatgctg | 2040 |
| ctttccggtt | catggaatgc | cattactctg | attgaatcaa | cgttaccgtt | gaaaggtgcc | 2100 |
| gaactggatc | ttttaatcgt | gatgaagcgc | acgacggcgc | gtccgcgtcc | gccaatgcca | 2160 |
| gcatctgtct | gggttcaggt | cgatgtgcca | gactccccgc | atttaattga | acgcttcaca | 2220 |
| gcacttttcg | acgcgcatca | tatgaacatt | gcggagctgg | tgtcgcgcac | gcaacctgct | 2280 |

-continued

```
gaaaatgaac gggctgcgca gttgcatatt cagataaccg cccacagccc cgcatctgcg    2340
gacgcagcaa atattgagca agcgttcaaa gccctatgta cagaactcaa tgcacaaggc    2400
agtattaacg tcgtcaatta ttcccaacat gatgaacagg atggagttaa gtaatgaatc    2460
cactgaaagc cggtgatatc gcaccgaaat ttagcttgcc ggatcaagac ggagaacaag    2520
ttaatttgac cgacttccag ggacagcgtg ttctggttta tttctacccg aaagccatga    2580
cccccggctg taccgtacag gcctgcggct tacgcgataa catggatgag ttgaaaaaag    2640
cgggcgttga tgtgctgggt atcagcaccg ataaacccga aaactctccc gttttgcgg    2700 aaaaagagct gcttaacttt acgctcctgt ctgatgagga ccaccaggtg tgcgaacaat    2760
tcggcgtctg gggtgaaaag tccttcatgg gcaaaaccta cgatggcatt catcgcatca    2820
gcttcctgat tgacgctgat ggcaaaatcg aacatgtctt tgacgatttc aaaaccagca    2880
atcaccacga cgttgtgctg aactggctga agaacacgc ctgattactt tgctccattc    2940
cgtgctggct gcgcttgcgg ccagcatacc tcacttctcg tgatcaagat cacattctcg    3000 cttttcccctg cgacacgggt gtcgaatcca tttttttgctg aacgttaatg accatcattt    3060
ttgtaccgtt cagaatccag ttaatacata acttattgaa tatattgagt taatcagaat    3120
ggcatccttt atgcaatatg aaatgcaatg tttcatatca ttttcaagga gccgacatga    3180
accgctttgt ggtggccgaa ccactgtggt gtacaggatg taatacctgt ctcgctgcct    3240
gttcggacgt gcataaaacg caaggtttac agcaacaccc gcgcctggcc ctggcgaaga    3300
cgtcaacaat cactgcccct gtcgtgtgtc atcactgtga ggaagcccct tgcctgcagg    3360
tctgcccggt caatgccatc tctcagaggg atgatgcgat ccaactcaac gaaagcctct    3420
gtattggctg caagctttgc gccgtggtct gcccatttgg cgcaatcagc gcttcaggaa    3480
gccgtccggt gaatgcccat gcgcaatatg tttttcaggc tgaaggctca ctcaaagacg    3540
gcgaagaaaa cgcgccaaca caacatgctt tgctgcgctg ggaacctggt gtccagaccg    3600
tcgcggtgaa atgcgacctg tgtgatttct tgccagaagg tccggcctgc gttcgcgctt    3660
gcccgaatca ggcgttacgg ctgatcaccg gtgatagcct gcaacgtcag atgaaagaaa    3720
aacagcgcct tgccgcaagc tggtttgcca atggcggga ggatcccctt tccctcactc    3780
aggagcaacg ctaatggatg ccctgcaatt attaacctgg tcgctgattc tctatctgtt    3840
tgctagtctg gcttcgctgt ttttactcgg tctggacaga ctggctatta agcttttccgg    3900 catcacatcg ctggtgggcg gcgtgattgg catcatcagc ggaattacgc aattacatgc    3960
tggtgtaact ttagtcgccc gttttgccac cccttttgaa tttgccgatt taaccctgcg    4020
aatggatagc ctctcggcat ttatggtgct ggttatctcc ttgctggtgg tggtttgttc    4080
tctctattca ttgacttata tgcgcgaata cgagggcaaa ggcgcggcgg cgatgggctt    4140
ctttatgaat attttcatcg catcgatggt tgccctgctg gtgatggaca acgctttttg    4200
gttcatcgtg ctgtttgaaa tgatgtcgct gtcttcctgg tttctggtca ttgccaggca    4260
ggataaaacg tcgatcaacg ctggcatgct ctactttttt atcgcccacg ccggatcggt    4320
gctgataatg atcgccttct tgctgatggg gcgcgaaagc ggcagcctcg attttgccag    4380
tttccgcacg ctttcacttt ctccgggct ggcgtcggcg tgttcctgc tggccttttt    4440 cggttttggc gcgaaagccg ggatgatgcc gttgcacagc tggttgccgc gcgctcaccc    4500
tgccgcacca tcgcacgctt cggcgttgat gtctggcgta atggtcaaaa taggtatttt    4560
cggcatcctg aaagtagcga tggatctgct ggcgcaaacg ggtttgcctc tgtggtgggg    4620
```

```
cattctggtg atggcgatcg gcgcaatctc cgcgctcctg ggcgtgctat atgcgctggc    4680
ggaacaggat atcaaacggc tgctggcctg gagtaccgtc gaaaacgtcg gcattatttt    4740
gctggcagtc ggtgtggcga tggtcggtct gtcactgcac gacccgctgc tcaccgtggt    4800
tggactgctc ggcgcactgt ttcatctgct caaccatgcg ctgttcaaag gctgctatt     4860 tctcggcgcg ggagcgatta tttcgcgttt gcatacccac gacatggaaa aaatgggggc    4920
actagcgaaa cggatgccgt ggacagccgc agcatgcctg attggttgcc tcgcgatatc    4980
agccattcct ccgctgaatg gttttatcag cgaatggtac acctggcagt cgctgttctc    5040
actaagtcgt gtggaagccg tagcgctaca acttgcgggt cctattgcta tggtaatgct    5100
ggcagtcact ggtgggctgg cagtaatgtg cttcgtaaaa atgtacggta ttactttctg    5160
tggtgcgccg cgcagtacac acgctgaaga ggcacaggaa gtgccaaata cgatgatcgt    5220
cgccatgcta ctgctcgcgg cactctgcgt attaattgcg ct                      5262
```

<210> SEQ ID NO 112
<211> LENGTH: 292
<212> TYPE: PRT
<213> ORGANISM: Escherichia coli

<400> SEQUENCE: 112

```
Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
```

```
                    260                 265                 270
Pro Ile Thr Asp Ser Gly Arg Glu Thr Val Arg Ala Ala Leu Lys His
            275                 280                 285

Ala Gly Leu Leu
        290

<210> SEQ ID NO 113
<211> LENGTH: 190
<212> TYPE: PRT
<213> ORGANISM: Escherichia coli

<400> SEQUENCE: 113

Met Thr Leu Ser Ser Gln His Tyr Leu Val Ile Thr Ala Leu Gly Ala
1               5                   10                  15

Asp Arg Pro Gly Ile Val Asn Thr Ile Thr Arg His Val Ser Ser Cys
            20                  25                  30

Gly Cys Asn Ile Glu Asp Ser Arg Leu Ala Met Leu Gly Glu Glu Phe
        35                  40                  45

Thr Phe Ile Met Leu Leu Ser Gly Ser Trp Asn Ala Ile Thr Leu Ile
    50                  55                  60

Glu Ser Thr Leu Pro Leu Lys Gly Ala Glu Leu Asp Leu Leu Ile Val
65                  70                  75                  80

Met Lys Arg Thr Thr Ala Arg Pro Arg Pro Met Pro Ala Ser Val
                85                  90                  95

Trp Val Gln Val Asp Val Ala Asp Ser Pro His Leu Ile Glu Arg Phe
            100                 105                 110

Thr Ala Leu Phe Asp Ala His His Met Asn Ile Ala Glu Leu Val Ser
        115                 120                 125

Arg Thr Gln Pro Ala Glu Asn Glu Arg Ala Ala Gln Leu His Ile Gln
    130                 135                 140

Ile Thr Ala His Ser Pro Ala Ser Ala Asp Ala Ala Asn Ile Glu Gln
145                 150                 155                 160

Ala Phe Lys Ala Leu Cys Thr Glu Leu Asn Ala Gln Gly Ser Ile Asn
                165                 170                 175

Val Val Asn Tyr Ser Gln His Asp Glu Gln Asp Gly Val Lys
            180                 185                 190

<210> SEQ ID NO 114
<211> LENGTH: 156
<212> TYPE: PRT
<213> ORGANISM: Escherichia coli

<400> SEQUENCE: 114

Met Asn Pro Leu Lys Ala Gly Asp Ile Ala Pro Lys Phe Ser Leu Pro
1               5                   10                  15

Asp Gln Asp Gly Glu Gln Val Asn Leu Thr Asp Phe Gln Gly Gln Arg
            20                  25                  30

Val Leu Val Tyr Phe Tyr Pro Lys Ala Met Thr Pro Gly Cys Thr Val
        35                  40                  45

Gln Ala Cys Gly Leu Arg Asp Asn Met Asp Glu Leu Lys Lys Ala Gly
    50                  55                  60

Val Asp Val Leu Gly Ile Ser Thr Asp Lys Pro Glu Lys Leu Ser Arg
65                  70                  75                  80

Phe Ala Glu Lys Glu Leu Leu Asn Phe Thr Leu Leu Ser Asp Glu Asp
                85                  90                  95

His Gln Val Cys Glu Gln Phe Gly Val Trp Gly Glu Lys Ser Phe Met
```

```
                        100                 105                 110
Gly Lys Thr Tyr Asp Gly Ile His Arg Ile Ser Phe Leu Ile Asp Ala
            115                 120                 125

Asp Gly Lys Ile Glu His Val Phe Asp Phe Lys Thr Ser Asn His
        130                 135                 140

His Asp Val Val Leu Asn Trp Leu Lys Glu His Ala
145                 150                 155

<210> SEQ ID NO 115
<211> LENGTH: 205
<212> TYPE: PRT
<213> ORGANISM: Escherichia coli

<400> SEQUENCE: 115

Met Asn Arg Phe Val Val Ala Glu Pro Leu Trp Cys Thr Gly Cys Asn
1               5                   10                  15

Thr Cys Leu Ala Ala Cys Ser Asp Val His Lys Thr Gln Gly Leu Gln
            20                  25                  30

Gln His Pro Arg Leu Ala Leu Ala Lys Thr Ser Thr Ile Thr Ala Pro
        35                  40                  45

Val Val Cys His His Cys Glu Glu Ala Pro Cys Leu Gln Val Cys Pro
    50                  55                  60

Val Asn Ala Ile Ser Gln Arg Asp Asp Ala Ile Gln Leu Asn Glu Ser
65                  70                  75                  80

Leu Cys Ile Gly Cys Lys Leu Cys Ala Val Val Cys Pro Phe Gly Ala
                85                  90                  95

Ile Ser Ala Ser Gly Ser Arg Pro Val Asn Ala His Ala Gln Tyr Val
            100                 105                 110

Phe Gln Ala Glu Gly Ser Leu Lys Asp Gly Glu Glu Asn Ala Pro Thr
        115                 120                 125

Gln His Ala Leu Leu Arg Trp Glu Pro Gly Val Gln Thr Val Ala Val
    130                 135                 140

Lys Cys Asp Leu Cys Asp Phe Leu Pro Glu Gly Pro Ala Cys Val Arg
145                 150                 155                 160

Ala Cys Pro Asn Gln Ala Leu Arg Leu Ile Thr Gly Asp Ser Leu Gln
                165                 170                 175

Arg Gln Met Lys Glu Lys Gln Arg Leu Ala Ala Ser Trp Phe Ala Asn
            180                 185                 190

Gly Gly Glu Asp Pro Leu Ser Leu Thr Gln Glu Gln Arg
        195                 200                 205

<210> SEQ ID NO 116
<211> LENGTH: 5223
<212> TYPE: DNA
<213> ORGANISM: Escherichia coli

<400> SEQUENCE: 116
cggctacgcc catttgggta agctgtgccg cccacggacg tactttctgc cagaatggca      60
ttttctgcca ttgatgcggc gcaggctggg cttccgggat caatgtcgcc ggttgacgta     120
ctggctcttc ttcaatggcg gccatcacgc gtgaagagat atcgaaatgg agcacctcgg     180
gagtatcacc ccgcattgag tcacggatta agtgatagct ttcccaggtt ttctgcattt     240
ctgggttatg agccagttcg ttaagcagct cactatccag cgtttcgcca tccattaaag     300
cggaaagttg ttctttctgc atgcctaata cccttatcca gtatcccgct atcgtcaacg     360
cctgataagc ggttgaactt tgttatcaat agcttccctc gctcggaaga tacgtgaacg     420
```

-continued

| | | | | |
|---|---|---|---|---|
| caccgtacct | accggacaat | ccatgatagc | ggctatctct | tcatagctca | ggccatccag | 480 |
| ctcccgcaag | gttattgcca | tgcgtaaatc | ttccgggagg | gactcaatag | ttcggaaaac | 540 |
| tatctgtctc | agttcttctg | acaacattaa | gttctcaggg | ttcgaaattt | ctttcaacgc | 600 |
| gccgccactt | tcgaagtttt | cagcttcaat | ggcatccaca | tcactggaag | gtggacgacg | 660 |
| cccctgagca | accaggtaat | ttttcgctgt | atttacagca | atccgataca | gccatgtata | 720 |
| aaaagcgcta | tctccccgga | acgaatccag | cgcacgatag | gctttaataa | aagcttcttg | 780 |
| taccacatcg | ggaacatcac | ccgacggcac | atagcgggaa | accagactcg | ccactttatg | 840 |
| ctgatagcgc | actaccagta | agttaaaggc | tttctgatct | cccttctgga | cccgttcaac | 900 |
| caggacctgg | tccgttaact | gctcgctcat | ccgaggtaaa | gtctccccaa | accaaatttc | 960 |
| cacgcgctat | cgaaacgcca | ctccattagc | tgcaatttga | gcaagcaaag | ggttagagtg | 1020 |
| tctcgttttt | gtaaagttcc | gtaacgcatc | tgttttgtt | tgtcatgctg | tagacggatc | 1080 |
| attatctatc | attataagtc | tacagaatct | gaacatcgca | ttatctgtgt | agaaatgccc | 1140 |
| atttaactgc | ctgaagagta | acccaacggc | cttttattt | caccacctaa | tcctccacca | 1200 |
| gccagtaact | tctcttttc | tcgccgccct | gcgtcagcgt | gtttagcaac | tgtaacaaat | 1260 |
| attaaaatag | caggtgttta | tccgcacaac | atgatgctat | gctgaccaaa | ccatgtttag | 1320 |
| taaattaaac | aaagaaaatg | aatactctcc | ctgaacattc | atgtgacgtg | ttgattatcg | 1380 |
| gtagcggcgc | agccggactt | tcactggcgc | tacgcctggc | tgaccagcat | caggtcatcg | 1440 |
| ttctaagtaa | aggcccggta | acggaaggtt | caacatttta | tgcccagggc | ggtattgccg | 1500 |
| ccgtgtttga | tgaaactgac | agcattgact | cgcatgtgga | agacacattg | attgccgggg | 1560 |
| ctggtatttg | cgatcgccat | gcagttgaat | ttgtcgccag | caatgcacga | tcctgtgtgc | 1620 |
| aatggctaat | cgaccagggg | gtgttgtttg | atacccacat | tcaaccgaat | ggcgaagaaa | 1680 |
| gttaccatct | gacccgtgaa | ggtggacata | gtcaccgtcg | tattcttcat | gccgccgacg | 1740 |
| ccaccggtag | agaagtagaa | accacgctgg | tgagcaaggc | gctgaaccat | ccgaatattc | 1800 |
| gcgtgctgga | gcgcagcaac | gcggttgatc | tgattgtttc | tgacaaaatt | ggcctgccgg | 1860 |
| gcacgcgacg | ggttgttggc | gcgtgggtat | ggaaccgtaa | taaagaaacg | gtggaaacct | 1920 |
| gccacgcaaa | agcggtggtg | ctggcaaccg | gcggtgcgtc | gaaggtttat | cagtacacca | 1980 |
| ccaatccgga | tatttcttct | ggcgatggca | ttgctatggc | gtggcgcgca | ggctgccggg | 2040 |
| ttgccaatct | cgaatttaat | cagttccacc | ctaccgcgct | atatcaccca | caggcacgca | 2100 |
| atttcctgtt | aacagaagca | ctgcgcgcg | aaggcgctta | tctcaagcgc | ccggatggta | 2160 |
| cgcgttttat | gcccgatttt | gatgagcgcg | gcgaactggc | cccgcgcgat | attgtcgccc | 2220 |
| gcgccattga | ccatgaaatg | aaacgcctcg | gcgcagattg | tatgttcctt | gatatcagcc | 2280 |
| ataagcccgc | cgattttatt | cgccagcatt | tcccgatgat | ttatgaaaag | ctgctcgggc | 2340 |
| tggggattga | tctcacacaa | gaaccggtac | cgattgtgcc | tgctgcacat | tatacctgcg | 2400 |
| gtggtgtaat | ggttgatgat | catgggcgta | cggacgtcga | gggcttgtat | gccattggcg | 2460 |
| aggtgagtta | taccggctta | cacggcgcta | accgcatggc | ctcgaattca | ttgctggagt | 2520 |
| gtctggtcta | tggctggtcg | gcggcggaag | atatcaccag | acgtatgcct | tatgccacg | 2580 |
| acatcagtac | gttaccgccg | tgggatgaaa | gccgcgttga | gaaccctgac | gaacgggtag | 2640 |
| taattcagca | taactggcac | gagctacgtc | tgtttatgtg | ggattacgtt | ggcattgtgc | 2700 |
| gcacaacgaa | gcgcctggaa | cgcgccctgc | ggcggataac | catgctccaa | caagaaatag | 2760 |

```
acgaatatta cgcccatttc cgcgtctcaa ataatttgct ggagctgcgt aatctggtac    2820
aggttgccga gttgattgtt cgctgtgcaa tgatgcgtaa agagagtcgg gggttgcatt    2880
tcacgctgga ttatccggaa ctgctcaccc attccggtcc gtcgatcctt tcccccggca    2940
atcattacat aaacagataa aaagcctggg tcagcgccgt atacgcttcg gaatagttct    3000
ggtctggccc acgaatgact aagcgatcgc taaagcattc tcccgcctgc ggggagaatg    3060
ccagcagcac ccgatgcggc agtcgcgctt cgttttccgc cacatccgtc cgcaaacgta    3120
aatgccagcc catgcttaat gccagctccg taaaaccatt accaatctgc tctggcagca    3180
ctacgcagaa aaatccctct tcggtaatgc actccgccgc acaggtcagc aacgatgggt    3240
gatcaagcgt agtggtatag cgagcctgtt cccgttgagg tgtcgagcac tctactccct    3300
gctgatagta aggtgggtta ctgatgatta aatcgaagcg tactgtctgc tgtgtgatcc    3360
actgctgaat atccgccgta tggacgttaa tccgctctgc ccacgggac tggttgatat     3420
tttcctgcgc ctgcgcggca gcttcacttt ccagttcaac tgcatcaatc atcacgctgt    3480
catcggttcg ctgcgccagc attaatgcca gcaacccgct acccgcgccg atatcaaggc    3540
aacgttttac cccagccacc ggtgcccatg cgcccaataa aataccatcc gttcccactt    3600
tcatcgcaca gcgatcgtga gcaacaaaaa actgttaa agtaaatcca ttacgacgaa     3660
gcacggatgt agactgtgac atgaaaataa aaccttgcag gaaaaacggc gatagcaccg    3720
ggtgagaaca atacccgaga agcgatatcc atacaaacag atgaagattg cagccgtaac    3780
gtctataatc agcgccccac acagaggtag aacatgactg taacgacttt ttccgaactt    3840
gaactcgacg aaaagcctgct ggaagccctc caggataaag gtttcactcg cccgaccgcc    3900
attcaggctg ccgccattcc gcctgcgctc gatggccgtg atgtactcgg ttctgcgccg    3960
acaggcaccg gtaaaacggc ggcgtatctg ctgccagcgt tgcagcacct gctcgatttc    4020
ccgcgtaaga aatccggtcc gccgcgtatt ttgatcctca ccccaactcg cgagctggcg    4080
atgcaggtgg ccgatcatgc ccgcgaactg gcgaaacata cgcatctgga tatcgccacc    4140
atcaccggcg gcgtagccta tgaaccac gcggaagtgt tcagcgaaaa tcaggacatc    4200
gtggtcgcca cgaccggacg tctgctgcaa tacataaaag aagagaactt cgattgccgc    4260
gcggttgaaa cgctgatcct cgacgaagca gaccgtatgc tggatatggg cttcgctcag    4320
gatatcgaac atattgctgg cgaaacgcgc tggcgtaaac agaccctgct cttttcggca    4380
acgctggaag gcgatgcgat tcaggacttt gccgagcgtc tgctggaaga tccggtggaa    4440
gtttctgcca atccctccac ccgtgagcgc aaaaaaattc atcagtggta ttaccgcgcc    4500
gatgatcttg agcataaaac cgcgttgctg gtgcatctgt aaaacagcc ggaagcgacc     4560
cgctcaattg tgtttgtgcg taagcgtgag cgtgtgcatg agctggcaaa ctggctgcgc    4620
gaagcgggca tcaacaactg ctatctcgaa ggtgagatgg tacagggcaa gcgtaacgaa    4680
gcgatcaagc gtttgaccga aggtcgcgta aacgtactgg tcgcaaccga tgttgccgcg    4740
cgcggtatcg acattcctga cgtcagccac gtctttaact tcgatatgcc gcgcagtggc    4800
gatacttatt tgcaccgtat cggacgtacc gcgcgcgccg gtcgtaaagg caccgcaatt    4860
tcgctggtgg aagcccatga ccatctgctg ctgggtaaag taggccgcta tattgaagag    4920
ccaattaaag ctcgcgttat tgatgagtta cgcccgaaaa cgcgtgcgcc aagcgaaaag    4980
cagaccggca agccatcgaa gaaagtactg gctaaacgtg ctgagaagaa aaaagctaaa    5040
gagaaagaga agccgcgggt gaaaaaacgc catcgcgaca ccaaaaatat tggtaagcgc    5100
cgtaaaccaa gcggaacggg cgtgccaccg caaacgacag aagagtaatc tcaatgccag    5160
```

```
gtttaagcct ggtattaaaa gtgctggcaa acgcaaaact gcctgatgcg ctacgcttat    5220
cag                                                                  5223
```

<210> SEQ ID NO 117
<211> LENGTH: 191
<212> TYPE: PRT
<213> ORGANISM: Escherichia coli

<400> SEQUENCE: 117

```
Met Ser Glu Gln Leu Thr Asp Gln Val Leu Val Glu Arg Val Gln Lys
1               5                   10                  15

Gly Asp Gln Lys Ala Phe Asn Leu Leu Val Val Arg Tyr Gln His Lys
            20                  25                  30

Val Ala Ser Leu Val Ser Arg Tyr Val Pro Ser Gly Asp Val Pro Asp
        35                  40                  45

Val Val Gln Glu Ala Phe Ile Lys Ala Tyr Arg Ala Leu Asp Ser Phe
    50                  55                  60

Arg Gly Asp Ser Ala Phe Tyr Thr Trp Leu Tyr Arg Ile Ala Val Asn
65                  70                  75                  80

Thr Ala Lys Asn Tyr Leu Val Ala Gln Gly Arg Arg Pro Pro Ser Ser
                85                  90                  95

Asp Val Asp Ala Ile Glu Ala Glu Asn Phe Glu Ser Gly Ala Leu
            100                 105                 110

Lys Glu Ile Ser Asn Pro Glu Asn Leu Met Leu Ser Glu Glu Leu Arg
        115                 120                 125

Gln Ile Val Phe Arg Thr Ile Glu Ser Leu Pro Glu Asp Leu Arg Met
    130                 135                 140

Ala Ile Thr Leu Arg Glu Leu Asp Gly Leu Ser Tyr Glu Glu Ile Ala
145                 150                 155                 160

Ala Ile Met Asp Cys Pro Val Gly Thr Val Arg Ser Arg Ile Phe Arg
                165                 170                 175

Ala Arg Glu Ala Ile Asp Asn Lys Val Gln Pro Leu Ile Arg Arg
            180                 185                 190
```

<210> SEQ ID NO 118
<211> LENGTH: 540
<212> TYPE: PRT
<213> ORGANISM: Escherichia coli

<400> SEQUENCE: 118

```
Met Asn Thr Leu Pro Glu His Ser Cys Asp Val Leu Ile Ile Gly Ser
1               5                   10                  15

Gly Ala Ala Gly Leu Ser Leu Ala Leu Arg Leu Ala Asp Gln His Gln
            20                  25                  30

Val Ile Val Leu Ser Lys Gly Pro Val Thr Glu Gly Ser Thr Phe Tyr
        35                  40                  45

Ala Gln Gly Gly Ile Ala Ala Val Phe Asp Glu Thr Asp Ser Ile Asp
    50                  55                  60

Ser His Val Glu Asp Thr Leu Ile Ala Gly Ala Gly Ile Cys Asp Arg
65                  70                  75                  80

His Ala Val Glu Phe Val Ala Ser Asn Ala Arg Ser Cys Val Gln Trp
                85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
```

-continued

```
            115                 120                 125
Ile Leu His Ala Ala Asp Ala Thr Gly Arg Glu Val Glu Thr Thr Leu
        130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285

Pro Arg Asp Ile Val Ala Arg Ala Ile Asp His Glu Met Lys Arg Leu
290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg
530                 535                 540
```

<210> SEQ ID NO 119
<211> LENGTH: 245
<212> TYPE: PRT
<213> ORGANISM: Escherichia coli

<400> SEQUENCE: 119

Met Ser Gln Ser Thr Ser Val Leu Arg Arg Asn Gly Phe Thr Phe Lys
1               5                   10                  15

Gln Phe Phe Val Ala His Asp Arg Cys Ala Met Lys Val Gly Thr Asp
                20                  25                  30

Gly Ile Leu Leu Gly Ala Trp Ala Pro Val Ala Gly Val Lys Arg Cys
            35                  40                  45

Leu Asp Ile Gly Ala Gly Ser Gly Leu Leu Ala Leu Met Leu Ala Gln
        50                  55                  60

Arg Thr Asp Asp Ser Val Met Ile Asp Ala Val Glu Leu Glu Ser Glu
65                  70                  75                  80

Ala Ala Ala Gln Ala Gln Glu Asn Ile Asn Gln Ser Pro Trp Ala Glu
                85                  90                  95

Arg Ile Asn Val His Thr Ala Asp Ile Gln Gln Trp Ile Thr Gln Gln
                100                 105                 110

Thr Val Arg Phe Asp Leu Ile Ile Ser Asn Pro Pro Tyr Tyr Gln Gln
            115                 120                 125

Gly Val Glu Cys Ser Thr Pro Gln Arg Glu Gln Ala Arg Tyr Thr Thr
        130                 135                 140

Thr Leu Asp His Pro Ser Leu Leu Thr Cys Ala Ala Glu Cys Ile Thr
145                 150                 155                 160

Glu Glu Gly Phe Phe Cys Val Val Leu Pro Glu Gln Ile Gly Asn Gly
                165                 170                 175

Phe Thr Glu Leu Ala Leu Ser Met Gly Trp His Leu Arg Leu Arg Thr
            180                 185                 190

Asp Val Ala Glu Asn Glu Ala Arg Leu Pro His Arg Val Leu Leu Ala
        195                 200                 205

Phe Ser Pro Gln Ala Gly Glu Cys Phe Ser Asp Arg Leu Val Ile Arg
    210                 215                 220

Gly Pro Asp Gln Asn Tyr Ser Glu Ala Tyr Thr Ala Leu Thr Gln Ala
225                 230                 235                 240

Phe Tyr Leu Phe Met
                245

<210> SEQ ID NO 120
<211> LENGTH: 444
<212> TYPE: PRT
<213> ORGANISM: Escherichia coli

<400> SEQUENCE: 120

Met Thr Val Thr Thr Phe Ser Glu Leu Glu Leu Asp Glu Ser Leu Leu
1               5                   10                  15

Glu Ala Leu Gln Asp Lys Gly Phe Thr Arg Pro Thr Ala Ile Gln Ala
                20                  25                  30

Ala Ala Ile Pro Pro Ala Leu Asp Gly Arg Asp Val Leu Gly Ser Ala
            35                  40                  45

Pro Thr Gly Thr Gly Lys Thr Ala Ala Tyr Leu Leu Pro Ala Leu Gln
        50                  55                  60

His Leu Leu Asp Phe Pro Arg Lys Lys Ser Gly Pro Pro Arg Ile Leu
65                  70                  75                  80

Ile Leu Thr Pro Thr Arg Glu Leu Ala Met Gln Val Ala Asp His Ala
            85                  90                  95

Arg Glu Leu Ala Lys His Thr His Leu Asp Ile Ala Thr Ile Thr Gly
            100                 105                 110

Gly Val Ala Tyr Met Asn His Ala Glu Val Phe Ser Glu Asn Gln Asp
        115                 120                 125

Ile Val Val Ala Thr Thr Gly Arg Leu Leu Gln Tyr Ile Lys Glu Glu
    130                 135                 140

Asn Phe Asp Cys Arg Ala Val Glu Thr Leu Ile Leu Asp Glu Ala Asp
145                 150                 155                 160

Arg Met Leu Asp Met Gly Phe Ala Gln Asp Ile Glu His Ile Ala Gly
                165                 170                 175

Glu Thr Arg Trp Arg Lys Gln Thr Leu Leu Phe Ser Ala Thr Leu Glu
            180                 185                 190

Gly Asp Ala Ile Gln Asp Phe Ala Glu Arg Leu Leu Glu Asp Pro Val
        195                 200                 205

Glu Val Ser Ala Asn Pro Ser Thr Arg Glu Arg Lys Lys Ile His Gln
    210                 215                 220

Trp Tyr Tyr Arg Ala Asp Asp Leu Glu His Lys Thr Ala Leu Leu Val
225                 230                 235                 240

His Leu Leu Lys Gln Pro Glu Ala Thr Arg Ser Ile Val Phe Val Arg
                245                 250                 255

Lys Arg Glu Arg Val His Glu Leu Ala Asn Trp Leu Arg Glu Ala Gly
            260                 265                 270

Ile Asn Asn Cys Tyr Leu Glu Gly Glu Met Val Gln Gly Lys Arg Asn
        275                 280                 285

Glu Ala Ile Lys Arg Leu Thr Glu Gly Arg Val Asn Val Leu Val Ala
    290                 295                 300

Thr Asp Val Ala Ala Arg Gly Ile Asp Ile Pro Asp Val Ser His Val
305                 310                 315                 320

Phe Asn Phe Asp Met Pro Arg Ser Gly Asp Thr Tyr Leu His Arg Ile
                325                 330                 335

Gly Arg Thr Ala Arg Ala Gly Arg Lys Gly Thr Ala Ile Ser Leu Val
            340                 345                 350

Glu Ala His Asp His Leu Leu Leu Gly Lys Val Gly Arg Tyr Ile Glu
        355                 360                 365

Glu Pro Ile Lys Ala Arg Val Ile Asp Glu Leu Arg Pro Lys Thr Arg
    370                 375                 380

Ala Pro Ser Glu Lys Gln Thr Gly Lys Pro Ser Lys Lys Val Leu Ala
385                 390                 395                 400

Lys Arg Ala Glu Lys Lys Ala Lys Glu Lys Glu Lys Pro Arg Val
                405                 410                 415

Lys Lys Arg His Arg Asp Thr Lys Asn Ile Gly Lys Arg Lys Pro
            420                 425                 430

Ser Gly Thr Gly Val Pro Pro Gln Thr Thr Glu Glu
        435                 440

<210> SEQ ID NO 121
<211> LENGTH: 1157
<212> TYPE: DNA
<213> ORGANISM: Escherichia coli

<400> SEQUENCE: 121
agagttgccc gacagcgaat tctgagcatg ctattgcgaa cagacaaacg ttatgcaggg      60

```
aagcactgga ccggcaaaca tcgaacctgg ttagctaatc aatcatttag tcagccatct    120
cagcagattg cttttcaaca ctattgtcaa agtctggagc agattgaaga tcgcatactt    180
caactcgacc aggaaatatc tcgcctgtta cctgagtggt ctctgtgcaa tctggtctgc    240
cagttgcagg ctctaaaagg tgttggtcag ctaattgcaa taaccctggt tgctgaactg    300
ggtgattttt cgcgattttc aatcccaaa cagctcatgg cttttctggg actggtgcca     360
ggtgaatatt ccagtggaaa cagtattcgt cccagaggaa taacaaaagt tggaaacagc    420
gaactgagac gtctgcttta cgaagccgcc tggtcttatc gtacacctgc aaaagttggc    480
gcatggctta tatattaccg accggactct gtaacacaat attccaaaga tattgcatgg    540
aaagctcaac aacgattgtg ttctcgttac cgaactctga cagcaaaagg gaaaaaatca    600
caagtagcca ttacggcggt ggctcgtgag ttgactggat ttatgtggga tattgcactt    660
gctgcccaat catcattcag tcagcagaag caaaattaaa ccctgaagca gtcagacacg    720
gaatgagtga tcctcgaaaa agaattcagg gaagccagaa tgcgctaata cctgcatgaa    780
ccgccccggg aatcctggag actaaattcc ctgagaaaga ggtaaacagg atgactaaaa    840
atacacgttt ttccccccgaa gtccgtcaac gggcagttcg tatggttctg aaagtcagg    900 acgaatatga ctcacaatgg gcggcaattt gttccattgc tccaaagatt ggctgtacgc    960
cagagactct gcgtgtctgg gttcgccagc atgagcggga taccgggggc ggtgatggtg   1020
ggctcaccac cgctgaacgt cagcgtctga agagctgga acgtgaaaat cgtgaactgc   1080
gccgcagtaa cgatatcctt cgccaggctt ccgcttattt tgcgaaggcg gagttcgacc   1140
gcctctggaa aaaataa                                                  1157

<210> SEQ ID NO 122
<211> LENGTH: 223
<212> TYPE: PRT
<213> ORGANISM: Escherichia coli

<400> SEQUENCE: 122

Met Leu Leu Arg Thr Asp Lys Arg Tyr Ala Gly Lys His Trp Thr Gly
1               5                   10                  15

Lys His Arg Thr Trp Leu Ala Asn Gln Ser Phe Ser Gln Pro Ser Gln
            20                  25                  30

Gln Ile Ala Phe Gln His Tyr Cys Gln Ser Leu Glu Gln Ile Glu Asp
        35                  40                  45

Arg Ile Leu Gln Leu Asp Gln Glu Ile Ser Arg Leu Leu Pro Glu Trp
    50                  55                  60

Ser Leu Cys Asn Leu Val Cys Gln Leu Gln Ala Leu Lys Gly Val Gly
65                  70                  75                  80

Gln Leu Ile Ala Ile Thr Leu Val Ala Glu Leu Gly Asp Phe Ser Arg
                85                  90                  95

Phe Ser Asn Pro Lys Gln Leu Met Ala Phe Leu Gly Leu Val Pro Gly
            100                 105                 110

Glu Tyr Ser Ser Gly Asn Ser Ile Arg Pro Arg Gly Ile Thr Lys Val
        115                 120                 125

Gly Asn Ser Glu Leu Arg Arg Leu Leu Tyr Glu Ala Ala Trp Ser Tyr
    130                 135                 140

Arg Thr Pro Ala Lys Val Gly Ala Trp Leu Ile Tyr Tyr Arg Pro Asp
145                 150                 155                 160

Ser Val Thr Gln Tyr Ser Lys Asp Ile Ala Trp Lys Ala Gln Gln Arg
                165                 170                 175
```

```
Leu Cys Ser Arg Tyr Arg Thr Leu Thr Ala Lys Gly Lys Lys Ser Gln
            180                 185                 190

Val Ala Ile Thr Ala Val Ala Arg Glu Leu Thr Gly Phe Met Trp Asp
        195                 200                 205

Ile Ala Leu Ala Ala Gln Ser Ser Phe Ser Gln Gln Lys Gln Asn
    210                 215                 220

<210> SEQ ID NO 123
<211> LENGTH: 108
<212> TYPE: PRT
<213> ORGANISM: Escherichia coli

<400> SEQUENCE: 123

Met Thr Lys Asn Thr Arg Phe Ser Pro Glu Val Arg Gln Arg Ala Val
1               5                   10                  15

Arg Met Val Leu Glu Ser Gln Asp Glu Tyr Asp Ser Gln Trp Ala Ala
            20                  25                  30

Ile Cys Ser Ile Ala Pro Lys Ile Gly Cys Thr Pro Glu Thr Leu Arg
        35                  40                  45

Val Trp Val Arg Gln His Glu Arg Asp Thr Gly Gly Gly Asp Gly Gly
    50                  55                  60

Leu Thr Thr Ala Glu Arg Gln Arg Leu Lys Glu Leu Glu Arg Glu Asn
65                  70                  75                  80

Arg Glu Leu Arg Arg Ser Asn Asp Ile Leu Arg Gln Ala Ser Ala Tyr
                85                  90                  95

Phe Ala Lys Ala Glu Phe Asp Arg Leu Trp Lys Lys
            100                 105

<210> SEQ ID NO 124
<211> LENGTH: 5518
<212> TYPE: DNA
<213> ORGANISM: Escherichia coli

<400> SEQUENCE: 124
cttcgccttt accgatcgtc agaaaattta cgatctggtg aagcaatca ctggtttccg      60 tatgcacccg gcgtggttcc gtattggcgg cgtagcgcac gacctgccgc gcggctggga     120
tcgcctgctg cgtgagttcc tcgactggat gccgaaacgt ctggcgtctt acgagaaagc     180
ggcgctgcaa acaccattc tgaaaggtcg ttcccagggc gttgccgcct atggcgcgaa      240
agaggcgctg agtgggca ccactggcgc gggcctgcgt gctaccggga tcgacttcga      300
cgtgcgtaag cgcgtcctt attctggcta tgaaaacttc gactttgaaa tcccggtggg     360
tggtggcgtt tctgactgct acacccgcgt aatgcttaaa gtggaagagc tgcgccagag     420
tctgcgcatt cttgagcagt gcctcaacaa catgccggaa ggcccgttca agcggatca     480 cccgctgacc acgccgccgc cgaaagagcg cacgctgcaa catatcgaaa ccctgatcac     540
ccacttcctg caagtgtcgt ggggtccggt gatgcctgcc aatgaatctt ccagatgat     600 tgaggcgacc aaagggatca acagttacta cctgaccagc gacggcagca ccatgagtta     660
ccgcacccgt gttcgtaccc cgagctttgc gcatttgcag caaattccgg cggcgatccg     720
cggcagcctg gtgtctgacc tgattgttta tctgggcagt atcgattttg ttatgtcaga     780
tgtggaccgc taattatgca cgagaatcaa caaccacaaa ccgaggcttt tgagctgagt     840
gcggcagagc gtgaagcgat cgagcacgag atgcaccact acgaagaccc gcgtgcggcg     900
tccattgaag cgctgaaaat cgttcagaag cagcgtggct gggtgccgga tggtgcgatc     960
```

-continued

```
cacgcgatcg ccgatgtgct gggtattccg gcaagcgacg tcgaaggtgt ggcaacgttc    1020
tacagtcaga tcttccgcca gccggttggt cgccatgtga tccgttattg tgacagcgtg    1080
gtctgtcata tcaacggtta tcagggtatt caggcggcgc tcgagaaaaa gctgaacatc    1140
aaaccagggc aaacgacatt tgatggccgc tttacgctgc tgccaacttg ctgcctgggg    1200
aactgtgata aagggccaaa catgatgatc gatgaggaca ctcacgcgca tctgaccccg    1260
gaagcgatcc ctgaactgct ggagcggtat aaatgaaaaa cattatccgt actcccgaaa    1320
cgcatccgct gacctggcgt ctgcgcgatg acaaacagcc agtgtggctg gacgaatacc    1380
gcagcaaaaa cggttacgaa ggcgcgcgta aggcgctgac cgggctgtct ccggacgaaa    1440
tcgttaatca ggtaaaagac gctggtctga aagggcgcgg cggcgcgggc ttctcgactg    1500
gcctgaaatg gagcctgatg ccgaaagacg aatccatgaa catccgttac ctgctgtgta    1560
atgccgatga atggagccg  gcacctata  aagaccgcct gttgatggag caactgccgc    1620
acctgctggt ggaaggtatg ctcatctccg cgtttgcgct gaaagcttac cgtggctaca    1680
tcttcctgcg tggcgaatat atcgaagcgg cagttaatct gcgccgtgcc attgccgaag    1740
ccaccgaagc gggtctgctt ggcaaaaaca ttatgggaac aggtttcgat ttcgaactgt    1800
tcgtccatac cggggcaggg cgctacatct gcggggaaga aacagcgtta atcaactccc    1860
tggaaggacg tcgtgctaac ccacgctcga agccacccct cccggcaacc tccggcgcat    1920
ggggtaaacc gacctgtgtc aacaacgtcg aaacccgtgt aacgttccg  gcgatcctcg    1980 ctaacggcgt ggagtggtat cagaacatct cgaaaagtaa agatgctggc accaagctga    2040
tgggcttctc cggtcgggtg aaaaatccgg gactgtggga actgccgttc ggcaccaccg    2100
cacgcgagat cctcgaagat tacgccggtg gtatgcgtga tggtctgaaa tttaaagcct    2160
ggcagccagg cggcgcgggg accgacttcc tgaccgaagc gcaccttgat ctgccgatgg    2220
aattcgaaag tatcggtaaa gcgggcagcc gtctgggtac ggcgctggcg atggcggttg    2280
accatgagat caacatggtg tcgctggtgc gtaacctgga agagttttc  gcccgtgagt    2340 cctgcggctg gtgtacgccg tgccgcgacg gtctgccgtg gagcgtgaaa attctgcgtg    2400
cgctggagcg tggtgaaggt cagccgggcg atatcgaaac acttgagcaa ctgtgtcgat    2460
tcttaggccc gggtaaaaact ttctgtgccc acgcacctgg tgcagtggag ccgttacaga    2520
gcgccatcaa atatttccgc gaagaatttg aggcgggaat caaacagccg ttcagcaata    2580
cccatttgat taatgggatt cagccgaacc tgctgaaaga gcgctggtaa ccgaatttcg    2640
attaacgctc agtctctgac tgagaaaact ggaagcatgc taatggctac aattcatgta    2700
gacggcaaag aatacgaggt caacggagcg gacaacctgc tggaagcttg tctgtctctg    2760
ggccttgata ttccttactt tgctggcat  ccggcgctgg gaagtgtcgg tgcttgccgc    2820
cagtgtgcgg tgaagcaata ccaaaacgcg gaagacacgc gtggtcgcct ggtgatgtcc    2880
tgtatgacac cggcttccga tggcacctttt atttccattg acgacgaaga agcgaaacag    2940
ttccgtgaaa gcgtggtcga gtggttgatg accaaccacc gcacgactg  tccggtatgt    3000 gaagagggcg gtaactgcca tcttcaggat atgactgtga tgaccggaca cagcttccgt    3060
cgctaccgtt tcaccaaacg tacccaccgt aatcaggatt tggggccatt catctctcac    3120
gaaatgaacc gctgcatcgc ctgctaccgc tgtgtgcgtt actacaaaga ttacgctgac    3180
ggtacagatc tgggcgttta cggtgcgcac gacaacgtct acttcggtcg cccggaagac    3240
ggcacgctgg aaagcgaatt ttccggtaac ctggtcgaaa tttgcccgac cggcgtattt    3300
accgacaaaa cgcactccga gcgttacaac cgtaaatggg atatgcagtt tgcgccgagc    3360
```

```
atctgccagc aatgttccat cggctgtaac atcagcccg gtgaacgtta cggcgaactg    3420
cgtcgtatcg aaaaccgtta caacggtacg gtaaaccact acttcctctg cgaccgtggt    3480
cgtttcggtt acggttacgt caacctgaag gatcgtccgc gtcagccagt acagcgtcgt    3540
ggcgatgatt tcattaccct caacgccgaa caggcaatgc agggcgcggc agatattctg    3600
cgtcagtcga agaaagtgat cggtattggt tctccgcgtg ccagcgtgga agcaacttt     3660
gcgctgcgtg aactggtggg cgaagaaaac ttctacaccg gtatcgctca cggtgagcag    3720
gaacgtctgc aactggcgct gaaagtgctg cgtgaaggcg gcatttatac tccggctctg    3780
cgcgaaatcg aatcttacga tgcggtactg gtgctgggcg aagacgttac ccagaccggc    3840
gcgcgcgtcg cgctggcagt gcgtcaggct gtgaaaggta agcgcgcga atggcggca      3900
gcacagaaag tggctgactg gcagattgcg gcaatcctca acatcggtca acgtgcgaag    3960
catccgctgt tgttaccaa cgttgatgac acccgtctgg atgatatcgc ggcgtggact    4020
taccgcgcac cggttgaaga tcaggcgcgt ttaggttttg ccatcgccca tgcgctggat    4080
aactctgcac cagcggttga cggtatcgaa cctgagctgc aaagcaaaat cgacgtcatc    4140
gtgcaggcac tggcaggtgc gaagaaaccg ttgattatct ccgggacgaa cgccggtagc    4200
ttagaggtga ttcaggcggc ggctaacgtc gcgaaagccc tgaaaggtcg cggcgctgac    4260
gtcggtatca ccatgattgc ccgttccgtc aacagcatgg ggctgggcat tatgggtggc    4320
ggttcgcttg aagaagcgtt aaccgaactg gaaaccggac gcgccgacgc ggtggtggtg    4380
ttggaaaacg atctgcatcg tcacgcttct gctatccgcg tgaatgctgc gctggctaaa    4440
gcaccgctgg tgatggtggt tgatcatcaa cgcacagcga ttatggaaaa cgcccatctg    4500
gtactttctg ctgccagctt tgctgaaagc gacggtacgg tgatcaacaa tgaaggccgc    4560
gcccaacgtt tcttccaggt ttacgatcct gcttattacg acagcaaaac tgtcatgctg    4620
gaaagctggc gctggttaca ctcgctgcac agcaccctgc tgagccgtga agtggactgg    4680
acgcagctcg accatgtgat tgacgctgtt gtggcgaaaa tcccggaact ggcaggtatc    4740
aaagatgctg cgccggatgc gacattccgt attcgtgggc agaaactggc ccgtgaaccg    4800
caccgttaca gcggtcgtac cgccatgcgc gccaatatca gcgttcatga gccgcgtcag    4860
ccgcaggata ttgacaccat gttcaccttc tcgatggaag gtaacaacca gccgactgcg    4920
caccgttcgc aagtgccgtt tgcctggcg ccgggctgga actccccgca ggcgtggaac    4980
aaattccagg acgaagtggg cggcaaactg cgctttggcg atccgggcgt gcgtctgttt    5040
gaaaccagcg aaaatggtct ggattacttc accagcgtac cggcacgctt ccagccgcag    5100
gacgggaaat ggcgtatcgc gccgtattac cacctgtttg gcagcgatga attgtcacag    5160
cgtgctccgg tcttccagag ccgtatgccg cagccgtaca tcaaactcaa cccagcggat    5220
gccgcgaagt tgggtgtgaa cgcaggtaca cgcgtctcct ttagttacga tggcaacacg    5280
gtcacgctgc cggttgaaat cgccgaagga ctgacggcag ggcaggtggg cttgccgatg    5340
ggtatgtccg gcattgctcc ggtgctggct ggcgcgcatc ttgaggatct caaggaggca    5400
caacaatgag ttggatatca ccggaactga ttgagatcct gctgaccatc ctcaaagcgg    5460
tggtgatcct gctggtggtt gtcacctgcg gggcattcat gagctttggc gaacgtcg     5518
```

<210> SEQ ID NO 125
<211> LENGTH: 166
<212> TYPE: PRT
<213> ORGANISM: Escherichia coli -continued

```
<400> SEQUENCE: 125

Met His Glu Asn Gln Gln Pro Gln Thr Glu Ala Phe Glu Leu Ser Ala
1               5                   10                  15

Ala Glu Arg Glu Ala Ile Glu His Glu Met His His Tyr Glu Asp Pro
            20                  25                  30

Arg Ala Ala Ser Ile Glu Ala Leu Lys Ile Val Gln Lys Gln Arg Gly
        35                  40                  45

Trp Val Pro Asp Gly Ala Ile His Ala Ile Ala Asp Val Leu Gly Ile
    50                  55                  60

Pro Ala Ser Asp Val Glu Gly Val Ala Thr Phe Tyr Ser Gln Ile Phe
65                  70                  75                  80

Arg Gln Pro Val Gly Arg His Val Ile Arg Tyr Cys Asp Ser Val Val
                85                  90                  95

Cys His Ile Asn Gly Tyr Gln Gly Ile Gln Ala Ala Leu Glu Lys Lys
            100                 105                 110

Leu Asn Ile Lys Pro Gly Gln Thr Thr Phe Asp Gly Arg Phe Thr Leu
        115                 120                 125

Leu Pro Thr Cys Cys Leu Gly Asn Cys Asp Lys Gly Pro Asn Met Met
    130                 135                 140

Ile Asp Glu Asp Thr His Ala His Leu Thr Pro Glu Ala Ile Pro Glu
145                 150                 155                 160

Leu Leu Glu Arg Tyr Lys
                165

<210> SEQ ID NO 126
<211> LENGTH: 445
<212> TYPE: PRT
<213> ORGANISM: Escherichia coli

<400> SEQUENCE: 126

Met Lys Asn Ile Ile Arg Thr Pro Glu Thr His Pro Leu Thr Trp Arg
1               5                   10                  15

Leu Arg Asp Asp Lys Gln Pro Val Trp Leu Asp Glu Tyr Arg Ser Lys
            20                  25                  30

Asn Gly Tyr Glu Gly Ala Arg Lys Ala Leu Thr Gly Leu Ser Pro Asp
        35                  40                  45

Glu Ile Val Asn Gln Val Lys Asp Ala Gly Leu Lys Gly Arg Gly Gly
    50                  55                  60

Ala Gly Phe Ser Thr Gly Leu Lys Trp Ser Leu Met Pro Lys Asp Glu
65                  70                  75                  80

Ser Met Asn Ile Arg Tyr Leu Leu Cys Asn Ala Asp Glu Met Glu Pro
                85                  90                  95

Gly Thr Tyr Lys Asp Arg Leu Leu Met Glu Gln Leu Pro His Leu Leu
            100                 105                 110

Val Glu Gly Met Leu Ile Ser Ala Phe Ala Leu Lys Ala Tyr Arg Gly
        115                 120                 125

Tyr Ile Phe Leu Arg Gly Glu Tyr Ile Glu Ala Ala Val Asn Leu Arg
    130                 135                 140

Arg Ala Ile Ala Glu Ala Thr Glu Ala Gly Leu Leu Gly Lys Asn Ile
145                 150                 155                 160

Met Gly Thr Gly Phe Asp Phe Glu Leu Phe Val His Thr Gly Ala Gly
                165                 170                 175

Arg Tyr Ile Cys Gly Glu Glu Thr Ala Leu Ile Asn Ser Leu Glu Gly
            180                 185                 190
```

Arg Arg Ala Asn Pro Arg Ser Lys Pro Pro Phe Pro Ala Thr Ser Gly
            195                 200                 205

Ala Trp Gly Lys Pro Thr Cys Val Asn Val Glu Thr Leu Cys Asn
    210                 215                 220

Val Pro Ala Ile Leu Ala Asn Gly Val Glu Trp Tyr Gln Asn Ile Ser
225                 230                 235                 240

Lys Ser Lys Asp Ala Gly Thr Lys Leu Met Gly Phe Ser Gly Arg Val
            245                 250                 255

Lys Asn Pro Gly Leu Trp Glu Leu Pro Phe Gly Thr Thr Ala Arg Glu
            260                 265                 270

Ile Leu Glu Asp Tyr Ala Gly Met Arg Asp Gly Leu Lys Phe Lys
            275                 280                 285

Ala Trp Gln Pro Gly Ala Gly Thr Asp Phe Leu Thr Glu Ala His
            290                 295                 300

Leu Asp Leu Pro Met Glu Phe Glu Ser Ile Gly Lys Ala Gly Ser Arg
305                 310                 315                 320

Leu Gly Thr Ala Leu Ala Met Ala Val Asp His Glu Ile Asn Met Val
            325                 330                 335

Ser Leu Val Arg Asn Leu Glu Glu Phe Phe Ala Arg Glu Ser Cys Gly
            340                 345                 350

Trp Cys Thr Pro Cys Arg Asp Gly Leu Pro Trp Ser Val Lys Ile Leu
            355                 360                 365

Arg Ala Leu Glu Arg Gly Glu Gly Gln Pro Gly Asp Ile Glu Thr Leu
            370                 375                 380

Glu Gln Leu Cys Arg Phe Leu Gly Pro Gly Lys Thr Phe Cys Ala His
385                 390                 395                 400

Ala Pro Gly Ala Val Glu Pro Leu Gln Ser Ala Ile Lys Tyr Phe Arg
            405                 410                 415

Glu Glu Phe Glu Ala Gly Ile Lys Gln Pro Phe Ser Asn Thr His Leu
            420                 425                 430

Ile Asn Gly Ile Gln Pro Asn Leu Leu Lys Glu Arg Trp
            435                 440                 445

<210> SEQ ID NO 127
<211> LENGTH: 908
<212> TYPE: PRT
<213> ORGANISM: Escherichia coli

<400> SEQUENCE: 127

Met Ala Thr Ile His Val Asp Gly Lys Glu Tyr Glu Val Asn Gly Ala
1               5                   10                  15

Asp Asn Leu Leu Glu Ala Cys Leu Ser Leu Gly Leu Asp Ile Pro Tyr
            20                  25                  30

Phe Cys Trp His Pro Ala Leu Gly Ser Val Gly Ala Cys Arg Gln Cys
        35                  40                  45

Ala Val Lys Gln Tyr Gln Asn Ala Glu Asp Thr Arg Gly Arg Leu Val
    50                  55                  60

Met Ser Cys Met Thr Pro Ala Ser Asp Gly Thr Phe Ile Ser Ile Asp
65                  70                  75                  80

Asp Glu Glu Ala Lys Gln Phe Arg Glu Ser Val Val Glu Trp Leu Met
            85                  90                  95

Thr Asn His Pro His Asp Cys Pro Val Cys Glu Glu Gly Gly Asn Cys
            100                 105                 110

His Leu Gln Asp Met Thr Val Met Thr Gly His Ser Phe Arg Arg Tyr
        115                 120                 125

```
Arg Phe Thr Lys Arg Thr His Arg Asn Gln Asp Leu Gly Pro Phe Ile
130                 135                 140

Ser His Glu Met Asn Arg Cys Ile Ala Cys Tyr Arg Cys Val Arg Tyr
145                 150                 155                 160

Tyr Lys Asp Tyr Ala Asp Gly Thr Asp Leu Gly Val Tyr Gly Ala His
                165                 170                 175

Asp Asn Val Tyr Phe Gly Arg Pro Glu Asp Gly Thr Leu Glu Ser Glu
            180                 185                 190

Phe Ser Gly Asn Leu Val Glu Ile Cys Pro Thr Gly Val Phe Thr Asp
        195                 200                 205

Lys Thr His Ser Glu Arg Tyr Asn Arg Lys Trp Asp Met Gln Phe Ala
210                 215                 220

Pro Ser Ile Cys Gln Gln Cys Ser Ile Gly Cys Asn Ile Ser Pro Gly
225                 230                 235                 240

Glu Arg Tyr Gly Glu Leu Arg Arg Ile Glu Asn Arg Tyr Asn Gly Thr
                245                 250                 255

Val Asn His Tyr Phe Leu Cys Asp Arg Gly Arg Phe Gly Tyr Gly Tyr
            260                 265                 270

Val Asn Leu Lys Asp Arg Pro Arg Gln Pro Val Gln Arg Arg Gly Asp
        275                 280                 285

Asp Phe Ile Thr Leu Asn Ala Glu Gln Ala Met Gln Gly Ala Ala Asp
290                 295                 300

Ile Leu Arg Gln Ser Lys Lys Val Ile Gly Ile Gly Ser Pro Arg Ala
305                 310                 315                 320

Ser Val Glu Ser Asn Phe Ala Leu Arg Glu Leu Val Gly Glu Glu Asn
                325                 330                 335

Phe Tyr Thr Gly Ile Ala His Gly Glu Gln Glu Arg Leu Gln Leu Ala
            340                 345                 350

Leu Lys Val Leu Arg Glu Gly Gly Ile Tyr Thr Pro Ala Leu Arg Glu
        355                 360                 365

Ile Glu Ser Tyr Asp Ala Val Leu Val Leu Gly Glu Asp Val Thr Gln
370                 375                 380

Thr Gly Ala Arg Val Ala Leu Ala Val Arg Gln Ala Val Lys Gly Lys
385                 390                 395                 400

Ala Arg Glu Met Ala Ala Ala Gln Lys Val Ala Asp Trp Gln Ile Ala
                405                 410                 415

Ala Ile Leu Asn Ile Gly Gln Arg Ala Lys His Pro Leu Phe Val Thr
            420                 425                 430

Asn Val Asp Asp Thr Arg Leu Asp Ile Ala Ala Trp Thr Tyr Arg
        435                 440                 445

Ala Pro Val Glu Asp Gln Ala Arg Leu Gly Phe Ala Ile Ala His Ala
450                 455                 460

Leu Asp Asn Ser Ala Pro Ala Val Asp Gly Ile Glu Pro Glu Leu Gln
465                 470                 475                 480

Ser Lys Ile Asp Val Ile Gln Ala Leu Ala Gly Ala Lys Lys Pro
                485                 490                 495

Leu Ile Ile Ser Gly Thr Asn Ala Gly Ser Leu Glu Val Ile Gln Ala
            500                 505                 510

Ala Ala Asn Val Ala Lys Ala Leu Lys Gly Arg Gly Ala Asp Val Gly
        515                 520                 525

Ile Thr Met Ile Ala Arg Ser Val Asn Ser Met Gly Leu Gly Ile Met
530                 535                 540
```

```
Gly Gly Gly Ser Leu Glu Glu Ala Leu Thr Glu Leu Glu Thr Gly Arg
545                 550                 555                 560

Ala Asp Ala Val Val Leu Glu Asn Asp Leu His Arg His Ala Ser
            565                 570                 575

Ala Ile Arg Val Asn Ala Ala Leu Ala Lys Ala Pro Leu Val Met Val
                580                 585                 590

Val Asp His Gln Arg Thr Ala Ile Met Glu Asn Ala His Leu Val Leu
595                 600                 605

Ser Ala Ala Ser Phe Ala Glu Ser Asp Gly Thr Val Ile Asn Asn Glu
        610                 615                 620

Gly Arg Ala Gln Arg Phe Phe Gln Val Tyr Asp Pro Ala Tyr Tyr Asp
625                 630                 635                 640

Ser Lys Thr Val Met Leu Glu Ser Trp Arg Trp Leu His Ser Leu His
                645                 650                 655

Ser Thr Leu Leu Ser Arg Glu Val Asp Trp Thr Gln Leu Asp His Val
            660                 665                 670

Ile Asp Ala Val Val Ala Lys Ile Pro Glu Leu Ala Gly Ile Lys Asp
        675                 680                 685

Ala Ala Pro Asp Ala Thr Phe Arg Ile Arg Gly Gln Lys Leu Ala Arg
690                 695                 700

Glu Pro His Arg Tyr Ser Gly Arg Thr Ala Met Arg Ala Asn Ile Ser
705                 710                 715                 720

Val His Glu Pro Arg Gln Pro Gln Asp Ile Asp Thr Met Phe Thr Phe
                725                 730                 735

Ser Met Glu Gly Asn Asn Gln Pro Thr Ala His Arg Ser Gln Val Pro
            740                 745                 750

Phe Ala Trp Ala Pro Gly Trp Asn Ser Pro Gln Ala Trp Asn Lys Phe
        755                 760                 765

Gln Asp Glu Val Gly Gly Lys Leu Arg Phe Gly Asp Pro Gly Val Arg
770                 775                 780

Leu Phe Glu Thr Ser Glu Asn Gly Leu Asp Tyr Phe Thr Ser Val Pro
785                 790                 795                 800

Ala Arg Phe Gln Pro Gln Asp Gly Lys Trp Arg Ile Ala Pro Tyr Tyr
                805                 810                 815

His Leu Phe Gly Ser Asp Glu Leu Ser Gln Arg Ala Pro Val Phe Gln
            820                 825                 830

Ser Arg Met Pro Gln Pro Tyr Ile Lys Leu Asn Pro Ala Asp Ala Ala
        835                 840                 845

Lys Leu Gly Val Asn Ala Gly Thr Arg Val Ser Phe Ser Tyr Asp Gly
850                 855                 860

Asn Thr Val Thr Leu Pro Val Glu Ile Ala Glu Gly Leu Thr Ala Gly
865                 870                 875                 880

Gln Val Gly Leu Pro Met Gly Met Ser Gly Ile Ala Pro Val Leu Ala
                885                 890                 895

Gly Ala His Leu Glu Asp Leu Lys Glu Ala Gln Gln
            900                 905

<210> SEQ ID NO 128
<211> LENGTH: 4547
<212> TYPE: DNA
<213> ORGANISM: Escherichia coli

<400> SEQUENCE: 128
ccctgacagg atgattacat aaataatagt gacaaaaata aattattat ttatccagaa        60
```

-continued

| | | | | | |
|---|---|---|---|---|---|
| aatgaattgg | aaaatcagga | gagcgttttc | aatcctacct | ctggcgcagt | tgatatgtaa | 120 |
| ggcaggttta | ttatatcgcg | ttgattattg | atgctgtttt | tagttttaac | ggcaattaat | 180 |
| atatgtgtta | ttaattgaat | gaattttatc | attcataata | agtatgtgta | ggatcaagct | 240 |
| caggttaaat | attcactcag | gaagttatta | ctcaggaagc | aaagaggatt | acagaattat | 300 |
| ctcataacaa | gtgttaaggg | atgttatttc | ccgattctct | gtggcataat | aaacgagtag | 360 |
| atgctcattc | catctcttat | gttcgcctta | gtgcctcata | aactccggaa | tgacgcagag | 420 |
| ccgtttacgg | tgcttatcgt | ccactgacag | atgtcgctta | tgcctcatca | gacaccatgg | 480 |
| acacaacgtt | gagtgaagca | cccacttgtt | gtcatacaga | cctgttttaa | cgcctgctcc | 540 |
| gtaataagag | caggcgtttt | tttatgtatc | aggaaggccc | cggaggtgct | tgcctccggg | 600 |
| tgagaaggaa | ctactgtggc | gggttattct | gcaacgttaa | catcaaaccg | tcgcgacgca | 660 |
| tcgctgcagc | ttcttccggc | ttgtgcagtc | tgtccagcgc | gtcggcaagc | catgcgtaat | 720 |
| cgtaggcgtc | cggacgttgt | tcagcgctg | cgcggaaggc | gagcgatgct | tcctgccatt | 780 |
| ctccgtgctt | catcagtgac | tggcccagtg | tgctccacaa | cagcgggcga | tcgccgacgt | 840 |
| ttttgatttg | ctggcgcagc | acttttcca | gctgttccgg | attgtttgtt | ttcagtcgag | 900 |
| gaatcggcag | cagtaggcga | tcgtcgtact | ggcgtttcag | gccatcgatg | ataatttgct | 960 |
| gggcagtatc | atgatcgtca | cattcaataa | gatgttccgc | cattgccacc | tgcaacgcta | 1020 |
| cctgatgacg | cgttttccgg | ctttggtttt | tccaccagtt | acgcaaacct | tcgctaccgt | 1080 |
| tatcggcacg | cgcctgatcc | atcaggccaa | tccatgcctg | ttgttccagc | attgcacgat | 1140 |
| gttcttcatc | accaacatgg | gctttcgcca | ttgatgggat | aatatccagc | agcgaactcc | 1200 |
| atgcacctgt | gcggatatac | gcctgttccg | ccagacgtaa | tacttccgga | tggcgtggcg | 1260 |
| taacttccag | cagcttatcc | acgccgtggc | gtgcagcatg | gttttcatta | cgggccagtt | 1320 |
| gcagacgtac | gcgggtgatt | tctaccggaa | tggtgtcgtt | gccggccagc | tccgctgcgc | 1380 |
| gttccagatg | ttggttggcg | cgtgcttcat | caccacgttg | ttgcgcggct | tcggcagcca | 1440 |
| gtagatagtt | caccaccggt | tgttccgcgt | gatcggcatt | tttcgccatc | agcttttcaa | 1500 |
| cttgctgata | atcgccttcc | gccagtttca | gcagcgcctg | ttcggtctgc | ttacgtgcac | 1560 |
| ggcgacgctt | acgtccgaca | aaccacccac | gggtgtgcgc | gccagtgcgg | aagatccgcc | 1620 |
| gcagtagcca | ctcaatggca | aacagcacta | ccatcgccag | aatcaatatg | atcgccaggc | 1680 |
| ccgtgacgct | ggtttcgata | ttgtagttgt | cggtctggat | cagcacataa | ccctgatggc | 1740 |
| cggcaatcat | cgggccaacc | acgatccccg | caatcagcaa | cacaaagagc | aataacactt | 1800 |
| ttagcatggt | tattctcctt | gcggcgcggc | tgccggagta | tcagcttgcg | gtgcaggtgc | 1860 |
| aggtttagct | tccgttgtcc | ccgctgccgg | ttgtgccagc | aggttacgca | cgcgagtctg | 1920 |
| catcagttttt | tccagcatcg | cctggctttg | cagggtttcc | ggaagatcca | tcgagatatt | 1980 |
| ttgctggctt | aactggtcca | cctcgtcgag | gaacgctttg | gtggtggcat | catcagtatc | 2040 |
| gtagtaagca | cgtacccagg | tggagacgtt | ctccagcgcc | tggcgataag | tctcttcctg | 2100 |
| gtgacgcggt | acagcttgtg | ctgcgaccag | caggcgagag | cgaatatttt | cgcgcagata | 2160 |
| gatatcctga | tttggcgcta | acagcggtac | ggcggtgtca | tcacgacggc | gaatcgtaat | 2220 |
| gaagttgtcc | ataaagttct | gccagctttt | ttgcagattg | atacgccatt | cgctgatgga | 2280 |
| actggaaagc | tcttcaccgt | ctgaatccat | cggcgaacca | tcgctgtcat | tatcggctag | 2340 |
| acgcaggtta | tctacctgat | ttgaaagctg | attaagctta | aggatgatgc | cgtcataatc | 2400 |
| cacctgcgat | actgcagaaa | ggctggcgat | atcatcggta | attgcccgac | gaacggtaat | 2460 |

```
cagactcggg tcattcatat ccgccaggct ggcgtctgca cttttcagca acgctgcagc     2520
ggtcgtgacg tcctgatcgc tccacagctt ccgtccggcg agtttcacca gaaaatcggc     2580
ctgagccagc agccaggttt tagcatcgct gccggaaatg gtggcgacct tttgttggac     2640
ttcatccaac tgttttgcca gcgtttcttg ctgacgattc gcctgcttaa gttgtgcagc     2700
ttgttgctta ataatgcctt ccagctcggc ttttttggctc tcctgggctt tttgcaatgc    2760
cgtcagttgg ttagccaggg catcgctggt ggcggtctga ttgacggcct gttgtttacc     2820
ccagccatac aaaccgatgc ccgccgccag agcaatagcg atagccaccg cgctgagaat     2880
caatgcggta ttgttcttac tctttttttc tgttgcgaca ggttgtgacg tggtgtccac     2940
ggcctccctg gtctcttcaa ccacggcgga ggttttttct tgttccgtca ttatggcttc     3000
ctgttatgag agttattgta atgcccgtaa aagcgcatcg ttgtcagcgt tatcggcgac     3060
cttaatgtct tgccagccca gttcccgggc gagtttcgcc aaacgctcac tgacgaccaa     3120
tagtcgacag tgtagtaacc agtgctcacg ataccattgt gggatcagcg accagagttg     3180
ctgcaacatt tcaccgctgg taacaacgac catcgtcacc tcgcgggctt gccagcgcat     3240
cgcttcttct gcaccatcgt aatggattgc gcatcgttga taacattcac aaaaagtgac     3300
ctcagcaccg cgcgccgtca gggtatcccc aattagctca cgaccaccat tgccacgtaa     3360
tatcagcgca cgtttgcccg caatattttg taattcaggt aattgtagca agacttcgct     3420
gatttcccga tcctgcgggt agagaatctt ctgtccgctt acggtatgta gtgccagtgc     3480
ggtggtgcgt ccaatggcga aataatcagg tagtcggggc catttacgat cttgctgatg     3540
cagctgtgat tgggcaaaag caaccgcgtg ttgcgagagg gcaaacaaca gatcgctctc     3600
ccccagcgct gccagttgat cagcaagttg cggtaattgt tgacccggag aaaactcaat     3660
cagcggaaaa tgccaggcca cctgccccag tgtgcgcaga cggctcacta actcttctcc     3720
agcgggagac gggcgggtga caaggatact catgccgggg cgtctccgtt atagacttca     3780
gcgaggatct cgcgcgcgcc gttattcagt agctcttctg ccagcgaaat ccccatttgt     3840
tcggcatctt gcggcgcacc gcggcgttca ccgcgaataa tctgcgaacc gtccggcgcg     3900
ccgaccagcg cacgcagcca gatttcgcca tcaataagct cggcgtagct accaattggc     3960
acctgacatc cgccttcgag acgggtattc atggcgcgtt ctgcggtaac gcgcagtgca     4020
gtttcgtggt gattcagcgc ggcaagcagc tcgcgagtgc gtgaatcatc aaggcggcat     4080 tcaatacccca ccgcaccttg tcctaccgcc ggaagagaaa tctcgggtgg caacgcggcg    4140
cgaatacgtg actccagacc taaacgtttt agtccggcta cggcaagaat gatggcatcg     4200
tattcgccgt tatccagttt gctcaggcga gtgccgacgt tgccgcgcag ggagcggata     4260
atcagatccg gacggcgttc agccagttgg cactggcgac gtaaactgga cgtcccgacg     4320
atactgcctg ccggtaacgc atccagactg tcatagttat tggacacaaa ggcatcgcga     4380
ggatcttcac gctcacaaat agtgaccagt cccagacctt gcgggaattc aaccggcaca     4440
tctttcattg agtgtacggc gatatcggcg cgattttcga ggagcgcgac ttccagctct     4500
tttacaaata agccttttcc gcctactttc gccagcggcg tatcaag                   4547
```

<210> SEQ ID NO 129
<211> LENGTH: 398
<212> TYPE: PRT
<213> ORGANISM: Escherichia coli

<400> SEQUENCE: 129

```
Met Leu Lys Val Leu Leu Leu Phe Val Leu Ile Ala Gly Ile Val
1               5                   10                  15

Val Gly Pro Met Ile Ala Gly His Gln Gly Tyr Val Leu Ile Gln Thr
            20                  25                  30

Asp Asn Tyr Asn Ile Glu Thr Ser Val Thr Gly Leu Ala Ile Ile Leu
            35                  40                  45

Ile Leu Ala Met Val Val Leu Phe Ala Ile Glu Trp Leu Leu Arg Arg
50                  55                  60

Ile Phe Arg Thr Gly Ala His Thr Arg Gly Trp Phe Val Gly Arg Lys
65                  70                  75                  80

Arg Arg Arg Ala Arg Lys Gln Thr Glu Gln Ala Leu Leu Lys Leu Ala
                85                  90                  95

Glu Gly Asp Tyr Gln Gln Val Glu Lys Leu Met Ala Lys Asn Ala Asp
                100                 105                 110

His Ala Glu Gln Pro Val Val Asn Tyr Leu Leu Ala Ala Glu Ala Ala
            115                 120                 125

Gln Gln Arg Gly Asp Glu Ala Arg Ala Asn Gln His Leu Glu Arg Ala
            130                 135                 140

Ala Glu Leu Ala Gly Asn Asp Thr Ile Pro Val Glu Ile Thr Arg Val
145                 150                 155                 160

Arg Leu Gln Leu Ala Arg Asn Glu Asn His Ala Ala Arg His Gly Val
                165                 170                 175

Asp Lys Leu Leu Glu Val Thr Pro Arg His Pro Glu Val Leu Arg Leu
            180                 185                 190

Ala Glu Gln Ala Tyr Ile Arg Thr Gly Ala Trp Ser Ser Leu Leu Asp
            195                 200                 205

Ile Ile Pro Ser Met Ala Lys Ala His Val Gly Asp Glu Glu His Arg
210                 215                 220

Ala Met Leu Glu Gln Gln Ala Trp Ile Gly Leu Met Asp Gln Ala Arg
225                 230                 235                 240

Ala Asp Asn Gly Ser Glu Gly Leu Arg Asn Trp Trp Lys Asn Gln Ser
                245                 250                 255

Arg Lys Thr Arg His Gln Val Ala Leu Gln Val Ala Met Ala Glu His
            260                 265                 270

Leu Ile Glu Cys Asp Asp His Asp Thr Ala Gln Gln Ile Ile Ile Asp
            275                 280                 285

Gly Leu Lys Arg Gln Tyr Asp Asp Arg Leu Leu Pro Ile Pro Arg
290                 295                 300

Leu Lys Thr Asn Asn Pro Glu Gln Leu Glu Lys Val Leu Arg Gln Gln
305                 310                 315                 320

Ile Lys Asn Val Gly Asp Arg Pro Leu Leu Trp Ser Thr Leu Gly Gln
                325                 330                 335

Ser Leu Met Lys His Gly Glu Trp Gln Glu Ala Ser Leu Ala Phe Arg
            340                 345                 350

Ala Ala Leu Lys Gln Arg Pro Asp Ala Tyr Asp Tyr Ala Trp Leu Ala
            355                 360                 365

Asp Ala Leu Asp Arg Leu His Lys Pro Glu Glu Ala Ala Ala Met Arg
            370                 375                 380

Arg Asp Gly Leu Met Leu Thr Leu Gln Asn Asn Pro Pro Gln
385                 390                 395

<210> SEQ ID NO 130
<211> LENGTH: 393
<212> TYPE: PRT
```

<213> ORGANISM: Escherichia coli

<400> SEQUENCE: 130

```
Met Thr Glu Gln Glu Lys Thr Ser Ala Val Val Glu Glu Thr Arg Glu
1               5                   10                  15

Ala Val Asp Thr Thr Ser Gln Pro Val Ala Thr Glu Lys Lys Ser Lys
            20                  25                  30

Asn Asn Thr Ala Leu Ile Leu Ser Ala Val Ala Ile Ala Ile Ala Leu
        35                  40                  45

Ala Ala Gly Ile Gly Leu Tyr Gly Trp Gly Lys Gln Gln Ala Val Asn
50                  55                  60

Gln Thr Ala Thr Ser Asp Ala Leu Ala Asn Gln Leu Thr Ala Leu Gln
65                  70                  75                  80

Lys Ala Gln Glu Ser Gln Lys Ala Glu Leu Glu Gly Ile Ile Lys Gln
                85                  90                  95

Gln Ala Ala Gln Leu Lys Gln Ala Asn Arg Gln Gln Glu Thr Leu Ala
            100                 105                 110

Lys Gln Leu Asp Glu Val Gln Gln Lys Val Ala Thr Ile Ser Gly Ser
        115                 120                 125

Asp Ala Lys Thr Trp Leu Leu Ala Gln Ala Asp Phe Leu Val Lys Leu
130                 135                 140

Ala Gly Arg Lys Leu Trp Ser Asp Gln Asp Val Thr Thr Ala Ala Ala
145                 150                 155                 160

Leu Leu Lys Ser Ala Asp Ala Ser Leu Ala Asp Met Asn Asp Pro Ser
                165                 170                 175

Leu Ile Thr Val Arg Arg Ala Ile Thr Asp Ile Ala Ser Leu Ser
            180                 185                 190

Ala Val Ser Gln Val Asp Tyr Asp Gly Ile Ile Leu Lys Leu Asn Gln
        195                 200                 205

Leu Ser Asn Gln Val Asp Asn Leu Arg Leu Ala Asp Asn Ser Asp
210                 215                 220

Gly Ser Pro Met Asp Ser Asp Gly Glu Glu Leu Ser Ser Ser Ile Ser
225                 230                 235                 240

Glu Trp Arg Ile Asn Leu Gln Lys Ser Trp Gln Asn Phe Met Asp Asn
                245                 250                 255

Phe Ile Thr Ile Arg Arg Arg Asp Asp Thr Ala Val Pro Leu Leu Ala
            260                 265                 270

Pro Asn Gln Asp Ile Tyr Leu Arg Glu Asn Ile Arg Ser Arg Leu Leu
        275                 280                 285

Val Ala Ala Gln Ala Val Pro Arg His Gln Glu Glu Thr Tyr Arg Gln
290                 295                 300

Ala Leu Glu Asn Val Ser Thr Trp Val Arg Ala Tyr Tyr Asp Thr Asp
305                 310                 315                 320

Asp Ala Thr Thr Lys Ala Phe Leu Asp Glu Val Asp Gln Leu Ser Gln
                325                 330                 335

Gln Asn Ile Ser Met Asp Leu Pro Glu Thr Leu Gln Ser Gln Ala Met
            340                 345                 350

Leu Glu Lys Leu Met Gln Thr Arg Val Arg Asn Leu Leu Ala Gln Pro
        355                 360                 365

Ala Ala Gly Thr Thr Glu Ala Lys Pro Ala Pro Gln Ala Asp
370                 375                 380

Thr Pro Ala Ala Ala Pro Gln Gly Glu
385                 390
```

<210> SEQ ID NO 131
<211> LENGTH: 246
<212> TYPE: PRT
<213> ORGANISM: Escherichia coli

<400> SEQUENCE: 131

Met Ser Ile Leu Val Thr Arg Pro Ser Pro Ala Gly Glu Glu Leu Val
1               5                   10                  15

Ser Arg Leu Arg Thr Leu Gly Gln Val Ala Trp His Phe Pro Leu Ile
            20                  25                  30

Glu Phe Ser Pro Gly Gln Gln Leu Pro Gln Leu Ala Asp Gln Leu Ala
        35                  40                  45

Ala Leu Gly Glu Ser Asp Leu Leu Phe Ala Leu Ser Gln His Ala Val
    50                  55                  60

Ala Phe Ala Gln Ser Gln Leu His Gln Gln Asp Arg Lys Trp Pro Arg
65                  70                  75                  80

Leu Pro Asp Tyr Phe Ala Ile Gly Arg Thr Thr Ala Leu Ala Leu His
                85                  90                  95

Thr Val Ser Gly Gln Lys Ile Leu Tyr Pro Gln Asp Arg Glu Ile Ser
            100                 105                 110

Glu Val Leu Leu Gln Leu Pro Glu Leu Gln Asn Ile Ala Gly Lys Arg
        115                 120                 125

Ala Leu Ile Leu Arg Gly Asn Gly Gly Arg Glu Leu Ile Gly Asp Thr
    130                 135                 140

Leu Thr Ala Arg Gly Ala Glu Val Thr Phe Cys Glu Cys Tyr Gln Arg
145                 150                 155                 160

Cys Ala Ile His Tyr Asp Gly Ala Glu Glu Ala Met Arg Trp Gln Ala
                165                 170                 175

Arg Glu Val Thr Met Val Val Thr Ser Gly Glu Met Leu Gln Gln
            180                 185                 190

Leu Trp Ser Leu Ile Pro Gln Trp Tyr Arg Glu His Trp Leu Leu His
        195                 200                 205

Cys Arg Leu Leu Val Ser Glu Arg Leu Ala Lys Leu Ala Arg Glu
    210                 215                 220

Leu Gly Trp Gln Asp Ile Lys Val Ala Asp Asn Ala Asp Asn Asp Ala
225                 230                 235                 240

Leu Leu Arg Ala Leu Gln
                245

<210> SEQ ID NO 132
<211> LENGTH: 3779
<212> TYPE: DNA
<213> ORGANISM: Escherichia coli

<400> SEQUENCE: 132
ccatttgttg atcgcgtctg gcgcaattcg cgcggtaaaa tgtgtgcccc aaacttcggt      60
tggtgcgtct tgtgtggcga atcagcaaa acgaacatat gcgctactgc catctggtgc     120
ggtgagatgc aagccatcat gcacaggtga aggagtaaac cgtaccatct ggggaaactg     180
gcgagcggta ataaacgtac cgtcaggttc cgtgatcata agatgcgat cgaaggccag     240 accactgaca tctgccagag catgtgtaag accaatgccg cgcatcgatt taacaggatg     300
aataaaaagc cggattaatg tcgccacggt gcggtcctca atgaaaata gcccctcaac     360 tttatgacat gacgcgctta ttagctataa tgcgcaacaa ttttcttagc gcctgtccca     420
ttaggctatt ttatttgtca gtttggccct gggttatgct cgaaatcctc acgtacttgt     480

```
gtacgctccg gtttctccgc gctgtccatg tccagactga ctgcaacaat tacgcctact    540
gcggtaggct cttagagtaa aagtgacgat atgaattctc tgtttgccag tacggcccgt    600
gggctggaag agctgttaaa aactgaactg gaaaacctgg gggccgttga atgccaggtg    660
gttcagggtg gggtccattt caagggcgac acacggcttg tttaccagag cctgatgtgg    720
agccgcctgg cctcgcgtat tatgttgccg ctgggcgagt gtaaggttta cagcgattta    780
gacctctatc tcggtgttca ggcgatcaac tggacagaga tgtttaatcc tggcgcgacc    840
ttcgctgtcc acttcagtgg tttgaatgac accatccgca acagtcagta cggtgcgatg    900
aaagtgaaag acgcgatcgt cgatgctttc acgcggaaaa atctgccgcg tccaaatgtt    960
gatcgcgatg cgccggatat ccgcgttaac gtctggctgc ataaagaaac cgccagtatc   1020
gctcttgatc tgagtggtga tggtttacat ctgcgtggct atcgcgatcg tgctggtatt   1080
gcgccgatca aagaaaccct ggcagccgct attgtgatgc gatccggctg cagccagga    1140
acaccgctgc tcgatccgat gtgtggttcc ggtacgttgc tgattgaagc agcgatgctg   1200
gcgaccgatc gcgcaccagg cttgcaccgt gggcgttggg gctttagcgg ctgggcgcag   1260
catgatgaag ctatctggca ggaagtgaaa gcggaagcgc aaactcgcgc cgtaaaggc    1320
ctggctgagt atagctctca tttttacggt tcggacagcg acgcacgggt gattcaacgt   1380
gcacgcacta acgcccgtct tgcggggatt ggtgaactga tcacctttga ggtgaaagat   1440
gtcgcgcaac tgaccaatcc gctgccgaaa gggccgtacg cacagtgtt gagcaacccg    1500
ccatacgggg aacgtctgga cagcgaaccg gcgctgattg cgctgcatag cctgctgggt   1560
cggatcatga aaaccagtt tggtggctgg aatctctctt tgtttagtgc ctcgccggat    1620
ctgctaagct gcttgcagct gcgtgcagac aaacagtaca aggcgaaaaa cggcccgctg   1680
gactgcgtac agaaaaatta ccacgttgcc gaaagcactc cagacagcaa accggcgatg   1740
gtagcggaag actacaccaa ccgcctgcgt aagaacctca aaaaattcga gaagtgggct   1800
cgccaggaag ggattgaatg ttaccgcctg tatgacgccg atctgccaga atataacgtt   1860
gccgttgacc gttatgccga ctgggtggtg gtgcaggagt atgcgccgcc aaaaaactatt  1920
gatgctcaca agcgcgtca gcgtctgttc gatattatcg ctgcaaccat ttcggtactg    1980
gggattgcgc caaacaaact ggtgctgaaa acccgtgaac gccagaaggg caaaaaccaa   2040
taccagaaac tgggcgagaa gggcgagttt cttgaagtta ccgaatataa cgctcacttg   2100
tgggtgaacc tgacggatta tctcgatact ggtctgttcc tcgatcaccg catcgcccgt   2160
cgtatgctcg gtcagatgag caaaggcaaa gatttcctca acctgttctc ttataccggc   2220
agcgccaccg tgcatgcggg attaggcggt gcacgcagca ccaccaccgt ggatatgtcg   2280
cgtacttatc tggaatgggc agaacgcaac ctgcgtctga tggcctgac cgggcgtgcg    2340
catcgcctga ttcaggccga ttgcctggcg tggctgcgtg aggcaaatga acagttcgat   2400
ctgatcttta tcgatccgcc aaccttctct aactcaaaac gaatggaaga tgcgtttgat   2460
gttcagcgcg atcatctggc gctgatgaaa gatttgaaac gtctgctgcg tgcaggtggg   2520
acgatcatgt tctcgaacaa caaacgtggc ttccgtatgg atctcgacgg cctggcaaaa   2580
ctgggactga aagcacaaga aattacgcaa aaaacgctct cccaggattt cgcccgtaac   2640
cgccagatcc acaactgctg gctgattacc gcagcctgaa aggaatagta atgtcattaa   2700
tcagtatgca tggcgcatgg ctgtcgttca gcgacgcgcc gcttctcgat aacgcagaac   2760
tgcatatcga agataacgaa cgtgtttgtc tggtgggccg caacggcgca ggcaaatcga   2820
```

-continued

```
cgttaatgaa atcctcaac cgtgaacaag gctggatga cggtcgcatt atttacgagc    2880
aagatttgat tgtagcgcgt ctgcaacagg atccgccgcg taacgttgag ggtagcgttt    2940
atgatttcgt tgccgaaggc attgaagaac aagcggaata tctgaaacgc tatcacgata    3000
tttcgcgcct ggtgatgaac gacccgagcg agaaaaatct caacgaactg gcgaaggttc    3060
aggaacagct ggatcaccac aacctgtggc agctggaaaa ccgcatcaac gaagtgctgg    3120
cgcaactggg gttagatcct aacgttgcgc tgtcgtcgct ttccggcggc tggttgcgta    3180
agcggcatt aggacgcgcg ctggtgagta atccgcgcgt gctgttgctt gatgaaccga    3240
caaaccacct ggatattgaa accatcgact ggctggaagg ttttttgaaa actttcaacg    3300
ggacgattat tttcatctcc cacgaccgtt cgtttatccg caatatggcg acgcgcattg    3360
ttgatctcga tcgcggcaag ctggtgacct atccagggaa ttacgaccag tacctgctgg    3420
aaaaagaaga agccctgcgc gtggaagaat acaaaatgc cgagttcgat cgcaaactgg    3480
cgcaggaaga ggtgtggatc cgccagggga tcaaagcacg ccgtacccgt aatgaaggcc    3540
gcgtacgcgc cctgaaagcg atgcgtcgcg aacgtggtga acgtcgcgaa gtgatgggta    3600
ccgcaaagat gcaggtggaa gaggccagcc gctccggtaa aatcgttttc gaaatggaag    3660
acgtttgcta ccaggttaac ggtaagcaac tggtgaaaga ttttttctgcc caggttctac    3720
gtggcgacaa aattgccctg attggtccga atgggtgcgg caaaaccacg ctgctaaaa    3779
```

<210> SEQ ID NO 133
<211> LENGTH: 702
<212> TYPE: PRT
<213> ORGANISM: Escherichia coli

<400> SEQUENCE: 133

```
Met Asn Ser Leu Phe Ala Ser Thr Ala Arg Gly Leu Glu Glu Leu Leu
1               5                   10                  15

Lys Thr Glu Leu Glu Asn Leu Gly Ala Val Glu Cys Gln Val Val Gln
            20                  25                  30

Gly Gly Val His Phe Lys Gly Asp Thr Arg Leu Val Tyr Gln Ser Leu
        35                  40                  45

Met Trp Ser Arg Leu Ala Ser Arg Ile Met Leu Pro Leu Gly Glu Cys
    50                  55                  60

Lys Val Tyr Ser Asp Leu Asp Leu Tyr Leu Gly Val Gln Ala Ile Asn
65                  70                  75                  80

Trp Thr Glu Met Phe Asn Pro Gly Ala Thr Phe Ala Val His Phe Ser
                85                  90                  95

Gly Leu Asn Asp Thr Ile Arg Asn Ser Gln Tyr Gly Ala Met Lys Val
            100                 105                 110

Lys Asp Ala Ile Val Asp Ala Phe Thr Arg Lys Asn Leu Pro Arg Pro
        115                 120                 125

Asn Val Asp Arg Asp Ala Pro Asp Ile Arg Val Asn Val Trp Leu His
    130                 135                 140

Lys Glu Thr Ala Ser Ile Ala Leu Asp Leu Ser Gly Asp Gly Leu His
145                 150                 155                 160

Leu Arg Gly Tyr Arg Asp Arg Ala Gly Ile Ala Pro Ile Lys Glu Thr
                165                 170                 175

Leu Ala Ala Ala Ile Val Met Arg Ser Gly Trp Gln Pro Gly Thr Pro
            180                 185                 190

Leu Leu Asp Pro Met Cys Gly Ser Gly Thr Leu Leu Ile Glu Ala Ala
        195                 200                 205
```

```
Met Leu Ala Thr Asp Arg Ala Pro Gly Leu His Arg Gly Arg Trp Gly
    210                 215                 220

Phe Ser Gly Trp Ala Gln His Asp Glu Ala Ile Trp Gln Glu Val Lys
225                 230                 235                 240

Ala Glu Ala Gln Thr Arg Ala Arg Lys Gly Leu Ala Glu Tyr Ser Ser
                245                 250                 255

His Phe Tyr Gly Ser Asp Ser Asp Ala Arg Val Ile Gln Arg Ala Arg
                260                 265                 270

Thr Asn Ala Arg Leu Ala Gly Ile Gly Glu Leu Ile Thr Phe Glu Val
                275                 280                 285

Lys Asp Val Ala Gln Leu Thr Asn Pro Leu Pro Lys Gly Pro Tyr Gly
290                 295                 300

Thr Val Leu Ser Asn Pro Pro Tyr Gly Glu Arg Leu Asp Ser Glu Pro
305                 310                 315                 320

Ala Leu Ile Ala Leu His Ser Leu Leu Gly Arg Ile Met Lys Asn Gln
                325                 330                 335

Phe Gly Gly Trp Asn Leu Ser Leu Phe Ser Ala Ser Pro Asp Leu Leu
                340                 345                 350

Ser Cys Leu Gln Leu Arg Ala Asp Lys Gln Tyr Lys Ala Lys Asn Gly
    355                 360                 365

Pro Leu Asp Cys Val Gln Lys Asn Tyr His Val Ala Glu Ser Thr Pro
    370                 375                 380

Asp Ser Lys Pro Ala Met Val Ala Glu Asp Tyr Thr Asn Arg Leu Arg
385                 390                 395                 400

Lys Asn Leu Lys Lys Phe Glu Lys Trp Ala Arg Gln Glu Gly Ile Glu
                405                 410                 415

Cys Tyr Arg Leu Tyr Asp Ala Asp Leu Pro Glu Tyr Asn Val Ala Val
                420                 425                 430

Asp Arg Tyr Ala Asp Trp Val Val Gln Glu Tyr Ala Pro Pro Lys
                435                 440                 445

Thr Ile Asp Ala His Lys Ala Arg Gln Arg Leu Phe Asp Ile Ile Ala
    450                 455                 460

Ala Thr Ile Ser Val Leu Gly Ile Ala Pro Asn Lys Leu Val Leu Lys
465                 470                 475                 480

Thr Arg Glu Arg Gln Lys Gly Lys Asn Gln Tyr Gln Lys Leu Gly Glu
                485                 490                 495

Lys Gly Glu Phe Leu Glu Val Thr Glu Tyr Asn Ala His Leu Trp Val
                500                 505                 510

Asn Leu Thr Asp Tyr Leu Asp Thr Gly Leu Phe Leu Asp His Arg Ile
                515                 520                 525

Ala Arg Arg Met Leu Gly Gln Met Ser Lys Gly Lys Asp Phe Leu Asn
    530                 535                 540

Leu Phe Ser Tyr Thr Gly Ser Ala Thr Val His Ala Gly Leu Gly Gly
545                 550                 555                 560

Ala Arg Ser Thr Thr Thr Val Asp Met Ser Arg Thr Tyr Leu Glu Trp
                565                 570                 575

Ala Glu Arg Asn Leu Arg Leu Asn Gly Leu Thr Gly Arg Ala His Arg
                580                 585                 590

Leu Ile Gln Ala Asp Cys Leu Ala Trp Leu Arg Glu Ala Asn Glu Gln
                595                 600                 605

Phe Asp Leu Ile Phe Ile Asp Pro Pro Thr Phe Ser Asn Ser Lys Arg
                610                 615                 620

Met Glu Asp Ala Phe Asp Val Gln Arg Asp His Leu Ala Leu Met Lys
```

```
                625                 630                 635                 640
Asp Leu Lys Arg Leu Leu Arg Ala Gly Gly Thr Ile Met Phe Ser Asn
                    645                 650                 655
Asn Lys Arg Gly Phe Arg Met Asp Leu Asp Gly Leu Ala Lys Leu Gly
                660                 665                 670
Leu Lys Ala Gln Glu Ile Thr Gln Lys Thr Leu Ser Gln Asp Phe Ala
            675                 680                 685
Arg Asn Arg Gln Ile His Asn Cys Trp Leu Ile Thr Ala Ala
        690                 695                 700
```

<210> SEQ ID NO 134
<211> LENGTH: 4731
<212> TYPE: DNA
<213> ORGANISM: Escherichia coli

<400> SEQUENCE: 134

| | | |
|---|---|---|
| caccagtgtt gatcagctga aaggcaaaaa agtcggcgta cagaacggga cgacacacca | 60 |
| gaaattcatt atggataagc acccggaaat cactaccgtt ccgtatgaca gctaccagaa | 120 |
| cgcaaaactg gatctgcaaa acgggcgtat cgacggcgtc ttcggtgaca ccgcagtggt | 180 |
| cactgagtgg ctgaaagata acccgaaact ggcggcggtg ggcgacaaag tgaccgataa | 240 |
| agattacttc ggcactggcc tcggcatcgc ggtacgtcag gcaacactg agctgcagca | 300 |
| gaaactcaac actgcgctgg aaaaagtgaa gaaagatggc acttacgaaa ccatctacaa | 360 |
| caaatggttc cagaagtaat tcctgatgaa tgaattttt cctttagcaa gcgccgccgg | 420 |
| gatgaccgtc ggccttgccg tttgtgcatt gattgtcggg ctggcgctgg cgatgttctt | 480 |
| tgcggtatgg gagtcggcaa atggcgtcc tgtcgcgtgg gcaggttcag cgctggtaac | 540 |
| cattctgcgt ggcctgccag aaattctggt ggtgctgttt atctattttg gctcctcgca | 600 |
| gctgctgctg acgctttcgg atggcttcac tatcaatctt gggttcgtgc agatcccagt | 660 |
| gcagatggac attgagaact cgacgttag cccgttcctt tgtggtgtca tcgctctgtc | 720 |
| actgctgtat gccgcctatg cctcgcaaac gcttcggggc gcgttgaaag cggtgccggt | 780 |
| gggtcagtgg gagtctggtc aggcgctggg gctgtcgaaa tcggctatct ttttccgtct | 840 |
| ggtgatgccg cagatgtggc gtcatgcgct gcctggcctc ggtaaccagt ggctggtgct | 900 |
| gctgaaagat accgcgctgg tcagtttgat tagtgtgaat gatttaatgc tgcaaacaaa | 960 |
| aagcatcgct actcgtaccc aggaaccatt tacctggtac attgtggcgg cggcgattta | 1020 |
| cctggtgatc accctgctca gtcagtacat tctcaaacgc attgacctgc gcgcgacacg | 1080 |
| ttttgagcgg aggcccagct aatgtttgag tatttacccg aactgatgaa agggctacac | 1140 |
| accagcctga cgctaaccgt tgcctcgctg attgtggcac tgattctggc attgattttt | 1200 |
| accatcatcc tgacgctgaa acgccggtg ctggtgtggc tggtgcgggg ttatatcacg | 1260 |
| ctgtttaccg gtacgccgct gctggtgcag atcttcctga tttattacgg gccgggccag | 1320 |
| tttccgactt gcaggagta tccggcactg tggcatttgt tgtcagaacc gtggttatgt | 1380 |
| gcgctgattg cgttgtcgct gaatagtgcg gcgtatacca cgcagctgtt ttacggtgca | 1440 |
| attcgtgcga tcccggaagg tcagtggcag tcctgtagcg ccctgggaat gagcaaaaaa | 1500 |
| gatacgctgg cgatcctgct gccgtatgcc tttaaacgct cgctctcttc ttattccaac | 1560 |
| gaagtggtgc tggtattcaa agtacctct ctggcataca ccattacgct gatggaagtg | 1620 |
| atgggataca gccagttgtt gtacggacgc acctacgatg taatggtgtt cggtgcggca | 1680 |
| gggattattt acctggtcgt taacggcctg ctgacgctga tgatgcgtct gatcgagcgc | 1740 |

```
aaagcgctgg cattcgaacg gcgaaattaa tgtggctgcg tacattcgcc ggggggtttt      1800
gtaggtctga taagacgcgc cagcgtcgca tcagacatca gcacggtgcc tgtgccggat      1860
gcggcgggga cgccttatcc ggcctacata gtgcataaat tcttataatg aagacggaca      1920
acccactaag ttgtccgtct tttttatttc atttaaatta tttaatcatg tttattgcat      1980
ataaattcac ttgatggcat tgttatccca tgccgcagac acggccaaaa atcataagat      2040
tgacagacgg gagttccatc atgaaaaagt tagttcttgc cgctttactt gcttccttta      2100
ctttcggtgc ttctgccgca gagaaaatca attttggcgt ttcagccacc tatccaccct      2160
ttgaatctat aggtgctaat aatgagattg tcggctttga tatcgatctg gcaaaagcct      2220
tgtgcaaaca aatgcaggca gaatgtactt ttactaatca cgcgttcgac agcctgatcc      2280
cgtccctgaa attcagaaaa tatgacgccg taatctccgg tatggatatc accccggagc      2340
gtagcaaaca ggtatcgttt accacgccct actatgaaaa ctcagccgtc gtgattgcca      2400
aaaagatac ctacaaaacg tttgccgatc tgaaaggcaa acgtattggg atggaaaacg      2460
gtactacgca ccagaaatat attcaggatc agcacccgga agtgaaaact gtctcttatg      2520
acagttatca gaatgccttt atcgatctga aaaatggtcg tattgatggg gtatttggtg      2580
acacagcggt ggtaaacgaa tggctgaaaa ccaatccaca acttggtgtt gctactgaga      2640
aagtgaccga tccgcaatat tttggcaccg gcctgggcat cgctgtacgt ccggataaca      2700
aagccctgct ggaaaaactg aataacgcgc tggcagcaat taaagctgac ggtacttatc      2760
aaaaaatcag tgaccagtgg ttcccacagt aagattcaga aagccgcaac cgcggcttga      2820
gactgatgac aaaggtaaaa ttgcctgatg cgctacgctt atcaggccta catggcccat      2880
gcaatgtatt gaatttgcac gcttttgtag gccggataag gcgttacgc cgcatccggc       2940
ataaacaacg cgcactttgt cagcaatctg aagccgcaca tgcggctttt ttattgcttc      3000
accagcagcg tcagcacttc atagtgcgcg gtatgcggga acatatcgaa aagctgcacc      3060
cgttcaatac gaaacccagg cagttcgcgg atatctttcg ccatagtttg ggcgttacag      3120
ctggagtaga tgataaaacg cggtgccatc gttgagagat aatcacacag cggtttacca      3180
atgccgcggc gcggcgggtt aaccagcacc agctccggca catccccctg agcggtggca      3240
aactgagtgg agtccagcgc ctgaaattgc aaacgcgtta agcccagttc agcggctgac      3300
tgctttgcac aggcaatggc ctctgatgca atttcgatcc cggttaactg catgtcaggc      3360
gtcgcgcagt gtaaaccaaa gcccccaca ccgcagaaca gatcccacat atgtttaacc       3420
ggcagctgtc gtacccagtc gcgcgcggtg gcgtacaact ggctggcgac cgccggatta      3480
gtctggaaga aactttgcgg acggatccac agcggtacgt cattaaaacg ctccgccagt      3540
gcctgttgtt cggtcaggta gatctccgtc tccccttcca taatcgccat atgtaccggc      3600
tgaatattga cggtaataac tttcagctgc ggtagttgtt cgtgtaacca cggcagcgcc      3660
ttacgcagtt gcgccagctt ggtatcagaa cgcagtacaa agcgcagcat catgcctcca      3720
tcactctggc tttcagtcag cagaatgtat ttcagttcgc cacgcttacg cgccacgttg      3780
tagggcgtta accccgctcg ggcgataaac ggttttagcg ccgcaaaaac gggcgcaaat      3840
gaggcaggat aaagcgggca gtcacaaagg tcttctggtg tgccatcgcg atgcagcata      3900
ccgagcagtg gttttcaac gctaccactc accaccattt tggctttatt acgaaaccct       3960
tgttccgggc ctgacaccgg cgcgcaccat tcctcaaccg gaaagtcggc gagcagattt      4020
ttaagatcgg cggttttagc ggagagttgc tctggaatcg gctgcattat ccactgacag      4080
```

-continued

```
gaacgacagc gacccgcgtc gtaaagtgcg cactgcatac attgaccttc acatcatcag    4140
gggcgacgat tatacacatt attgcaactg gaagaaccgc cgactggtcg agggaacgaa    4200
cagcagcatc aggatgagca tatccggcag cttctgcagc atcaggctat ggaagatttc    4260
acgttttgat tcaccgggaa tgctgaacag ctccggataa ccgtacccca gcgaagccgc    4320
ccacaagtaa cttgcggcgg tgatttgtgt cagcagatat agccagcgcg cccagcgacg    4380
cccttttcacc agtgaaaacg cacaccagat ctcaatgaaa accagcacca gactgcttaa    4440
aaagaccagc gttaaactcc aggtttgtac gctgcgatga atgaactcgc caataccgcg    4500
cacgcccagc gtattgaaaa tcatcagcac gtcgaggcca cggatcataa taatggcgag    4560
cgccgccacc tgcaccagcg caggcacatt caggcgagca tgagatgaag atgttttctt    4620
aaaaaatccc aacgtttcgt cttccatgaa acaatgccg cgacatgcgc ggcattatgt    4680
agccaggttg gcaaatttta gtgtcttcag ccacgtcttg cacgctggat g             4731
```

<210> SEQ ID NO 135
<211> LENGTH: 238
<212> TYPE: PRT
<213> ORGANISM: Escherichia coli

<400> SEQUENCE: 135

Met Asn Glu Phe Phe Pro Leu Ala Ser Ala Ala Gly Met Thr Val Gly
1               5                   10                  15

Leu Ala Val Cys Ala Leu Ile Val Gly Leu Ala Leu Ala Met Phe Phe
            20                  25                  30

Ala Val Trp Glu Ser Ala Lys Trp Arg Pro Val Ala Trp Ala Gly Ser
        35                  40                  45

Ala Leu Val Thr Ile Leu Arg Gly Leu Pro Glu Ile Leu Val Val Leu
    50                  55                  60

Phe Ile Tyr Phe Gly Ser Ser Gln Leu Leu Leu Thr Leu Ser Asp Gly
65                  70                  75                  80

Phe Thr Ile Asn Leu Gly Phe Val Gln Ile Pro Val Gln Met Asp Ile
                85                  90                  95

Glu Asn Phe Asp Val Ser Pro Phe Leu Cys Gly Val Ile Ala Leu Ser
            100                 105                 110

Leu Leu Tyr Ala Ala Tyr Ala Ser Gln Thr Leu Arg Gly Ala Leu Lys
        115                 120                 125

Ala Val Pro Val Gly Gln Trp Glu Ser Gly Gln Ala Leu Gly Leu Ser
    130                 135                 140

Lys Ser Ala Ile Phe Phe Arg Leu Val Met Pro Gln Met Trp Arg His
145                 150                 155                 160

Ala Leu Pro Gly Leu Gly Asn Gln Trp Leu Val Leu Leu Lys Asp Thr
                165                 170                 175

Ala Leu Val Ser Leu Ile Ser Val Asn Asp Leu Met Leu Gln Thr Lys
            180                 185                 190

Ser Ile Ala Thr Arg Thr Gln Glu Pro Phe Thr Trp Tyr Ile Val Ala
        195                 200                 205

Ala Ala Ile Tyr Leu Val Ile Thr Leu Leu Ser Gln Tyr Ile Leu Lys
    210                 215                 220

Arg Ile Asp Leu Arg Ala Thr Arg Phe Glu Arg Arg Pro Ser
225                 230                 235

<210> SEQ ID NO 136
<211> LENGTH: 222
<212> TYPE: PRT

<213> ORGANISM: Escherichia coli

<400> SEQUENCE: 136

Met Phe Glu Tyr Leu Pro Glu Leu Met Lys Gly Leu His Thr Ser Leu
1               5                   10                  15

Thr Leu Thr Val Ala Ser Leu Ile Val Ala Leu Ile Leu Ala Leu Ile
            20                  25                  30

Phe Thr Ile Ile Leu Thr Leu Lys Thr Pro Val Leu Val Trp Leu Val
        35                  40                  45

Arg Gly Tyr Ile Thr Leu Phe Thr Gly Thr Pro Leu Leu Val Gln Ile
    50                  55                  60

Phe Leu Ile Tyr Tyr Gly Pro Gly Gln Phe Pro Thr Leu Gln Glu Tyr
65                  70                  75                  80

Pro Ala Leu Trp His Leu Leu Ser Glu Pro Trp Leu Cys Ala Leu Ile
                85                  90                  95

Ala Leu Ser Leu Asn Ser Ala Ala Tyr Thr Thr Gln Leu Phe Tyr Gly
            100                 105                 110

Ala Ile Arg Ala Ile Pro Glu Gly Gln Trp Gln Ser Cys Ser Ala Leu
        115                 120                 125

Gly Met Ser Lys Lys Asp Thr Leu Ala Ile Leu Leu Pro Tyr Ala Phe
130                 135                 140

Lys Arg Ser Leu Ser Ser Tyr Ser Asn Glu Val Val Leu Val Phe Lys
145                 150                 155                 160

Ser Thr Ser Leu Ala Tyr Thr Ile Thr Leu Met Glu Val Met Gly Tyr
                165                 170                 175

Ser Gln Leu Leu Tyr Gly Arg Thr Tyr Asp Val Met Val Phe Gly Ala
            180                 185                 190

Ala Gly Ile Ile Tyr Leu Val Val Asn Gly Leu Leu Thr Leu Met Met
        195                 200                 205

Arg Leu Ile Glu Arg Lys Ala Leu Ala Phe Glu Arg Arg Asn
    210                 215                 220

<210> SEQ ID NO 137
<211> LENGTH: 243
<212> TYPE: PRT
<213> ORGANISM: Escherichia coli

<400> SEQUENCE: 137

Met Lys Lys Leu Val Leu Ala Ala Leu Leu Ala Ser Phe Thr Phe Gly
1               5                   10                  15

Ala Ser Ala Ala Glu Lys Ile Asn Phe Gly Val Ser Ala Thr Tyr Pro
            20                  25                  30

Pro Phe Glu Ser Ile Gly Ala Asn Asn Glu Ile Val Gly Phe Asp Ile
        35                  40                  45

Asp Leu Ala Lys Ala Leu Cys Lys Gln Met Gln Ala Glu Cys Thr Phe
    50                  55                  60

Thr Asn His Ala Phe Asp Ser Leu Ile Pro Ser Leu Lys Phe Arg Lys
65                  70                  75                  80

Tyr Asp Ala Val Ile Ser Gly Met Asp Ile Thr Pro Glu Arg Ser Lys
                85                  90                  95

Gln Val Ser Phe Thr Thr Pro Tyr Tyr Glu Asn Ser Ala Val Val Ile
            100                 105                 110

Ala Lys Lys Asp Thr Tyr Lys Thr Phe Ala Asp Leu Lys Gly Lys Arg
        115                 120                 125

Ile Gly Met Glu Asn Gly Thr Thr His Gln Lys Tyr Ile Gln Asp Gln

```
            130                 135                 140
His Pro Glu Val Lys Thr Val Ser Tyr Asp Ser Tyr Gln Asn Ala Phe
145                 150                 155                 160

Ile Asp Leu Lys Asn Gly Arg Ile Asp Gly Val Phe Gly Asp Thr Ala
                165                 170                 175

Val Val Asn Glu Trp Leu Lys Thr Asn Pro Gln Leu Gly Val Ala Thr
            180                 185                 190

Glu Lys Val Thr Asp Pro Gln Tyr Phe Gly Thr Gly Leu Gly Ile Ala
                195                 200                 205

Val Arg Pro Asp Asn Lys Ala Leu Leu Glu Lys Leu Asn Asn Ala Leu
            210                 215                 220

Ala Ala Ile Lys Ala Asp Gly Thr Tyr Gln Lys Ile Ser Asp Gln Trp
225                 230                 235                 240

Phe Pro Gln

<210> SEQ ID NO 138
<211> LENGTH: 375
<212> TYPE: PRT
<213> ORGANISM: Escherichia coli

<400> SEQUENCE: 138

Met Gln Cys Ala Leu Tyr Asp Ala Gly Arg Cys Arg Ser Cys Gln Trp
1               5                   10                  15

Ile Met Gln Pro Ile Pro Glu Gln Leu Ser Ala Lys Thr Ala Asp Leu
            20                  25                  30

Lys Asn Leu Leu Ala Asp Phe Pro Val Glu Glu Trp Cys Ala Pro Val
        35                  40                  45

Ser Gly Pro Glu Gln Gly Phe Arg Asn Lys Ala Lys Met Val Val Ser
    50                  55                  60

Gly Ser Val Glu Lys Pro Leu Leu Gly Met Leu His Arg Asp Gly Thr
65                  70                  75                  80

Pro Glu Asp Leu Cys Asp Cys Pro Leu Tyr Pro Ala Ser Phe Ala Pro
                85                  90                  95

Val Phe Ala Ala Leu Lys Pro Phe Ile Ala Arg Ala Gly Leu Thr Pro
            100                 105                 110

Tyr Asn Val Ala Arg Lys Arg Gly Glu Leu Lys Tyr Ile Leu Leu Thr
        115                 120                 125

Glu Ser Gln Ser Asp Gly Gly Met Met Leu Arg Phe Val Leu Arg Ser
    130                 135                 140

Asp Thr Lys Leu Ala Gln Leu Arg Lys Ala Leu Pro Trp Leu His Glu
145                 150                 155                 160

Gln Leu Pro Gln Leu Lys Val Ile Thr Val Asn Ile Gln Pro Val His
                165                 170                 175

Met Ala Ile Met Glu Gly Glu Thr Glu Ile Tyr Leu Thr Glu Gln Gln
            180                 185                 190

Ala Leu Ala Glu Arg Phe Asn Asp Val Pro Leu Trp Ile Arg Pro Gln
        195                 200                 205

Ser Phe Phe Gln Thr Asn Pro Ala Val Ala Ser Gln Leu Tyr Ala Thr
    210                 215                 220

Ala Arg Asp Trp Val Arg Gln Leu Pro Val Lys His Met Trp Asp Leu
225                 230                 235                 240

Phe Cys Gly Val Gly Gly Phe Gly Leu His Cys Ala Thr Pro Asp Met
                245                 250                 255

Gln Leu Thr Gly Ile Glu Ile Ala Ser Glu Ala Ile Ala Cys Ala Lys
```

```
                    260                 265                 270
Gln Ser Ala Ala Glu Leu Gly Leu Thr Arg Leu Gln Phe Gln Ala Leu
        275                 280                 285

Asp Ser Thr Gln Phe Ala Thr Ala Gln Gly Asp Val Pro Glu Leu Val
        290                 295                 300

Leu Val Asn Pro Pro Arg Arg Gly Ile Gly Lys Pro Leu Cys Asp Tyr
305                 310                 315                 320

Leu Ser Thr Met Ala Pro Arg Phe Ile Ile Tyr Ser Ser Cys Asn Ala
                325                 330                 335

Gln Thr Met Ala Lys Asp Ile Arg Glu Leu Pro Gly Phe Arg Ile Glu
            340                 345                 350

Arg Val Gln Leu Phe Asp Met Phe Pro His Thr Ala His Tyr Glu Val
                355                 360                 365

Leu Thr Leu Leu Val Lys Gln
                370                 375

<210> SEQ ID NO 139
<211> LENGTH: 162
<212> TYPE: PRT
<213> ORGANISM: Escherichia coli

<400> SEQUENCE: 139

Met Glu Asp Glu Thr Leu Gly Phe Phe Lys Lys Thr Ser Ser Ser His
1               5                   10                  15

Ala Arg Leu Asn Val Pro Ala Leu Val Gln Val Ala Ala Leu Ala Ile
                20                  25                  30

Ile Met Ile Arg Gly Leu Asp Val Leu Met Ile Phe Asn Thr Leu Gly
            35                  40                  45

Val Arg Gly Ile Gly Glu Phe Ile His Arg Ser Val Gln Thr Trp Ser
        50                  55                  60

Leu Thr Leu Val Phe Leu Ser Ser Leu Val Leu Val Phe Ile Glu Ile
65                  70                  75                  80

Trp Cys Ala Phe Ser Leu Val Lys Gly Arg Arg Trp Ala Arg Trp Leu
                85                  90                  95

Tyr Leu Leu Thr Gln Ile Thr Ala Ala Ser Tyr Leu Trp Ala Ala Ser
                100                 105                 110

Leu Gly Tyr Gly Tyr Pro Glu Leu Phe Ser Ile Pro Gly Glu Ser Lys
            115                 120                 125

Arg Glu Ile Phe His Ser Leu Met Leu Gln Lys Leu Pro Asp Met Leu
        130                 135                 140

Ile Leu Met Leu Leu Phe Val Pro Ser Thr Ser Arg Arg Phe Phe Gln
145                 150                 155                 160

Leu Gln

<210> SEQ ID NO 140
<211> LENGTH: 5079
<212> TYPE: DNA
<213> ORGANISM: Escherichia coli

<400> SEQUENCE: 140
aaaactacaa ccttgtcgtt cgctttggca tcatttttcat tataaagacg gaattttgca    60
tcagcttctc atcaagaaaa acaactaaaa aatcaatcac aatacttgtg catttcttta   120
aacagttttt aaaaactgac tccgggtatg gagctatggg tattttctgt acccaatgct   180
tttaacagca attaatttca taggatgaaa gctcaatgca tcaatctggt tctgtttctc   240
```

-continued

```
tttgtcgttc cgcaatatct gttctggtgg ctacagcgtt atattcaccc atagcattgg    300
catcaactgt tgagtatggt gagacagttg atggtgttgt cctggaaaaa gatatccagc    360
tggtttatgg gaccgccaat aatacgaaaa tcaatcctgg cggagaacag catataaaag    420
aatttggtgt aagtaataat actgaaatta acggagggta tcagtacatt gaaatgaatg    480
gcgccgcaga atactcagta ttaaatgacg gttatcaaat tgttcaaatg ggtggcgcgg    540
caaaccagac tacgctcaat aatggtgtgc tacaggttta tggcgcagcg aatgatacca    600
cgattaaagg cgggcgctta atcgttgaaa aagatggggg ggccgtcttt gtcgctatcg    660
aaaagggagg actactggag gttaagagg ggggatttgc atttgcggta gatcagaaag    720
caggcggtgc tattaaaaca accacgcggg ccatggaggt attcggaaca aaccgtctcg    780
gtcagttcga tatcaagaat ggtattgcta ataatatgtt gttggaaaac ggcggaagtt    840
tgcgagttga agaaaatgac ttcgcttata ataccactgt agatagtggc ggcttactgg    900
aggttatgga tggcgggact gtaactggcg ttgataaaaa agcaggcgga aaattaattg    960
tctcaacgaa tgcgctggaa gtgagtggtc caaacagtaa aggccaattt agtataaaag   1020
atggtgtgtc aaaaaattat gaactggatg atggttccgg gctcattgtt atggaggaca   1080
cgcaggccat tgatactatc cttgataagc atgccactat gcaatcgctg ggaaaggata   1140
ctggtacgaa agtgcaggca aatgcggtat atgatctcgg tcgatcatat cagaatggaa   1200
gtatcacgta ttcctcaaaa gccatctctg aaaatatggt tatcaacaat ggccgcgcta   1260
acgtctgggc tggcacaatg gttaacgttt cagtcagagg gaatgatggc attcttgagg   1320
tcatgaagcc gcaaataaat tatgcacccg caatgttggt gggtaaggta gtggtttctg   1380
agggcgcttc ttttagaacg catggtgccg tggataccag caaagcggac gtttcgctcg   1440
aaaatagcgt atggaccatc attgccgata tcactacgac gaaccaaaac accctcctca   1500
acttagccaa ccttgcgatg tctgacgcaa atgtgattat gatggatgag ccagtgactc   1560
gttcatcagt gacggcaagt gcggaaaatt tcattacgtt gaccaccaat accctgtcgg   1620
gaaacggcaa tttttatatg cgtaccgata tggctaatca tcagagcgat cagctcaacg   1680
tcaccggtca ggcaacaggt gatttcaaaa tattcgtgac ggacaccggt gccagcccgg   1740
cagcaggaga tagccttaca ctggtaacaa cgggcggcgg tgatgctgca tttacgttgg   1800
gcaatgccgg aggcgttgtt gatatcggta cgtatgaata taccttgctg gataatggca   1860
accatagctg gagtctggca gagaatcgcg cgcaaattac cccttcaacc actgatgtgc   1920
tgaatatggc ggccgcacaa ccgctggtat ttgatgcaga actggacacc gtgcgtgagc   1980
gtcttggtag cgtaaaaggc gttagttacg atacggcgat gtggagttcg gcaattaaca   2040
cccgcaacaa cgtgaccact gatgcgggag ctggttttga gcaaacattg acgggcctga   2100
cgctcggtat cgatagccgt ttctcccgtg aagaaagcag tacaattcgc ggcttgatct   2160
ttggttactc tcattctgat attggttttg atcgcggcgg caaaggtaat atcgatagct   2220
ataccctggg ggcttatgcc ggttgggagc atcagaacgg tgcctatgtt gatggggtgg   2280
tgaaagttga ccgttttgcc aacaccatcc atggcaagat gagtaatggg gcaacagcgt   2340
ttggcgatta caatagtaac ggcgcggtg ctcatgttga gagcgggttc cgttgggttg    2400
acggattgtg gagtgttaga ccctatctgg cctttaccgg ctttaccaca gatggtcagg   2460
actacacgtt atcaaacggc atgcgcgcgg atgtgggaaa tacccggata ttacgcgctg   2520
aagcgggaac ggcggtaagc tatcacatgg acctgcaaaa cggtacgacg ctggaacccc   2580
ggctgaaagc ggccgtgcgt caggaatacg ccgattctaa ccaggtgaaa gttaatgacg   2640
```

```
atggcaaatt taataatgat gtggctggaa ccagtggcgt ttatcaggct ggtataaggt    2700
catcgtttac cccgacgtta agcggtcatt tgtcagtcag ctatggcaat ggcgcagggg    2760
tagaatcgcc gtggaatact caggcgggtg tggtctggac gttctgataa cagaaaataa    2820
acaggctgtg atgtgtcacg gtctgtttat cgaattaatt gcagatataa aaaaaccaac    2880
cgtaagggtt ggttttttct tgggattttt ggtcggcacg agaggatttg aacctccgac    2940
ccccgacacc ccatgacggt gcgctaccag gctgcgctac gtgccgactc gtggctgcta    3000
atactaccgt tttccacacc gattgcaagt aagatatttc gctaactgat ttataattaa    3060
tcagttagcg ataaaacgct tctcgtctgt cagcacttgc aataacaaac ttaactgtgg    3120
tttttcatct ttcactcttt caccacgtaa gttgtaagtg cggtatttac cgttattgtt    3180
cagtaccagc gtcttttttcg gggtggtaat tgccagcgta tcgttatccg ctgcggtaac    3240
ccagtaatga cggcgttgag ggttgaacaa atcctgacct tgcgaatatt cgctggcagg    3300
tgtgctgaca gtagcaggc gttgcatcag cgtcgtcatc agatcggtat gatcagtcag    3360
agcattaata cgctgcgccg gcgtgcctgg ccagtgaatc actaatggca cctgcagatg    3420
accgtgggac cagtcaaagg tttcttcctc ttcgctcagt ggaataccc gaccggcagt    3480 gataatcacc accgtattgt ccagtttgcc agaatcacgc agtgcattga gcacgcggtt    3540
gatctggtca tcgacattgc ctgccgcccg gctatatttc cgtgcaaatg cctgctgatt    3600
gctgtcgtca atgttagtac cattgaaaga aacccacgag aaccagcggt tatcttcttg    3660
tgcgtagcgt cccagccagt tgatccactg cgtggcggtc tgctcgtcgg attgggtgcg    3720
tacgctcggc atcgagaaat ctgacaacaa tgcctggcga tacagcgggc tggtaaagcc    3780
atctgatgag aataacccca gctgatagcc ttgctgatta agcgcagtaa ttaatgccgc    3840
aggcgtacgg gtcgacagaa tgccgtccat atagctcggc gagatgccat agaacaggcc    3900
aaagatgccg ttgtctgtag tgttgccgga gctcatatgg cgcgtgaacg aaatattttg    3960
ctcagcaaaa cctgccagcg caggcatctg cttctcgaag cgtgagtagt tcaggccatc    4020
gacagtaatc aacagcacat tctgcccggt gcccatatcg cgatagcgca gttcgcttaa    4080
cggatactga acggaaacgg cgtctggatt accttgctca ataagacggc gttgatactc    4140
ctgcgcatca agcagaccat gcttctcaag aaaacgtcgc gccgtcatcg ggtacgaaag    4200
cggcaggtta gcgcgctgca tggtgatcgg gcgatagaaa ttggcatcgg cccagatata    4260
caccacatgc gaggcgataa aggcgataaa taagaatgcg ccagcgggc gcgcgaagcg    4320 tcgacgacgt gtcaggctgc gcagcttttg ccagctccac gtcgcaaaca ccagttcaag    4380
caataaaata accggcacgc tgatgaacat cagctgccag tcgcgcgcca tctcatttc    4440 gtctgggttg ataaccagtt gccagacgat gggattaaga tggagatgga aacgagtaaa    4500
gacttcgcta tcgatcagta atagcgtcat tcccgccgtt gccagaatga cggacaaaaa    4560
cctcatcagc ctctgggagc cgacgataaa ggtcagcggg aagaggatca gcaagtaggt    4620
ggcgaacacc aggaagctga aatggccgat aatgcttacg taggaataaa tgcgaccagc    4680
aagcgttgtc ggccagtcgg cgataaacag gtaacggctg ccaatgacga gcgaaagcag    4740
aatattgaac agtgcaaacc agtgccccca actgaccatc tgggagactt tttcacggta    4800
gcgctgacga tgagttacca taacctgtta tctgtttccc ttagtgcgct ttgtcttcgt    4860
tgatagagga ctgtaaggcg cgggcaaaag agttggcaat tgcctggcgt tgggccgggg    4920
caatgctggt gttgataagg ttagtgacca tgttgcctaa caccatcagg gaaaggtcgg    4980
```

```
tcggagcctt atgttttcc agtacgttga gcagctctgc gagcaattgt tcaacctgtt    5040
catcactgta gcgggaaatt tgtggcataa atcgaaatc                          5079
```

<210> SEQ ID NO 141
<211> LENGTH: 863
<212> TYPE: PRT
<213> ORGANISM: Escherichia coli

<400> SEQUENCE: 141

```
Met His Gln Ser Gly Ser Val Ser Leu Cys Arg Ser Ala Ile Ser Val
1               5                   10                  15

Leu Val Ala Thr Ala Leu Tyr Ser Pro Ile Ala Leu Ala Ser Thr Val
            20                  25                  30

Glu Tyr Gly Glu Thr Val Asp Gly Val Val Leu Glu Lys Asp Ile Gln
        35                  40                  45

Leu Val Tyr Gly Thr Ala Asn Asn Thr Lys Ile Asn Pro Gly Gly Glu
    50                  55                  60

Gln His Ile Lys Glu Phe Gly Val Ser Asn Asn Thr Glu Ile Asn Gly
65                  70                  75                  80

Gly Tyr Gln Tyr Ile Glu Met Asn Gly Ala Ala Glu Tyr Ser Val Leu
                85                  90                  95

Asn Asp Gly Tyr Gln Ile Val Gln Met Gly Gly Ala Ala Asn Gln Thr
            100                 105                 110

Thr Leu Asn Asn Gly Val Leu Gln Val Tyr Gly Ala Ala Asn Asp Thr
        115                 120                 125

Thr Ile Lys Gly Gly Arg Leu Ile Val Glu Lys Asp Gly Gly Ala Val
    130                 135                 140

Phe Val Ala Ile Glu Lys Gly Gly Leu Leu Glu Val Lys Glu Gly Gly
145                 150                 155                 160

Phe Ala Phe Ala Val Asp Gln Lys Ala Gly Gly Ala Ile Lys Thr Thr
                165                 170                 175

Thr Arg Ala Met Glu Val Phe Gly Thr Asn Arg Leu Gly Gln Phe Asp
            180                 185                 190

Ile Lys Asn Gly Ile Ala Asn Asn Met Leu Leu Glu Asn Gly Gly Ser
        195                 200                 205

Leu Arg Val Glu Glu Asn Asp Phe Ala Tyr Asn Thr Thr Val Asp Ser
    210                 215                 220

Gly Gly Leu Leu Glu Val Met Asp Gly Gly Thr Val Thr Gly Val Asp
225                 230                 235                 240

Lys Lys Ala Gly Gly Lys Leu Ile Val Ser Thr Asn Ala Leu Glu Val
                245                 250                 255

Ser Gly Pro Asn Ser Lys Gly Gln Phe Ser Ile Lys Asp Gly Val Ser
            260                 265                 270

Lys Asn Tyr Glu Leu Asp Asp Gly Ser Gly Leu Ile Val Met Glu Asp
        275                 280                 285

Thr Gln Ala Ile Asp Thr Ile Leu Asp Lys His Ala Thr Met Gln Ser
    290                 295                 300

Leu Gly Lys Asp Thr Gly Thr Lys Val Gln Ala Asn Ala Val Tyr Asp
305                 310                 315                 320

Leu Gly Arg Ser Tyr Gln Asn Gly Ser Ile Thr Tyr Ser Ser Lys Ala
                325                 330                 335

Ile Ser Glu Asn Met Val Ile Asn Asn Gly Arg Ala Asn Val Trp Ala
            340                 345                 350

Gly Thr Met Val Asn Val Ser Val Arg Gly Asn Asp Gly Ile Leu Glu
```

-continued

```
                355                 360                 365
Val Met Lys Pro Gln Ile Asn Tyr Ala Pro Ala Met Leu Val Gly Lys
370                 375                 380

Val Val Val Ser Glu Gly Ala Ser Phe Arg Thr His Gly Ala Val Asp
385                 390                 395                 400

Thr Ser Lys Ala Asp Val Ser Leu Glu Asn Ser Val Trp Thr Ile Ile
                405                 410                 415

Ala Asp Ile Thr Thr Thr Asn Gln Asn Thr Leu Leu Asn Leu Ala Asn
                420                 425                 430

Leu Ala Met Ser Asp Ala Asn Val Ile Met Met Asp Glu Pro Val Thr
                435                 440                 445

Arg Ser Ser Val Thr Ala Ser Ala Glu Asn Phe Ile Thr Leu Thr Thr
                450                 455                 460

Asn Thr Leu Ser Gly Asn Gly Asn Phe Tyr Met Arg Thr Asp Met Ala
465                 470                 475                 480

Asn His Gln Ser Asp Gln Leu Asn Val Thr Gly Gln Ala Thr Gly Asp
                485                 490                 495

Phe Lys Ile Phe Val Thr Asp Thr Gly Ala Ser Pro Ala Ala Gly Asp
                500                 505                 510

Ser Leu Thr Leu Val Thr Thr Gly Gly Asp Ala Ala Phe Thr Leu
                515                 520                 525

Gly Asn Ala Gly Gly Val Val Asp Ile Gly Thr Tyr Glu Tyr Thr Leu
530                 535                 540

Leu Asp Asn Gly Asn His Ser Trp Ser Leu Ala Glu Asn Arg Ala Gln
545                 550                 555                 560

Ile Thr Pro Ser Thr Thr Asp Val Leu Asn Met Ala Ala Gln Pro
                565                 570                 575

Leu Val Phe Asp Ala Glu Leu Asp Thr Val Arg Glu Arg Leu Gly Ser
                580                 585                 590

Val Lys Gly Val Ser Tyr Asp Thr Ala Met Trp Ser Ser Ala Ile Asn
                595                 600                 605

Thr Arg Asn Asn Val Thr Thr Asp Ala Gly Ala Gly Phe Glu Gln Thr
610                 615                 620

Leu Thr Gly Leu Thr Leu Gly Ile Asp Ser Arg Phe Ser Arg Glu Glu
625                 630                 635                 640

Ser Ser Thr Ile Arg Gly Leu Ile Phe Gly Tyr Ser His Ser Asp Ile
                645                 650                 655

Gly Phe Asp Arg Gly Gly Lys Gly Asn Ile Asp Ser Tyr Thr Leu Gly
                660                 665                 670

Ala Tyr Ala Gly Trp Glu His Gln Asn Gly Ala Tyr Val Asp Gly Val
                675                 680                 685

Val Lys Val Asp Arg Phe Ala Asn Thr Ile His Gly Lys Met Ser Asn
                690                 695                 700

Gly Ala Thr Ala Phe Gly Asp Tyr Asn Ser Asn Gly Ala Gly Ala His
705                 710                 715                 720

Val Glu Ser Gly Phe Arg Trp Val Asp Gly Leu Trp Ser Val Arg Pro
                725                 730                 735

Tyr Leu Ala Phe Thr Gly Phe Thr Thr Asp Gly Gln Asp Tyr Thr Leu
                740                 745                 750

Ser Asn Gly Met Arg Ala Asp Val Gly Asn Thr Arg Ile Leu Arg Ala
                755                 760                 765

Glu Ala Gly Thr Ala Val Ser Tyr His Met Asp Leu Gln Asn Gly Thr
770                 775                 780
```

```
Thr Leu Glu Pro Trp Leu Lys Ala Ala Val Arg Gln Glu Tyr Ala Asp
785                 790                 795                 800

Ser Asn Gln Val Lys Val Asn Asp Asp Gly Lys Phe Asn Asn Asp Val
                805                 810                 815

Ala Gly Thr Ser Gly Val Tyr Gln Ala Gly Ile Arg Ser Ser Phe Thr
            820                 825                 830

Pro Thr Leu Ser Gly His Leu Ser Val Ser Tyr Gly Asn Gly Ala Gly
                835                 840                 845

Val Glu Ser Pro Trp Asn Thr Gln Ala Gly Val Val Trp Thr Phe
        850                 855                 860

<210> SEQ ID NO 142
<211> LENGTH: 586
<212> TYPE: PRT
<213> ORGANISM: Escherichia coli

<400> SEQUENCE: 142

Met Val Thr His Arg Gln Arg Tyr Arg Glu Lys Val Ser Gln Met Val
1               5                   10                  15

Ser Trp Gly His Trp Phe Ala Leu Phe Asn Ile Leu Leu Ser Leu Val
                20                  25                  30

Ile Gly Ser Arg Tyr Leu Phe Ile Ala Asp Trp Pro Thr Thr Leu Ala
            35                  40                  45

Gly Arg Ile Tyr Ser Tyr Val Ser Ile Ile Gly His Phe Ser Phe Leu
        50                  55                  60

Val Phe Ala Thr Tyr Leu Leu Ile Leu Phe Pro Leu Thr Phe Ile Val
65                  70                  75                  80

Gly Ser Gln Arg Leu Met Arg Phe Leu Ser Val Ile Leu Ala Thr Ala
                85                  90                  95

Gly Met Thr Leu Leu Leu Ile Asp Ser Glu Val Phe Thr Arg Phe His
                100                 105                 110

Leu His Leu Asn Pro Ile Val Trp Gln Leu Val Ile Asn Pro Asp Glu
            115                 120                 125

Asn Glu Met Ala Arg Asp Trp Gln Leu Met Phe Ile Ser Val Pro Val
130                 135                 140

Ile Leu Leu Leu Glu Leu Val Phe Ala Thr Trp Ser Trp Gln Lys Leu
145                 150                 155                 160

Arg Ser Leu Thr Arg Arg Arg Phe Ala Arg Pro Leu Ala Ala Phe
                165                 170                 175

Leu Phe Ile Ala Phe Ile Ala Ser His Val Val Tyr Ile Trp Ala Asp
            180                 185                 190

Ala Asn Phe Tyr Arg Pro Ile Thr Met Gln Arg Ala Asn Leu Pro Leu
                195                 200                 205

Ser Tyr Pro Met Thr Ala Arg Arg Phe Leu Glu Lys His Gly Leu Leu
210                 215                 220

Asp Ala Gln Glu Tyr Gln Arg Arg Leu Ile Glu Gln Gly Asn Pro Asp
225                 230                 235                 240

Ala Val Ser Val Gln Tyr Pro Leu Ser Glu Leu Arg Tyr Arg Asp Met
            245                 250                 255

Gly Thr Gly Gln Asn Val Leu Leu Ile Thr Val Asp Gly Leu Asn Tyr
                260                 265                 270

Ser Arg Phe Glu Lys Gln Met Pro Ala Leu Ala Gly Phe Ala Glu Gln
            275                 280                 285

Asn Ile Ser Phe Thr Arg His Met Ser Ser Gly Asn Thr Thr Asp Asn
```

```
            290                 295                 300
Gly Ile Phe Gly Leu Phe Tyr Gly Ile Ser Pro Ser Tyr Met Asp Gly
305                 310                 315                 320

Ile Leu Ser Thr Arg Thr Pro Ala Ala Leu Ile Thr Ala Leu Asn Gln
                325                 330                 335

Gln Gly Tyr Gln Leu Gly Leu Phe Ser Ser Asp Gly Phe Thr Ser Pro
                340                 345                 350

Leu Tyr Arg Gln Ala Leu Leu Ser Asp Phe Ser Met Pro Ser Val Arg
                355                 360                 365

Thr Gln Ser Asp Glu Gln Thr Ala Thr Gln Trp Ile Asn Trp Leu Gly
                370                 375                 380

Arg Tyr Ala Gln Glu Asp Asn Arg Trp Phe Ser Trp Val Ser Phe Asn
385                 390                 395                 400

Gly Thr Asn Ile Asp Asp Ser Asn Gln Gln Ala Phe Ala Arg Lys Tyr
                405                 410                 415

Ser Arg Ala Ala Gly Asn Val Asp Asp Gln Ile Asn Arg Val Leu Asn
                420                 425                 430

Ala Leu Arg Asp Ser Gly Lys Leu Asp Asn Thr Val Val Ile Ile Thr
                435                 440                 445

Ala Gly Arg Gly Ile Pro Leu Ser Glu Glu Glu Thr Phe Asp Trp
                450                 455                 460

Ser His Gly His Leu Gln Val Pro Leu Val Ile His Trp Pro Gly Thr
465                 470                 475                 480

Pro Ala Gln Arg Ile Asn Ala Leu Thr Asp His Thr Asp Leu Met Thr
                485                 490                 495

Thr Leu Met Gln Arg Leu Leu His Val Ser Thr Pro Ala Ser Glu Tyr
                500                 505                 510

Ser Gln Gly Gln Asp Leu Phe Asn Pro Gln Arg Arg His Tyr Trp Val
                515                 520                 525

Thr Ala Ala Asp Asn Asp Thr Leu Ala Ile Thr Thr Pro Lys Lys Thr
                530                 535                 540

Leu Val Leu Asn Asn Asn Gly Lys Tyr Arg Thr Tyr Asn Leu Arg Gly
545                 550                 555                 560

Glu Arg Val Lys Asp Glu Lys Pro Gln Leu Ser Leu Leu Leu Gln Val
                565                 570                 575

Leu Thr Asp Glu Lys Arg Phe Ile Ala Asn
                580                 585

<210> SEQ ID NO 143
<211> LENGTH: 75
<212> TYPE: PRT
<213> ORGANISM: Escherichia coli

<400> SEQUENCE: 143

Met Pro Gln Ile Ser Arg Tyr Ser Asp Glu Gln Val Glu Gln Leu Leu
1               5                   10                  15

Ala Glu Leu Leu Asn Val Leu Glu Lys His Lys Ala Pro Thr Asp Leu
                20                  25                  30

Ser Leu Met Val Leu Gly Asn Met Val Thr Asn Leu Ile Asn Thr Ser
                35                  40                  45

Ile Ala Pro Ala Gln Arg Gln Ala Ile Ala Asn Ser Phe Ala Arg Ala
                50                  55                  60

Leu Gln Ser Ser Ile Asn Glu Asp Lys Ala His
65                  70                  75
```

<210> SEQ ID NO 144
<211> LENGTH: 4791
<212> TYPE: DNA
<213> ORGANISM: Escherichia coli

<400> SEQUENCE: 144

| | | | | | |
|---|---|---|---|---|---|
| gcagatggcc | gcgttgttta | tgctggtaac | gcgctgcgcg | gctacggtaa | tctgattatc | 60 |
| atcaaacata | atgatgatta | cctgagtgcc | tacgcccata | acgacacaat | gctggtccgg | 120 |
| gaacaacaag | aagttaaggc | ggggcaaaaa | atagcgacca | tgggtagcac | cggaaccagt | 180 |
| tcaacacgct | tgcattttga | aattcgttac | aaggggaaat | ccgtaaaccc | gctgcgttat | 240 |
| ttgccgcagc | gataaatcgg | cggaaccagg | cttttgcttg | aatgttccgt | caagggatca | 300 |
| cgggtaggag | ccaccttatg | agtcagaata | cgctgaaagt | tcatgattta | aatgaagatg | 360 |
| cggaatttga | tgagaacgga | gttgaggttt | ttgacgaaaa | ggccttagta | aagaggaac | 420 |
| ccagtgataa | cgatttggcc | gaagaggaac | tgttatcgca | gggagccaca | cagcgtgtgt | 480 |
| tggacgcgac | tcagctttac | cttggtgaga | ttggttattc | accactgtta | acggccgaag | 540 |
| aagaagttta | ttttgcgcgt | cgcgcactgc | gtggagatgt | cgcctctcgc | cgccggatga | 600 |
| tcgagagtaa | cttgcgtctg | gtggtaaaaa | ttgcccgccg | ttatggcaat | cgtggtctgg | 660 |
| cgttgctgga | ccttatcgaa | gagggcaacc | tgggctgat | ccgcgcggta | gagaagtttg | 720 |
| acccggaacg | tggtttccgc | ttctcaacat | acgcaacctg | gtggattcgc | cagacgattg | 780 |
| aacgggcgat | tatgaaccaa | acccgtacta | ttcgtttgcc | gattcacatc | gtaaaggagc | 840 |
| tgaacgttta | cctgcgaacc | gcacgtgagt | tgtcccataa | gctggaccat | gaaccaagtg | 900 |
| cggaagagat | cgcagagcaa | ctggataagc | cagttgatga | cgtcagccgt | atgcttcgtc | 960 |
| ttaacgagcg | cattacctcg | gtagacaccc | cgctgggtgg | tgattccgaa | aaagcgttgc | 1020 |
| tggacatcct | ggccgatgaa | aaagagaacg | gtccggaaga | taccacgcaa | gatgacgata | 1080 |
| tgaagcagag | catcgtcaaa | tggctgttcg | agctgaacgc | caaacagcgt | gaagtgctgg | 1140 |
| cacgtcgatt | cggtttgctg | gggtacgaag | cggcaacact | ggaagatgta | ggtcgtgaaa | 1200 |
| ttggcctcac | ccgtgaacgt | gttcgccaga | ttcaggttga | aggcctgcgc | cgtttgcgcg | 1260 |
| aaatcctgca | aacgcagggg | ctgaatatcg | aagcgctgtt | ccgcgagtaa | gtaagcatct | 1320 |
| gtcagaaagg | ccagtctcaa | gcgaggctgg | ccttttctgt | gcacaataaa | aggtccgatg | 1380 |
| cccatcggac | cttttatta | aggtcaaatt | accgcccata | cgcaccaggt | aattaagaat | 1440 |
| ccggtaaaac | cgagaatggt | cgttaacact | gtccaggttt | tcagaccgtc | tgctaccgac | 1500 |
| aaccccagat | atttggtcac | aatccagaac | cctgagtcat | aatatgtga | cgcaccaagc | 1560 |
| ccaccaaagc | aggctgccag | cgtcaccaat | acgcactgaa | tcggattcaa | tcccatcacc | 1620 |
| gcttctgaga | gtaacccgcc | ggttgtcagt | attgctacgg | ttgctgaccc | ctgcgatgca | 1680 |
| cgcagcgcca | gtgaaataat | aaatgcggct | ggtaacagag | gcaggtcaat | catttgtagc | 1740 |
| atgttggcaa | gggctttgcc | gacgcccgat | tccaccagca | ctttgccaaa | tacccctcca | 1800 |
| gcaccagtaa | ccaaaatcac | taccgccgca | gtaggaagcg | ctgagcccat | aatgtcgctg | 1860 |
| gtgtgttgta | agctccagcc | gcgacgtaaa | gccaataacc | agaatgccag | caccagcgca | 1920 |
| atcattagag | ctaccattgg | tgagccgatc | agctgtagcg | taccaagcag | gggatgcgaa | 1980 |
| ggcggcatca | gtgttgcgga | aaccgtaccc | gccatgataa | tcgcgatagg | aataacaatt | 2040 |
| agcgaggtga | ccagcgcgac | gcccggtgga | tttatttat | cgcttaattt | tgtcgcgcct | 2100 |
| tcctcactgg | ccggagccag | ttgcatctgt | tccagtactt | ctactgacat | cgcatattgg | 2160 |

```
cgcttattga ttattttcgc tgcaaagtag ccaacaaccc ctacgggaat agaaatcgca    2220
ataccgatga tggttagcca gccgatgtct gcgtggagta accccgctgc ggcgacaggg    2280
cctggatgcg gcggtaccgc cacgtgaaca gtgagcatga tcccagcgac aggcaggcca    2340
aatttgagtg gcgatatttt ggcaaccttg gcaaaaccgt aaatgattgg cgcaagaata    2400
ataaagccga catcaaagaa gacgggaata ccgaggaaga acgctgccag agtcagcgca    2460
gcgatagttc gtttgtcacc taacttgcga ctgaaataat tagccagtga ctctgcacca    2520
ccagagtgtt cgatcatacg ccccagcata gcgcccagac caataataat agtgacggaa    2580
ccaagcacac cgcccatccc ggcgatcatc actttaccca cttcgcccgc cggtatacct    2640
gccgcaagtg cgactaacag gctgacgagg agcaaagcaa cgaatggttg tacctttgcc    2700
ttgatgacca gcagcaacag catgattacg ccagctaacg caatgcataa caatgtaatt    2760
gtggacatgg gaaaccctgt ctgaaagtta tagttaacct accccatccg tagatggggg    2820
gatgtatggg tacgttgtaa ttagggattt aacgaattag cgccaggcgt caaaccagcc    2880
aagcccttct tcggtgaggc cacgaggttt atattcacaa ccgatccagc cctgatatcc    2940
cacctcatcg aacaggcgga acagccacgg atagttgatt tctccatcgt ccggttcatg    3000
tcgatcaggt agtccggcaa tttgtacgtg cgcatatttc ccggcgtagt cgcggattaa    3060
atgcgtcagg ttgccatcta cttttttgcgc atgaaaagta tctagttgaa taaacacgtt    3120
atctcgcgca acctcttcaa caatagccag tgcctgatac tggctggaga agagataatg    3180
aggcttaacg ccggggctga gtgcttcaac taatattcgc ttgccgtgtg gcgcaaagcg    3240
gtcggcagcg tagcggatat tatcgataaa tactgcccgg taccgttcag catcttcgcc    3300
agcgggcacg acgcctgcca tcacatggac ttgttcacaa ttgagcgcca atgcatattc    3360
cagtgccagg tcgatgtctg cgtgtgcttc gtgctcacgt ccgggaaggg cggataatcc    3420
ccattccccc gcattaatat ctccgggagc ggtattgaac agcgccagtg tcagatggtt    3480
ttgctccagt tgcttttgga tttgcagggt ggagtagtta tagggaaaca gaaattccac    3540
agcatcgaac ccggcttttc gcgctgcggc gaagcgttca ataaaaggca cttcggtgaa    3600
catcatggat aaattagctg caaaacgagg cattgcatta actccttaat tccgcaattt    3660
cacctgcggt cagataacgg atcgggcggt caccgagaat aaaaatcagc tttgccgttt    3720
cctccagctc ttccatattg ttggcggctt cttgcaggct ttcaccgcaa accactgggc    3780
catgatttgc cagtaaaaaa gcctgattgt ctgctgccag ttcgccagat cctgtgcga    3840 tgcgtttatc gcccggtcgg taataaggca ccagcggac atttcccatc cgcatcacca    3900
cgtatggtgt gaacggacga ataacgttgc tgctgtccag cccttgcagg caggaaagcg    3960
ccgtcgacca tgtgctgtgc aaatgcacca ccgctttaca gcgcggattg ttgcgataca    4020
gcgccagatg aaagagcacc tctttcgagg gtttgtcacc acttaaccat cgccatccg    4080 cggcgacttt ggaaagccgc tgcggatcga gattgcccag gcatgaacct gtcggtgtcg    4140
ccagtaaatt cccgtcaggt aaaagcagcg acagattgcc agccgaaccg gttgcatagc    4200
cgcgctgaaa gaatgaactg gcaatccgcg tcatctcctc tcgcaaagac tgctctactt    4260
ttgcgaaatc gctcatgata aaaactctct ttgggctcgt gaaaaaaagg cgtcatcacc    4320
gaagttgcca gatttaaggg cgagtgagac aggcttatcc agtgcgttta cccacggcac    4380
gccgggggaa atggttgggc caatatgaaa ccctttttatt cccaggctct gtgtgactac    4440
gccggaggtc tcaccgcctg cgacaataaa gcgtgtcacg ccttccgctg ctaaccgcgc    4500
```

```
cgctagttga gaaaacagtg tttctactgc ctgactggct ttttgtgcac cgtattgctg   4560
ttgaattgct gccaatgcgt cagtgctggc ggtggcaaaa accagtggag caagtacact   4620
ttcctggccc agaacccact ctgccagttc gtgtgcataa gcggccagag tttcaattga   4680
gaggcagcgt gccacatcaa cttcacgggc tggtgcaatt tgacggtaat gtgctacctg   4740
gcggttggtc atttgagagc atgaaccgga gagcactacg ccgcgcccag c            4791
```

<210> SEQ ID NO 145
<211> LENGTH: 330
<212> TYPE: PRT
<213> ORGANISM: Escherichia coli

<400> SEQUENCE: 145

```
Met Ser Gln Asn Thr Leu Lys Val His Asp Leu Asn Glu Asp Ala Glu
1               5                   10                  15

Phe Asp Glu Asn Gly Val Glu Val Phe Asp Glu Lys Ala Leu Val Glu
                20                  25                  30

Glu Glu Pro Ser Asp Asn Asp Leu Ala Glu Glu Leu Leu Ser Gln
                35                  40                  45

Gly Ala Thr Gln Arg Val Leu Asp Ala Thr Gln Leu Tyr Leu Gly Glu
    50                  55                  60

Ile Gly Tyr Ser Pro Leu Leu Thr Ala Glu Glu Val Tyr Phe Ala
65              70                  75                  80

Arg Arg Ala Leu Arg Gly Asp Val Ala Ser Arg Arg Met Ile Glu
                85                  90                  95

Ser Asn Leu Arg Leu Val Val Lys Ile Ala Arg Arg Tyr Gly Asn Arg
            100                 105                 110

Gly Leu Ala Leu Leu Asp Leu Ile Glu Glu Gly Asn Leu Gly Leu Ile
        115                 120                 125

Arg Ala Val Glu Lys Phe Asp Pro Glu Arg Gly Phe Arg Phe Ser Thr
    130                 135                 140

Tyr Ala Thr Trp Trp Ile Arg Gln Thr Ile Glu Arg Ala Ile Met Asn
145                 150                 155                 160

Gln Thr Arg Thr Ile Arg Leu Pro Ile His Ile Val Lys Glu Leu Asn
                165                 170                 175

Val Tyr Leu Arg Thr Ala Arg Glu Leu Ser His Lys Leu Asp His Glu
            180                 185                 190

Pro Ser Ala Glu Glu Ile Ala Glu Gln Leu Asp Lys Pro Val Asp Asp
        195                 200                 205

Val Ser Arg Met Leu Arg Leu Asn Glu Arg Ile Thr Ser Val Asp Thr
    210                 215                 220

Pro Leu Gly Gly Asp Ser Glu Lys Ala Leu Leu Asp Ile Leu Ala Asp
225                 230                 235                 240

Glu Lys Glu Asn Gly Pro Glu Asp Thr Thr Gln Asp Asp Met Lys
                245                 250                 255

Gln Ser Ile Val Lys Trp Leu Phe Glu Leu Asn Ala Lys Gln Arg Glu
            260                 265                 270

Val Leu Ala Arg Arg Phe Gly Leu Leu Gly Tyr Glu Ala Ala Thr Leu
        275                 280                 285

Glu Asp Val Gly Arg Glu Ile Gly Leu Thr Arg Glu Val Arg Gln
    290                 295                 300

Ile Gln Val Glu Gly Leu Arg Arg Leu Arg Glu Ile Leu Gln Thr Gln
305                 310                 315                 320

Gly Leu Asn Ile Glu Ala Leu Phe Arg Glu
                325                 330
```

<210> SEQ ID NO 146
<211> LENGTH: 454
<212> TYPE: PRT
<213> ORGANISM: Escherichia coli

<400> SEQUENCE: 146

```
Met Ser Thr Ile Thr Leu Leu Cys Ile Ala Leu Ala Gly Val Ile Met
1               5                   10                  15

Leu Leu Leu Leu Val Ile Lys Ala Lys Val Gln Pro Phe Val Ala Leu
            20                  25                  30

Leu Leu Val Ser Leu Leu Val Ala Leu Ala Ala Gly Ile Pro Ala Gly
        35                  40                  45

Glu Val Gly Lys Val Met Ile Ala Gly Met Gly Val Leu Gly Ser
    50                  55                  60

Val Thr Ile Ile Ile Gly Leu Gly Ala Met Leu Gly Arg Met Ile Glu
65                  70                  75                  80

His Ser Gly Gly Ala Glu Ser Leu Ala Asn Tyr Phe Ser Arg Lys Leu
                85                  90                  95

Gly Asp Lys Arg Thr Ile Ala Ala Leu Thr Leu Ala Ala Phe Phe Leu
            100                 105                 110

Gly Ile Pro Val Phe Phe Asp Val Gly Phe Ile Ile Leu Ala Pro Ile
        115                 120                 125

Ile Tyr Gly Phe Ala Lys Val Ala Lys Ile Ser Pro Leu Lys Phe Gly
130                 135                 140

Leu Pro Val Ala Gly Ile Met Leu Thr Val His Val Ala Val Pro Pro
145                 150                 155                 160

His Pro Gly Pro Val Ala Ala Gly Leu Leu His Ala Asp Ile Gly
                165                 170                 175

Trp Leu Thr Ile Ile Gly Ile Ala Ile Ser Ile Pro Val Gly Val Val
            180                 185                 190

Gly Tyr Phe Ala Ala Lys Ile Ile Asn Lys Arg Gln Tyr Ala Met Ser
        195                 200                 205

Val Glu Val Leu Glu Gln Met Gln Leu Ala Pro Ala Ser Glu Glu Gly
    210                 215                 220

Ala Thr Lys Leu Ser Asp Lys Ile Asn Pro Pro Gly Val Ala Leu Val
225                 230                 235                 240

Thr Ser Leu Ile Val Ile Pro Ile Ala Ile Met Ala Gly Thr Val
                245                 250                 255

Ser Ala Thr Leu Met Pro Pro Ser His Pro Leu Leu Gly Thr Leu Gln
            260                 265                 270

Leu Ile Gly Ser Pro Met Val Ala Leu Met Ile Ala Leu Val Leu Ala
        275                 280                 285

Phe Trp Leu Leu Ala Leu Arg Arg Gly Trp Ser Leu Gln His Thr Ser
    290                 295                 300

Asp Ile Met Gly Ser Ala Leu Pro Thr Ala Ala Val Val Ile Leu Val
305                 310                 315                 320

Thr Gly Ala Gly Gly Val Phe Gly Lys Val Leu Val Glu Ser Gly Val
                325                 330                 335

Gly Lys Ala Leu Ala Asn Met Leu Gln Met Ile Asp Leu Pro Leu Leu
            340                 345                 350

Pro Ala Ala Phe Ile Ile Ser Leu Ala Leu Arg Ala Ser Gln Gly Ser
        355                 360                 365
```

```
Ala Thr Val Ala Ile Leu Thr Thr Gly Gly Leu Leu Ser Glu Ala Val
    370                 375                 380

Met Gly Leu Asn Pro Ile Gln Cys Val Leu Val Thr Leu Ala Ala Cys
385                 390                 395                 400

Phe Gly Gly Leu Gly Ala Ser His Ile Asn Asp Ser Gly Phe Trp Ile
                405                 410                 415

Val Thr Lys Tyr Leu Gly Leu Ser Val Ala Asp Gly Leu Lys Thr Trp
                420                 425                 430

Thr Val Leu Thr Thr Ile Leu Gly Phe Thr Gly Phe Leu Ile Thr Trp
                435                 440                 445

Cys Val Trp Ala Val Ile
    450
```

<210> SEQ ID NO 147
<211> LENGTH: 258
<212> TYPE: PRT
<213> ORGANISM: Escherichia coli

<400> SEQUENCE: 147

```
Met Pro Arg Phe Ala Ala Asn Leu Ser Met Met Phe Thr Glu Val Pro
1               5                   10                  15

Phe Ile Glu Arg Phe Ala Ala Arg Lys Ala Gly Phe Asp Ala Val
            20                  25                  30

Glu Phe Leu Phe Pro Tyr Asn Tyr Ser Thr Leu Gln Ile Gln Lys Gln
        35                  40                  45

Leu Glu Gln Asn His Leu Thr Leu Ala Leu Phe Asn Thr Ala Pro Gly
    50                  55                  60

Asp Ile Asn Ala Gly Glu Trp Gly Leu Ser Ala Leu Pro Gly Arg Glu
65                  70                  75                  80

His Glu Ala His Ala Asp Ile Asp Leu Ala Leu Glu Tyr Ala Leu Ala
                85                  90                  95

Leu Asn Cys Glu Gln Val His Val Met Ala Gly Val Val Pro Ala Gly
            100                 105                 110

Glu Asp Ala Glu Arg Tyr Arg Ala Val Phe Ile Asp Asn Ile Arg Tyr
        115                 120                 125

Ala Ala Asp Arg Phe Ala Pro His Gly Lys Arg Ile Leu Val Glu Ala
    130                 135                 140

Leu Ser Pro Gly Val Lys Pro His Tyr Leu Phe Ser Ser Gln Tyr Gln
145                 150                 155                 160

Ala Leu Ala Ile Val Glu Glu Val Ala Arg Asp Asn Val Phe Ile Gln
                165                 170                 175

Leu Asp Thr Phe His Ala Gln Lys Val Asp Gly Asn Leu Thr His Leu
            180                 185                 190

Ile Arg Asp Tyr Ala Gly Lys Tyr Ala His Val Gln Ile Ala Gly Leu
        195                 200                 205

Pro Asp Arg His Glu Pro Asp Asp Gly Glu Ile Asn Tyr Pro Trp Leu
    210                 215                 220

Phe Arg Leu Phe Asp Glu Val Gly Tyr Gln Gly Trp Ile Gly Cys Glu
225                 230                 235                 240

Tyr Lys Pro Arg Gly Leu Thr Glu Glu Gly Leu Gly Trp Phe Asp Ala
                245                 250                 255

Trp Arg
```

<210> SEQ ID NO 148
<211> LENGTH: 212

<212> TYPE: PRT
<213> ORGANISM: Escherichia coli

<400> SEQUENCE: 148

```
Met Ser Asp Phe Ala Lys Val Glu Gln Ser Leu Arg Glu Glu Met Thr
1               5                   10                  15
Arg Ile Ala Ser Ser Phe Phe Gln Arg Gly Tyr Ala Thr Gly Ser Ala
            20                  25                  30
Gly Asn Leu Ser Leu Leu Leu Pro Asp Gly Asn Leu Leu Ala Thr Pro
        35                  40                  45
Thr Gly Ser Cys Leu Gly Asn Leu Asp Pro Gln Arg Leu Ser Lys Val
    50                  55                  60
Ala Ala Asp Gly Glu Trp Leu Ser Gly Asp Lys Pro Ser Lys Glu Val
65                  70                  75                  80
Leu Phe His Leu Ala Leu Tyr Arg Asn Asn Pro Arg Cys Lys Ala Val
                85                  90                  95
Val His Leu His Ser Thr Trp Ser Thr Ala Leu Ser Cys Leu Gln Gly
            100                 105                 110
Leu Asp Ser Ser Asn Val Ile Arg Pro Phe Thr Pro Tyr Val Val Met
        115                 120                 125
Arg Met Gly Asn Val Pro Leu Val Pro Tyr Tyr Arg Pro Gly Asp Lys
    130                 135                 140
Arg Ile Ala Gln Asp Leu Ala Glu Leu Ala Ala Asp Asn Gln Ala Phe
145                 150                 155                 160
Leu Leu Ala Asn His Gly Pro Val Val Cys Gly Glu Ser Leu Gln Glu
                165                 170                 175
Ala Ala Asn Asn Met Glu Glu Leu Glu Glu Thr Ala Lys Leu Ile Phe
            180                 185                 190
Ile Leu Gly Asp Arg Pro Ile Arg Tyr Leu Thr Ala Gly Glu Ile Ala
        195                 200                 205
Glu Leu Arg Ser
    210
```

<210> SEQ ID NO 149
<211> LENGTH: 4859
<212> TYPE: DNA
<213> ORGANISM: Escherichia coli

<400> SEQUENCE: 149

```
cgttctgctt atcttcgatt catgacagcc aatcatcttt gccagaccgc gctgggtaat      60
agctgacaga ttgataagta aatctgtttc tgcgcgatca acttcacgct gtgatagttt     120
gctgtaactt gttctttcca tttcttaaga tttccaatag tgaatagtta gttgaaaggt     180
atgcgtggaa acgcatatgg ccttagttgg tcagatatct tggaactcgc ttttcagcga     240
cgtaggacga atgtccgttg ttacaaagag cggatccgct tattaagcgg ctttgtgttc     300
cggcgggaac acgtcatcaa gactgacttt tgcgcctaac ttgtttaggc acgcaacaag     360
agcacggcat gttttaaggt ctgggaagcg acgaccagat tcccaatgtc cgatagctcc     420
ctgtgtgcat ccaactgcct tagcaagtgt tgtttgagag atattcagtg actctcgata     480
ttttcgtagg ttgctcatat gccctccata gtaaacacga ataaaaaata caatatgtac     540
tttaagaata caagtaaaaa tacacattgt gcatggatgg ttccagtaca aagcgtaata     600
ataagaacat gaaaatgaaa tggtatgaac tggctagatc cagaatgaaa gagctcggca     660
taactcaaga gaagttagcc gaagagctag gtatgacgca gggtgggatt ggacactggt     720
```

-continued

```
tgcgcggatc tcgtcatcca tctcttagtg atattggagt ggtgtttaaa taccttggta    780
ttgataacat atcattcaac cacgacggga cattttcacc tgttggcgaa tactcatcgg    840
ccccagttaa aaacaatat gagtaccctg ttttttctca tgttcaggct gggatgttct    900
ctccagaact cagaaccttt accaaaggcg atgcggagag attggtaagc acaaccaaaa    960
aagccagtga ctctgcattc tggcttgagg ttgaaggtaa ctcaatgacc gcaccaacag   1020
gttccaagcc cagcttttcct gacgggatgt taattctggt tgaccctgag caggctgttg   1080
agccaggcga tttctgtata gccagacttg gtggtgatga gtttaccttc aagaaactga   1140
tcagggatag cggtcaggtg tttctacagc cactaaaccc acaataccca atgatcccat   1200
gcaatgagag ttgttccgtt gtggggaaag ttatcgctag tcagtggcct gaagagacgt   1260
ttgggtgatg tgactgcatg taatttatca aaagcgcaca taccctatgc taaacaactt   1320
actgattaat ttactgaaaa tcatttatta aaaataagg attgccaatg aattttttcgg   1380
aagaaaaaaa taaagatttc cccaaaaaag tacaaacttc gctatttgaa gtagattgta   1440
atgacggatg ctcatttgta gatgtcttga agacatgcga aaatttcaaa caaaactatg   1500
actttgagta ctctaacgac actcgggcaa ggataaaaag tctaatagtt aacgatgacc   1560
aaatctttgc tgggataaca ctctatgagc ccaaagctt ggtcccggta actccaaaag   1620
atggagacca taacgatttg caggatgtag ataattatga taaatgccat atattcttgc   1680
ttgcaacaga aagcaatatt ctaacaattt ttcaactatc aggaactcat cctttatcta   1740
agttaaaaaa aatatttagc ctcatgaata tcaatgtgaa tatttctgag aaactcaaca   1800
aagatgcact tggcaagata taaaagatg gaatacgctc catcagccta agtattgaaa   1860
caacaaaaga agatctagaa gaggcaaaag caacatcatt aggtatcact ggaaaagcta   1920
aagaagcttt gtcaagatta tttgagaaag agcaagatga tgacaactct ttctatgggc   1980
ttctgactct tgacaagaga cataacccaa aactcttaaa tattgcgaac aaaaatccaa   2040
gcctgatcat tgatgaatta tcggaagagt tcttcatcac aacatcaaaa ggccaagcga   2100
tcaaaagctc tgaaatcaaa acaaaaaaag attattacac aagaaagtat ggctctacca   2160
ccataaaagc ggaacacgct aaggaaattc ttgagcactt caaggatttc atactataat   2220
ggagggtcgt acgtataacc aaaggggag gtgtgaatga gaggtaaaga ttggagttat   2280
atttttttcca taatcttttt tatctgcctt tctcttgtat taacttatta tttacatgat   2340
aaggttagat ataacaaaga gttgcttgga cttgtggcaa atatattttc aatattaaca   2400
gggtttctgt tacttgttat aaccacaagt ggagacgtag catcgtttac agaaggtaaa   2460
tcaagatcag aaaagtatgc aactaagagg aaattcgaaa ttcggttttc tcgttacatg   2520
atgctttttt acctctatct tacagtcttg tgcttaatat tcttctacta catgctgctg   2580
ccaccaggag acaccagtaa aatcttagca agcaagccgc ctgtgaccaa cctgagtctg   2640
gcacttgagt ttattatatg ctggctaagc ataatttcat ttggatgctc ttttttcata   2700
ccaataaagc tgaaacagat ttataacgaa aaactcaagc aacaataacc cggcctcagc   2760
gccgggtttt ctttgcctca cgatcgcccc acctaaaaac acataaccaa ttgtatttat   2820
tgaaaaataa atagatacaa cccactaaac cacgcaattc tgatctctcc ttacatcgcc   2880
gaggcaatac atccacgcta aaaacaaca ctattaaata caaagcgtta taaaaaacca   2940
cgccaactta caacaaattg tattgatctt gtaaagtaca tatcgtacta tttaaccgtc   3000
agcaggacgc tggaagccaa atggaacaga ctggcaggct ctttaaacaa cgtcgactct   3060
cgactacgtg gctgaaaagc cagatcaccc aaccacataa gctgtgggat gcaatgccga   3120
```

```
agcaaccgtc tcaggaggag cttcgagatt gcatcgccaa agtttattcg ggaggaatcc   3180
atgtccagaa aaacagaatt taaaggcacc gcagcttctc gccgtagagc tcgtcgcgca   3240
aatctgcaaa gtcaggaggc gatcagctcc gacaagctac acaggccaac cccttcacga   3300
gtggtcttgc aatgcaagcg caaaccagca atgagagcag aagtgataac tctgacaacg   3360
ttgaccagaa aatatgaagg ttcaacttgt cttccgaacg tagctcttta cgcggcaggc   3420
taccggaaat caaaacaact gacggcgaga tgataaattc atttgctaat tacttgtttt   3480
tgccatgctt atcctgagcg ataagttcat ccataaggct gtctgccttc ccggcaaacc   3540
gaatgtagca ctcatgtcta tagctttcag gaataacaaa acggtcggta tcaggatatc   3600
caacagcagg aggccttcga acgaggagtc cttttttgag caatgaaatt gattcatgaa   3660
ctcccttttc cgtttgtagc tggttattag cggctacagc gaatgccaaa tacgctcttt   3720
ctccaagagt taacgaatca aacaaatctt gcacatattt ttcttcttta gatttgcgct   3780
tctgagcagc ggatacctca attctttcag tcacagcgtg ataagcggaa ttaacaacgc   3840
cgttaagcac atagctaacg caaaacaaca ggatgtaata catccagtaa tgaggaagga   3900
tttctggatt atgcaggttt atccattctt ttacgcttac cggcataaca ataatcaata   3960
tgatcaggat gattagcata tgaatcaact gtttaagtgt cattccttgc aggaaaaaat   4020
gcattagttc ctgccaccat gagttgttca tcggcgtttc tcttttgctc tctgtagggg   4080
tgaatagagt ttatctgggg cggttcaatc cgatttctcg ctgtaggggt acacgagaac   4140
cagcgagcct gatgtggtta aaagacaggc acaatcttta ctaccgcaat ccactattta   4200
aggtgatata tggaagaaga atttgaagag ttcgaagagc atcctcagga tgtgatggaa   4260
caataccagg actatccgta tgactacgac tattgataaa aatcaatggt gtggacaatt   4320
caagcgatgc aatggatgca agctgcaatc gaaatgcatg gttaagcctg aagaaatgtt   4380
tcctgtaatg gaagatggga aatatgtcga taaatgggca atacgaacga cggcaatgat   4440
tgccagagaa cttggtaaac agaacaacaa ggctgcctga tggtggcctt cattttttggc   4500
ataaacaaca gaggcgaaga tgttgacagt tggaaaggca tattcaacta aaaatggaaa   4560
gacatttagt tgtgaaaaag atattggaga atagacact atctttccat ttggtggatg   4620
ggtatacaat tctgatggaa gcaaagacag atttgcatat tacaccagag gaggtactta   4680
taaactaacc aaatcagaat atgatttaat tatttagcac agagaagcac tgtgtattca   4740
ttccaacgag tgaatacacg gagcaatgtc gctcgtaact aaacaggagc cgacttgttc   4800
tgattattgg aaatcttctt tgccctccaa tgtgagggcg attttttatc tgtgaggat    4859
```

<210> SEQ ID NO 150
<211> LENGTH: 217
<212> TYPE: PRT
<213> ORGANISM: Escherichia coli

<400> SEQUENCE: 150

```
Met Lys Trp Tyr Glu Leu Ala Arg Ser Arg Met Lys Glu Leu Gly Ile
1               5                   10                  15

Thr Gln Glu Lys Leu Ala Glu Glu Leu Gly Met Thr Gln Gly Gly Ile
            20                  25                  30

Gly His Trp Leu Arg Gly Ser Arg His Pro Ser Leu Ser Asp Ile Gly
        35                  40                  45

Val Val Phe Lys Tyr Leu Gly Ile Asp Asn Ile Ser Phe Asn His Asp
    50                  55                  60
```

```
Gly Thr Phe Ser Pro Val Gly Glu Tyr Ser Ser Ala Pro Val Lys Lys
 65                  70                  75                  80

Gln Tyr Glu Tyr Pro Val Phe Ser His Val Gln Ala Gly Met Phe Ser
             85                  90                  95

Pro Glu Leu Arg Thr Phe Thr Lys Gly Asp Ala Glu Arg Leu Val Ser
            100                 105                 110

Thr Thr Lys Lys Ala Ser Asp Ser Ala Phe Trp Leu Glu Val Glu Gly
        115                 120                 125

Asn Ser Met Thr Ala Pro Thr Gly Ser Lys Pro Ser Phe Pro Asp Gly
    130                 135                 140

Met Leu Ile Leu Val Asp Pro Glu Gln Ala Val Glu Pro Gly Asp Phe
145                 150                 155                 160

Cys Ile Ala Arg Leu Gly Gly Asp Glu Phe Thr Phe Lys Lys Leu Ile
                165                 170                 175

Arg Asp Ser Gly Gln Val Phe Leu Gln Pro Leu Asn Pro Gln Tyr Pro
            180                 185                 190

Met Ile Pro Cys Asn Glu Ser Cys Ser Val Val Gly Lys Val Ile Ala
        195                 200                 205

Ser Gln Trp Pro Glu Glu Thr Phe Gly
    210                 215

<210> SEQ ID NO 151
<211> LENGTH: 283
<212> TYPE: PRT
<213> ORGANISM: Escherichia coli

<400> SEQUENCE: 151

Met Asn Phe Ser Glu Glu Lys Asn Lys Asp Phe Pro Lys Lys Val Gln
  1               5                  10                  15

Thr Ser Leu Phe Glu Val Asp Cys Asn Asp Gly Cys Ser Phe Val Asp
             20                  25                  30

Val Leu Lys Thr Cys Glu Asn Phe Lys Gln Asn Tyr Asp Phe Glu Tyr
         35                  40                  45

Ser Asn Asp Thr Arg Ala Arg Ile Lys Ser Leu Ile Val Asn Asp Asp
     50                  55                  60

Gln Ile Phe Ala Gly Ile Thr Leu Tyr Glu Pro Lys Ala Leu Val Pro
 65                  70                  75                  80

Val Thr Pro Lys Asp Gly Asp His Asn Asp Leu Gln Asp Val Asp Asn
             85                  90                  95

Tyr Asp Lys Cys His Ile Phe Leu Leu Ala Thr Glu Ser Asn Ile Leu
            100                 105                 110

Thr Ile Phe Gln Leu Ser Gly Thr His Pro Leu Ser Lys Leu Lys Lys
        115                 120                 125

Ile Phe Ser Leu Met Asn Ile Asn Val Asn Ile Ser Glu Lys Leu Asn
    130                 135                 140

Lys Asp Ala Leu Gly Lys Ile Lys Asp Gly Ile Arg Ser Ile Ser
145                 150                 155                 160

Leu Ser Ile Glu Thr Thr Lys Glu Asp Leu Glu Glu Ala Lys Ala Thr
                165                 170                 175

Ser Leu Gly Ile Thr Gly Lys Ala Lys Glu Ala Leu Ser Arg Leu Phe
            180                 185                 190

Glu Lys Glu Gln Asp Asp Asp Asn Ser Phe Tyr Gly Leu Leu Thr Leu
        195                 200                 205

Asp Lys Arg His Asn Pro Lys Leu Leu Asn Ile Ala Asn Lys Asn Pro
    210                 215                 220
```

```
Ser Leu Ile Ile Asp Glu Leu Ser Glu Phe Phe Ile Thr Thr Ser
225                 230                 235                 240

Lys Gly Gln Ala Ile Lys Ser Ser Glu Ile Lys Thr Lys Lys Asp Tyr
                    245                 250                 255

Tyr Thr Arg Lys Tyr Gly Ser Thr Thr Ile Lys Ala Glu His Ala Lys
                260                 265                 270

Glu Ile Leu Glu His Phe Lys Asp Phe Ile Leu
            275                 280

<210> SEQ ID NO 152
<211> LENGTH: 163
<212> TYPE: PRT
<213> ORGANISM: Escherichia coli

<400> SEQUENCE: 152

Met Arg Gly Lys Asp Trp Ser Tyr Ile Phe Ser Ile Ile Phe Phe Ile
1               5                   10                  15

Cys Leu Ser Leu Val Leu Thr Tyr Tyr Leu His Asp Lys Val Arg Tyr
            20                  25                  30

Asn Lys Glu Leu Leu Gly Leu Val Ala Asn Ile Phe Ser Ile Leu Thr
        35                  40                  45

Gly Phe Leu Leu Val Ile Thr Thr Ser Gly Asp Val Ala Ser Phe
    50                  55                  60

Thr Glu Gly Lys Ser Arg Ser Glu Lys Tyr Ala Thr Lys Arg Lys Phe
65                  70                  75                  80

Glu Ile Arg Phe Ser Arg Tyr Met Met Leu Phe Tyr Leu Tyr Leu Thr
                85                  90                  95

Val Leu Cys Leu Ile Phe Phe Tyr Tyr Met Leu Leu Pro Pro Gly Asp
            100                 105                 110

Thr Ser Lys Ile Leu Ala Ser Lys Pro Pro Val Thr Asn Leu Ser Leu
        115                 120                 125

Ala Leu Glu Phe Ile Ile Cys Trp Leu Ser Ile Ser Phe Gly Cys
    130                 135                 140

Ser Phe Phe Ile Pro Ile Lys Leu Lys Gln Ile Tyr Asn Glu Lys Leu
145                 150                 155                 160

Lys Gln Gln

<210> SEQ ID NO 153
<211> LENGTH: 60
<212> TYPE: PRT
<213> ORGANISM: Escherichia coli

<400> SEQUENCE: 153

Met Glu Gln Thr Gly Arg Leu Phe Lys Gln Arg Arg Leu Ser Thr Thr
1               5                   10                  15

Trp Leu Lys Ser Gln Ile Thr Gln Pro His Lys Leu Trp Asp Ala Met
            20                  25                  30

Pro Lys Gln Pro Ser Gln Glu Glu Leu Arg Asp Cys Ile Ala Lys Val
        35                  40                  45

Tyr Ser Gly Gly Ile His Val Gln Lys Asn Arg Ile
    50                  55                  60

<210> SEQ ID NO 154
<211> LENGTH: 193
<212> TYPE: PRT
<213> ORGANISM: Escherichia coli
```

<400> SEQUENCE: 154

```
Met Asn Asn Ser Trp Trp Gln Glu Leu Met His Phe Leu Gln Gly
1               5                   10                  15

Met Thr Leu Lys Gln Leu Ile His Met Leu Ile Ile Leu Ile Leu
            20                  25                  30

Ile Ile Val Met Pro Val Ser Val Lys Glu Trp Ile Asn Leu His Asn
        35                  40                  45

Pro Glu Ile Leu Pro His Tyr Trp Met Tyr Tyr Ile Leu Leu Phe Cys
    50                  55                  60

Val Ser Tyr Val Leu Asn Gly Val Asn Ser Ala Tyr His Ala Val
65                  70                  75                  80

Thr Glu Arg Ile Glu Val Ser Ala Ala Gln Lys Arg Lys Ser Lys Glu
                85                  90                  95

Glu Lys Tyr Val Gln Asp Leu Phe Asp Ser Leu Thr Leu Gly Glu Arg
            100                 105                 110

Ala Tyr Leu Ala Phe Ala Val Ala Ala Asn Asn Gln Leu Gln Thr Glu
        115                 120                 125

Lys Gly Val His Glu Ser Ile Ser Leu Leu Lys Gly Leu Leu Val
130                 135                 140

Arg Arg Pro Pro Ala Val Gly Tyr Pro Asp Thr Asp Arg Phe Val Ile
145                 150                 155                 160

Pro Glu Ser Tyr Arg His Glu Cys Tyr Ile Arg Phe Ala Gly Lys Ala
                165                 170                 175

Asp Ser Leu Met Asp Glu Leu Ile Ala Gln Asp Lys His Gly Lys Asn
            180                 185                 190

Lys
```

<210> SEQ ID NO 155
<211> LENGTH: 66
<212> TYPE: PRT
<213> ORGANISM: Escherichia coli

<400> SEQUENCE: 155

```
Met Thr Thr Thr Ile Asp Lys Asn Gln Trp Cys Gly Gln Phe Lys Arg
1               5                   10                  15

Cys Asn Gly Cys Lys Leu Gln Ser Lys Cys Met Val Lys Pro Glu Glu
            20                  25                  30

Met Phe Pro Val Met Glu Asp Gly Lys Tyr Val Asp Lys Trp Ala Ile
        35                  40                  45

Arg Thr Thr Ala Met Ile Ala Arg Glu Leu Gly Lys Gln Asn Asn Lys
    50                  55                  60

Ala Ala
65
```

<210> SEQ ID NO 156
<211> LENGTH: 65
<212> TYPE: PRT
<213> ORGANISM: Escherichia coli

<400> SEQUENCE: 156

```
Met Leu Thr Val Gly Lys Ala Tyr Ser Thr Lys Asn Gly Lys Thr Phe
1               5                   10                  15

Ser Cys Glu Lys Asp Ile Gly Glu Ile Asp Thr Ile Phe Pro Phe Gly
            20                  25                  30

Gly Trp Val Tyr Asn Ser Asp Gly Ser Lys Asp Arg Phe Ala Tyr Tyr
        35                  40                  45
```

Thr Arg Gly Gly Thr Tyr Lys Leu Thr Lys Ser Glu Tyr Asp Leu Ile
    50                  55                  60

Ile
65

<210> SEQ ID NO 157
<211> LENGTH: 4289
<212> TYPE: DNA
<213> ORGANISM: Escherichia coli

<400> SEQUENCE: 157

| | | | | | |
|---|---|---|---|---|---|
| gcagattagc | ccacagaccc | atcacgatag | aaccgagtcc | ggcaaccaga | caggttgcaa | 60 |
| cgaaaactgc | cgcaggcggg | aagcctgctt | tacccaacat | acctggaacg | acgatgaccg | 120 |
| agtagaccat | cgccagaaac | gttgttaacc | cggcaaccac | ttcctgacgg | acagtgcttc | 180 |
| cacgttgtga | aattttaaac | caggcgtcga | gtgaaccgcc | ggtacgcgct | gatggcgtag | 240 |
| acataagaaa | acatcccctg | agagtttaat | tttcgtcaag | atgcgtggcg | gacaatcccc | 300 |
| tgccagcgaa | acgttatctt | cctgctccag | gtttgcgaca | atttgctgcg | tcgcaaaaaa | 360 |
| gcaaacgttt | agctccgcgc | atacaaaacg | ggtggtaaaa | aaagcaaacg | attatccggc | 420 |
| gatcatagcg | gcttttttcaa | ccgaagtttg | ctgctttttt | ctcttttatt | gtcttgacga | 480 |
| tgaaaaacca | ggcaattgat | gcgcaaacgt | tatcgtcggt | gcgcaagatt | gcagcgttat | 540 |
| cgagccgtat | accgttcagg | attgcgataa | aaaatcgtct | gagatgacaa | aaatattgcg | 600 |
| gttaaaaagt | atacttttac | actggcgaag | aaacgtcggt | gacatacaat | taaagcatca | 660 |
| acaccaaccg | gaacctccac | cacgtgctcg | aatgaggtgt | gttgacgtcg | ggggaaaccc | 720 |
| tcctgtgtac | cagcgggata | gagagaaaga | caaagaccgg | aaaacaaact | aaagcgccct | 780 |
| tgtggcgctt | tagttttgtt | catcttccag | caagcgtgcg | ccggtacctt | cttctcctaa | 840 |
| gcggtcgccc | gggttacgca | acgggcaatc | actgcgcgaa | aggcagccac | aaccaataca | 900 |
| tccgtccagt | tcgtcacgca | gcgccactaa | ggtatgaatg | cgccgatcca | actcttctcg | 960 |
| ccattgggac | gaaagctgtt | tccactcttt | cgcacttaac | gtatgccctt | cgggcaacac | 1020 |
| gccaaacgct | tcaccaatgg | tcgccagcgg | aatgccaata | cgctgagcaa | ttttgataat | 1080 |
| tgcaacatat | cgcaacacat | cacgtttata | tcgccgctga | ttgccgctgt | tacggatact | 1140 |
| ggtaatcaac | cctttacttt | catagaaatg | cagcgccgat | accgccacac | cgctgcgttt | 1200 |
| cgccacttcg | ccgggggtta | gcagcgcttt | aatgcgggt | aatttcttttt | ccataaatcg | 1260 |
| ctttacctca | agttaacttg | aggaattata | ctccccaaca | gatgaattaa | cgaactgaac | 1320 |
| actgaaaaga | ggcagattta | tgtcccatca | gaaaattatt | caggatctta | tcgcatggat | 1380 |
| tgacgagcat | attgaccagc | cgcttaacat | tgatgtagtc | gcaaaaaaat | caggctattc | 1440 |
| aaagtggtac | ttgcaacgaa | tgttccgcac | ggtgacgcat | cagacgcttg | gcgattacat | 1500 |
| tcgccaacgc | cgcctgttac | tggccgcccgt | tgagttgcgc | accaccgagc | gtccgatttt | 1560 |
| tgatatcgca | atggacctgg | gttatgtctc | gcagcagacc | ttctcccgcg | ttttccgtcg | 1620 |
| gcagtttgat | cgcactccca | gcgattatcg | ccaccgcctg | taattttatt | gcccgcgcgt | 1680 |
| taactcccgc | gcgggtaatt | gctccatcca | ttgcataaac | acctgcggcg | gcatcgcctt | 1740 |
| cgcaaagaac | catccctggc | aatagcgcac | gccgcgtttg | cgcagccagt | taacctgctc | 1800 |
| ctcagtttcg | acgccttcag | cgatcgtttt | taacccccagg | ctgtgcgcca | gctcgatgat | 1860 |
| gtgttccgca | atcaaatgac | tggttttgtg | ggtggtcagc | gtttcaacaa | acgatttgtc | 1920 |

```
gattttcaaa atatcgacat tcaatgattt aaggttatgc aagttagagt agccaatacc    1980
aaaatcatca attgccactt cgtaacctgc ctggcggaaa gccagaataa tcggcgtcat    2040
tttgtcaaca tcaagaaatg catgctcagt cacttcaaat ttaatttgct gcggacgcac    2100
cgcgtattgc tctgttttct gattgattcg cgctatcaac cgtgacgtat gaaaatcgga    2160
ggccgacagg ttaatagaaa catagcgatc tgcatgtgtt gccaggtaat cgcccagatc    2220
gcggaagaca ttatcaataa cataatcagt tatctgttct atcatcccct ccttttctgc    2280
cagcggaata aactctgccg gattcattat ttgcccctgc tcaccaggcc aacgtaacaa    2340
cgcttcagcg ccgatacatt tttctgtttt gatatcgatt attggctggt aataaagaca    2400
aagttgatgt ttttcgaggg cgcgttgcaa tttacgtttg ggagataaat agttttgtcg    2460
aatacgtagc cagagtaata gcagaacaag actccccaaa ataccggcgg gcaacgcaaa    2520
aataagatga ttataaaaat gggttataag acgttgatat gaagtcgcaa caatggctgc    2580
aattgggcgt tttgtcgaat aaactgtcgc atataaatag ccatttcttt gtacggttaa    2640
atccttcaaa tgaatcagcg gagaaaacgt tgctgccgag gcctcttgc ttaacgagaa    2700
aaaggttttc gtcaccgtat catacacacc ccattgcaat gtcgggtcat cagacatcac    2760
ttcactccag aagagagggt tgataaccgc cacataattt ccccgctgca tataggtcat    2820
tttatagcca gagaaaaaag gcgtatcgcg gtaataatag atagaaacgt taggttcacg    2880
cttataatcg gccggtgcaa tcgtatagcc gtttacaggc gctatcagcg atgagcataa    2940
aaaatggtta tcacgggcat agatcaattc attaatataa agatagccac gaataatatt    3000
caacattcgc ttttgatggg ctggagtgca aacttgcccc tgatagcgtt cagctgcatc    3060
gctcactaaa tctgcctggc gaatgaccag ctcggattta ccagtgcca gttgagcaaa    3120
ggttcggagc tgattattca cttctgattt tgcccaaagg aaggcaatcc atagcgaaag    3180
aatgatggga aagagaacta aaaagataat gcccggcaac gccagtaatt ggtgtcgtgc    3240
acgatgactc attgctatca atttcctgcc tgtttatacc cggccattgc aaggtgaaaa    3300
ccctgggtac cgacgtcttt agataaatct tacggtataa atagcacttt tgcctgattt    3360
gaaattgata cctttctaat cgtcacctgg atgaaaataa ttcattgata ttcaaaatta    3420
atttcctaca ggaatgcaga ggcggcggga agatatgccc ttaatgccac tgaaaaacca    3480
cataatctgt acagcaataa aagtcacggc ctaatatggc taacaaacaa tcaattgtga    3540
tatagttcac aaaattaatg aaacaaacag agtgtttcat ttttgtgttc tgcaagcccc    3600
gcgatagcca gagtgtacca cgcctcccgt gaacaacgcc gcgctgtcca gggcatcggc    3660
tcttttcaga ggaattgttt gatggctacc ctcaccactg gcgtggttct tcttcgctgg    3720
caacttctta gtgccgtaat gatgtttctg ccagcacac tcaacatccg ttttcgtcgg    3780
tctgattatg tcgggcttgc ggtgatcagc agcggtctgg gcgttgtttc cgcctgttgg    3840
ttcgcaatgg ggttgcttgg catcacaatg gcggacatca ccgctatctg gcacaacatc    3900
gagtcggtga tgatagaaga gatgaatcag acaccgccac aatggccaat gattttgacc    3960
tgatacgtag aagcctccat aacggaggct tcttttttat ggctggcaga tgctttaatc    4020
atccaccttta aaacaatata acctattgtt ttaatgacaa atcagaacgg aatgtcatca    4080
tcaaagtcca tcggcggctc gttagacggc gctgccggag cggactgctg cgggcgagac    4140
tgcgcgccgc cgctgaactg attgccaccc tgcggctgct gaggctgacc ccaaccgccc    4200
tgcggctgac caccaccgat attgccacct gccggagcgc caccaccctg acgaccaccc    4260
agcatctgca tggtgccgcc aacgttcac                                      4289
```

<210> SEQ ID NO 158
<211> LENGTH: 154
<212> TYPE: PRT
<213> ORGANISM: Escherichia coli

<400> SEQUENCE: 158

Met Glu Lys Lys Leu Pro Arg Ile Lys Ala Leu Leu Thr Pro Gly Glu
1               5                   10                  15

Val Ala Lys Arg Ser Gly Val Ala Val Ser Ala Leu His Phe Tyr Glu
            20                  25                  30

Ser Lys Gly Leu Ile Thr Ser Ile Arg Asn Ser Gly Asn Gln Arg Arg
        35                  40                  45

Tyr Lys Arg Asp Val Leu Arg Tyr Val Ala Ile Ile Lys Ile Ala Gln
    50                  55                  60

Arg Ile Gly Ile Pro Leu Ala Thr Ile Gly Glu Ala Phe Gly Val Leu
65                  70                  75                  80

Pro Glu Gly His Thr Leu Ser Ala Lys Glu Trp Lys Gln Leu Ser Ser
                85                  90                  95

Gln Trp Arg Glu Glu Leu Asp Arg Arg Ile His Thr Leu Val Ala Leu
            100                 105                 110

Arg Asp Glu Leu Asp Gly Cys Ile Gly Cys Gly Cys Leu Ser Arg Ser
        115                 120                 125

Asp Cys Pro Leu Arg Asn Pro Gly Asp Arg Leu Gly Glu Glu Gly Thr
    130                 135                 140

Gly Ala Arg Leu Leu Glu Asp Glu Gln Asn
145                 150

<210> SEQ ID NO 159
<211> LENGTH: 107
<212> TYPE: PRT
<213> ORGANISM: Escherichia coli

<400> SEQUENCE: 159

Met Ser His Gln Lys Ile Ile Gln Asp Leu Ile Ala Trp Ile Asp Glu
1               5                   10                  15

His Ile Asp Gln Pro Leu Asn Ile Asp Val Val Ala Lys Lys Ser Gly
            20                  25                  30

Tyr Ser Lys Trp Tyr Leu Gln Arg Met Phe Arg Thr Val Thr His Gln
        35                  40                  45

Thr Leu Gly Asp Tyr Ile Arg Gln Arg Leu Leu Leu Ala Ala Val
    50                  55                  60

Glu Leu Arg Thr Thr Glu Arg Pro Ile Phe Asp Ile Ala Met Asp Leu
65                  70                  75                  80

Gly Tyr Val Ser Gln Gln Thr Phe Ser Arg Val Phe Arg Arg Gln Phe
                85                  90                  95

Asp Arg Thr Pro Ser Asp Tyr Arg His Arg Leu
            100                 105

<210> SEQ ID NO 160
<211> LENGTH: 528
<212> TYPE: PRT
<213> ORGANISM: Escherichia coli

<400> SEQUENCE: 160

Met Ser His Arg Ala Arg His Gln Leu Leu Ala Leu Pro Gly Ile Ile
1               5                   10                  15

-continued

```
Phe Leu Val Leu Phe Pro Ile Ile Leu Ser Leu Trp Ile Ala Phe Leu
             20                  25                  30

Trp Ala Lys Ser Glu Val Asn Asn Gln Leu Arg Thr Phe Ala Gln Leu
         35                  40                  45

Ala Leu Asp Lys Ser Glu Leu Val Ile Arg Gln Ala Asp Leu Val Ser
     50                  55                  60

Asp Ala Ala Glu Arg Tyr Gln Gly Gln Val Cys Thr Pro Ala His Gln
 65                  70                  75                  80

Lys Arg Met Leu Asn Ile Ile Arg Gly Tyr Leu Tyr Ile Asn Glu Leu
                 85                  90                  95

Ile Tyr Ala Arg Asp Asn His Phe Leu Cys Ser Ser Leu Ile Ala Pro
             100                 105                 110

Val Asn Gly Tyr Thr Ile Ala Pro Ala Asp Tyr Lys Arg Glu Pro Asn
         115                 120                 125

Val Ser Ile Tyr Tyr Tyr Arg Asp Thr Pro Phe Phe Ser Gly Tyr Lys
     130                 135                 140

Met Thr Tyr Met Gln Arg Gly Asn Tyr Val Ala Val Ile Asn Pro Leu
145                 150                 155                 160

Phe Trp Ser Glu Val Met Ser Asp Asp Pro Thr Leu Gln Trp Gly Val
                 165                 170                 175

Tyr Asp Thr Val Thr Lys Thr Phe Phe Ser Leu Ser Lys Glu Ala Ser
             180                 185                 190

Ala Ala Thr Phe Ser Pro Leu Ile His Leu Lys Asp Leu Thr Val Gln
         195                 200                 205

Arg Asn Gly Tyr Leu Tyr Ala Thr Val Tyr Ser Thr Lys Arg Pro Ile
     210                 215                 220

Ala Ala Ile Val Ala Thr Ser Tyr Gln Arg Leu Ile Thr His Phe Tyr
225                 230                 235                 240

Asn His Leu Ile Phe Ala Leu Pro Ala Gly Ile Leu Gly Ser Leu Val
                 245                 250                 255

Leu Leu Leu Leu Trp Leu Arg Ile Arg Gln Asn Tyr Leu Ser Pro Lys
             260                 265                 270

Arg Lys Leu Gln Arg Ala Leu Glu Lys His Gln Leu Cys Leu Tyr Tyr
         275                 280                 285

Gln Pro Ile Ile Asp Ile Lys Thr Glu Lys Cys Ile Gly Ala Glu Ala
     290                 295                 300

Leu Leu Arg Trp Pro Gly Glu Gln Gly Gln Ile Met Asn Pro Ala Glu
305                 310                 315                 320

Phe Ile Pro Leu Ala Glu Lys Glu Gly Met Ile Glu Gln Ile Thr Asp
                 325                 330                 335

Tyr Val Ile Asp Asn Val Phe Arg Asp Leu Gly Asp Tyr Leu Ala Thr
             340                 345                 350

His Ala Asp Arg Tyr Val Ser Ile Asn Leu Ser Ala Ser Asp Phe His
         355                 360                 365

Thr Ser Arg Leu Ile Ala Arg Ile Asn Gln Lys Thr Glu Gln Tyr Ala
     370                 375                 380

Val Arg Pro Gln Gln Ile Lys Phe Glu Val Thr Glu His Ala Phe Leu
385                 390                 395                 400

Asp Val Asp Lys Met Thr Pro Ile Ile Leu Ala Phe Arg Gln Ala Gly
                 405                 410                 415

Tyr Glu Val Ala Ile Asp Asp Phe Gly Ile Gly Tyr Ser Asn Leu His
             420                 425                 430

Asn Leu Lys Ser Leu Asn Val Asp Ile Leu Lys Ile Asp Lys Ser Phe
```

| | | | | | 435 | | | | | 440 | | | | | 445 | | | |
|---|---|---|---|---|---|---|---|---|---|---|---|---|---|---|---|---|---|---|
| Val | Glu | Thr | Leu | Thr | Thr | His | Lys | Thr | Ser | His | Leu | Ile | Ala | Glu | His |
| | | | | 450 | | | | | 455 | | | | | 460 | |
| Ile | Ile | Glu | Leu | Ala | His | Ser | Leu | Gly | Leu | Lys | Thr | Ile | Ala | Glu | Gly |
| 465 | | | | | 470 | | | | | 475 | | | | | 480 |
| Val | Glu | Thr | Glu | Gln | Val | Asn | Trp | Leu | Arg | Lys | Arg | Gly | Val | Arg |
| | | | | 485 | | | | | 490 | | | | | 495 |
| Tyr | Cys | Gln | Gly | Trp | Phe | Phe | Ala | Lys | Ala | Met | Pro | Pro | Gln | Val | Phe |
| | | | 500 | | | | | 505 | | | | | 510 | |
| Met | Gln | Trp | Met | Glu | Gln | Leu | Pro | Ala | Arg | Glu | Leu | Thr | Arg | Gly | Gln |
| | | 515 | | | | | 520 | | | | | 525 | |

<210> SEQ ID NO 161
<211> LENGTH: 93
<212> TYPE: PRT
<213> ORGANISM: Escherichia coli

<400> SEQUENCE: 161

| Met | Ala | Thr | Leu | Thr | Thr | Gly | Val | Val | Leu | Leu | Arg | Trp | Gln | Leu | Leu |
|---|---|---|---|---|---|---|---|---|---|---|---|---|---|---|---|
| 1 | | | | 5 | | | | | 10 | | | | | 15 | |
| Ser | Ala | Val | Met | Met | Phe | Leu | Ala | Ser | Thr | Leu | Asn | Ile | Arg | Phe | Arg |
| | | | 20 | | | | | 25 | | | | | 30 | | |
| Arg | Ser | Asp | Tyr | Val | Gly | Leu | Ala | Val | Ile | Ser | Ser | Gly | Leu | Gly | Val |
| | | | 35 | | | | | 40 | | | | | 45 | | |
| Val | Ser | Ala | Cys | Trp | Phe | Ala | Met | Gly | Leu | Leu | Gly | Ile | Thr | Met | Ala |
| | 50 | | | | | 55 | | | | | 60 | | | | |
| Asp | Ile | Thr | Ala | Ile | Trp | His | Asn | Ile | Glu | Ser | Val | Met | Ile | Glu | Glu |
| 65 | | | | | 70 | | | | | 75 | | | | | 80 |
| Met | Asn | Gln | Thr | Pro | Pro | Gln | Trp | Pro | Met | Ile | Leu | Thr |
| | | | | 85 | | | | | 90 | | | |

<210> SEQ ID NO 162
<211> LENGTH: 3157
<212> TYPE: DNA
<213> ORGANISM: Escherichia coli

<400> SEQUENCE: 162

```
atgatcatcg gtgcgctgac ggttatcgtc tggaaacagt tcggctggct gggactgtac      60
gaaattattc cgggctttat cttcggcagt attgggattg tagtgtttag tttgctgggt     120
aaagcgccgt cagcggcgat gcaaaaacgc tttgccgagg ccgatgcgca ctatcattcg     180
gctccgccgt cacggttgca ggaaagctaa gggacttagc ctgcggcggt tttgtttggc     240
ttcagcagcg ggttgcgctc ccttaatgtg cctcgccata taaattgaat ggtgcaggga     300
gcgcgcaggg ggcggccaat cgccgccgcc cctgctgtc ccggccttcg gggaacgctt      360
cagcgatttt gacgccacca acacccgagc tgttattatg ttccgggcaa aaagttagat     420
ttgataatcg cggatggacg aaattgcttg atacaccccgc ttatcagttt tacatggaag    480
ctctgatgca ttgagtctgg acagttttgt cggctggata cggcgtttac gcggcatccg     540
gcaagaacac atggttcttt gcaaacaatc ccatctttct accctggaat aatcgtttat     600
atcccttggc attacctctc tttgtttaca ttccaacatc attttataaa cattccgctt     660
gtgtttttct ttgctgtaat gataatcgct atcactgcga tttacttttc tttgcataga     720
ttgactcaga aaaacgtttta agggtgggtg gcatgtttgt tccgtttctc attatgttgc    780
gcgaaggact tgaagccgcg ctgattgtca gtttgattgc cagctatctt aagcgtaccc     840
```

```
agcgaggccg atggattggt gtgatgtgga ttggcgtgtt gcttgccgct gcgttgtgcc    900
tgggcttggg tatcttcatt aacgaaacca ccggcgaatt ccgcaaaaaa gaacaggaac    960
tgtttgaagg tatcgtggcg gtgatcgccg tggtgatcct tacctggatg gttttctgga   1020
tgcgcaaagt gtcgcgcaac gtcaaagtgc aactggaaca ggcagtcgat agcgcattgc   1080
agcgtggaaa tcatcatggc tgggcgctgg tgatgatggt cttttttgcc gttgcaaggg   1140
aagggctgga gtcggtcttt ttcctgctgg cggcatttca acaagatgtc gggatctggc   1200
cgccgctggg tgcaatgctc ggtcttgcta ctgccgtggt gctaggcttc ctgctctact   1260
ggggcggtat tcgcctcaat cttggtgcat tttttaaatg gaccagcctg tttattctct   1320
tcgtcgccgc agggctggca gctggtgcca ttcgcgcatt tcatgaagcc ggattgtgga   1380
accactttca ggaaatcgcc ttcgatatga gtgcggtgct ctcaactcac tcgctgtttg   1440
gcacgctgat ggaagggatt tttggctatc aggaagcgcc gagcgtcagc gaagtcgccg   1500
tctggtttat ttatctcatc ccggcgctgg tggcatttgc tctgccacca cgcgcagggg   1560
cgacagcgtc tcgctccgcg taacaaatac gacgcaaact cttgcttagt tacaacatac   1620
tttaaaggga tagtctcgtc atgaccatta acttccgccg taacgcattg cagttgagcg   1680
tggctgcgct gttttcttct gcttttatgg ctaacgccgc tgatgtgccg caggtcaaag   1740
tgaccgtgac ggataagcag tgcgaaccga tgaccattac ggttaacgcc gggaaaacac   1800
agttcattat tcagaaccac agccagaagg cgctggagtg ggagatcctc aaaggcgtga   1860
tggtggtgga agagcgggaa aatatcgccc ctggctttag ccagaaaatg acggcgaatt   1920
tacagcctgg cgaatacgat atgacctgcg gtctgctgac taacccgaaa gggaagttga   1980
tcgtcaaagg tgaggcaacg gcggatgcgg cgcaaagtga tgcgctgtta agtcttggtg   2040
gtgcaattac tgcatataaa gcgtatgtca tggcggaaac cacgcagctg gtgaccgaca   2100
ccaaagcctt taccgacgcg attaaagcag gcgatatcga aaaagcgaaa gcactgtatg   2160
caccgacgcg ccagcactat gagcgtattg aaccgattgc tgaactgttc tccgatctgg   2220
atggcagcat tgacgcccgt gaagatgatt acgagcaaaa agccgccgac ccaaaattca   2280
ctggtttcca ccgtctggaa aaagcattgt ttggcgacaa caccaccaaa gggatggatc   2340
agtacgctga gcagctttat accgatgtgg tcgatttgca aaaacgcatc agtgaactgg   2400
ctttcccacc ttcaaaagtg gtcggcggcg cagccggact gattgaggaa gtggcagcca   2460
gcaaaattag cggtgaagaa gatcgctaca gccacaccga tctgtgggat ttccaggcta   2520
acgttgaagg ctcgcagaaa attgtcgatt tgctgcgtcc acaactgcaa aaagccaacc   2580
cggaactgct ggcaaaagtc gatgccaact ttaaaaaggt cgataccatt ctggcgaaat   2640
accgtactaa agacggtttt gaaacctacg acaaattgac cgatgccgac cggaatgcac   2700
tgaaaggacc gattactgcg ctggcggaag atctggcgca acttcgcggt gtgctgggac   2760
tggattaagc gttatgcagt ataaagatga aaacggcgtg aatgaaccgt cacgccgacg   2820
tttactgaaa gtgataggtg cactggcgct ggcgggaagt tgtccggtcg ctcatgcaca   2880
aaaaacgcaa agtgcgccgg gtacgctttc accggatgct cgcaatgaga aacagccgtt   2940
ttatggtgag catcaggcag ggatcctgac gccacaacag gccgcaatga tgctggtggc   3000
gtttgatgtg cttgccagcg ataaagccga tcttgagcgg ttgtttcgct tgttgactca   3060
gcgttttgct tttctgactc agggcggagc agcaccagaa acgccaaatc cgcgcctgcc   3120
accactcgat tccggcattc ttggcggcta cattgcg                            3157
```

<210> SEQ ID NO 163
<211> LENGTH: 276
<212> TYPE: PRT
<213> ORGANISM: Escherichia coli

<400> SEQUENCE: 163

Met Phe Val Pro Phe Leu Ile Met Leu Arg Glu Gly Leu Glu Ala Ala
1               5                   10                  15

Leu Ile Val Ser Leu Ile Ala Ser Tyr Leu Lys Arg Thr Gln Arg Gly
            20                  25                  30

Arg Trp Ile Gly Val Met Trp Ile Gly Val Leu Leu Ala Ala Ala Leu
        35                  40                  45

Cys Leu Gly Leu Gly Ile Phe Ile Asn Glu Thr Thr Gly Glu Phe Pro
    50                  55                  60

Gln Lys Glu Gln Glu Leu Phe Glu Gly Ile Val Ala Val Ile Ala Val
65                  70                  75                  80

Val Ile Leu Thr Trp Met Val Phe Trp Met Arg Lys Val Ser Arg Asn
                85                  90                  95

Val Lys Val Gln Leu Glu Gln Ala Val Asp Ser Ala Leu Gln Arg Gly
            100                 105                 110

Asn His His Gly Trp Ala Leu Val Met Met Val Phe Ala Val Ala
        115                 120                 125

Arg Glu Gly Leu Glu Ser Val Phe Phe Leu Leu Ala Ala Phe Gln Gln
    130                 135                 140

Asp Val Gly Ile Trp Pro Pro Leu Gly Ala Met Leu Gly Leu Ala Thr
145                 150                 155                 160

Ala Val Val Leu Gly Phe Leu Leu Tyr Trp Gly Gly Ile Arg Leu Asn
                165                 170                 175

Leu Gly Ala Phe Phe Lys Trp Thr Ser Leu Phe Ile Leu Phe Val Ala
            180                 185                 190

Ala Gly Leu Ala Ala Gly Ala Ile Arg Ala Phe His Glu Ala Gly Leu
        195                 200                 205

Trp Asn His Phe Gln Glu Ile Ala Phe Asp Met Ser Ala Val Leu Ser
    210                 215                 220

Thr His Ser Leu Phe Gly Thr Leu Met Glu Gly Ile Phe Gly Tyr Gln
225                 230                 235                 240

Glu Ala Pro Ser Val Ser Glu Val Ala Val Trp Phe Ile Tyr Leu Ile
                245                 250                 255

Pro Ala Leu Val Ala Phe Ala Leu Pro Pro Arg Ala Gly Ala Thr Ala
            260                 265                 270

Ser Arg Ser Ala
        275

<210> SEQ ID NO 164
<211> LENGTH: 375
<212> TYPE: PRT
<213> ORGANISM: Escherichia coli

<400> SEQUENCE: 164

Met Thr Ile Asn Phe Arg Arg Asn Ala Leu Gln Leu Ser Val Ala Ala
1               5                   10                  15

Leu Phe Ser Ser Ala Phe Met Ala Asn Ala Ala Asp Val Pro Gln Val
            20                  25                  30

Lys Val Thr Val Thr Asp Lys Gln Cys Glu Pro Met Thr Ile Thr Val
        35                  40                  45

Asn Ala Gly Lys Thr Gln Phe Ile Ile Gln Asn His Ser Gln Lys Ala

```
              50                  55                  60
Leu Glu Trp Glu Ile Leu Lys Gly Val Met Val Glu Arg Glu
 65                  70                  75                  80

Asn Ile Ala Pro Gly Phe Ser Gln Lys Met Thr Ala Asn Leu Gln Pro
                 85                  90                  95

Gly Glu Tyr Asp Met Thr Cys Gly Leu Leu Thr Asn Pro Lys Gly Lys
                100                 105                 110

Leu Ile Val Lys Gly Glu Ala Thr Ala Asp Ala Ala Gln Ser Asp Ala
                115                 120                 125

Leu Leu Ser Leu Gly Gly Ala Ile Thr Ala Tyr Lys Ala Tyr Val Met
130                 135                 140

Ala Glu Thr Thr Gln Leu Val Thr Asp Thr Lys Ala Phe Thr Asp Ala
145                 150                 155                 160

Ile Lys Ala Gly Asp Ile Glu Lys Ala Lys Ala Leu Tyr Ala Pro Thr
                165                 170                 175

Arg Gln His Tyr Glu Arg Ile Glu Pro Ile Ala Glu Leu Phe Ser Asp
                180                 185                 190

Leu Asp Gly Ser Ile Asp Ala Arg Glu Asp Tyr Glu Gln Lys Ala
                195                 200                 205

Ala Asp Pro Lys Phe Thr Gly Phe His Arg Leu Glu Lys Ala Leu Phe
210                 215                 220

Gly Asp Asn Thr Thr Lys Gly Met Asp Gln Tyr Ala Glu Gln Leu Tyr
225                 230                 235                 240

Thr Asp Val Val Asp Leu Gln Lys Arg Ile Ser Glu Leu Ala Phe Pro
                245                 250                 255

Pro Ser Lys Val Val Gly Gly Ala Ala Gly Leu Ile Glu Glu Val Ala
                260                 265                 270

Ala Ser Lys Ile Ser Gly Glu Glu Asp Arg Tyr Ser His Thr Asp Leu
                275                 280                 285

Trp Asp Phe Gln Ala Asn Val Glu Gly Ser Gln Lys Ile Val Asp Leu
                290                 295                 300

Leu Arg Pro Gln Leu Gln Lys Ala Asn Pro Glu Leu Leu Ala Lys Val
305                 310                 315                 320

Asp Ala Asn Phe Lys Lys Val Asp Thr Ile Leu Ala Lys Tyr Arg Thr
                325                 330                 335

Lys Asp Gly Phe Glu Thr Tyr Asp Lys Leu Thr Asp Ala Asp Arg Asn
                340                 345                 350

Ala Leu Lys Gly Pro Ile Thr Ala Leu Ala Glu Asp Leu Ala Gln Leu
                355                 360                 365

Arg Gly Val Leu Gly Leu Asp
370                 375

<210> SEQ ID NO 165
<211> LENGTH: 146
<212> TYPE: DNA
<213> ORGANISM: Artificial Sequence
<220> FEATURE:
<223> OTHER INFORMATION: promoter

<400> SEQUENCE: 165
aaaacgtgag gaaatacctg gatttttcct ggttattttg ccgcaggtca gcgtataatg      60
aagatctttt ccagtgttca gtagggtcct tgcacggtaa ttatgtcact ggttattaac     120 caattttttcc tgggggataa atgagc                                          146
```

```
<210> SEQ ID NO 166
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 166
atcgtgaaga tcttttccag tgttnannag ggtgccttgc acggtnatna ngtcactgg      59

<210> SEQ ID NO 167
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(20)
<223> OTHER INFORMATION: n is a, c, g, or t

<400> SEQUENCE: 167
tggaaaagat cttcannnnn cgctgacctg cg                                   32

<210> SEQ ID NO 168
<211> LENGTH: 146
<212> TYPE: DNA
<213> ORGANISM: Artificial Sequence
<220> FEATURE:
<223> OTHER INFORMATION: promoter

<400> SEQUENCE: 168
aaaacgtgag gaaatacctg gattttcct ggttatttg ccgcaggtca gcgtataatg       60
aagatctttt ccagtgttga caagggtcct tgcacggtta taatgtcact ggttattaac    120 caattttcc tgggggataa atgagc                                          146

<210> SEQ ID NO 169
<211> LENGTH: 314
<212> TYPE: DNA
<213> ORGANISM: Artificial Sequence
<220> FEATURE:
<223> OTHER INFORMATION: promoter

<400> SEQUENCE: 169
gcatgcattc caactgcgct aatgacgcag ctggacgaag gcgggattct cgtcttaccc     60
gtaggggagg agcaccagta tttgaaacgg gtgcgtcgtc ggggaggcga atttattatc   120
gataccgtgg aggccgtgcg ctttgtccct ttagtgaagg gtgagctggc ttaaaacgtg   180
```

```
aggaaatacc tggattttc ctggttattt tgccgcaggt cagcgtataa tgaagatctt      240
ttccagtgtt gacaagggtg ccttgcacgg ttataatgtc actggttatt aaccaatttt      300
tcctgggggt cgac                                                        314

<210> SEQ ID NO 170
<211> LENGTH: 45
<212> TYPE: DNA
<213> ORGANISM: Artificial Sequence
<220> FEATURE:
<223> OTHER INFORMATION: primer

<400> SEQUENCE: 170 ttcctgggg tcgacatgaa aaagattctc gtatcatttg ttgcc                        45

<210> SEQ ID NO 171
<211> LENGTH: 45
<212> TYPE: DNA
<213> ORGANISM: Artificial Sequence
<220> FEATURE:
<223> OTHER INFORMATION: primer

<400> SEQUENCE: 171
attctgtttt ctagattaat tctgggtgat ctgactgcga tgctt                       45

<210> SEQ ID NO 172
<211> LENGTH: 30
<212> TYPE: DNA
<213> ORGANISM: Artificial Sequence
<220> FEATURE:
<223> OTHER INFORMATION: primer

<400> SEQUENCE: 172
tctagaaaac agaatttgcc tggcggcagt                                        30

<210> SEQ ID NO 173
<211> LENGTH: 30
<212> TYPE: DNA
<213> ORGANISM: Artificial Sequence
<220> FEATURE:
<223> OTHER INFORMATION: primer

<400> SEQUENCE: 173 gtcgacccccc aggaaaaatt ggttaataac                                       30

<210> SEQ ID NO 174
<211> LENGTH: 576
<212> TYPE: DNA
<213> ORGANISM: Escherichia coli

<400> SEQUENCE: 174
atgagcgagc agttaacgga ccaggtcctg gttgaacggg tccagaaggg agatcagaaa       60
gcctttaact tactggtagt gcgctatcag cataaagtgg cgagtctggt ttcccgctat      120
gtgccgtcgg gtgatgttcc cgatgtggta caagaagctt ttattaaagc ctatcgtgcg      180
ctggattcgt tccggggaga tagcgctttt tatacatggc tgtatcggat tgctgtaaat      240
acagcgaaaa attactggt tgctcagggg cgtcgtccac cttccagtga tgtggatgcc      300
attgaagctg aaaacttcga aagtggcggc gcgttgaaag aaatttcgaa ccctgagaac      360
```

```
ttaatgttgt cagaagaact gagacagata gtttccgaa ctattgagtc cctcccggaa    420
gatttacgca tggcaataac cttgcgggag ctggatggcc tgagctatga agagatagcc    480
gctatcatgg attgtccggt aggtacggtg cgttcacgta tcttccgagc gagggaagct    540
attgataaca aagttcaacc gcttatcagg cgttga                              576
```